US012600696B2

(12) United States Patent
Reinmüller

(10) Patent No.: US 12,600,696 B2
(45) Date of Patent: Apr. 14, 2026

(54) AROMATIC COMPOUNDS

(71) Applicant: XENIOPRO GMBH, Kelkheim (Taunus (DE)

(72) Inventor: Viktoria Reinmüller, Allschwil (CH)

(73) Assignee: XENIOPRO GMBH, Kelkheim (DE)

(*) Notice: Subject to any disclaimer, the term of this patent is extended or adjusted under 35 U.S.C. 154(b) by 211 days.

(21) Appl. No.: 18/064,576

(22) Filed: Dec. 12, 2022

(65) Prior Publication Data

US 2023/0150923 A1 May 18, 2023
US 2023/0406814 A2 Dec. 21, 2023

Related U.S. Application Data

(62) Division of application No. 16/488,458, filed as application No. PCT/EP2018/054686 on Feb. 26, 2018, now Pat. No. 11,591,289.

(60) Provisional application No. 62/463,212, filed on Feb. 24, 2017.

(30) Foreign Application Priority Data

Mar. 10, 2017 (EP) .................................... 17160326
Dec. 7, 2017 (EP) .................................... 17205950

(51) Int. Cl.

| | |
|---|---|
| ***C07C 233/65*** | (2006.01) |
| ***A61K 31/192*** | (2006.01) |
| ***A61K 31/44*** | (2006.01) |
| ***C07C 65/24*** | (2006.01) |
| ***C07C 69/94*** | (2006.01) |
| ***C07D 213/80*** | (2006.01) |

(52) U.S. Cl.

CPC .......... *C07C 233/65* (2013.01); *A61K 31/192* (2013.01); *C07C 65/24* (2013.01); *C07C 69/94* (2013.01); *C07D 213/80* (2013.01); *A61K 31/44* (2013.01)

(58) Field of Classification Search

CPC ........ C07C 233/65; C07C 65/24; C07C 69/94
See application file for complete search history.

(56) References Cited

U.S. PATENT DOCUMENTS

| | | | | |
|---|---|---|---|---|
| 2,754,286 | A | 7/1956 | Elmore | |
| 3,113,849 | A | 12/1963 | McCoy | |
| 3,940,403 | A | 2/1976 | Maeda et al. | |
| 7,456,292 | B2 * | 11/2008 | Neogi | C07C 311/19 546/339 |
| 9,296,682 | B2 | 3/2016 | Radtke | |
| 10,772,876 | B2 | 9/2020 | Reinmueller | |

FOREIGN PATENT DOCUMENTS

| | | | | |
|---|---|---|---|---|
| EP | 1145718 | A1 | 10/2001 | |
| EP | 1710233 | A1 | 10/2006 | |
| GB | 2380193 | A | 4/2003 | |
| JP | 2011001294 | A | 1/2011 | |
| WO | 9303012 | A1 | 2/1993 | |
| WO | WO-9324442 | A1 * | 12/1993 | C07C 217/80 |
| WO | 2007022371 | A2 | 2/2007 | |
| WO | 2009032249 | A1 | 3/2009 | |
| WO | 2013093885 | A1 | 6/2013 | |
| WO | 2017158190 | A1 | 9/2017 | |
| WO | 2018096510 | A1 | 5/2018 | |

OTHER PUBLICATIONS

Li et al: "Synthesis of Diaryl Ethers, Diaryl Sulfides, Heteroaryl Ethers and Heteroaryl Sulfides under Microwave Dielectric Heating", Synthesis, Georg Thieme Verlag, Stuttgart, De, No. 8, Apr. 19, 2005 (Apr. 19, 2005), pp. 1305-1313, XP002435109.

Koden et al: "Effect of Chain Length on Mesomorphism of Steroid Esters of 4-(4-Alkylphenyl-X)benzoic Acids with X=Co, O, S, and CH2", Journal of Physical Chemistry, Jan. 1, 1973 (Jan. 1, 1973), pp. 4730-4737, XP055470685.

Ito et al: "Notiz uber einige neue Diphenylather-aldehyde und deren Thiosemicarbazone.", Pharmaceutical Bulletin, vol. 5, No. 6, Jan. 1, 1957 (Jan. 1, 1957), pp. 619-621, XP055486381.

Guan et al: "Design, Synthesis, and Structure-Activity Relationship of New Pyrimidinamine Derivatives Containing an Aryloxy Pyridine Moiety", Journal of Agricultural and Food Chemistry, vol. 65, No. 6, Feb. 6, 2017 (Feb. 6, 2017), pp. 1272-1280, XP055485673.

Hergenrother et al: "Synthesis and thermal reaction of 2-[4-(4-ethynylphenoxy)phenylene]-3-phenyl quinoxaline", Journal of Heterocyclic Chemistry, vol. 13, No. 5,Oct. 1, 1976 (Oct. 1, 1976), pp. 993-999, XP055485851.

Hou et al: "Evaluation of Novel N-(piperidine-4-yl)benzamide Derivatives as Potential Cell Cycle Inhibitors in HepG2 Cells", Chemical Biology & Drug Design., vol. 86, No. 2, Aug. 1, 2015 (Aug. 1, 2015), pp. 223-231, XP055485858.

Buck et al: "Ullmann diaryl ether synthesis: rate acceleration by 2,2,6,6-tetramethylheptane-3,5-dione", Organic Letters , 14(23), 6012-6015 Coden: ORLEF7; ISSN: 1523-7052, vol. 4, No. 9, Jan. 1, 2002 (Jan. 1, 2002), pp. 1623-1626, XP002403679.

Database Registry [Online] Chemical Abstracts Service, Columbus, Ohio, US; May 15, 2008 (May 15, 2008), XP002782250, accession No. 1020936-29-1 Database accession No. 1020936-29-1 RN 1020936-29-1.

Database Registry [Online] Chemical Abstracts Service, Columbus, Ohio, US; Jul. 27, 2008 (Jul. 27, 2008), XP002782251, accession No. 1036524-79-4 Database accession No. 1036524-79-4 RN 1036524-79-4.

(Continued)

*Primary Examiner* — Kevin E Weddington

(74) *Attorney, Agent, or Firm* — Rothwell, Figg, Ernst & Manbeck, P.C.

(57) ABSTRACT

The present invention comprises novel aromatic molecules, which can be used in the treatment of pathological conditions, such as cancer, skin diseases, muscle disorders, and immune system-related disorders such as disorders of the hematopoietic system including the hematologic system in human and veterinary medicine.

29 Claims, No Drawings

(56) References Cited

OTHER PUBLICATIONS

Database Registry [Online] Chemical Abstracts Service, Columbus, Ohio, US; Jul. 28, 2008 (Jul. 28, 2008), XP002782252, accession No. 1036598-46-5 Database accession No. 1036598-46-5 RN 1036598-46-5.
Database Registry [Online] Chemical Abstracts Service, Columbus, Ohio, US; Aug. 17, 2008 (Aug. 17, 2008), XP002782253, accession No. 1041517-52-5 Database accession No. 1041517-52-5 RN 1041517-52-5.
Database Registry [Online] Chemical Abstracts Service, Columbus, Ohio, US; Nov. 25, 2013 (Nov. 25, 2013), XP002782254, accession No. 1480752-41-7 Database accession No. 1480752-41-7 RN 1480752-41-7.
Database Registry [Online] Chemical Abstracts Service, Columbus, Ohio, US; Feb. 1, 2009 (Feb. 1, 2009), XP002782255, accession No. 1099130-61-6 Database accession No. 1099130-61-6 RN 1099130-61-6.
Database Registry [Online] Chemical Abstracts Service, Columbus, Ohio, US; Feb. 20, 2014 (Feb. 20, 2014), XP002782256, accession No. 1550449-98-3 Database accession No. 1550449-98-3 RN 1550449-98-3.
Database Registry [Online] Chemical Abstracts Service, Columbus, Ohio, US; Dec. 5, 2012 (Dec. 5, 2012), XP002782257, accession No. 1411168-77-8 Database accession No. 1411168-77-8 RN 1411168-77-8.
Database Registry [Online] Chemical Abstracts Service, Columbus, Ohio, US; Jun. 22, 2016 (Jun. 22, 2016), XP002782258, accession No. 1937165-19-9 Database accession No. 1937165-19-9 RN 1937165-19-9.
Database Registry [Online] Chemical Abstracts Service, Columbus, Ohio, US; Nov. 15, 2007 (Nov. 15, 2007), XP002782259, accession No. 953720-22-4 Database accession No. 953720-22-4 RN 953720-22-4.
Database Registry [Online] Chemical Abstracts Service, Columbus, Ohio, US; Nov. 19, 2007 (Nov. 19, 2007), XP002782260, accession No. 954564-77-3 Database accession No. 954564-77-3 RN 954564-77-3.
Database Registry [Online] Chemical Abstracts Service, Columbus, Ohio, US; Feb. 1, 2009 (Feb. 1, 2009), XP002782261, accession No. 1098368-66-1 Database accession No. 1098368-66-1 RN 1098368-66-1.
Database Registry [Online] Chemical Abstracts Service, Columbus, Ohio, US; Nov. 4, 2013 (Nov. 4, 2013), XP002782262, accession No. 1468989-97-0 Database accession No. 1468989-97-0 RN 1468989-97-0.
Database Registry [Online] Chemical Abstracts Service, Columbus, Ohio, US; Dec. 29, 2013 (Dec. 29, 2013), XP002782264, accession No. 1506498-75-4 Database accession No. 1506498-75-4 RN 1506498-75-4.
Database Registry [Online] Chemical Abstracts Service, Columbus, Ohio, US; Feb. 20, 2014 (Feb. 20, 2014), XP002782265, accession No. 1550451-20-1 Database accession No. 1550451-20-1 RN 1550451-20-1.
Database Registry [Online] Chemical Abstracts Service, Columbus, Ohio, US; May 25, 2016 (May 25, 2016), XP002782266, accession No. 1917642-56-8 Database accession No. 1917642-56-8 RN 1917642-56-8.
Database Registry [Online] Chemical Abstracts Service, Columbus, Ohio, US; Jul. 3, 2016 (Jul. 3, 2016), XP002782267, accession No. 1944481-23-5 Database accession No. 1944481-23-5 RN 1944481-23-5.
Database Registry [Online] Chemical Abstracts Service, Columbus, Ohio, US; Jul. 25, 2016 (Jul. 25, 2016), XP002782268, accession No. 1958884-22-4 Database accession No. 1958884-22-4 RN 1958884-22-4.
Database Registry [Online] Chemical Abstracts Service, Columbus, Ohio, US; Jul. 29, 2016 (Jul. 29, 2016), XP002782269, accession No. 1962787-08-1 Database accession No. 1962787-08-1 RN 1962787-08-1.
Yabunaka et al: "Hybrid ubiquinone: novel inhibitor of mitochondrial complex I", Biochimica Et Biophysica Acta. Bioenerget, Amsterdam, NL, vol. 1556, No. 2-3, Dec. 2, 2002 (Dec. 2, 2002), pp. 106-112, XP004396758.
Carrasco et al: "Probing the aurone scaffold against Plasmodium falciparum: Design, synthesis and antimalarial activity", European Journal of Medicinal Chemistry, vol. 80, Jun. 1, 2014 (Jun. 1, 2014), pp. 523-534, XP055513880.
Carrasco et al: "Probing the Azaaurone Scaffold against the Hepatic and Erythrocytic Stages of Malaria Parasites", CHEMMEDCHEM, vol. 11, No. 19, Aug. 19, 2016 (Aug. 19, 2016), pp. 2194-2204, XP0055513882.
International Search Report cited in PCT/EP2018/054686 dated Oct. 23, 2018, 14 pgs.
Partial International Search Report dated Jul. 11, 2018, cited in PCT/EP2018/054686, 31 pages.
Notification Concerning Transmittal of International Preliminary Report on Patentability (Chapter I) cited in PCT/EP2018/54696 dated Aug. 27, 2019, 23 pages.
Koden et al: "Effect of Chain Length on Mesomorphism of Steroid Esters of 4-(4-Alkylphenyl-X)benzoic Acids with X=Co, O, S, and CH2", Journal of Physical Chemistry, Jan. 1, 1983 (Jan. 1, 1983), pp. 4730-4737, XP055470685.

* cited by examiner

AROMATIC COMPOUNDS

This application is a divisional from Ser. No. 16/488,458 filed Aug. 23, 2019, which is a 35 U.S.C. 371 National Phase Entry Application from PCT/EP2018/054686 filed Feb. 26, 2018, which claims priority to European Application No. 17160326.9 filed Mar. 10, 2017 and European Application No. 17205950.3 filed Dec. 7, 2017, and claims the benefit of U.S. Patent Application No. 62/463,212, filed on Feb. 24, 2017, the disclosures of which are incorporated herein by reference in their entirety.

The present invention relates to novel aromatic compounds and their use as therapeutic agents, which can be used in the treatment of pathological conditions, such as cancer, skin disorders, muscle disorders, and immune system-related disorders such as disorders of the hematopoietic system including the hematologic system in human and veterinary medicine.

BACKGROUND

Notch signaling is a fundamental cell-to-cell communication pathway that regulates central processes in embryonic development as well as in the maintenance of adult tissues. The effect of a Notch signal is highly dependent on the signal strength, duration, and most importantly on the cellular context. In this regard, Notch activity leads to numerous cell-type specific responses, which implicate for example cell fate decisions, the induction or inhibition of differentiation, and the regulation of cell proliferation.

If a signaling event is not correctly controlled, a consequent loss of balance in according cellular processes may drive abnormal cellular changes and finally end in diverse disease situations, such as cancer.

Initially, Notch signaling was discovered as an oncogenic pathway. Corresponding pathological conditions are linked to abnormally augmented signaling levels. In these particular cases, the use of Notch inhibiting agents represents a promising strategy for therapeutic intervention and numerous corresponding drugs are currently in development.

Conversely, there is increasing evidence for tumor-suppressor functions of the Notch pathway in other cellular contexts (Lobry et al., *J. Exp. Med.* 2011, 208, 1931-1935; South et al., *Semin. Cell Dev. Biol.* 2012, 23, 458-464), most notably concerning organs, in which Notch negatively impacts proliferation or triggers differentiation, such as in the skin or in the neuroendocrine system (Dotto, *Oncogene* 2008, 27, 5115-5123; Kunnimalaiyaan et al., *The Oncologist* 2007, 12, 535-542). This finding is not only based on observations that certain tumors display impairments in Notch activity. Additionally, various successful demonstrations confirmed that the artificial activation of Notch signaling has a beneficial impact on according malignant degenerations (Jaskula-Sztul et al, *J. Surg. Res.* 2011, 171, 23-27; Yu et al., *Cancer* 2013, 119, 774-781; Ye et al., *Sci. Rep.* 2016, 6, 26510). Prominent examples comprise non-melanoma skin cancer, neuroendocrine tumors and certain cancers of the hematopoietic system.

In a broader sense, due to the central role of this pathway, the potential use of Notch enhancers is not only limited to the treatment of cancer, but likewise expected to be beneficial in other pathologic conditions that have been shown to be responsive to Notch induction, such as diseases of the skin, muscle or immune system.

To this end, it is highly desirable to develop therapeutic agents that enhance Notch signaling.

Notch Enhancers State of the Art

Current methods to enhance Notch signaling for a potential therapeutic use entail the application of receptor-activating peptides or of small molecules that show Notch-augmenting properties. However, no approved Notch enhancer is available yet in the clinics. Besides, only a small number of according agents is known to date and much less have so far entered a drug development program. Reported small molecule Notch enhancers comprise resveratrol (Pinchot et al., *Cancer* 2011, 117, 1386-1398; Truong et al., *Ann. Surg. Oncol.* 2011, 18, 1506-1511; Yu et al., *Mol. Cancer Ther.* 2013, 12, 1276-1287), valproic acid (Greenblatt et al., *Oncologist* 2007, 12, 942-951; Platta et al., *J. Surg. Res.* 2008, 148, 31-37; Mohammed et al., *Oncologist* 2011, 16, 835-843), hesperetin (Patel et al., *Ann. Surg. Oncol.* 2014, 21, 497-504), chrysin (Yu et al., *Cancer* 2013, 119, 774-778), phenethyl isothiocyanate (Kim et al., *PLoS One* 2011, 6, 10), thiocoraline (Wyche et al., *Cancer Gene Ther.* 2014, 21, 518-525) and N-methylhemeanthidine chloride (Ye et al., *Sci. Rep.* 2016, 6, 26510).

A common drawback associated with most of the mentioned compounds is the lack of potency.

Hence, it is absolutely crucial to provide novel Notch enhancers with high therapeutic efficacy.

The screening of a small library of chemical molecules in a Notch-dependent luciferase reporter assay revealed a novel compound family with Notch-augmenting properties (Reinmüller et al., 2015, EPFL Thesis 6887, published in March 2016), the content of which is herein incorporated by reference.

DESCRIPTION OF THE INVENTION

The present invention covers refined structures to the initially discovered limited set of Notch enhancer molecules. These second generation compounds have been designed and are supposed to exhibit increased potency and greater metabolic stability. Alternatively, they present specific modifications of chemical residues, which are supposed to not impair the Notch-augmenting activity, but yet provide novel molecular features that may turn out to beneficially influence pharmacological and physicochemical parameters addressed in the general drug development process.

Thus, the present invention relates to compounds as defined herein that feature Notch enhancing activity, which can be used in the treatment of pathological conditions that are responsive for Notch-regulation, such as cancer, skin diseases, muscle disorders, and immune system-related disorders such as disorders of the hematopoietic system including the hematologic system in human and veterinary medicine.

The biological activity, e.g. the antiproliferative activity of the claimed compounds can be attributed to but may not be limited to Notch signaling enhancing activity. Thus, the present invention also relates to compounds as defined herein that feature antiproliferative activity, which can be used in the treatment of benign and malignant hyperproliferative disorders in human and veterinary medicine. In particular, the present invention relates to compounds as defined herein for the treatment of immune system-related disorders such as disorders of the hematopoietic system including the hematologic system, such as malignancies of the myeloid lineage, malignant and non-malignant disorders of the skin and mucosa, such as squamous and basal cell carcinoma, actinic keratosis, and hyperproliferative disorders of the skin and mucosa, e.g. cornification disorders, malignant and non-malignant disorders of the muscle, including hyperproliferative disorders of the muscle, such as muscle hyperplasia and muscle hypertrophy, disorders of the neuroendocrine system, such as medullary thyroid cancer, and hyperproliferative disorders of the genitourinary tract, e.g. cervical cancer in human and veterinary medicine.

A first aspect of the present invention relates to compounds of formula I and salts and solvates thereof:

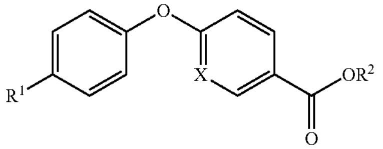

(I)

wherein X is CH or N, $R^1$=$C_1$-$C_{12}$ preferably $C_1$-$C_6$ alkyl, $C_2$-$C_{12}$ preferably $C_2$-$C_6$ alkenyl, $C_2$-$C_{12}$ preferably $C_2$-$C_6$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents in particular independently selected from: —F, —Cl, —Br, —I, —CN, —NCO, —NCS; and $OC_1$-$C_3$ alkyl optionally halogenated or perhalogenated, particularly perfluorinated;

wherein all cycloalkyl, cycloalkenyl, bicycloalkyl, bicycloalkenyl and tricycloalkyl residues can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all alkyl, alkenyl, alkynyl, cycloalkyl, cycloalkenyl, bicycloalkyl, bicycloalkenyl and tricycloalkyl residues can be perhalogenated, particularly perfluorinated;

and wherein $R^1$ is preferably selected from methyl, ethyl, n-propyl, n-butyl, n-pentyl, n-hexyl, iso-propyl, tert-butyl, tert-pentyl, 3-pentyl, —$CF_3$, —$CF_2CF_3$, —$(CF_2)_2CF_3$, —$(CF_2)_3CF_3$, —$CH(CF_3)_2$, —$CF(CF_3)_2$, cyclopropyl, cyclobutyl, cyclopentyl, cyclohexyl, cycloheptyl, norbornyl, bicyclo[2.2.2]octyl, adamantyl, and 9-methylbicyclo[3.3.1]nonyl;

$R^2$=H, $C_1$-$C_6$ alkyl, $C_3$-$C_6$ cycloalkyl, wherein all alkyl residues can be linear or branched, and can be unsubstituted or substituted with one or more substituents in particular independently selected from: —F, —Cl, —Br, —I; and $OC_1$-$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all alkyl and cycloalkyl residues can be perhalogenated, particularly perfluorinated;

and wherein $R^2$ is preferably selected from H, methyl and ethyl.

In some embodiments, the following compounds shown in Table Ia are explicitly excluded from the scope of the invention:

TABLE Ia

| Compound | $R^1$ | $R^2$ | X |
|---|---|---|---|
| I-A | tert-butyl | H | CH |
| I-B | tert-butyl | ethyl | CH |
| I-C | tert-pentyl | H | CH |
| I-D | tert-pentyl | ethyl | CH |
| I-E | cyclo-hexyl | H | CH |
| I-F | cyclo-hexyl | ethyl | CH |
| I-G | adamant-1-yl | H | CH |
| I-H | adamant-1-yl | ethyl | CH |
| I-I | methyl | H | N |
| I-J | methyl | ethyl | N |
| I-K | tert-butyl | H | N |
| I-L | tert-butyl | ethyl | N |
| I-M | tert-pentyl | H | N |
| I-N | tert-pentyl | ethyl | N |
| I-O | cyclo-hexyl | H | N |
| I-P | cyclo-hexyl | ethyl | N |
| I-Q | isopropyl | H | CH |
| I-R | phenyl | H | CH |
| I-S | methyl | H | CH |
| I-T | tert-butyl | methyl | N |
| I-U | methyl | methyl | N |
| I-V | methyl | methyl | CH |
| I-W | methyl | ethyl | CH |
| I-X | n-hexyl | H | CH |
| I-Y | n-octyl | H | CH |
| I-Z | n-dodecyl | H | CH |
| I-AA | iso-propyl | H | N |

Compounds I-A to I-T of Table Ia are known in the art for certain applications in the field of medicine whereas to the best of the inventor's knowledge, compounds I-U to I-AA are not known for any use in medicine. Thus, the invention encompasses any medical use for compounds I-U to I-AA.

Specific examples of compounds falling under the scope of formula I are shown in Table Ib. The compounds in Table Ib are defined by their chemical structure, the indicated nomenclature is only for illustrative purposes.

TABLE Ib

X = CH, $R^2$ = H

001

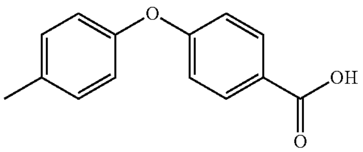 [SMILES: Cc1ccc(Oc2ccc(C(=O)O)cc2)cc1]

4(p-tolyloxy)benzoic acid

002

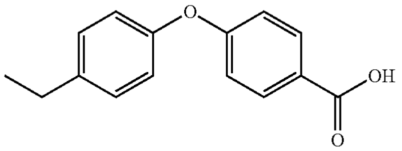 [SMILES: CCc1ccc(Oc2ccc(C(=O)O)cc2)cc1]

4-(4-ethylphenoxy)benzoic acid

TABLE Ib-continued

003

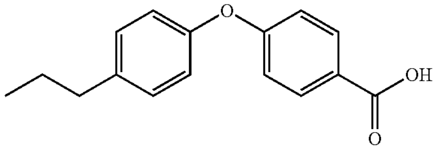 [SMILES: CCCc1ccc(Oc2ccc(C(=O)O)cc2)cc1]

4-(4-propylphenoxy)benzoic acid

004

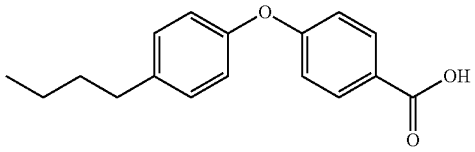 [SMILES: CCCCc1ccc(Oc2ccc(C(=O)O)cc2)cc1]

4-(4-butylphenoxy)benzoic acid

005

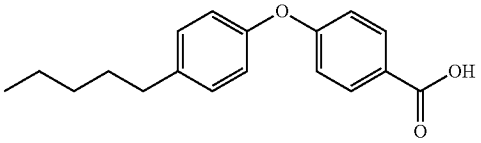 [SMILES: CCCCCc1ccc(Oc2ccc(C(=O)O)cc2)cc1]

4-(4-pentylphenoxy)benzoic acid

006

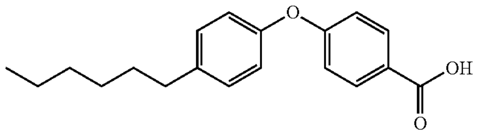 [SMILES: CCCCCCc1ccc(Oc2ccc(C(=O)O)cc2)cc1]

4-(4-hexylphenoxy)benzoic acid

007

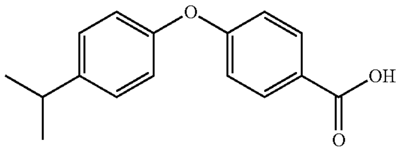 [SMILES: CC(C)c1ccc(Oc2ccc(C(=O)O)cc2)cc1]

4-(4-isopropylphenoxy)benzoic acid

008

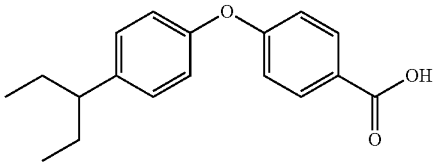 [SMILES: CCC(CC)c1ccc(Oc2ccc(C(=O)O)cc2)cc1]

4-(4-(pentan-3-yl)phenoxy)benzoic acid

009

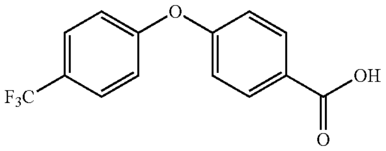 [SMILES: O=C(O)c1ccc(Oc2ccc(C(F)(F)F)cc2)cc1]

4-(4-(trifluoromethyl)phenoxy)benzoic acid

010

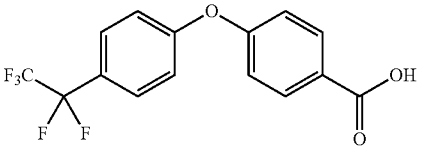 [SMILES: O=C(O)c1ccc(Oc2ccc(C(F)(F)C(F)(F)F)cc2)cc1]

4-(4-(perfluoroethyl)phenoxy)benzoic acid

TABLE Ib-continued

011

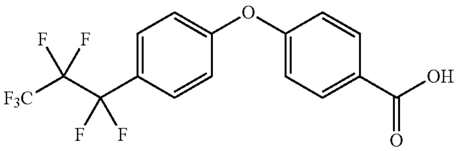

4-(4-(perfluoropropyl)phenoxy)benzoic acid

012

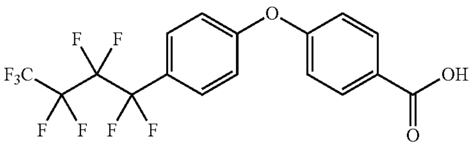 [SMILES: O=C(O)c1ccc(Oc2ccc(C(F)(F)C(F)(F)C(F)(F)C(F)(F)F)cc2)cc1]

4-(4-(perfluorobutyl)phenoxy)benzoic acid

013

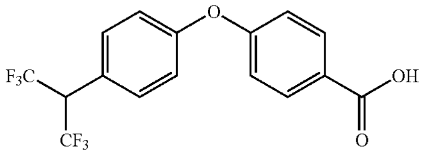

4-(4-(1,1,1,3,3,3-hexafluoropropan-2-yl)phenoxy) benzoic acid

014

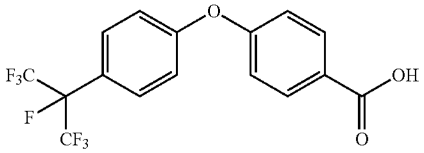

4-(4-(perfluoropropan-2-yl)phenoxy)benzoic acid

015

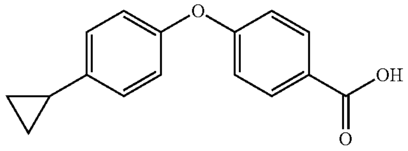 [SMILES: O=C(O)c1ccc(Oc2ccc(C3CC3)cc2)cc1]

4-(4-cyclopropylphenoxy)benzoic acid

016

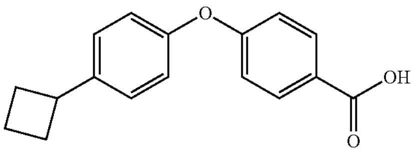 [SMILES: O=C(O)c1ccc(Oc2ccc(C3CCC3)cc2)cc1]

4-(4-cyclobutylphenoxy)benzoic acid

017

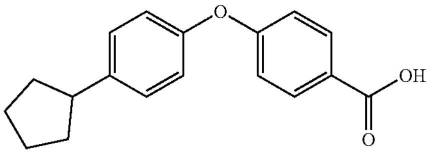

4-(4-cyclopentylphenoxy)benzoic acid

TABLE Ib-continued

018

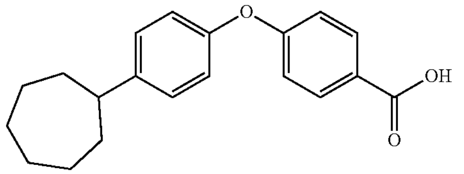 [SMILES: O=C(O)c1ccc(Oc2ccc(C3CCCCCC3)cc2)cc1]

4-(4-cycloheptylphenoxy)benzoic acid

019

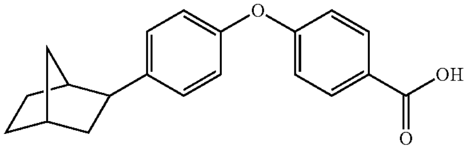 [SMILES: O=C(O)c1ccc(Oc2ccc(C3CC4CCC3C4)cc2)cc1]

4-(4-((1S,4R)-bicyclo[2.2.1]heptan-2-yl) phenoxy)benzoic acid

020

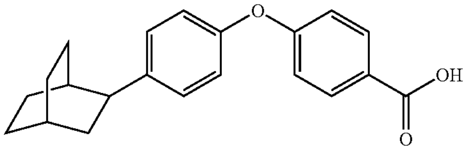 [SMILES: O=C(O)c1ccc(Oc2ccc(C3CC4CCC3CC4)cc2)cc1]

4-(4-((1s,4s)-bicyclo[2.2.2]octan-2-yl) phenoxy)benzoic acid

021

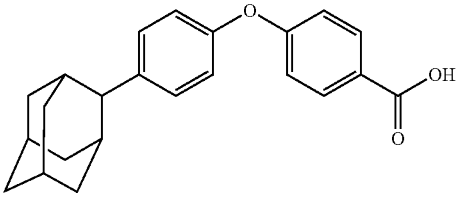 [SMILES: O=C(O)c1ccc(Oc2ccc(C3C4CC5CC(C4)CC3C5)cc2)cc1]

4-(4-((1r,3r,5r,7r)-adamantan-2-yl) phenoxy)benzoic acid

022

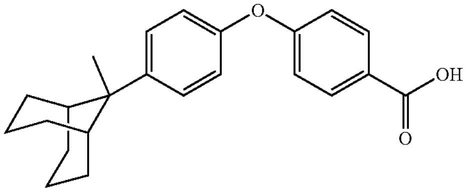 [SMILES: CC1(c2ccc(Oc3ccc(C(=O)O)cc3)cc2)C2CCCC1CCC2]

4-(4-((1R,5S)-9-methylbicyclo[3.3.1]nonan-9-yl) phenoxy)benzoic acid

X = CH, $R^2$ = Me

023

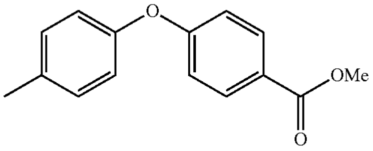

methyl 4-(p-tolyloxy)benzoate

TABLE Ib-continued

024

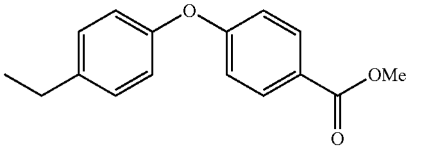 [SMILES: CCc1ccc(Oc2ccc(C(=O)OC)cc2)cc1]

methyl 4-(4-ethylphenoxy)benzoate

025

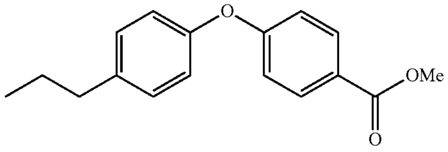 [SMILES: CCCc1ccc(Oc2ccc(C(=O)OC)cc2)cc1]

methyl 4-(4-propylphenoxy)benzoate

026

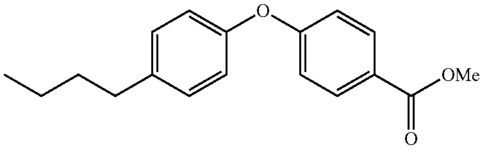 [SMILES: CCCCc1ccc(Oc2ccc(C(=O)OC)cc2)cc1]

methyl 4-(4-butylphenoxy)benzoate

027

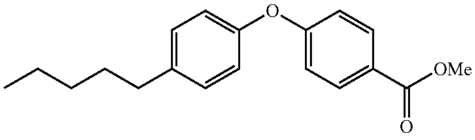 [SMILES: CCCCCc1ccc(Oc2ccc(C(=O)OC)cc2)cc1]

methyl 4-(4-pentylphenoxy)benzoate

028

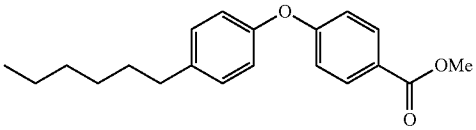 [SMILES: CCCCCCc1ccc(Oc2ccc(C(=O)OC)cc2)cc1]

methyl 4-(4-hexylphenoxy)benzoate

029

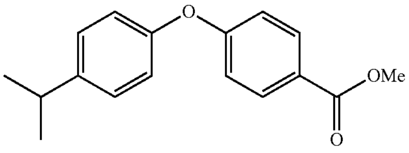 [SMILES: COC(=O)c1ccc(Oc2ccc(C(C)C)cc2)cc1]

methyl 4-(4-isopropylphenoxy)benzoate

030

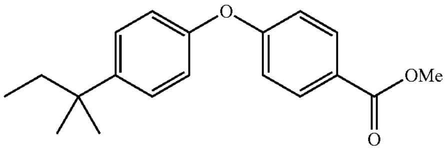 [SMILES: CCC(C)(C)c1ccc(Oc2ccc(C(=O)OC)cc2)cc1]

methyl 4-(4-(tert-pentyl)phenoxy)benzoate

031

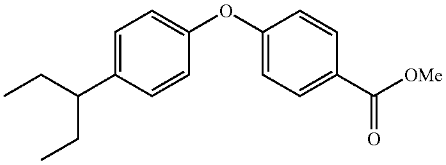 [SMILES: CCC(CC)c1ccc(Oc2ccc(C(=O)OC)cc2)cc1]

methyl 4-(4-(pentan-3-yl)phenoxy)benzoate

TABLE Ib-continued

032
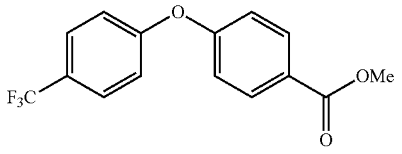 [SMILES: COC(=O)c1ccc(Oc2ccc(C(F)(F)F)cc2)cc1]
methyl 4-(4-(trifluoromethyl)phenoxy)benzoate

033
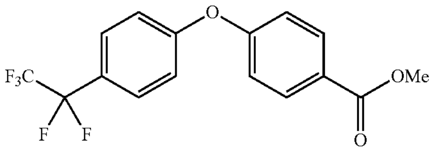 [SMILES: COC(=O)c1ccc(Oc2ccc(C(F)(F)C(F)(F)F)cc2)cc1]
methyl 4-(4-(perfluoroethyl)phenoxy)benzoate

034
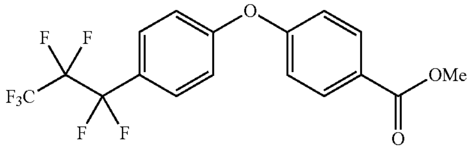
methyl 4-(4-(perfluoropropyl)phenoxy)benzoate

035
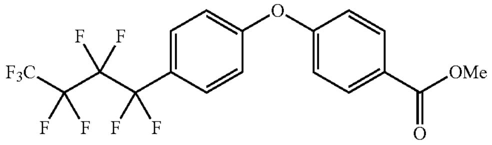
methyl 4-(4-(perfluorobutyl)phenoxy)benzoate

036
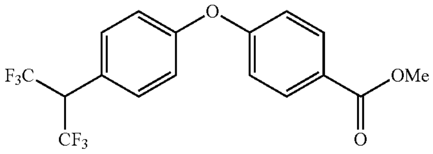
methyl 4-(4-(1,1,1,3,3,3-hexafluoropropan-2-yl) phenoxy)benzoate

037
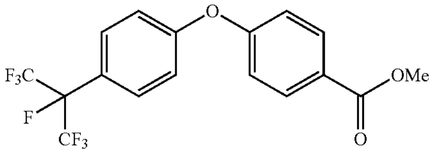 [SMILES: COC(=O)c1ccc(Oc2ccc(C(F)(C(F)(F)F)C(F)(F)F)cc2)cc1]
methyl 4-(4-(perfluoropropan-2-yl)phenoxy)benzoate

038
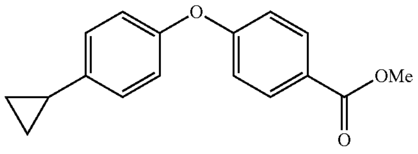 [SMILES: COC(=O)c1ccc(Oc2ccc(C3CC3)cc2)cc1]
methyl 4-(4-(cyclopropyl)phenoxy)benzoate

039
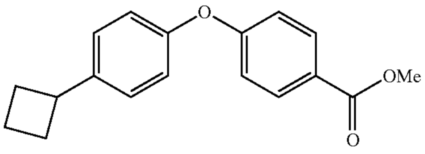 [SMILES: COC(=O)c1ccc(Oc2ccc(C3CCC3)cc2)cc1]
methyl 4-(4-(cyclobutyl)phenoxy)benzoate

TABLE Ib-continued

040
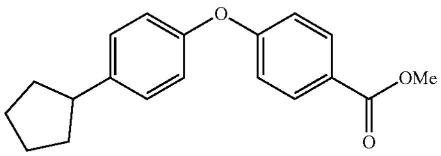 [SMILES: COC(=O)c1ccc(Oc2ccc(C3CCCC3)cc2)cc1]
methyl 4-(4-(cyclopentyl)phenoxy)benzoate

041
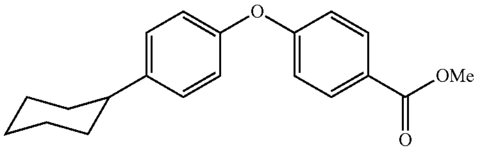 [SMILES: COC(=O)c1ccc(Oc2ccc(C3CCCCC3)cc2)cc1]
methyl 4-(4-(cyclohexyl)phenoxy)benzoate

042
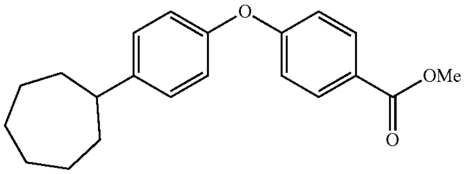 [SMILES: COC(=O)c1ccc(Oc2ccc(C3CCCCCC3)cc2)cc1]
methyl 4-(4-(cycloheptylphenoxy)benzoate

043
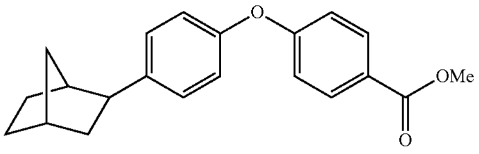
methyl 4-(4-((1S,4R)-bicyclo[2.2.1]heptan-2-yl) phenoxy)benzoate

044
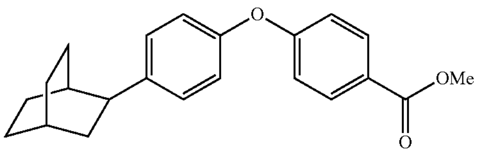 [SMILES: COC(=O)c1ccc(Oc2ccc(C3CC4CCC3CC4)cc2)cc1]
methyl 4-(4-((1s,4s)-bicyclo[2.2.2]octan-2-yl) phenoxy)benzoate

045
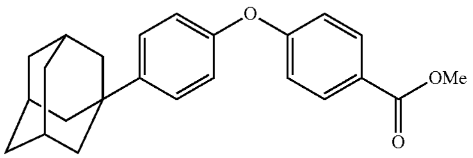
methyl 4-(4-((3r,5r,7r)-adamantan-1-yl) phenoxy)benzoate

046
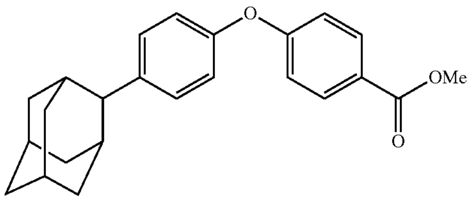 [SMILES: COC(=O)c1ccc(Oc2ccc(C3C4CC5CC(C4)CC3C5)cc2)cc1]
methyl 4-(4-((1r,3r,5r,7r)-adamantan-2-yl) phenoxy)benzoate

TABLE Ib-continued

047

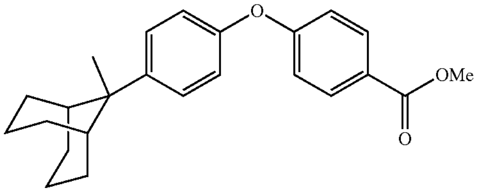

methyl 4-(4-((1R,5S)-9-methylbicyclo[3.3.1]nonan-9-yl) phenoxy)benzoate

X = CH, $R^2$ = Et

048

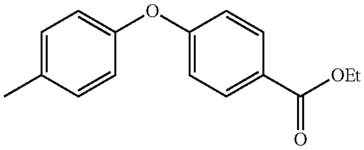 [SMILES: CCOC(=O)c1ccc(Oc2ccc(C)cc2)cc1]

ethyl 4-(p-tolyoxy)benzoate

049

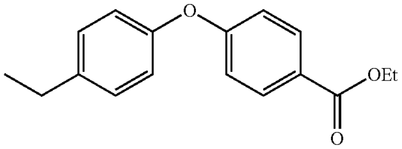 [SMILES: CCOC(=O)c1ccc(Oc2ccc(CC)cc2)cc1]

ethyl 4-(4-ethylphenoxy)benzoate

050

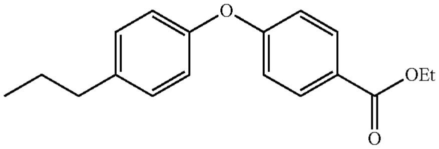 [SMILES: CCCc1ccc(Oc2ccc(C(=O)OCC)cc2)cc1]

ethyl 4-(4-propylphenoxy)benzoate

051

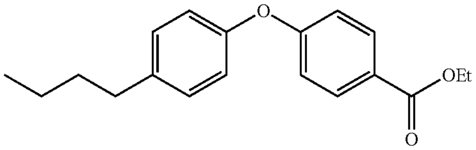 [SMILES: CCCCc1ccc(Oc2ccc(C(=O)OCC)cc2)cc1]

ethyl 4-(4-butylphenoxy)benzoate

052

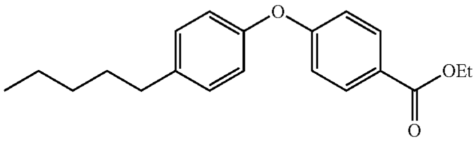 [SMILES: CCCCCc1ccc(Oc2ccc(C(=O)OCC)cc2)cc1]

ethyl 4-(4-pentylphenoxy)benzoate

053

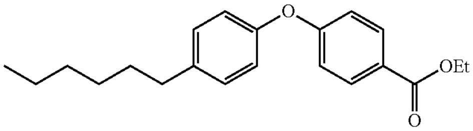 [SMILES: CCCCCCc1ccc(Oc2ccc(C(=O)OCC)cc2)cc1]

ethyl 4-(4-hexylphenoxy)benzoate

TABLE Ib-continued

054

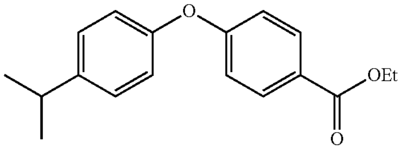 [SMILES: CCOC(=O)c1ccc(Oc2ccc(C(C)C)cc2)cc1]

ethyl 4-(4-isopropylphenoxy)benzoate

055

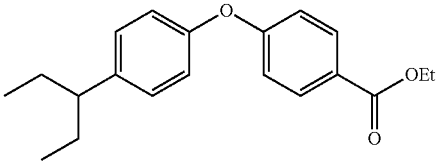 [SMILES: CCOC(=O)c1ccc(Oc2ccc(C(CC)CC)cc2)cc1]

ethyl 4-(4-(pentan-3-yl)phenoxy)benzoate

056

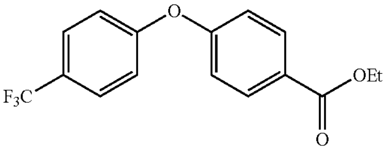 [SMILES: CCOC(=O)c1ccc(Oc2ccc(C(F)(F)F)cc2)cc1]

ethyl 4-(4-(trifluoromethyl)phenoxy)benzoate

057

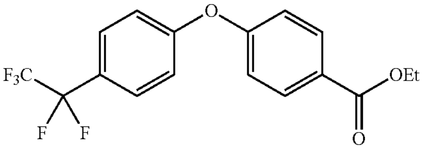 [SMILES: CCOC(=O)c1ccc(Oc2ccc(C(F)(F)C(F)(F)F)cc2)cc1]

ethyl 4-(4-(perfluoroethyl)phenoxy)benzoate

058

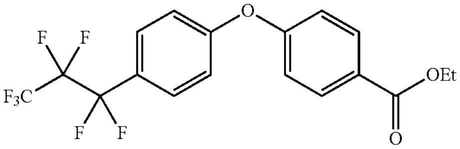 [SMILES: CCOC(=O)c1ccc(Oc2ccc(C(F)(F)C(F)(F)C(F)(F)F)cc2)cc1]

ethyl 4-(4-(perfluoropropyl)phenoxy)benzoate

059

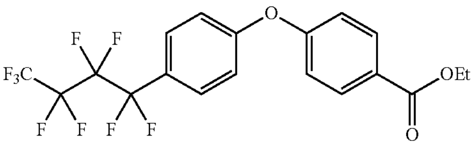 [SMILES: CCOC(=O)c1ccc(Oc2ccc(C(F)(F)C(F)(F)C(F)(F)C(F)(F)F)cc2)cc1]

ethyl 4-(4-(perfluorobutyl)phenoxy)benzoate

060

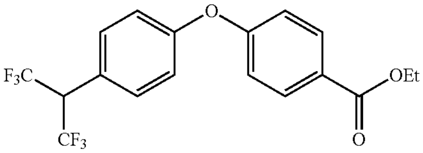

ethyl 4-(4-(1,1,1,3,3,3-hexafluoropropan-2-yl)phenoxy)benzoate

TABLE Ib-continued

061

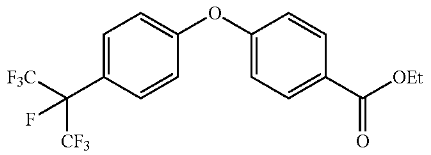 [SMILES: CCOC(=O)c1ccc(Oc2ccc(C(F)(C(F)(F)F)C(F)(F)F)cc2)cc1]

ethyl 4-(4-(perfluoropropan-2-yl)phenoxy)benzoate

062

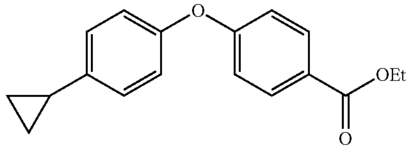

ethyl 4-(4-cyclopropylphenoxy)benzoate

063

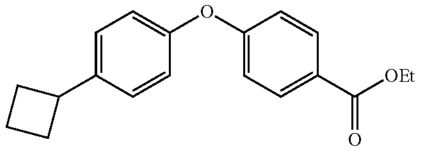 [SMILES: CCOC(=O)c1ccc(Oc2ccc(C3CCC3)cc2)cc1]

ethyl 4-(4-cyclobutylphenoxy)benzoate

064

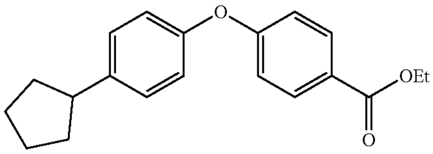 [SMILES: CCOC(=O)c1ccc(Oc2ccc(C3CCCC3)cc2)cc1]

ethyl 4-(4-cyclopentylphenoxy)benzoate

065

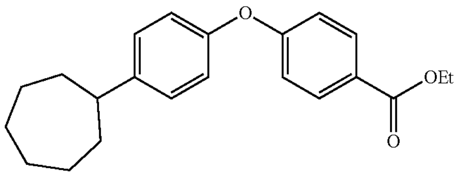 [SMILES: CCOC(=O)c1ccc(Oc2ccc(C3CCCCCC3)cc2)cc1]

ethyl 4-(4-cycloheptylphenoxy)benzoate

066

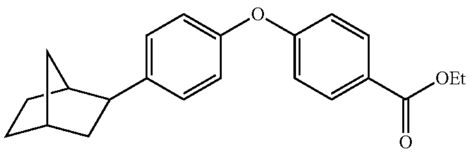 [SMILES: CCOC(=O)c1ccc(Oc2ccc(C3CC4CCC3C4)cc2)cc1]

ethyl 4-(4-((1S,4R)-bicyclo[2.2.1]heptan-2yl) phenoxy)benzoate

067

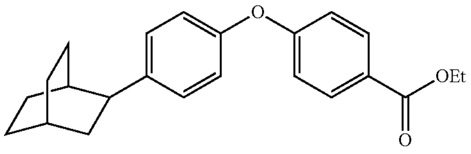 [SMILES: CCOC(=O)c1ccc(Oc2ccc(C3CC4CCC3CC4)cc2)cc1]

ethyl 4-(4-((1s,4s)-bicyclo[2.2.2]octan-2-yl) phenoxy)benzoate

TABLE Ib-continued

068

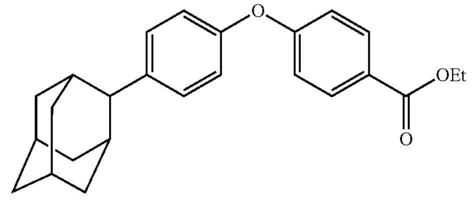

ethyl 4-(4-((1r,3r,5r,7r)-adamantan-2-yl) phenoxy)benzoate

069

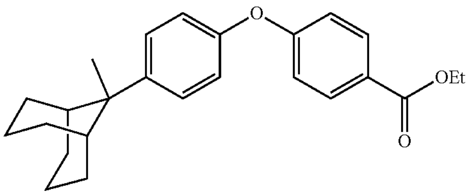 [SMILES: CCOC(=O)c1ccc(Oc2ccc(C3(C)C4CCCC3CCC4)cc2)cc1]

ethyl 4-(4-((1R,5S)-9-methylbicyclo[3.3.1]nonan-9-yl) phenoxy)benzoate

X = N, $R^2$ = H

070

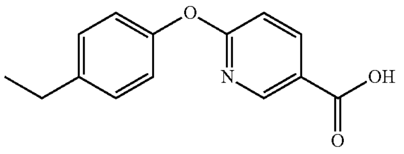

6-(4-ethylphenoxy)nicotinic acid

071

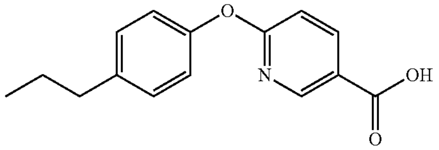 [SMILES: CCCc1ccc(Oc2ccc(C(=O)O)cn2)cc1]

6-(4-propylphenoxy)nicotinic acid

072

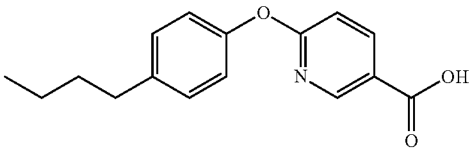 [SMILES: CCCCc1ccc(Oc2ccc(C(=O)O)cn2)cc1]

6-(4-butylphenoxy)nicotinic acid

073

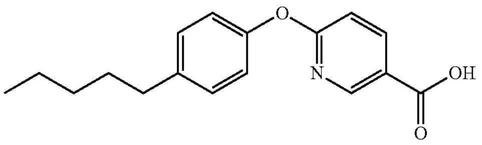

6-(4-pentylphenoxy)nicotinic acid

074

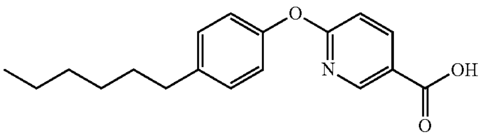

6-(4-hexylphenoxy)nicotinic acid

TABLE Ib-continued

075

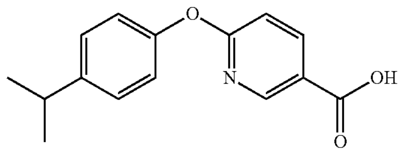

6-(4-isopropylphenoxy)nicotinic acid

076

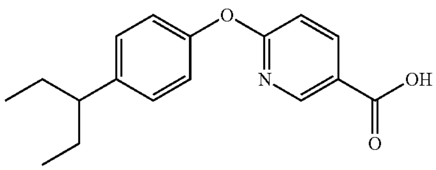 [SMILES: CCC(CC)c1ccc(Oc2ccc(C(=O)O)cn2)cc1]

6-(4-(pentan-3-ylphenoxy)nicotinic acid

077

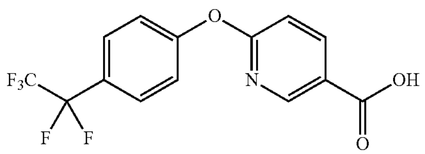

6-(4-(perfluoroethyl)phenoxy)nicotinic acid

078

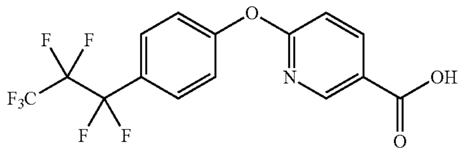 [SMILES: O=C(O)c1ccc(Oc2ccc(C(F)(F)C(F)(F)C(F)(F)F)cc2)nc1]

6-(4-(perfluoropropyl)phenoxy)nicotinic acid

079

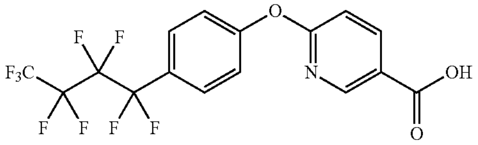

6-(4-(perfluorobutyl)phenoxy)nicotinic acid

080

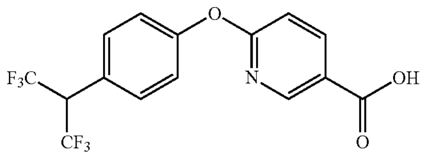 [SMILES: O=C(O)c1ccc(Oc2ccc(C(C(F)(F)F)C(F)(F)F)cc2)nc1]

6-(4-(1,1,1,3,3,3-hexafluoropropan-2-yl)phenoxy)nicotinic acid

081

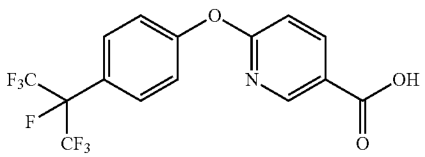 [SMILES: O=C(O)c1ccc(Oc2ccc(C(F)(C(F)(F)F)C(F)(F)F)cc2)nc1]

6-(4-(perfluoropropan-2-yl)phenoxy)nicotinic acid

TABLE Ib-continued

082

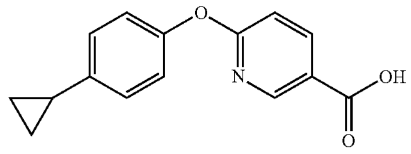 [SMILES: O=C(O)c1ccc(Oc2ccc(C3CC3)cc2)nc1]

6-(4-cyclopropylphenoxy)nicotinic acid

083

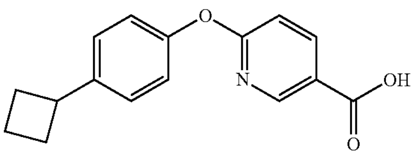

6-(4-cyclobutylphenoxy)nicotinic acid

084

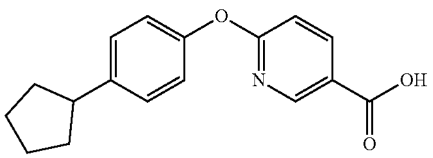 [SMILES: O=C(O)c1ccc(Oc2ccc(C3CCCC3)cc2)nc1]

6-(4-cyclopentylphenoxy)nicotinic acid

085

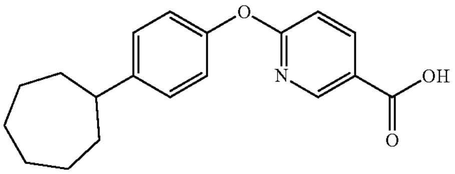 [SMILES: O=C(O)c1ccc(Oc2ccc(C3CCCCCC3)cc2)nc1]

6-(4-cycloheptylphenoxy)nicotinic acid

086

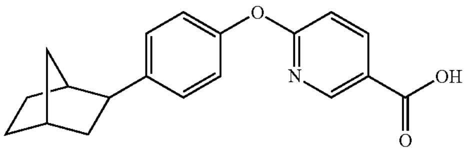

6-(4-((1S,4R)-bicyclo[2.2.1]heptan-2-yl)phenoxy)nicotinic acid

087

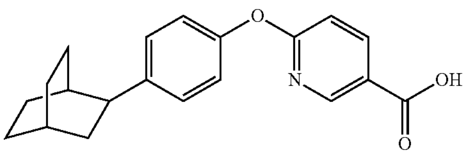

6-(4-((1s,4s)-bicyclo[2.2.2]octan-2-yl)phenoxy)nicotinic acid

088

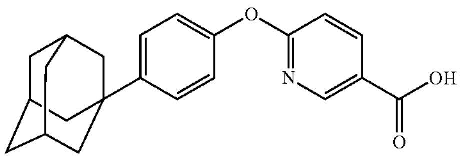 [SMILES: O=C(O)c1ccc(Oc2ccc(C34CC5CC(CC(C5)C3)C4)cc2)nc1]

6-(4-((3r,5r,7r)-adamantan-1-yl)phenoxy)nicotinic acid

TABLE Ib-continued

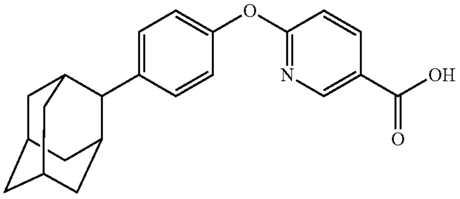
089

6-(4-((1r,3r,5r,7r)-adamantan-2-yl)phenoxy)nicotinic acid

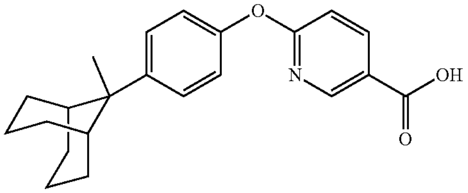 [SMILES: CC1(c2ccc(Oc3ccc(C(=O)O)cn3)cc2)C2CCCC1CCC2]
090

6-(4-((1R,5S)-9-methylbicyclo[3.3.1]nonan-9-yl)phenoxy)nicotinic acid

X = N, $R^2$ = Me

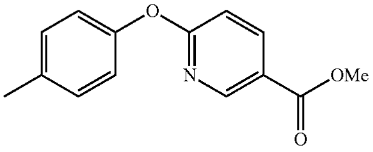 [SMILES: COC(=O)c1ccc(Oc2ccc(C)cc2)nc1]
091 methyl 6-(p-tolyloxy)nicotinate

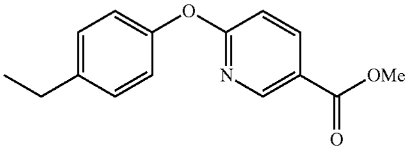
092 methyl 6-(4-ethylphenoxy)nicotinate

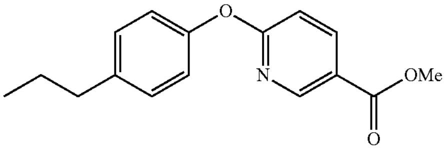 [SMILES: CCCc1ccc(Oc2ccc(C(=O)OC)cn2)cc1]
093 methyl 6-(4-propylphenoxy)nicotinate

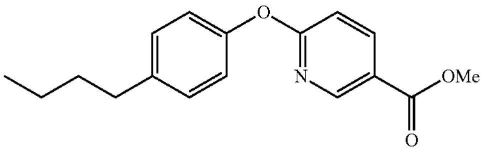 [SMILES: CCCCc1ccc(Oc2ccc(C(=O)OC)cn2)cc1]
094 methyl 6-(4-butylphenoxy)nicotinate

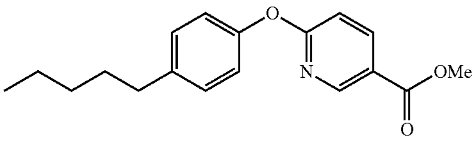 [SMILES: CCCCCc1ccc(Oc2ccc(C(=O)OC)cn2)cc1]
095 methyl 6-(4-pentylphenoxy)nicotinate

TABLE Ib-continued

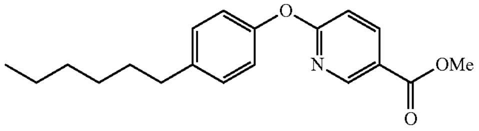 [SMILES: CCCCCCc1ccc(Oc2ccc(C(=O)OC)cn2)cc1]
096 methyl 6-(4-hexylphenoxy)nicotinate

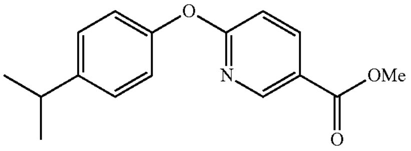
097 methyl 6-(4-isopropylphenoxy)nicotinate

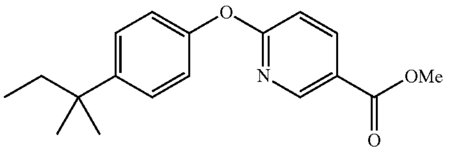 [SMILES: CCC(C)(C)c1ccc(Oc2ccc(C(=O)OC)cn2)cc1]
099 methyl 6-(4-(tert-pentyl)phenoxy)nicotinate

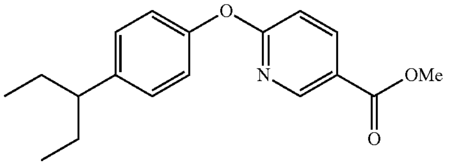 [SMILES: CCC(CC)c1ccc(Oc2ccc(C(=O)OC)cn2)cc1]
100 methyl 6-(4-(pentan-3-yl)phenoxy)nicotinate

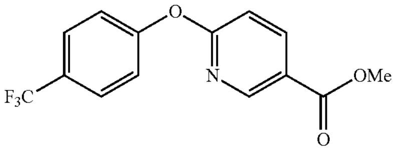 [SMILES: COC(=O)c1ccc(Oc2ccc(C(F)(F)F)cc2)nc1]
101 methyl 6-(4-(trifluoromethyl)phenoxy)nicotinate

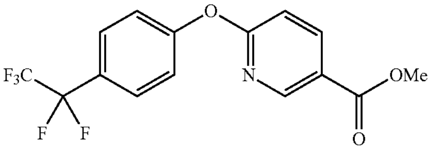 [SMILES: COC(=O)c1ccc(Oc2ccc(C(F)(F)C(F)(F)F)cc2)nc1]
102 methyl 6-(4-(perfluoroethyl)phenoxy)nicotinate

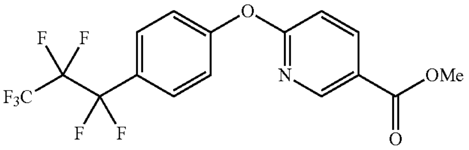 [SMILES: COC(=O)c1ccc(Oc2ccc(C(F)(F)C(F)(F)C(F)(F)F)cc2)nc1]
103 methyl 6-(4-(perfluoropropyl)phenoxy)nicotinate

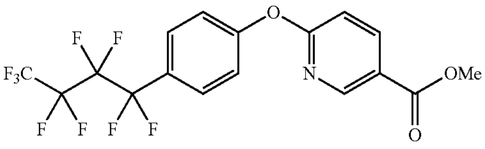 [SMILES: COC(=O)c1ccc(Oc2ccc(C(F)(F)C(F)(F)C(F)(F)C(F)(F)F)cc2)nc1]
104 methyl 6-(4-(perfluorobutyl)phenoxy)nicotinate

TABLE Ib-continued

105

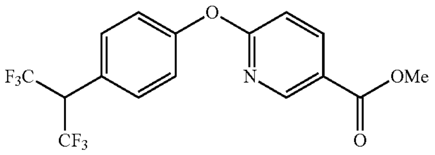

methyl 6-(4-(1,1,1,3,3,3-hexafluoropropan-2-yl)phenoxy)nicotinate

106

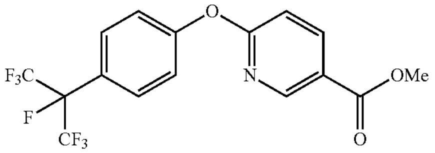

methyl 6-(4-(perfluoropropan-2-yl)phenoxy)nicotinate

107

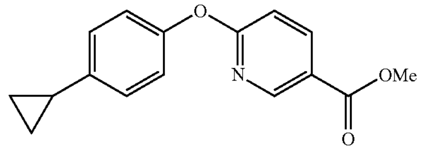 [SMILES: COC(=O)c1ccc(Oc2ccc(C3CC3)cc2)nc1]

methyl 6-(4-cyclopropyl)phenoxy)nicotinate

108

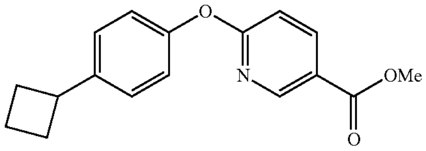

methyl 6-(4-cyclobutylphenoxy)nicotinate

109

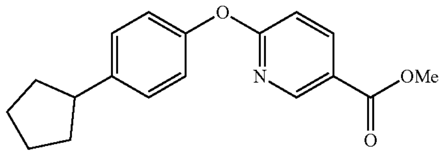 [SMILES: COC(=O)c1ccc(Oc2ccc(C3CCCC3)cc2)nc1]

methyl 6-(4-cyclobutylphenoxy)nicotinate

110

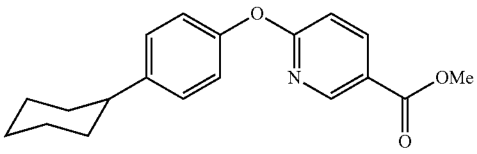

methyl 6-(4-cyclohexylphenoxy)nicotinate

111

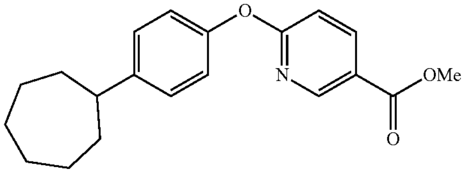 [SMILES: COC(=O)c1ccc(Oc2ccc(C3CCCCCC3)cc2)nc1]

methyl 6-(4-cycloheptylphenoxy)nicotinate

TABLE Ib-continued

112

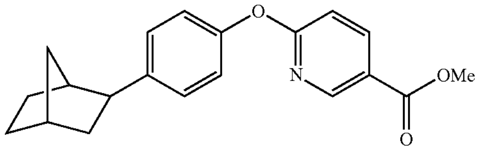 [SMILES: COC(=O)c1ccc(Oc2ccc(C3CC4CCC3C4)cc2)nc1]

methyl 6-(4-((1S,4R)-bicyclo[2.2.1]heptan-2-yl)phenoxy)nicotinate

113

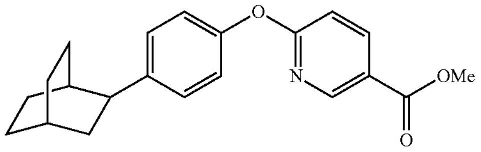 [SMILES: COC(=O)c1ccc(Oc2ccc(C3CC4CCC3CC4)cc2)nc1]

methyl 6-(4-((1s,4s)-bicyclo[2.2.2]octan-2-yl)phenoxy)nicotinate

114

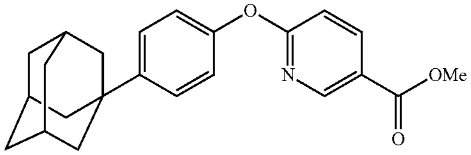 [SMILES: COC(=O)c1ccc(Oc2ccc(C34CC5CC(CC(C5)C3)C4)cc2)nc1]

methyl 6-(4-((3r,5r,7r)-adamantan-1-yl)phenoxy)nicotinate

115

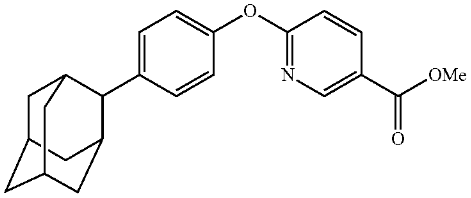

methyl 6-(4-((1r,3r,5r,7r)-adamantan-2-yl)phenoxy)nicotinate

116

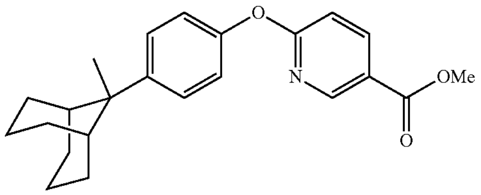 [SMILES: COC(=O)c1ccc(Oc2ccc(C3(C)C4CCCC3CCC4)cc2)nc1]

methyl 6-(4-((1R,5S)-9-methylbicyclo[3.3.1]nonan-9-yl)phenoxy)nicotinate

X = N, $R^2$ = Et

117

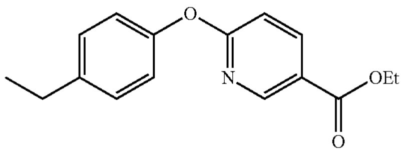 [SMILES: CCOC(=O)c1ccc(Oc2ccc(CC)cc2)nc1]

ethyl 6-(4-ethylphenoxy)nicotinate

118

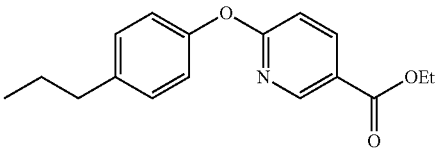 [SMILES: CCCc1ccc(Oc2ccc(C(=O)OCC)cn2)cc1]

ethyl 6-(4-propylphenoxy)nicotinate

TABLE Ib-continued

119

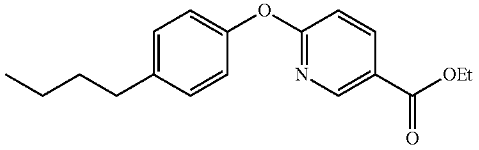 [SMILES: CCCCc1ccc(Oc2ccc(C(=O)OCC)cn2)cc1]

ethyl 6-(4-butylphenoxy)nicotinate

120

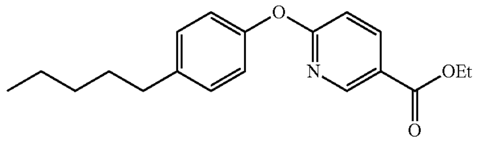

ethyl 6-(4-pentylphenoxy)nicotinate

121

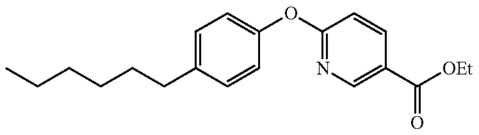 [SMILES: CCCCCCc1ccc(Oc2ccc(C(=O)OCC)cn2)cc1]

ethyl 6-(4-hexylphenoxy)nicotinate

122

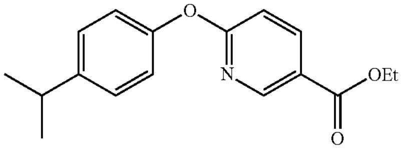 [SMILES: CCOC(=O)c1ccc(Oc2ccc(C(C)C)cc2)nc1]

ethyl 6-(4-isopropylphenoxy)nicotinate

123

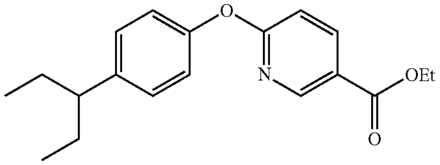 [SMILES: CCOC(=O)c1ccc(Oc2ccc(C(CC)CC)cc2)nc1]

ethyl 6-(4-(pentan-3-yl)phenoxy)nicotinate

124

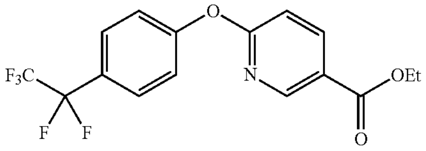 [SMILES: CCOC(=O)c1ccc(Oc2ccc(C(F)(F)C(F)(F)F)cc2)nc1]

ethyl 6-(4-(perfluoroethylphenoxy)nicotinate

125

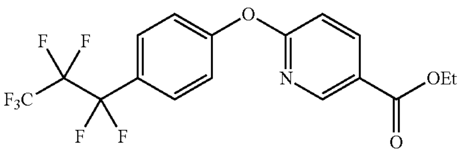 [SMILES: CCOC(=O)c1ccc(Oc2ccc(C(F)(F)C(F)(F)C(F)(F)F)cc2)nc1]

ethyl 6-(4-(perfluoropropyl)phenoxy)nicotinate

126

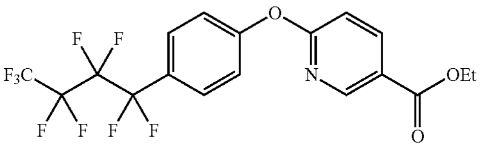 [SMILES: CCOC(=O)c1ccc(Oc2ccc(C(F)(F)C(F)(F)C(F)(F)C(F)(F)F)cc2)nc1]

ethyl 6-(4-(perfluorobutyl)phenoxy)nicotinate

TABLE Ib-continued

127

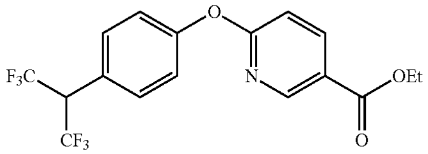 [SMILES: CCOC(=O)c1ccc(Oc2ccc(C(C(F)(F)F)C(F)(F)F)cc2)nc1]

ethyl 6-(4-(1,1,1,3,3,3-hexafluoropropan-2-yl)phenoxy)nicotinate

128

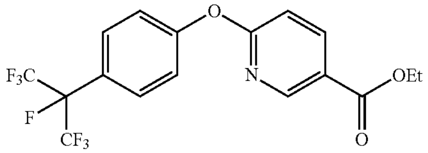 [SMILES: CCOC(=O)c1ccc(Oc2ccc(C(F)(C(F)(F)F)C(F)(F)F)cc2)nc1]

ethyl 6-(4-(perfluoropropan-2-yl)phenoxy)nicotinate

129

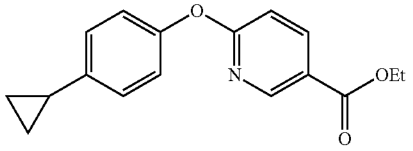

ethyl 6-(4-(4-cyclopropyl)phenoxy)nicotinate

130

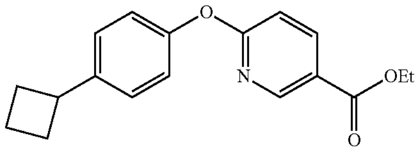 [SMILES: CCOC(=O)c1ccc(Oc2ccc(C3CCC3)cc2)nc1]

ethyl 6-(4-(4-cyclobutyl)phenoxy)nicotinate

131

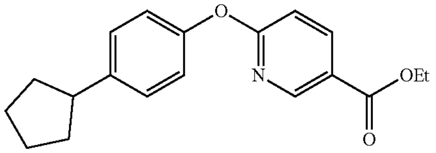 [SMILES: CCOC(=O)c1ccc(Oc2ccc(C3CCCC3)cc2)nc1]

ethyl 6-(4-cyclopentylphenoxy)nicotinate

132

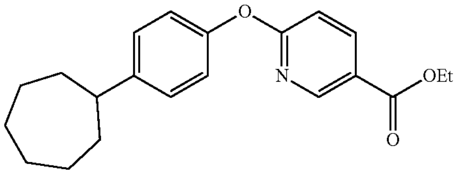 [SMILES: CCOC(=O)c1ccc(Oc2ccc(C3CCCCCC3)cc2)nc1]

ethyl 6-(4-cycloheptylphenoxy)nicotinate

133

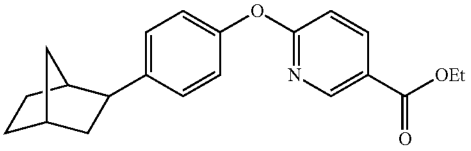 [SMILES: CCOC(=O)c1ccc(Oc2ccc(C3CC4CCC3C4)cc2)nc1]

ethyl 6-(4-((1S,4R)-bicyclo[2.2.1]heptan-2-yl)phenoxy)nicotinate

TABLE Ib-continued

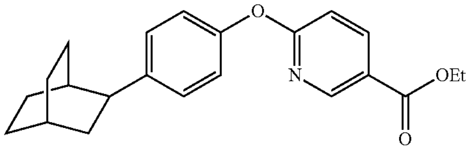 [SMILES: CCOC(=O)c1ccc(Oc2ccc(C3CC4CCC3CC4)cc2)nc1]

134 ethyl 6-(4-((1s,4s)-bicyclo[2.2.2]octan-2-yl)phenoxy)nicotinate

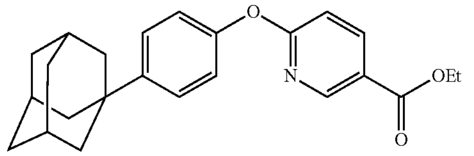 [SMILES: CCOC(=O)c1ccc(Oc2ccc(C34CC5CC(CC(C5)C3)C4)cc2)nc1]

135 ethyl 6-(4-((3r,5r,7r)-adamantan-1-yl)phenoxy)nicotinate

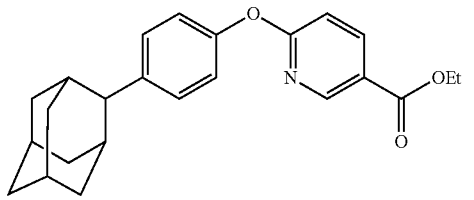 [SMILES: CCOC(=O)c1ccc(Oc2ccc(C3C4CC5CC(C4)CC3C5)cc2)nc1]

136 ethyl 6-(4-((1r,3r,5r,7r)-adamantan-2-yl)phenoxy)nicotinate

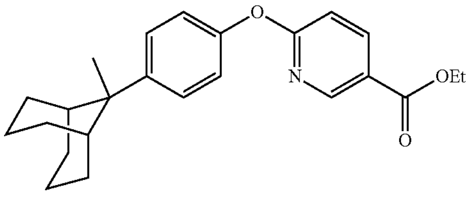 [SMILES: CCOC(=O)c1ccc(Oc2ccc(C3(C)C4CCCC3CCC4)cc2)nc1]

137 ethyl 6-(4-((1R,5S)-9-methylbicyclo[3.3.1]nonan-9-yl)phenoxy)nicotinate

Also included are isomers, e.g. enantiomers or diastereomers or mixtures of isomers, salts, particularly pharmaceutically acceptable salts, and solvates of the compounds listed above.

A second aspect of the present invention relates to compounds of formula II and salts and solvates thereof:

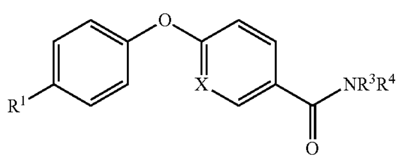

(II)

wherein X and $R^1$ are defined as in formula I, including the preferred definition of $R^1$, $R^3$=H, $C_1$-$C_6$ alkyl, or $C_3$-$C_6$ cycloalkyl, wherein all alkyl residues can be linear or branched, and can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all alkyl and cycloalkyl residues can be perhalogenated, particularly perfluorinated;

and wherein $R^3$ is preferably H or methyl;

$R^4$=H, $C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein all alkyl and cycloalkyl residues can be perhalogenated, particularly perfluorinated;

and wherein $R^4$ is preferably H, OH or methyl.

In especially preferred embodiments, $R^3$ and $R^4$ are in each case H; H and OH; H and —$CH_3$; or in each case —$CH_3$.

In some embodiments, the following compounds shown in Table IIa are explicitly excluded from the scope of the invention:

TABLE IIa

| Compound | $R^1$ | $R^3$ | $R^4$ | X |
|---|---|---|---|---|
| II-A | tert-butyl | H | H | N |
| II-B | methyl | H | methyl | CH |
| II-C | methyl | methyl | methyl | CH |

Compound II-A and II-B of Table IIa are known in the art for certain applications in the field of medicine whereas to the best of the inventor's knowledge, compound II-C is not known for any use in medicine. Thus, the invention encompasses any medical use for compound II-C.

Specific examples of compounds falling under the scope of formula II are shown in Table IIb. The compounds in Table IIb are defined by their chemical structure, the indicated nomenclature is only for illustrative purposes.

TABLE IIb

X = CH, $R^3$ = H, $R^4$ = H

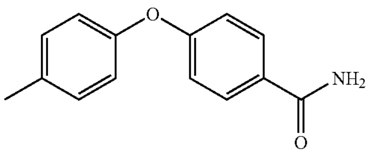 [SMILES: Cc1ccc(Oc2ccc(C(N)=O)cc2)cc1]

138

4-(p-tolyloxy)benzamide

TABLE IIb-continued

139

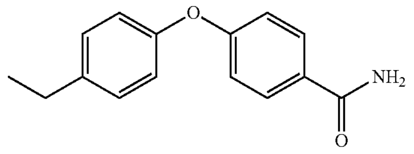 [SMILES: CCc1ccc(Oc2ccc(C(N)=O)cc2)cc1]

4-(4-ethylphenoxy)benzamide

140

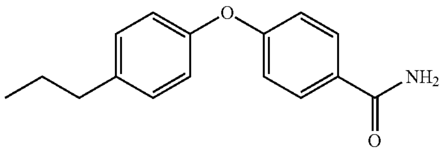 [SMILES: CCCc1ccc(Oc2ccc(C(N)=O)cc2)cc1]

4-(4-propylphenoxy)benzamide

141

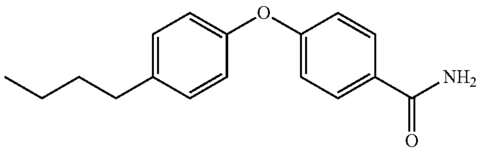 [SMILES: CCCCc1ccc(Oc2ccc(C(N)=O)cc2)cc1]

4-(4-butylphenoxy)benzamide

142

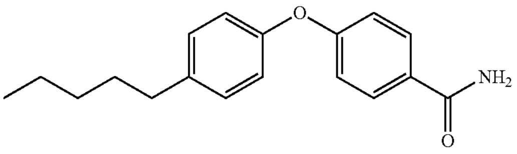 [SMILES: CCCCCc1ccc(Oc2ccc(C(N)=O)cc2)cc1]

4-(4-pentylphenoxy)benzamide

143

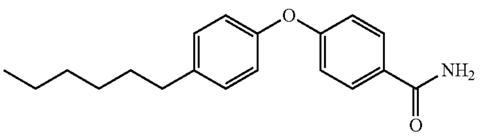 [SMILES: CCCCCCc1ccc(Oc2ccc(C(N)=O)cc2)cc1]

4-(4-hexylphenoxy)benzamide

144

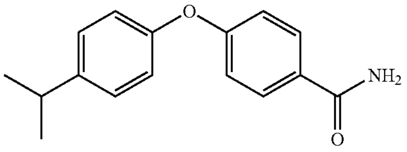

4-(4-isopropylphenoxy)benzamide

145

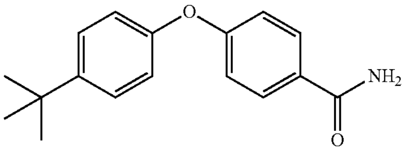 [SMILES: CC(C)(C)c1ccc(Oc2ccc(C(N)=O)cc2)cc1]

4-(4-(tert-butyl)phenoxy)benzamide

146

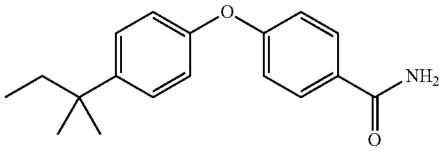 [SMILES: CCC(C)(C)c1ccc(Oc2ccc(C(N)=O)cc2)cc1]

4-(4-(tert-pentyl)phenoxy)benzamide

TABLE IIb-continued

147

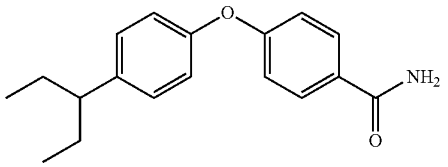 [SMILES: CCC(CC)c1ccc(Oc2ccc(C(N)=O)cc2)cc1]

4-(4-(pentan-3-yl)phenoxy)benzamide

148

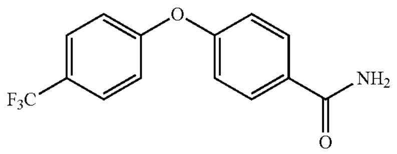

4-(4-(trifluoromethyl)phenoxy)benzamide

149

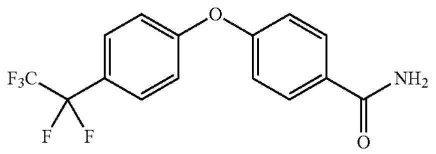 [SMILES: NC(=O)c1ccc(Oc2ccc(C(F)(F)C(F)(F)F)cc2)cc1]

4-(4-(perfluoroethyl)phenoxy)benzamide

150

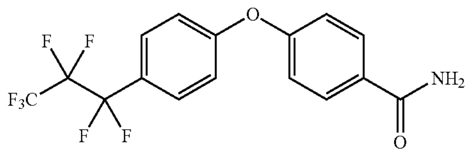 [SMILES: NC(=O)c1ccc(Oc2ccc(C(F)(F)C(F)(F)C(F)(F)F)cc2)cc1]

4-(4-(perfluoropropyl)phenoxy)benzamide

151

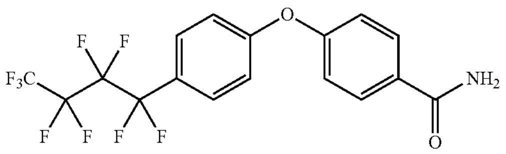 [SMILES: NC(=O)c1ccc(Oc2ccc(C(F)(F)C(F)(F)C(F)(F)C(F)(F)F)cc2)cc1]

4-(4-(perfluorobutyl)phenoxy)benzamide

152

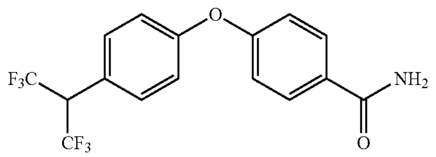 [SMILES: NC(=O)c1ccc(Oc2ccc(C(C(F)(F)F)C(F)(F)F)cc2)cc1]

4-(4-(1,1,1,3,3,3-hexafluoropropan-2-yl)phenoxy)benzamide

153

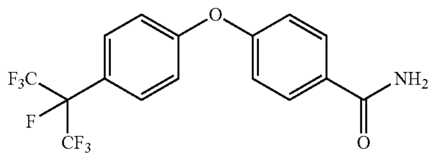 [SMILES: NC(=O)c1ccc(Oc2ccc(C(F)(C(F)(F)F)C(F)(F)F)cc2)cc1]

4-(4-(perfluoropropan-2-yl)phenoxy)benzamide

154

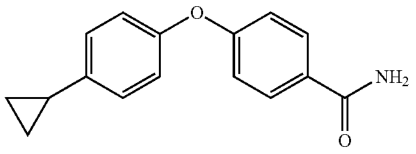 [SMILES: NC(=O)c1ccc(Oc2ccc(C3CC3)cc2)cc1]

4-(4-cyclopropylphenoxy)benzamide

TABLE IIb-continued

155

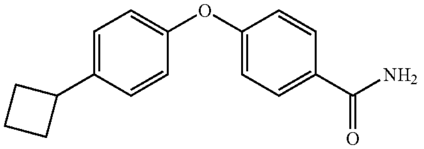

4-(4-cyclobutylphenoxy)benzamide

156

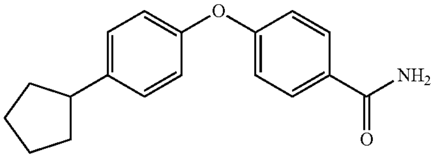 [SMILES: NC(=O)c1ccc(Oc2ccc(C3CCCC3)cc2)cc1]

4-(4-cyclopentylphenoxy)benzamide

157

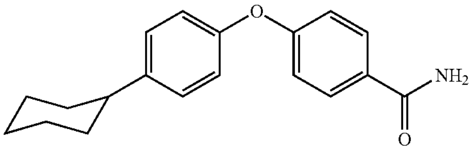

4-(4-cyclohexylphenoxy)benzamide

158

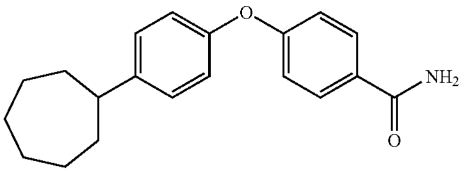 [SMILES: NC(=O)c1ccc(Oc2ccc(C3CCCCCC3)cc2)cc1]

4-(4-cycloheptylphenoxy)benzamide

159

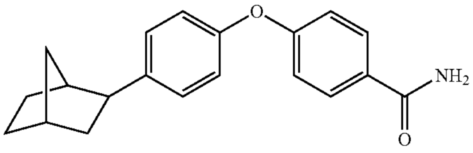

4-(4-((1S,4R)-bicyclo[2.2.1]heptan-2-yl)phenoxy)benzamide

160

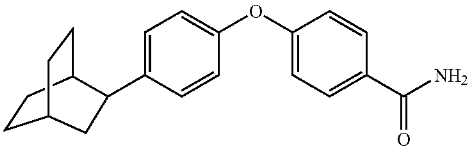

4-(4-((1s,4s)-bicyclo[2.2.2]octan-2-yl)phenoxy)benzamide

161

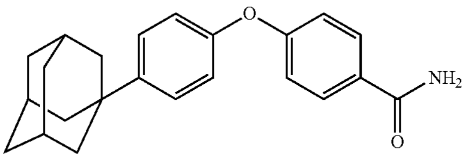 [SMILES: NC(=O)c1ccc(Oc2ccc(C34CC5CC(CC(C5)C3)C4)cc2)cc1]

4-(4-((3r,5r,7r)-adamantan-1-yl)phenoxy)benzamide

TABLE IIb-continued

162

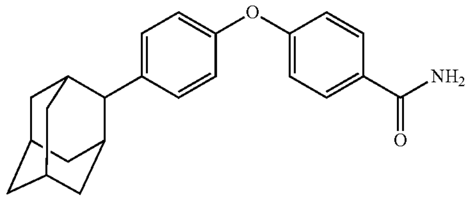 [SMILES: NC(=O)c1ccc(Oc2ccc(C3C4CC5CC(C4)CC3C5)cc2)cc1]

4-(4-((1r,3r,5r,7r)-adamantan-2-yl)phenoxy)benzamide

163

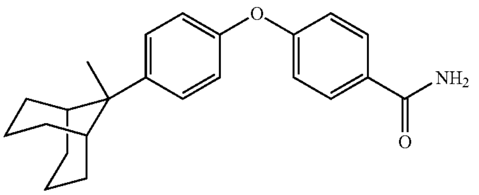 [SMILES: CC1(c2ccc(Oc3ccc(C(N)=O)cc3)cc2)C2CCCC1CCC2]

4-(4-((1R,5S)-9-methylbicyclo[3.3.1]nonan-9-yl)phenoxy)benzamide

X = CH, $R^3$ = H, $R^4$ = OH

164

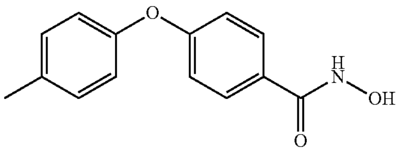 [SMILES: Cc1ccc(Oc2ccc(C(=O)NO)cc2)cc1]

N-hydroxy-4-(p-tolyltoxy)benzamide

165

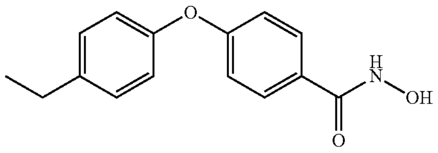

4-(4-ethylphenoxy)-N-hydroxybenzamide

166

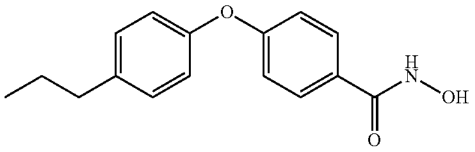

N-hydroxy-4-(4-propylphenoxy)benzamide

167

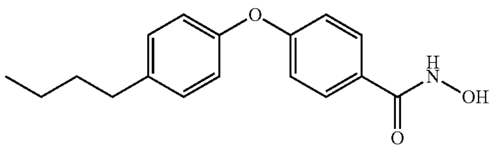 [SMILES: CCCCc1ccc(Oc2ccc(C(=O)NO)cc2)cc1]

4-(4-butylphenoxy)-N-hydroxybenzamide

168

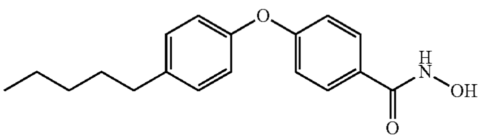 [SMILES: CCCCCc1ccc(Oc2ccc(C(=O)NO)cc2)cc1]

N-hydroxy-4-(4-pentylphenoxy)benzamide

TABLE IIb-continued

169

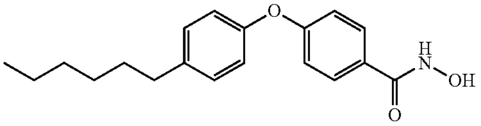 [SMILES: CCCCCCc1ccc(Oc2ccc(C(=O)NO)cc2)cc1]

4-(4-hexylphenoxy)-N-hydroxybenzamide

170

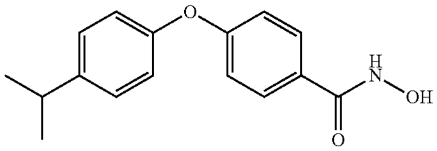

N-hydroxy-4-(4-isopropylphenoxy)benzamide

171

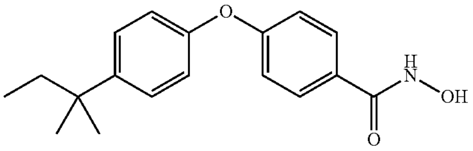 [SMILES: CCC(C)(C)c1ccc(Oc2ccc(C(=O)NO)cc2)cc1]

N-hydroxy-4-(4-(tert-pentyl)phenoxy)benzamide

172

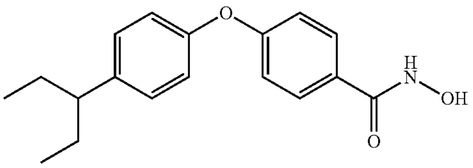

N-hydroxy-4-(4-(pentan-3-yl)phenoxy)benzamide

173

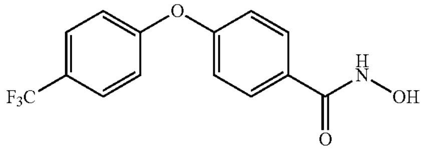 [SMILES: O=C(NO)c1ccc(Oc2ccc(C(F)(F)F)cc2)cc1]

N-hydroxy-4-(4-(trifluoromethyl)phenoxy)benzamide

174

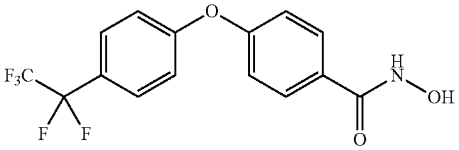 [SMILES: O=C(NO)c1ccc(Oc2ccc(C(F)(F)C(F)(F)F)cc2)cc1]

N-hydroxy-4-(4-(perfluoroethyl)phenoxy)benzamide

175

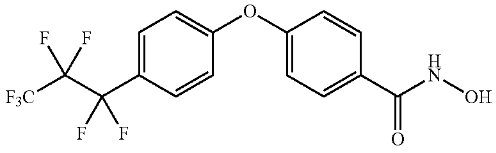 [SMILES: O=C(NO)c1ccc(Oc2ccc(C(F)(F)C(F)(F)C(F)(F)F)cc2)cc1]

N-hydroxy-4-(4-(perfluoropropyl)phenoxy)benzamide

176

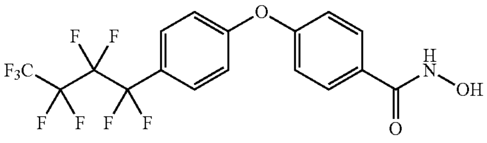 [SMILES: O=C(NO)c1ccc(Oc2ccc(C(F)(F)C(F)(F)C(F)(F)C(F)(F)F)cc2)cc1]

N-hydroxy-4-(4-(perfluorobutyl)phenoxy)benzamide

TABLE IIb-continued

177

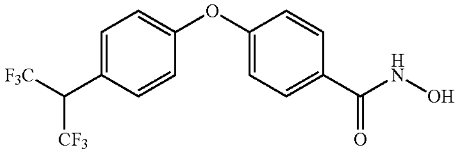 [SMILES: O=C(NO)c1ccc(Oc2ccc(C(C(F)(F)F)C(F)(F)F)cc2)cc1]

4-(4-(1,1,1,3,3,3-hexafluoropropan-2-yl)phenoxy)-N-hydroxybenzamide

178

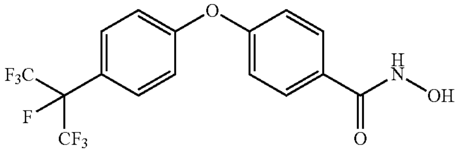 [SMILES: O=C(NO)c1ccc(Oc2ccc(C(F)(C(F)(F)F)C(F)(F)F)cc2)cc1]

N-hydroxy-4-(4-(perfluoropropan-2-yl)phenoxy)benzamide

179

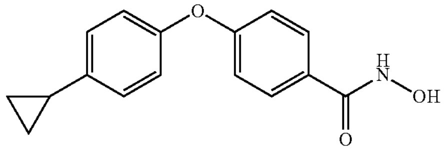 [SMILES: O=C(NO)c1ccc(Oc2ccc(C3CC3)cc2)cc1]

4-(4-cyclopropylphenoxy)-N-hydroxybenzamide

180

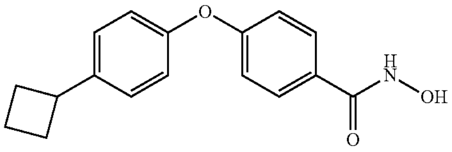 [SMILES: O=C(NO)c1ccc(Oc2ccc(C3CCC3)cc2)cc1]

4-(4-cyclobutylphenoxy)-N-hydroxybenzamide

181

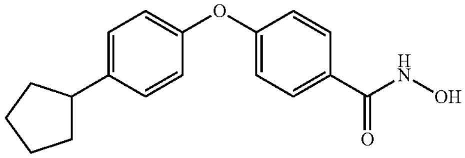 [SMILES: O=C(NO)c1ccc(Oc2ccc(C3CCCC3)cc2)cc1]

4-(4-cyclopentylphenoxy)-N-hydroxybenzamide

182

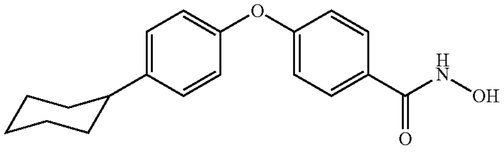 [SMILES: O=C(NO)c1ccc(Oc2ccc(C3CCCCC3)cc2)cc1]

4-(4-cyclohexylphenoxy)-N-hydroxybenzamide

183

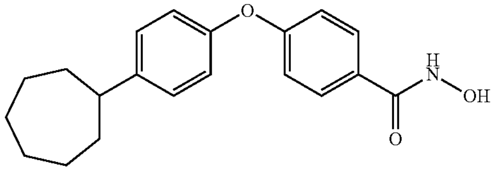 [SMILES: O=C(NO)c1ccc(Oc2ccc(C3CCCCCC3)cc2)cc1]

4-(4-cycloheptylphenoxy)-N-hydroxybenzamide

TABLE IIb-continued

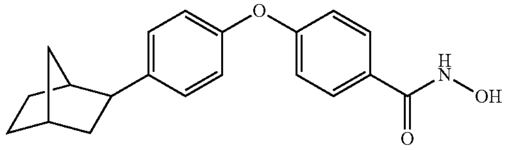 [SMILES: O=C(NO)c1ccc(Oc2ccc(C3CC4CCC3C4)cc2)cc1]
184

4-(4-((1S,4R)-bicyclo[2.2.1]heptan-2-yl)phenoxy)-N-hydroxybenzamide

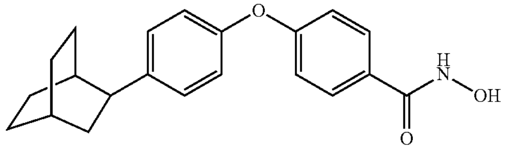
185

4-(4-((1s,4s)-bicyclo[2.2.2]octan-2-yl)phenoxy)-N-hydroxybenzamide

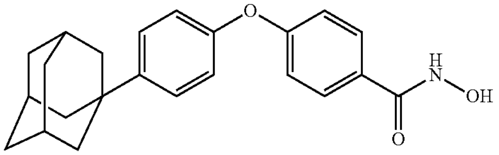 [SMILES: O=C(NO)c1ccc(Oc2ccc(C34CC5CC(CC(C5)C3)C4)cc2)cc1]
186

4-(4-((3r,5r,7r)-adamantan-1-yl)phenoxy)-N-hydroxybenzamide

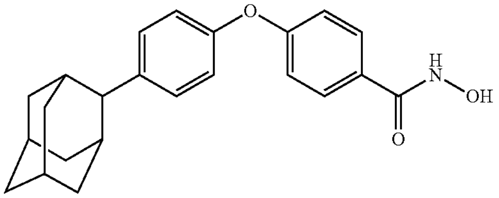 [SMILES: O=C(NO)c1ccc(Oc2ccc(C3C4CC5CC(C4)CC3C5)cc2)cc1]
187

4-(4-((1r,3r,7r)-adamantan-2-yl)phenoxy)-N-hydroxybenzamide

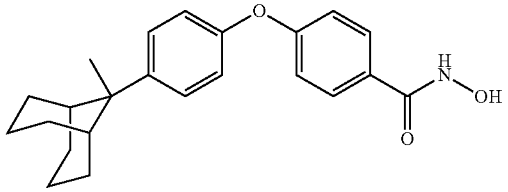 [SMILES: CC1(c2ccc(Oc3ccc(C(=O)NO)cc3)cc2)C2CCCC1CCC2]
188

N-hydroxy-4-(4-((1R,5S)-9-methylbicyclo[3.3.1]nonan-9-yl)phenoxy)benzamide

X = CH, $R^3$ = H, $R^4$ = Me

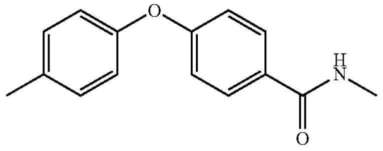
189

N-methyl-4-(p-tolyloxy)benzamide

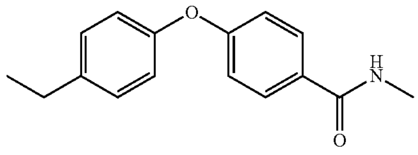 [SMILES: CCc1ccc(Oc2ccc(C(=O)NC)cc2)cc1]
190

4-(4-ethylphenoxy)-N-methylbenzamide

TABLE IIb-continued

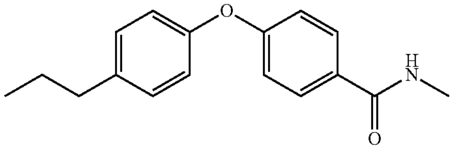 [SMILES: CCCc1ccc(Oc2ccc(C(=O)NC)cc2)cc1]
191

N-methyl-4-(4-propylphenoxy)benzamide

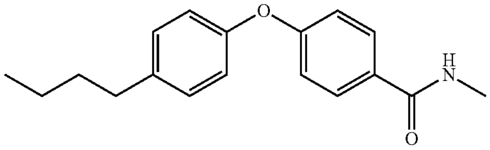 [SMILES: CCCCc1ccc(Oc2ccc(C(=O)NC)cc2)cc1]
192

4-(4-butylphenoxy)-N-methylbenzamide

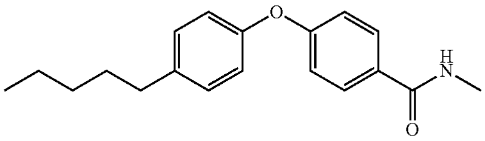 [SMILES: CCCCCc1ccc(Oc2ccc(C(=O)NC)cc2)cc1]
193

N-methyl-4-(4-pentylphenoxy)benzamide

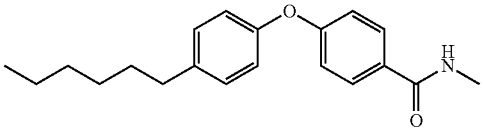 [SMILES: CCCCCCc1ccc(Oc2ccc(C(=O)NC)cc2)cc1]
194

4-(4-hexylphenoxy)-N-methylbenzamide

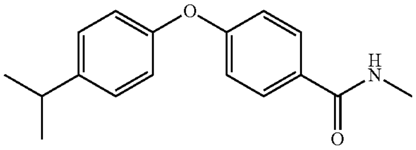 [SMILES: CNC(=O)c1ccc(Oc2ccc(C(C)C)cc2)cc1]
195

4-(4-isopropylphenoxy)-N-methylbenzamide

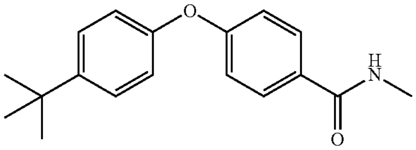
196

4-(4-(tert-butyl)phenoxy)-N-methylbenzamide

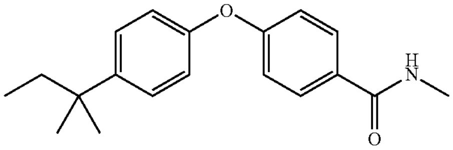 [SMILES: CCC(C)(C)c1ccc(Oc2ccc(C(=O)NC)cc2)cc1]
197

N-methyl-4-(4-(tert-pentyl)phenoxy)benzamide

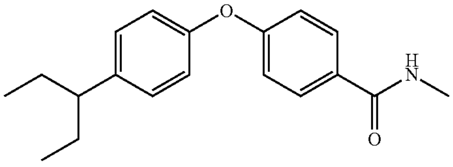 [SMILES: CCC(CC)c1ccc(Oc2ccc(C(=O)NC)cc2)cc1]
198

N-methyl-4-(4-(pentan-3-yl)phenoxy)benzamide

TABLE IIb-continued

199

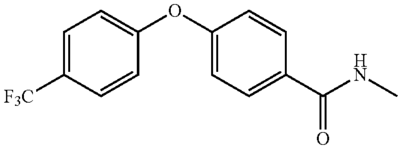 [SMILES: CNC(=O)c1ccc(Oc2ccc(C(F)(F)F)cc2)cc1]

N-methyl-4-(4-(trifluoromethyl)phenoxy)benzamide

200

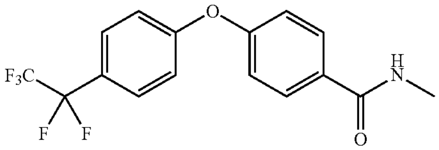 [SMILES: CNC(=O)c1ccc(Oc2ccc(C(F)(F)C(F)(F)F)cc2)cc1]

N-4-methyl-4-(4-(perfluoroethyl)phenoxy)benzamide

201

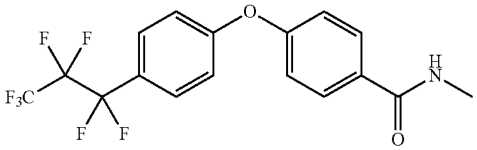

N-methyl-4-(4-(perfluoropropyl)phenoxy)benzamide

202

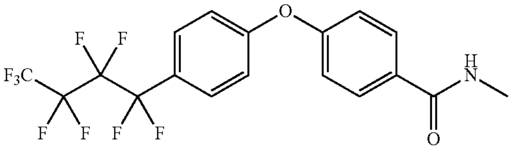 [SMILES: CNC(=O)c1ccc(Oc2ccc(C(F)(F)C(F)(F)C(F)(F)C(F)(F)F)cc2)cc1]

N-methyl-4-(4-(perfluorobutyl)phenoxy)benzamide

203

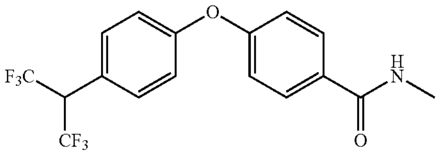

4-(4-(1,1,1,3,3,3-hexafluoropropan-2-yl)phenoxy)-N-methylbenzamide

204

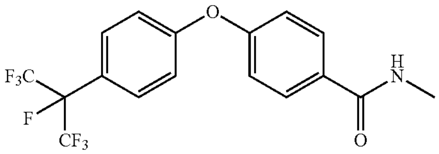

N-methyl-4-(4-(perfluoropropan-2-yl)phenoxy)benzamide

205

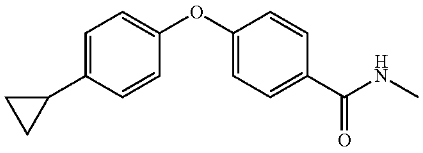 [SMILES: CNC(=O)c1ccc(Oc2ccc(C3CC3)cc2)cc1]

4-(4-cyclopropylphenoxy)-N-methylbenzamide

206

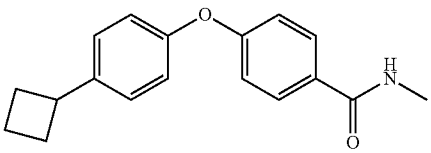 [SMILES: CNC(=O)c1ccc(Oc2ccc(C3CCC3)cc2)cc1]

4-(4-cyclobutylphenoxy)-N-methylbenzamide

TABLE IIb-continued

207

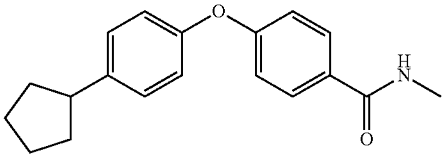 [SMILES: CNC(=O)c1ccc(Oc2ccc(C3CCCC3)cc2)cc1]

4-(4-cyclopentylphenoxy)-N-methylbenzamide

208

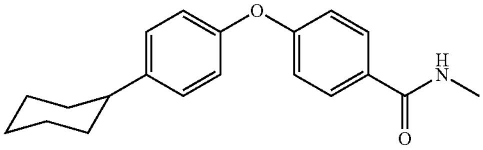 [SMILES: CNC(=O)c1ccc(Oc2ccc(C3CCCCC3)cc2)cc1]

4-(4-cyclohexylphenoxy)-N-methylbenzamide

209

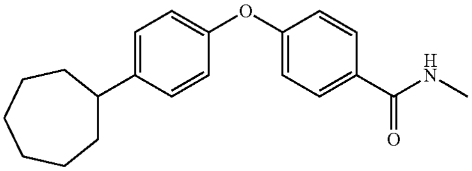

4-(4-cycloheptylphenoxy)-N-methylbenzamide

210

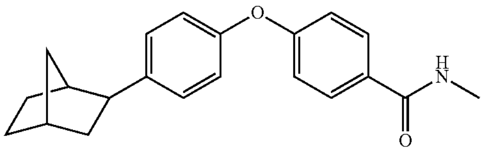 [SMILES: CNC(=O)c1ccc(Oc2ccc(C3CC4CCC3C4)cc2)cc1]

4-(4-((1S,4R)-bicyclo[2.2.1]heptan-2-yl)phenoxy)-N-methylbenzamide

211

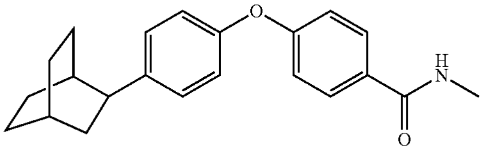 [SMILES: CNC(=O)c1ccc(Oc2ccc(C3CC4CCC3CC4)cc2)cc1]

4-(4-((1s,4s)-bicyclo[2.2.2]octan-2-yl)phenoxy)-N-methylbenzamide

212

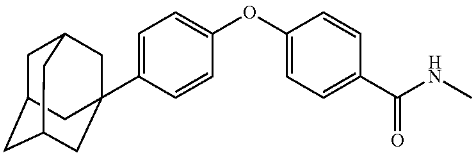 [SMILES: CNC(=O)c1ccc(Oc2ccc(C34CC5CC(CC(C5)C3)C4)cc2)cc1]

4-(4-((3r,5r,7r)-adamantan-1-yl)phenoxy)-N-methylbenzamide

213

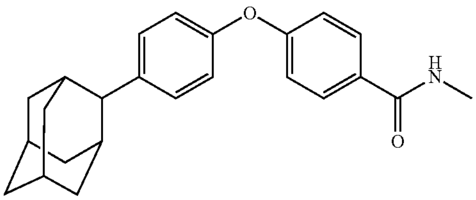 [SMILES: CNC(=O)c1ccc(Oc2ccc(C3C4CC5CC(C4)CC3C5)cc2)cc1]

4-(4-((1r,3r,5r,7r)-adamantan-2-yl)phenoxy)-N-methylbenzamide

TABLE IIb-continued

214

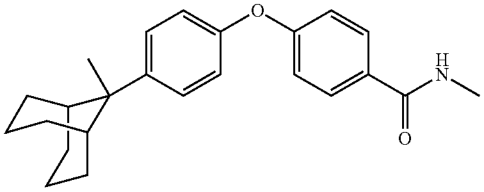 [SMILES: CNC(=O)c1ccc(Oc2ccc(C3(C)C4CCCC3CCC4)cc2)cc1]

N-methyl-4-(4-((1R,5S)-9-methylbicyclo[3.3.1]nonan-9-yl)phenoxy)benzamide

X = CH, $R^3$ = Me, $R^4$ = Me

215

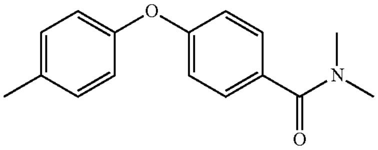

N,N-dimethyl-4-(p-tolyloxy)benzamide

216

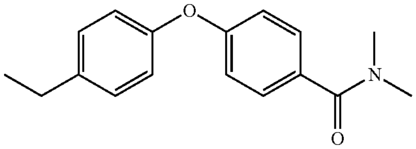

4-(4-ethylphenoxy)-N,N-dimethylbenzamide

217

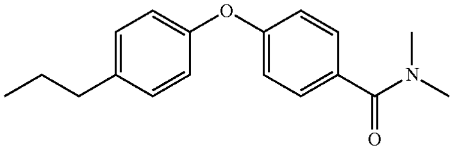 [SMILES: CCCc1ccc(Oc2ccc(C(=O)N(C)C)cc2)cc1]

N,N-dimethyl-4-(4-propylphenoxy)benzamide

218

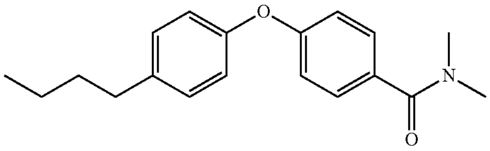 [SMILES: CCCCc1ccc(Oc2ccc(C(=O)N(C)C)cc2)cc1]

4-(4-butylphenoxy)-N,N-dimethylbenzamide

219

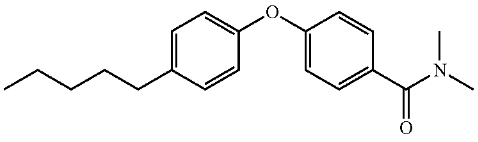 [SMILES: CCCCCc1ccc(Oc2ccc(C(=O)N(C)C)cc2)cc1]

N,N-dimethyl-4-(4-pentylphenoxy)benzamide

220

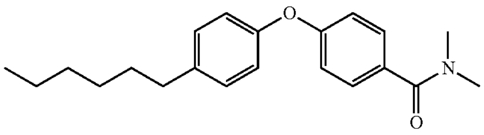 [SMILES: CCCCCCc1ccc(Oc2ccc(C(=O)N(C)C)cc2)cc1]

4-(4-hexylphenoxy)-N,N-dimethylbenzamide

TABLE IIb-continued

221

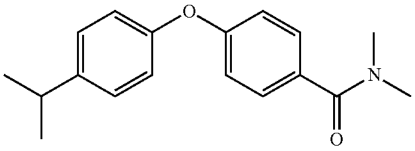 [SMILES: CC(C)c1ccc(Oc2ccc(C(=O)N(C)C)cc2)cc1]

4-(4-isopropylphenoxy)-N,N-dimethylbenzamide

222

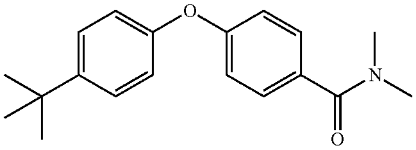 [SMILES: CN(C)C(=O)c1ccc(Oc2ccc(C(C)(C)C)cc2)cc1]

4-(4-(tert-butyl)phenoxy)-N,N-dimethylbenzamide

223

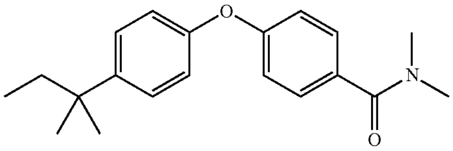 [SMILES: CCC(C)(C)c1ccc(Oc2ccc(C(=O)N(C)C)cc2)cc1]

N,N-dimethyl-4-(4-(tert-pentyl)phenoxy)benzamide

224

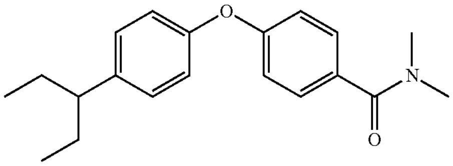 [SMILES: CCC(CC)c1ccc(Oc2ccc(C(=O)N(C)C)cc2)cc1]

N,N-dimethyl-4-(4-(pentan-3-yl)phenoxy)benzamide

225

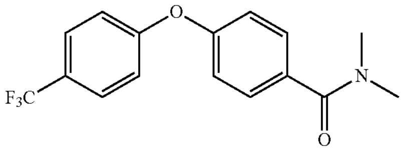 [SMILES: CN(C)C(=O)c1ccc(Oc2ccc(C(F)(F)F)cc2)cc1]

N,N-dimethyl-4-(4-(trifluoromethyl)phenoxy)benzamide

226

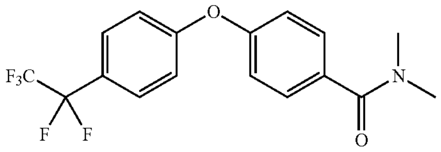 [SMILES: CN(C)C(=O)c1ccc(Oc2ccc(C(F)(F)C(F)(F)F)cc2)cc1]

N,N-dimethyl-4-(4-(perfluoroethyl)phenoxy)benzamide

227

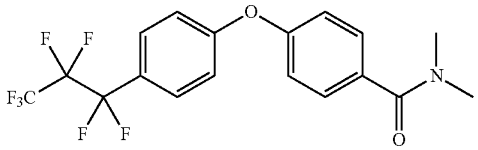 [SMILES: CN(C)C(=O)c1ccc(Oc2ccc(C(F)(F)C(F)(F)C(F)(F)F)cc2)cc1]

N,N-dimethyl-4-(4-(perfluoropropyl)phenoxy)benzamide

228

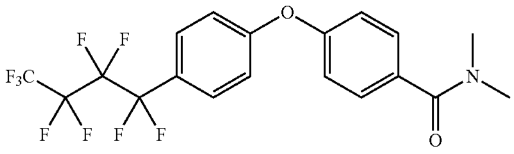 [SMILES: CN(C)C(=O)c1ccc(Oc2ccc(C(F)(F)C(F)(F)C(F)(F)C(F)(F)F)cc2)cc1]

N,N-dimethyl-4-(4-(perfluorobutyl)phenoxy)benzamide

TABLE IIb-continued

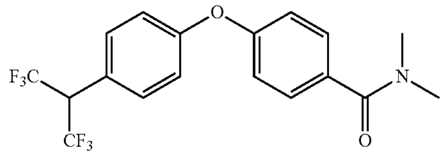

229

4-(4-(1,1,1,3,3,3-hexafluoropropan-2-yl)phenoxy)-N,N-dimethylbenzamide

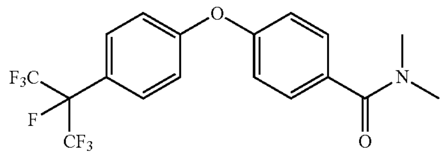 [SMILES: CN(C)C(=O)c1ccc(Oc2ccc(C(F)(C(F)(F)F)C(F)(F)F)cc2)cc1]

230

N,N-dimethyl-4-(4-(perfluoropropan-2-yl)phenoxy)benzamide

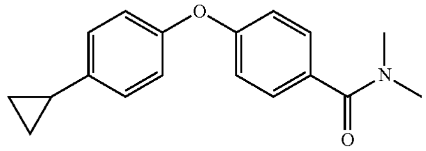 [SMILES: CN(C)C(=O)c1ccc(Oc2ccc(C3CC3)cc2)cc1]

231

4-(4-cyclopropylphenoxy)-N,N-dimethylbenzamide

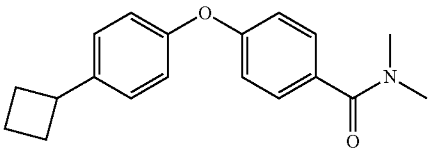 [SMILES: CN(C)C(=O)c1ccc(Oc2ccc(C3CCC3)cc2)cc1]

232

4-(4-cyclobutylphenoxy)-N,N-dimethylbenzamide

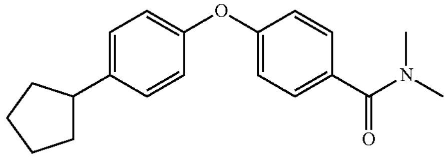

233

4-(4-cyclopentylpheoxy)-N,N-dimethylbenzamide

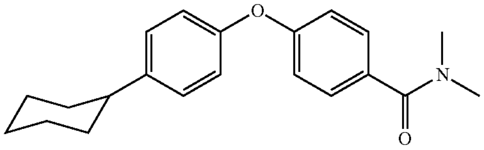 [SMILES: CN(C)C(=O)c1ccc(Oc2ccc(C3CCCCC3)cc2)cc1]

234

4-(4-cyclohexylphenoxy)-N,N-dimethylbenzamide

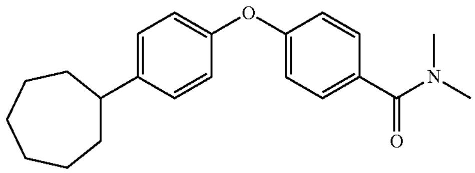 [SMILES: CN(C)C(=O)c1ccc(Oc2ccc(C3CCCCCC3)cc2)cc1]

235

4-(4-cycloheptylphenoxy)-N,N-dimethylbenzamide

TABLE IIb-continued

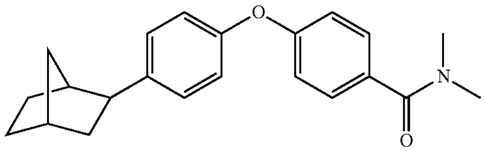 [SMILES: CN(C)C(=O)c1ccc(Oc2ccc(C3CC4CCC3C4)cc2)cc1]

236

4-(4-((1S,4R)-bicyclo[2.2.1]heptan-2-yl)phenoxy)-N,N-dimethylbenzamide

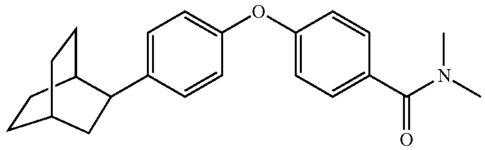 [SMILES: CN(C)C(=O)c1ccc(Oc2ccc(C3CC4CCC3CC4)cc2)cc1]

237

4-(4-((1s,4s)-bicyclo[2.2.2]octan-2-yl)phenoxy)-N,N-dimethylbenzamide

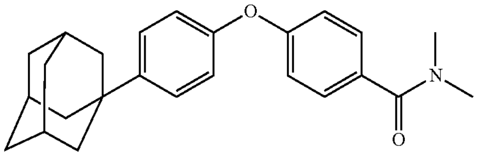

238

4-(4-((3r,5r,7r)-adamantan-1-yl)pheoxy)-N,N-dimethylbenzamide

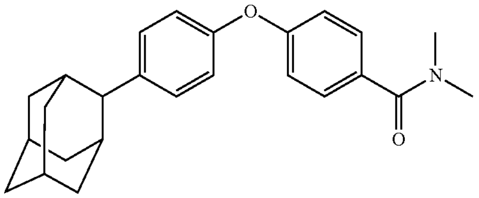

239

4-(4-((1r,3r,5r,7r)-adamantan-2-yl)-phenoxy)-N,N-dimethylbenzamide

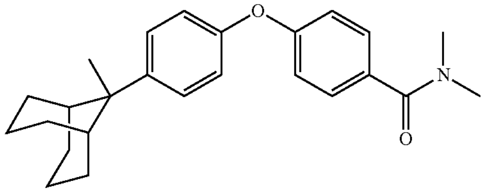

240

N,N-dimethyl-4-(4-((1R,5S)-9-methylbicyclo[3.3.1]nonan-9-yl)phenoxy)benzamide

X = N, $R^3$ = H, $R^4$ = H

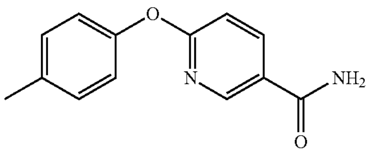 [SMILES: Cc1ccc(Oc2ccc(C(N)=O)cn2)cc1]

241

6-(p-tolyloxy)nicolinamide

TABLE IIb-continued

242

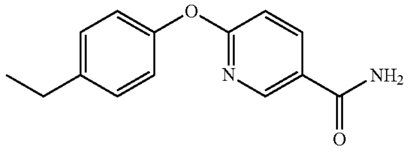 [SMILES: CCc1ccc(Oc2ccc(C(N)=O)cn2)cc1]

6-(4-ethylphenoxy)nicotinamide

243

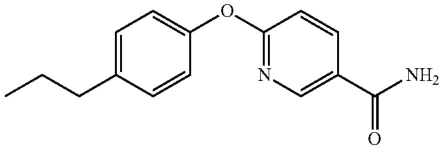

6-(4-propylphenoxy)nicotinamide

244

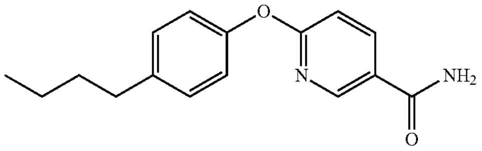

6-(4-butylphenoxy)nicotinamide

245

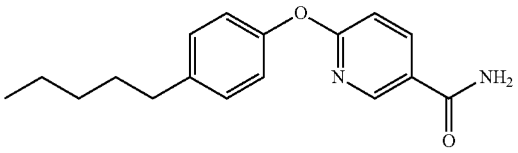

6-(4-pentylphenoxy)nicotinamide

246

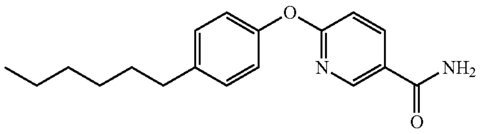 [SMILES: CCCCCCc1ccc(Oc2ccc(C(N)=O)cn2)cc1]

6-(4-hexylphenoxy)nicotinamide

247

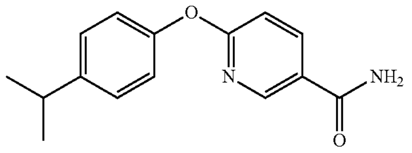

6-(4-isopropylphenoxy)nicotinamide

248

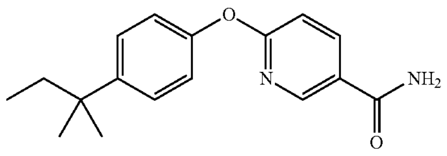 [SMILES: CCC(C)(C)c1ccc(Oc2ccc(C(N)=O)cn2)cc1]

6-(4-(tert-pentyl)phenoxy)nicotinamide

249

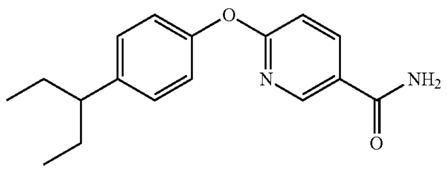 [SMILES: CCC(CC)c1ccc(Oc2ccc(C(N)=O)cn2)cc1]

6-(4-pentan-3-yl)phenoxy)nicotinamide

TABLE IIb-continued

250

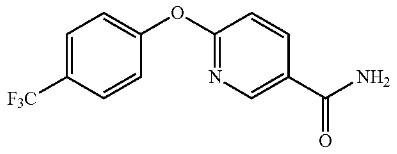 [SMILES: NC(=O)c1ccc(Oc2ccc(C(F)(F)F)cc2)nc1]

6-(4-(trifluoromethyl)phenoxy)nicotinamide

251

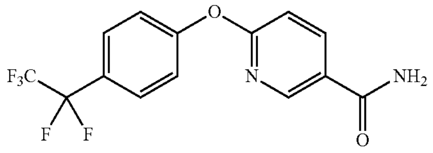 [SMILES: NC(=O)c1ccc(Oc2ccc(C(F)(F)C(F)(F)F)cc2)nc1]

6-(4-(perfluoroethyl)phenoxy)nicotinamide

252

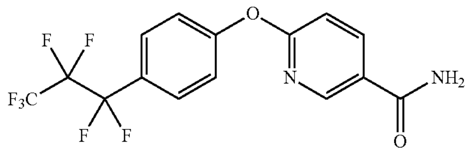 [SMILES: NC(=O)c1ccc(Oc2ccc(C(F)(F)C(F)(F)C(F)(F)F)cc2)nc1]

6-(4-(perfluoropropyl)phenoxy)nicotinamide

253

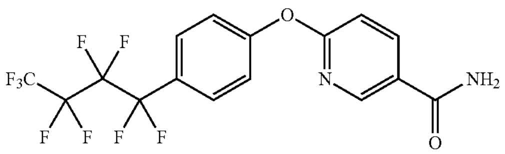 [SMILES: NC(=O)c1ccc(Oc2ccc(C(F)(F)C(F)(F)C(F)(F)C(F)(F)F)cc2)nc1]

6-(4-(perfluorobutylphenoxy)nicotinamide

254

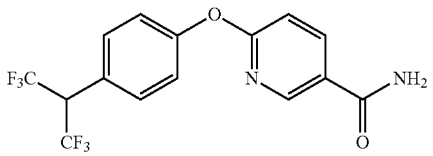

6-(4-(1,1,1,3,3,3-hexafluoropropan-2-yl)phenoxy) nicotinamide

255

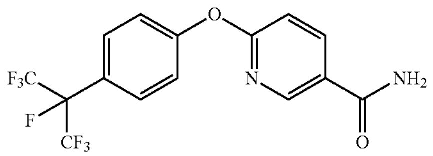

(6-(4-(perfluoropropan-2-yl)phenoxy)nicotinamide

256

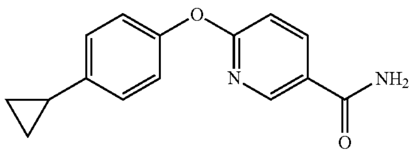 [SMILES: NC(=O)c1ccc(Oc2ccc(C3CC3)cc2)nc1]

6-(4-cyclopropylphenoxy)nicotinamide

TABLE IIb-continued

257

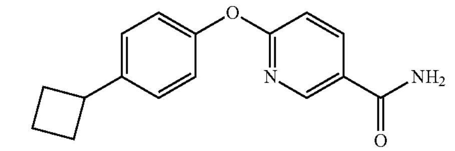 [SMILES: NC(=O)c1ccc(Oc2ccc(C3CCC3)cc2)nc1]

6-(4-cyclobutylphenoxy)nicotinamide

258

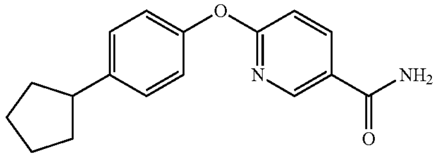 [SMILES: NC(=O)c1ccc(Oc2ccc(C3CCCC3)cc2)nc1]

6-(4-cyclopentylphenoxy)nicotinamide

259

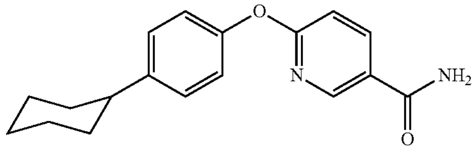 [SMILES: NC(=O)c1ccc(Oc2ccc(C3CCCCC3)cc2)nc1]

6-(4-cyclohexylphenoxy)nicotinamide

260

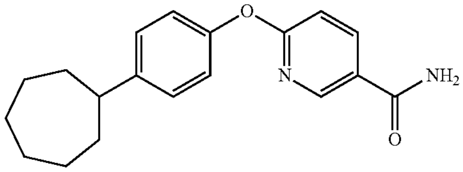

6-(4-cycloheptylphenoxy)nicotinamide

261

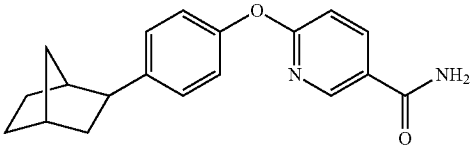 [SMILES: NC(=O)c1ccc(Oc2ccc(C3CC4CCC3C4)cc2)nc1]

6-(4-((1S,4R)-bicyclo[2.2.1]heptan-2-yl)phenoxy)nicotinamide

262

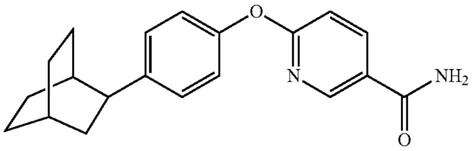 [SMILES: NC(=O)c1ccc(Oc2ccc(C3CC4CCC3CC4)cc2)nc1]

6-(4-((1s,4s)-bicyclo[2.2.2]octan-2-yl)phenoxy)nicotinamide

263

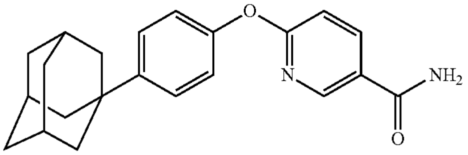 [SMILES: NC(=O)c1ccc(Oc2ccc(C34CC5CC(CC(C5)C3)C4)cc2)nc1]

6-(4-((3r,5r,7r)-adamantan-1-yl)phenoxy)nicotinamide

TABLE IIb-continued

264

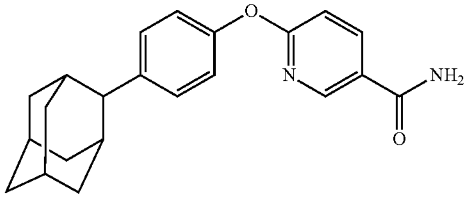

6-(4-((1r,3r,5r,7r)-adamantan-2-yl)phenoxy)nicotinamide

265

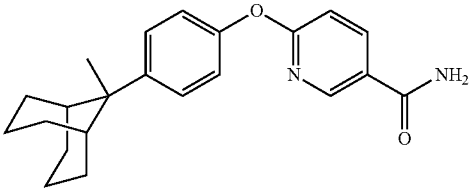

6-(4-((1R,5S)-9-methylbicyclo[3.3.1]nonan-9-yl)phenoxy)nicotinamide

X = N, $R^3$ = H, $R^4$ = OH

266

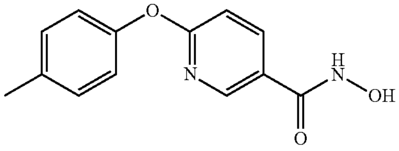 [SMILES: Cc1ccc(Oc2ccc(C(=O)NO)cn2)cc1]

N-hydroxy-6-(p-tolyloxy)nicotinamide

267

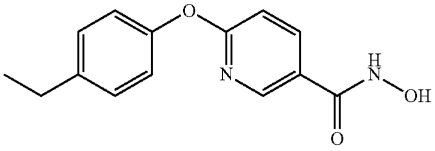 [SMILES: CCc1ccc(Oc2ccc(C(=O)NO)cn2)cc1]

6-(4-ethylphenoxy)-N-hydroxynicotinamide

268

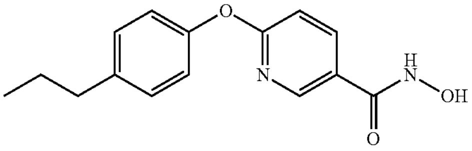 [SMILES: CCCc1ccc(Oc2ccc(C(=O)NO)cn2)cc1]

N-hydroxy-6-(4-propylphenoxy)nicotinamide

269

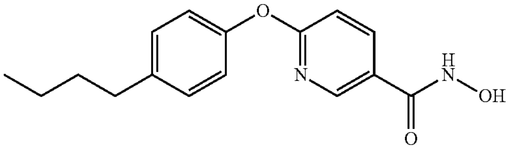 [SMILES: CCCCc1ccc(Oc2ccc(C(=O)NO)cn2)cc1]

6-(4-butylphenoxy)-N-hydroxynicotinamide

270

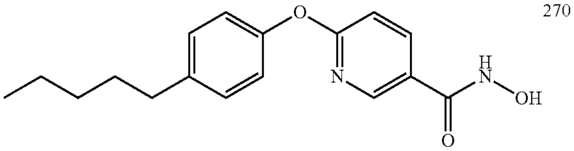

N-hydroxy-6-(4-pentylphenoxy)nicotinamide

TABLE IIb-continued

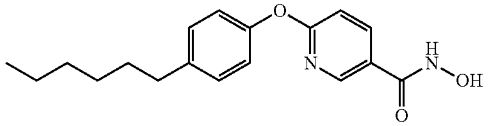

271

6-(4-hexylphenoxy)-N-hydroxynicotinamide

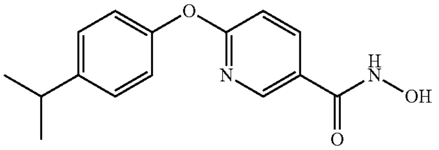 [SMILES: CC(C)c1ccc(Oc2ccc(C(=O)NO)cn2)cc1]

272

N-hydroxy-6-(4-isopropylphenoxy)nicotinamide

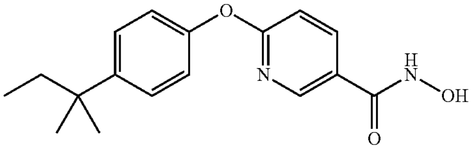 [SMILES: CCC(C)(C)c1ccc(Oc2ccc(C(=O)NO)cn2)cc1]

273

N-hydroxy-6-(4-(tert-pentyl)phenoxy)nicotinamide

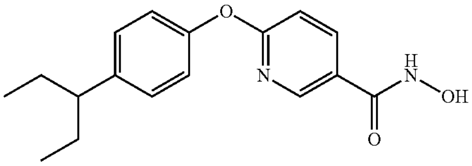 [SMILES: CCC(CC)c1ccc(Oc2ccc(C(=O)NO)cn2)cc1]

274

N-hydroxy-6-(4-(pentan-3-yl)phenoxy)nicotinamide

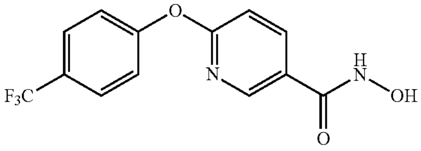 [SMILES: O=C(NO)c1ccc(Oc2ccc(C(F)(F)F)cc2)nc1]

275

N-hydroxy-6-(4-(trifluoromethyl)phenoxy)nicotinamide

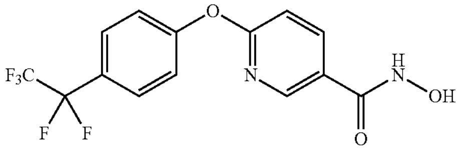 [SMILES: O=C(NO)c1ccc(Oc2ccc(C(F)(F)C(F)(F)F)cc2)nc1]

276

N-hydroxy-6-(4-(perfluoroethyl)phenoxy)nicotinamide

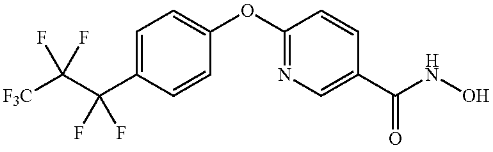

277

N-hydroxy-6-(4-(perfluoropropyl)phenoxy)nicotinamide

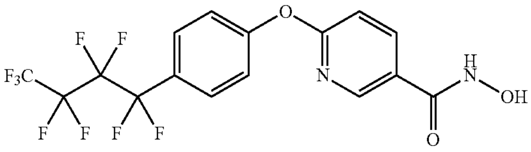 [SMILES: O=C(NO)c1ccc(Oc2ccc(C(F)(F)C(F)(F)C(F)(F)C(F)(F)F)cc2)nc1]

278

TABLE IIb-continued

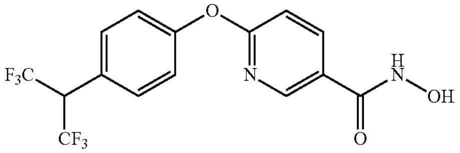 [SMILES: O=C(NO)c1ccc(Oc2ccc(C(C(F)(F)F)C(F)(F)F)cc2)nc1]

279

6-(4-(1,1,1,3,3,3-hexafluoropropan-2-yl)phenoxy)-N-hydroxynicotinamide

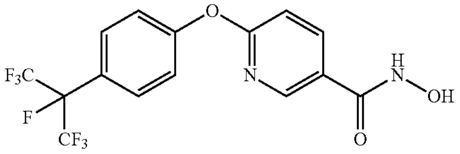 [SMILES: O=C(NO)c1ccc(Oc2ccc(C(F)(C(F)(F)F)C(F)(F)F)cc2)nc1]

280

N-hydroxy-6-(4-(perfluoropropan-2-yl)phenoxy)nicotinamide

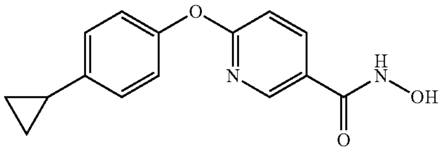 [SMILES: O=C(NO)c1ccc(Oc2ccc(C3CC3)cc2)nc1]

281

6-(4-cyclopropylphenoxy)-N-hydroxynicotinamide

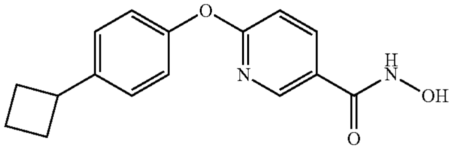 [SMILES: O=C(NO)c1ccc(Oc2ccc(C3CCC3)cc2)nc1]

282

6-(4-cyclobutylphenoxy)-N-hydroxynicotinamide

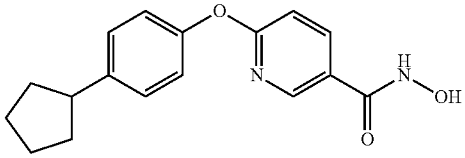 [SMILES: O=C(NO)c1ccc(Oc2ccc(C3CCCC3)cc2)nc1]

283

6-(4-cyclopentylphenoxy)-N-hydroxynicotinamide

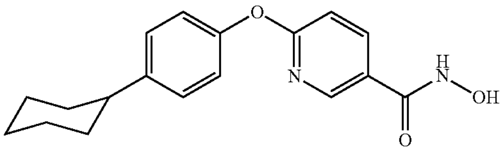

284

6-(4-cyclohexylphenoxy)-N-hydroxynicotinamide

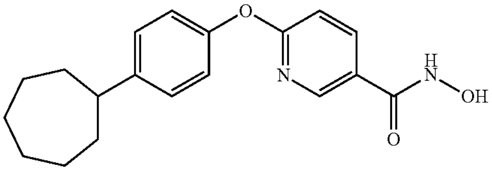 [SMILES: O=C(NO)c1ccc(Oc2ccc(C3CCCCCC3)cc2)nc1]

285

6-(4-cycloheptylphenoxy)-N-hydroxynicotinamide

TABLE IIb-continued

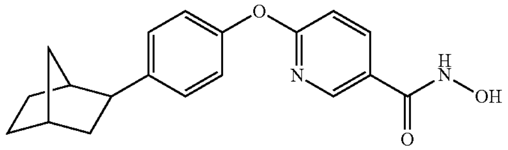 [SMILES: O=C(NO)c1ccc(Oc2ccc(C3CC4CCC3C4)cc2)nc1]
286

6-(4-((1S,4R)-bicyclo[2.2.1]heptan-2-yl)phenoxy)-N-hydroxynicotinamide

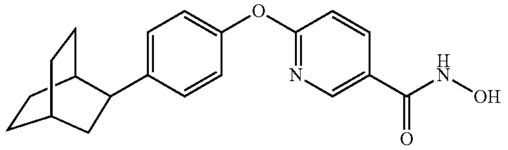 [SMILES: O=C(NO)c1ccc(Oc2ccc(C3CC4CCC3CC4)cc2)nc1]
287

6-(4-((1s,4s)-bicyclo[2.2.2]octan-2-yl)phenoxy)-N-hydroxynicotinamide

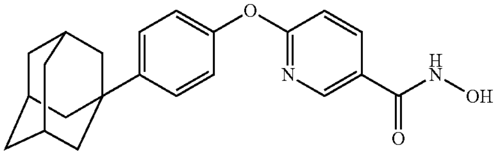
288

6-(4-((3r,5r,7r)-adamantan-1-yl)phenoxy)-N-hydroxynicotinamide

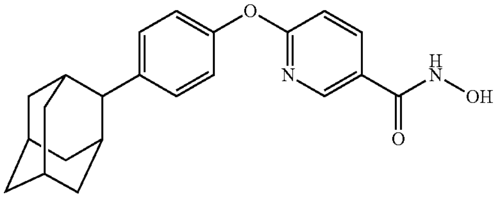 [SMILES: O=C(NO)c1ccc(Oc2ccc(C3C4CC5CC(C4)CC3C5)cc2)nc1]
289

6-(4-((1r,3r,5r,7r)-adamantan-2-yl)phenoxy)-N-hydroxynicotinamide

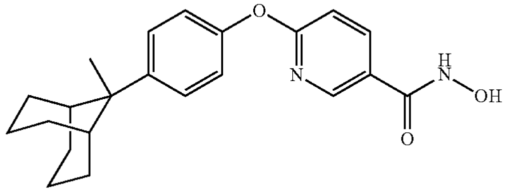 [SMILES: CC1(c2ccc(Oc3ccc(C(=O)NO)cn3)cc2)C2CCCC1CCC2]
290

N-hydroxy-6-(4-((1R,5S)-9-methylbicyclo[3.3.1]nonan-9-yl)phenoxy)nicotinamide

X = N, $R^3$ = H, $R^4$ = Me

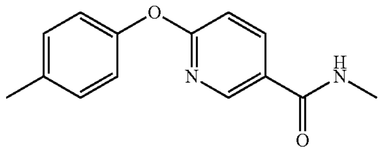
291

N-methyl-6-(p-tolyloxy)nicotinamide

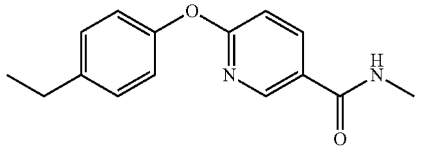 [SMILES: CCc1ccc(Oc2ccc(C(=O)NC)cn2)cc1]
292

6-(4-ethylphenoxy)-N-mtehylnicotinamide

TABLE IIb-continued

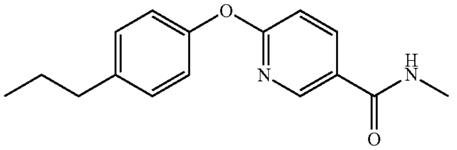 [SMILES: CCCc1ccc(Oc2ccc(C(=O)NC)cn2)cc1]
293

N-methyl-6-(4-propylphenoxy)nicotinamide

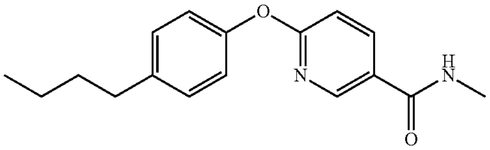 [SMILES: CCCCc1ccc(Oc2ccc(C(=O)NC)cn2)cc1]
294

6-(4-butylphenoxy)-N-methylnicotinamide

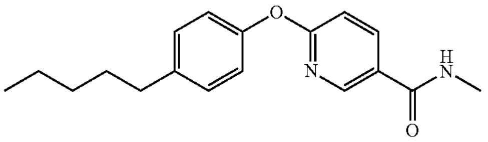 [SMILES: CCCCCc1ccc(Oc2ccc(C(=O)NC)cn2)cc1]
295

N-methyl-6-(4-pentylphenoxy)nicotinamide

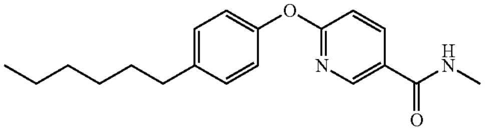 [SMILES: CCCCCCc1ccc(Oc2ccc(C(=O)NC)cn2)cc1]
296

6-(4-hexylphenoxy)-N-methylnicotinamide

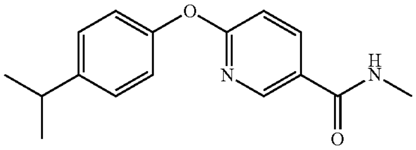
297

6-(4-isopropylphenoxy)-N-methylnicotinamide

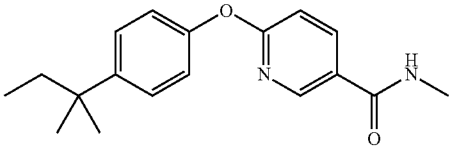 [SMILES: CCC(C)(C)c1ccc(Oc2ccc(C(=O)NC)cn2)cc1]
298

N-methyl-6-(4-(tert-pentyl)phenoxy)nicotinamide

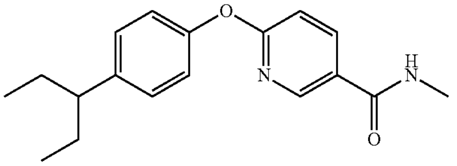 [SMILES: CCC(CC)c1ccc(Oc2ccc(C(=O)NC)cn2)cc1]
299

N-mtehyl-6-(4-(pentan-3-yl)phenoxy)nicotinamide

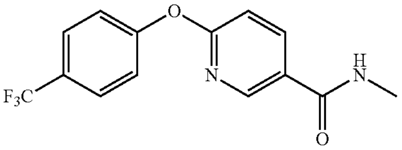 [SMILES: CNC(=O)c1ccc(Oc2ccc(C(F)(F)F)cc2)nc1]
300

N-methyl-6-(4-(trifluoromethyl)phenoxy)nicotinamide

TABLE IIb-continued

301

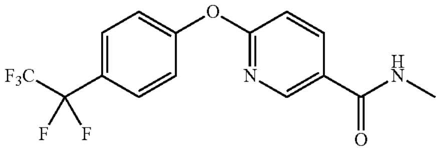 [SMILES: CNC(=O)c1ccc(Oc2ccc(C(F)(F)C(F)(F)F)cc2)nc1]

N-methyl-6-(4-(perfluoroethyl)phenoxy)nicotinamide

302

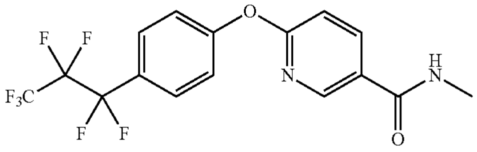 [SMILES: CNC(=O)c1ccc(Oc2ccc(C(F)(F)C(F)(F)C(F)(F)F)cc2)nc1]

N-methyl-6-(4-(perfluoropropyl)phenoxy)nicotinamide

303

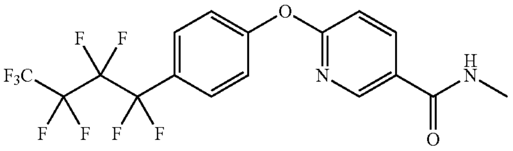 [SMILES: CNC(=O)c1ccc(Oc2ccc(C(F)(F)C(F)(F)C(F)(F)C(F)(F)F)cc2)nc1]

N-methyl-6-(4-(perfluorobutyl)phenoxy)nicotinamide

304

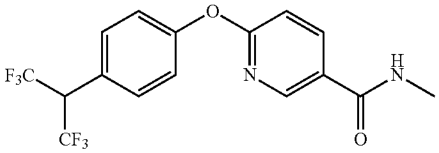 [SMILES: CNC(=O)c1ccc(Oc2ccc(C(C(F)(F)F)C(F)(F)F)cc2)nc1]

6-(4-(1,1,1,3,3,3-hexafluoropropan-2-yl)phenoxy)-N-methylnicotinamide

305

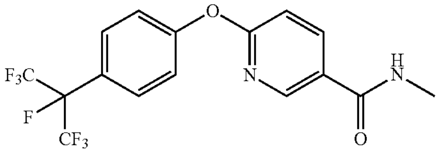 [SMILES: CNC(=O)c1ccc(Oc2ccc(C(F)(C(F)(F)F)C(F)(F)F)cc2)nc1]

N-methyl-6-(4-(perfluoropropan-2-yl)phenoxy)nicotinamide

306

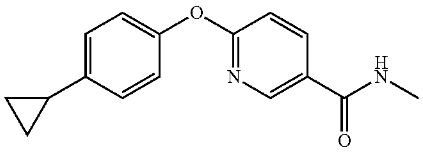 [SMILES: CNC(=O)c1ccc(Oc2ccc(C3CC3)cc2)nc1]

6-(4-cyclopropylphenoxy)-N-mtehylnicotinamide

307

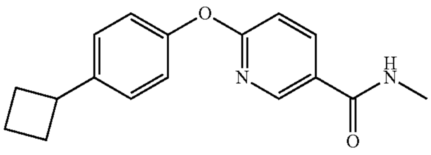 [SMILES: CNC(=O)c1ccc(Oc2ccc(C3CCC3)cc2)nc1]

6-(4-cyclobutylphenoxy)-N-methylnicotinamide

TABLE IIb-continued

308

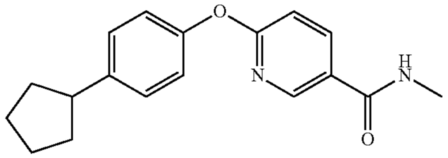 [SMILES: CNC(=O)c1ccc(Oc2ccc(C3CCCC3)cc2)nc1]

6-(4-cyclopentylphenoxy)-N-mtehylnicotinamide

309

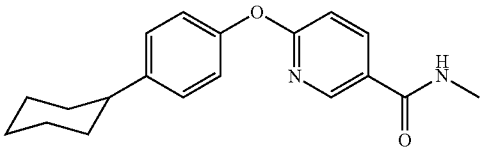

6-(4-cyclohexylphenoxy)-N-methylnicotinamide

310

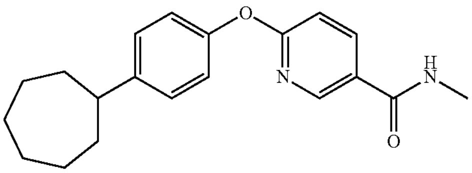 [SMILES: CNC(=O)c1ccc(Oc2ccc(C3CCCCCC3)cc2)nc1]

6-(4-cycloheptylphenoxy)-N-methylnicotinamide

311

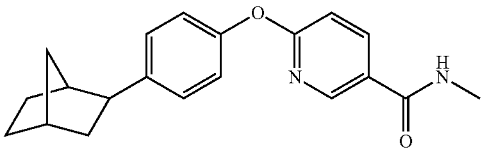 [SMILES: CNC(=O)c1ccc(Oc2ccc(C3CC4CCC3C4)cc2)nc1]

6-(4-((1S,4R)-bicyclo[2.2.1]heptan-2-yl)phenoxy)-N-methylnicotinamide

312

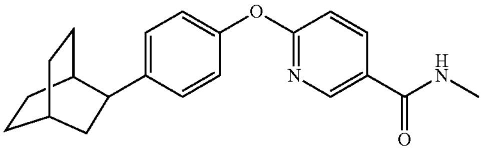

6-(4-((1s,4s)-bicyclo[2.2.2]octan-2-yl)phenoxy)-N-methylnicotinamide

313

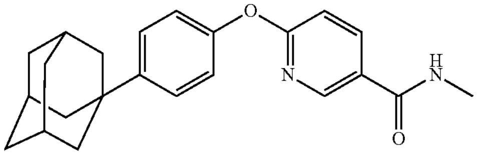 [SMILES: CNC(=O)c1ccc(Oc2ccc(C34CC5CC(CC(C5)C3)C4)cc2)nc1]

6-(4-((3r,5r,7r)-adamantan-1-yl)phenoxy)-N-methylnicotinamide

314

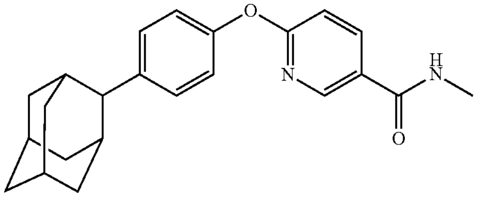

6-(4-((1r,3r,5r,7r)-adamantan-2-yl)phenoxy)-N-methylnicotinamide

TABLE IIb-continued

315

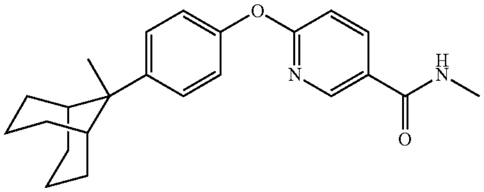 [SMILES: CNC(=O)c1ccc(Oc2ccc(C3(C)C4CCCC3CCC4)cc2)nc1]

N-methyl-6-(4-((1R,5S)-9-methylbicyclo[3.3.1]nonan-9-yl)phenoxy)nicotinamide

X = N, $R^3$ = Me, $R^4$ = Me

316

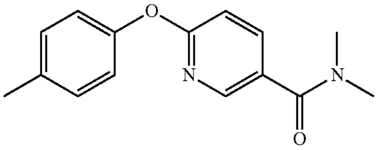

N,N-dimethyl-6-(p-tolyloxy)nicotinamide

317

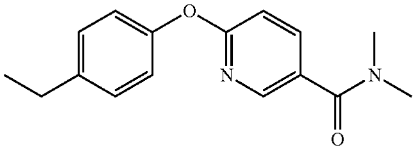 [SMILES: CCc1ccc(Oc2ccc(C(=O)N(C)C)cn2)cc1]

6-(4-ethylphenoxy)-N,N-dimethylnicotinamide

318

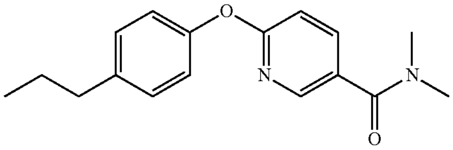 [SMILES: CCCc1ccc(Oc2ccc(C(=O)N(C)C)cn2)cc1]

N,N-dimethyl-6-(4-propylphenoxy)nicotinamide

319

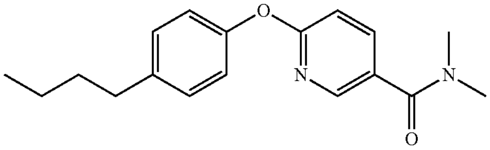 [SMILES: CCCCc1ccc(Oc2ccc(C(=O)N(C)C)cn2)cc1]

6-(4-butylphenoxy)-N,N-dimethylnicotinamide

320

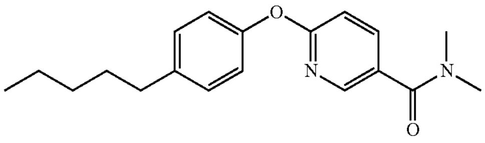 [SMILES: CCCCCc1ccc(Oc2ccc(C(=O)N(C)C)cn2)cc1]

N,N-dimethyl-6-(4-pentylphenoxy)nicotinamide

321

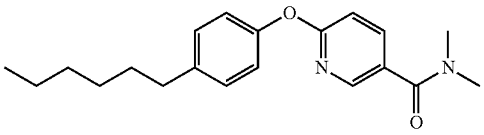 [SMILES: CCCCCCc1ccc(Oc2ccc(C(=O)N(C)C)cn2)cc1]

6-(4-hexylphenoxy)-N,N-dimethylnicotinamide

TABLE IIb-continued

322

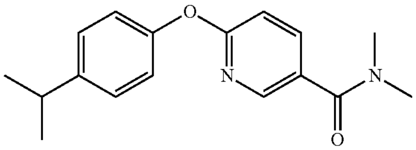

6-(4-isopropylphenoxy)-N,N-dimethylnicotinamide

323

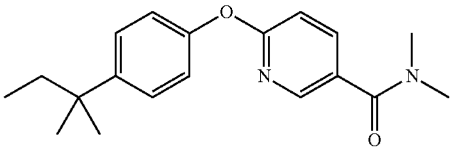 [SMILES: CCC(C)(C)c1ccc(Oc2ccc(C(=O)N(C)C)cn2)cc1]

N,N-dimethyl-6-(4-(tert-pentyl)phenoxy)nicotinamide

324

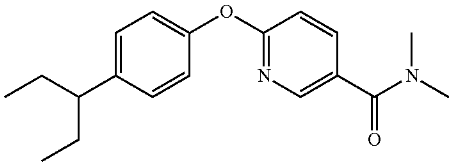 [SMILES: CCC(CC)c1ccc(Oc2ccc(C(=O)N(C)C)cn2)cc1]

N,N-dimethyl-6-(4-(pentan-3-yl)phenoxy)nicotinamide

325

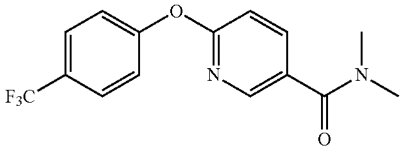 [SMILES: CN(C)C(=O)c1ccc(Oc2ccc(C(F)(F)F)cc2)nc1]

N,N-dimethyl-6-(4-(trifluoromethyl)phenoxy)nicotinamide

326

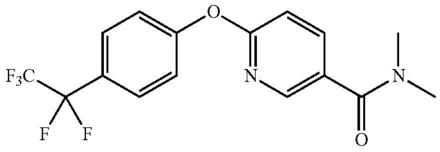 [SMILES: CN(C)C(=O)c1ccc(Oc2ccc(C(F)(F)C(F)(F)F)cc2)nc1]

N,N-dimethyl-6-(4-(perfluoroethyl)phenoxy)nicotinamide

327

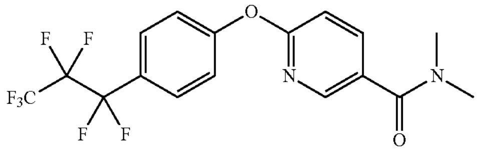 [SMILES: CN(C)C(=O)c1ccc(Oc2ccc(C(F)(F)C(F)(F)C(F)(F)F)cc2)nc1]

N,N-dimethyl-6-(4-(perfluoropropyl)phenoxy)nicotinamide

328

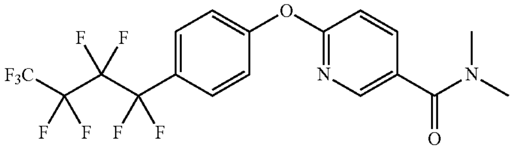

N,N-dimethyl-6-(4-(perfluorobutyl)phenoxy)nicotinamide

TABLE IIb-continued

329

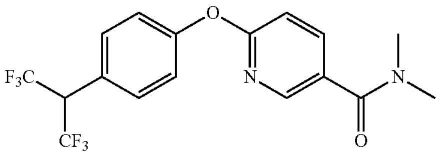 [SMILES: CN(C)C(=O)c1ccc(Oc2ccc(C(C(F)(F)F)C(F)(F)F)cc2)nc1]

6-(4-(1,1,1,3,3,3-hexafluoropropan-2-yl)phenoxy)-N,N-dimethylnicotinamide

330

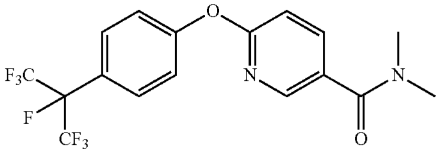 [SMILES: CN(C)C(=O)c1ccc(Oc2ccc(C(F)(C(F)(F)F)C(F)(F)F)cc2)nc1]

N,N-dimethyl-6-(4-(perfluoropropan-2-yl)phenoxy)nicotinamide

331

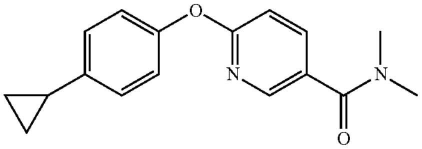

6-(4-cyclopropylphenoxy)-N,N-dimethylnicotinamide

332

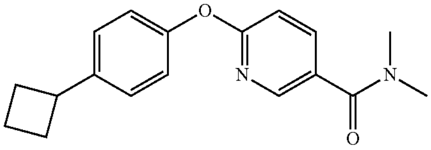

6-(4-cyclobutylphenoxy)-N,N-dimethylnicotinamide

333

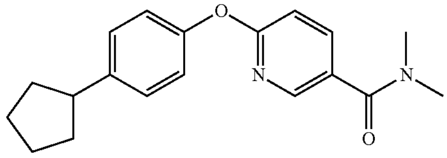 [SMILES: CN(C)C(=O)c1ccc(Oc2ccc(C3CCCC3)cc2)nc1]

6-(4-cyclopentylphenoxy)-N,N-dimethylnicotinamide

334

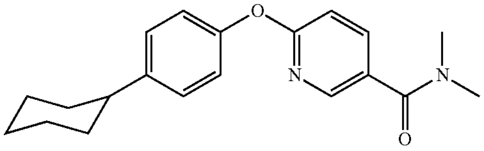 [SMILES: CN(C)C(=O)c1ccc(Oc2ccc(C3CCCCC3)cc2)nc1]

6-(4-cyclohexylphenoxy)-N,N-dimethylnicotinamide

335

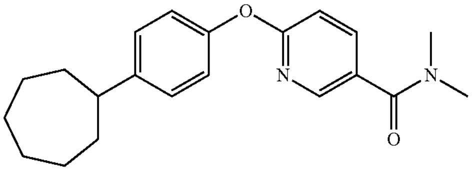 [SMILES: CN(C)C(=O)c1ccc(Oc2ccc(C3CCCCCC3)cc2)nc1]

6-(4-cycloheptylphenoxy)-N,N-dimethylnicotinamide

TABLE IIb-continued

336

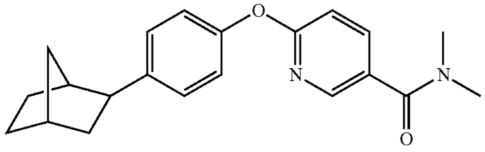

6-(4-((1S,4R)-bicyclo[2.2.1]heptan-2-yl)phenoxy)-N,N-dimethylnicotinamide

337

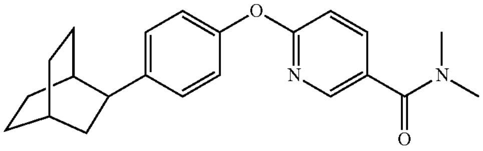 [SMILES: CN(C)C(=O)c1ccc(Oc2ccc(C3CC4CCC3CC4)cc2)nc1]

6-(4-((1s,4s)-bicyclo[2.2.2]octan-2-yl)phenoxy)-N,N-dimethylnicotinamide

338

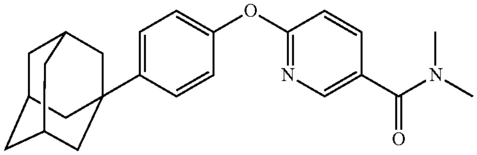 [SMILES: CN(C)C(=O)c1ccc(Oc2ccc(C34CC5CC(CC(C5)C3)C4)cc2)nc1]

6-(4-((3r,5r,7r)-adamantan-1-yl)phenoxy)-N,N-dimethylnicotinamide

339

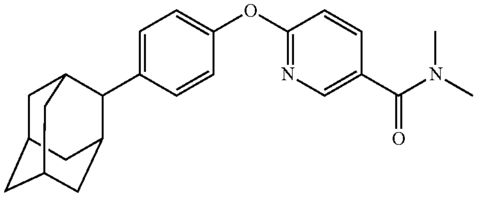 [SMILES: CN(C)C(=O)c1ccc(Oc2ccc(C3C4CC5CC(C4)CC3C5)cc2)nc1]

6-(4-((1r,3r,5r,7r)-adamantan-2-yl)phenoxy)-N,N-dimethylnicotinamide

340

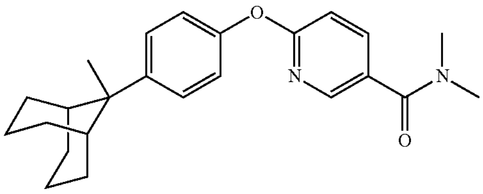

N,N-dimethyl-6-(4-((1R,5S)-9-methylbicyclo[3.3.1]nonan-9-yl)phenoxy)nicotinamide Also included are isomers, e.g. enantiomers or diastereomers or rotamers or mixtures of isomers, salts, particularly pharmaceutically acceptable salts, and solvates of the compounds listed above.

A third aspect of the present invention relates to compounds of formula III and salts and solvates thereof:

(III)

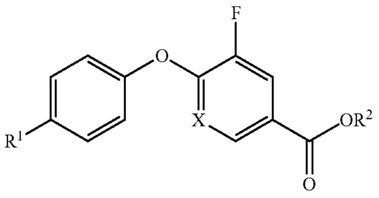

wherein X, $R^1$ and $R^2$ are defined as in formula I, including the preferred definitions of $R^1$ and $R^2$.

In some embodiments, the following compounds shown in Table IIIa are explicitly excluded from the scope of the invention:

TABLE IIIa

| Compound | $R^1$ | $R^2$ | X |
|---|---|---|---|
| III-A | tert-butyl | H | CH |
| III-B | tert-butyl | ethyl | CH |
| III-C | phenyl | H | CH |

Specific examples of compounds falling under the scope of formula III are shown in Table IIIb. The compounds in Table IIIb are defined by their chemical structure, the indicated nomenclature is only for illustrative purposes.

TABLE IIIb

X = CH, $R^2$ = H

341

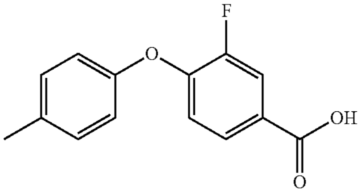 [SMILES: Cc1ccc(Oc2ccc(C(=O)O)cc2F)cc1]

3-fluoro-4-(p-tolyloxy)benzoic acid

342

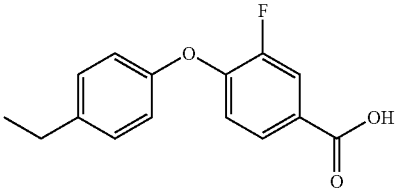

4-(4-ethylphenoxy)-3-fluorobenzoic acid

343

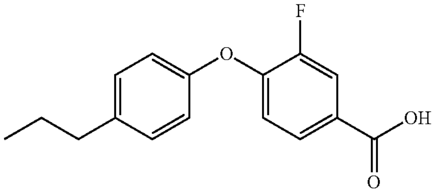

3-fluoro-4-(4-propylphenoxy)benzoic acid

TABLE IIIb-continued

344

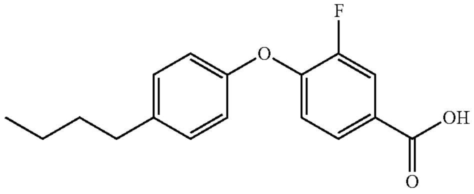

4-(4-butylphenoxy)-3-fluorobenzoic acid

345

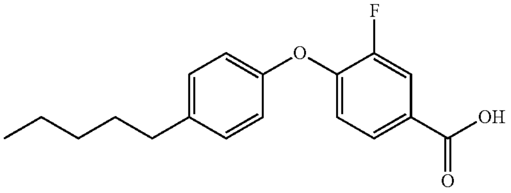 [SMILES: CCCCCc1ccc(Oc2ccc(C(=O)O)cc2F)cc1]

3-fluoro-4-(4-pentylphenoxy)benzoic acid

346

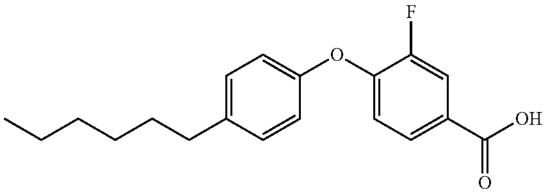

3-fluoro-4-(4-hexylphenoxy)benzoic acid

347

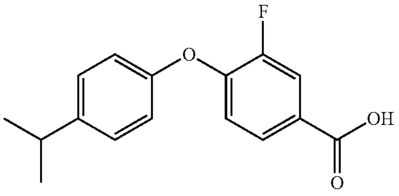 [SMILES: CC(C)c1ccc(Oc2ccc(C(=O)O)cc2F)cc1]

3-fluoro-4-(4-isopropylphenoxy)benzoic acid

348

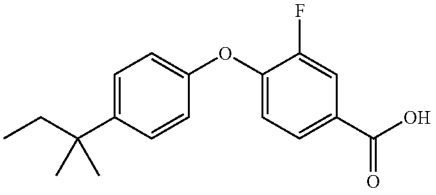

3-fluoro-4-(4-(tert-pentyl)phenoxy)benzoic acid

349

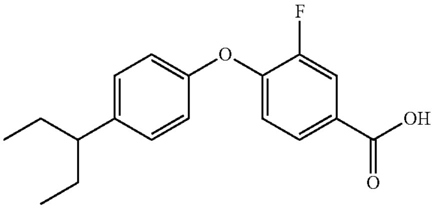 [SMILES: CCC(CC)c1ccc(Oc2ccc(C(=O)O)cc2F)cc1]

3-fluoro-4-(4-(pentan-3-yl)phenoxy)benzoic acid

TABLE IIIb-continued

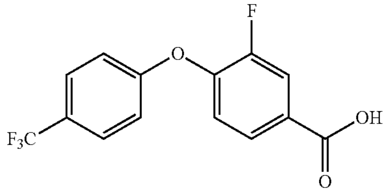

350

3-fluoro-4-(4-trifluoromethyl)phenoxy)benzoic acid

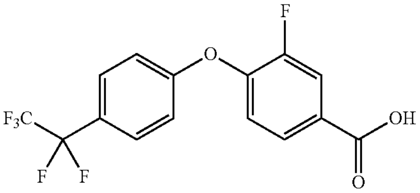

351

3-fluoro-4-(4-(perfluoroethyl)phenoxy)benzoic acid

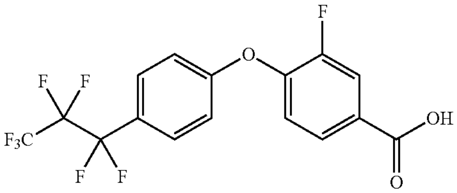

352

3-fluoro-4-(4-(perfluoropropyl)phenoxy)benzoic acid

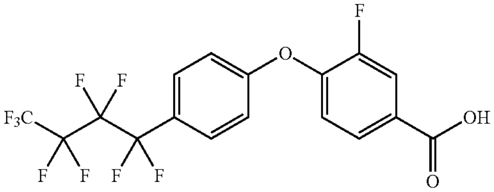 [SMILES: O=C(O)c1ccc(Oc2ccc(C(F)(F)C(F)(F)C(F)(F)C(F)(F)F)cc2)c(F)c1]

353

3-fluoro-4-(4-(perfluorobutyl)phenoxy)benzoic acid

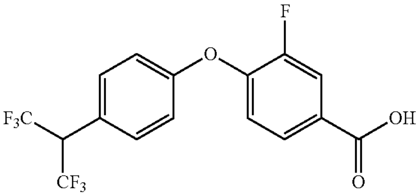

354

3-fluoro-4-(4-(1,1,1,3,3,3-hexafluoropropan-2-yl)phenoxy) benzoic acid

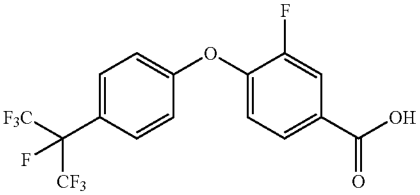

355

3-fluoro-4-(4-(perfluoropropan-2-yl)phenoxy)benzoic acid

TABLE IIIb-continued

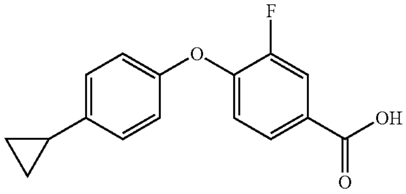 [SMILES: O=C(O)c1ccc(Oc2ccc(C3CC3)cc2)c(F)c1]

356

4-(4-cyclopropylphenoxy)-3-fluorobenzoic acid

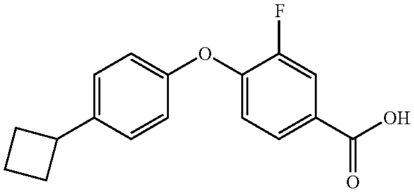 [SMILES: O=C(O)c1ccc(Oc2ccc(C3CCC3)cc2)c(F)c1]

357

4-(4-cyclobutylphenoxy)-3-fluorobenzoic acid

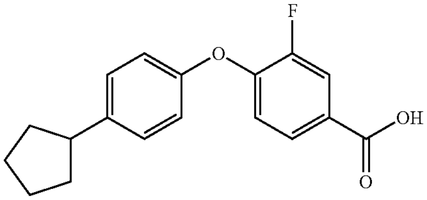 [SMILES: O=C(O)c1ccc(Oc2ccc(C3CCCC3)cc2)c(F)c1]

358

4-(4-cyclopentylphenoxy)-3-fluorobenzoic acid

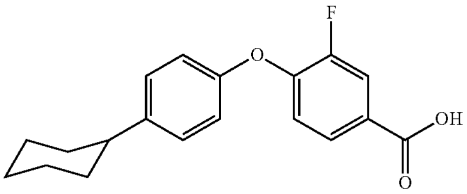 [SMILES: O=C(O)c1ccc(Oc2ccc(C3CCCCC3)cc2)c(F)c1]

359

4-(4-cyclohexylphenoxy)-3-fluorobenzoic acid

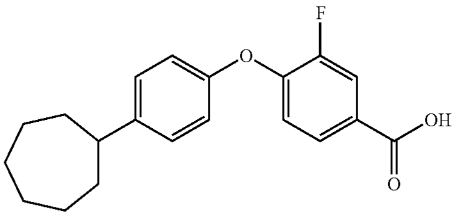 [SMILES: O=C(O)c1ccc(Oc2ccc(C3CCCCCC3)cc2)c(F)c1]

360

4-(4-cycloheptylphenoxy)-3-fluorobenzoic acid

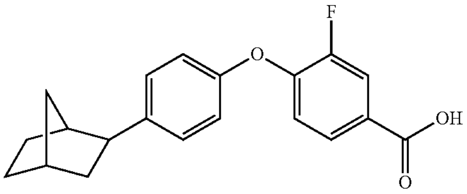

361

4-(4-((1S,4R)-bicyclo[2.2.1]heptan-2-yl)phenoxy)-3-fluorobenzoic acid

TABLE IIIb-continued

362

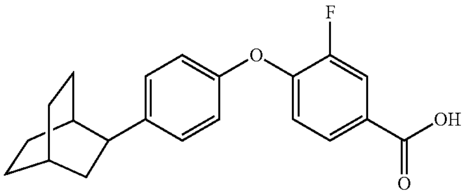 [SMILES: O=C(O)c1ccc(Oc2ccc(C3CC4CCC3CC4)cc2)c(F)c1]

4-(4-((1s,4s)-bicyclo[2.2.2]octan-2-yl)phenoxy)-3-fluorobenzoic acid

363

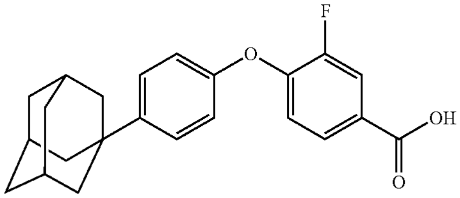 [SMILES: O=C(O)c1ccc(Oc2ccc(C34CC5CC(CC(C5)C3)C4)cc2)c(F)c1]

4-(4-((3r,5r,7r)-adamantan-1-yl)phenoxy)-3-fluorobenzoic acid

364

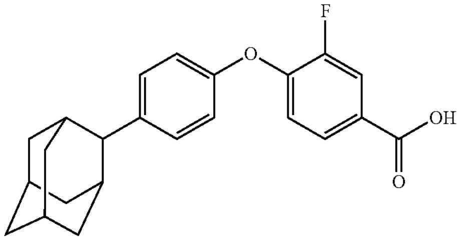 [SMILES: O=C(O)c1ccc(Oc2ccc(C3C4CC5CC(C4)CC3C5)cc2)c(F)c1]

4-(4-((1r,3r,5r,7r)-adamantan-2-yl)phenoxy)-3-fluorobenzoic acid

365

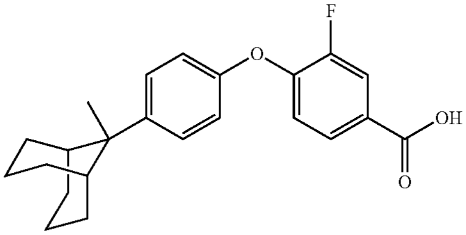 [SMILES: CC1(c2ccc(Oc3ccc(C(=O)O)cc3F)cc2)C2CCCC1CCC2]

3-fluoro-4-(4-((1R,5S)-9-methylbicyclo[3.3.1]nonan-9-yl)phenoxy)benzoic acid

X = CH, $R^2$ = Me

366

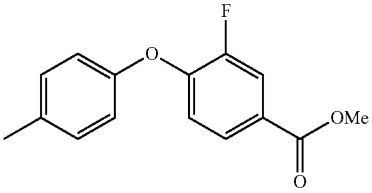

methyl 3-fluoro-4-(p-tolyloxy)benzoate

TABLE IIIb-continued

367

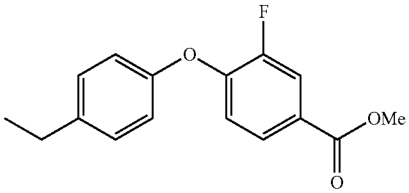 [SMILES: CCc1ccc(Oc2ccc(C(=O)OC)cc2F)cc1]

methyl 4-(4-ethylphenoxy)-3-fluorobenzoate

368

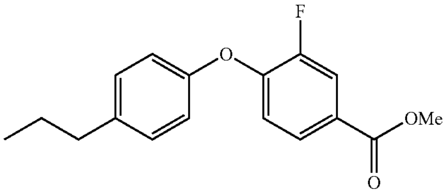 [SMILES: CCCc1ccc(Oc2ccc(C(=O)OC)cc2F)cc1]

methyl 3-fluoro-4-(4-propylphenoxy)benzoate

369

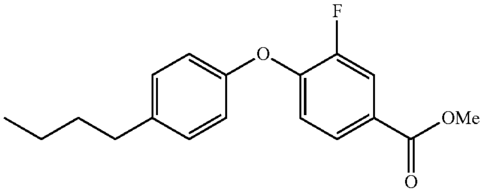

methyl 4-(4-butylphenoxy)-3-fluorobenzoate

370

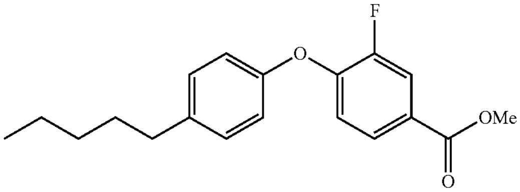 [SMILES: CCCCCc1ccc(Oc2ccc(C(=O)OC)cc2F)cc1]

methyl 3-fluoro-4-(4-pentylphenoxy)benzoate

371

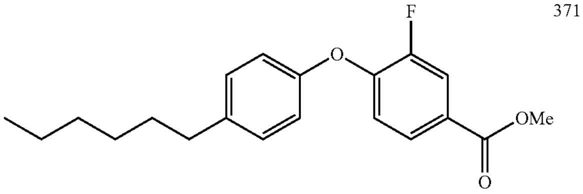

methyl 3-fluoro-4-(4-hexylphenoxy)benzoate

372

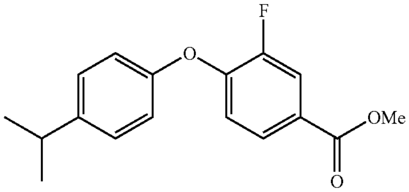 [SMILES: COC(=O)c1ccc(Oc2ccc(C(C)C)cc2)c(F)c1]

methyl 3-fluoro-4-(4-isopropylphenoxy)benzoate

TABLE IIIb-continued

373

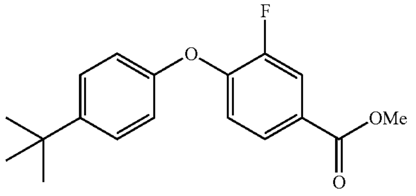 [SMILES: COC(=O)c1ccc(Oc2ccc(C(C)(C)C)cc2)c(F)c1]

methyl 4-(4-(tert-butyl)phenoxy)-3-fluorobenzoate

374

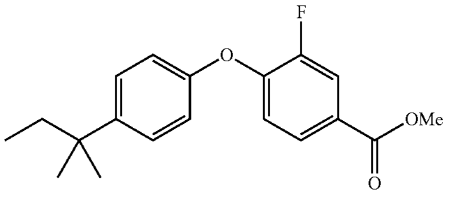 [SMILES: CCC(C)(C)c1ccc(Oc2ccc(C(=O)OC)cc2F)cc1]

methyl 3-fluoro-4-(4-(tert-pentyl)phenoxy)benzoate

375

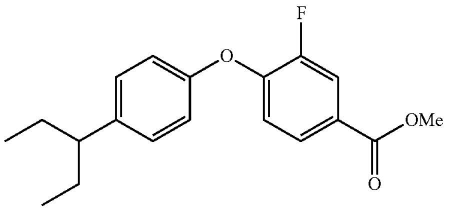 [SMILES: CCC(CC)c1ccc(Oc2ccc(C(=O)OC)cc2F)cc1]

methyl 3-fluoro-4-(4-(pentan-3-yl)phenoxy)benzoate

376

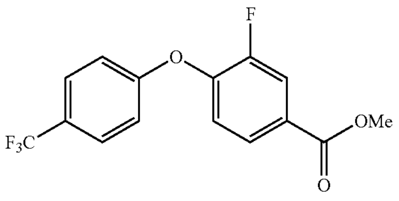 [SMILES: COC(=O)c1ccc(Oc2ccc(C(F)(F)F)cc2)c(F)c1]

methyl 3-fluoro-4-(4-(trifluoromethyl)phenoxy) benzoate

377

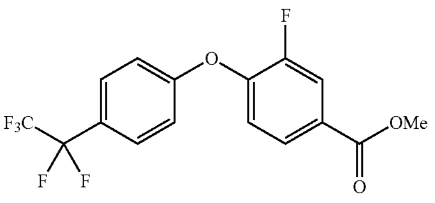 [SMILES: COC(=O)c1ccc(Oc2ccc(C(F)(F)C(F)(F)F)cc2)c(F)c1]

methyl 3-fluoro-4-(4-(perfluoroethyl)phenoxy)benzoate

378

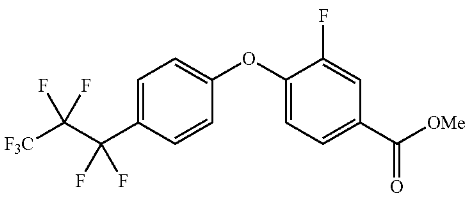 [SMILES: COC(=O)c1ccc(Oc2ccc(C(F)(F)C(F)(F)C(F)(F)F)cc2)c(F)c1]

methyl 3-fluoro-4-(4-(perfluoropropyl)phenoxy)benzoate

TABLE IIIb-continued

379

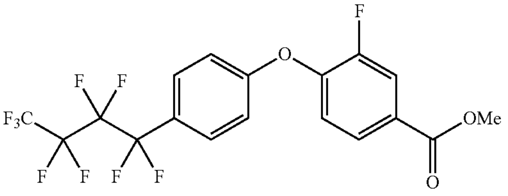 [SMILES: COC(=O)c1ccc(Oc2ccc(C(F)(F)C(F)(F)C(F)(F)C(F)(F)F)cc2)c(F)c1]

methyl 3-fluoro-4-(4-(perfluorobutyl)phenoxy)benzoate

380

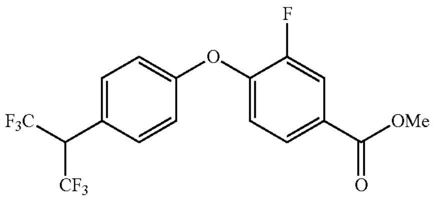 [SMILES: COC(=O)c1ccc(Oc2ccc(C(C(F)(F)F)C(F)(F)F)cc2)c(F)c1]

methyl 3-fluoro-4-(4-(1,1,1,3,3,3-hexafluoropropan-2-yl)phenoxy)benzoate

381

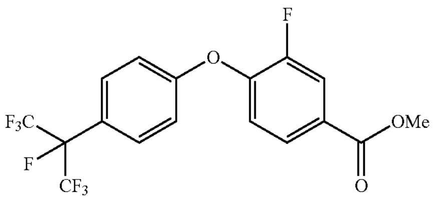 [SMILES: COC(=O)c1ccc(Oc2ccc(C(F)(C(F)(F)F)C(F)(F)F)cc2)c(F)c1]

methyl 3-fluoro-4-(4-(perfluoropropan-2-yl)phenoxy) benzoate

382

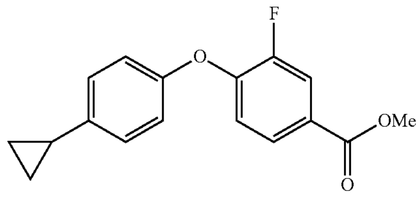

methyl 4-(4-cyclopropylphenoxy)-3-fluorobenzoate

383

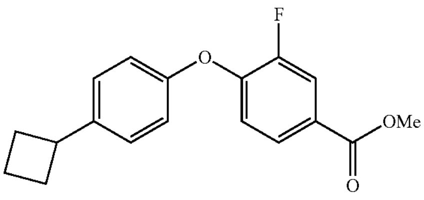 [SMILES: COC(=O)c1ccc(Oc2ccc(C3CCC3)cc2)c(F)c1]

methyl 4-(4-cyclobutylphenoxy)-3-fluorobenzoate

384

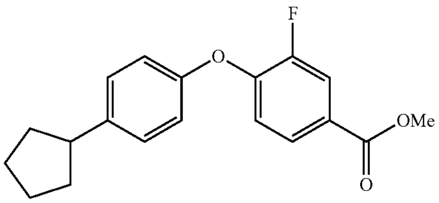

methyl 4-(4-cyclopentylphenoxy)-3-fluorobenzoate

TABLE IIIb-continued

385

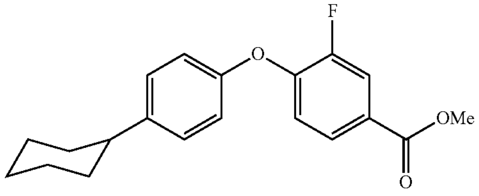

methyl 4-(4-cyclohexylphenoxy)-3-fluorobenzoate

386

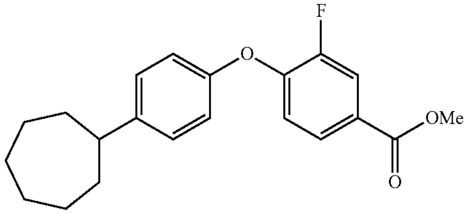 [SMILES: COC(=O)c1ccc(Oc2ccc(C3CCCCCC3)cc2)c(F)c1]

methyl 4-(4-cycloheptylphenoxy)-3-fluorobenzoate

387

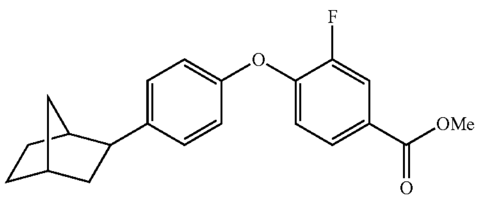 [SMILES: COC(=O)c1ccc(Oc2ccc(C3CC4CCC3C4)cc2)c(F)c1]

methyl 4-(4-((1S,4R)-bicyclo[2.2.1]heptan-2-yl)phenoxy)-3-fluorobenzoate

388

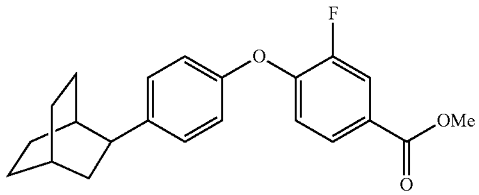 [SMILES: COC(=O)c1ccc(Oc2ccc(C3CC4CCC3CC4)cc2)c(F)c1]

methyl 4-(4-((1s,4s)-bicyclo[2.2.2]octan-2-yl)phenoxy)-3-fluorobenzoate

389

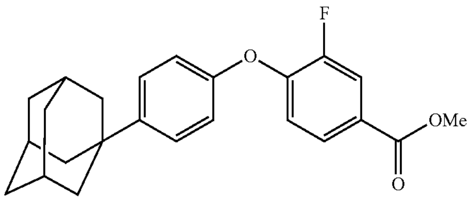 [SMILES: COC(=O)c1ccc(Oc2ccc(C34CC5CC(CC(C5)C3)C4)cc2)c(F)c1]

methyl 4-(4-((3r,5r,7r)-adamantan-1-yl)phenoxy)-3-fluorobenzoate

390

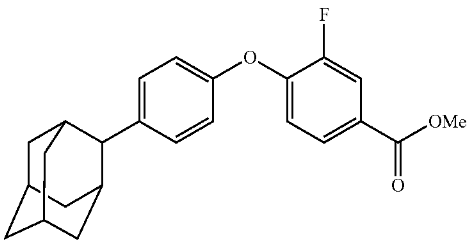 [SMILES: COC(=O)c1ccc(Oc2ccc(C3C4CC5CC(C4)CC3C5)cc2)c(F)c1]

methyl 4-(4-((1r,3r,5r,7r)-adamantan-2-yl)phenoxy)-3-fluorobenzoate

TABLE IIIb-continued

391

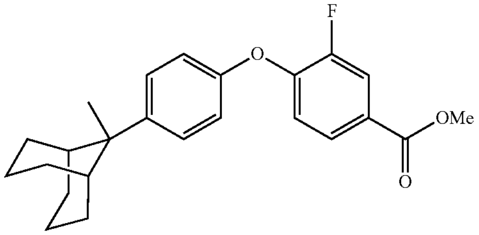 [SMILES: COC(=O)c1ccc(Oc2ccc(C3(C)C4CCCC3CCC4)cc2)c(F)c1]

methyl 3-fluoro-4-(4-((1R,5S)-9-methylbicyclo[3.3.1]nonan-9-yl)phenoxy)benzoate

X = CH, $R^2$ = Et

392

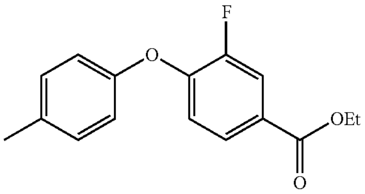 [SMILES: CCOC(=O)c1ccc(Oc2ccc(C)cc2)c(F)c1]

ethyl 3-fluoro-4-(p-tolyloxy)benzoate

393

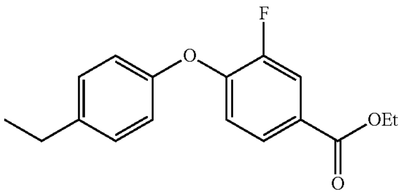

ethyl 4-(4-ethylphenoxy)-3-fluorobenzoate

394

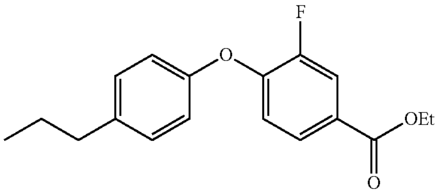

ethyl 3-fluoro-4-(4-propylphenoxy)benzoate

395

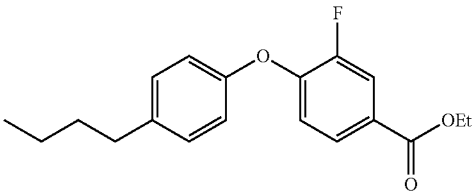

ethyl 4-(4-butylphenoxy)-3-fluorobenzoate

396

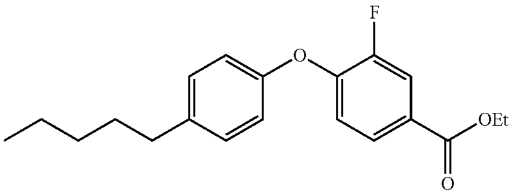 [SMILES: CCCCCc1ccc(Oc2ccc(C(=O)OCC)cc2F)cc1]

ethyl 3-fluoro-4-(4-pentylphenoxy)benzoate

TABLE IIIb-continued

397

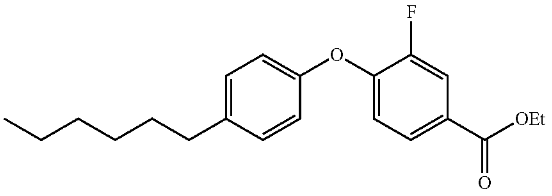 [SMILES: CCCCCCc1ccc(Oc2ccc(C(=O)OCC)cc2F)cc1]

ethyl 3-fluoro-4-(4-hexylphenoxy)benzoate

398

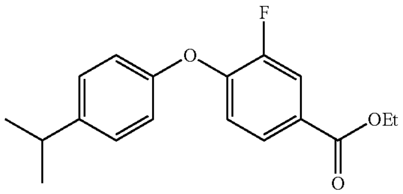 [SMILES: CCOC(=O)c1ccc(Oc2ccc(C(C)C)cc2)c(F)c1]

ethyl 3-fluoro-4-(4-isopropylphenoxy)benzoate

399

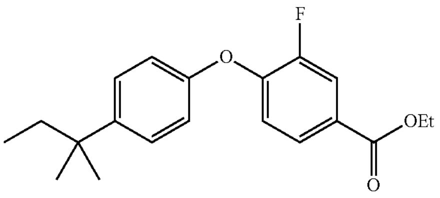

ethyl 3-fluoro-4-(4-(tert-pentyl)phenoxy)benzoate

400

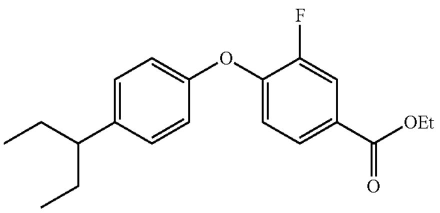 [SMILES: CCOC(=O)c1ccc(Oc2ccc(C(CC)CC)cc2)c(F)c1]

ethyl 3-fluoro-4-(4-(pentan-3-yl)phenoxy)benzoate

401

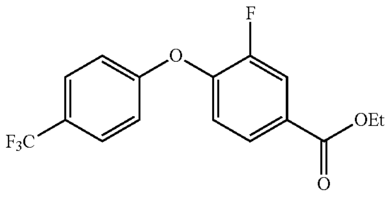 [SMILES: CCOC(=O)c1ccc(Oc2ccc(C(F)(F)F)cc2)c(F)c1]

ethyl 3-fluoro-4-(4-trifluoromethyl)phenoxy)benzoate

402

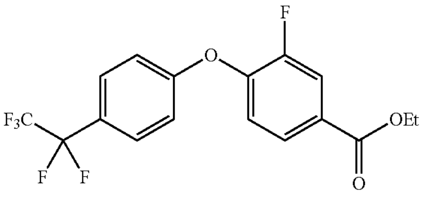 [SMILES: CCOC(=O)c1ccc(Oc2ccc(C(F)(F)C(F)(F)F)cc2)c(F)c1]

ethyl 3-fluoro-4-(4-(perfluoroethyl)phenoxy)benzoate

TABLE IIIb-continued

403

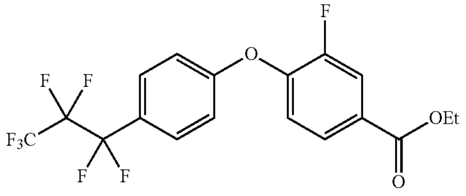

ethyl 3-fluoro-4-(4-(perfluoropropyl)phenoxy)benzoate

404

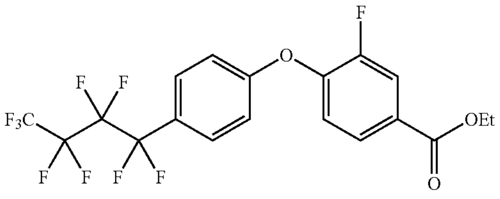 [SMILES: CCOC(=O)c1ccc(Oc2ccc(C(F)(F)C(F)(F)C(F)(F)C(F)(F)F)cc2)c(F)c1]

ethyl 3-fluoro-4-(4-(perfluorobutyl)phenoxy)benzoate

405

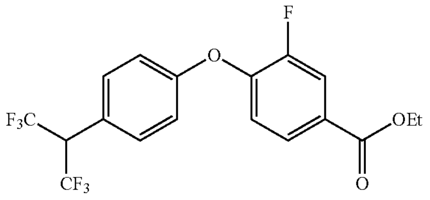

ethyl 3-fluoro-4-(4-(1,1,1,3,3,3-hexafluoropropan-2-yl)phenoxy)benzoate

406

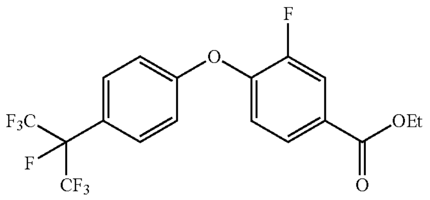

ethyl 3-fluoro-4-(4-(perfluoropropan-2-yl)phenoxy) benzoate

407

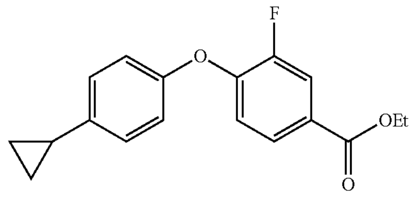 [SMILES: CCOC(=O)c1ccc(Oc2ccc(C3CC3)cc2)c(F)c1]

ethyl 4-(4-cyclopropylphenoxy)-3-fluorobenzoate

408

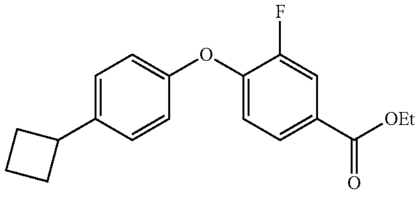 [SMILES: CCOC(=O)c1ccc(Oc2ccc(C3CCC3)cc2)c(F)c1]

ethyl 4-(4-cyclobutylphenoxy)-3-fluorobenzoate

TABLE IIIb-continued

409

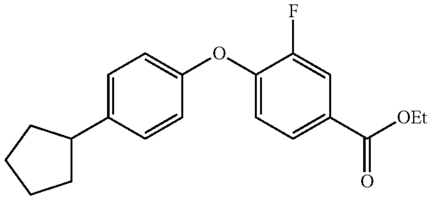 [SMILES: CCOC(=O)c1ccc(Oc2ccc(C3CCCC3)cc2)c(F)c1]

ethyl 4-(4-cyclopentylphenoxy)-3-fluorobenzoate

410

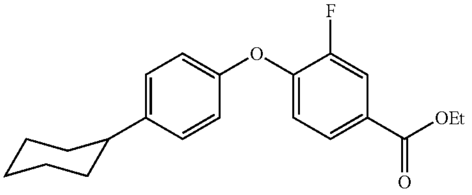 [SMILES: CCOC(=O)c1ccc(Oc2ccc(C3CCCCC3)cc2)c(F)c1]

ethyl 4-(4-cyclohexylphenoxy)-3-fluorobenzoate

411

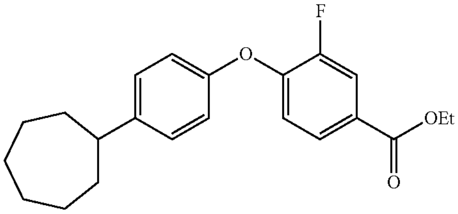

ethyl 4-(4-cycloheptylphenoxy)-3-fluorobenzoate

412

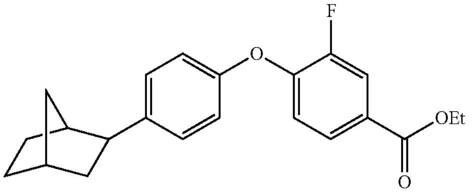 [SMILES: CCOC(=O)c1ccc(Oc2ccc(C3CC4CCC3C4)cc2)c(F)c1]

ethyl 4-(4-((1S,4R)-bicyclo[2.2.1]heptan-2-yl)phenoxy)-3-fluorobenzoate

413

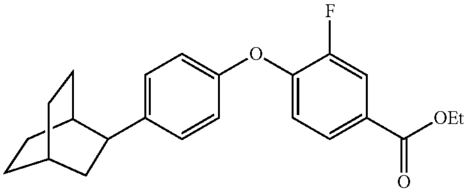 [SMILES: CCOC(=O)c1ccc(Oc2ccc(C3CC4CCC3CC4)cc2)c(F)c1]

ethyl 4-(4-((1s,4s)-bicyclo[2.2.2]octan-2-yl)phenoxy)-3-fluorobenzoate

414

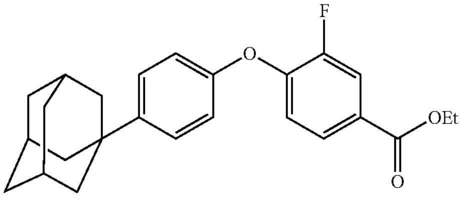

ethyl 4-(4-((3r,5r,7r)-adamantan-1-yl)phenoxy)-3-fluorobenzoate

TABLE IIIb-continued

415

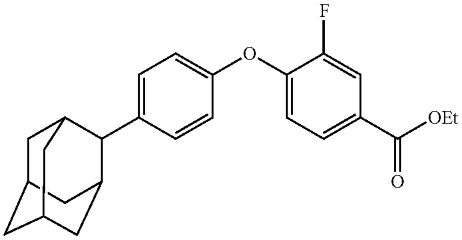 [SMILES: CCOC(=O)c1ccc(Oc2ccc(C3C4CC5CC(C4)CC3C5)cc2)c(F)c1]

ethyl 4-(4-((1r,3r,5r,7r)-adamantan-2-yl)phenoxy)-3-fluorobenzoate

416

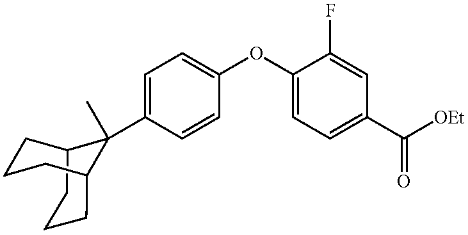

ethyl 3-fluoro-4-(4-((1R,5S)-9-methylbiccyclo[3.3.1]nonan-9-yl)phenoxy)benzoate

X = N, $R^2$ = H

417

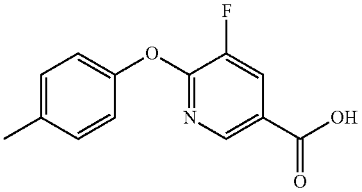 [SMILES: Cc1ccc(Oc2ncc(C(=O)O)cc2F)cc1]

5-fluoro-6-(p-tolyloxy)nicotinic acid

418

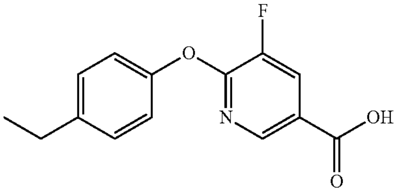 [SMILES: CCc1ccc(Oc2ncc(C(=O)O)cc2F)cc1]

6-(4-ethylphenoxy)-5-fluoronicotinic acid

419

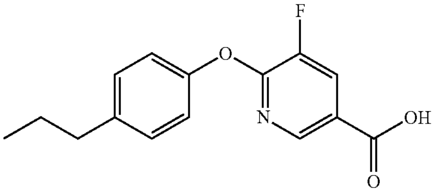 [SMILES: CCCc1ccc(Oc2ncc(C(=O)O)cc2F)cc1]

5-fluoro-6-(4-propylphenoxy)nicotinic acid

420

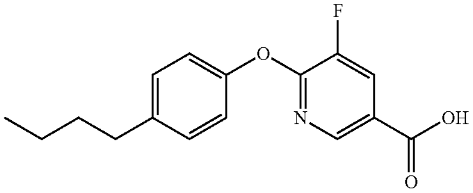

6-(4-butylphenoxy)-5-fluoronicotinic acid

TABLE IIIb-continued

421
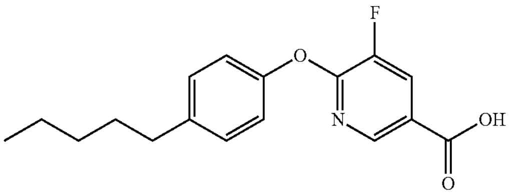 [SMILES: CCCCCc1ccc(Oc2ncc(C(=O)O)cc2F)cc1]
5-fluoro-6-(4-pentylphenoxy)nicotinic acid

422
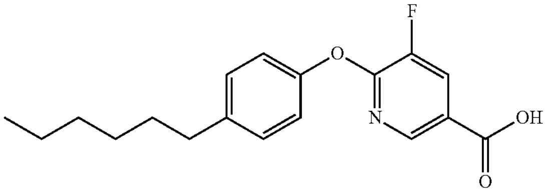 [SMILES: CCCCCCc1ccc(Oc2ncc(C(=O)O)cc2F)cc1]
5-fluoro-6-(4-hexylphenoxy)nicotinic acid

423
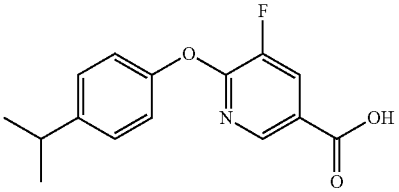 [SMILES: CC(C)c1ccc(Oc2ncc(C(=O)O)cc2F)cc1]
5-fluoro-6-(4-isopropylphenoxy)nicotinic acid

424
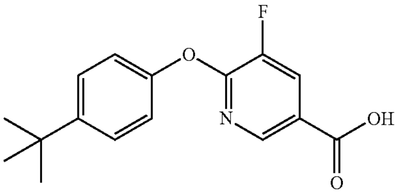 [SMILES: CC(C)(C)c1ccc(Oc2ncc(C(=O)O)cc2F)cc1]
6-(4-(tert-butyl)phenoxy)-5-fluoronicotinic acid

425
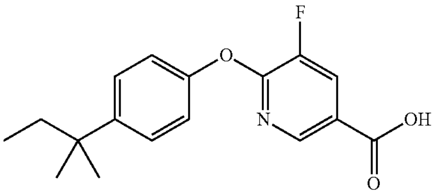 [SMILES: CCC(C)(C)c1ccc(Oc2ncc(C(=O)O)cc2F)cc1]
5-fluoro-6-(4-(tert-pentyl)phenoxy)nicotinic acid

426
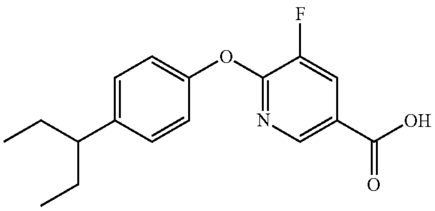 [SMILES: CCC(CC)c1ccc(Oc2ncc(C(=O)O)cc2F)cc1]
5-fluoro-6-(4-(pentan-3-yl)phenoxy)nicotinic acid

TABLE IIIb-continued

427
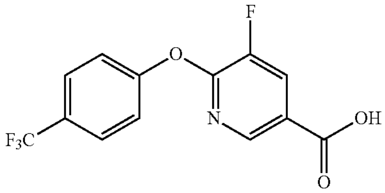 [SMILES: O=C(O)c1cnc(Oc2ccc(C(F)(F)F)cc2)c(F)c1]
5-fluoro-6-(4-(trifluoromethyl)phenoxy)nicotinic acid

428
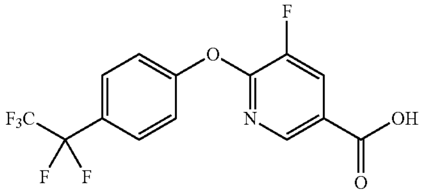 [SMILES: O=C(O)c1cnc(Oc2ccc(C(F)(F)C(F)(F)F)cc2)c(F)c1]
5-fluoro-6-(4-(perfluoroethyl)phenoxy)nicotinic acid

429
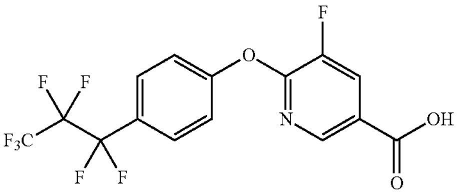 [SMILES: O=C(O)c1cnc(Oc2ccc(C(F)(F)C(F)(F)C(F)(F)F)cc2)c(F)c1]
5-fluoro-6-(4-(perfluoropropyl)phenoxy)nicotinic acid

430
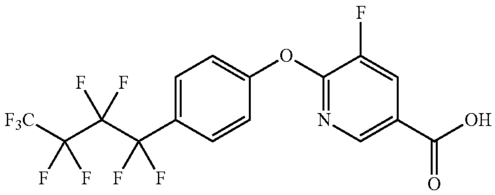 [SMILES: O=C(O)c1cnc(Oc2ccc(C(F)(F)C(F)(F)C(F)(F)C(F)(F)F)cc2)c(F)c1]
5-fluoro-6-(4-(perfluorobutyl)phenoxy)nicotinic acid

431
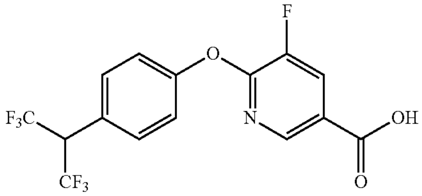
5-fluoro-6-(4-(1,1,1,3,3,3-hexafluoropropan-2-yl)phenoxy) nicotinic acid 432
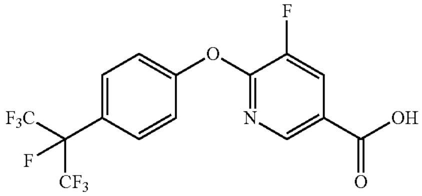
5-fluoro-6-(4-(perfluoropropan-2-yl)phenoxy)nicotinic acid TABLE IIIb-continued

433

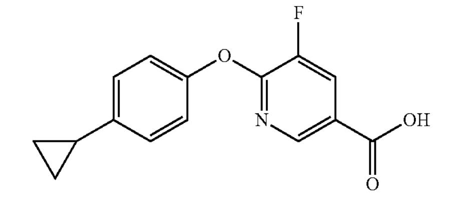 [SMILES: O=C(O)c1cnc(Oc2ccc(C3CC3)cc2)c(F)c1]

6-(4-cyclopropylphenoxy)-5-fluoronicotinic acid

434

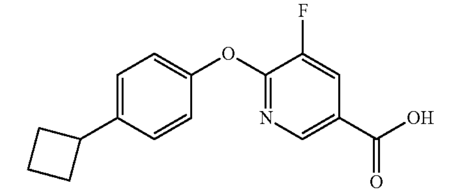 [SMILES: O=C(O)c1cnc(Oc2ccc(C3CCC3)cc2)c(F)c1]

6-(4-cyclobutylphenoxy)-5-fluoronicotinic acid

435

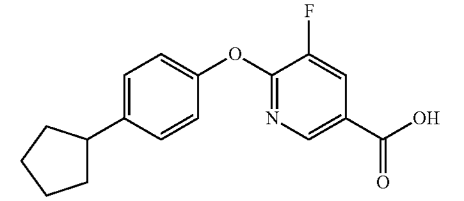

6-(4-cyclopentylphenoxy)-5-fluoronicotinic acid

436

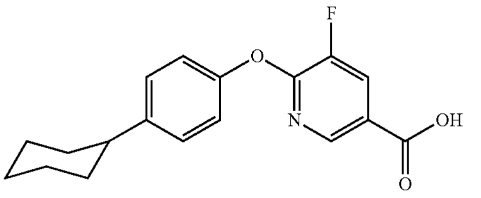

6-(4-cyclohexylphenoxy)-5-fluoronicotinic acid

437

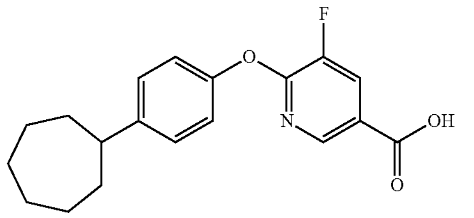 [SMILES: O=C(O)c1cnc(Oc2ccc(C3CCCCCC3)cc2)c(F)c1]

6-(4-cylcloheptylphenoxy)-5-fluoronicotinic acid

438

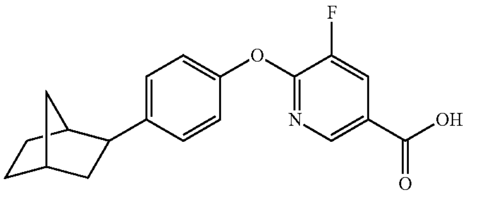 [SMILES: O=C(O)c1cnc(Oc2ccc(C3CC4CCC3C4)cc2)c(F)c1]

6-(4-((1S,4R)-bicyclo[2.2.1]heptan-2-yl)phenoxy)-5-fluoronicotinic acid

TABLE IIIb-continued

439

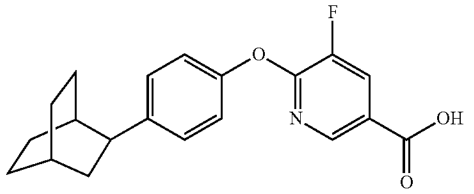 [SMILES: O=C(O)c1cnc(Oc2ccc(C3CC4CCC3CC4)cc2)c(F)c1]

6-(4-((1s,4s)-bicyclo[2.2.2]octan-2-yl)phenoxy)-5-fluoronicotinic acid

440

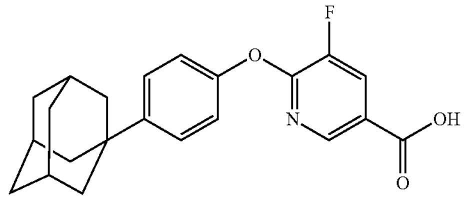 [SMILES: O=C(O)c1cnc(Oc2ccc(C34CC5CC(CC(C5)C3)C4)cc2)c(F)c1]

6-(4-((3r,5r,7r)-adamantan-1-yl)phenoxy)-5-fluoronicotinic acid

441

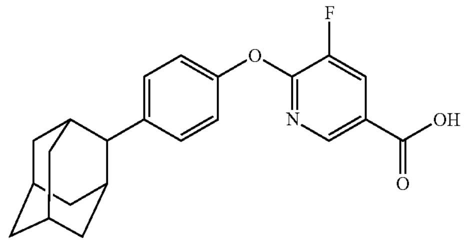 [SMILES: O=C(O)c1cnc(Oc2ccc(C3C4CC5CC(C4)CC3C5)cc2)c(F)c1]

6-(4-((1r,3r,5r,7r)-adamantan-2-yl)phenoxy)-5-fluoronicotinic acid

442

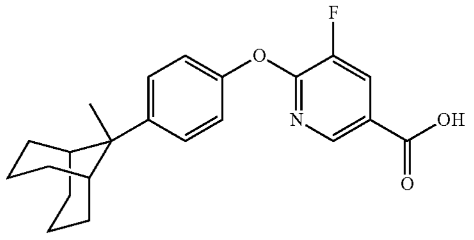 [SMILES: CC1(c2ccc(Oc3ncc(C(=O)O)cc3F)cc2)C2CCCC1CCC2]

5-fluoro-6-(4-((1R,5S)-9-methylbicyclo[3.3.1]nonan-9-yl)phenoxy)nicotinic acid

X = N, $R^2$ = Me

443

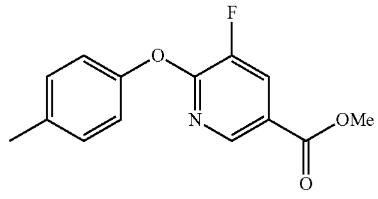 [SMILES: COC(=O)c1cnc(Oc2ccc(C)cc2)c(F)c1]

methyl 5-fluoro-6-(p-tolyloxy)nicotinate

TABLE IIIb-continued

444

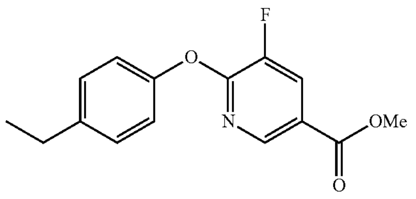 [SMILES: CCc1ccc(Oc2ncc(C(=O)OC)cc2F)cc1]

methyl 6-(4-ethylphenoxy)-5-fluoronicotinate

445

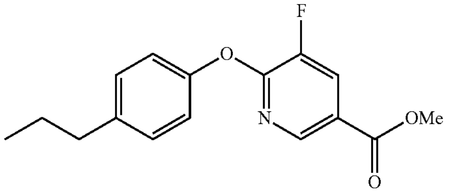 [SMILES: CCCc1ccc(Oc2ncc(C(=O)OC)cc2F)cc1]

methyl 5-fluoro-6-(4-propylphenoxy)nicotinate

446

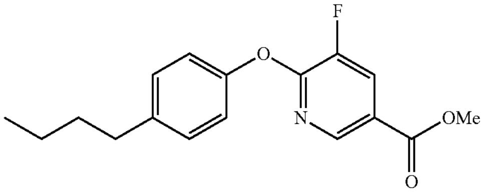 [SMILES: CCCCc1ccc(Oc2ncc(C(=O)OC)cc2F)cc1]

methyl 6-(4-butylphenoxy)5-fluoronicotinate

447

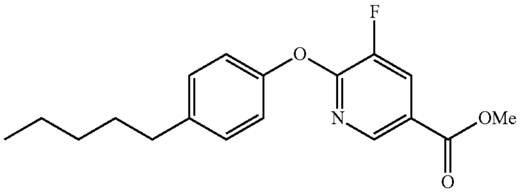 [SMILES: CCCCCc1ccc(Oc2ncc(C(=O)OC)cc2F)cc1]

methyl 5-fluoro-6-(4-pentylphenoxy)nicotinate

448

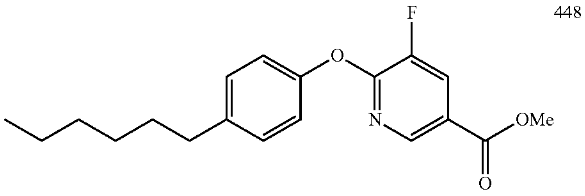

methyl 5-fluoro-6-(4-hexylphenoxy)nicotinate

449

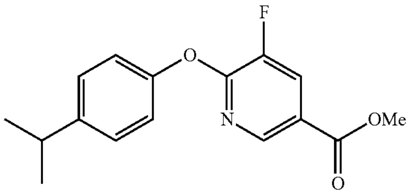 [SMILES: COC(=O)c1cnc(Oc2ccc(C(C)C)cc2)c(F)c1]

methyl 5-fluoro-6-(4-isopropylphenoxy)nicotinate

TABLE IIIb-continued

450

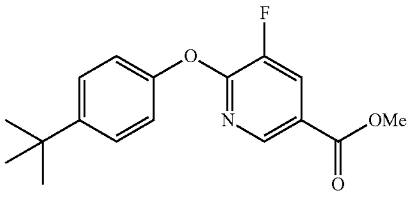 [SMILES: COC(=O)c1cnc(Oc2ccc(C(C)(C)C)cc2)c(F)c1]

methyl 6-(4-(tert-butyl)phenoxy)-5-fluoronicotinate

451

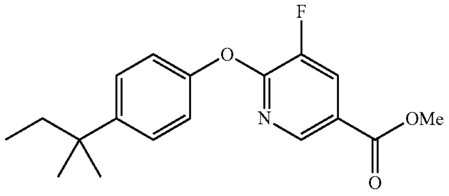 [SMILES: CCC(C)(C)c1ccc(Oc2ncc(C(=O)OC)cc2F)cc1]

methyl 5-fluoro-6-(4-(tert-pentyl)phenoxy)nicotinate

452

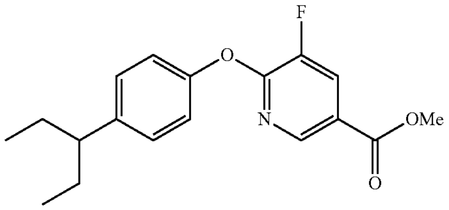 [SMILES: CCC(CC)c1ccc(Oc2ncc(C(=O)OC)cc2F)cc1]

methyl 5-fluoro-6-(4-(pentan-3-yl)phenoxy)nicotinate

453

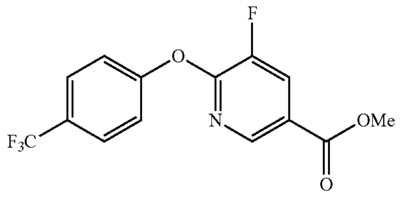 [SMILES: COC(=O)c1cnc(Oc2ccc(C(F)(F)F)cc2)c(F)c1]

methyl 5-fluoro-6-(4-(trifluoromethyl)phenoxy)nicotinate

454

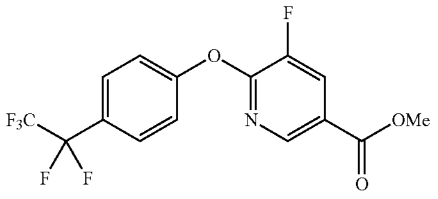 [SMILES: COC(=O)c1cnc(Oc2ccc(C(F)(F)C(F)(F)F)cc2)c(F)c1]

methyl 5-fluoro-6-(4-(perfluoroethyl)phenoxy)nicotinate

455

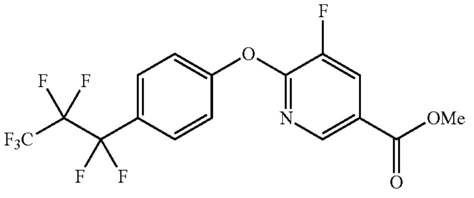 [SMILES: COC(=O)c1cnc(Oc2ccc(C(F)(F)C(F)(F)C(F)(F)F)cc2)c(F)c1]

methyl 5-fluoro-6-(4-(perfluoropropyl)phenoxy)nicotinate

TABLE IIIb-continued

456

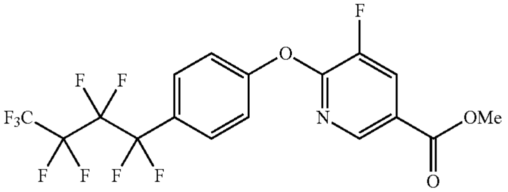 [SMILES: COC(=O)c1cnc(Oc2ccc(C(F)(F)C(F)(F)C(F)(F)C(F)(F)F)cc2)c(F)c1]

methyl 5-fluoro-6-(4-(perfluorobutyl)phenoxy)nicotinate

457

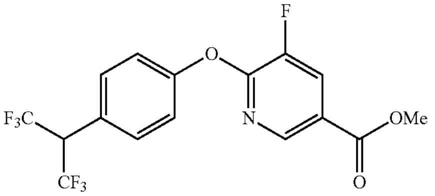

methyl 5-fluoro-6-(4-(1,1,1,3,3,3-hexafluoropropan-2-yl) phenoxy)nicotinate

458

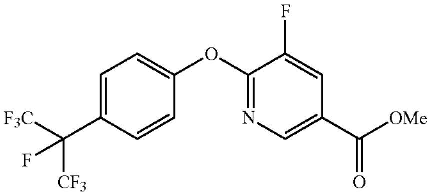 [SMILES: COC(=O)c1cnc(Oc2ccc(C(F)(C(F)(F)F)C(F)(F)F)cc2)c(F)c1]

methyl 5-fluoro-6-(4-(perfluoropropan-2-yl)phenoxy) nicotinate

459

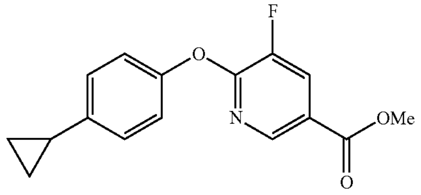

methyl 6-(4-cyclopropylphenoxy)-5-fluoronicotinate

460

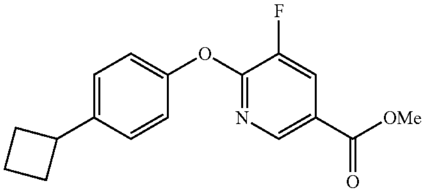

methyl 6-(4-cyclobutylphenoxy)-5-fluoronicotinate

461

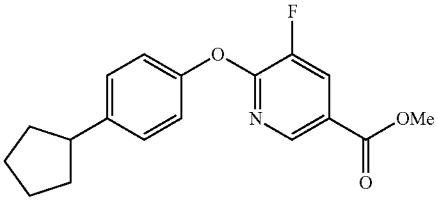 [SMILES: COC(=O)c1cnc(Oc2ccc(C3CCCC3)cc2)c(F)c1]

methyl 6-(4-cyclopentylphenoxy)-5-fluoronicotinate

TABLE IIIb-continued

462

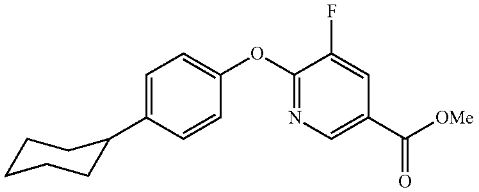 [SMILES: COC(=O)c1cnc(Oc2ccc(C3CCCCC3)cc2)c(F)c1]

methyl 6-(4-cyclohexylphenoxy)-5-fluoronicotinate

463

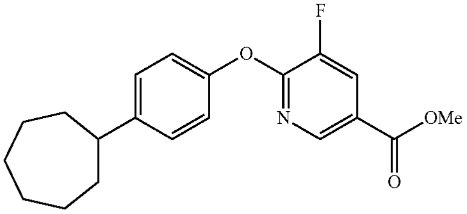

methyl 6-(4-cycloheptylphenoxy)-5-fluoronicotinate

464

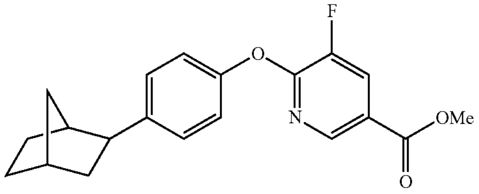

methyl 6-(4-((1S,4R)-bicyclo[2.2.1]heptan-2-yl)phenoxy)-5-fluoronicotinate

465

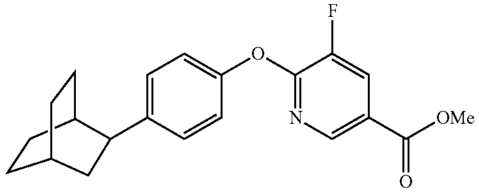 [SMILES: COC(=O)c1cnc(Oc2ccc(C3CC4CCC3CC4)cc2)c(F)c1]

methyl 6-(4-((1s,4s)-bicyclo[2.2.2]octan-2-yl)phenoxy)-5-fluoronicotinate

466

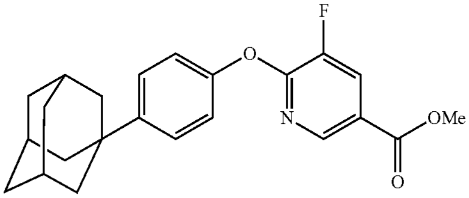 [SMILES: COC(=O)c1cnc(Oc2ccc(C34CC5CC(CC(C5)C3)C4)cc2)c(F)c1]

methyl 6-(4-((3r,5r,7r)-adamantan-1-yl)phenoxy)-5-fluoronicotinate

467

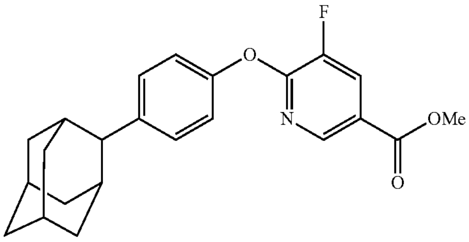

methyl 6-(4-((1r,3r,5r,7r)-adamantan-2-yl)phenoxy)-5-fluoronictinate

TABLE IIIb-continued

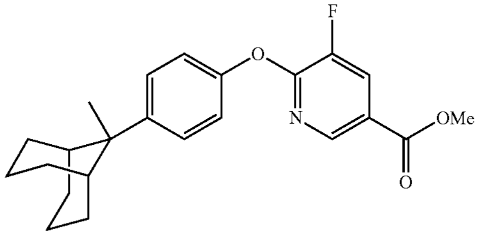 [SMILES: COC(=O)c1cnc(Oc2ccc(C3(C)C4CCCC3CCC4)cc2)c(F)c1]

468 methyl 5-fluoro-6-(4-((1R,5S)-9-methylbicyclo[3.3.1]nonan-9-yl)phenoxy)nicotinate X = N, $R^2$ = Et

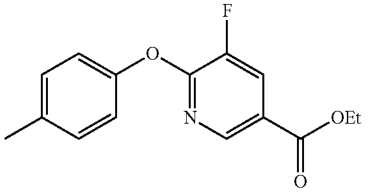 [SMILES: CCOC(=O)c1cnc(Oc2ccc(C)cc2)c(F)c1]

469 ethyl 5-fluoro-6-(p-tolyloxy)nicotinate

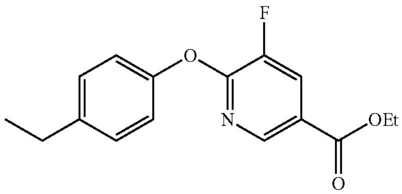 [SMILES: CCOC(=O)c1cnc(Oc2ccc(CC)cc2)c(F)c1]

470 ethyl 6-(4-ethylphenoxy)-5-fluoronicotinate

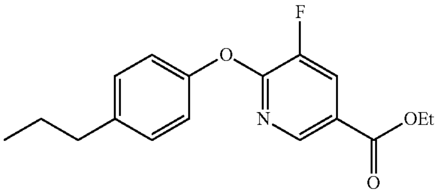 [SMILES: CCCc1ccc(Oc2ncc(C(=O)OCC)cc2F)cc1]

471 ethyl 5-fluoro-6-(4-propylphenoxy)nicotinate

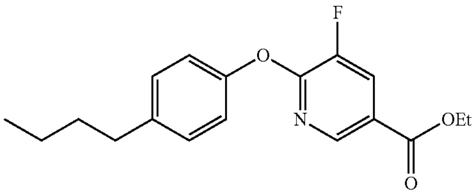 [SMILES: CCCCc1ccc(Oc2ncc(C(=O)OCC)cc2F)cc1]

472 ethyl 6-(4-butylphenoxy)-5-fluoronicotinate

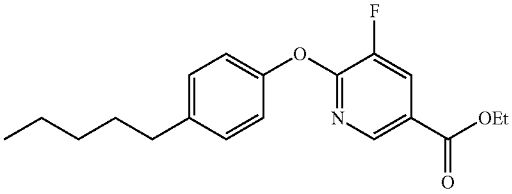 [SMILES: CCCCCc1ccc(Oc2ncc(C(=O)OCC)cc2F)cc1]

473 ethyl 5-fluoro-6-(4-pentylphenoxy)nicotinate

TABLE IIIb-continued

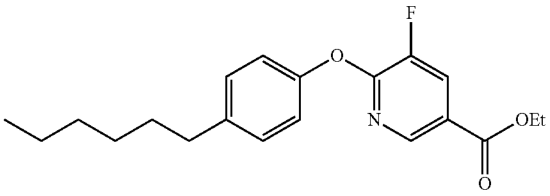 [SMILES: CCCCCCc1ccc(Oc2ncc(C(=O)OCC)cc2F)cc1]

474 ethyl 5-fluoro-6-(4-hexylphenoxy)nicotinate

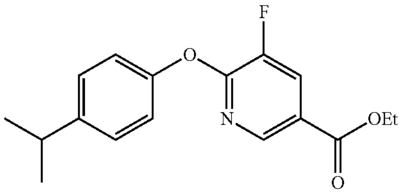 [SMILES: CCOC(=O)c1cnc(Oc2ccc(C(C)C)cc2)c(F)c1]

475 ethyl 5-fluoro-6-(4-isopropylphenoxy)nicotinate

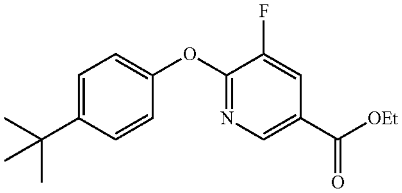 [SMILES: CCOC(=O)c1cnc(Oc2ccc(C(C)(C)C)cc2)c(F)c1]

476 ethyl 6-(4-(tert-butyl)phenoxy)-5-fluoronicotinate

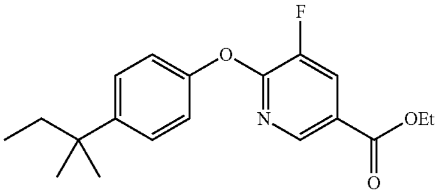 [SMILES: CCOC(=O)c1cnc(Oc2ccc(C(C)(C)CC)cc2)c(F)c1]

477 ethyl 5-fluoro-6-(4-(tert-pentyl)phenoxy)nicotinate

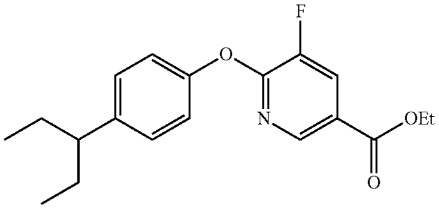 [SMILES: CCOC(=O)c1cnc(Oc2ccc(C(CC)CC)cc2)c(F)c1]

478 ethyl 5-fluoro-6-(4-(pentan-3-yl)phenoxy)nicotinate

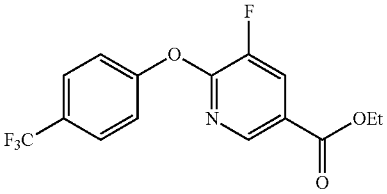 [SMILES: CCOC(=O)c1cnc(Oc2ccc(C(F)(F)F)cc2)c(F)c1]

479 ethyl 5-fluoro-6-(4-(trifluoromethyl)phenoxy)nicotinate

TABLE IIIb-continued

480

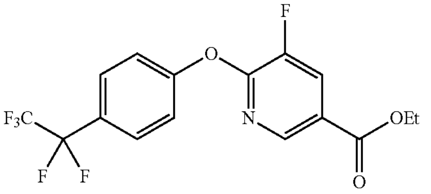 [SMILES: CCOC(=O)c1cnc(Oc2ccc(C(F)(F)C(F)(F)F)cc2)c(F)c1]

ethyl 5-fluoro-6-(4-(perfluoroethyl)phenoxy)nicotinate

481

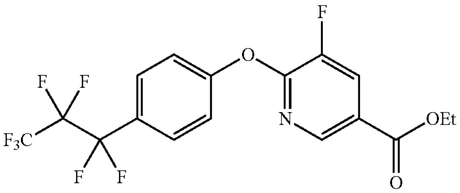 [SMILES: CCOC(=O)c1cnc(Oc2ccc(C(F)(F)C(F)(F)C(F)(F)F)cc2)c(F)c1]

ethyl 5-fluoro-6-(4-(perfluoropropyl)phenoxy)nicotinate

482

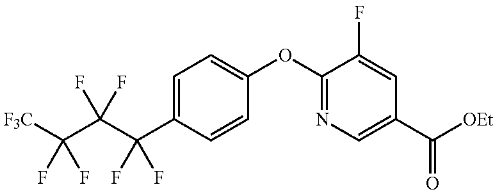 [SMILES: CCOC(=O)c1cnc(Oc2ccc(C(F)(F)C(F)(F)C(F)(F)C(F)(F)F)cc2)c(F)c1]

ethyl 5-fluoro-6-(4-(perfluorobutyl)phenoxy)nicotinate

483

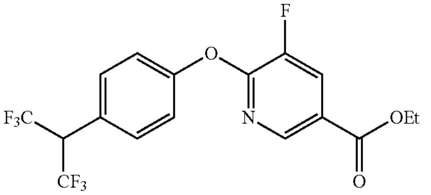

ethyl 5-fluoro-6-(4-(1,1,1,3,3,3-hexafluoropropan-2-yl)phenoxy)nicotinate

484

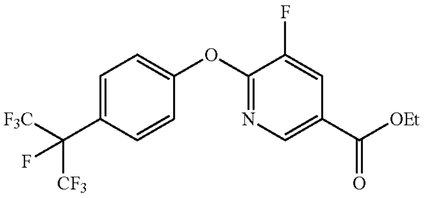 [SMILES: CCOC(=O)c1cnc(Oc2ccc(C(F)(C(F)(F)F)C(F)(F)F)cc2)c(F)c1]

ethyl 5-fluoro-6-(4-(perfluoropropan-2-yl)phenoxy) nicotinate

485

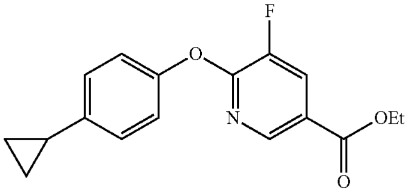 [SMILES: CCOC(=O)c1cnc(Oc2ccc(C3CC3)cc2)c(F)c1]

ethyl 6-(4-cyclopropylphenoxy)-5-fluoronictinate

TABLE IIIb-continued

486

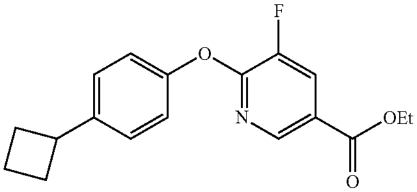

ethyl 6-(4-cyclobutylphenoxy)-5-fluoronicotinate

487

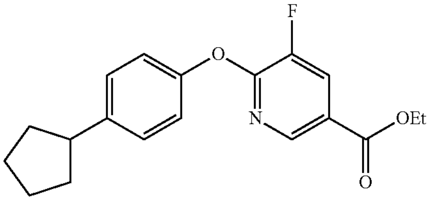 [SMILES: CCOC(=O)c1cnc(Oc2ccc(C3CCCC3)cc2)c(F)c1]

ethyl 6-(4-cyclopentylphenoxy)-5-fluoronicotinate

488

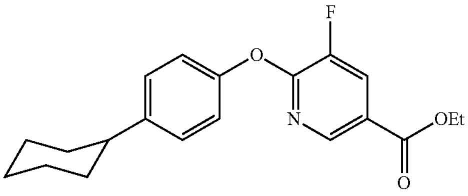 [SMILES: CCOC(=O)c1cnc(Oc2ccc(C3CCCCC3)cc2)c(F)c1]

ethyl 6-(4-cyclohexylphenoxy)-5-fluoronicotinate

489

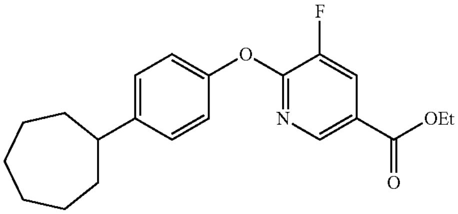 [SMILES: CCOC(=O)c1cnc(Oc2ccc(C3CCCCCC3)cc2)c(F)c1]

ethyl 6-(4-cycloheptylphenoxy)-5-fluoronicotinate

490

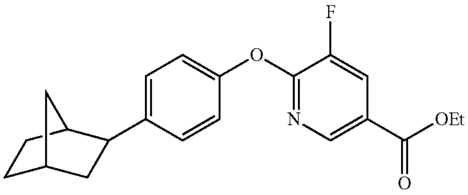 [SMILES: CCOC(=O)c1cnc(Oc2ccc(C3CC4CCC3C4)cc2)c(F)c1]

ethyl 6-(4-((1S,4R)-bicyclo[2.2.1]heptan-2-yl)phenoxy)-5-fluoronicotinate

491

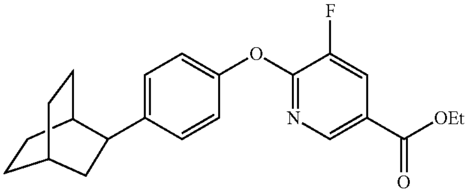

ethyl 6-(4-((1s,4s)-bicyclo[2.2.2]octan-2-yl)phenoxy)-5-fluoronicotinate

TABLE IIIb-continued

492

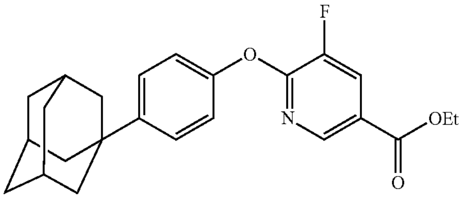 [SMILES: CCOC(=O)c1cnc(Oc2ccc(C34CC5CC(CC(C5)C3)C4)cc2)c(F)c1]

ethyl 6-(4-((3r,5r,7r)-adamantan-1-yl)phenoxy)-5-fluoronicotinate

493

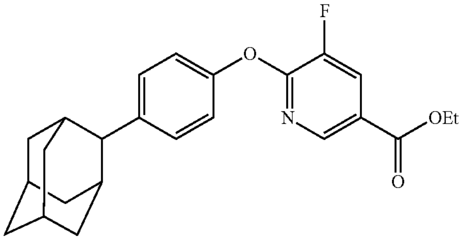

ethyl 6-(4-((1r,3r,5r,7r)-adamantan-2-yl)phenoxy)-5-fluoronicotinate

494

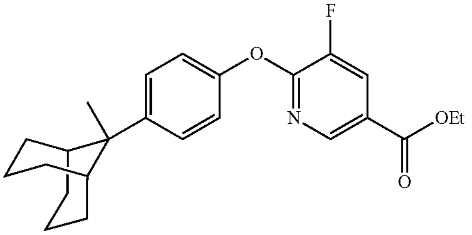 [SMILES: CCOC(=O)c1cnc(Oc2ccc(C3(C)C4CCCC3CCC4)cc2)c(F)c1]

ethyl 5-fluoro-6-(4-((1R,5S)-9-methylbicyclo[3.3.1]nonan-9-yl)phenoxy)nicotinate Also included are isomers, e.g. enantiomers or diastereomers or mixtures of isomers, salts, particularly pharmaceutically acceptable salts, and solvates of the compounds listed above.

A fourth aspect of the present invention relates to compounds of formula IV and salts and solvates thereof:

(IV)

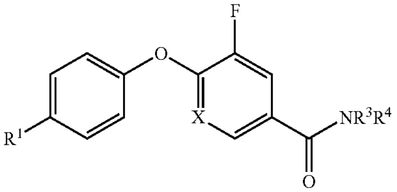

wherein X and $R^1$ are defined as in formula I, including the preferred definition of $R^1$, and $R^3$ and $R^4$ are defined as in formula II, including the preferred definitions of $R^3$ and $R^4$.

Specific examples of compounds falling under the scope of formula IV are shown in Table IV. The compounds in Table IV are defined by their chemical structure, the indicated nomenclature is only for illustrative purposes.

TABLE IV

X = CH, $R^3$ = H, $R^4$ = H

495

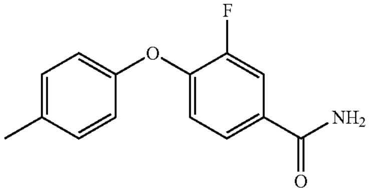 [SMILES: Cc1ccc(Oc2ccc(C(N)=O)cc2F)cc1]

3-fluoro-4-(p-tolyloxy)benzamide

496

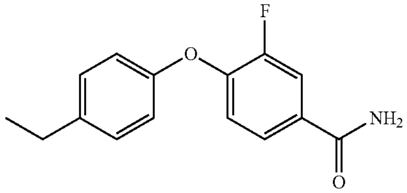 [SMILES: CCc1ccc(Oc2ccc(C(N)=O)cc2F)cc1]

4-(4-ethylphenoxy)-3-fluorobenzamide

497

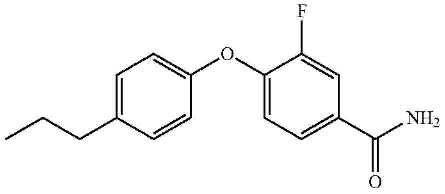 [SMILES: CCCc1ccc(Oc2ccc(C(N)=O)cc2F)cc1]

3-fluoro-4-(4-propylphenoxy)benzamide

498

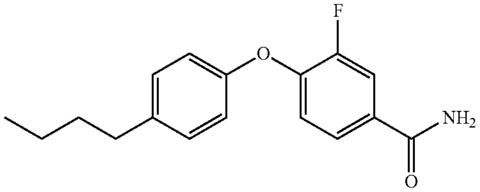 [SMILES: CCCCc1ccc(Oc2ccc(C(N)=O)cc2F)cc1]

4-(4-butylphenoxy)-3-fluorobenzamide

499

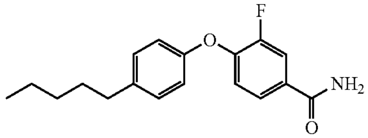 [SMILES: CCCCCc1ccc(Oc2ccc(C(N)=O)cc2F)cc1]

3-fluoro-4-(4-pentylphenoxy)benzamide

500

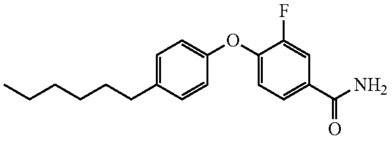 [SMILES: CCCCCCc1ccc(Oc2ccc(C(N)=O)cc2F)cc1]

3-fluoro-4-(4-hexylphenoxy)benzamide

501

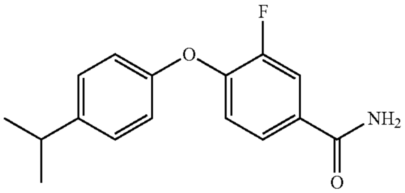 [SMILES: CC(C)c1ccc(Oc2ccc(C(N)=O)cc2F)cc1]

3-fluoro-4-(4-isopropylphenoxy)benzamide

TABLE IV-continued

502

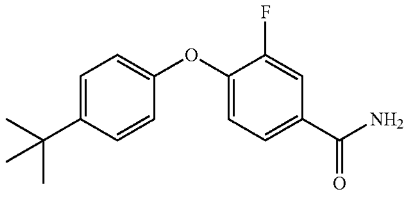 [SMILES: CC(C)(C)c1ccc(Oc2ccc(C(N)=O)cc2F)cc1]

4-(4-(tert-butyl)phenoxy)-3-fluorobenzamide

503

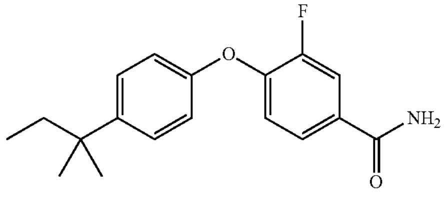 [SMILES: CCC(C)(C)c1ccc(Oc2ccc(C(N)=O)cc2F)cc1]

3-fluoro-4-(4-(tert-pentyl)phenoxy)benzamide

504

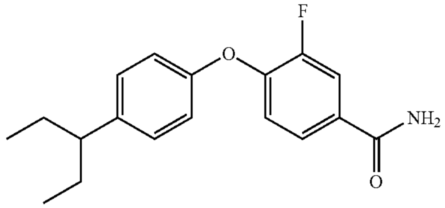 [SMILES: CCC(CC)c1ccc(Oc2ccc(C(N)=O)cc2F)cc1]

3-fluoro-4-(4-(pentan-3-yl)phenoxy)benzamide

505

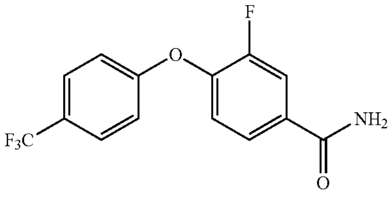

3-fluoro-4-(4-(trifluoromethyl)phenoxy)benzamide

506

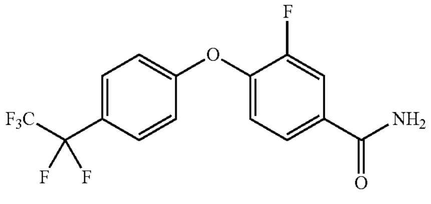 [SMILES: NC(=O)c1ccc(Oc2ccc(C(F)(F)C(F)(F)F)cc2)c(F)c1]

3-fluoro-4-(4-(perfluoroethyl)phenoxy)benzamide

507

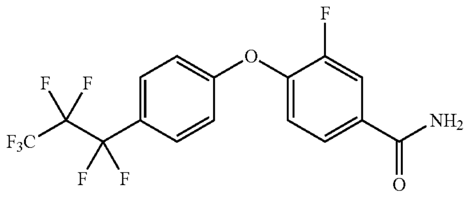 [SMILES: NC(=O)c1ccc(Oc2ccc(C(F)(F)C(F)(F)C(F)(F)F)cc2)c(F)c1]

3-fluoro-4-(4-(perfluoropropyl)phenoxy)benzamide

TABLE IV-continued

508

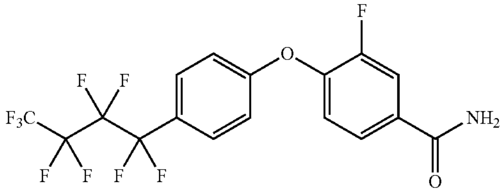 [SMILES: NC(=O)c1ccc(Oc2ccc(C(F)(F)C(F)(F)C(F)(F)C(F)(F)F)cc2)c(F)c1]

3-fluoro-4-(4-(perfluorobutyl)phenoxy)benzamide

509

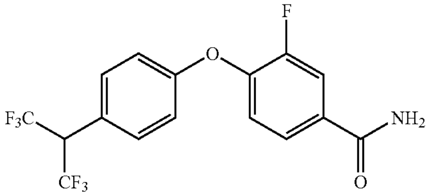

3-fluoro-4-(4-(1,1,1,3,3,3-hexafluoropropan-2-yl) phenoxy)benzamide

510

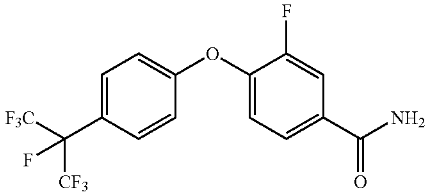

3-fluoro-4-(4-(perfluoropropan-2-yl)phenoxy)benzamide

511

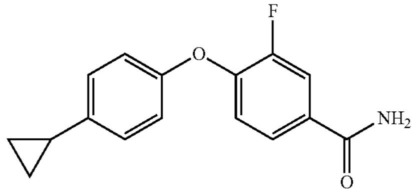 [SMILES: NC(=O)c1ccc(Oc2ccc(C3CC3)cc2)c(F)c1]

4-(4-cyclopropylphenoxy)-3-fluorobenzamide

512

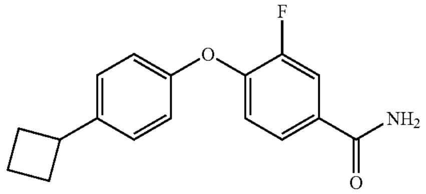 [SMILES: NC(=O)c1ccc(Oc2ccc(C3CCC3)cc2)c(F)c1]

4-(4-cyclobutylphenoxy)-3-fluorobenzamide

513

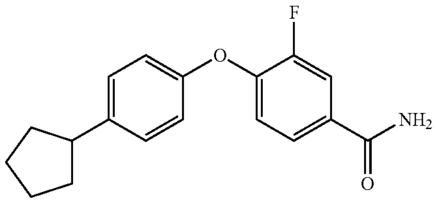 [SMILES: NC(=O)c1ccc(Oc2ccc(C3CCCC3)cc2)c(F)c1]

4-(4-cyclopentylphenoxy)-3-fluorobenzamide

TABLE IV-continued

514

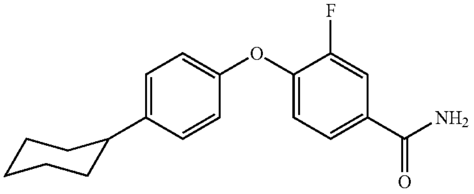 [SMILES: NC(=O)c1ccc(Oc2ccc(C3CCCCC3)cc2)c(F)c1]

4-(4-cyclohexylphenoxy)-3-fluorobenzamide

515

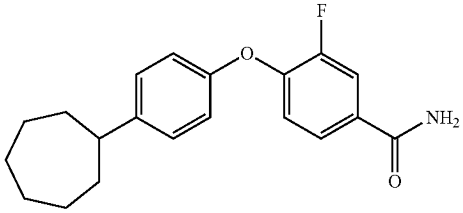 [SMILES: NC(=O)c1ccc(Oc2ccc(C3CCCCCC3)cc2)c(F)c1]

4-(4-cycloheptylphenoxy)-3-fluorobenzamide

516

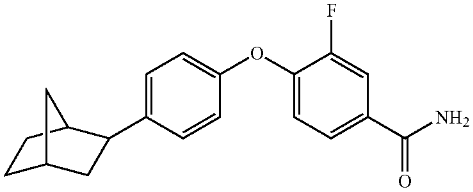 [SMILES: NC(=O)c1ccc(Oc2ccc(C3CC4CCC3C4)cc2)c(F)c1]

4-(4-((1S,4R)-bicyclo[2.2.1]heptan-2-yl)phenoxy)-3-fluorobenzamide

517

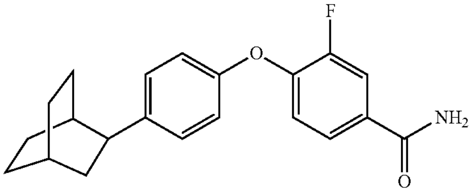 [SMILES: NC(=O)c1ccc(Oc2ccc(C3CC4CCC3CC4)cc2)c(F)c1]

4-(4-((1s,4s)-bicyclo[2.2.2]octan-2-yl)phenoxy)-3-fluorobenzamide

518

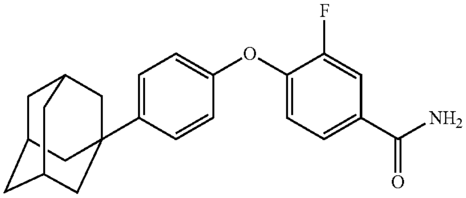 [SMILES: NC(=O)c1ccc(Oc2ccc(C34CC5CC(CC(C5)C3)C4)cc2)c(F)c1]

4-(4-((3r,5r,7r)-adamantan-1-yl)phenoxy)-3-fluorobenzamide

519

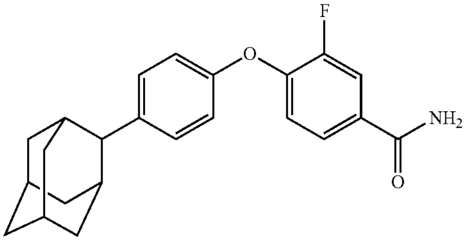 [SMILES: NC(=O)c1ccc(Oc2ccc(C3C4CC5CC(C4)CC3C5)cc2)c(F)c1]

4-(4-((1r,3r,5r,7r)-adamantan-2-yl)phenoxy)-3-fluorobenzamide

TABLE IV-continued

520

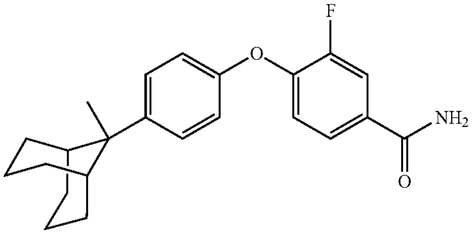 [SMILES: CC1(c2ccc(Oc3ccc(C(N)=O)cc3F)cc2)C2CCCC1CCC2]

3-fluoro-4-(4-((1R,5S)-9-methylbicyclo[3.3.1]nonan-9-yl)phenoxy)benzamide

X = CH, $R^3$ = H, $R^4$ = OH

521

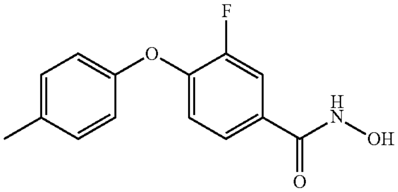 [SMILES: Cc1ccc(Oc2ccc(C(=O)NO)cc2F)cc1]

3-fluoro-N-hydroxy-4-(p-tolyloxy)benzamide

522

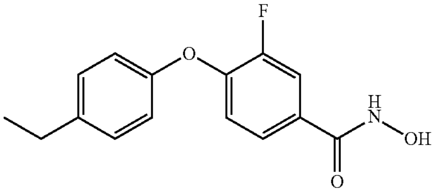 [SMILES: CCc1ccc(Oc2ccc(C(=O)NO)cc2F)cc1]

4-(4-ethylphenoxy)-3-fluoro-N-hydroxybenzamide

523

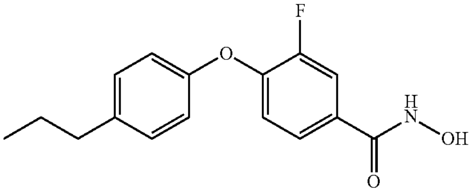 [SMILES: CCCc1ccc(Oc2ccc(C(=O)NO)cc2F)cc1]

3-fluoro-N-hydroxy-4-(4-propylphenoxy)benzamide

524

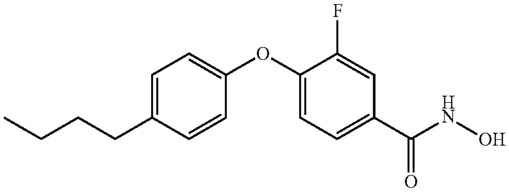 [SMILES: CCCCc1ccc(Oc2ccc(C(=O)NO)cc2F)cc1]

4-(4-butylphenoxy)-3-fluoro-N-hydroxybenzamide

525

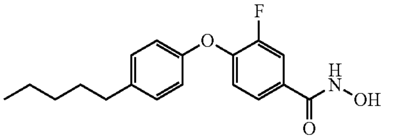 [SMILES: CCCCCc1ccc(Oc2ccc(C(=O)NO)cc2F)cc1]

3-fluoro-N-hydroxy-4-(4-pentylphenoxy)benzamide

TABLE IV-continued

526

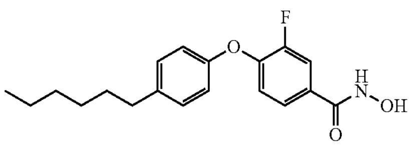 [SMILES: CCCCCCc1ccc(Oc2ccc(C(=O)NO)cc2F)cc1]

3-fluoro-4-(4-hexylphenoxy)-N-hydroxybenzamide

527

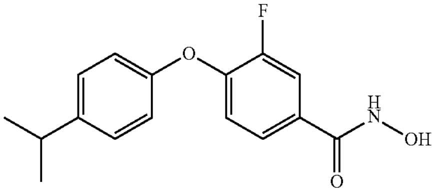

3-fluooro-N-hydroxy-4-(4-isopropylphenoxy)benzamide

528

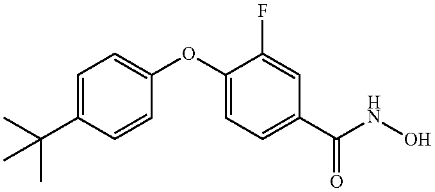

4-(4-(tert-butyl)phenoxy)-3-fluoro-N-hydroxybenzamide

529

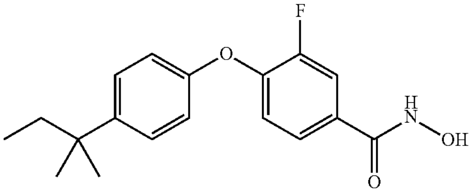 [SMILES: CCC(C)(C)c1ccc(Oc2ccc(C(=O)NO)cc2F)cc1]

3-fluoro-N-hydroxy-4-(4-(tert-pentyl)phenoxy)benzamide

530

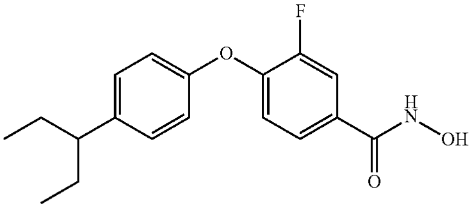 [SMILES: CCC(CC)c1ccc(Oc2ccc(C(=O)NO)cc2F)cc1]

3-fluoro-N-hydroxy-4-(4-(pentan-3-yl)phenoxy)benzamide

531

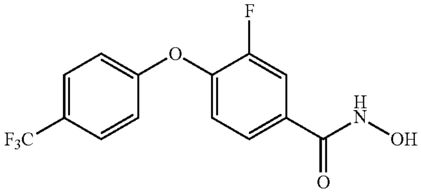 [SMILES: O=C(NO)c1ccc(Oc2ccc(C(F)(F)F)cc2)c(F)c1]

3-fluoro-N-hydroxy-4-(4-(trifluoromethyl)phenoxy)benzamide

TABLE IV-continued

532

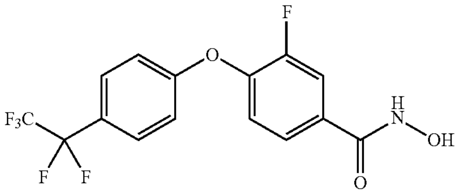 [SMILES: O=C(NO)c1ccc(Oc2ccc(C(F)(F)C(F)(F)F)cc2)c(F)c1]

3-fluoro-N-hydroxy-4-(4-(perfluoroethyl)phenoxy)benzamide

533

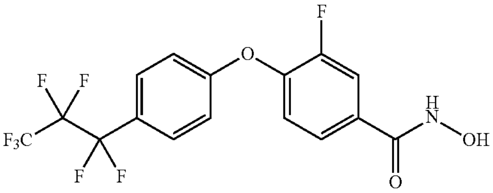 [SMILES: O=C(NO)c1ccc(Oc2ccc(C(F)(F)C(F)(F)C(F)(F)F)cc2)c(F)c1]

3-fluoro-N-hydroxy-4-(4-(perfluoropropyl)phenoxy)benzamide

534

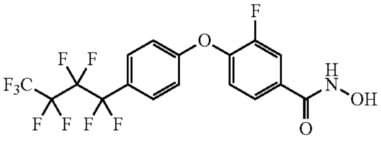 [SMILES: O=C(NO)c1ccc(Oc2ccc(C(F)(F)C(F)(F)C(F)(F)C(F)(F)F)cc2)c(F)c1]

3-fluoro-N-hydroxy-4-(4-(perfluorobutyl)phenoxy)benzamide

535

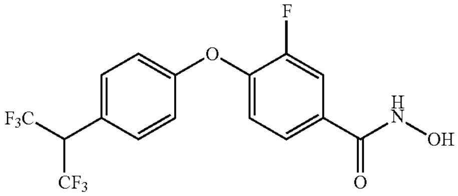

3-fluoro-4-(4-(1,1,1,3,3,3-hexafluoropropan-2-yl)phenoxy)-N-hydroxybenzamide

536

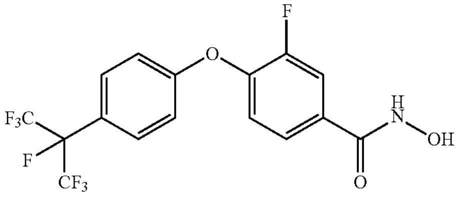

3-fluoro-N-hydroxy-4-(4-(perfluoropropan-2-yl)phenoxy)benzamide

537

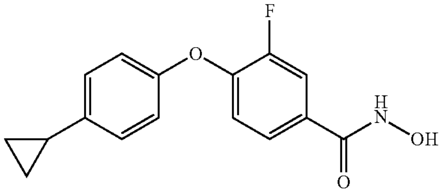 [SMILES: O=C(NO)c1ccc(Oc2ccc(C3CC3)cc2)c(F)c1]

4-(4-cyclopropylphenoxy)-3-fluoro-N-hydroxybenzamide

TABLE IV-continued

538

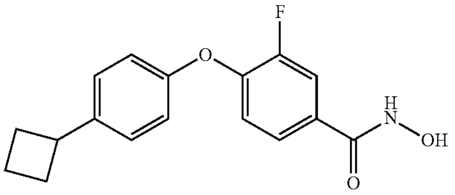 [SMILES: O=C(NO)c1ccc(Oc2ccc(C3CCC3)cc2)c(F)c1]

4-(4-cyclobutylphenoxy)-3-fluoro-N-hydroxybenzamide

539

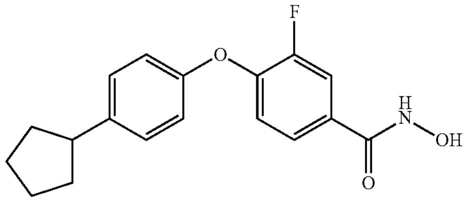 [SMILES: O=C(NO)c1ccc(Oc2ccc(C3CCCC3)cc2)c(F)c1]

4-(4-cyclopentylphenoxy)-3-fluoro-N-hydroxybenzamide

540

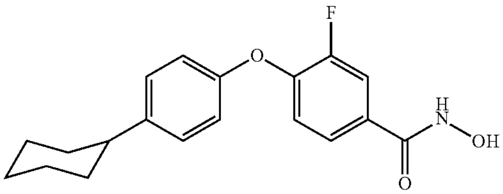 [SMILES: O=C(NO)c1ccc(Oc2ccc(C3CCCCC3)cc2)c(F)c1]

4-(4-cyclohexylphenoxy)-3-fluoro-N-hydroxybenzamide

541

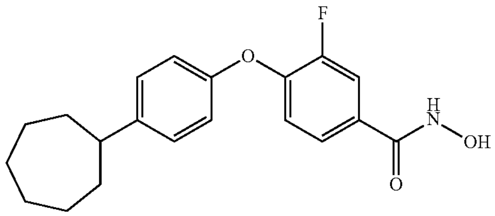 [SMILES: O=C(NO)c1ccc(Oc2ccc(C3CCCCCC3)cc2)c(F)c1]

4-(4-cycloheptylphenoxy)-3-fluoro-N-hydroxybenzamide

542

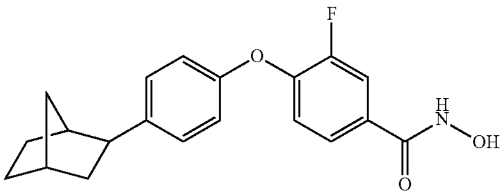 [SMILES: O=C(NO)c1ccc(Oc2ccc(C3CC4CCC3C4)cc2)c(F)c1]

4-(4-((1S,4R)-bicyclo[2.2.1]heptan-2-yl)phenoxy)-3-fluoro-N-hydroxybenzamide

543

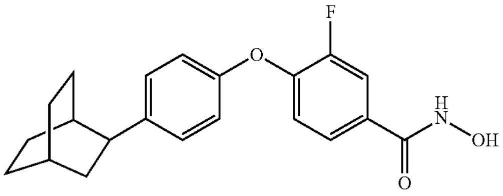 [SMILES: O=C(NO)c1ccc(Oc2ccc(C3CC4CCC3CC4)cc2)c(F)c1]

4-(4-((1s,4s)-bicyclo[2.2.2]octan-2-yl)phenoxy)-3-fluoro-N-hydroxybenzamide

TABLE IV-continued

544

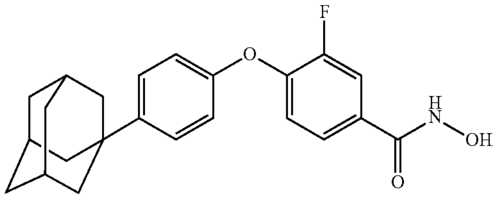 [SMILES: O=C(NO)c1ccc(Oc2ccc(C34CC5CC(CC(C5)C3)C4)cc2)c(F)c1]

4-(4-((3r,5r,7r)-adamantan-1-yl)phenoxy)-3-fluoro-N-hydroxybenzamide

545

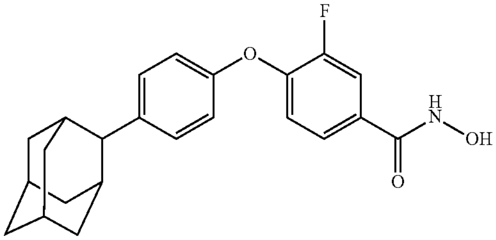

4-(4-((1r,3r,5r,7r)-adamantan-2-yl)phenoxy)-3-fluoro-N-hydroxybenzamide

546

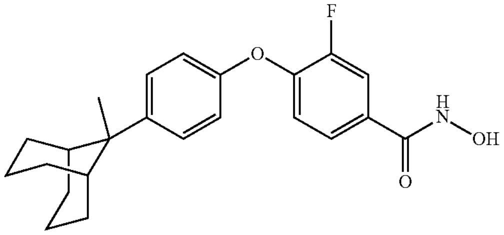 [SMILES: CC1(c2ccc(Oc3ccc(C(=O)NO)cc3F)cc2)C2CCCC1CCC2]

3-fluoro-N-hydroxy-4-(4-((1R,5S)-9-methylbicyclo[3.3.1]nonan-9-yl)phenoxy)benzamide X = CH, $R^3$ = H, $R^4$ = Me

547

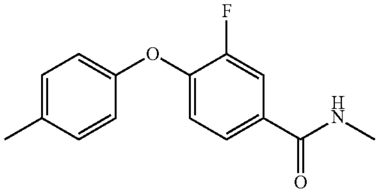

3-fluoro-N-mtehyl-4-(p-tolyloxy)benzamide

548

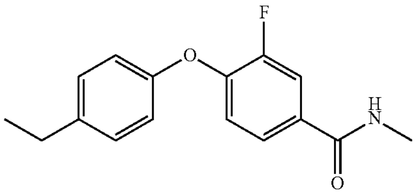 [SMILES: CCc1ccc(Oc2ccc(C(=O)NC)cc2F)cc1]

4-(4-ethylphenoxy)-3-fluoro-N-methylbenzamide

549

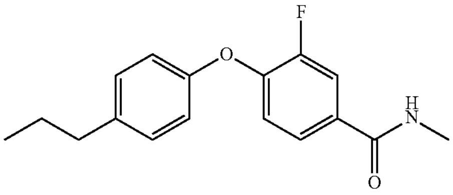 [SMILES: CCCc1ccc(Oc2ccc(C(=O)NC)cc2F)cc1]

3-fluoro-N-methyl-4-(4-propylphenoxy)benzamide

TABLE IV-continued

550

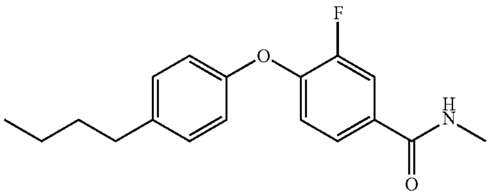 [SMILES: CCCCc1ccc(Oc2ccc(C(=O)NC)cc2F)cc1]

4-(4-butylphenoxy)-3-fluoro-N-methylbenzamide

551

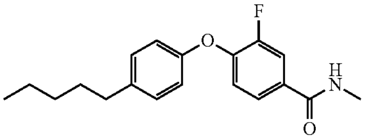 [SMILES: CCCCCc1ccc(Oc2ccc(C(=O)NC)cc2F)cc1]

3-fluoro-N-methyl-4-(4-pentylphenoxy)benzamide

552

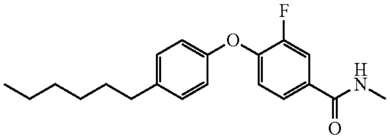 [SMILES: CCCCCCc1ccc(Oc2ccc(C(=O)NC)cc2F)cc1]

3-fluoro-4-(4-hexylphenoxy)-N-methylbenzamide

553

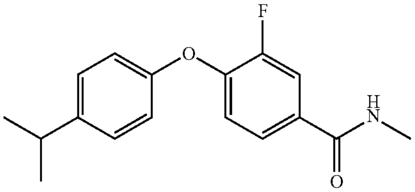

3-fluoro-4-(4-isopropylphenoxy)-N-methylbenzamide

554

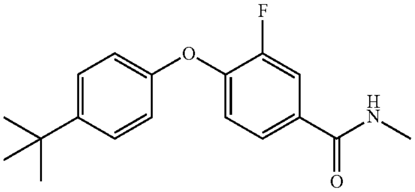

4-(4-(tert-butyl)phenxoy)-3-fluoro-N-methylbenzamide

555

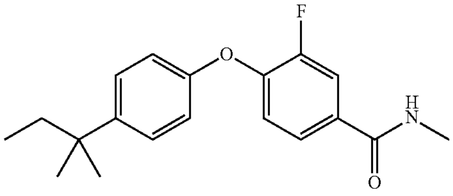 [SMILES: CCC(C)(C)c1ccc(Oc2ccc(C(=O)NC)cc2F)cc1]

3-fluoro-N-methyl-4-(4-(tert-pentyl)phenoxy)benzamide

556

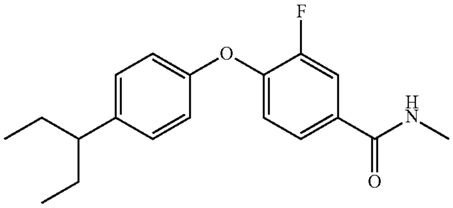 [SMILES: CCC(CC)c1ccc(Oc2ccc(C(=O)NC)cc2F)cc1]

3-fluoro-N-methyl-4-(4-(pentan-3-yl)phenoxy)benzamide

TABLE IV-continued

557

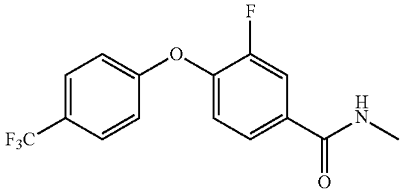 [SMILES: CNC(=O)c1ccc(Oc2ccc(C(F)(F)F)cc2)c(F)c1]

3-fluoro-N-methyl-4-(4-(trifluoromethyl)phenoxy) benzamide

558

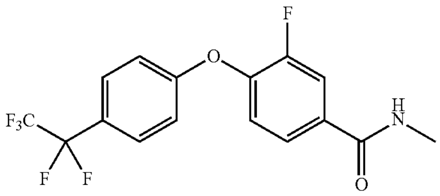 [SMILES: CNC(=O)c1ccc(Oc2ccc(C(F)(F)C(F)(F)F)cc2)c(F)c1]

3-fluoro-N-methyl-4-(4-(perfluoroethyl)phenoxy) benzamide

559

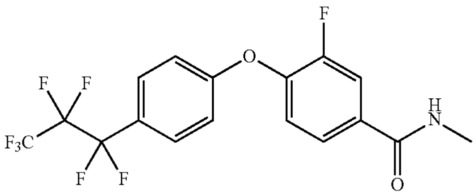 [SMILES: CNC(=O)c1ccc(Oc2ccc(C(F)(F)C(F)(F)C(F)(F)F)cc2)c(F)c1]

3-fluoro-N-methyl-4-(4-(perfluoropropyl)phenoxy)benzamide

560

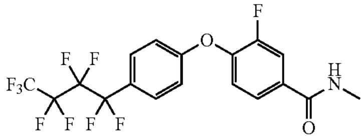 [SMILES: CNC(=O)c1ccc(Oc2ccc(C(F)(F)C(F)(F)C(F)(F)C(F)(F)F)cc2)c(F)c1]

3-fluoro-N-methyl-4-(4-(perfluorobutyl)phenoxy)benzamide

561

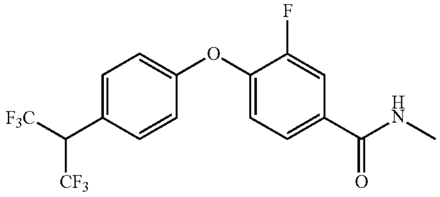

3-fluoro-4-(4-(1,1,1,3,3,3-hexafluoropropan-2-yl) phenoxy)-N-methylbenzamide

562

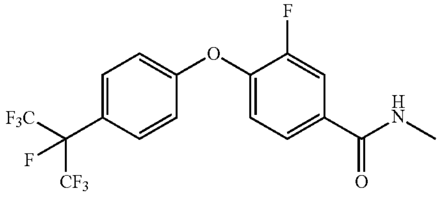

3-fluoro-N-methyl-4-(4-(perfluoropropan-2-yl)phenoxy) benzamide

TABLE IV-continued

563

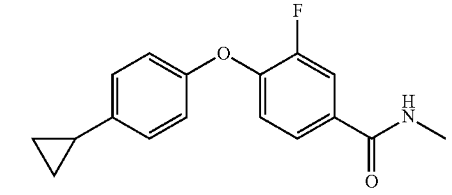 [SMILES: CNC(=O)c1ccc(Oc2ccc(C3CC3)cc2)c(F)c1]

4-(4-cyclopropylphenoxy)-3-fluoro-N-methylbenzamide

564

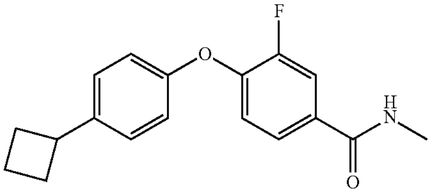 [SMILES: CNC(=O)c1ccc(Oc2ccc(C3CCC3)cc2)c(F)c1]

4-(4-cyclobutylphenoxy)-3-fluoro-N-methylbenzamide

565

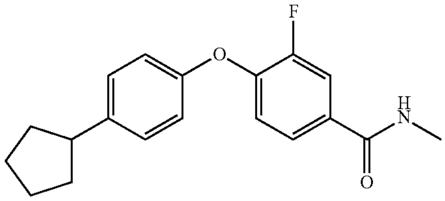

4-(4-cyclopentylphenoxy)-3-fluoro-N-methylbenzamide

566

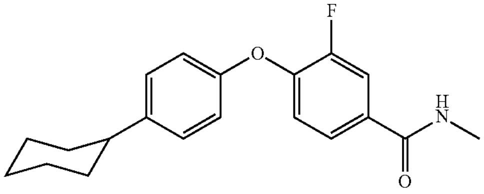 [SMILES: CNC(=O)c1ccc(Oc2ccc(C3CCCCC3)cc2)c(F)c1]

4-(4-cyclohexylphenoxy)-3-fluoro-N-methylbenzamide

567

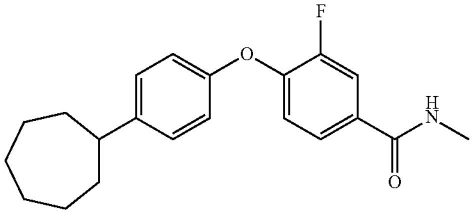

4-(4-cycloheptylphenoxy)-3-fluoro-N-methylbenzamide

568

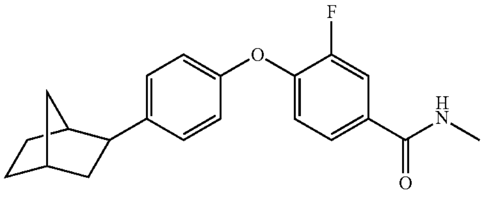 [SMILES: CNC(=O)c1ccc(Oc2ccc(C3CC4CCC3C4)cc2)c(F)c1]

4-(4-((1S,4R)-bicyclo[2.2.1]heptan-2-yl)phenoxy)-3-fluoro-N-methylbenzamide

TABLE IV-continued

569

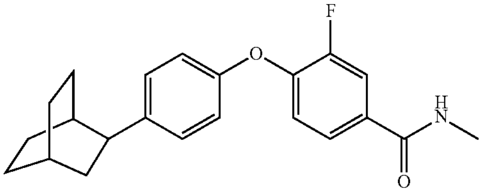 [SMILES: CNC(=O)c1ccc(Oc2ccc(C3CC4CCC3CC4)cc2)c(F)c1]

4-(4-((1s,4s)-bicyclo[2.2.2]octan-2-yl)phenoxy)-3-fluoro-N-methylbenzamide

570

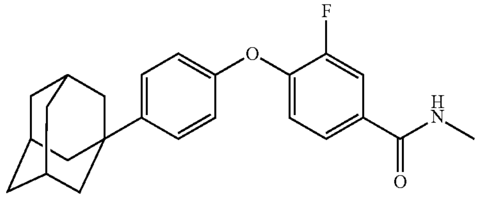

4-(4-((3r,5r,7r)-adamantan-1-yl)phenoxy)-3-fluoro-N-methylbenzamide

571

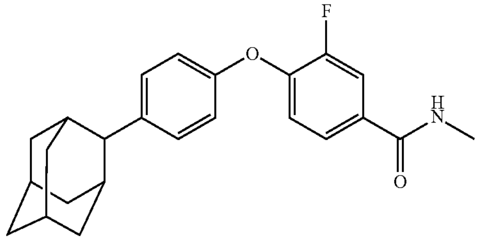 [SMILES: CNC(=O)c1ccc(Oc2ccc(C3C4CC5CC(C4)CC3C5)cc2)c(F)c1]

4-(4-((1r,3r,5r,7r)-adamantan-2-yl)phenoxy)-3-fluoro-N-methylbenzamide

572

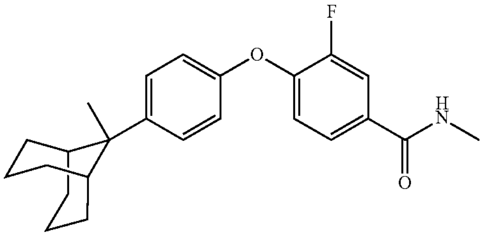 [SMILES: CNC(=O)c1ccc(Oc2ccc(C3(C)C4CCCC3CCC4)cc2)c(F)c1]

3-fluoro-N-methyl-4-(4-((1R,5S)-9-methylbicyclo[3.3.1]nonan-9-yl)phenoxy)benzamide X = CH, $R^3$ = Me, $R^4$ = Me

573

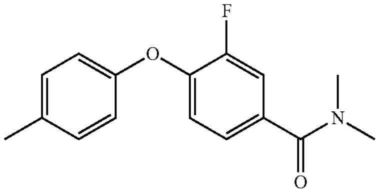

3-fluoro-N,N-dimethyl-4-(p-tolyloxy)benzamide

TABLE IV-continued

574

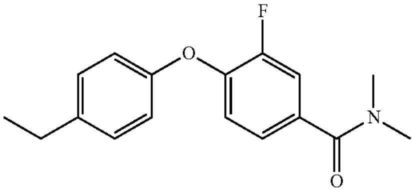

4-(4-ethylphenoxy)-3-fluoro-N,N-dimethylbenzamide

575

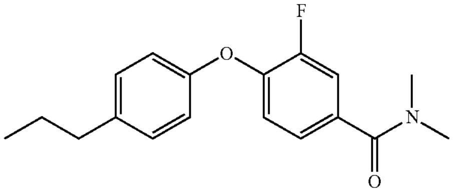 [SMILES: CCCc1ccc(Oc2ccc(C(=O)N(C)C)cc2F)cc1]

3-fluoro-N,N-dimethyl-4-(4-propylphenoxy)benzamide

576

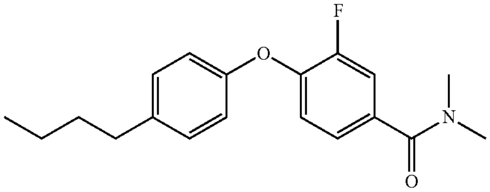 [SMILES: CCCCc1ccc(Oc2ccc(C(=O)N(C)C)cc2F)cc1]

4-(4-butylphenoxy)-3-fluoro-N,N-dimethylbenzamide

577

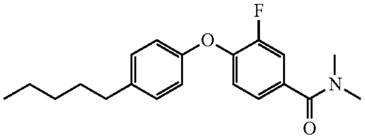 [SMILES: CCCCCc1ccc(Oc2ccc(C(=O)N(C)C)cc2F)cc1]

3-fluoro-N,N-dimethyl-4-(4-pentylphenoxy)benzamide

578

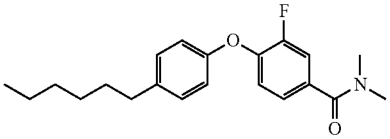 [SMILES: CCCCCCc1ccc(Oc2ccc(C(=O)N(C)C)cc2F)cc1]

3-fluoro-4-(4-hexylphenoxy)-N,N-dimethylbenzamide

579

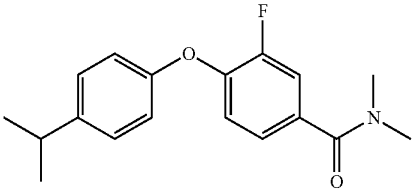

3-fluoro-4-(4-isopropylphenoxy)-N,N-dimethyl-benzamide

580

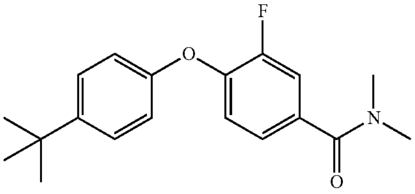

4-(4-(tert-butyl)phenoxy)-3-fluoro-N,N-dimethyl-benzamide

TABLE IV-continued

581

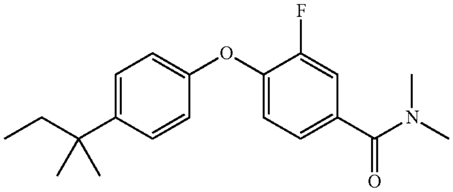 [SMILES: CCC(C)(C)c1ccc(Oc2ccc(C(=O)N(C)C)cc2F)cc1]

3-fluoro-N,N-dimethyl-4-(4-(tert-pentyl)phenoxy)benzamide

582

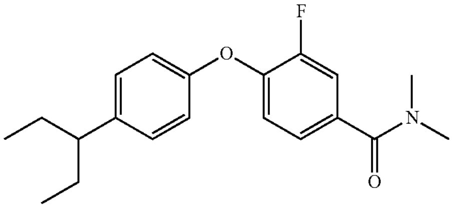 [SMILES: CCC(CC)c1ccc(Oc2ccc(C(=O)N(C)C)cc2F)cc1]

3-fluoro-N,N-dimethyl-4-(4-pentan-3-yl)phenoxy)benzamide

583

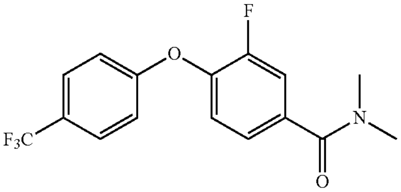

3-fluoro-N,N-dimethyl-4-(4-(trifluoromethyl)phenoxy) benzamide

584

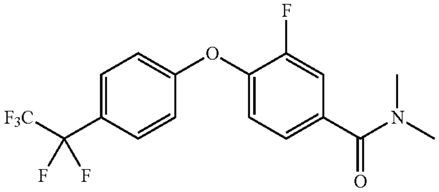 [SMILES: CN(C)C(=O)c1ccc(Oc2ccc(C(F)(F)C(F)(F)F)cc2)c(F)c1]

3-fluoro-N,N-dimethyl-4-(4-(perfluoroethyl)phenoxy) benzamide

585

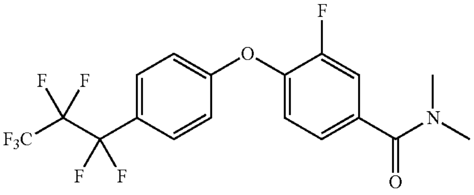 [SMILES: CN(C)C(=O)c1ccc(Oc2ccc(C(F)(F)C(F)(F)C(F)(F)F)cc2)c(F)c1]

3-fluoro-N,N-dimethyl-4-(4-(perfluoropropyl)phenoxy) benzamide

586

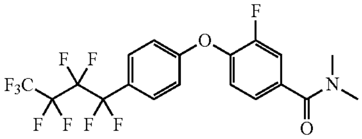 [SMILES: CN(C)C(=O)c1ccc(Oc2ccc(C(F)(F)C(F)(F)C(F)(F)C(F)(F)F)cc2)c(F)c1]

3-fluoro-N,N-dimethyl-4-(4-(perfluorobutyl)phenoxy)benzamide

TABLE IV-continued

587

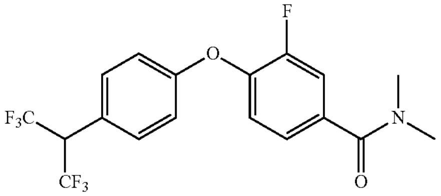 [SMILES: CN(C)C(=O)c1ccc(Oc2ccc(C(C(F)(F)F)C(F)(F)F)cc2)c(F)c1]

3-fluoro-4-(4-(1,1,1,3,3,3-hexafluoropropan-2-yl)phenoxy)-N,N-dimethylbenzamide

588

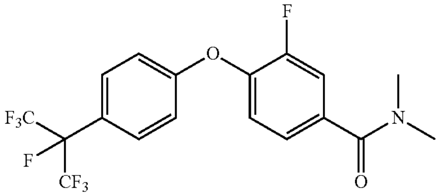 [SMILES: CN(C)C(=O)c1ccc(Oc2ccc(C(F)(C(F)(F)F)C(F)(F)F)cc2)c(F)c1]

3-fluoro-N,N-dimethyl-4-(4-(perfluoropropan-2-yl)phenoxy)benzamide

589

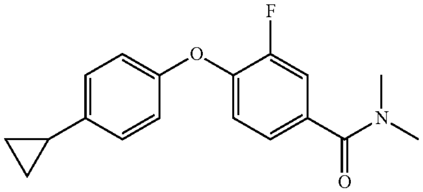 [SMILES: CN(C)C(=O)c1ccc(Oc2ccc(C3CC3)cc2)c(F)c1]

4-(4-cyclopropylphenoxy)-3-fluoro-N,N-dimethyl-benzamide

590

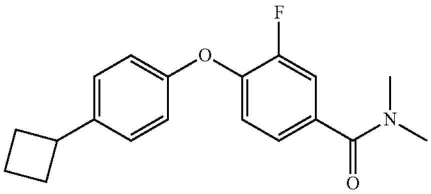 [SMILES: CN(C)C(=O)c1ccc(Oc2ccc(C3CCC3)cc2)c(F)c1]

4-(4-cyclobutylphenoxy)-3-fluoro-N,N-dimethyl-benzamide

591

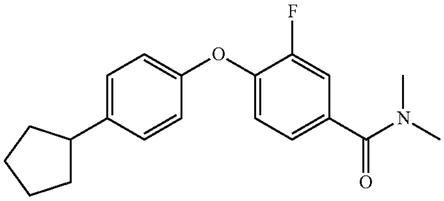 [SMILES: CN(C)C(=O)c1ccc(Oc2ccc(C3CCCC3)cc2)c(F)c1]

4-(4-cyclopentylphenoxy)-3-fluoro-N,N-dimethyl-benzamide

592

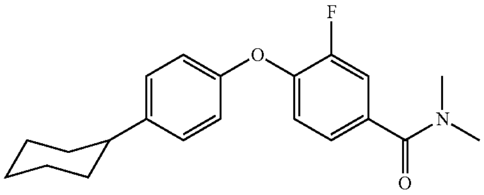 [SMILES: CN(C)C(=O)c1ccc(Oc2ccc(C3CCCCC3)cc2)c(F)c1]

4-(4-cyclohexylphenoxy)-3-fluoro-N,N-dimethylbenzamide

TABLE IV-continued

593

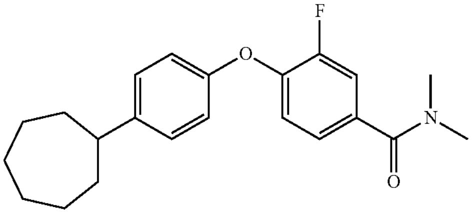

4-(4-cycloheptylphenoxy)-3-fluoro-N,N-dimethylbenzamide

594

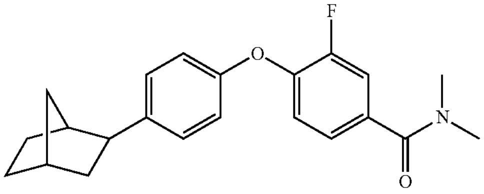 [SMILES: CN(C)C(=O)c1ccc(Oc2ccc(C3CC4CCC3C4)cc2)c(F)c1]

4-(4-((1S,4R)-bicyclo[2.2.1]heptan-2-yl)phenoxy-3-fluoro-N,N-dimethylbenzamide

595

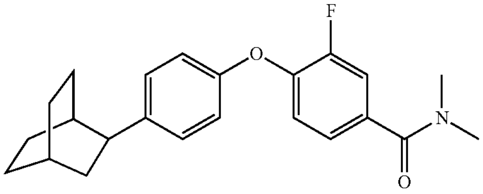 [SMILES: CN(C)C(=O)c1ccc(Oc2ccc(C3CC4CCC3CC4)cc2)c(F)c1]

4-(4-((1s,4s)-bicyclo[2.2.2]octan-2-yl)phenoxy)-3-fluoro-N,N-dimethylbenzamide

596

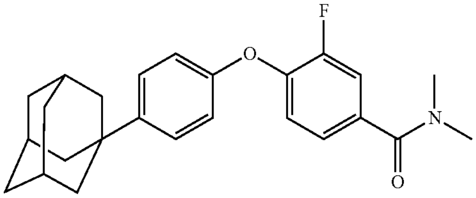 [SMILES: CN(C)C(=O)c1ccc(Oc2ccc(C34CC5CC(CC(C5)C3)C4)cc2)c(F)c1]

4-(4-((3r,5r,7r)-adamantan-1-yl)phenoxy)-3-fluoro-N,N-dimethylbenzamide

597

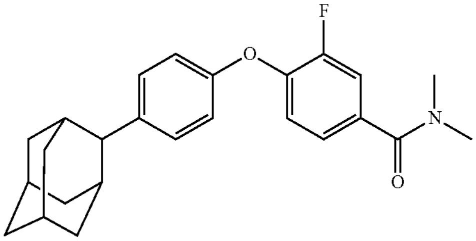 [SMILES: CN(C)C(=O)c1ccc(Oc2ccc(C3C4CC5CC(C4)CC3C5)cc2)c(F)c1]

4-(4-((1r,3r,5r,7r)-adamantan-2-yl)phenoxy)-3-fluoro-N,N-dimethylbenzamide

598

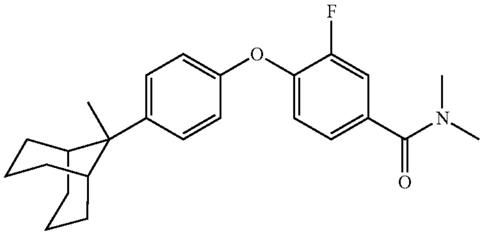 [SMILES: CN(C)C(=O)c1ccc(Oc2ccc(C3(C)C4CCCC3CCC4)cc2)c(F)c1]

3-fluoro-N,N-dimethyl-4-(4-((1R,5S)-9-methylbicyclo[3.3.1]

TABLE IV-continued nonan-9-yl)phenoxy)benzamide

X = N, $R^3$ = H, $R^4$ = H

599

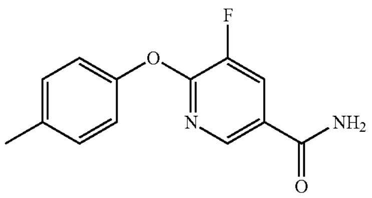 [SMILES: Cc1ccc(Oc2ncc(C(N)=O)cc2F)cc1]

5-fluoro-6-(p-tolyloxy)nicotinamide

600

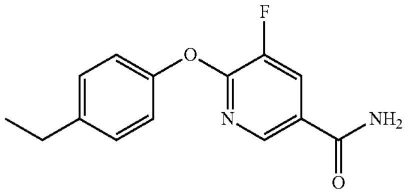

6-(4-ethylphenoxy)-5-fluoronicotinamide

601

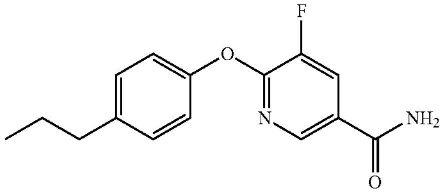 [SMILES: CCCc1ccc(Oc2ncc(C(N)=O)cc2F)cc1]

5-fluoro-6-(4-propylphenoxy)nicotinamide

602

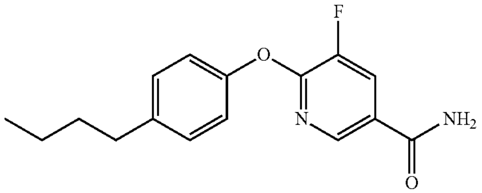

6-(4-butylphenoxy)-5-fluoronicotinamide

603

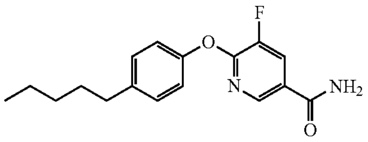 [SMILES: CCCCCc1ccc(Oc2ncc(C(N)=O)cc2F)cc1]

5-fluoro-6-(4-pentylphenoxy)nicotinamide

604

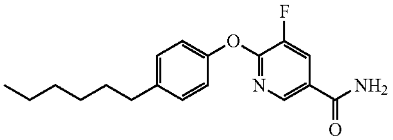 [SMILES: CCCCCCc1ccc(Oc2ncc(C(N)=O)cc2F)cc1]

5-fluoro-6-(4-hexylphenoxy)nicotinamide

TABLE IV-continued

605

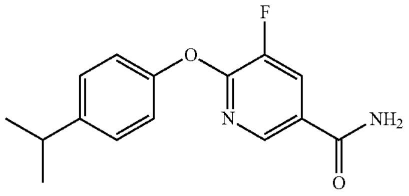 [SMILES: CC(C)c1ccc(Oc2ncc(C(N)=O)cc2F)cc1]

5-fluoro-6-(4-isopropylphenoxy)nictinamide

606

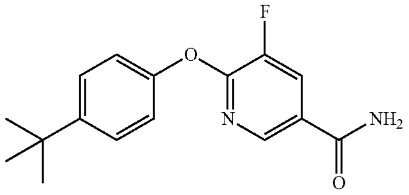 [SMILES: CC(C)(C)c1ccc(Oc2ncc(C(N)=O)cc2F)cc1]

6-(4-(tert-butyl)phenoxy)-5-fluoronicotinamide

607

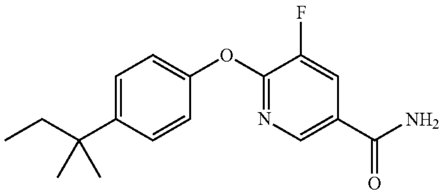 [SMILES: CCC(C)(C)c1ccc(Oc2ncc(C(N)=O)cc2F)cc1]

5-fluoro-6-(4-(tert-pentyl)phenoxy)nicotinamide

608

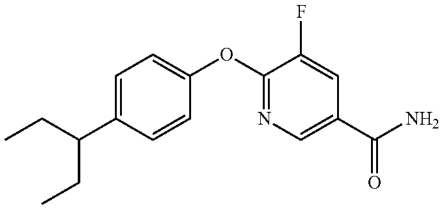 [SMILES: CCC(CC)c1ccc(Oc2ncc(C(N)=O)cc2F)cc1]

5-fluoro-6-(4-(pentan-3-yl)phenoxy)nicotinamide

609

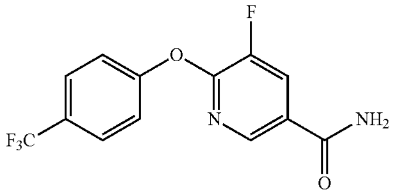 [SMILES: NC(=O)c1cnc(Oc2ccc(C(F)(F)F)cc2)c(F)c1]

5-fluoro-6-(4-(trifluoromethyl)phenoxy)nicotinamide

610

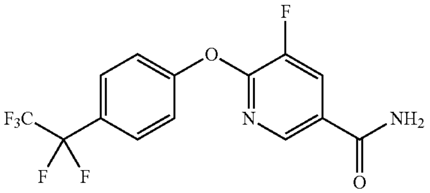 [SMILES: NC(=O)c1cnc(Oc2ccc(C(F)(F)C(F)(F)F)cc2)c(F)c1]

5-fluoro-6-(4-(perfluoroethyl)phenoxy)nicotinamdie

TABLE IV-continued

611

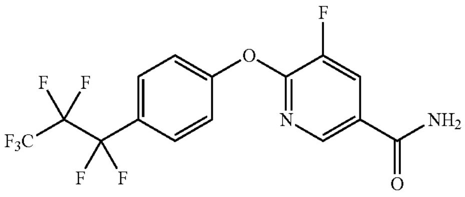 [SMILES: NC(=O)c1cnc(Oc2ccc(C(F)(F)C(F)(F)C(F)(F)F)cc2)c(F)c1]

5-fluoro-6-(4-(perfluoropropyl)phenoxy)nicotinamide

612

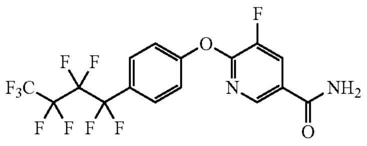 [SMILES: NC(=O)c1cnc(Oc2ccc(C(F)(F)C(F)(F)C(F)(F)C(F)(F)F)cc2)c(F)c1]

5-fluoro-6-(4-(perfluorobutyl)phenoxy)nicotinamide

613

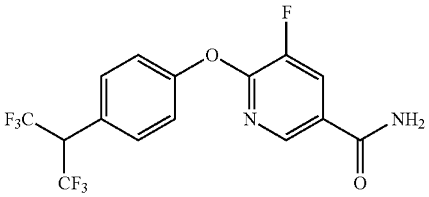 [SMILES: NC(=O)c1cnc(Oc2ccc(C(C(F)(F)F)C(F)(F)F)cc2)c(F)c1]

5-fluoro-6-(4-(1,1,1,3,3,3-hexafluoropropan-2-yl)phenoxy) nicotinamide

614

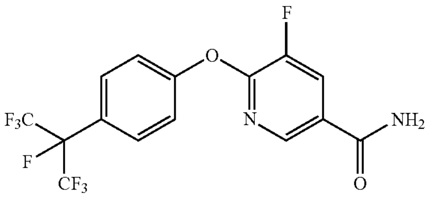 [SMILES: NC(=O)c1cnc(Oc2ccc(C(F)(C(F)(F)F)C(F)(F)F)cc2)c(F)c1]

5-fluoro-6-(4-(perfluoropropan-2-yl)phenoxy)nicotinamide

615

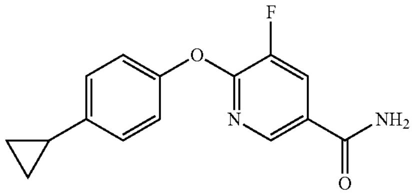 [SMILES: NC(=O)c1cnc(Oc2ccc(C3CC3)cc2)c(F)c1]

6-(4-cyclopropylphenoxy)-5-fluoronicotinamide

616

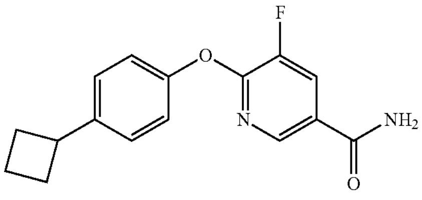 [SMILES: NC(=O)c1cnc(Oc2ccc(C3CCC3)cc2)c(F)c1]

6-(4-cyclobutylphenoxy)-5-fluoronicotinamide

TABLE IV-continued

617

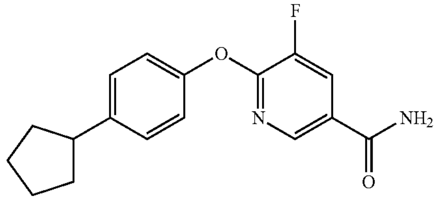 [SMILES: NC(=O)c1cnc(Oc2ccc(C3CCCC3)cc2)c(F)c1]

6-(4-cyclopentylphenoxy)-5-fluoronicotinamide

618

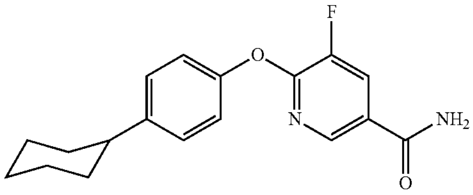 [SMILES: NC(=O)c1cnc(Oc2ccc(C3CCCCC3)cc2)c(F)c1]

6-(4-cyclohexylphenoxy)-5-fluoronicotinamide

619

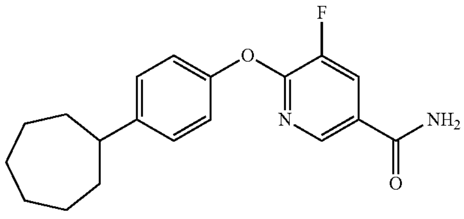 [SMILES: NC(=O)c1cnc(Oc2ccc(C3CCCCCC3)cc2)c(F)c1]

6-(4-cycloheptylphenoxy)-5-fluoronicotinamide

620

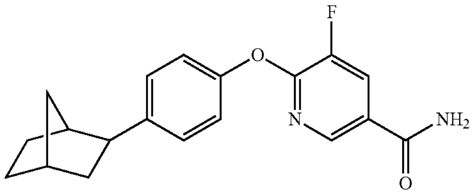 [SMILES: NC(=O)c1cnc(Oc2ccc(C3CC4CCC3C4)cc2)c(F)c1]

6-(4-((1S,4R)-bicyclo[2.2.1]heptan-2-yl)phenoxy)-5-fluoronicotinamide

621

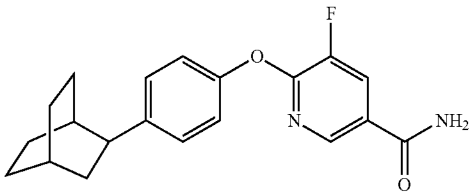 [SMILES: NC(=O)c1cnc(Oc2ccc(C3CC4CCC3CC4)cc2)c(F)c1]

6-(4-((1s,4s)-bicyclo[2.2.2]octan-2-yl)phenoxy)-5-fluoronicotinamide

622

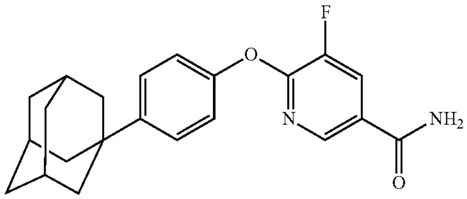 [SMILES: NC(=O)c1cnc(Oc2ccc(C34CC5CC(CC(C5)C3)C4)cc2)c(F)c1]

6-(4-((3r,5r,7r)-adamantan-1-yl)phenoxy)-5-fluoronicotinamide

TABLE IV-continued

623

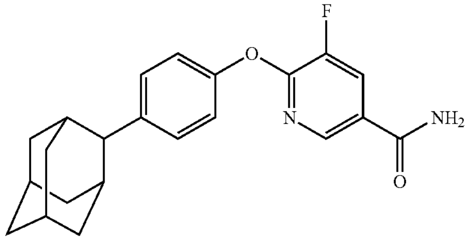

6-(4-((1r,3r,5r,7r)-adamantan-2-yl)phenoxy)-5-fluoro-nicotinamide

624

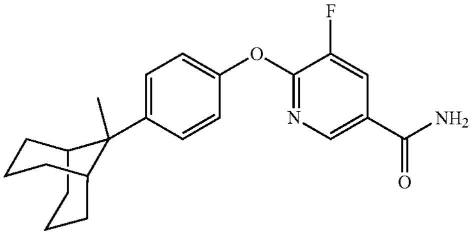 [SMILES: CC1(c2ccc(Oc3ncc(C(N)=O)cc3F)cc2)C2CCCC1CCC2]

5-fluoro-6-(4-((1R,5S)-9-methybicyclo[3.3.1]nonan-9-yl)phenoxy)nicotinamide

X = N, $R^3$ = H, $R^4$ = OH

625

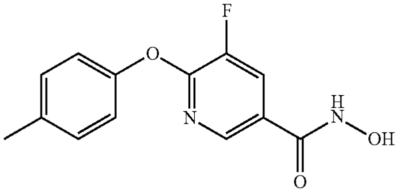 [SMILES: Cc1ccc(Oc2ncc(C(=O)NO)cc2F)cc1]

5-fluoro-N-hydroxy-6-(p-tolyloxy)nicotinamide

626

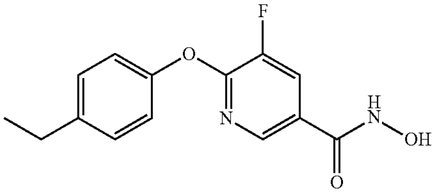 [SMILES: CCc1ccc(Oc2ncc(C(=O)NO)cc2F)cc1]

6-(4-ethylphenoxy)-5-fluoro-N-hydroxynicotinamide

627

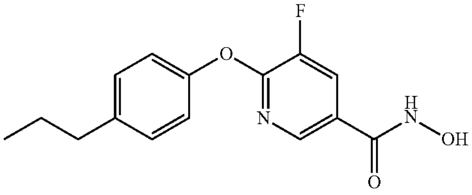 [SMILES: CCCc1ccc(Oc2ncc(C(=O)NO)cc2F)cc1]

5-fluoro-N-hydroxy-6-(4-propylphenoxy)nicotinamide

628

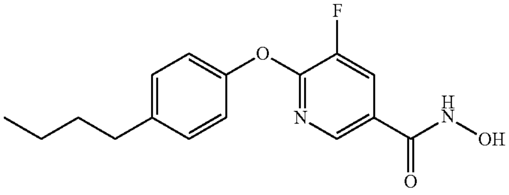 [SMILES: CCCCc1ccc(Oc2ncc(C(=O)NO)cc2F)cc1]

6-(4-butylphenoxy)-5-fluoro-N-hydroxynicotinamide

TABLE IV-continued

629

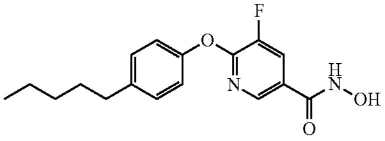 [SMILES: CCCCCc1ccc(Oc2ncc(C(=O)NO)cc2F)cc1]

5-fluoro-N-hydroxy-6-(4-pentylphenoxy)nicotinamide

630

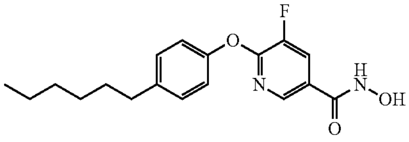 [SMILES: CCCCCCc1ccc(Oc2ncc(C(=O)NO)cc2F)cc1]

5-fluoro-6-(4-hexylphenoxy)-N-hydroxynicotinamide

631

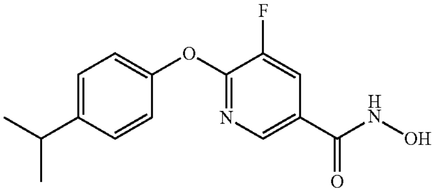 [SMILES: CC(C)c1ccc(Oc2ncc(C(=O)NO)cc2F)cc1]

5-fluoro-N-hydroxy-6-(4-isopropylphenoxy)nicotinamide

632

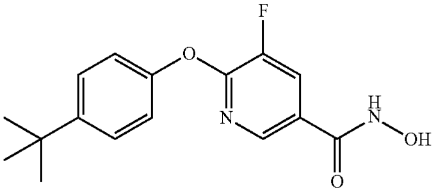 [SMILES: CC(C)(C)c1ccc(Oc2ncc(C(=O)NO)cc2F)cc1]

6-(4-(tert-butyl)phenoxy)-5-fluoro-N-hydroxynicotinamide

633

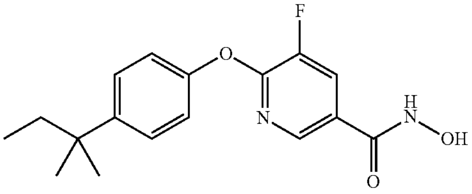 [SMILES: CCC(C)(C)c1ccc(Oc2ncc(C(=O)NO)cc2F)cc1]

634

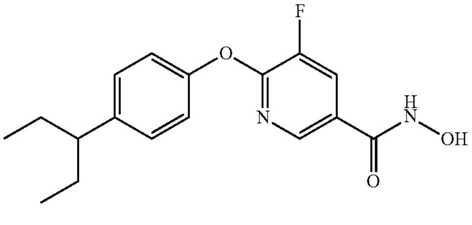 [SMILES: CCC(CC)c1ccc(Oc2ncc(C(=O)NO)cc2F)cc1]

5-fluoro-N-hydroxy-6-(4-(pentan-3-yl)phenoxy)nicotinamide

635

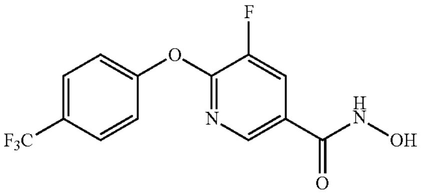 [SMILES: O=C(NO)c1cnc(Oc2ccc(C(F)(F)F)cc2)c(F)c1]

5-fluoro-N-hydroxy-6-(4-(trifluoromethyl)phenoxy) nicotinamide

TABLE IV-continued

636

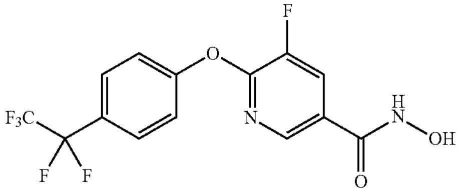 [SMILES: O=C(NO)c1cnc(Oc2ccc(C(F)(F)C(F)(F)F)cc2)c(F)c1]

5-fluoro-N-hydroxy-6-(4-(perfluoroethyl)phenoxy) nicotinamide

637

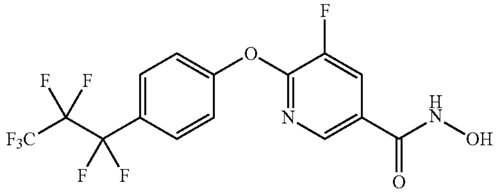 [SMILES: O=C(NO)c1cnc(Oc2ccc(C(F)(F)C(F)(F)C(F)(F)F)cc2)c(F)c1]

5-fluoro-N-hydroxy-6-(4-(perfluoropropyl)phenoxy)nicotinamide

638

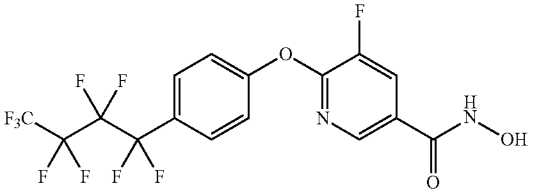 [SMILES: O=C(NO)c1cnc(Oc2ccc(C(F)(F)C(F)(F)C(F)(F)C(F)(F)F)cc2)c(F)c1]

5-fluoro-N-hydroxy-6-(4-(perfluorobutyl)phenoxy)nicotinamide

639

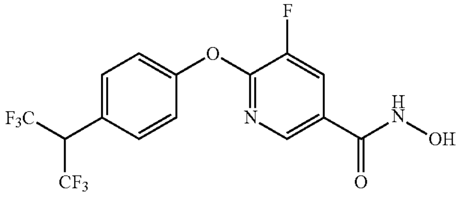 [SMILES: O=C(NO)c1cnc(Oc2ccc(C(C(F)(F)F)C(F)(F)F)cc2)c(F)c1]

5-fluoro-6-(4-(1,1,1,3,3,3-hexafluoropropan-2-yl)phenoxy)-N-hydroxynicotinamide

640

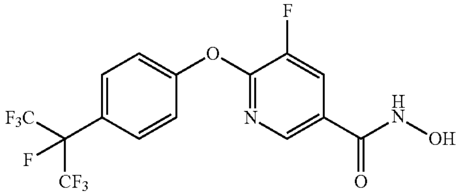

5-fluoro-N-hydroxy-6-(4-(perfluoropropan-2-yl)phenoxy)nicotinamide

641

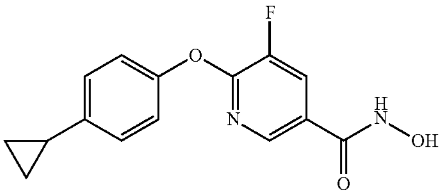

6-(4-cyclopropylphenoxy)-5-fluoro-N-hydroxy-nicotinamide

TABLE IV-continued

642

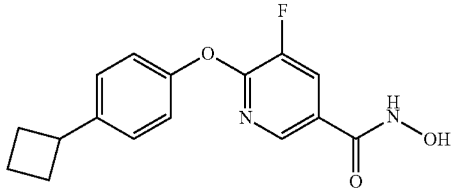 [SMILES: O=C(NO)c1cnc(Oc2ccc(C3CCC3)cc2)c(F)c1]

6-(4-cyclobutylphenoxy)-5-fluoro-N-hydroxynicotinamide

643

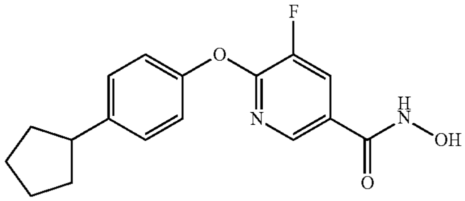 [SMILES: O=C(NO)c1cnc(Oc2ccc(C3CCCC3)cc2)c(F)c1]

6-(4-cyclopentylphenoxy)-5-fluoro-N-hydroxynicotinamide

644

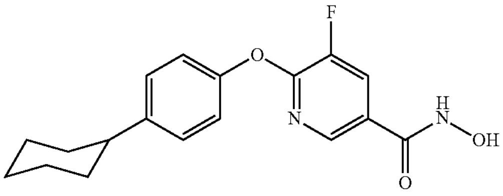 [SMILES: O=C(NO)c1cnc(Oc2ccc(C3CCCCC3)cc2)c(F)c1]

6-(4-cyclohexylphenoxy)-5-fluoro-N-hydroxynicotinamide

645

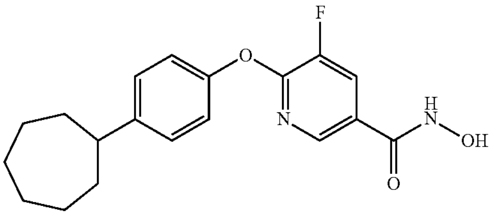 [SMILES: O=C(NO)c1cnc(Oc2ccc(C3CCCCCC3)cc2)c(F)c1]

6-(4-cycloheptylphenoxy)-5-fluoro-N-hydroxynicotinamide

646

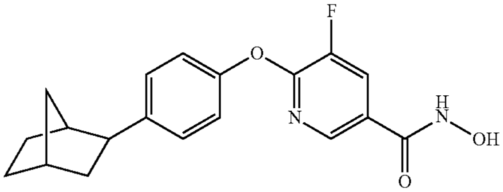 [SMILES: O=C(NO)c1cnc(Oc2ccc(C3CC4CCC3C4)cc2)c(F)c1]

6-(4-((1S,4R)-bicyclo[2.2.1]heptan-2-yl)phenoxy)-5-fluoro-N-hydroxynicotinamide

647

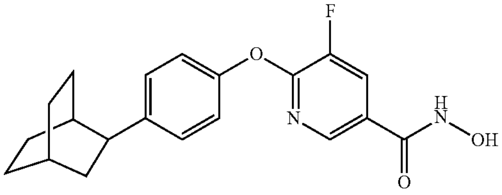 [SMILES: O=C(NO)c1cnc(Oc2ccc(C3CC4CCC3CC4)cc2)c(F)c1]

6-(4-((1s,4s)-bicyclo[2.2.2]octan-2-yl)phenoxy)-5-fluoro-N-hydroxynicotinamide

TABLE IV-continued

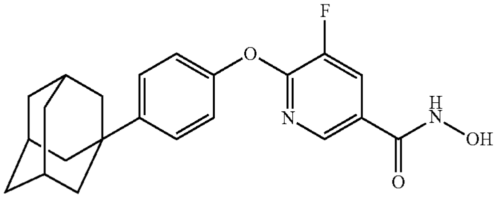 [SMILES: O=C(NO)c1cnc(Oc2ccc(C34CC5CC(CC(C5)C3)C4)cc2)c(F)c1]

648

6-(4-((3r,5r,7r)-adamantan-1-yl)phenoxy)-5-fluoro-N-hydroxynictinamide

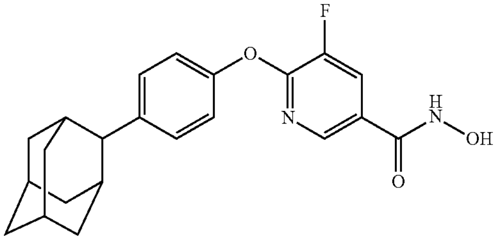 [SMILES: O=C(NO)c1cnc(Oc2ccc(C3C4CC5CC(C4)CC3C5)cc2)c(F)c1]

649

6-(4-((1r,3r,5r,7r)-adamantan-2-yl)phenoxy)-5-fluoro-N-hydroxynicotinamide

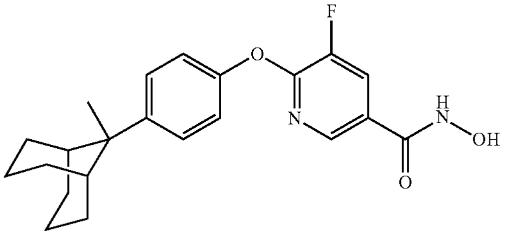 [SMILES: CC1(c2ccc(Oc3ncc(C(=O)NO)cc3F)cc2)C2CCCC1CCC2]

650

5-fluoro-N-hydroxy-6-(4-((1R,5S)-9-methylbicyclo[3.3.1]nonan-9-yl)phenoxy)nicotinamide X = N, $R^3$ = H, $R^4$ = Me

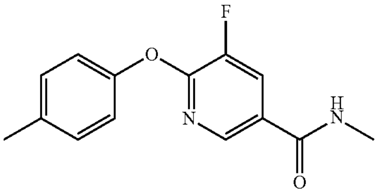

651

5-fluoro-N-methyl-6-(p-tolyloxy)nicotinamide

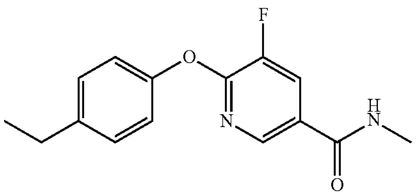 [SMILES: CCc1ccc(Oc2ncc(C(=O)NC)cc2F)cc1]

652

6-(4-ethylphenoxy)-5-fluoro-N-methylnicotinamide

TABLE IV-continued

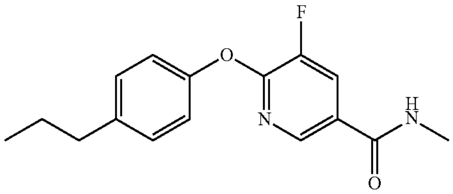 [SMILES: CCCc1ccc(Oc2ncc(C(=O)NC)cc2F)cc1]

653

5-fluoro-N-methyl-6-(4-propylphenoxy)nicotinamide

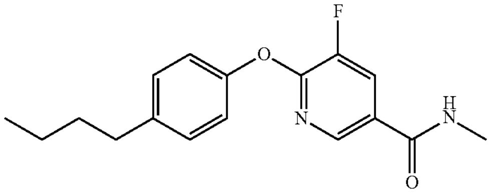 [SMILES: CCCCc1ccc(Oc2ncc(C(=O)NC)cc2F)cc1]

654

6-(4-butylphenoxy)-5-fluoro-N-methylnicotinamide

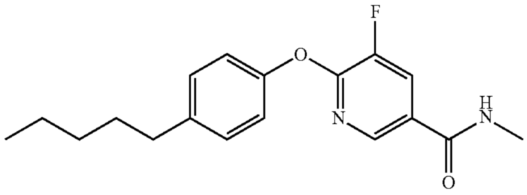 [SMILES: CCCCCc1ccc(Oc2ncc(C(=O)NC)cc2F)cc1]

655

5-fluoro-N-methyl-6-(4-pentylphenoxy)nicotinamide

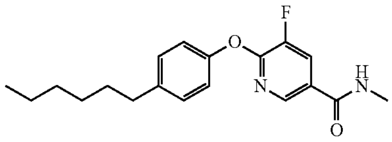 [SMILES: CCCCCCc1ccc(Oc2ncc(C(=O)NC)cc2F)cc1]

656

5-fluoro-6-(4-hexylphenoxy)-N-methylnicotinamide

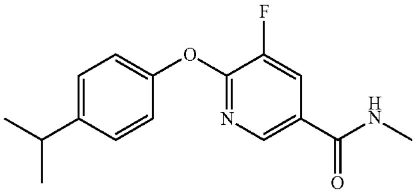

657

5-fluoro-6-(4-isopropylphenoxy)-N-methylnicotinamide

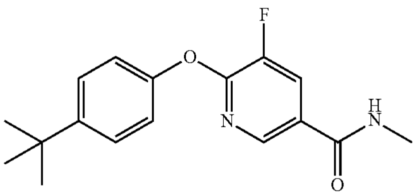

658

6-(4-(tert-butyl)phenoxy)-5-fluoro-N-methylnicotinamide

TABLE IV-continued

659

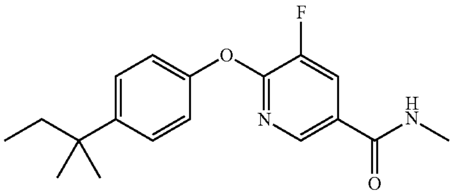 [SMILES: CCC(C)(C)c1ccc(Oc2ncc(C(=O)NC)cc2F)cc1]

5-fluoro-N-methyl-6-(4-(tert-pentyl)phenoxy)nicotinamide

660

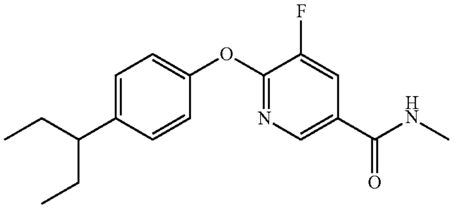 [SMILES: CCC(CC)c1ccc(Oc2ncc(C(=O)NC)cc2F)cc1]

5-fluoro-N-methyl-6-(4-(pentan-3-yl)phenoxy)nicotinamide

661

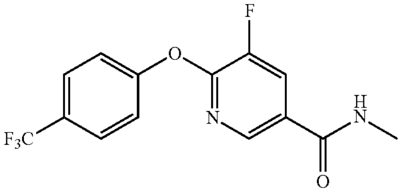

5-fluoro-N-methyl-6-(4-(trifluoromethyl)phenoxy) nicotinamide

662

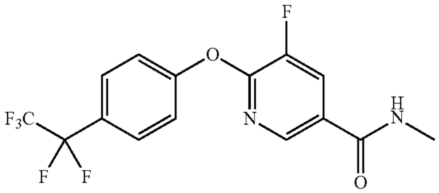

5-fluoro-N-methyl-6-(4-(perfluoroethyl)phenoxy) nicotinamide

663

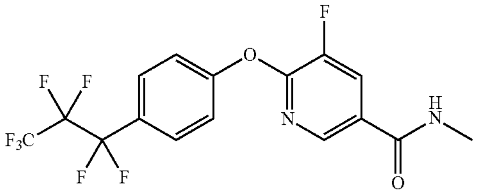 [SMILES: CNC(=O)c1cnc(Oc2ccc(C(F)(F)C(F)(F)C(F)(F)F)cc2)c(F)c1]

5-fluoro-N-methyl-6-(4-(perfluoropropyl)phenoxy)nicotinamide

664

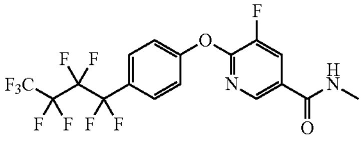 [SMILES: CNC(=O)c1cnc(Oc2ccc(C(F)(F)C(F)(F)C(F)(F)C(F)(F)F)cc2)c(F)c1]

5-fluoro-N-methyl-6-(4-(perfluorobutyl)phenoxy)nicotinamide

TABLE IV-continued

665

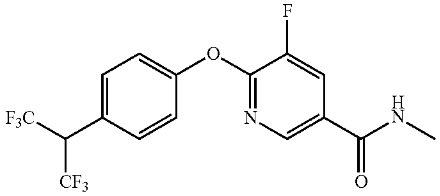 [SMILES: CNC(=O)c1cnc(Oc2ccc(C(C(F)(F)F)C(F)(F)F)cc2)c(F)c1]

5-fluoro-6-(4-(1,1,1,3,3,3-hexafluoropropan-2-yl) phenoxy)-N-methylnicotinamide

666

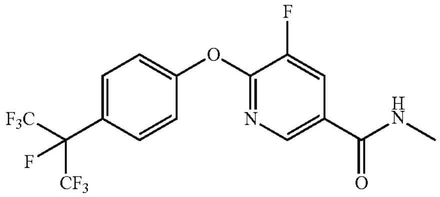 [SMILES: CNC(=O)c1cnc(Oc2ccc(C(F)(C(F)(F)F)C(F)(F)F)cc2)c(F)c1]

5-fluoro-N-methyl-6-(4-(perfluoropropan-2-yl)phenoxy) nicotinamide

667

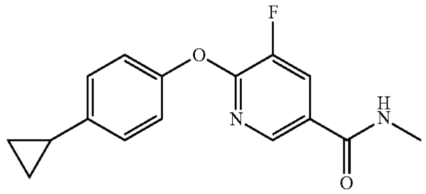

6-(4-cyclopropylphenoxy)-5-fluoro-N-methylnicotinamide

668

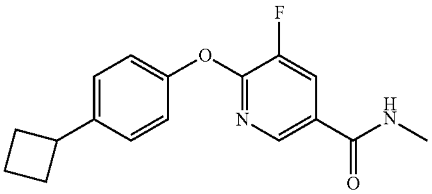 [SMILES: CNC(=O)c1cnc(Oc2ccc(C3CCC3)cc2)c(F)c1]

6-(4-cyclobutylphenoxy)-5-fluoro-N-methylnicotinamide

669

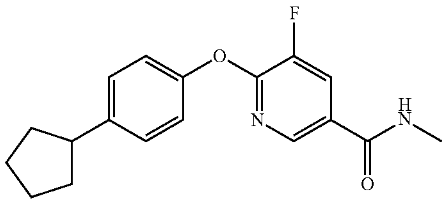 [SMILES: CNC(=O)c1cnc(Oc2ccc(C3CCCC3)cc2)c(F)c1]

6-(4-cyclopentylphenoxy)-5-fluoro-N-methylnicotinamide

670

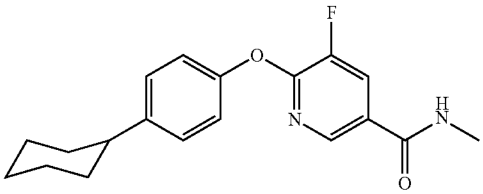

6-(4-cyclohexylphenoxy)-5-fluoro-N-methylnicotinamide

TABLE IV-continued

671

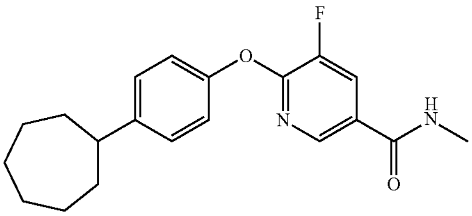 [SMILES: CNC(=O)c1cnc(Oc2ccc(C3CCCCCC3)cc2)c(F)c1]

6-(4-cycloheptylphenoxy)-5-fluoro-N-methylnicotinamide

672

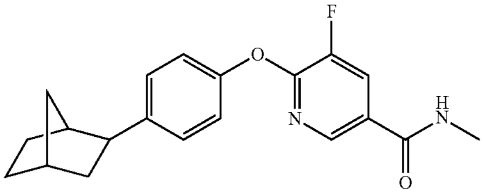 [SMILES: CNC(=O)c1cnc(Oc2ccc(C3CC4CCC3C4)cc2)c(F)c1]

6-(4-((1S,4R)-bicyclo[2.2.1]heptan-2-yl)phenoxy)-5-fluoro-N-methylnicotinamide

673

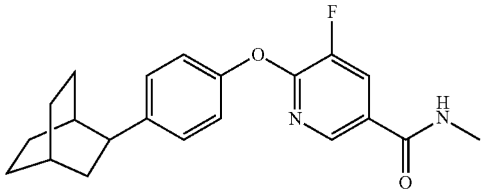

6-(4-((1s,4s)-bicyclo[2.2.2]octan-2-yl)phenoxy)-5-fluoro-N-methylnictinamide

674

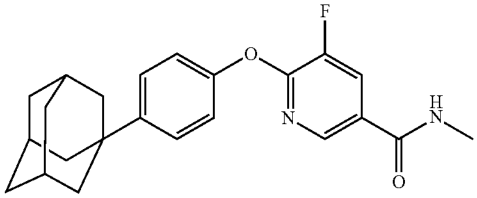

6-(4-((3r,5r,7r)-adamantan-1-yl)phenoxy)-5-fluoro-N-methylnicotinamide

675

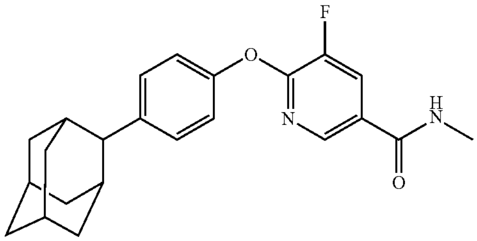 [SMILES: CNC(=O)c1cnc(Oc2ccc(C3C4CC5CC(C4)CC3C5)cc2)c(F)c1]

6-(4-((1r,3r,5r,7r)-adamantan-2-yl)phenoxy)-5-fluoro-N-methylnicotinamide

TABLE IV-continued

676

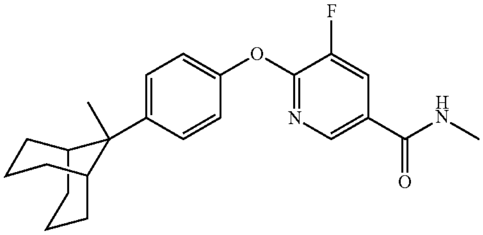 [SMILES: CNC(=O)c1cnc(Oc2ccc(C3(C)C4CCCC3CCC4)cc2)c(F)c1]

5-fluoro-N-methyl-6-(4-((1R,5S)-9-methylbicyclo[3.3.1]nonan-9-yl)phenoxy)nicotinamide X = N, $R^3$ = Me, $R^4$ = Me

677

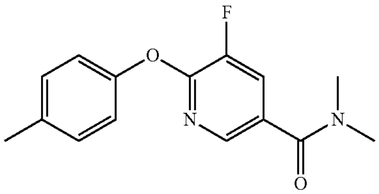

5-fluoro-N,N-dimethyl-6-(p-tolyloxy)nicotinamide

678

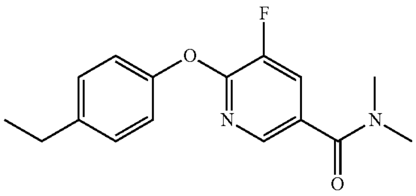 [SMILES: CCc1ccc(Oc2ncc(C(=O)N(C)C)cc2F)cc1]

6-(4-ethylphenoxy)-5-fluoro-N,N-dimethylnicotinamide

679

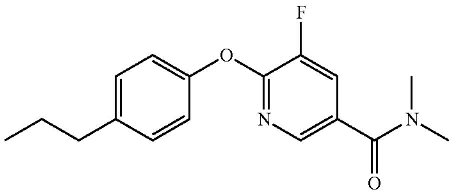

5-fluoro-N,N-dimethyl-6-(4-propylphenoxy)nicotinamide

680

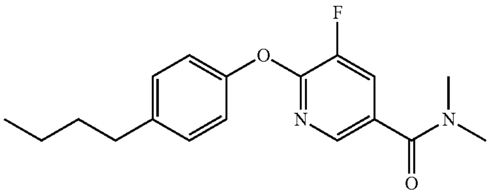 [SMILES: CCCCc1ccc(Oc2ncc(C(=O)N(C)C)cc2F)cc1]

6-(4-butylphenoxy)-5-fluoro-N,N-dimethylnicotinamide

681

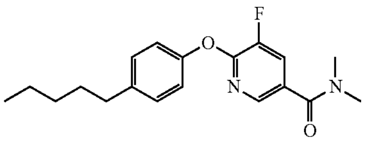 [SMILES: CCCCCc1ccc(Oc2ncc(C(=O)N(C)C)cc2F)cc1]

5-fluoro-N,N-dimethyl-6-(4-pentylphenoxy)nicotinamide

TABLE IV-continued

682

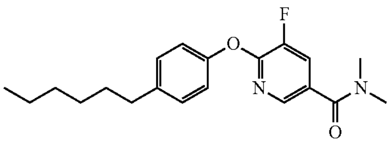 [SMILES: CCCCCCc1ccc(Oc2ncc(C(=O)N(C)C)cc2F)cc1]

5-fluoro-6-(4-hexylphenoxy)-N,N-dimethylnicotinamide

683

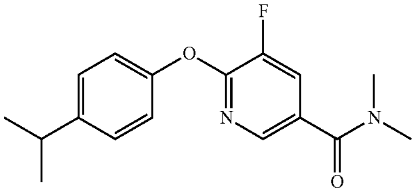

5-fluoro-6-(4-isopropylphenoxy)-N,N-dimethylnicotinamide

684

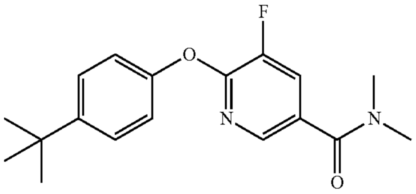

6-(4-(tert-butyl)phenoxy)-5-fluoro-N,N-dimethylnicotinamide

685

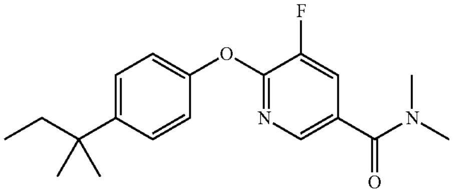 [SMILES: CCC(C)(C)c1ccc(Oc2ncc(C(=O)N(C)C)cc2F)cc1]

5-fluoro-N,N-dimethyl-6-(4-(tert-pentyl)phenoxy)nicotinamide

686

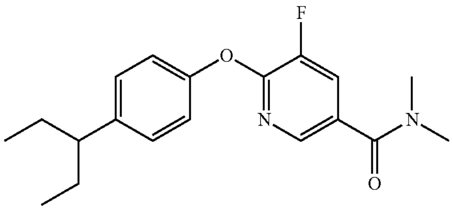 [SMILES: CCC(CC)c1ccc(Oc2ncc(C(=O)N(C)C)cc2F)cc1]

5-fluoro-N,N-dimethyl-6-(4-(pentan-3-yl)phenoxy)nicotinamide

687

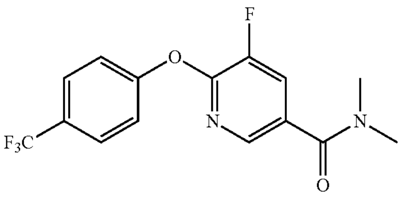 [SMILES: CN(C)C(=O)c1cnc(Oc2ccc(C(F)(F)F)cc2)c(F)c1]

5-fluoro-N,N-dimethyl-6-(4-(trifluoromethyl) phenoxy)nicotinamide

TABLE IV-continued

688

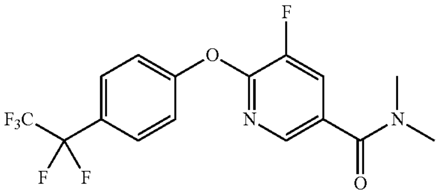 [SMILES: CN(C)C(=O)c1cnc(Oc2ccc(C(F)(F)C(F)(F)F)cc2)c(F)c1]

5-fluoro-N,N-dimethyl-6-(4-(perfluoroethyl)phenoxy) nicotinamide

689

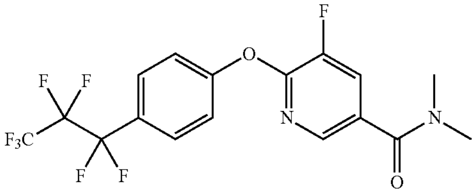

5-fluoro-N,N-dimethyl-6-(4-(perfluoropropyl)phenoxy) nicotinamide

690

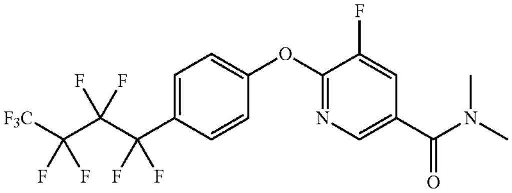 [SMILES: CN(C)C(=O)c1cnc(Oc2ccc(C(F)(F)C(F)(F)C(F)(F)C(F)(F)F)cc2)c(F)c1]

5-fluoro-N,N-dimethyl-6-(4-(perfluorobutyl)phenoxy)nicotinamide

691

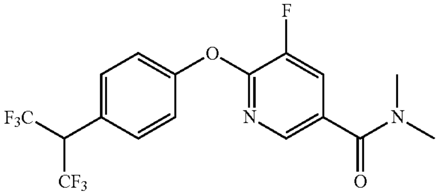 [SMILES: CN(C)C(=O)c1cnc(Oc2ccc(C(C(F)(F)F)C(F)(F)F)cc2)c(F)c1]

5-fluoro-6-(4-(1,1,1,3,3,3-hexafluoropropan-2-yl)phenoxy)-N,N-dimethylnicotinamide

692

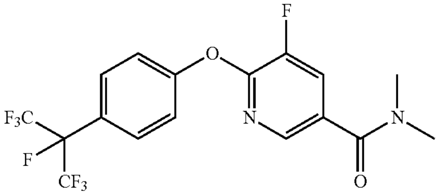 [SMILES: CN(C)C(=O)c1cnc(Oc2ccc(C(F)(C(F)(F)F)C(F)(F)F)cc2)c(F)c1]

5-fluoro-N,N-dimethyl-6-(4-(perfluoropropan-2-yl)phenoxy)nicotinamide

693

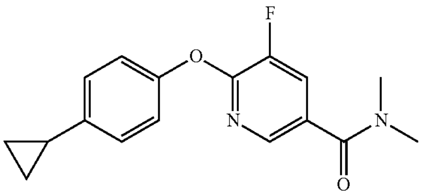

6-(4-cyclopropylphenoxy)-5-fluoro-N,N-dimethyl-nicotinamide

TABLE IV-continued

694

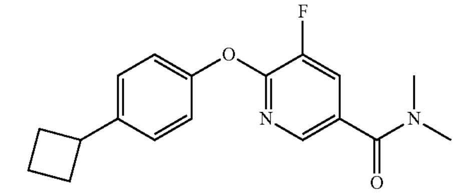 [SMILES: CN(C)C(=O)c1cnc(Oc2ccc(C3CCC3)cc2)c(F)c1]

6-(4-cyclobutylphenoxy)-5-fluoro-N,N-dimethyl-nicotinamide

695

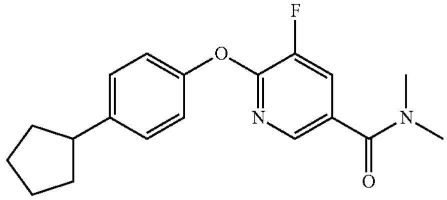 [SMILES: CN(C)C(=O)c1cnc(Oc2ccc(C3CCCC3)cc2)c(F)c1]

6-(4-cyclopentylphenoxy)-5-fluoro-N,N-dimethyl-nicotinamide

696

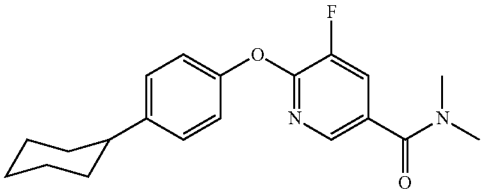 [SMILES: CN(C)C(=O)c1cnc(Oc2ccc(C3CCCCC3)cc2)c(F)c1]

6-(4-cyclohexylphenoxy)-5-fluoro-N,N-dimethylnicotinamide

697

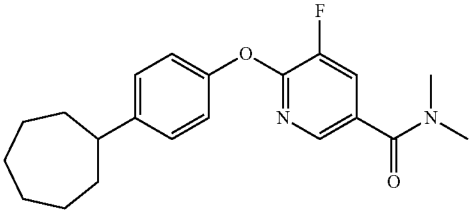 [SMILES: CN(C)C(=O)c1cnc(Oc2ccc(C3CCCCCC3)cc2)c(F)c1]

6-(4-cycloheptylphenoxy)-5-fluoro-N,N-dimethylnicotinamide

698

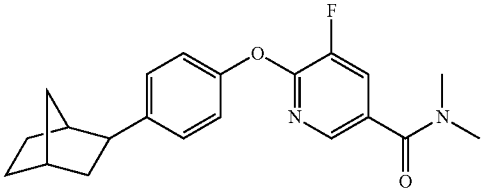

6-(4-((1S,4R)-bicyclo[2.2.1]heptan-2-yl)phenoxy)-5-fluoro-N,N-dimethylnicotinamide

699

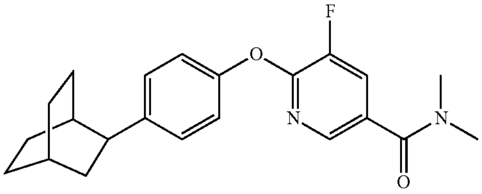 [SMILES: CN(C)C(=O)c1cnc(Oc2ccc(C3CC4CCC3CC4)cc2)c(F)c1]

6-(4-((1s,4s)-bicyclo[2.2.2]octan-2-yl)phenoxy)-5-fluoro-N,N-dimethylnicotinamide TABLE IV-continued

700

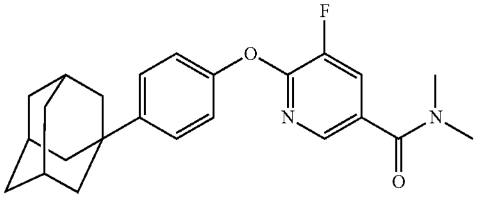 [SMILES: CN(C)C(=O)c1cnc(Oc2ccc(C34CC5CC(CC(C5)C3)C4)cc2)c(F)c1]

6-(4-((3r,5r,7r)-adamantan-1-yl)phenoxy)-5-fluoro-N,N-dimethylnicotinamide

701

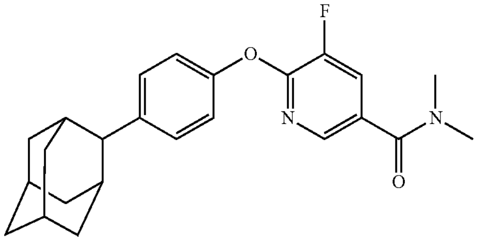 [SMILES: CN(C)C(=O)c1cnc(Oc2ccc(C3C4CC5CC(C4)CC3C5)cc2)c(F)c1]

6-(4-((1r,3r,5r,7r)-adamantan-2-yl)phenoxy)-5-fluoro-N,N-dimethylnictinamide

702

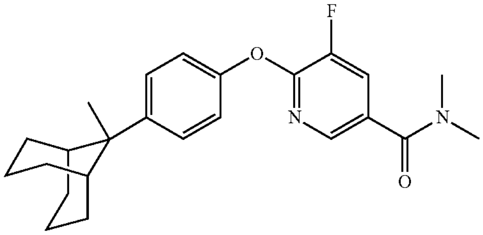 [SMILES: CN(C)C(=O)c1cnc(Oc2ccc(C3(C)C4CCCC3CCC4)cc2)c(F)c1]

5-fluoro-N,N-dimethyl-6-(4-((1R,5S)-9-methylbicyclo[3.3.1]nonan-9-yl)phenoxy)nicotinamide Also included are isomers, e.g. enantiomers or diastereomers or rotamers or mixtures of isomers, salts, particularly pharmaceutically acceptable salts, and solvates of the compounds listed above.

A fifth aspect of the present invention relates to compounds of formula V and salts and solvates thereof:

(V)

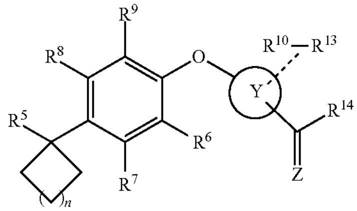

wherein n=0-5, which comprises cyclopropyl (n=0), cyclobutyl (n=1), cyclopentyl (n=2), cyclohexyl (n=3), cycloheptyl (n=4) and cyclooctyl (n=5), wherein the said cyclopropyl, cyclobutyl, cyclopentyl, cyclohexyl, cycloheptyl and cyclooctyl groups can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein the said cyclopropyl, cyclobutyl, cyclopentyl, cyclohexyl, cycloheptyl and cyclooctyl groups can be perhalogenated, particularly perfluorinated;

and wherein n is preferably 0 as constituting cyclopropyl, particularly as constituting cyclopropyl being unsubstituted;

$R^5$=$C_1$-$C_{12}$ preferably $C_1$-$C_6$ alkyl, $C_2$-$C_{12}$ preferably $C_2$-$C_6$ alkenyl, $C_2$-$C_{12}$ preferably $C_2$-$C_6$ alkynyl, $C_3$-$C_8$ cycloalkyl, $C_3$-$C_8$ cycloalkenyl, wherein all alkyl, alkenyl and alkynyl residues can be linear or branched, and are perhalogenated, particularly perfluorinated, and wherein all cycloalkyl and cycloalkenyl residues are perhalogenated, particularly perfluorinated;

or wherein all alkyl, alkenyl and alkynyl residues can be linear or branched, and can be unsubstituted or substituted with one or more substituents in particular independently selected from: —F, —Cl, —Br, —I, —CN, —NCO, —NCS; and $OC_1$-$C_3$ alkyl optionally halogenated or perhalogenated, particularly perfluorinated;

and wherein all cycloalkyl and cycloalkenyl residues can be unsubstituted or substituted with one or more substituents in particular independently selected from: —F, —Cl, —Br, —I, —CN, —NCO, —NCS; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein $R^5$ is preferably —$CF_3$ or —$CF_2CF_3$;

$R^6$-$R^9$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from: —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

wherein $R^6$-$R^8$ each are preferably H, and $R^9$ is preferably —H, —F, —Cl, or —$CH_3$;

Y=a six-membered aromatic ring selected from benzene, pyridine, pyrimidine, pyridazine or pyrazine;

wherein the benzene ring is not substituted, or it is substituted with one to four of the substituents independently selected from $R^{10}$-$R^{13}$, and wherein the pyridine ring is not substituted, or it is substituted at the carbon positions with one to three of the substituents independently selected from $R^{10}$-$R^{12}$, and wherein preferably the N-atom of the pyridine ring is in ortho-position relative to the ether bond, and wherein the pyrimidine ring is not substituted, or it is substituted at the carbon positions with one or two of the substituents independently selected from $R^{10}$-$R^{11}$, and wherein preferably an N-atom of the pyrimidine ring is in ortho-position relative to the ether bond, and wherein the pyridazine ring is not substituted, or it is substituted at the carbon positions with one or two of the substituents independently selected from $R^{10}$-$R^{11}$, and wherein preferably an N-atom of the pyridazine ring is in ortho-position relative to the ether bond, and wherein the pyrazine ring is not substituted, or it is substituted at the carbon positions with one or two of the substituents independently selected from $R^{10}$-$R^{11}$, and wherein preferably an N-atom of the pyrazine ring is in ortho-position relative to the ether bond, wherein preferably Y=benzene or pyridine being not substituted with any of the residues selected from $R^{10}$-$R^{13}$, or being substituted with one of the substituents selected from $R^{10}$-$R^{13}$ being F at the carbon atom in ortho-position relative to the ether bond;

$R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated;

Z=O or S, and preferably Z=O;

$R^{14}$=$OR^2$ or $NR^3R^4$ wherein $R^2$ is defined as in formula I including the preferred definition of $R^2$ as H, methyl or ethyl;

wherein $R^3$ and $R^4$ are defined as in formula II, including the preferred definitions of $R^3$ as H or —$CH_3$ and $R^4$ as H, OH or —$CH_3$;

In a particularly preferred embodiment of the compounds of formula V, the present invention relates to compounds of formula Va and salts and solvates thereof:

(Va)

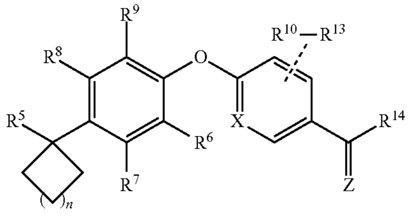

wherein n is defined as in formula V, including the preferred definition of n being n=0 as constituting cyclopropyl, particularly as constituting cyclopropyl being unsubstituted, wherein Z is defined as in formula V, including the preferred definition of Z as Z=O, wherein $R^5$ is defined as in formula V, including all preferred definitions of $R^5$, $R^6$-$R^9$ are defined as in formula V, including all preferred definitions of $R^6$-$R^9$, wherein $R^{14}$ is defined as in formula V, wherein X is N or $CR^{13}$, and wherein $R^{10}$-$R^{13}$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents in particular independently selected from —F, —Cl, —Br, —I; and $C_1$-$C_3$ alkyl such as —$CH_3$ optionally halogenated or perhalogenated, particularly perfluorinated such as —$CF_3$; and $OC_1$-$C_3$ alkyl optionally halogenated or perhalogenated, particularly perfluorinated.

Specific examples of compounds falling under the scope of formula V are shown in Table V. The compounds in Table V are defined by their chemical structure, the indicated nomenclature is only for illustrative purposes.

TABLE V

703

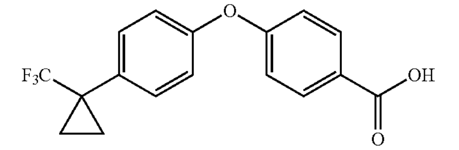

4-(4-(1-(trifluoromethyl)cyclopropyl)phenoxy) benzoic acid

704

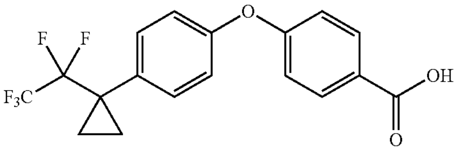 [SMILES: O=C(O)c1ccc(Oc2ccc(C3(C(F)(F)C(F)(F)F)CC3)cc2)cc1]

4-(4-(1-(perfluoroethyl)cyclopropyl)phenoxy) benzoic acid

705

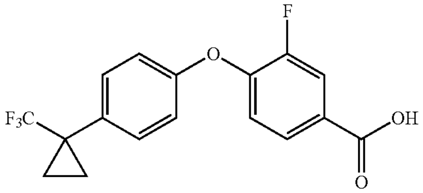 [SMILES: O=C(O)c1ccc(Oc2ccc(C3(C(F)(F)F)CC3)cc2)c(F)c1]

3-fluoro-4-(4-(1-(trifluoromethyl)cyclopropyl)phenoxy) benzoic acid

706

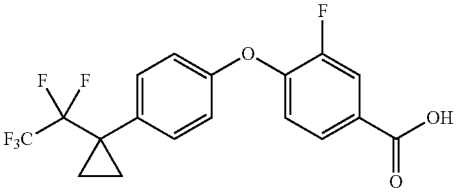 [SMILES: O=C(O)c1ccc(Oc2ccc(C3(C(F)(F)C(F)(F)F)CC3)cc2)c(F)c1]

3-fluoro-4-(4-(1-(perfluoroethyl)cyclopropyl)phenoxy) benzoic acid

707

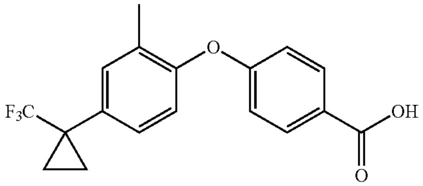 [SMILES: Cc1cc(C2(C(F)(F)F)CC2)ccc1Oc1ccc(C(=O)O)cc1]

4-(2-methyl-4-(1-trifluoromethyl)cyclopropyl)phenoxy) benzoic acid

708

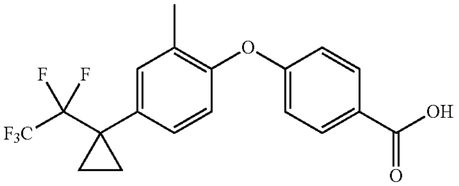 [SMILES: Cc1cc(C2(C(F)(F)C(F)(F)F)CC2)ccc1Oc1ccc(C(=O)O)cc1]

4-(2-methyl-4-(1-(perfluoroethyl)cyclopropyl)phenoxy) benzoic acid

TABLE V-continued

709

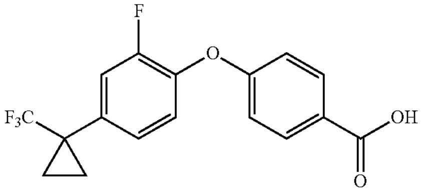 [SMILES: O=C(O)c1ccc(Oc2ccc(C3(C(F)(F)F)CC3)cc2F)cc1]

4-(2-fluoro-4-(1-(trifluoromethyl)cyclopropyl)phenoxy) benzoic acid

710

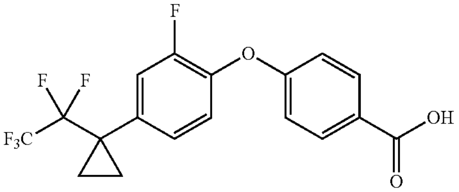 [SMILES: O=C(O)c1ccc(Oc2ccc(C3(C(F)(F)C(F)(F)F)CC3)cc2F)cc1]

4-(2-fluoro-4-(1-(perfluoroethyl)cyclopropyl)phenoxy) benzoic acid

711

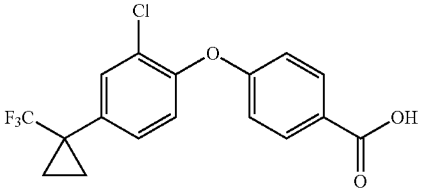

4-(2-chloro-4-(1-(trifluoromethyl)cyclopropyl)phenoxy) benzoic acid

712

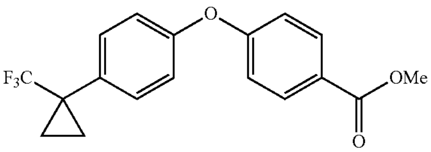

methyl 4-(4-(1-trifluoromethyl)cyclopropyl) phenoxy)benzoate

713

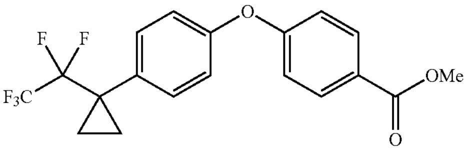 [SMILES: COC(=O)c1ccc(Oc2ccc(C3(C(F)(F)C(F)(F)F)CC3)cc2)cc1]

methyl 4-(4-(1-(perfluoroethyl)cyclopropyl) phenoxy)benzoate

714

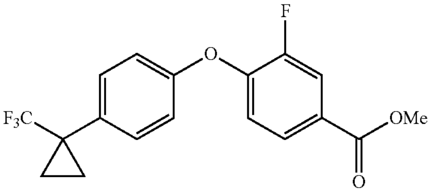

methyl 3-fluoro-4-(4-(1-(trifluoromethyl)cyclopropyl) phenoxy)benzoate

TABLE V-continued

715

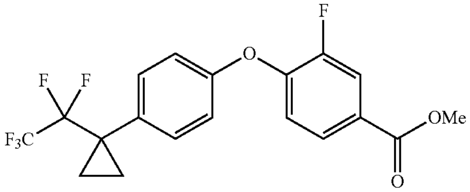 [SMILES: COC(=O)c1ccc(Oc2ccc(C3(C(F)(F)C(F)(F)F)CC3)cc2)c(F)c1]

methyl 3-fluoro-4-(4-(1-(perfluoroethyl)cyclopropyl) phenoxy)benzoate

716

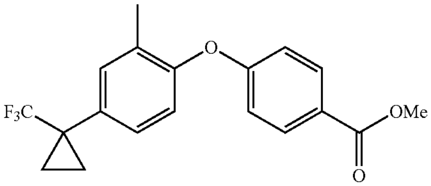

methyl 4-(2-methyl-4-(1-(trifluoromethyl)cyclopropyl) phenoxy)benzoate

717

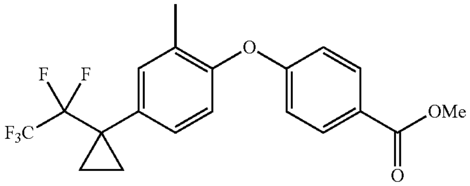 [SMILES: COC(=O)c1ccc(Oc2ccc(C3(C(F)(F)C(F)(F)F)CC3)cc2C)cc1]

methyl 4-(2-methyl-4-(1-(perfluoroethyl)cyclopropyl) phenoxy)benzoate

718

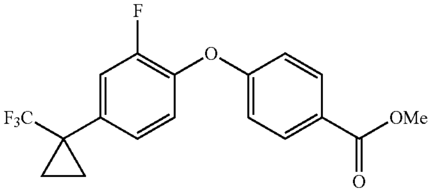 [SMILES: COC(=O)c1ccc(Oc2ccc(C3(C(F)(F)F)CC3)cc2F)cc1]

methyl 4-(2-fluoro-4-(1-(trifluoromethyl)cyclopropyl) phenoxy)benzoate

719

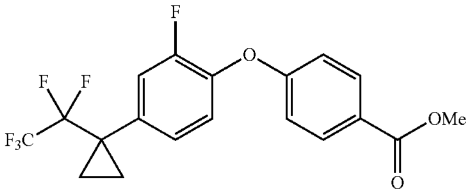 [SMILES: COC(=O)c1ccc(Oc2ccc(C3(C(F)(F)C(F)(F)F)CC3)cc2F)cc1]

methyl 4-(2-fluoro-4-(1-(perfluoroethyl)cyclopropyl) phenoxy)benzoate

720

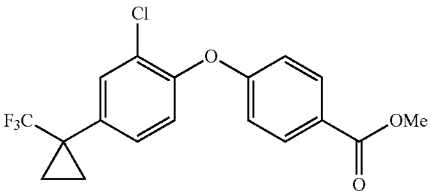

methyl 4-(2-chloro-4-(1-(trifluoromethyl)cyclopropyl) phenoxy)benzoate

TABLE V-continued

721

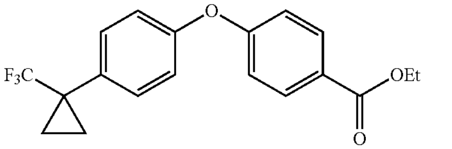 [SMILES: CCOC(=O)c1ccc(Oc2ccc(C3(C(F)(F)F)CC3)cc2)cc1]

ethyl 4-(4-(1-(trifluoromethyl)cyclopropyl) phenoxy)benzoate

722

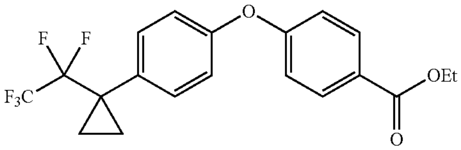 [SMILES: CCOC(=O)c1ccc(Oc2ccc(C3(C(F)(F)C(F)(F)F)CC3)cc2)cc1]

ethyl 4-(4-(1-perfluoroethyl)cyclopropyl) pheoxy)benzoate

723

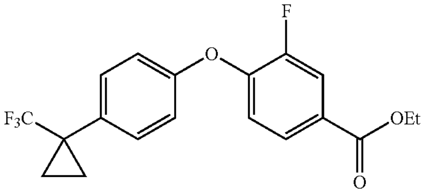 [SMILES: CCOC(=O)c1ccc(Oc2ccc(C3(C(F)(F)F)CC3)cc2)c(F)c1]

ethyl 3-fluoro-4-(4-(1-(trifluoromethyl)cyclopropyl) phenoxy)benzoate

724

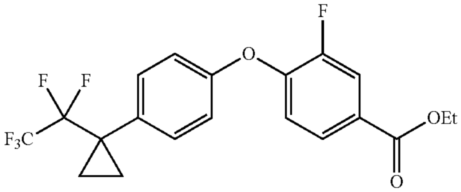 [SMILES: CCOC(=O)c1ccc(Oc2ccc(C3(C(F)(F)C(F)(F)F)CC3)cc2)c(F)c1]

ethyl 3-fluoro-4-(4-(1-(perfluoroethyl)cyclopropyl) phenoxy)benzoate

725

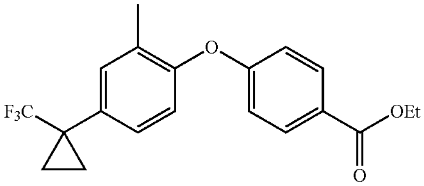 [SMILES: CCOC(=O)c1ccc(Oc2ccc(C3(C(F)(F)F)CC3)cc2C)cc1]

ethyl 4-(2-methyl-4-(1-(trifluoromethyl)cyclopropyl) phenoxy)benzoate

726

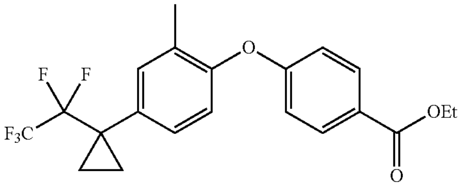 [SMILES: CCOC(=O)c1ccc(Oc2ccc(C3(C(F)(F)C(F)(F)F)CC3)cc2C)cc1]

ethyl 4-(2-methyl-4-(1-(perfluoroethyl)cyclopropyl) phenoxy)benzoate

TABLE V-continued

727

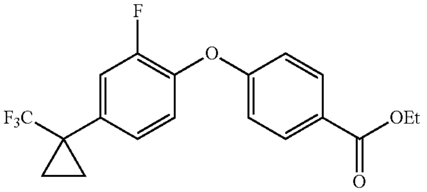 [SMILES: CCOC(=O)c1ccc(Oc2ccc(C3(C(F)(F)F)CC3)cc2F)cc1]

ethyl 4-(2-fluoro-4-(1-(trifluoromethyl)cyclopropyl) phenoxy)benozate

728

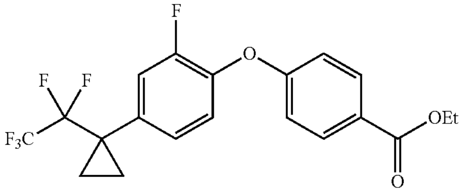 [SMILES: CCOC(=O)c1ccc(Oc2ccc(C3(C(F)(F)C(F)(F)F)CC3)cc2F)cc1]

ethyl 4-(2-fluoro-4-(1-(perfluoroethyl)cyclopropyl) phenoxy)benzoate

729

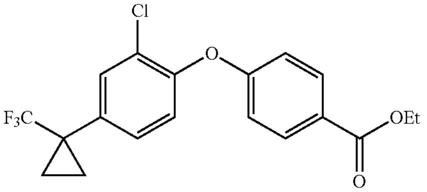

ethyl 4-(2-chloro-4-(1-(trifluoromethyl)cyclopropyl) phenoxy)benzoate

730

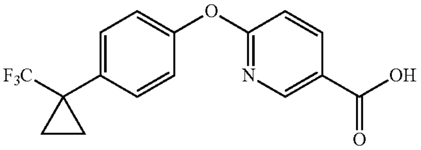

6-(4-(1-(trifluoromethyl)cyclopropyl)phenoxy) phenoxy)nicotinic acid

731

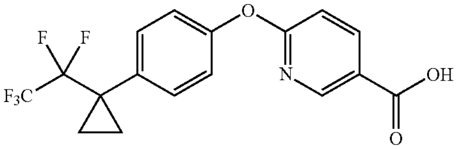

6-(4-(1-(perfluoroethyl)cyclopropyl)phenoxy) phenoxy)nicotinic acid

732

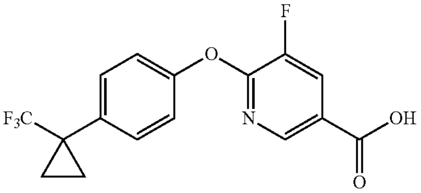 [SMILES: O=C(O)c1cnc(Oc2ccc(C3(C(F)(F)F)CC3)cc2)c(F)c1]

5-fluoro-6-(4-(1-(trifluoromethyl)cyclopropyl)phenoxy) nicotinic acid

TABLE V-continued

733

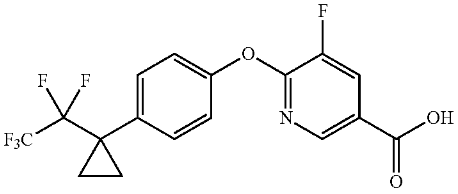 [SMILES: O=C(O)c1cnc(Oc2ccc(C3(C(F)(F)C(F)(F)F)CC3)cc2)c(F)c1]

5-fluoro-6-(4-(1-(perfluoroethyl)cyclopropyl)phenoxy) nicotinic acid

734

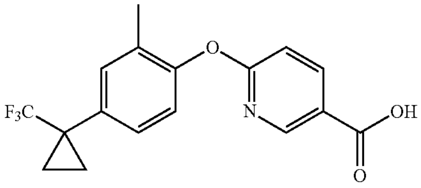 [SMILES: Cc1cc(C2(C(F)(F)F)CC2)ccc1Oc1ccc(C(=O)O)cn1]

6-(2-methyl-4-(1-(trifluoromethyl)cyclopropyl)phenoxy) nicotinic acid

735

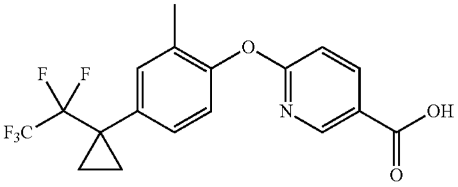 [SMILES: Cc1cc(C2(C(F)(F)C(F)(F)F)CC2)ccc1Oc1ccc(C(=O)O)cn1]

6-(2-methyl-4-(1-(perfluoroethyl)cyclopropyl)phenoxy) nicotinic acid

736

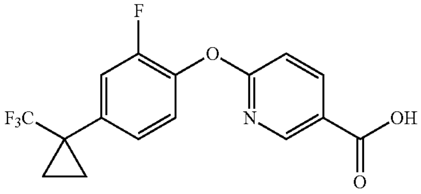 [SMILES: O=C(O)c1ccc(Oc2ccc(C3(C(F)(F)F)CC3)cc2F)nc1]

6-(2-fluoro-4-(1-(trifluoromethyl)cyclopropyl)phenoxy) nicotinic acid

737

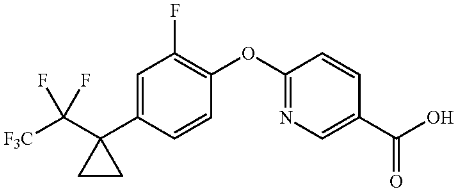 [SMILES: O=C(O)c1ccc(Oc2ccc(C3(C(F)(F)C(F)(F)F)CC3)cc2F)nc1]

6-(2-fluoro-4-(1-(perfluoroethyl)cyclopropyl)phenoxy) nicotinic acid

738

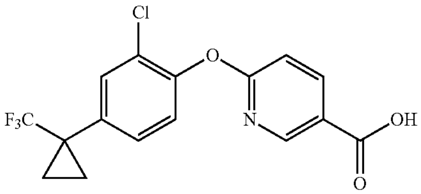

6-(2-chloro-4-(1-(trifluoromethyl)cyclopropyl)phenoxy) nicotinic acid

TABLE V-continued

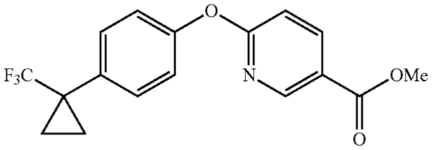 [SMILES: COC(=O)c1ccc(Oc2ccc(C3(C(F)(F)F)CC3)cc2)nc1]
739 methyl 6-(4-(1-(trifluoromethyl)cyclopropyl) phenoxy)nicotinate

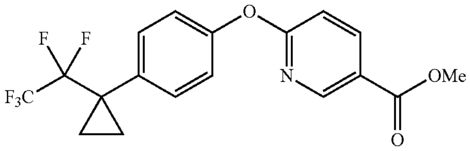 [SMILES: COC(=O)c1ccc(Oc2ccc(C3(C(F)(F)C(F)(F)F)CC3)cc2)nc1]
740 methyl 6-(4-(1-(perfluoroethyl)cyclopropyl) phenoxy)nicotinate

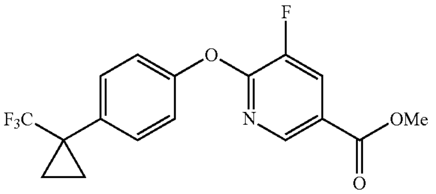
741 methyl 5-fluoro-6-(4-(1-(trifluoromethyl)cyclopropyl) phenoxy)nicotinate

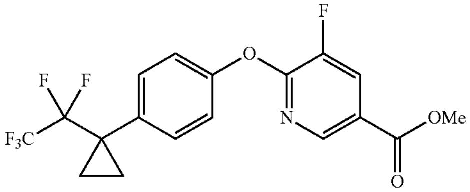 [SMILES: COC(=O)c1cnc(Oc2ccc(C3(C(F)(F)C(F)(F)F)CC3)cc2)c(F)c1]
742 methyl 5-fluoro-6-(4-(1-(perfluoroethyl)cyclopropyl) phenoxy)nicotinate

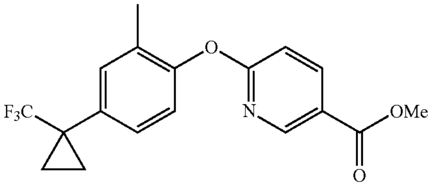
743 methyl 6-(2-methyl-4-(1-(trifluoromethyl)cyclopropyl) phenoxy)nicotinate

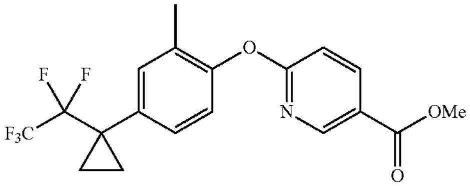 [SMILES: COC(=O)c1ccc(Oc2ccc(C3(C(F)(F)C(F)(F)F)CC3)cc2C)nc1]
744 methyl 6-(2-methyl-4-(1-(perfluoroethyl)cyclopropyl) phenoxy)nicotinate

TABLE V-continued

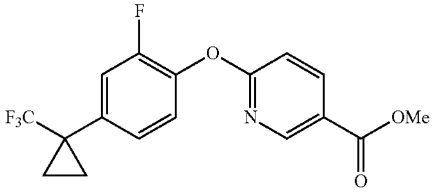 [SMILES: COC(=O)c1ccc(Oc2ccc(C3(C(F)(F)F)CC3)cc2F)nc1]
745 methyl 6-(2-fluoro-4-(1-(trifluoromethyl)cyclopropyl) phenoxy)nicotinate

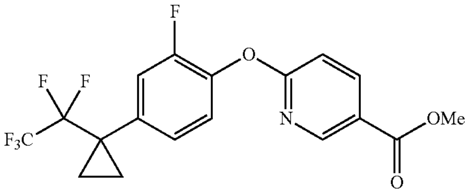 [SMILES: COC(=O)c1ccc(Oc2ccc(C3(C(F)(F)C(F)(F)F)CC3)cc2F)nc1]
746 methyl 6-(2-fluoro-4-(1-(perfluoroethyl)cyclopropyl) phenoxy)nicotinate

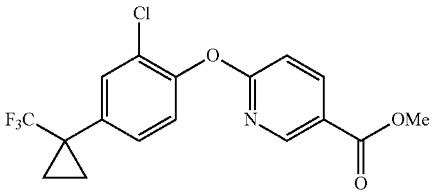
747 methyl 6-(2-chloro-4-(1-(trifluoromethyl)cyclopropyl) phenoxy)nicotinate

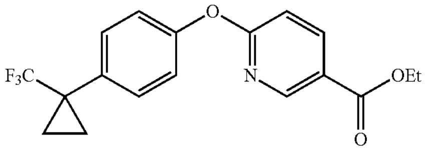 [SMILES: CCOC(=O)c1ccc(Oc2ccc(C3(C(F)(F)F)CC3)cc2)nc1]
748 ethyl 6-(4-(1-(trifluoromethyl)cyclopropyl) phenoxy)nicotinate

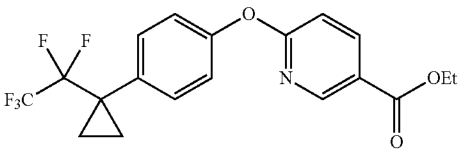 [SMILES: CCOC(=O)c1ccc(Oc2ccc(C3(C(F)(F)C(F)(F)F)CC3)cc2)nc1]
749 ethyl 6-(4-(1-(perfluoroethyl)cyclopropyl) phenoxy)nicotinate

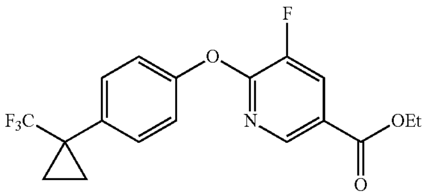 [SMILES: CCOC(=O)c1cnc(Oc2ccc(C3(C(F)(F)F)CC3)cc2)c(F)c1]
750 ethyl 5-fluoro-6-(4-(1-(trifluoromethyl)cyclopropyl) phenoxy)nicotinate

TABLE V-continued

751

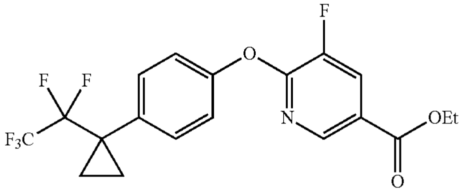 [SMILES: CCOC(=O)c1cnc(Oc2ccc(C3(C(F)(F)C(F)(F)F)CC3)cc2)c(F)c1]

ethyl 5-fluoro-6-(4-(1-(perfluoroethyl)cyclopropyl)phenoxy)nicotinate

752

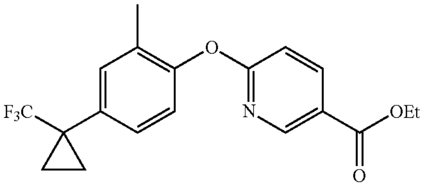 [SMILES: CCOC(=O)c1ccc(Oc2ccc(C3(C(F)(F)F)CC3)cc2C)nc1]

ethyl 6-(2-methyl-4-(1-(trifluoromethyl)cyclopropyl)phenoxy)nicotinate

753

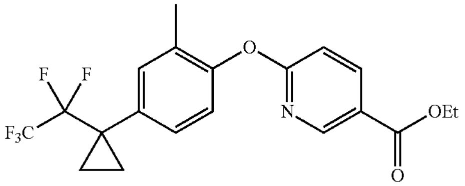 [SMILES: CCOC(=O)c1ccc(Oc2ccc(C3(C(F)(F)C(F)(F)F)CC3)cc2C)nc1]

ethyl 6-(2-methyl-4-(1-(perfluoroethyl)cyclopropyl)phenoxy)nicotinate

754

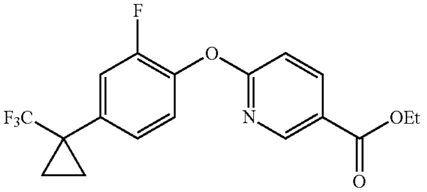

ethyl 6-(2-fluoro-4-(1-(trifluoromethyl)cyclopropyl)phenoxy)nicotinate

755

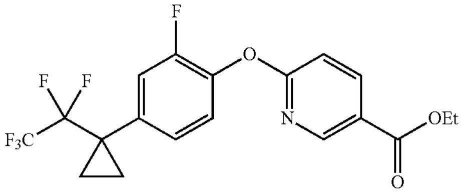 [SMILES: CCOC(=O)c1ccc(Oc2ccc(C3(C(F)(F)C(F)(F)F)CC3)cc2F)nc1]

ethyl 6-(2-fluoro-4-(1-(perfluoroethyl)cyclopropyl)phenoxy)nicotinate

756

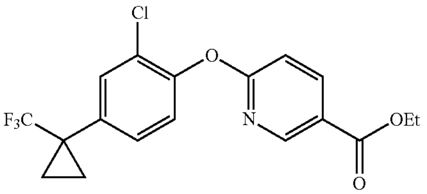

ethyl 6-(2-chloro-4-(1-(trifluoromethyl)cyclopropyl)phenoxy)nicotinate

TABLE V-continued

757

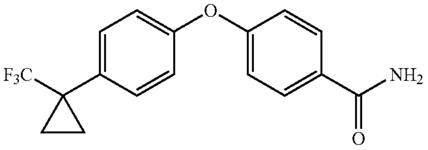

4-(4-(1-(trifluoromethyl)cyclopropyl)phenoxy)benzamide

758

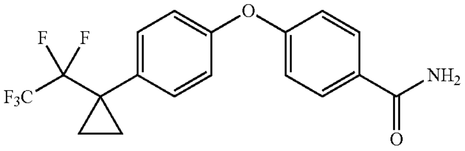 [SMILES: NC(=O)c1ccc(Oc2ccc(C3(C(F)(F)C(F)(F)F)CC3)cc2)cc1]

4-(4-(1-(perfluoroethyl)cyclopropyl)phenoxy)benzamide

759

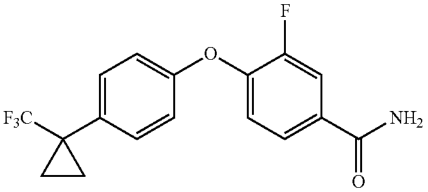 [SMILES: NC(=O)c1ccc(Oc2ccc(C3(C(F)(F)F)CC3)cc2)c(F)c1]

3-fluoro-4-(4-(1-(trifluoromethyl)cyclopropyl)phenoxy)benzamide

760

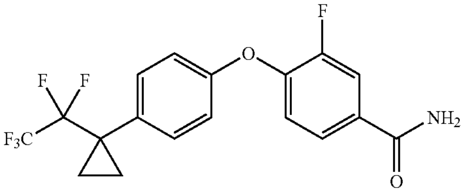 [SMILES: NC(=O)c1ccc(Oc2ccc(C3(C(F)(F)C(F)(F)F)CC3)cc2)c(F)c1]

3-fluoro-4-(4-(1-(perfluoroethyl)cyclopropyl)phenoxy)benzamide

761

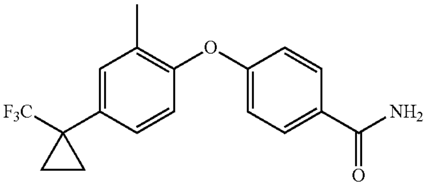 [SMILES: Cc1cc(C2(C(F)(F)F)CC2)ccc1Oc1ccc(C(N)=O)cc1]

4-(2-methyl-4-(1-(trifluoromethyl)cyclopropyl)phenoxy)benzamide

762

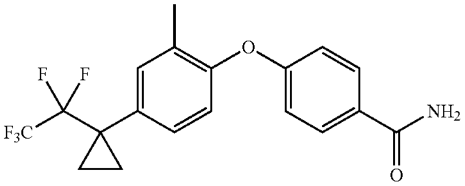 [SMILES: Cc1cc(C2(C(F)(F)C(F)(F)F)CC2)ccc1Oc1ccc(C(N)=O)cc1]

4-(2-methyl-4-(1-(perfluoroethyl)cyclopropyl)phenoxy)benzamide

TABLE V-continued

763

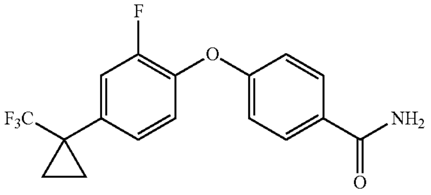 [SMILES: NC(=O)c1ccc(Oc2ccc(C3(C(F)(F)F)CC3)cc2F)cc1]

4-(2-fluoro-4-(1-(trifluoromethyl)cyclopropyl) phenoxy)benzamide

764

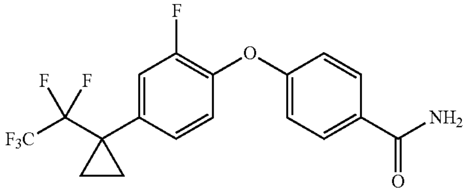 [SMILES: NC(=O)c1ccc(Oc2ccc(C3(C(F)(F)C(F)(F)F)CC3)cc2F)cc1]

4-(2-fluoro-4-(1-(perfluoroethyl)cyclopropyl) phenoxy)benzamide

765

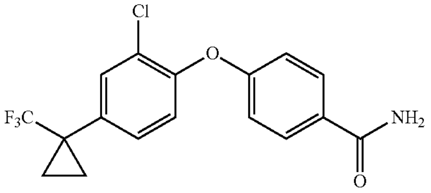 [SMILES: NC(=O)c1ccc(Oc2ccc(C3(C(F)(F)F)CC3)cc2Cl)cc1]

4-(2-chloro-4-(1-(trifluoromethyl)cyclopropyl) phenoxy)benzamide

766

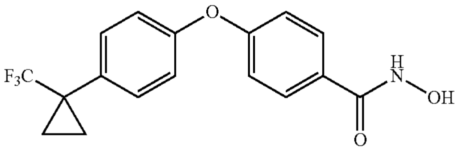 [SMILES: O=C(NO)c1ccc(Oc2ccc(C3(C(F)(F)F)CC3)cc2)cc1]

N-hydroxy-4-(4-(1-(trifluoromethyl)cyclopropyl) phenoxy)benzamide

767

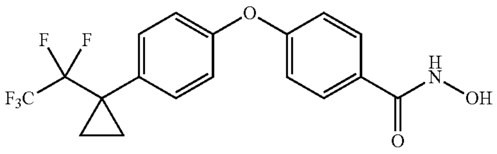 [SMILES: O=C(NO)c1ccc(Oc2ccc(C3(C(F)(F)C(F)(F)F)CC3)cc2)cc1]

N-hydroxy-4-(4-(1-(perfluoroethyl)cyclopropyl) phenoxy)benzamide

768

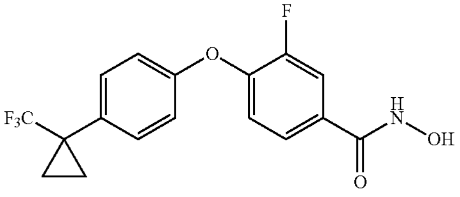 [SMILES: O=C(NO)c1ccc(Oc2ccc(C3(C(F)(F)F)CC3)cc2)c(F)c1]

3-fluoro-N-hydroxy-4-(4-(1-(trifluoromethyl)cyclopropyl) phenoxy)benzamide

TABLE V-continued

769

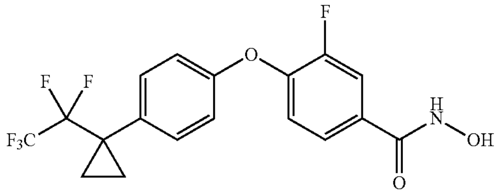 [SMILES: O=C(NO)c1ccc(Oc2ccc(C3(C(F)(F)C(F)(F)F)CC3)cc2)c(F)c1]

3-fluoro-N-hydroxy-4-(4-(1-(perfluoroethyl)cyclopropyl) phenoxy)benzamide

770

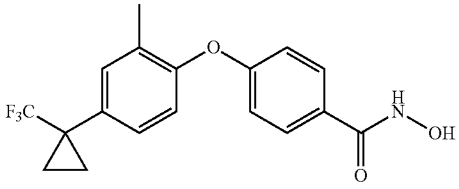 [SMILES: Cc1cc(C2(C(F)(F)F)CC2)ccc1Oc1ccc(C(=O)NO)cc1]

N-hydroxy-4-(2-methyl-4-(1-(trifluoromethyl)cyclopropyl) phenoxy)benzamide

771

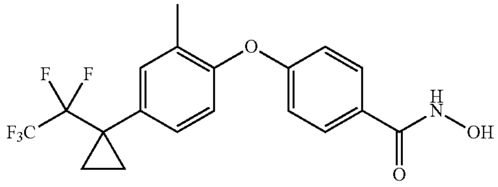 [SMILES: Cc1cc(C2(C(F)(F)C(F)(F)F)CC2)ccc1Oc1ccc(C(=O)NO)cc1]

N-hydroxy-4-(2-methyl-4-(1-(perfluoroethyl)cyclopropyl) phenoxy)benzamide

772

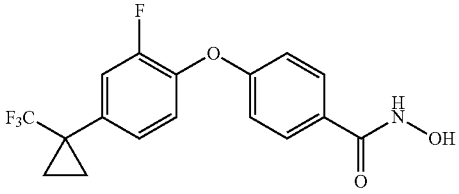 [SMILES: O=C(NO)c1ccc(Oc2ccc(C3(C(F)(F)F)CC3)cc2F)cc1]

4-(2-fluoro-4-(1-(trifluoromethyl)cyclopropyl)phenoxy)-N-hydroxybenzamide

773

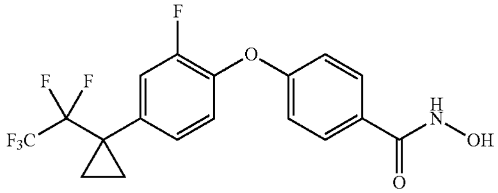 [SMILES: O=C(NO)c1ccc(Oc2ccc(C3(C(F)(F)C(F)(F)F)CC3)cc2F)cc1]

4-(2-fluoro-4-(1-(perfluoroethyl)cyclopropyl)phenoxy)-N-hydroxybenzamide

774

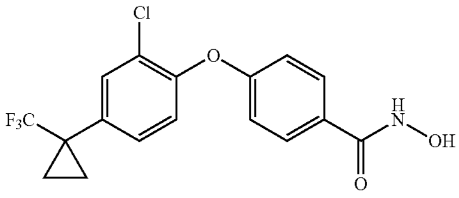 [SMILES: O=C(NO)c1ccc(Oc2ccc(C3(C(F)(F)F)CC3)cc2Cl)cc1]

4-(2-chloro-4-(1-(trifluoromethyl)cyclopropyl)phenoxy)-N-hydroxybenzamide

TABLE V-continued

775

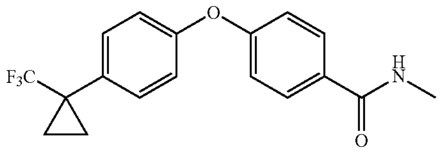

N-methyl-4-(4-(1-(trifluoromethyl)cyclopropyl)phenoxy)benzamide

776

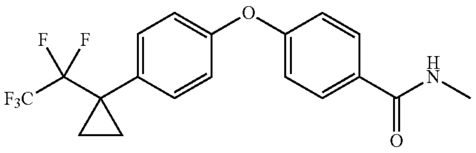 [SMILES: CNC(=O)c1ccc(Oc2ccc(C3(C(F)(F)C(F)(F)F)CC3)cc2)cc1]

N-methyl-4-(4-(1-(perfluoroethyl)cyclopropyl)phenoxy)benzamide

777

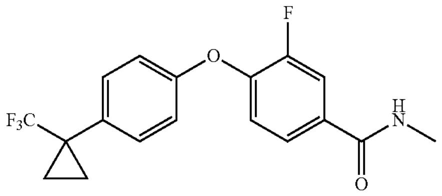 [SMILES: CNC(=O)c1ccc(Oc2ccc(C3(C(F)(F)F)CC3)cc2)c(F)c1]

3-fluoro-N-methyl-4-(4-(1-(trifluoromethyl)cyclopropyl)phenoxy)benzamide

778

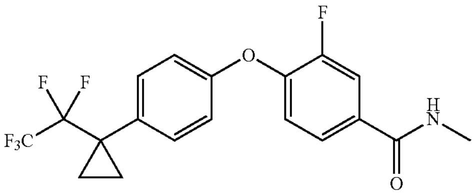 [SMILES: CNC(=O)c1ccc(Oc2ccc(C3(C(F)(F)C(F)(F)F)CC3)cc2)c(F)c1]

3-fluoro-N-methyl-4-(4-(1-(perfluoroethyl)cyclopropyl)phenoxy)benzamide

779

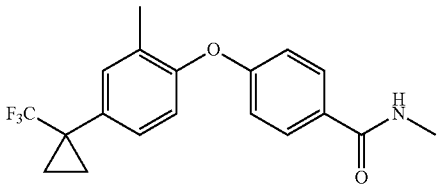 [SMILES: CNC(=O)c1ccc(Oc2ccc(C3(C(F)(F)F)CC3)cc2C)cc1]

N-methyl-4-(2-methyl-4-(1-(trifluoromethyl)cyclopropyl)phenoxy)benzamide

780

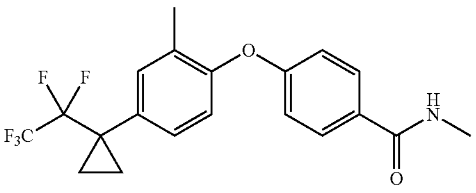 [SMILES: CNC(=O)c1ccc(Oc2ccc(C3(C(F)(F)C(F)(F)F)CC3)cc2C)cc1]

N-methyl-4-(2-methyl-4-(1-(perfluoroethyl)cyclopropyl)phenoxy)benzamide

TABLE V-continued

781

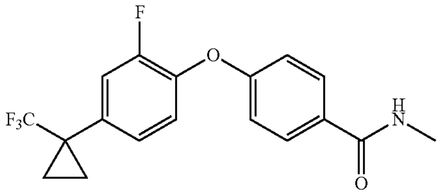 [SMILES: CNC(=O)c1ccc(Oc2ccc(C3(C(F)(F)F)CC3)cc2F)cc1]

4-(2-fluoro-4-(1-(trifluoromethyl)cyclopropyl)phenoxy)-N-methylbenzamide

782

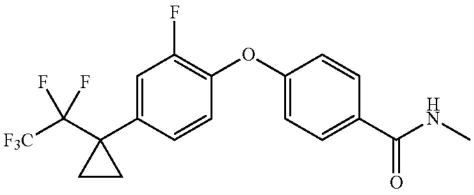 [SMILES: CNC(=O)c1ccc(Oc2ccc(C3(C(F)(F)C(F)(F)F)CC3)cc2F)cc1]

4-(2-fluoro-4-(1-(perfluoroethyl)cyclopropyl)phenoxy)-N-methylbenzamide

783

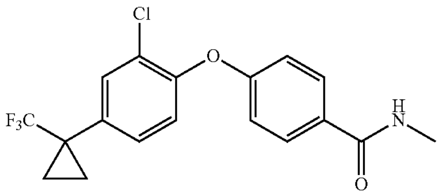 [SMILES: CNC(=O)c1ccc(Oc2ccc(C3(C(F)(F)F)CC3)cc2Cl)cc1]

4-(2-chloro-4-(1-(trifluoromethyl)cyclopropyl)phenoxy)-N-methylbenzamide

784

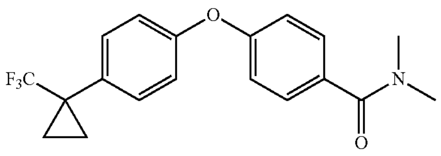 [SMILES: CN(C)C(=O)c1ccc(Oc2ccc(C3(C(F)(F)F)CC3)cc2)cc1]

N,N-dimethyl-4-(4-(1-(trifluoromethyl)cyclopropyl)phenoxy)benzamide

785

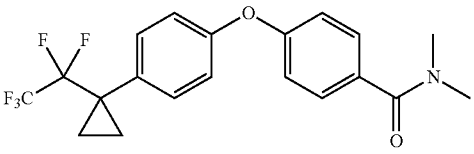 [SMILES: CN(C)C(=O)c1ccc(Oc2ccc(C3(C(F)(F)C(F)(F)F)CC3)cc2)cc1]

N,N-dimethyl-4-(4-(1-(perfluoroethyl)cyclopropyl)phenoxy)benzamide

786

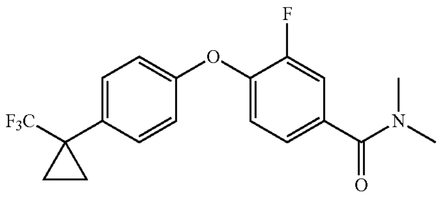 [SMILES: CN(C)C(=O)c1ccc(Oc2ccc(C3(C(F)(F)F)CC3)cc2)c(F)c1]

3-fluoro-N,N-dimethyl-4-(4-(1-(trifluoromethyl)cyclopropyl)phenoxy)benzamide

TABLE V-continued

787

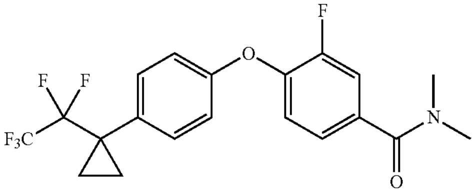 [SMILES: CN(C)C(=O)c1ccc(Oc2ccc(C3(C(F)(F)C(F)(F)F)CC3)cc2)c(F)c1]

3-fluoro-N,N-dimethyl-4-(4-(1-(perfluoroethyl)cyclopropyl) phenoxy)benzamide

788

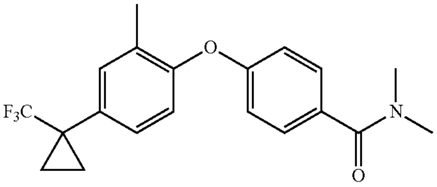 [SMILES: Cc1cc(C2(C(F)(F)F)CC2)ccc1Oc1ccc(C(=O)N(C)C)cc1]

N,N-dimethyl-4-(2-methyl-4-(1-(trifluoromethyl)cyclopropyl)phenoxy)benzamide

789

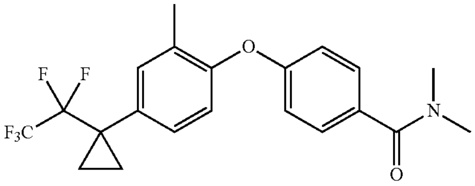 [SMILES: Cc1cc(C2(C(F)(F)C(F)(F)F)CC2)ccc1Oc1ccc(C(=O)N(C)C)cc1]

N,N-dimethyl-4-(2-methyl-4-(1-(perfluoroethyl)cyclopropyl) phenoxy)benzamide

790

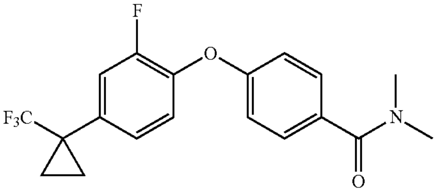 [SMILES: CN(C)C(=O)c1ccc(Oc2ccc(C3(C(F)(F)F)CC3)cc2F)cc1]

4-(2-fluoro-4-(1-(trifluoromethyl)cyclopropyl)phenoxy)-N,N-dimethylbenzamide

791

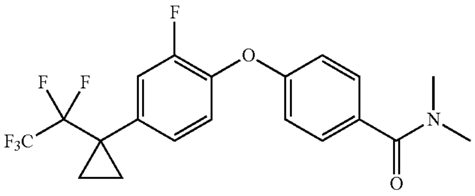 [SMILES: CN(C)C(=O)c1ccc(Oc2ccc(C3(C(F)(F)C(F)(F)F)CC3)cc2F)cc1]

4-(2-fluoro-4-(1-(perfluoroethyl)cyclopropyl)phenoxy)-N,N-dimethylbenzamide

792

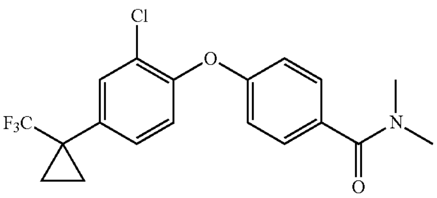 [SMILES: CN(C)C(=O)c1ccc(Oc2ccc(C3(C(F)(F)F)CC3)cc2Cl)cc1]

4-(2-chloro-4-(1-(trifluoromethyl)cyclopropyl)phenoxy)-N,N-dimethylbenzamide

TABLE V-continued

793

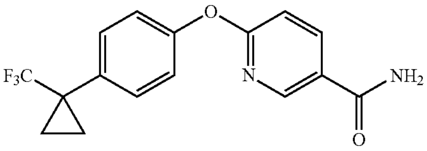

6-(4-(1-(trifluoromethyl)cyclopropyl) phenoxy)nicotinamide

794

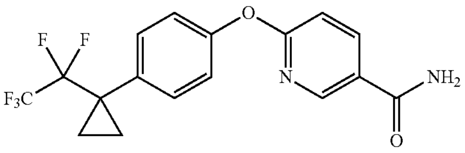 [SMILES: NC(=O)c1ccc(Oc2ccc(C3(C(F)(F)C(F)(F)F)CC3)cc2)nc1]

6-(4-(1-(perfluoroethyl)cyclopropyl) phenoxy)nicotinamide

795

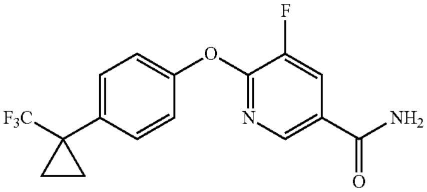 [SMILES: NC(=O)c1cnc(Oc2ccc(C3(C(F)(F)F)CC3)cc2)c(F)c1]

5-fluoro-6-(4-(1-(trifluoromethyl)cyclopropyl) phenoxy)nicotinamide

796

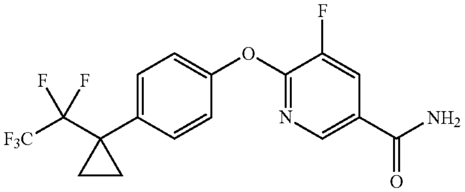 [SMILES: NC(=O)c1cnc(Oc2ccc(C3(C(F)(F)C(F)(F)F)CC3)cc2)c(F)c1]

5-fluoro-6-(4-(1-(perfluoroethyl)cyclopropyl) phenoxy)nicotinamide

797

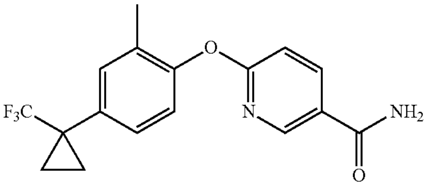 [SMILES: Cc1cc(C2(C(F)(F)F)CC2)ccc1Oc1ccc(C(N)=O)cn1]

6-(2-methyl-4-(1-(trifluoromethyl)cyclopropyl) phenoxy)nicotinamide

798

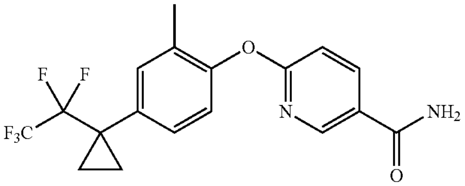 [SMILES: Cc1cc(C2(C(F)(F)C(F)(F)F)CC2)ccc1Oc1ccc(C(N)=O)cn1]

6-(2-methyl-4-(1-(perfluoroethyl)cyclopropyl) phenoxy)nicotinamide

TABLE V-continued

799

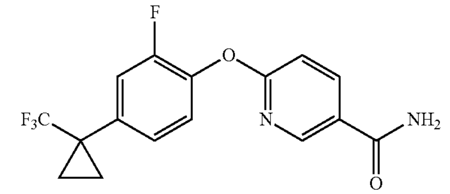 [SMILES: NC(=O)c1ccc(Oc2ccc(C3(C(F)(F)F)CC3)cc2F)nc1]

6-(2-fluoro-4-(1-(trifluoromethyl)cyclopropyl)phenoxy)nicotinamide

800

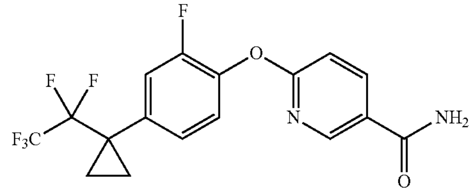 [SMILES: NC(=O)c1ccc(Oc2ccc(C3(C(F)(F)C(F)(F)F)CC3)cc2F)nc1]

6-(2-fluoro-4-(1-(perfluoroethyl)cyclopropyl)phenoxy)nicotinamide

801

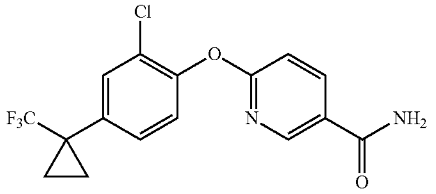 [SMILES: NC(=O)c1ccc(Oc2ccc(C3(C(F)(F)F)CC3)cc2Cl)nc1]

6-(2-chloro-4-(1-(trifluoromethyl)cyclopropyl)phenoxy)nicotinamide

802

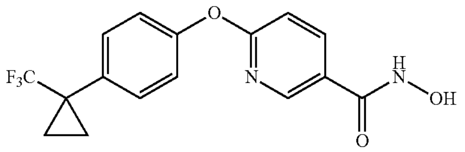 [SMILES: O=C(NO)c1ccc(Oc2ccc(C3(C(F)(F)F)CC3)cc2)nc1]

N-hydroxy-6-(4-(1-(trifluoromethyl)cyclopropyl)phenoxy)nicotinamide

803

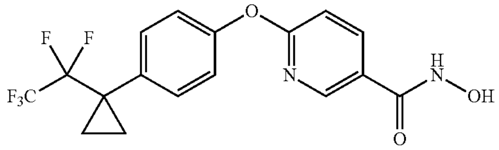 [SMILES: O=C(NO)c1ccc(Oc2ccc(C3(C(F)(F)C(F)(F)F)CC3)cc2)nc1]

N-hydroxy-6-(4-(1-(perfluoroethyl)cyclopropyl)phenoxy)nicotinamide

804

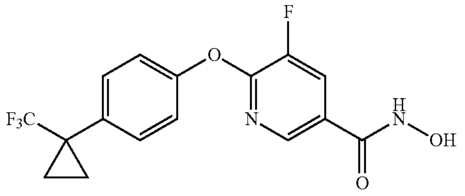 [SMILES: O=C(NO)c1cnc(Oc2ccc(C3(C(F)(F)F)CC3)cc2)c(F)c1]

5-fluoro-N-hydroxy-6-(4-(1-(trifluoromethyl)cyclopropyl)phenoxy)nicotinamide

TABLE V-continued

805

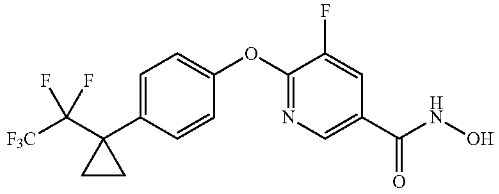 [SMILES: O=C(NO)c1cnc(Oc2ccc(C3(C(F)(F)C(F)(F)F)CC3)cc2)c(F)c1]

5-fluoro-N-hydroxy-6-(4-(1-(perfluoroethyl)cyclopropyl)phenoxy)nicotinamide

806

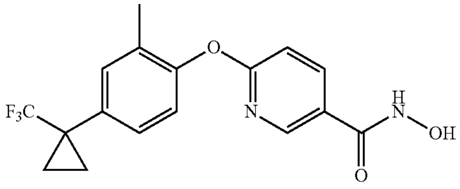 [SMILES: Cc1cc(C2(C(F)(F)F)CC2)ccc1Oc1ccc(C(=O)NO)cn1]

N-hydroxy-6-(2-methyl-4-(1-(trifluoroemthyl)cyclopropyl)phenoxy)nicotinamide

807

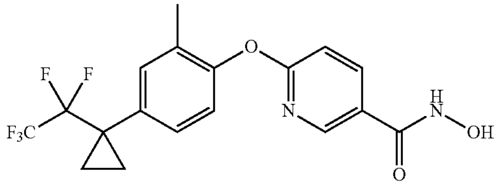 [SMILES: Cc1cc(C2(C(F)(F)C(F)(F)F)CC2)ccc1Oc1ccc(C(=O)NO)cn1]

N-hydroxy-6-(2-methyl-4-(1-(perfluoroethyl)cyclopropyl)phenoxy)nicotinamide

808

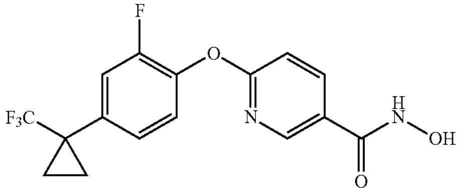

6-(2-fluoro-4-(1-(trifluoromethyl)cyclopropyl)phenoxy)-N-hydroxynicotinamide

809

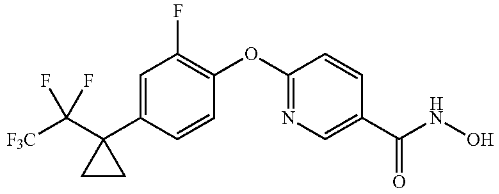 [SMILES: O=C(NO)c1ccc(Oc2ccc(C3(C(F)(F)C(F)(F)F)CC3)cc2F)nc1]

6-(2-fluoro-4-(1-(perfluoroethyl)cyclopropyl)phenoxy)-N-hydroxynicotinamide

810

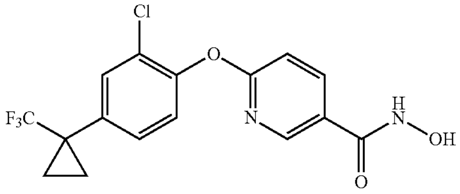

6-(2-chloro-4-(1-(trifluoromethyl)cyclopropyl)phenoxy)-N-hydroxynicotinamide

TABLE V-continued

811

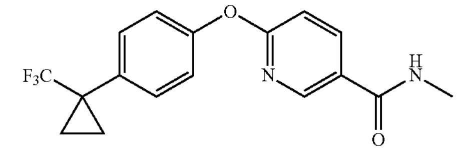 [SMILES: CNC(=O)c1ccc(Oc2ccc(C3(C(F)(F)F)CC3)cc2)nc1]

N-methyl-4-(4-(1-(trifluoromethyl)cyclopropyl) phenoxy)benzamide

812

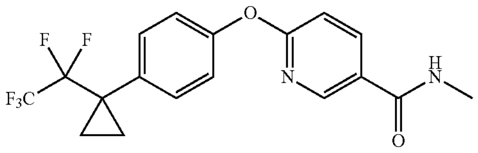 [SMILES: CNC(=O)c1ccc(Oc2ccc(C3(C(F)(F)C(F)(F)F)CC3)cc2)nc1]

N-methyl-4-(4-(1-(perfluoroethyl)cyclopropyl) phenoxy)benzamide

813

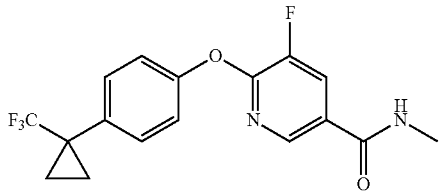 [SMILES: CNC(=O)c1cnc(Oc2ccc(C3(C(F)(F)F)CC3)cc2)c(F)c1]

3-fluoro-N-methyl-4-(4-(1-(trifluoromethyl)cyclopropyl) phenoxy)benzamide

814

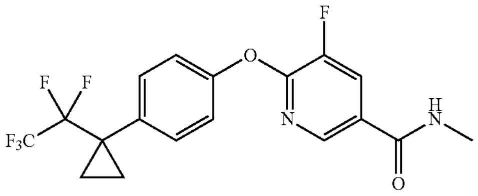 [SMILES: CNC(=O)c1cnc(Oc2ccc(C3(C(F)(F)C(F)(F)F)CC3)cc2)c(F)c1]

3-fluoro-N-methyl-4-(4-(1-(perfluoroethyl)cyclopropyl) phenoxy)benzamide

815

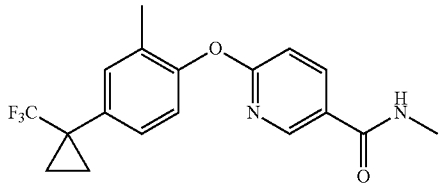 [SMILES: CNC(=O)c1ccc(Oc2ccc(C3(C(F)(F)F)CC3)cc2C)nc1]

N-methyl-4-(2-methyl-4-(1-(trifluoromethyl)cyclopropyl) phenoxy)benzamide

816

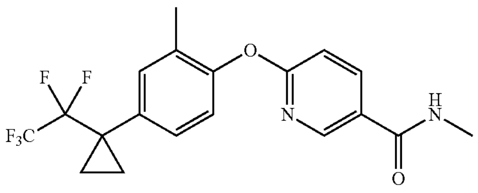 [SMILES: CNC(=O)c1ccc(Oc2ccc(C3(C(F)(F)C(F)(F)F)CC3)cc2C)nc1]

N-methyl-4-(2-methyl-4-(1-(perfluoroethyl)cyclopropyl) phenoxy)benzamide

TABLE V-continued

817

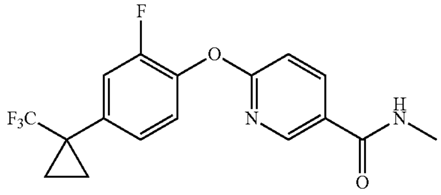 [SMILES: CNC(=O)c1ccc(Oc2ccc(C3(C(F)(F)F)CC3)cc2F)nc1]

4-(2-fluoro-4-(1-(trifluoromethyl)cyclopropyl)phenoxy)-N-methylbenzamide

818

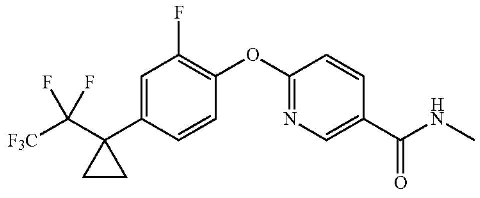 [SMILES: CNC(=O)c1ccc(Oc2ccc(C3(C(F)(F)C(F)(F)F)CC3)cc2F)nc1]

4-(2-fluoro-4-(1-(perfluoroethyl)cyclopropyl)phenoxy)-N-methylbenzamide

819

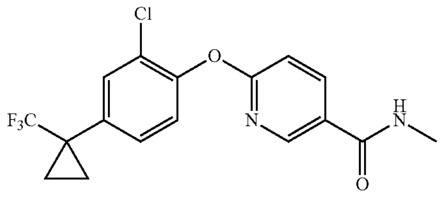 [SMILES: CNC(=O)c1ccc(Oc2ccc(C3(C(F)(F)F)CC3)cc2Cl)nc1]

4-(2-chloro-4-(1-(trifluoromethyl)cyclopropyl)phenoxy)-N-methylbenzamide

820

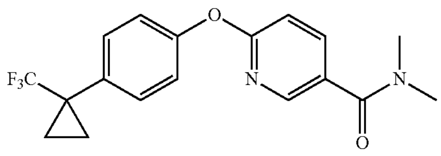 [SMILES: CN(C)C(=O)c1ccc(Oc2ccc(C3(C(F)(F)F)CC3)cc2)nc1]

N,N-dimethyl-6-(4-(1-(trifluoromethyl)cyclopropyl) phenoxy)nicotinamide

821

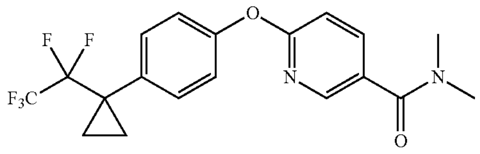 [SMILES: CN(C)C(=O)c1ccc(Oc2ccc(C3(C(F)(F)C(F)(F)F)CC3)cc2)nc1]

N,N-dimethyl-6-(4-(1-(perfluoroethyl)cyclopropyl) phenoxy)nicotinamide

822

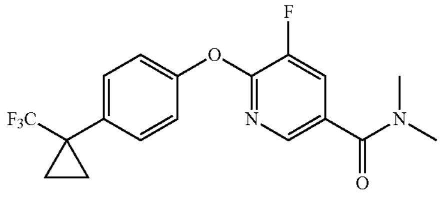 [SMILES: CN(C)C(=O)c1cnc(Oc2ccc(C3(C(F)(F)F)CC3)cc2)c(F)c1]

5-fluoro-N,N-dimethyl-6-(4-(1-(trifluoromethyl)cyclopropyl) phenoxy)nicotinamide TABLE V-continued

823

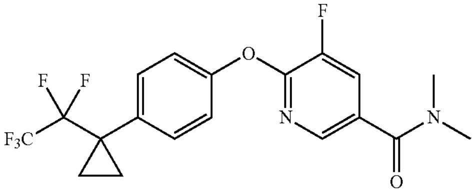 [SMILES: CN(C)C(=O)c1cnc(Oc2ccc(C3(C(F)(F)C(F)(F)F)CC3)cc2)c(F)c1]

5-fluoro-N,N-dimethyl-6-(4-(1-(perfluoroethyl)cyclopropyl) phenoxy)nicotinamide

824

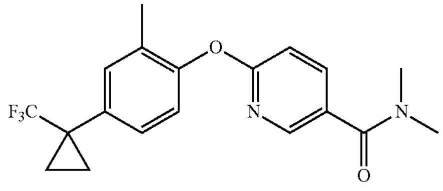 [SMILES: Cc1cc(C2(C(F)(F)F)CC2)ccc1Oc1ccc(C(=O)N(C)C)cn1]

N,N-dimethyl-6-(2-methyl-4-(1-(trifluoromethyl)cyclopropyl) phenoxy)nicotinamide

825

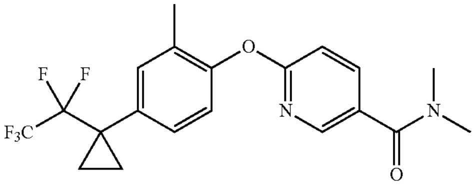 [SMILES: Cc1cc(C2(C(F)(F)C(F)(F)F)CC2)ccc1Oc1ccc(C(=O)N(C)C)cn1]

N,N-dimethyl-6-(2-methyl-4-(1-(perfluoroethyl)cyclopropyl) phenoxy)nicotinamide

826

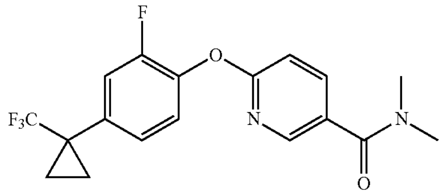 [SMILES: CN(C)C(=O)c1ccc(Oc2ccc(C3(C(F)(F)F)CC3)cc2F)nc1]

6-(2-fluoro-4-(1-(trifluoromethyl)cyclopropyl)phenoxy)-N,N-dimethylnicotinamide

827

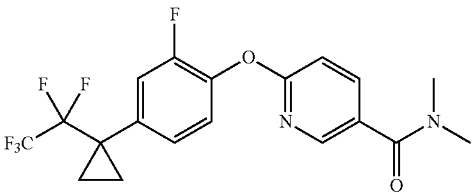 [SMILES: CN(C)C(=O)c1ccc(Oc2ccc(C3(C(F)(F)C(F)(F)F)CC3)cc2F)nc1]

6-(2-fluoro-4-(1-(perfluoroethyl)cyclopropyl)phenoxy)-N,N-dimethylnicotinamide

828

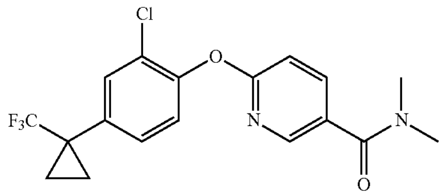 [SMILES: CN(C)C(=O)c1ccc(Oc2ccc(C3(C(F)(F)F)CC3)cc2Cl)nc1]

6-(2-chloro-4-(1-(trifluoromethyl)cyclopropyl)phenoxy)-N,N-dimethylnicotinamide

Also included are isomers, e.g. enantiomers or diastereomers or rotamers or mixtures of isomers, salts, particularly pharmaceutically acceptable salts, and solvates of the compounds listed above.

Further Definitions

The term "$C_1$-$C_{12}$ alkyl" comprises all isomers of the corresponding saturated aliphatic hydrocarbon groups containing one to twelve carbon atoms; this includes methyl, ethyl, n-propyl, iso-propyl, n-butyl, sec-butyl, iso-butyl, tert-butyl, n-pentyl, sec-pentyl, 3-pentyl, 2-methylbutyl, iso-pentyl, 2-methylbut-2-yl, 3-methylbut-2-yl, all hexyl-isomers, all heptyl-isomers, all octyl-isomers, all nonyl-isomers, all decyl-isomers, all undecyl-isomers and all dodecyl-isomers. The term "$C_2$-$C_{12}$ alkenyl" comprises all isomers of the corresponding unsaturated olefinic hydrocarbon groups containing two to twelve carbon atoms linked by one or more double bonds; this includes vinyl, all propenyl-isomers, all butenyl-isomers, all pentenyl-isomers, all hexenyl-isomers, all heptenyl-isomers, all octenyl-isomers, all nonenyl-isomers, all decenyl-isomers, all undecenyl-isomers and all dodecenyl-isomers.

The term "$C_2$-$C_{12}$ alkynyl" comprises all isomers of the corresponding unsaturated olefinic hydrocarbon groups containing two to twelve carbon atoms linked by one or more triple bonds; this includes ethynyl, all propynyl-isomers, all butynyl-isomers, all pentynyl-isomers, all hexynyl-isomers, all heptynyl-isomers, all octynyl-isomers, all nonynyl-isomers, all decynyl-isomers, all undecynyl-isomers and all dodecynyl-isomers. The term "alkynyl" also includes compounds having one or more triple bonds and one or more double bonds.

The term "$C_3$-$C_8$ cycloalkyl" comprises the corresponding saturated hydrocarbon groups containing three to eight carbon atoms arranged in a monocyclic ring structure; this includes cyclopropyl, cyclobutyl, cyclopentyl, cyclohexyl, cycloheptyl, cyclooctyl.

The term "$C_3$-$C_8$ cycloalkenyl" comprises the corresponding unsaturated non-aromatic, anti-aromatic or aromatic hydrocarbon groups containing three to eight carbon atoms arranged in a monocyclic ring structure and linked by one or more double bonds; this includes cyclopropenyl, all cyclobutenyl-isomers, all cyclopentenyl-isomers, all cyclohexenyl-isomers, all cycloheptenyl-isomers, all cyclooctenyl-isomers.

The term "$C_4$-$C_{12}$ bicycloalkyl" comprises the corresponding saturated hydrocarbon groups containing four to twelve carbon atoms arranged in a bicyclic ring structure;

The term "$C_6$-$C_{12}$ bicycloalkenyl" comprises the corresponding unsaturated hydrocarbon groups containing six to twelve carbon atoms arranged in a bicyclic ring structure and linked by one or more double bonds;

The term "$C_5$-$C_{14}$ tricycloalkyl" comprises the corresponding saturated hydrocarbon groups containing five to fourteen carbon atoms arranged in a tricyclic ring structure;

The term "perhalogenated" relates to the exhaustive halogenation of the carbon scaffold; according residues comprise the corresponding perfluorinated, perchlorinated, perbrominated and periodinated groups. Preferably, the term "perhalogenated" relates to perfluorinated or perchlorinated groups, more preferably to perfluorinated groups.

The following contains definitions of terms used in this specification. The initial definition provided for a group or term herein applies to that group or term throughout the present specification, individually or as part of another group, unless otherwise indicated.

The compounds of the present invention may form salts, which are also within the scope of this invention. Reference to a compound of the invention herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the substituents comprise an acid moiety such as a carboxyl group). Also included herein are quaternary ammonium salts such as alkylammonium salts. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, tert-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, $17^{th}$ ed., Mack Publishing Company, Easton, Pa., 1985, p. 1418 and *Journal of Pharmaceutical Science* 1977, 66 (2), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Furthermore, in the case of the compounds of the invention which contain an asymmetric carbon atom, the invention relates to the D form, the L form and D,L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

Also included are solvates and hydrates of the compounds of the invention and solvates and hydrates of their pharmaceutically acceptable salts.

The term “compound” as used herein is meant to include all stereoisomers, geometric isomers, tautomers, rotamers, and isotopes of the structures depicted, unless otherwise indicated.

In some embodiments, the compound can be provided as a prodrug. The term “prodrug”, as employed herein, denotes a compound, which, upon administration to a subject, undergoes chemical conversion by metabolic or chemical processes to yield a compound of the invention, or a salt and/or solvate thereof.

In some embodiments, the compounds of the invention, and salts thereof, are substantially isolated. By “substantially isolated” is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

Pharmaceutical Methods

The compounds according to the invention have been found to have pharmacologically important properties, which can be used therapeutically. The compounds of the invention can be used alone, in combination with each other or in combination with other active compounds.

In certain embodiments, compounds of the present invention may be enhancers of Notch signalling.

The communication between cells via Notch signaling (reviewed in Kopan et al., *Cell* 2009, 137, 216-233; Bray, *Nat. Rev. Mol. Cell Biol.* 2016, 17, 722-735) is in the first step mediated by two types of transmembrane proteins: The Notch receptors being distributed within the cell membrane of the signal-receiving cell and the Notch ligands covering the membrane of the signal-sending cell. Mechanistically, Notch signaling is activated by receptor-ligand interaction, which leads to the proteolytic release of the intra cellular domain (NICD) of the membrane bound Notch receptor into the inside of the signal receiving cell. Subsequent translocation of NICD into the nucleus in turn leads to the transcriptional activation of certain and cell type specific genes. The Notch-mediated alteration of the previous gene-expression program of a cell is manifested in according cellular changes, which represent the response of the cell to a Notch signal.

The activation level of Notch signaling can be quantified in vitro most reliably by measuring the expression levels of Notch specific target genes. This can be accomplished by the quantification of corresponding mRNA or protein of a particular Notch target gene. Alternatively, cells can be genetically modified to carry a luciferase gene as an artificial Notch target gene, which is expressed in dependence of Notch activity. In this setting, Notch signaling levels can be quantified by measuring the luciferase-derived bioluminescence values.

An according Notch-reporter assay, i.e. a luciferase-based luminescence readout, was used here to quantify the ability of the claimed small molecules to augment Notch signaling in a cellular system. For this purpose, HeLa cells, obtainable from the American Type Culture Collection (ATCC) under the accession number ATCC-CCL-2, were transiently transfected for 24 hours using FuGENE® HD (Promega, #E2311) as transfection reagent with expression vectors of a membrane-tethered form of the constitutively active intracellular domain of the human Notch1 receptor (hNotch1ΔE) to activate the signaling cascade (BPS Bioscience, human analogue to Notch Pathway Reporter Kit #60509 component C), a Firefly luciferase being expressed under the control of a Notch-responsive promoter to monitor Notch signaling (BPS Bioscience, Notch Pathway Reporter Kit #60509, CSL luciferase reporter vector from component A not premixed with Renilla luciferase vector), and a Renilla luciferase being constitutively expressed in a Notch signaling independent manner to include a measure for the cell number per sample (Promega, pRL-SV40, #E2231). HeLa cells were cultivated according to the protocol of the provider in DMEM medium (Fisherscientific, #11584456) containing 10% fetal bovine serum (Fisherscientific, #15517589). The transfection was carried out in a 100 mm-culture dish (StarLab, #CC7682-3394) with cells being properly attached to the plate at a cell confluency of 80-90% in a total volume of 7 mL culture medium. Per dish to be transfected, a transfection mix was prepared by adding to 238 μL Opti-MEM (Fisherscientific, #10149832) 40 μL of the hNotch1ΔE expression vector (100 ng/μL), 80 μL of the CSL luciferase reporter vector (40 ng/μL), 4 μL of the pRL-SV40-Renilla luciferase vector (10 ng/μL), and in the last step 18.1 μL of FuGENE® HD. After addition of FuGENE® HD the transfection mix was let stand for 15 min at room temperature and hereafter equally distributed into the culture dish. Subsequently, i.e. after 24 hours of transfection, the transfected cells (10.000 cells per well) were incubated with the test-compounds at a final concentration of 10 μM (diluted from 10 mM stock-solutions in DMSO to a final DMSO concentration of 0.1% v/v) or with the empty carrier DMSO at 0.1% v/v as control for 20 hours in 96-well plates suitable for luminescence readouts (CORNING, #3610). Hereafter, the cells were lysed with 30 μL per well of Passive Lysis Buffer (Promega, #E194A, component of Dual-Luciferase® Reporter Assay System, #E1910) and the Firefly as well as Renilla luciferase values were measured with a luminescence reader with applying 15 μL per well each of the corresponding enzyme substrates needed to create the luminescence signals (Promega, Dual-Luciferase® Reporter Assay System, #E1910).

The suitability of the assays for monitoring Notch signaling was controlled by additionally including a generally accepted commercial Notch inhibitor, i.e. DAPT, as negative control, as well as the reported Notch enhancer resveratrol (RES) as positive control (Pinchot et al., *Cancer* 2011, 117, 1386-1398; Truong et al., *Ann. Surg. Oncol.* 2011, 18, 1506-1511; Yu et al., *Mol. Cancer Ther.* 2013, 12, 1276-1287). Both control compounds were likewise tested at 10 μM.

Per single experiment the measurement was performed in six replicates per compound. For every compound, this experiment was repeated in three or more independent replicates. The values of the Notch-reporter luciferase were normalized by division through the corresponding individual Notch-independent Renilla values in order to eliminate the impact of variation in the absolute cell-numbers in between the samples. For every individual plate, a second normalization was performed against the equally weighted arithmetic mean (here abbreviated as AVE) of the six associated Renilla-normalized DMSO-control values within a single experiment in order to obtain the relative values to a baseline level of 1.0. Two independent outlier analyses were performed according to the methods by Peirce and Chauvenet (Ross, *Journal of Engineering Technology* 2003, 1-12). Outliers confirmed by at least one of the methods were excluded from the calculations but not more than one value out of six per compound within a single experiment. The weighted arithmetic mean (here abbreviated as $AVE_w$)

for each compound was calculated from the double-normalized values over all independent replicates of the single experiments comprising the six replicates each. The corresponding standard deviation for the weighted arithmetic mean was calculated according to the method described by Bronstein et al. (Bronstein, Semendjajew, Musiol, Mühlig, Taschenbuch der Mathematik, 5th edition 2001 (German), publisher: Verlag Harri Deutsch, Frankfurt am Main and Thun) and was combined with the Gauß' error propagation associated with the performed calculation for the normalization. The resulting standard deviation is herein referred to as "combined standard deviation".

A compound is considered as a Notch augmenting molecule, i.e. an enhancer of Notch signaling, if the weighted arithmetic mean of the luminescence values after subtraction of the corresponding combined standard deviation amounts to 1.1 or higher, in particular to 1.2 or higher, 1.3 or higher, 1.4 or higher, 1.5 or higher, 1.7 or higher, and 2.0 or higher relative to the overall basis level of 1.0. The overall basis level was calculated as the weighted arithmetic mean of all double-normalized values from the DMSO control measurements in analogy to the calculations performed for the test-compounds. The corresponding combined standard deviation for the DMSO values amounts to less than $1 \cdot 10^{-2}$.

According to the method described above, several molecules falling under the scope of the five compound families herein defined in formula I, formula II, formula III, formula IV and formula V have been identified as enhancers of Notch signaling. The so far identified Notch enhancers relate to the compounds listed in Table VI. The entries of Table VI are categorized by the corresponding weighted arithmetic mean of the compounds falling into the activity ranges as indicated.

TABLE VI

| Notch reporter assay | | | |
|---|---|---|---|
| Activity Range | Entry | Compound | Specification |
| $AVE_w \geq 2.0$ | 1 | 030 | |
| | 2 | 186 | |
| | 3 | 322 | |
| $1.7 \leq AVE_w < 2.0$ | 4 | 003 | |
| | 5 | 005 | |
| | 6 | 027 | |
| | 7 | 043 | |
| | 8 | 045 | |
| | 9 | 051 | |
| | 10 | 114 | |
| | 11 | 272 | |
| | 12 | 284 | |
| | 13 | 288 | |
| | 14 | 318 | |
| $1.4 \leq AVE_w < 1.7$ | 15 | 004 | |
| | 16 | 026 | |
| | 17 | 041 | |
| | 18 | 050 | |
| | 19 | 052 | |
| | 20 | 067 | |
| | 21 | 071 | |
| | 22 | 072 | |
| | 23 | 073 | |
| | 24 | 075 | |
| | 25 | 117 | |
| | 26 | 120 | |
| | 27 | 134 | |
| | 28 | 216 | |
| | 29 | 266 | |
| | 30 | 269 | |
| | 31 | 291 | |
| | 32 | 297 | |
| | 33 | 317 | |

TABLE VI-continued

| Notch reporter assay | | | |
|---|---|---|---|
| Activity Range | Entry | Compound | Specification |
| | 34 | 336 | |
| | 35 | 337 | |
| | 36 | 385 | |
| | 37 | 394 | |
| | 38 | 395 | |
| | 39 | 410 | |
| | 40 | 544 | |
| | 41 | 820 | |
| 1.5 ± 0.0 | 42 | RES | Positive control |
| $1.3 \leq AVE_w < 1.4$ | 43 | 044 | |
| | 44 | 066 | |
| | 45 | 122 | |
| | 46 | 168 | |
| | 47 | 182 | |
| | 48 | 184 | |
| | 49 | 268 | |
| | 50 | 286 | |
| | 51 | 292 | |
| | 52 | 319 | |
| | 53 | 334 | |
| | 54 | 344 | |
| $1.2 \leq AVE_w < 1.3$ | 55 | 007 | |
| | 56 | 019 | |
| | 57 | 025 | |
| | 58 | 091 | |
| | 59 | 092 | |
| | 60 | 133 | |
| | 61 | 166 | |
| | 62 | 195 | |
| | 63 | 217 | |
| | 64 | 222 | |
| | 65 | 241 | |
| | 66 | 242 | |
| | 67 | 247 | |
| | 68 | 273 | |
| | 69 | 275 | |
| | 70 | 316 | |
| | 71 | 325 | |
| | 72 | 363 | |
| | 73 | 396 | |
| | 74 | 784 | |
| $1.1 \leq AVE_w < 1.2$ | 75 | 086 | |
| | 76 | 118 | |
| | 77 | 159 | |
| | 78 | 170 | |
| | 79 | 171 | |
| | 80 | 189 | |
| | 81 | 215 | |
| | 82 | 221 | |
| | 83 | 234 | |
| | 84 | 267 | |
| | 85 | 287 | |
| | 86 | 300 | |
| | 87 | 323 | |
| | 88 | 343 | |
| | 89 | 374 | |
| | 90 | 399 | |
| | 91 | 451 | |
| | 92 | 644 | |
| | 93 | 703 | |
| | 94 | 712 | |
| | 95 | 721 | |
| | 96 | 730 | |
| 1.0 ± 0.0 | 97 | DMSO | Baseline control |
| 0.1 ± 0.0 | 98 | DAPT | Negative control |

Several other molecules have not been identified as enhancers of Notch signaling according to the above method.

In the course of the evaluation of molecules falling under formula I, formula II, formula III, formula IV and formula V in further cellular assays, results indicate that compounds of said molecule families exhibit growth inhibiting properties in hyperproliferative processes. In some cases, the growth inhibiting properties correlate with Notch enhancing properties, in other cases the growth inhibiting properties do not correlate with Notch enhancing properties.

The biological activity of the claimed compounds can be attributed to but may not be limited to Notch signaling enhancing activity. The secondary mechanisms of the claimed compounds leading to antiproliferative effects can be used alternatively or in combination with the Notch enhancing properties in medicinal treatments, preferably in the treatment of hyperproliferative disorders including cancer and non-malignant hyperproliferative disorders.

The antiproliferative activities of compounds falling under formula I, formula II, formula III, formula IV and formula V were investigated on cells or cell lines originating from a disorder of the myeloid cell compartment, the neuroendocrine system, the cervix, and the mucosal epithelium, as well as from the skin epithelium. To this end, HL-60 cells, TT cells, HeLa cells, CAL-27 cells and human primary epidermal keratinocytes (HPEK) were seeded into 96-well plates suitable for fluorescence assays (CORNING #3598) at following initial cell numbers: 1000 cells per well for HL-60; 9000 cells per well for TT; 2000 cells per well for HeLa, 2000 cells per well for CAL-27, 2000 cells per well for HPEK. The cells were treated with compounds at indicated final concentrations (diluted from the 1000× stock-solutions in DMSO to a final DMSO concentration of 0.1% v/v) or with the empty carrier DMSO at 0.1% v/v as control for 5 days. At day 5 after starting the treatments the cells were subjected to the alamarBlue® Proliferation Assay (Bio-Rad Serotec GmbH, BUF012B) according to the protocol of the manufacturer. The readout was taken with a multi-well plate-reader in the fluorescence mode with applying a filter for excitation at 560 nm (band width 10 nm) and for emission at 590 nm (band width 10 nm). Resveratrol (RES) treatment was included as control for growth inhibition.

The assays were performed in duplicate or more replicates of independent single experiments each containing a six-fold replicate for every condition. For every individual plate, the measured fluorescence intensity values of the conditions with compound treatment were normalized against the corresponding equally weighted arithmetic mean of the fluorescence intensity values of the six DMSO treated control wells in order to obtain the relative values to a baseline level of 1.0. The statistical calculations were performed in analogy to the luciferase assay as described above. To this end, two independent outlier analyses were performed according to the methods by Peirce and Chauvenet (Ross, *Journal of Engineering Technology* 2003, 1-12). Outliers confirmed by at least one of the methods were excluded from the calculations but not more than one value out of six per compound within a single experiment. The weighted arithmetic mean $AVE_w$ for each compound was calculated from the normalized values over all independent replicates of the single experiments comprising the six replicates each. The corresponding standard deviation for the weighted arithmetic mean was calculated according to the method described by Bronstein et al. (Bronstein, Semendjajew, Musiol, Mühlig, Taschenbuch der Mathematik, $5^{th}$ edition 2001 (German), publisher: Verlag Harri Deutsch, Frankfurt am Main and Thun) and was combined with the Gauß' error propagation associated with the performed calculation for the normalization. The resulting standard deviation is herein referred to as "combined standard deviation".

In certain embodiments, the compounds of the present invention may be growth inhibitors in hyperproliferative processes, including malignant and non-malignant hyperproliferative processes.

In one embodiment, several compounds of the invention were found to inhibit the growth of HL-60 cells (human acute myeloid leukemia cells) obtainable from the Deutsche Sammlung von Mikroorganismen and Zellkulturen GmbH (DSMZ) under the accession number ACC 3. HL-60 cells were cultivated according to the protocol of the provider in RPMI 1640 medium (Fisherscientific, #11554526) containing 10% fetal bovine serum (Fisherscientific, #15517589).

A compound is considered as a growth inhibitor of HL-60 cells, if—at a reference concentration of 20 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling under the scope of the five compound families herein defined in formula I, formula II, formula III, formula IV and formula V have been identified as growth inhibitors of HL-60 cells. The so far identified HL-60 growth inhibitors relate to the compounds listed in Table VII. The entries of Table VII are categorized by the corresponding weighted arithmetic means of the compounds falling into the activity ranges as indicated.

TABLE VII

Proliferation assay with HL-60 cells at 20 μM

| Activity Range | Entry | Compound | Specification |
|---|---|---|---|
| 1.0 ± 0.0 | 1 | DMSO | Baseline control |
| $0.8 < AVE_w \leq 0.9$ | 2 | 002 | |
| | 3 | 030 | |
| | 4 | 054 | |
| | 5 | 072 | |
| | 6 | 073 | |
| | 7 | 075 | |
| | 8 | 087 | |
| | 9 | 092 | |
| | 10 | 165 | |
| | 11 | 245 | |
| | 12 | 248 | |
| | 13 | 298 | |
| | 14 | 300 | |
| | 15 | 316 | |
| | 16 | 317 | |
| | 17 | 325 | |
| | 18 | 337 | |
| | 19 | 374 | |
| | 20 | 385 | |
| | 21 | 395 | |
| | 22 | 399 | |
| | 23 | 427 | |
| | 24 | 477 | |
| | 25 | 592 | |
| | 26 | 712 | |
| | 27 | 723 | |
| | 28 | 731 | |
| | 29 | 738 | |
| | 30 | 739 | |
| | 31 | 740 | |
| | 32 | 792 | |

TABLE VII-continued

| Proliferation assay with HL-60 cells at 20 μM | | | |
|---|---|---|---|
| Activity Range | Entry | Compound | Specification |
| | 33 | 793 | |
| | 34 | 811 | |
| | 35 | 812 | |
| | 36 | 819 | |
| $0.7 < AVE_w \leq 0.8$ | 37 | 041 | |
| | 38 | 134 | |
| | 39 | 215 | |
| | 40 | 223 | |
| | 41 | 322 | |
| | 42 | 410 | |
| | 43 | 440 | |
| | 44 | 488 | |
| | 45 | 581 | |
| | 46 | 674 | |
| | 47 | 685 | |
| | 48 | 756 | |
| | 49 | 785 | |
| | 50 | 786 | |
| | 51 | 822 | |
| $0.6 < AVE_w \leq 0.7$ | 52 | 067 | |
| | 53 | 217 | |
| | 54 | 222 | |
| | 55 | 334 | |
| | 56 | 336 | |
| | 57 | 414 | |
| | 58 | 492 | |
| | 59 | 700 | |
| | 60 | 821 | |
| | 61 | 828 | |
| $0.4 < AVE_w \leq 0.6$ | 62 | 043 | |
| | 63 | 044 | |
| | 64 | 045 | |
| | 65 | 066 | |
| | 66 | 133 | |
| | 67 | 159 | |
| | 68 | 164 | |
| | 69 | 167 | |
| | 70 | 218 | |
| | 71 | 221 | |
| | 72 | 236 | |
| | 73 | 238 | |
| | 74 | 313 | |
| | 75 | 318 | |
| | 76 | 319 | |
| | 77 | 320 | |
| | 78 | 323 | |
| | 79 | 389 | |
| | 80 | 721 | |
| | 81 | 722 | |
| | 82 | 729 | |
| | 83 | 784 | |
| | 84 | 820 | |
| 0.4 ± 0.0 | 85 | RES 20 μM | Control |
| $0.2 < AVE_w \leq 0.4$ | 86 | 161 | |
| | 87 | 210 | |
| | 88 | 211 | |
| | 89 | 237 | |
| | 90 | 596 | |
| $0.0 \leq AVE_w \leq 0.2$ | 91 | 166 | |
| | 92 | 168 | |
| | 93 | 170 | |
| | 94 | 171 | |
| | 95 | 182 | |
| | 96 | 184 | |
| | 97 | 185 | |
| | 98 | 186 | |
| | 99 | 216 | |
| | 100 | 266 | |
| | 101 | 267 | |
| | 102 | 268 | |
| | 103 | 269 | |
| | 104 | 270 | |
| | 105 | 272 | |
| | 106 | 273 | |
| | 107 | 275 | |
| | 108 | 284 | |

TABLE VII-continued

| Proliferation assay with HL-60 cells at 20 μM | | | |
|---|---|---|---|
| Activity Range | Entry | Compound | Specification |
| | 109 | 286 | |
| | 110 | 287 | |
| | 111 | 288 | |
| | 112 | 529 | |
| | 113 | 540 | |
| | 114 | 544 | |
| | 115 | 633 | |
| | 116 | 644 | |
| | 117 | 648 | |
| | 118 | 766 | |
| | 119 | 767 | |
| | 120 | 768 | |
| | 121 | 774 | |
| | 122 | 802 | |
| | 123 | 803 | |
| | 124 | 804 | |
| | 125 | 810 | |

In one embodiment, several compounds of the invention were found to inhibit the growth of CAL-27 cells (human tongue squamous cell carcinoma cells) obtainable from the Deutsche Sammlung von Mikroorganismen and Zellkulturen GmbH (DSMZ) under the accession number ACC 446. CAL-27 cells were cultivated according to the protocol of the provider (but at 5% instead of 10% $CO_2$) in DMEM medium (Fisherscientific, #11584456) containing 10% fetal bovine serum (Fisherscientific, #15517589).

A compound is considered as a growth inhibitor of CAL-27 cells, if—at a reference concentration of 20 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the three compound families herein defined in formula II, formula IV and formula V have been identified as growth inhibitors of CAL-27 cells. The so far identified CAL-27 growth inhibitors relate to the compounds listed in Table VIIIa and VIIIb. The entries of Table VIIIa and VIIIb are categorized by the corresponding weighted arithmetic means of the compounds falling into the activity ranges as indicated.

TABLE VIIIa

| Proliferation assay with CAL-27 cells at 20 μM | | | |
|---|---|---|---|
| Activity Range | Entry | Compound | Specification |
| 1.0 ± 0.0 | 1 | DMSO | Baseline control |
| 0.9 ± 0.0 | 2 | RES 20 μM | Control |
| $0.8 < AVE_w \leq 0.9$ | 3 | 236 | |
| | 4 | 300 | |
| | 5 | 596 | |
| | 6 | 820 | |
| | 7 | 822 | |
| $0.7 < AVE_w \leq 0.8$ | 8 | 164 | |
| | 9 | 210 | |
| | 10 | 313 | |
| | 11 | 774 | |

TABLE VIIIa-continued

| Proliferation assay with CAL-27 cells at 20 μM | | | |
|---|---|---|---|
| Activity Range | Entry | Compound | Specification |
| $0.6 < AVE_w \le 0.7$ | 12 | 167 | |
| | 13 | 238 | |
| $0.4 < AVE_w \le 0.6$ | 14 | 211 | |
| | 15 | 237 | |
| | 16 | 266 | |
| 0.4 ± 0.0 | 17 | RES 40 μM | Control |
| $0.2 < AVE_w \le 0.4$ | 18 | 166 | |
| | 19 | 170 | |
| | 20 | 182 | |
| | 21 | 267 | |
| | 22 | 287 | |
| | 23 | 288 | |
| | 24 | 768 | |
| $0.0 \le AVE_w \le 0.2$ | 25 | 168 | |
| | 26 | 171 | |
| | 27 | 184 | |
| | 28 | 185 | |
| | 29 | 186 | |
| | 30 | 268 | |
| | 31 | 269 | |
| | 32 | 270 | |
| | 33 | 272 | |
| | 34 | 273 | |
| | 35 | 275 | |
| | 36 | 284 | |
| | 37 | 286 | |
| | 38 | 529 | |
| | 39 | 540 | |
| | 40 | 544 | |
| | 41 | 633 | |
| | 42 | 644 | |
| | 43 | 648 | |
| | 44 | 766 | |
| | 45 | 767 | |
| | 46 | 802 | |
| | 47 | 803 | |
| | 48 | 804 | |
| | 49 | 810 | |

TABLE VIIIb

| Proliferation assay with CAL-27 cells at 40 μM | | | |
|---|---|---|---|
| Activity Range | Entry | Compound | Specification |
| 1.0 ± 0.0 | 1 | DMSO | Baseline control |
| 0.9 ± 0.0 | 2 | RES 20 μM | Control |
| $0.8 < AVE_w \le 0.9$ | 3 | 300 | |
| | 4 | 334 | |
| $0.7 < AVE_w \le 0.8$ | 5 | 722 | |
| $0.6 < AVE_w \le 0.7$ | 6 | 159 | |
| 0.5 ± 0.0 | 7 | RES 40 μM | Control |
| $0.2 < AVE_w \le 0.4$ | 8 | 161 | |
| | 9 | 237 | |
| | 10 | 729 | |
| | 11 | 768 | |
| $0.0 \le AVE_w \le 0.2$ | 12 | 166 | |
| | 13 | 167 | |
| | 14 | 210 | |
| | 15 | 272 | |
| | 16 | 287 | |

In one embodiment, several compounds of the invention were found to inhibit the growth of TT cells (human medullary thyroid carcinoma cells) obtainable from the American Type Culture Collection (ATCC) under the accession number ATCC-CRL-1803. TT cells were cultivated according to the protocol of the provider in F-12K medium (Fisherscientific, #11580556, or ATCC, #ATCC-30-2004) containing 10% fetal bovine serum (Fisherscientific, #15517589).

A compound is considered as a growth inhibitor of TT cells, if—at a reference concentration of 40 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the three compound families herein defined in formula II, formula IV and formula V have been identified as growth inhibitors of TT cells. The so far identified TT growth inhibitors relate to the compounds listed in Table IX. The entries of Table IX are categorized by the corresponding weighted arithmetic means of the compounds falling into the activity ranges as indicated.

TABLE IX

| Proliferation assay with TT cells at 40 μM | | | |
|---|---|---|---|
| Activity Range | Entry | Compound | Specification |
| 1.0 ± 0.0 | 1 | DMSO | Baseline control |
| 0.9 ± 0.0 | 2 | RES 20 μM | Control |
| $0.8 < AVE_w \le 0.9$ | 3 | 159 | |
| | 4 | 309 | |
| | 5 | 334 | |
| 0.8 ± 0.0 | 6 | RES 40 μM | Control |
| $0.7 < AVE_w \le 0.8$ | 7 | 748 | |
| $0.6 < AVE_w \le 0.7$ | 8 | 210 | |
| $0.4 < AVE_w \le 0.6$ | 9 | 161 | |
| | 10 | 237 | |
| $0.2 < AVE_w \le 0.4$ | 11 | 166 | |
| | 12 | 167 | |
| | 13 | 171 | |
| | 14 | 182 | |
| | 15 | 186 | |
| | 16 | 287 | |
| | 17 | 540 | |
| | 18 | 544 | |
| | 19 | 644 | |
| | 20 | 729 | |
| $0.0 \le AVE_w \le 0.2$ | 21 | 272 | |
| | 22 | 284 | |
| | 23 | 288 | |
| | 24 | 768 | |

In one embodiment, several compounds of the invention were found to inhibit the growth of HeLa cells (human cervical adenocarcinoma cells) obtainable from the American Type Culture Collection (ATCC) under the accession number ATCC-CCL-2. HeLa cells were cultivated according to the protocol of the provider in DMEM medium (Fisherscientific, #11584456) containing 10% fetal bovine serum (Fisherscientific, #15517589).

A compound is considered as a growth inhibitor of HeLa cells, if—at a reference concentration of 40 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the compound family herein defined in formula II have been identified as growth inhibitors of HeLa cells. The so far identified HeLa growth inhibitors relate to the compounds listed in Table X. The entries of Table X are categorized by the corresponding weighted arithmetic means of the compounds falling into the activity ranges as indicated.

TABLE X

Proliferation assay with HeLa cells at 40 μM

| Activity Range | Entry | Compound | Specification |
|---|---|---|---|
| 1.0 ± 0.0 | 1 | DMSO | Baseline control |
| 0.9 ± 0.0 | 2 | RES 20 μM | Control |
| 0.4 < $AVE_w$ ≤ 0.6 | 3 | 166 | |
| 0.4 ± 0.0 | 4 | RES 40 μM | Control |
| 0.2 < $AVE_w$ ≤ 0.4 | 5 | 167 | |
| | 6 | 287 | |
| 0.0 ≤ $AVE_w$ ≤ 0.2 | 7 | 272 | |

In one embodiment, several compounds of the invention were found to inhibit the growth of human epidermal keratinocyte progenitors, (HPEKp, pooled), obtainable from CELLnTEC Advanced Cell Systems AG under the accession number HPEKp. HPEKp cells were cultivated according to the protocol of the provider in CnT-Prime epithelial culture medium (CELLnTEC, #CnT-PR, a fully defined, low calcium formulation, completely free of animal or human-derived components) without addition of further components.

A compound is considered as a growth inhibitor of HPEKp cells, if—at a reference concentration of 10 μM—the weighted arithmetic mean of the normalized fluorescence intensity values after addition of the corresponding combined standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean of all normalized values from the DMSO control measurements in analogy to the calculations performed for the test-compounds. The corresponding combined standard deviation for the DMSO values amounts to less than $1 \cdot 10^{-2}$.

According to the method described above, several molecules falling so far under the scope of the four compound families herein defined in formula II, formula III, formula IV and formula V have been identified as growth inhibitors of HPEKp cells. The so far identified HPEKp growth inhibitors relate to the compounds listed in Table XI. The entries of Table XI are categorized by the corresponding weighted arithmetic means of the compounds falling into the activity ranges as indicated.

TABLE XI

Proliferation assay with HPEKp cells at 10 μM

| Activity Range | Entry | Compound | Specification |
|---|---|---|---|
| 1.0 ± 0.0 | 1 | DMSO | Baseline control |
| 0.8 < $AVE_w$ ≤ 0.9 | 3 | 140 | |
| | 4 | 374 | |
| | 5 | 731 | |
| | 6 | 747 | |
| | 7 | 749 | |
| | 8 | 801 | |
| 0.7 < $AVE_w$ ≤ 0.8 | 10 | 312 | |
| | 11 | 323 | |
| | 12 | 424 | |
| | 13 | 721 | |
| | 14 | 819 | |
| | 15 | 828 | |
| 0.6 < $AVE_w$ ≤ 0.7 | 16 | 086 | |
| | 17 | 190 | |
| | 18 | 334 | |
| 0.4 < $AVE_w$ ≤ 0.6 | 19 | 112 | |
| | 20 | 722 | |
| 0.4 ± 0.0 | 21 | RES 10 μM | Control |
| 0.2 < $AVE_w$ ≤ 0.4 | 22 | 389 | |
| | 23 | 440 | |
| | 24 | 540 | |
| 0.0 ≤ $AVE_w$ ≤ 0.2 | 25 | 159 | |
| | 26 | 182 | |
| | 27 | 185 | |
| | 28 | 273 | |
| | 29 | 287 | |
| | 30 | 644 | |
| | 31 | 810 | |

Preliminary results from a single proliferation assay of six replicates per condition using cells derived from murine muscle tissue show that compounds of the invention may exhibit antiproliferative activity on muscle cells. Compounds were tested on C2C12 cells using the alamarBlue® proliferation assay in analogy to the above described method with seeding the cells at an initial number of 2000 cells per 96-well and a duration of treatment with compounds for 3 days.

In one embodiment, two compounds of the invention were found so far to inhibit the growth of C2C12 cells (murine myoblast cells) obtainable from the Deutsche Sammlung von Mikroorganismen und Zellkulturen GmbH (DSMZ) under the accession number ACC 565. C2C12 cells were cultivated according to the protocol of the provider in RPMI 1640 medium (Fisherscientific, #11554526) containing 10% fetal bovine serum (Fisherscientific, #15517589).

A compound is considered as a growth inhibitor of C2C12 cells, if—at a reference concentration of 40 μM—the equally weighted arithmetic mean (AVE) of the six normalized fluorescence intensity values after addition of the corresponding standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the equally weighted arithmetic mean (AVE) of the six normalized values from the DMSO control measurements in analogy to the calculations performed for the test-compounds. The corresponding standard deviations for the tested compounds were calculated including the Gauß' error propagation associated with the performed calculation for the normalization and amounts for the DMSO values to less than $3 \cdot 10^{-2}$. Outlier analyses were performed as described above.

According to the method described above, molecules falling so far under the scope of the two compound families herein defined in formula II and formula V have been identified as growth inhibitors of C2C12 cells. The so far identified C2C12 growth inhibitors relate to the compounds listed in Table XII. The entries of Table XII are categorized by the corresponding equally weighted arithmetic means of the compounds falling into the activity ranges as indicated.

TABLE XII

| Proliferation assay with C2C12 cells at 40 μM | | | |
|---|---|---|---|
| Activity Range | Entry | Compound | Specification |
| 1.0 ± 0.0 | 1 | DMSO | Baseline control |
| 0.8 < AVE ≤ 0.9 | 2 | 748 | |
| 0.3 ± 0.0 | 3 | RES 40 μM | Control |
| 0.2 < AVE ≤ 0.4 | 4 | 288 | |

Preliminary results from a single proliferation assay of six replicates per condition using squamous cell carcinoma (SC C) cells derived from the human oral mucosa may confirm that compounds of the invention exhibit antiproliferative activity on SCC of the mucosal epithelium. Compounds were tested on BHY cells using the alamarBlue® proliferation assay in analogy to the above described method with seeding the cells at an initial number of 4000 cells per 96-well and a duration of treatment with compounds for 3 days.

In one embodiment, several compounds of the invention were found to inhibit the growth of BHY cells (human oral squamous cell carcinoma cells) obtainable from the Deutsche Sammlung von Mikroorganismen and Zellkulturen GmbH (DSMZ) under the accession number ACC 404. BHY cells were cultivated according to the protocol of the provider (but at 5% instead of 10% $CO_2$) in DMEM medium (Fisherscientific, #11584456) containing 10% fetal bovine serum (Fisherscientific, #15517589).

A compound is considered as a growth inhibitor of BHY cells, if—at a reference concentration of 40 μM—the equally weighted arithmetic mean (AVE) of the six normalized fluorescence intensity values after addition of the corresponding standard deviation amounts to 0.9 or lower, in particular to 0.8 or lower, 0.7 or lower, 0.6 or lower, 0.4 or lower, and 0.2 or lower, relative to the overall basis level of 1.0. The overall basis level was calculated as the weighted arithmetic mean ($AVE_w$) of all normalized values from the DMSO control measurements. The corresponding combined standard deviation for the DMSO values amounts to less than $1 \cdot 10^{-2}$. The corresponding standard deviations for the tested compounds were calculated including the Gauß' error propagation associated with the performed calculation for the normalization. The weighted arithmetic mean ($AVE_w$) and the combined standard deviation for RES was calculated in analogy to DMSO. Outlier analyses were performed as described above.

According to the method described above, molecules falling so far under the scope of the two compound families herein defined in formula II and formula IV have been identified as growth inhibitors of BHY cells. The so far identified BHY growth inhibitors relate to the compounds listed in Table XIII. The entries of Table XIII are categorized by the corresponding equally weighted arithmetic means of the compounds falling into the activity ranges as indicated.

TABLE XIII

| Proliferation assay with BHY cells at 40 μM | | | |
|---|---|---|---|
| Activity Range | Entry | Compound | Specification |
| 1.0 ± 0.0 | 1 | DMSO | Baseline control |
| 0.6 < AVE ≤ 0.7 | 2 | 644 | |
| 0.6 ± 0.0 | 3 | RES 40 μM | Control |
| 0.4 < AVE ≤ 0.6 | 4 | 171 | |
| 0.2 < AVE ≤ 0.4 | 5 | 182 | |
| | 6 | 186 | |

TABLE XIII-continued

| Proliferation assay with BHY cells at 40 μM | | | |
|---|---|---|---|
| Activity Range | Entry | Compound | Specification |
| | 7 | 272 | |
| | 8 | 284 | |
| | 9 | 288 | |
| | 10 | 544 | |
| | 11 | 633 | |
| 0.0 ≤ AVE ≤ 0.2 | 12 | 540 | |

In one aspect, the present invention relates to the treatment of skin, skin appendages, mucosa, mucosal appendages, cornea, and all kinds of epithelial tissue. The term “skin” relates to tissue including epidermis and dermis. The term “mucosa” relates to mucous and submucous tissues including oral mucosa, nasal mucosa, ocular mucosa, mucosa of the ear, respiratory mucosa, genital mucosa, urothelial mucosa, anal mucosa and rectal mucosa. The term “appendages” relates to tissue including hair follicles, hair, fingernails, toenails and glands including sebaceous glands, sweat glands, e.g. apocrine or eccrine sweat glands and mammary glands.

In one embodiment, the present invention relates to treatment of non-melanoma skin cancer and pre-cancerous lesions, such as basal cell carcinoma (BCC), squamous cell carcinoma (SCC), e.g. cutaneous SCC, lung SCC, head and neck SCC, oral SCC, esophageal SCC, cervical SCC, periocular SCC, SCC of the thyroid, SCC of the penis, SCC of the vagina, SCC of the prostate, SCC of the bladder, sebaceous gland carcinoma, Merkel cell carcinoma, angiosarcoma, cutaneous B-cell lymphoma, cutaneous T-cell lymphoma, dermatofibrosarcoma, actinic keratosis (AK) or Bowen's disease (BD).

In a further embodiment, the present invention relates to the treatment of skin and mucosal disorders with cornification defects (keratoses) and/or abnormal keratinocyte proliferation, such as Psoriasis, Darier's disease, Lichen planus, Lupus erythematosus, Ichthyosis or Verruca vulgaris (senilis).

In a further embodiment, the invention relates to the treatment of skin and mucosal diseases related to and caused by viral infections, such as warts, HPV-related warts, papillomas, HPV-related papillomas, papillomatoses and HPV-related papillomatoses, e.g. Verruca (plantar warts), Verruca plana (flat warts/plane warts), Verruca filiformis (filiform warts), mosaic warts, periungual warts, subungual warts, oral warts, genital warts, fibroepithelial papilloma, intracanalicular papilloma, intraductal papilloma, inverted papilloma, basal cell papilloma, squamous papilloma, cutaneous papilloma, fibrovasular papilloma, plexus papilloma, nasal papilloma, pharyngeal papilloma, Papillomatosis cutis carcinoides, Papillomatosis cutis lymphostatica, Papillomatosis confluens et reticularis or laryngeal papillomatosis (respiratory papillomatosis), Herpes-related diseases, e.g. Herpes labialis, Herpes genitalis, Herpes zoster, Herpes corneae or Kaposi's sarcoma.

In a further embodiment, the invention relates to the treatment of atopic dermatitis.

In a further embodiment, the invention relates to the treatment of acne.

In a further embodiment, the invention relates to the treatment of wounds of the skin, wherein the process of wound healing is accelerated.

A further aspect of the present invention relates to the treatment of immune system-related disorders. The term "immune system-related" as used herein applies to a pathological condition of the hematopoietic system including the hematologic system, as well as to the intervention into proliferation, differentiation and/or activation of cell lineages of the hematopoietic system including the hematologic system in order to modulate an immune response (immune modulation).

Examples are diseases of the hematopoietic system including the hematologic system, such as malignancies of the myeloid lineage, e.g. chronic myelomonocytic leukemia (CMML) or acute myeloid leukemia (AML), including acute promyelocytic leukemia (APL); malignancies of the lymphoid lineage, e.g. B-cell acute lymphoblastic leukemia (B-ALL), pre-B-cell acute lymphoblastic leukemia (pre-B-ALL), Hodgkin lymphoma or myeloma; or acute lymphoblastic and acute myeloid mixed lineage leukemia with MLL gene translocation.

Furthermore, the compounds of the invention may be used in immunotherapy, alone or together with other immunotherapeutic methods or compounds, or as adjuvant for immunotherapy. The term "immunotherapy" as used herein applies to activation-immunotherapy in patients without immune deficiency or with acquired or congenital immune deficiency, and as immune recovery to enhance the functionality of the immune system in the response against pathogens or pathologically transformed endogenous cells, such as cancer cells.

The term "other immunotherapy methods" as used herein applies to vaccinations, antibody treatment, cytokine therapy, the use of immune checkpoint inhibitors and immune response-stimulating drugs, as well as to autologous transplantations of genetically modified or non-modified immune cells, which may be stimulated with intercellular signals, or signaling molecules, or antigens, or antibodies, i.e. adoptive immune-cell transfer.

Specific examples are activation of peripheral T-lymphocytes in order to amplify an immune response, particularly the stimulation of proliferation and/or cytokine production and/or secretion upon antigen recognition in order to amplify an immune response, such as the activation of B-lymphocytes in order to amplify an immune response, particularly the stimulation of proliferation and/or antibody production and/or secretion, such as the enhancement of an immune response through augmentation of the number of specific immune-cell subtypes, by regulation of differentiation and/or cell fate decision during immune-cell development, as for example to augment the number of marginal zone B-cells, or T-helper (Th) subsets in particular Th1, Th2 and regulatory T-cells; or the use as vaccine adjuvant.

A still further aspect of the invention relates to the treatment of muscular diseases including diseases of skeletal muscle, cardiac muscle and smooth muscle.

In one embodiment, the invention relates to the treatment of muscular dystrophies (MD).

Specific examples are Duchenne MD, Becker MD, congenital MD, Limb-Girdle MD, facioscapulohumeral MD, Emery-Dreifuss MD, distal MD, myotonic MD or oculopharyngeal MD.

In a further embodiment, the invention relates to the treatment of hyperproliferative disorders of the muscle, including myoblastoma, rhabdomyoma, and rhabdomyosarcoma, as well as muscle hyperplasia and muscle hypertrophy.

In a further embodiment, the compounds of the invention may be used for muscle regeneration after pathologic muscle degeneration or atrophy, e.g. caused by traumata, caused by muscle ischemia or caused by inflammation, in aging-related muscle-atrophy or in disease-related muscle atrophy such as myositis and fibromyositis or poliomyelitis.

A still further aspect relates to the treatment of disorders of the neuroendocrine system such as cancer of the neuroendocrine system, comprising neuroendocrine small cell carcinomas, neuroendocrine large cell carcinomas and carcinoid tumors, e.g. of the brain, thyroid, pancreas, gastrointestinal tract, liver, esophagus, and lung, such as neuroendocrine tumor of the pituitary gland, neuroendocrine tumor of the adrenal gland, medullary thyroid cancer (MTC), C-cell hyperplasia, anaplastic thyroid cancer (ATC), parathyroid adenoma, intrathyroidal nodules, insular carcinoma, hyalinizing trabecular neoplasm, paraganglioma, small-cell lung cancer (SCLC), lung carcinoid tumors, neuroblastoma, gastrointestinal carcinoid, Goblet-cell carcinoid, pancreatic carcinoid, gastrinoma, glucagenoma, somatostatinoma, VIPoma, insulinoma, non-functional islet cell tumor, multiple endocrine neoplasia type-1, or pulmonary carcinoid.

A still further aspect relates to the treatment of cancers or precancerous lesions of the brain, pancreas, liver, thyroid, genitourinary tract and endothelial tissue, including glioma, mixed glioma, glioblastoma multiforme, astrocytoma, anaplastic astrocytoma, glioblastoma, oligodendroglioma, anaplastic oligodendroglioma, anaplastic oligoastrocytoma, ependymoma, anaplastic ependymoma, myxopapillary ependymoma, subependymoma, brain stem glioma, optic nerve glioma, and forebrain tumors, pancreatic adenocarcinoma, pancreatic ductal adenocarcinoma, pancreatic acinar cell carcinoma, pancreatic pseudopapillary neoplasm, pancreatic intraductal papillary-mucinous neoplasm, pancreatic mucinous cystadenocarcinoma, pancreatoblastoma and pancreatic intraepithelial neoplesia, hepatocellular carcinoma, fibrolamellar hepatocellular carcinoma, papillary thyroid cancer and follicular thyroid cancer, cervical cancer and angiosarcoma.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. The term "treating" also encompasses post-treatment care.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

The compounds of the invention may be used in human and veterinary medicine, which includes the treatment of companion animals, e.g. horses, dogs, cats, rabbits, guinea pigs, birds, fishes; and livestock, e.g. cattle, poultry, pig, sheep, goat, donkey, yak and camel.

Pharmaceutical Compositions

The present invention further provides pharmaceutical compositions comprising a compound as described herein or a pharmaceutically acceptable salt thereof for use in medicine, e.g. in human or veterinary medicine. In some embodiments, the composition further comprises a pharmaceutically acceptable carrier.

An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are topical or systemical including enteral, oral, rectal, and parenteral, as infusion and injection, intravenous, intra-arterial, intraperitoneal, intramuscular, intracardial, epidural, intracerebral, intracerebroventricular, intraosseous, intra-articular, intraocular, intravitreal, intrathecal, intravaginal, intracavernous, intravesical, subcutaneous, intradermal, transdermal, transmucosal, inhalative, intranasal, buccal, sublingual and intralesional preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, gels, hydrogels, ointments, creams, lotions, shampoos, lip balms, mouthwashes, foams, pastes, tinctures, dermal patches and tapes, forms in occlusion or in combination with time release drug delivery systems, with electrophoretic dermal delivery systems including implants and devices, and with jet injectors, liposome and transfersome vesicles, vapors, sprays, syrups, juices or drops and eye drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable, synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy, as sequence therapy or as simultaneous combination therapy, with further active agents, e.g. therapeutically active compounds useful in the treatment of the above indicated disorders. These therapeutically active compounds may include but are not limited to chemotherapeutic agents such as nucleoside analogs, e.g. Cytarabin, Gemcitabine, Azathioprine, Mercaptopurine, Fluorouracil, Thioguanine, Hydroxyurea, Azacitidine, Capecitabine, Doxifluridine, and Methotrexate; such as platinum-based drugs, e.g. Cisplatin, Oxaliplatin, Carboplatin and Nedaplatin; such as anthracyclines, e.g. Doxorubicin, Epirubicin, Valrubicin, Idarubicin, Daunorubicin, Sabarubicin, Pixantrone and Mitoxantrone; such as peptide antibiotics, e.g. Actinomycin and Bleomycin; such as alkylating agents e.g. Mechlorethamine, Chlorambucil, Melphalan, Nitrosoureas, Dacarbazine, Temozolomide and Cyclophosphamide; such as antimitotic agents including taxanes and vinca alkaloids, e.g. Docetaxel, Paclitaxel, Abraxane, Cabazitaxel, Vinblastine, Vindesine, Vinorelbine and Vincristine; such as topoisomerase inhibitors, e.g. Irinotecan, Topotecan, Teniposide and Etoposide; and targeted therapeutic agents such as kinase inhibitors, regulators i.e. inhibitors and activators of signaling pathways including growth factor signaling, cytokine signaling, NF-kappaB signaling, AP1 signaling, JAK/STAT signaling, EGFR signaling, TGF-beta signaling, Notch signaling, Wnt signaling, Hedgehog signaling, hormone and nuclear receptor signaling, e.g. Erlotinib, Lapatinib, Dasatinib, Imatinib, Afatinib, Vemurafenib, Dabrafenib, Nilotinib, Cetuximab, Trametinib, Palbociclib, Cobimetinib, Cabozantinib, Pegaptanib, Crizotinib, Olaparib, Panitumumab, Cabozantinib, Ponatinib, Regorafenib, Entrectinib, Ranibizumab, Ibrutinib, Trastuzumab, Rituximab, Alemtuzumab, Gefitinib, Bevacizumab, Lenvatinib, Bosutinib, Axitinib, Pazopanib, Everolimus, Temsirolimus, Ruxolitinib, Tofacitinib, Sorafenib, Sunitinib, Aflibercept, Bortezomib, Vandetanib; Vismodegib and Sonidegib; retinoids such as retinol, tretinoin, isotretinoin, alitretinoin, bexarotene, tazarotene, acitretin, adapalene and etretinate; hormone signaling modulators including estrogen receptor modulators, androgen receptor modulators and aromatase inhibitors e.g. Raloxifene, Tamoxifen, Fulvestrant, Lasofoxifene, Toremifene, Bicalutamide, Flutamide, Anastrozole, Letrozole and Exemestane; histone deacetylase inhibitors, e.g. Vorinostat, Romidepsin, Panobinostat, Belinostat and Chidamide; and Ingenol mebutate; and other Notch enhancers not encompassed by the compounds of the present invention, e.g. Valproic acid, Resveratrol, hesperetin, chrysin, phenethyl isothiocyanate, thiocoraline, N-methylhemeanthidine chloride and Notch Signaling-activating peptides or antibodies; and immune response modulating agents e.g. Imiquimod, Ipilimumab, Atezolizumab, Ofatumumab, Rituximab, Nivolumab and Pembrolizumab; and anti-inflammatory agents including glucocorticoids and non-steroidal anti-inflammatory drugs, e.g. cortisol-based preparations, Dexamethason, Betamethason, Prednisone, Prednisolone, Methylprednisolone, Triamcinolon-hexacetonid, Mometasonfuroat, Clobetasolpropionat, acetylsalicylic acid, salicylic acid and other salicylates, Diflunisal, Ibuprofen, Dexibuprofen, Naproxen, Fenoprofen, Ketoprofen, Dexketoprofen, Loxoprofen, Flurbiprofen, Oxaprozin, Indomethacin, Ketorolac, Tolmetin, Diclofenac, Etodolac, Aceclofenac, Nabumetone, Sulindac, Mefenamic acid, Meclofenamic acid, Flufenamic acid, Tolfenamic acid, Celecoxib, Parecoxib, Etoricoxib and Firocoxib; and ACE inhibitors; and beta-blockers; and myostatin inhibitors; and PDE-5 inhibitors; and antihistamines. For a combination therapy, the active ingredients may be formulated as compositions containing several active ingredients in a single dose form and/or as kits containing individual active ingredients in separate dose forms. The active ingredients used in combination therapy may be co-administered or administered separately.

The compounds of the invention may be administered as antibody-drug conjugates.

The compounds of the invention may be administered in combination with surgery, cryotherapy, electrodessication, radiotherapy, photodynamic therapy, laser therapy, chemotherapy, targeted therapy, immunotherapy, gene therapy, antisense therapy, cell-based transplantation therapy, stem cell therapy, physical therapy and occupational therapy.

The compounds of the invention falling under the scope of formula I, formula II, formula III, formula IV and formula V can be synthesized in analogy to the methods described in Reinmüller et al., 2015, EPFL Thesis 6887 by a coupling step to establish the diaryl ether scaffold, which can be prepared by a method of reacting a phenol and an electron-deficient aryl halide in the presence of a base such as potassium carbonate or cesium carbonate in a non-protic organic solvent such as DMSO or DMF at room temperature or at elevated temperature or reflux, preferably at 80° C. or 100° C., with optional assistance of microwave irradiation (Li et al., Org. Lett. 2003, 5, 2169-2171);

- or by a method of reacting a phenol and a nitroarene in the presence of a base such as potassium carbonate or cesium carbonate in a non-protic organic solvent such as DMSO or DMF at elevated temperature or reflux, with assistance of microwave irradiation (Sarkate et al., Synlett 2013, 24, 1513-1516);
- or by a method of reacting an aryl silyl ether with an electron-deficient aryl halide in the presence of a base such as DBU and trace water in a non-protic organic solvent such as DMSO or DMF at elevated temperature or reflux (Yeom et al., Synlett 2007, 146-150);
- or by a method of reacting a phenol with a diaryliodonium triflate or tosylate in the presence of a base such as potassium carbonate or cesium carbonate in a non-protic organic solvent such as acetonitrile at ambient or elevated temperature (Kakinuma et al., Synthesis 2013, 45, 183-184);
- or by a method of reacting under Buchwald-Hartwig conditions a phenol with an aryl halide in the presence of a transition metal-based catalyst system such as palladium(II) acetate, an organophosphorus-based ligand such as dppf, a base such as potassium phosphate in an organic solvent such as toluene at elevated temperature or reflux (Burgos et al., Angew. Chem. Int. Ed. 2006, 45, 4321-4326);
- or by a method of reacting under Chan-Lam conditions a phenol with an arylboronic acid or ester in the presence of air, a copper-based catalyst system such as copper(II)

acetate, a base such as pyridine or triethylamine in a non-protic organic solvent such as DCM, chloroform at ambient temperature (Evans et al., Tetrahedron Letters 1998, 39, 2937-2940);

wherein all said methods of preparation may require a subsequent derivatisation step by standard chemical procedures known to the person skilled in the art, such as saponification, hydrolysis, esterification or amidation to obtain the corresponding carboxylic acids, esters, primary amides, secondary amides, tertiary amides, hydroxamic acids and hydroxamates.

For example, the corresponding carboxylic acids are synthesized by saponification of the corresponding benzoate esters, fluorobenzoate esters, nicotinate esters, or fluoronicotinate esters in the presence of potassium hydroxide or sodium hydroxide in a binary solvent mixture of water and an alcohol, preferably ethanol, or water and tetrahydrofuran at ambient or elevated temperature (Becker et al., Organikum, 22nd edition 2004 (German), pp. 488, publisher: Wiley-VCH Weinheim);

the esters, primary amides, secondary amides, tertiary amides, and hydroxamic acids are synthesized by in situ transformation of the corresponding benzoic acid, fluorobenzoic acid, nicotinic acid, or fluoronicotinic acid to the corresponding acid chlorides in the presence of thionyl chloride and catalytic amounts of DMF in toluene at ambient or elevated temperature, preferably at 80° C., and under inert gas atmosphere, followed by the addition of the respective nucleophile, i.e. alcohol, ammonia, secondary amine, tertiary amine, or hydroxylamine in the presence or absence of a non-nucleophilic base such as triethylamine, at ambient temperature under inert gas atmosphere (Becker et al., Organikum, 22nd edition 2004 (German), pp. 459, publisher: Wiley-VCH Weinheim).

The perfluoroalkylcyclopropyl moiety associated with the compounds of the invention falling under the scope of formula V is synthesized in three steps according to the procedure described in Barnes-Seeman et al., ACS Med. Chem. Lett. 2013, 4, 514-516; first, a bromoperfluoroalkenylbenzene such as 1-bromo-4-(3,3,3-trifluoroprop-1-en-2-yl)benzene or 1-bromo-4-(3,3,4,4,4-pentafluorobut-1-en-2-yl)benzene is obtained by a method of reacting 1-(4-bromophenyl)-2,2,2-trifluoroethan-1-one or 1-(4-bromophenyl)-2,2,3,3,3-pentafluoropropan-1-one, respectively, in the presence of methanesulfonyl chloride and a base such as potassium fluoride in a crown ether such as 18-crown-6 in a non-protic organic solvent such as DMF at elevated temperature, preferably at 80° C.;

second, a bromophenylperfluoroalkyldihydropyrazole such as 3-(4-bromophenyl)-3-(trifluoromethyl)-4,5-dihydro-3H-pyrazole or 3-(4-bromophenyl)-3-(perfluoroethyl)-4,5-dihydro-3H-pyrazole is obtained by a method of reacting a bromoperfluoroalkenylbenzene such as 1-bromo-4-(3,3,3-trifluoroprop-1-en-2-yl)benzene or 1-bromo-4-(3,3,4,4,4-pentafluorobut-1-en-2-yl)benzene, respectively, in the presence of diazomethane in an ether such as diethyl ether or methyl tert-butyl ether at ambient temperature;

and third, the perfluoroalkylcyclopropylarylbromide such as 1-bromo-4-(1-(trifluoromethyl)cyclopropyl)benzene or 1-bromo-4-(1-(perfluoroethyl)cyclopropyl)benzene is obtained by a method of reacting 3-(4-bromophenyl)-3-(trifluoromethyl)-4,5-dihydro-3H-pyrazole or 3-(4-bromophenyl)-3-(perfluoroethyl)-4,5-dihydro-3H-pyrazole, respectively, in an organic solvent such as toluene or xylenes or a mixture thereof.

The obtained perfluoroalkylcyclopropylarylbromide can subsequently be converted into the corresponding phenol for one of the above said coupling reactions with an electron-deficient aryl halide, a nitroarene, a diaryliodonium triflate or tosylate by a method of reaction in the presence of a transition metal-based catalyst system such as Pd2dba3, an organophosphorus-based ligand such as 2-di-tert-butylphosphino-2',4',6'-triisopropylbiphenyl (t-Bu XPhos), a base such as potassium hydroxide or sodium hydroxide in a biphasic solvent system such as water/dioxane or water/toluene at elevated temperature or reflux, preferably at 100° C., and under an inert gas atmosphere (Anderson et al., J. Am. Chem. Soc. 2006, 128, 10694-10695);

or by a method of reaction in the presence of a copper-based catalyst system such as CuI, a pyridyl based ligand such as 2-methylquinolin-8-ol or preferably 8-hydroxyquinoline-N-oxide, and tetrabutyl-ammonium hydroxide or preferably cesium hydroxide monohydrate in a non-protic organic solvent such as DMSO or DMF at elevated temperature or reflux, preferably at 110° C., and under an inert gas atmosphere (Paul et al., Synthesis 2010, 4268-4272; Yang et el., Org. Lett. 2011, 13, 4340-4343).

The compounds of the invention falling under the scope of formula I, formula II, formula III, formula IV and formula V, as well as intermediates, can be isolated by column chromatography using silica gel as stationary phase and common organic solvents such as petroleum ether, ethyl acetate, dichloromethane, methanol, or acetic acids as eluent, preferably as binary or tertiary solvent mixtures thereof;

or by crystallization from common organic solvents such as petroleum ether, ethyl acetate, dichloromethane, chloroform, methanol, ethanol, toluene, or tert-butyl methyl ether, and mixtures thereof.

The compounds of the invention falling under the scope of formula I, formula II, formula III, formula IV and formula V, as well as starting materials and intermediates, can be identified by conventional methods such as nuclear magnetic resonance (NMR) spectroscopy, mass spectrometry (MS), or thin layer chromatography (TLC).

Chemical Synthesis

The compounds of the invention falling under the scope of formula I, formula II, formula III, formula IV and formula V can be synthesized and purified by those persons skilled in the art and are preferably synthesized according to the general procedure A, or general procedure B, or general procedure C, or general procedure D, respectively, and according to the detailed synthesis procedures described herein;

Abbreviations

Ac acetyl
BRSM based on recovered starting material (yield)
Bu butyl
δ chemical shift in parts per million (ppm)
dba dibenzylideneacetone
DCE 1,2-dichloroethane
DCM dichloromethane
DMF N,N-dimethylformamide
DMSO dimethyl sulfoxide
Et ethyl
ESI electron spray ionization
M mol/L
Me methyl
Ms methanesulfonyl
PE petroleum ether TBAF tetrabutylammonium fluoride THF tetrahydrofuran TMS trimethylsilyl General Procedure A: Synthesis of Diaryl Ether Esters Diaryl ether esters according to formula I, formula III, and formula V can be prepared by nucleophilic aromatic substitution, e.g. by reaction of an alkyl 4-fluorobenzoate, or an alkyl 3,4-difluorobenzoate, or an alkyl 6-chloronicotinate, or an alkyl 6-chloro-5-fluoronicotinate, with a phenol derivative (nucleophile, see Table XIV) in the presence of a base like potassium carbonate in a solvent like dimethyl sulfoxide at a temperature between 80° C. and 150° C. and in an inert atmosphere such as argon.

General Procedure B: Synthesis of Diaryl Ether Acids

Diaryl ether acids according to formula I, formula III, and formula V can be prepared by saponification, e.g. by reaction of the corresponding diaryl ether esters with an aqueous base solution like sodium hydroxide (nucleophile, see Table XIV) in a solvent like ethanol, methanol, tetrahydrofuran or a mixture thereof at a temperature between room temperature and reflux.

General Procedure C: Synthesis of Diaryl Ether Esters

Diaryl ether esters according to formula I, formula III, and formula V can be prepared by esterification via the corresponding acid chloride, e.g by reaction of a diaryl ether acid with thionyl chloride in the presence of catalytic amounts of DMF in a solvent like toluene at a temperature between 50° C. and 100° C. and in an inert atmosphere such as argon. After removal of the volatiles, the such obtained acid chloride intermediate is reacted with the alcohol corresponding to the desired ester (nucleophile, see Table XIV) in the presence of an organic base like triethylamine at a temperature between 0° C. and room temperature and in an inert atmosphere such as argon.

Alternatively, diaryl ether esters according to formula I, formula III, and formula V can be prepared by esterification via the corresponding acid chloride, e.g. by reaction of a diaryl ether acid with thionyl chloride in the presence of the alcohol corresponding to the desired ester (nucleophile, see Table XIV), preferably as the solvent at a temperature between 50° C. and reflux.

General Procedure D: Synthesis of Diaryl Ether Amides

Diaryl ether amides according to formula II, formula IV, and formula V can be prepared by amidation via the corresponding acid chloride, e.g by reaction of a diaryl ether acid with thionyl chloride in the presence of catalytic amounts of DMF in a solvent like toluene at a temperature between 50° C. and 100° C. and in an inert atmosphere such as argon. After removal of the volatiles, the such obtained acid chloride intermediate is reacted with the amine corresponding to the desired amide (nucleophile, see Table XIV) in a solvent like methanol, ethanol, or tetrahydrofuran at a temperature between 0° C. and room temperature and in an inert atmosphere such as argon. The presence of an organic base like triethylamine is needed if the hydrochloride salt of the amine is used.

TABLE XIV

List of Synthesized compounds

| Compound Number | m/z | ESI Ion Type | General Procedure | Nucleophile used in the General Procedure |
|---|---|---|---|---|
| 002 | 241.17 | $[M-H]^-$ | B | NaOH |
| 003 | 255.18 | $[M-H]^-$ | B | NaOH |
| 004 | 269.18 | $[M-H]^-$ | B | NaOH |
| 005 | 283.21 | $[M-H]^-$ | B | NaOH |

TABLE XIV-continued

List of Synthesized compounds

| Compound Number | m/z | ESI Ion Type | General Procedure | Nucleophile used in the General Procedure |
|---|---|---|---|---|
| 019 | 307.28 | $[M-H]^-$ | B | NaOH |
| 020 | 321.34 | $[M-H]^-$ | B | NaOH |
| 023 | 243.09 | $[M+H]^+$ | C | methanol |
| 024 | 257.10 | $[M+H]^+$ | C | methanol |
| 025 | 271.11 | $[M+H]^+$ | C | methanol |
| 026 | 285.13 | $[M+H]^+$ | C | methanol |
| 027 | 299.20 | $[M+H]^+$ | C | methanol |
| 029 | 271.11 | $[M+H]^+$ | C | methanol |
| 030 | 299.20 | $[M+H]^+$ | C | methanol |
| 041 | 311.21 | $[M+H]^+$ | C | methanol |
| 043 | 323.24 | $[M+H]^+$ | C | methanol |
| 044 | 337.25 | $[M+H]^+$ | C | methanol |
| 045 | 362.32 | $[M+H]^+$ | C | methanol |
| 048 | 257.11 | $[M+H]^+$ | A | 4-methylphenol |
| 049 | 271.12 | $[M+H]^+$ | A | 4-ethylphenol |
| 050 | 285.15 | $[M+H]^+$ | A | 4-n-propylphenol |
| 051 | 299.21 | $[M+H]^+$ | A | 4-n-butylphenol |
| 052 | 313.26 | $[M+H]^+$ | A | 4-n-pentylphenol |
| 054 | 285.15 | $[M+H]^+$ | A | 4-isopropylphenol |
| 056 | 311.17 | $[M+H]^+$ | A | 4-(trifluoromethyl)phenol |
| 066 | 337.25 | $[M+H]^+$ | A | (±)-4-(bicyclo[2.2.1]heptan-2-yl)phenol (7:1 endo:exo) |
| 067 | 351.26 | $[M+H]^+$ | A | (±)-4-(bicyclo[2.2.2]octan-2-yl)phenol |
| 070 | 244.00 | $[M-H]^-$ | B | NaOH |
| 071 | 258.09 | $[M-H]^-$ | B | NaOH |
| 072 | 272.11 | $[M-H]^-$ | B | NaOH |
| 073 | 286.16 | $[M-H]^-$ | B | NaOH |
| 075 | 258.10 | $[M-H]^-$ | B | NaOH |
| 086 | 308.25 | $[M-H]^-$ | B | NaOH |
| 087 | 322.30 | $[M-H]^-$ | B | NaOH |
| 091 | 244.07 | $[M+H]^+$ | C | methanol |
| 092 | 258.09 | $[M+H]^+$ | C | methanol |
| 093 | 272.11 | $[M+H]^+$ | C | methanol |
| 094 | 286.15 | $[M+H]^+$ | C | methanol |
| 095 | 300.19 | $[M+H]^+$ | C | methanol |
| 097 | 272.11 | $[M+H]^+$ | C | methanol |
| 099 | 300.19 | $[M+H]^+$ | C | methanol |
| 101 | 298.09 | $[M+H]^+$ | C | methanol |
| 110 | 312.19 | $[M+H]^+$ | C | methanol |
| 112 | 324.22 | $[M+H]^+$ | C | methanol |
| 113 | 338.24 | $[M+H]^+$ | C | methanol |
| 114 | 364.29 | $[M+H]^+$ | C | methanol |
| 117 | 272.12 | $[M+H]^+$ | A | 4-ethylphenol |
| 118 | 286.16 | $[M+H]^+$ | A | 4-n-propylphenol |
| 119 | 300.20 | $[M+H]^+$ | A | 4-n-butylphenol |
| 120 | 314.24 | $[M+H]^+$ | A | 4-n-pentylphenol |
| 122 | 286.16 | $[M+H]^+$ | A | 4-isopropylphenol |
| 133 | 338.24 | $[M+H]^+$ | A | (±)-4-(bicyclo[2.2.1]heptan-2-yl)phenol (7:1 endo:exo) |
| 134 | 352.28 | $[M+H]^+$ | A | (±)-4-(bicyclo[2.2.2]octan-2-yl)phenol |
| 138 | 228.10 | $[M+H]^+$ | D | ammonia |
| 139 | 242.10 | $[M+H]^+$ | D | ammonia |
| 140 | 256.12 | $[M+H]^+$ | D | ammonia |
| 141 | 270.11 | $[M+H]^+$ | D | ammonia |
| 142 | 284.16 | $[M+H]^+$ | D | ammonia |
| 144 | 256.12 | $[M+H]^+$ | D | ammonia |
| 145 | 270.12 | $[M+H]^+$ | D | ammonia |
| 146 | 284.16 | $[M+H]^+$ | D | ammonia |
| 157 | 296.20 | $[M+H]^+$ | D | ammonia |
| 159 | 308.22 | $[M+H]^+$ | D | ammonia |
| 160 | 322.26 | $[M+H]^+$ | D | ammonia |
| 161 | 348.27 | $[M+H]^+$ | D | ammonia |
| 164 | 244.07 | $[M+H]^+$ | D | hydroxylamine |
| 165 | 258.09 | $[M+H]^+$ | D | hydroxylamine |
| 166 | 272.11 | $[M+H]^+$ | D | hydroxylamine |
| 167 | 286.15 | $[M+H]^+$ | D | hydroxylamine |
| 168 | 300.19 | $[M+H]^+$ | D | hydroxylamine |
| 170 | 272.11 | $[M+H]^+$ | D | hydroxylamine |
| 171 | 300.19 | $[M+H]^+$ | D | hydroxylamine |
| 182 | 312.20 | $[M+H]^+$ | D | hydroxylamine |
| 184 | 324.22 | $[M+H]^+$ | D | hydroxylamine |
| 185 | 338.25 | $[M+H]^+$ | D | hydroxylamine |
| 186 | 364.36 | $[M+H]^+$ | D | hydroxylamine |

TABLE XIV-continued

List of Synthesized compounds

| Compound Number | m/z | ESI Ion Type | General Procedure | Nucleophile used in the General Procedure |
|---|---|---|---|---|
| 190 | 256.12 | $[M + H]^+$ | D | methylamine |
| 191 | 270.12 | $[M + H]^+$ | D | methylamine |
| 192 | 284.15 | $[M + H]^+$ | D | methylamine |
| 193 | 298.21 | $[M + H]^+$ | D | methylamine |
| 195 | 270.12 | $[M + H]^+$ | D | methylamine |
| 196 | 284.15 | $[M + H]^+$ | D | methylamine |
| 197 | 298.22 | $[M + H]^+$ | D | methylamine |
| 208 | 310.23 | $[M + H]^+$ | D | methylamine |
| 210 | 322.26 | $[M + H]^+$ | D | methylamine |
| 211 | 336.28 | $[M + H]^+$ | D | methylamine |
| 212 | 362.30 | $[M + H]^+$ | D | methylamine |
| 215 | 256.12 | $[M + H]^+$ | D | dimethylamine |
| 216 | 270.12 | $[M + H]^+$ | D | dimethylamine |
| 217 | 284.16 | $[M + H]^+$ | D | dimethylamine |
| 218 | 298.21 | $[M + H]^+$ | D | dimethylamine |
| 219 | 312.23 | $[M + H]^+$ | D | dimethylamine |
| 221 | 284.15 | $[M + H]^+$ | D | dimethylamine |
| 222 | 298.21 | $[M + H]^+$ | D | dimethylamine |
| 223 | 312.24 | $[M + H]^+$ | D | dimethylamine |
| 234 | 324.27 | $[M + H]^+$ | D | dimethylamine |
| 236 | 336.28 | $[M + H]^+$ | D | dimethylamine |
| 237 | 350.30 | $[M + H]^+$ | D | dimethylamine |
| 238 | 376.33 | $[M + H]^+$ | D | dimethylamine |
| 241 | 229.09 | $[M + H]^+$ | D | ammonia |
| 242 | 243.09 | $[M + H]^+$ | D | ammonia |
| 243 | 257.11 | $[M + H]^+$ | D | ammonia |
| 244 | 271.12 | $[M + H]^+$ | D | ammonia |
| 245 | 285.15 | $[M + H]^+$ | D | ammonia |
| 247 | 257.11 | $[M + H]^+$ | D | ammonia |
| 248 | 285.16 | $[M + H]^+$ | D | ammonia |
| 250 | 283.04 | $[M + H]^+$ | D | ammonia |
| 259 | 297.17 | $[M + H]^+$ | D | ammonia |
| 261 | 309.21 | $[M + H]^+$ | D | ammonia |
| 262 | 323.26 | $[M + H]^+$ | D | ammonia |
| 263 | 349.29 | $[M + H]^+$ | D | ammonia |
| 266 | 245.07 | $[M + H]^+$ | D | hydroxylamine |
| 267 | 259.09 | $[M + H]^+$ | D | hydroxylamine |
| 268 | 273.11 | $[M + H]^+$ | D | hydroxylamine |
| 269 | 287.14 | $[M + H]^+$ | D | hydroxylamine |
| 270 | 301.18 | $[M + H]^+$ | D | hydroxylamine |
| 272 | 273.12 | $[M + H]^+$ | D | hydroxylamine |
| 273 | 301.19 | $[M + H]^+$ | D | hydroxylamine |
| 275 | 299.08 | $[M + H]^+$ | D | hydroxylamine |
| 284, | 313.20 | $[M + H]^+$ | D | hydroxylamine |
| 286 | 325.21 | $[M + H]^+$ | D | hydroxylamine |
| 287 | 339.24 | $[M + H]^+$ | D | hydroxylamine |
| 288 | 365.29 | $[M + H]^+$ | D | hydroxylamine |
| 291 | 243.10 | $[M + H]^+$ | D | methylamine |
| 292 | 257.11 | $[M + H]^+$ | D | methylamine |
| 293 | 271.12 | $[M + H]^+$ | D | methylamine |
| 294 | 285.15 | $[M + H]^+$ | D | methylamine |
| 295 | 299.21 | $[M + H]^+$ | D | methylamine |
| 297 | 271.12 | $[M + H]^+$ | D | methylamine |
| 298 | 299.21 | $[M + H]^+$ | D | methylamine |
| 300 | 297.08 | $[M + H]^+$ | D | methylamine |
| 309 | 311.22 | $[M + H]^+$ | D | methylamine |
| 311 | 323.25 | $[M + H]^+$ | D | methylamine |
| 312 | 337.26 | $[M + H]^+$ | D | methylamine |
| 313 | 363.32 | $[M + H]^+$ | D | methylamine |
| 316 | 257.11 | $[M + H]^+$ | D | dimethylamine |
| 317 | 271.12 | $[M + H]^+$ | D | dimethylamine |
| 318 | 285.15 | $[M + H]^+$ | D | dimethylamine |
| 319 | 299.21 | $[M + H]^+$ | D | dimethylamine |
| 320 | 313.24 | $[M + H]^+$ | D | dimethylamine |
| 322 | 285.16 | $[M + H]^+$ | D | dimethylamine |
| 323 | 313.25 | $[M + H]^+$ | D | dimethylamine |
| 325 | 311.13 | $[M + H]^+$ | D | dimethylamine |
| 334 | 325.26 | $[M + H]^+$ | D | dimethylamine |
| 336 | 337.26 | $[M + H]^+$ | D | dimethylamine |
| 337 | 351.28 | $[M + H]^+$ | D | dimethylamine |
| 338 | 377.32 | $[M + H]^+$ | D | dimethylamine |
| 341 | 245.13 | $[M - H]^-$ | B | NaOH |
| 342 | 259.15 | $[M - H]^-$ | B | NaOH |
| 343 | 273.17 | $[M - H]^-$ | B | NaOH |
| 344 | 287.18 | $[M - H]^-$ | B | NaOH |
| 345 | 301.21 | $[M - H]^-$ | B | NaOH |
| 347 | 273.15 | $[M - H]^-$ | B | NaOH |
| 348 | 301.24 | $[M - H]^-$ | B | NaOH |
| 350 | 299.12 | $[M - H]^-$ | B | NaOH |
| 359 | 313.24 | $[M - H]^-$ | B | NaOH |
| 363 | 365.39 | $[M - H]^-$ | B | NaOH |
| 374 | 317.22 | $[M + H]^+$ | C | methanol |
| 385 | 329.24 | $[M + H]^+$ | C | methanol |
| 389 | 381.34 | $[M + H]^+$ | C | methanol |
| 392 | 275.09 | $[M + H]^+$ | A | 4-methylphenol |
| 393 | 289.13 | $[M + H]^+$ | A | 4-ethylphenol |
| 394 | 303.17 | $[M + H]^+$ | A | 4-n-propylphenol |
| 395 | 317.23 | $[M + H]^+$ | A | 4-n-butylphenol |
| 396 | 331.24 | $[M + H]^+$ | A | 4-n-pentylphenol |
| 398 | 303.19 | $[M + H]^+$ | A | 4-isopropylphenol |
| 399 | 331.25 | $[M + H]^+$ | A | 4-tert-pentylphenol |
| 401 | 329.17 | $[M + H]^+$ | A | 4-(trifluoromethyl)phenol |
| 410 | 343.28 | $[M + H]^+$ | A | 4-cyclohexylphenol |
| 414 | 395.33 | $[M + H]^+$ | A | 4-(1-adamantyl)phenol |
| 417 | 246.12 | $[M - H]^-$ | B | NaOH |
| 423 | 274.15 | $[M - H]^-$ | B | NaOH |
| 424 | 288.17 | $[M - H]^-$ | B | NaOH |
| 425 | 304.16 | $[M + H]^+$ | B | NaOH |
| 427 | 300.10 | $[M - H]^-$ | B | NaOH |
| 436 | 314.24 | $[M - H]^-$ | B | NaOH |
| 440 | 368.29 | $[M + H]^+$ | B | NaOH |
| 451 | 318.21 | $[M + H]^+$ | C | methanol |
| 462 | 330.23 | $[M + H]^+$ | C | methanol |
| 466 | 382.29 | $[M + H]^+$ | C | methanol |
| 469 | 276.08 | $[M + H]^+$ | A | 4-methylphenol |
| 475 | 304.15 | $[M + H]^+$ | A | 4-isopropylphenol |
| 476 | 318.20 | $[M + H]^+$ | A | 4-tert-butylphenol |
| 477 | 332.24 | $[M + H]^+$ | A | 4-tert-pentylphenol |
| 479 | 330.14 | $[M + H]^+$ | A | 4-(trifluoromethyl)phenol |
| 488 | 344.24 | $[M + H]^+$ | A | 4-cyclohexylphenol |
| 492 | 396.29 | $[M + H]^+$ | A | 4-(1-adamantyl)phenol |
| 503 | 302.20 | $[M + H]^+$ | D | ammonia |
| 514 | 314.20 | $[M + H]^+$ | D | ammonia |
| 518 | 366.29 | $[M + H]^+$ | D | ammonia |
| 529 | 318.21 | $[M + H]^+$ | D | hydroxylamine |
| 540 | 330.23 | $[M + H]^+$ | D | hydroxylamine |
| 544 | 382.30 | $[M + H]^+$ | D | hydroxylamine |
| 555 | 316.23 | $[M + H]^+$ | D | methylamine |
| 566 | 328.25 | $[M + H]^+$ | D | methylamine |
| 570 | 380.31 | $[M + H]^+$ | D | methylamine |
| 581 | 330.26 | $[M + H]^+$ | D | dimethylamine |
| 592 | 342.28 | $[M + H]^+$ | D | dimethylamine |
| 596 | 394.33 | $[M + H]^+$ | D | dimethylamine |
| 607 | 303.19 | $[M + H]^+$ | D | ammonia |
| 618 | 315.21 | $[M + H]^+$ | D | ammonia |
| 622 | 367.36 | $[M + H]^+$ | D | ammonia |
| 633 | 319.21 | $[M + H]^+$ | D | hydroxylamine |
| 644 | 331.21 | $[M + H]^+$ | D | hydroxylamine |
| 648 | 383.27 | $[M + H]^+$ | D | hydroxylamine |
| 659 | 317.22 | $[M + H]^+$ | D | methylamine |
| 670 | 329.25 | $[M + H]^+$ | D | methylamine |
| 674 | 381.31 | $[M + H]^+$ | D | methylamine |
| 685 | 331.25 | $[M + H]^+$ | D | dimethylamine |
| 696 | 343.28 | $[M + H]^+$ | D | dimethylamine |
| 700 | 395.31 | $[M + H]^+$ | D | dimethylamine |
| 703 | 321.22 | $[M - H]^-$ | B | NaOH |
| 704 | 371.30 | $[M - H]^-$ | B | NaOH |
| 705 | 339.22 | $[M - H]^-$ | B | NaOH |
| 711 | 355.21 | $[M - H]^-$ | B | NaOH |
| 712 | 337.16 | $[M + H]^+$ | C | methanol |
| 714 | 353.31 | $[M - H]^-$ | C | methanol |
| 721 | 351.20 | $[M + H]^+$ | A | 4-(1-(trifluoromethyl) cyclopropyl)phenol |
| 722 | 401.25 | $[M + H]^+$ | A | 4-(1-(perfluoroethyl) cyclopropyl)phenol |
| 723 | 369.24 | $[M + H]^+$ | A | 4-(1-(trifluoromethyl) cyclopropyl)phenol |
| 729 | 385.18 | $[M + H]^+$ | A | 2-chloro-4-(1-(trifluoromethyl) cyclopropyl)phenol |

TABLE XIV-continued

List of Synthesized compounds

| Compound Number | m/z | ESI Ion Type | General Procedure | Nucleophile used in the General Procedure |
|---|---|---|---|---|
| 730 | 322.22 | $[M - H]^-$ | B | NaOH |
| 731 | 374.19 | $[M + H]^+$ | B | NaOH |
| 732 | 340.21 | $[M - H]^-$ | B | NaOH |
| 738 | 358.13 | $[M + H]^+$ | B | NaOH |
| 739 | 338.17 | $[M + H]^+$ | C | methanol |
| 740 | 388.21 | $[M + H]^+$ | C | methanol |
| 741 | 356.19 | $[M + H]^+$ | C | methanol |
| 747 | 372.15 | $[M + H]^+$ | C | methanol |
| 748 | 352.21 | $[M + H]^+$ | A | 4-(1-(trifluoromethyl) cyclopropyl)phenol |
| 749 | 402.25 | $[M + H]^+$ | A | 4-(1-(perfluoroethyl) cyclopropyl)phenol |
| 750 | 370.20 | $[M + H]^+$ | A | 4-(1-(trifluoromethyl) cyclopropyl)phenol |
| 756 | 386.17 | $[M + H]^+$ | A | 2-chloro-4-(1-(trifluoromethyl) cyclopropyl)phenol |
| 757 | 322.18 | $[M + H]^+$ | D | ammonia |
| 759 | 340.18 | $[M + H]^+$ | D | ammonia |
| 766 | 338.17 | $[M + H]^+$ | D | hydroxylamine |
| 767 | 388.22 | $[M + H]^+$ | D | hydroxylamine |
| 768 | 356.19 | $[M + H]^+$ | D | hydroxylamine |
| 774 | 372.19 | $[M + H]^+$ | D | hydroxylamine |
| 775 | 336.20 | $[M + H]^+$ | D | methylamine |
| 777 | 354.19 | $[M + H]^+$ | D | methylamine |
| 784 | 350.21 | $[M + H]^+$ | D | dimethylamine |
| 785 | 400.26 | $[M + H]^+$ | D | dimethylamine |
| 786 | 368.22 | $[M + H]^+$ | D | dimethylamine |
| 792 | 384.23 | $[M + H]^+$ | D | dimethylamine |
| 793 | 323.17 | $[M + H]^+$ | D | ammonia |
| 794 | 373.21 | $[M + H]^+$ | D | ammonia |
| 795 | 341.17 | $[M + H]^+$ | D | ammonia |
| 801 | 357.14 | $[M + H]^+$ | D | ammonia |
| 802 | 339.17 | $[M + H]^+$ | D | hydroxylamine |
| 803 | 389.22 | $[M + H]^+$ | D | hydroxylamine |
| 804 | 357.17 | $[M + H]^+$ | D | hydroxylamine |
| 810 | 373.17 | $[M + H]^+$ | D | hydroxylamine |
| 811 | 337.18 | $[M + H]^+$ | D | methylamine |
| 812 | 387.23 | $[M + H]^+$ | D | methylamine |
| 813 | 355.20 | $[M + H]^+$ | D | methylamine |
| 819 | 371.17 | $[M + H]^+$ | D | methylamine |
| 820 | 351.21 | $[M + H]^+$ | D | dimethylamine |
| 821 | 401.26 | $[M + H]^+$ | D | dimethylamine |
| 822 | 369.21 | $[M + H]^+$ | D | dimethylamine |
| 828 | 385.21 | $[M + H]^+$ | D | dimethylamine |

Synthesis of Representative Compounds

Compound 005

4-(4-Pentylphenoxy)benzoic acid

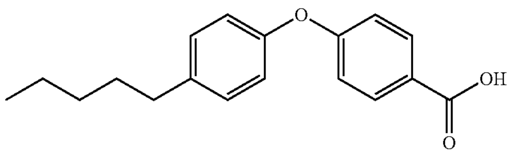 [SMILES: CCCCCc1ccc(Oc2ccc(C(=O)O)cc2)cc1]

Following general procedure B, to a solution of ethyl 4-(4-pentylphenoxy)benzoate (1.69 g, 5.4 mmol) in THF (25 mL) and MeOH (3 mL) was added 2 M aqueous NaOH (10 mL, 20 mmol) and the reaction was stirred at room temperature for 48 hours. The organic solvents were evaporated and the residue acidified with 5 M aqueous HCl to adjust a pH of 1-2. The aqueous layer was extracted with EtOAc (3×). The combined organics were washed with brine (1×), dried over $Na_2SO_4$, filtered and concentrated in vacuo. The residue was purified by recrystallization from hot EtOAc to give the title compound as colorless solid (1.21 g, 79%). $^1H$ NMR (300 MHz, $CDCl_3$) δ 8.12-8.01 (m, 2H), 7.25-7.15 (m, 2H), 7.05-6.94 (m, 4H), 2.68-2.57 (m, 2H), 1.72-1.56 (m, 2H), 1.46-1.33 (m, 2H), 1.38-1.23 (m, 2H), 0.97-0.86 (m, 3H). $^{13}C$ NMR (75 MHz, $CDCl_3$) δ 171.9, 163.3, 153.2, 139.7, 132.5, 130.0, 123.3, 120.4, 117.0, 35.4, 31.6, 31.4, 22.7, 14.2. HRMS ($C_{18}H_{19}O_3^-$): expected: 283.1339. found: 283.1326.

Compound 030

Methyl 4-(4-(tert-Pentyl)phenoxy)benzoate

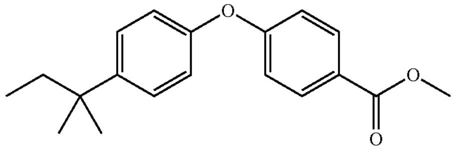 [SMILES: CCC(C)(C)c1ccc(Oc2ccc(C(=O)OC)cc2)cc1]

Following general procedure C, to a solution of 4-(4-(tert-pentyl)phenoxy)benzoic acid (122 mg, 0.43 mmol) in MeOH (2 mL) was added $SOCl_2$ (0.1 mL, 1.4 mmol) at 0° C. and the reaction was then stirred at 80° C. in a sealed vessel for 3 hours in an argon atmosphere. The reaction was cooled to room temperature and quenched by the addition of saturated aqueous $NaHCO_3$. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 90% PE-EtOAc gradient to give the title compound as colorless oil (120 mg, 94%). $^1H$ NMR (300 MHz, $CDCl_3$) δ 8.05-7.94 (m, 2H), 7.39-7.28 (m, 2H), 7.04-6.92 (m, 4H), 3.89 (s, 3H), 1.65 (q, J=7.4 Hz, 2H), 1.30 (s, 6H), 0.71 (t, J=7.4 Hz, 3H). $^{13}C$ NMR (75 MHz, $CDCl_3$) δ 166.8, 162.3, 153.1, 146.0, 131.8, 127.6, 124.3, 119.7, 117.2, 52.1, 37.8, 37.1, 28.7, 9.3. HRMS ($C_{19}H_{23}O_3^+$): expected: 299.1642. found: 299.1640.

Compound 044

(±)-Methyl 4-(4-(bicyclo[2.2.2]octan-2-yl)phenoxy) benzoate

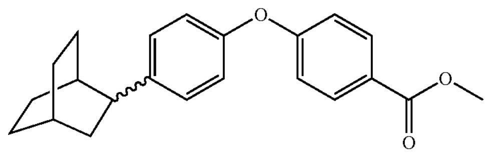 [SMILES: COC(=O)c1ccc(Oc2ccc(C3CC4CCC3CC4)cc2)cc1]

Following general procedure C, to a solution of (±)-4-(4-(Bicyclo[2.2.2]octan-2-yl)phenoxy)benzoic acid (30.3 mg, 0.1 mmol) in toluene (1 mL) was added one drop of DMF followed by $SOCl_2$ (0.02 mL, 0.3 mmol) at room temperature and the reaction was then stirred at 80° C. for 3.5 hours in an argon atmosphere. The reaction was cooled to room temperature and the volatiles evaporated on a rotary evaporator. A solution of $NEt_3$ (0.2 mL, 1.4 mmol) in MeOH (1 mL) was added and the reaction was stirred at room temperature overnight in an argon atmosphere. The reaction was quenched by the addition of 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 85% PE-EtOAc gradient to give the title compound as colorless oil (29.3 mg, 93%). $^1H$ NMR (300 MHz, $CDCl_3$) δ 8.05-7.94 (m, 2H), 7.35-7.21 (m, 2H), 7.06-6.91 (m, 4H), 3.89 (s, 3H), 3.11-2.94 (m, 1H), 2.01 (dddd, J=12.9, 10.6, 3.9, 1.9 Hz, 1H), 1.85-1.45 (m, 10H), 1.43-1.23 (m, 1H). $^{13}C$ NMR (75 MHz, $CDCl_3$) δ 166.8, 162.3, 153.3, 143.1, 131.8, 129.3, 124.3, 120.0, 117.1, 52.1, 41.4, 32.6, 31.2, 27.6, 26.1, 25.4, 24.9, 20.6. HRMS ($C_{22}H_{25}O_3^+$): expected: 337.1798. found: 337.1778.

Compound 051

Ethyl 4-(4-butylphenoxy)benzoate

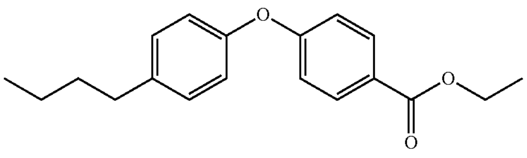 [SMILES: CCCCc1ccc(Oc2ccc(C(=O)OCC)cc2)cc1]

Following general procedure A, to 4-butylphenol (1.75 mL, 11.4 mmol) and $K_2CO_3$ (1.89 g, 13.7 mmol) in DMSO (18 mL) was added ethyl 4-fluorobenzoate (1.35 mL, 9.2 mmol) and the reaction was then stirred at 120° C. for 3 days in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over $Na_2SO_4$, filtered and concentrated in vacuo. The residue was purified by silica gel flash chromatography eluting with a 100% to 70% PE-DCM gradient to give the title compound as colorless oil (1.72 g, 63%). $^1H$ NMR (300 MHz, $CDCl_3$) δ 8.05-7.94 (m, 2H), 7.24-7.13 (m, 2H), 7.02-6.91 (m, 4H), 4.36 (q, J=7.1 Hz, 2H), 2.67-2.56 (m, 2H), 1.69-1.53 (m, 2H), 1.47-1.23 (m, 5H), 0.95 (t, J=7.3 Hz, 3H). $^{13}C$ NMR (75 MHz, $CDCl_3$) δ 166.3, 162.3, 153.5, 139.4, 131.7, 130.0, 124.7, 120.1, 117.1, 60.9, 35.1, 33.8, 22.5, 14.5, 14.1. HRMS ($C_{19}H_{23}O_3^+$): expected: 299.1642. found: 299.1642.

Compound 071

6-(4-Propylphenoxy)nicotinic acid

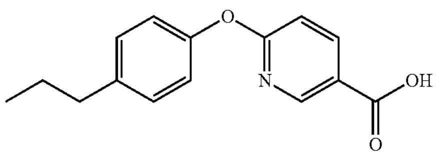 [SMILES: CCCc1ccc(Oc2ccc(C(=O)O)cn2)cc1]

Following general procedure B, to a solution of ethyl 6-(4-propylphenoxy)nicotinate (2.11 g, 7.4 mmol) in EtOH (15 mL) was added 2 M aqueous NaOH (10 mL, 20 mmol) and the reaction was stirred at room temperature for 48 hours. The reaction was acidified with 5 M aqueous HCl to adjust a pH of 1-2. The aqueous layer was extracted with EtOAc (3×). The combined organics were washed with brine (1×), dried over $Na_2SO_4$, filtered and concentrated in vacuo. The residue was purified by recrystallization from hot EtOAc to give the title compound as colorless solid (1.26 g, 66%). $^1H$ NMR (300 MHz, $CDCl_3$) δ 11.01 (br, s, 1H), 8.92 (dd, J=2.4, 0.7 Hz, 1H), 8.31 (dd, J=8.7, 2.4 Hz, 1H), 7.28-7.18 (m, 2H), 7.12-7.02 (m, 2H), 6.94 (dd, J=8.7, 0.7 Hz, 1H), 2.61 (dd, J=8.7, 6.7 Hz, 2H), 1.76-1.58 (m, 2H), 0.97 (t, J=7.3 Hz, 3H). $^{13}C$ NMR (75 MHz, $CDCl_3$) δ 170.5, 167.4, 151.4, 151.2, 141.2, 140.2, 129.9, 121.3, 120.3, 110.9, 37.6, 24.6, 14.0. HRMS ($C_{15}H_{14}NO_3^-$): expected: 256.0979. found: 256.0979.

Compound 114

Methyl 6-(4-(adamantan-1-yl)phenoxy)nicotinate

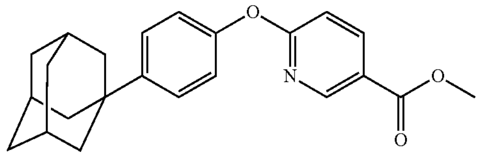 [SMILES: COC(=O)c1ccc(Oc2ccc(C34CC5CC(CC(C5)C3)C4)cc2)nc1]

Following general procedure C, to a solution of 6-(4-(adamantan-1-yl)phenoxy)nicotinic acid (170 mg, 0.49 mmol) in MeOH (2 mL) was added $SOCl_2$ (0.1 mL, 1.37 mmol) at room temperature and the reaction was then stirred at 80° C. in a sealed vessel for 3.5 hours in an argon atmosphere. The reaction was cooled to room temperature and quenched by the addition of saturated aqueous $NaHCO_3$. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 90% PE-EtOAc gradient to give the title compound as colorless solid (47 mg, 27%). $^1H$ NMR (300 MHz, $CDCl_3$) δ 8.84 (dd, J=2.4, 0.7 Hz, 1H), 8.25 (dd, J=8.6, 2.4 Hz, 1H), 7.46-7.35 (m, 2H), 7.15-7.04 (m, 2H), 6.90 (dd, J=8.6, 0.7 Hz, 1H), 3.91 (s, 3H), 2.11 (p, J=3.0 Hz, 4H), 1.93 (d, J=2.9 Hz, 6H), 1.87-1.68 (m, 6H). $^{13}C$ NMR (75 MHz, $CDCl_3$) δ 166.7, 165.6, 150.9, 150.5, 148.4, 140.5, 126.3, 121.0, 120.7, 110.7, 52.2, 43.3, 36.8, 36.0, 29.0. HRMS ($C_{23}H_{26}NO_3^+$): expected: 364.1907. found: 364.1900.

Compound 117

Ethyl 6-(4-Ethylphenoxy)nicotinate

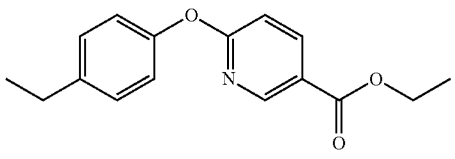 [SMILES: CCOC(=O)c1ccc(Oc2ccc(CC)cc2)nc1]

Following general procedure A, to 4-ethylphenol (1.36 g, 11.1 mmol) and $K_2CO_3$ (1.89 g, 13.7 mmol) in DMSO (18 mL) was added ethyl 6-chloronicotinate (1.65 mL, 10.9 mmol) and the reaction was then stirred at 80° C. for 48 hours in an argon atmosphere. The reaction was cooled to room temperature and quenched by the addition of water.

The aqueous layer was extracted with EtOAc (3×). The combined organics were washed first with 1 M aqueous NaOH (1×) then washed with brine (1×), dried over $Na_2SO_4$, filtered and concentrated in vacuo. The residue was purified by silica gel flash chromatography eluting with a 90% to 60% PE-MeOH gradient to give the title compound as colorless oil (1.78 g, 60%). $^1H$ NMR (300 MHz, $CDCl_3$) δ 8.83 (dd, J=2.4, 0.7 Hz, 1H), 8.25 (dd, J=8.6, 2.4 Hz, 1H), 7.28-7.20 (m, 2H), 7.11-7.00 (m, 2H), 6.90 (dd, J=8.7, 0.8 Hz, 1H), 4.37 (q, J=7.1 Hz, 2H), 2.68 (q, J=7.6 Hz, 2H), 1.38 (t, J=7.1 Hz, 3H), 1.26 (t, J=7.6 Hz, 3H). $^{13}C$ NMR (75 MHz, $CDCl_3$) δ 166.8, 165.2, 151.3, 150.5, 141.4, 140.6, 129.3, 121.4, 121.3, 110.7, 61.2, 28.4, 15.6, 14.4. HRMS ($C_{16}H_{18}NO_3^+$): expected: 272.1281. found: 272.1271.

Compound 159

(±)-4-(4-(Bicyclo[2.2.1]heptan-2-yl)phenoxy)benzamide, mixture of endo and exo

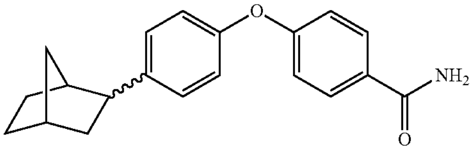 [SMILES: NC(=O)c1ccc(Oc2ccc(C3CC4CCC3C4)cc2)cc1]

Following general procedure D, to a solution of (±)-4-(4-(bicyclo[2.2.1]heptan yl)phenoxy)benzoic acid (50.2 mg, 0.16 mmol) in toluene (0.8 mL) was added one drop of DMF followed by $SOCl_2$ (0.04 mL, 0.55 mmol) at room temperature and the reaction was then stirred at 80° C. for 3 hours in an argon atmosphere. The reaction was cooled to room temperature and the volatiles evaporated on a rotary evaporator. 2 M ammonia in MeOH (0.6 mL, 1.3 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 10% PE-EtOAc gradient to give the title compound as colorless solid (46.6 mg, 93%, 6:1 mixture endo:exo). $^1H$ NMR (300 MHz, $CDCl_3$, mixture of rotamers 0.3:1, and diastereoisomers 6:1) δ 7.82-7.72 (m, 2H), 7.26-7.13 (m, 2H), 7.08-6.91 (m, 4H), 6.05 (s, 2H), 3.20 (major diastereomer, tt, J=14.0, 4.8 Hz, 0.85H), 2.79-2.70 (minor diastereomer, m, 0.15H), 2.46-2.29 (major diastereomer, m, 1.7H), 2.28-2.14 (minor diastereomer, m, 0.3H), 2.12-1.10 (m, 8H). $^{13}C$ NMR (75 MHz, $CDCl_3$, mixture of rotamers 0.3:1, and diastereoisomers 6:1) δ 169.0, 161.5, 161.4, 153.5, 153.3, 144.1, 140.1, 139.9, 129.8, 129.7, 129.5, 128.6, 127.5, 127.4, 119.9, 119.7, 119.6, 117.6, 117.5, 117.4, 50.3, 46.9, 46.6, 45.6, 43.6, 43.1, 42.7, 42.4, 42.2, 42.1, 41.6, 41.1, 40.7, 39.4, 37.7, 37.7, 37.0, 36.7, 36.4, 36.2, 34.6, 30.7, 30.3, 29.0, 24.7, 24.6, 23.0. HRMS ($C_{20}H_{22}NO_2^+$): expected: 308.1645. found: 308.1624.

Compound 186

4-(4-(Adamantan-1-yl)phenoxy)-N-hydroxybenzamide

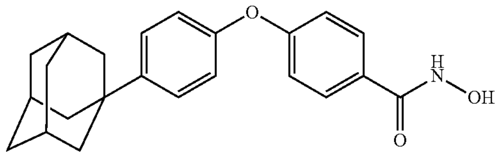 [SMILES: O=C(NO)c1ccc(Oc2ccc(C34CC5CC(CC(C5)C3)C4)cc2)cc1]

Following general procedure D, to a solution of 4-(4-(adamantan yl)phenoxy)benzoic acid (200 mg, 0.57 mmol) in toluene (2 mL) was added two drops of DMF followed by $SOCl_2$ (0.1 mL, 1.37 mmol) at room temperature and the reaction was then stirred at 80° C. for 3.5 hours in an argon atmosphere. The reaction was cooled to room temperature and the volatiles evaporated on a rotary evaporator. Hydroxylamine hydrochloride (208 mg, 3 mmol) in a solution of $NEt_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed first with 1 M aqueous HCl (1×) then washed with brine (1×), dried over $Na_2SO_4$, filtered and concentrated in vacuo. The residue was purified by silica gel flash chromatography eluting with a 90% to 30% PE-EtOAc gradient to give the title compound as colorless solid (176 mg, 84%). $^1H$ NMR (300 MHz, $CDCl_3$/DMSO-$d_6$) δ 11.10 (s, 1H), 8.87 (s, 1H), 7.80-7.69 (m, 2H), 7.37-7.26 (m, 2H), 6.98-6.86 (m, 4H), 2.09-2.01 (m, 4H), 1.85 (d, J=2.8 Hz, 6H), 1.81-1.63 (m, 6H). $^{13}C$ NMR (75 MHz, $CDCl_3$/DMSO-$d_6$) δ 163.8, 159.7, 152.9, 146.7, 128.6, 126.7, 126.0, 118.9, 116.7, 42.6, 36.1, 35.3, 28.2. HRMS ($C_{23}H_{24}NO_3^-$): expected: 362.1761. found: 362.1672.

Compound 195

4-(4-Isopropylphenoxy)-N-methylbenzamide

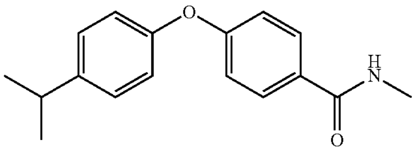 [SMILES: CNC(=O)c1ccc(Oc2ccc(C(C)C)cc2)cc1]

Following general procedure D, to a solution of 4-(4-isopropylphenoxy)benzoic acid (177 mg, 0.7 mmol) in toluene (2.5 mL) was added two drops of DMF followed by $SOCl_2$ (0.15 mL, 2.1 mmol) at room temperature and the reaction was then stirred at 80° C. for 3 hours in an argon atmosphere. The reaction was cooled to room temperature and the volatiles evaporated on a rotary evaporator. 33 wt % methylamine in EtOH (2 mL, 16 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 40% PE-EtOAc gradient to give the title compound as colorless solid (178 mg, 94%). $^{1}H$ NMR (300 MHz, $CDCl_3$) δ 7.78-7.67 (m, 2H), 7.27-7.16 (m, 2H), 7.01-6.90 (m, 4H), 6.31 (s, 1H), 2.98 (d, J=4.6 Hz, 3H), 2.90 (hept, J=6.9 Hz, 1H), 1.26 (d, J=6.9 Hz, 6H). $^{13}C$ NMR (75 MHz, $CDCl_3$) δ 167.8, 160.8, 153.8, 145.1, 128.8, 128.8, 127.9, 119.8, 117.5, 33.6, 26.9, 24.2. HRMS ($C_{17}H_{18}NO_2^-$): expected: 268.1343. found: 268.1384.

Compound 222

4-(4-(tert-Butyl)phenoxy)-N,N-dimethylbenzamide

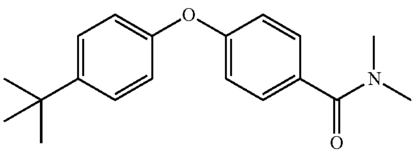 [SMILES: CN(C)C(=O)c1ccc(Oc2ccc(C(C)(C)C)cc2)cc1]

Following general procedure D, to a solution of 4-(4-(tert-butyl)phenoxy)benzoic acid (154 mg, 0.57 mmol) in toluene (2.5 mL) was added two drops of DMF followed by $SOCl_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 40% PE-EtOAc gradient to give the title compound as colorless oil (166 mg, 98%). $^{1}H$ NMR (300 MHz, $CDCl_3$) δ 7.44-7.31 (m, 4H), 7.03-6.91 (m, 4H), 3.06 (s, 6H), 1.33 (s, 9H). $^{13}C$ NMR (75 MHz, $CDCl_3$) δ 171.4, 159.1, 153.9, 147.0, 130.6, 129.2, 126.8, 119.2, 117.8, 39.9 (br), 35.6 (br), 34.5, 31.6. HRMS ($C_{19}H_{24}NO_2^+$): expected: 298.1802. found: 298.1820.

Compound 241

6-(p-Tolyloxy)nicotinamide

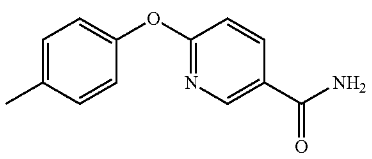 [SMILES: Cc1ccc(Oc2ccc(C(N)=O)cn2)cc1]

Following general procedure D, to a solution of 6-(p-tolyloxy)nicotinic acid (148 mg, 0.66 mmol) in toluene (2.5 mL) was added two drops of DMF followed by $SOCl_2$ (0.12 mL, 1.6 mmol) at room temperature and the reaction was then stirred at 80° C. for 3.5 hours in an argon atmosphere. The reaction was cooled to room temperature and the volatiles evaporated on a rotary evaporator. 2 M ammonia in MeOH (3 mL, 1.3 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 20% PE-EtOAc gradient to give the title compound as colorless solid (104 mg, 70%). $^{1}H$ NMR (300 MHz, $CDCl_3$/DMSO-$d_6$, mixture of rotamers 0.3:1) δ 8.89 (d, J=2.5 Hz, 0.25H, minor rotamer), 8.65 (d, J=2.4 Hz, 0.75H, major rotamer), 8.25 (dt, J=8.6, 2.9 Hz, 1H), 7.96 (br, s, 1H), 7.49 (d, J=8.4 Hz, 0.25H, minor rotamer), 7.27 (br, s, 1H), 7.21 (d, J=8.2 Hz, 2H), 7.06-6.97 (m, 2H), 6.93 (d, J=8.6 Hz, 0.75H, major rotamer), 2.35 (s, 3H). $^{13}C$ NMR (75 MHz, $CDCl_3$/DMSO-$d_6$, mixture of rotamers 0.3:1) δ 166.6, 165.9 (minor rotamer), 165.4 (major rotamer), 153.3 (minor rotamer), 151.5 (major rotamer), 149.7 (minor rotamer), 148.0 (major rotamer), 139.5 (major rotamer), 138.9 (minor rotamer), 134.4, 130.3, 129.3 (minor rotamer), 125.2 (major rotamer), 124.1 (minor rotamer), 121.4, 110.5 (major rotamer), 20.9. HRMS ($C_{13}H_{13}N_2O_2^+$): expected: 229.0972. found: 229.0978.

Compound 275

N-Hydroxy-6-(4-(trifluoromethyl)phenoxy)nicotinamide

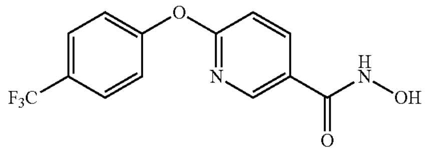 [SMILES: O=C(NO)c1ccc(Oc2ccc(C(F)(F)F)cc2)nc1]

Following general procedure D, to a solution of 6-(4-(trifluoromethyl)phenoxy)nicotinic acid (62.9 mg, 0.22 mmol) in toluene (1.5 mL) was added two drops of DMF followed by $SOCl_2$ (0.06 mL, 0.82 mmol) at room temperature and the reaction was then stirred at 80° C. for 3 hours in an argon atmosphere. The reaction was cooled to room temperature and the volatiles evaporated on a rotary evaporator. Hydroxylamine hydrochloride (94 mg, 1.35 mmol) in a solution of $NEt_3$ (0.5 mL, 3.6 mmol) and MeOH (1 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 40% PE-EtOAc (+0.2% AcOH) gradient to give the title compound as colorless solid (42.7 mg, 65%). $^{1}H$ NMR (300 MHz, $CDCl_3$/DMSO-$d_6$) δ 11.29 (s, 1H), 9.07 (s, 1H), 8.52 (d, J=2.4 Hz, 1H), 8.19 (dd, J=8.6, 2.4 Hz, 1H), 7.69 (d, J=8.4 Hz, 2H), 7.29 (d, J=8.4 Hz, 2H), 7.06 (d, J=8.5 Hz, 1H). $^{13}C$ NMR (75 MHz, $CDCl_3$/DMSO-$d_6$) δ 163.6, 161.9, 156.2 (d, J=1.5 Hz), 146.4, 138.8, 126.6 (q, J=3.8 Hz), 125.6 (q, J=32.4 Hz), 124.2, 123.8 (q, J=273.0 Hz), 121.5, 111.1. HRMS ($C_{13}H_8F_3N_2O_3^-$): expected: 297.0492. found: 297.0597.

Compound 284

6-(4-Cyclohexylphenoxy)-N-hydroxynicotinamide

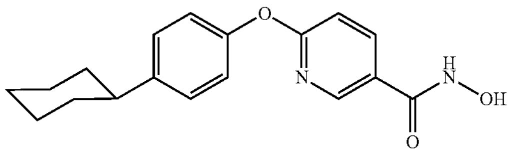 [SMILES: O=C(NO)c1ccc(Oc2ccc(C3CCCCC3)cc2)nc1]

Following general procedure D, to a solution of 6-(4-cyclohexylphenoxy)nicotinic acid (150 mg, 0.5 mmol) in toluene (2 mL) was added two drops of DMF followed by $SOCl_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. Hydroxylamine hydrochloride (208 mg, 3 mmol) in a solution of $NEt_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 95% PE-EtOAc gradient to give the title compound as colorless solid (150 mg, 95%). $^1$H NMR (300 MHz, $CDCl_3$/DMSO-$d_6$) δ 11.27 (s, 1H), 9.05 (s, 1H), 8.54 (s, 1H), 8.20-8.06 (m, 1H), 7.23 (d, J=8.0 Hz, 2H), 7.02 (d, J=8.0 Hz, 2H), 6.95 (d, J=8.6 Hz, 1H), 1.86 (d, J=8.3 Hz, 4H), 1.74 (d, J=12.6 Hz, 1H), 1.43 (q, J=11.3, 10.1 Hz, 4H), 1.35-1.16 (m, 2H). $^{13}$C NMR (75 MHz, $CDCl_3$/DMSO-$d_6$) δ 163.4, 160.9, 149.8, 145.2, 142.8, 137.1, 126.2, 122.0, 119.5, 109.0, 41.9, 32.7, 25.0, 24.2. HRMS ($C_{18}H_{21}N_2O_3^+$): expected: 313.1547. found: 313.1622.

Compound 297

6-(4-Isopropylphenoxy)-N-methylnicotinamide

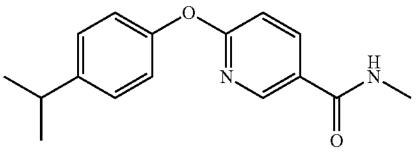

Following general procedure D, to a solution of 6-(4-isopropylphenoxy)nicotinic acid (151 mg, 0.6 mmol) in toluene (2.5 mL) was added two drops of DMF followed by $SOCl_2$ (0.1 mL, 1.5 mmol) at room temperature and the reaction was then stirred at 80° C. for 3 hours in an argon atmosphere. 33 wt % methylamine in EtOH (2.5 mL, 20 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 20% PE-EtOAc gradient to give the title compound as colorless solid (150 mg, 96%). $^1$H NMR (300 MHz, $CDCl_3$) δ 8.55 (dd, J=2.5, 0.7 Hz, 1H), 8.11 (dd, J=8.6, 2.5 Hz, 1H), 7.32-7.21 (m, 2H), 7.11-7.00 (m, 2H), 6.90 (dd, J=8.6, 0.7 Hz, 1H), 6.47 (d, J=5.3 Hz, 1H), 2.98 (d, J=4.7 Hz, 3H), 2.94 (hept, J=7.0 Hz, 1H), 1.27 (d, J=6.9 Hz, 6H). $^{13}$C NMR (75 MHz, $CDCl_3$) δ 166.1, 165.8, 151.4, 146.6, 145.9, 139.0, 127.8, 125.3, 121.1, 111.0, 33.7, 26.9, 24.1. HRMS ($C_{16}H_{19}N_2O_2^+$): expected: 271.1441. found: 271.1491.

Compound 322

6-(4-Isopropylphenoxy)-N,N-dimethylnicotinamide

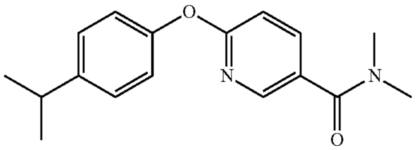

Following general procedure D, to a solution of 6-(4-isopropylphenoxy)nicotinic acid (156 mg, 0.6 mmol) in toluene (2.5 mL) was added two drops of DMF followed by $SOCl_2$ (0.1 mL, 1.5 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5.4 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 30% PE-EtOAc gradient to give the title compound as colorless oil (169 mg, 98%). $^1$H NMR (300 MHz, $CDCl_3$) δ 8.28 (dd, J=2.4, 0.8 Hz, 1H), 7.79 (dd, J=8.5, 2.4 Hz, 1H), 7.31-7.20 (m, 2H), 7.11-7.00 (m, 2H), 6.91 (dd, J=8.5, 0.7 Hz, 1H), 3.07 (s, 6H), 2.92 (hept, J=7.0 Hz, 1H), 1.26 (d, J=6.9 Hz, 6H). $^{13}$C NMR (75 MHz, $CDCl_3$) δ 168.9, 164.5, 151.4, 146.8, 145.6, 139.2, 127.7, 126.6, 121.0, 111.0, 39.7 (br), 35.6 (br), 33.6, 24.1. HRMS ($C_{17}H_{21}N_2O_2^+$): expected: 285.1598. found: 285.1643.

Compound 344

4-(4-(Butylphenoxy)-3-fluorobenzoic acid

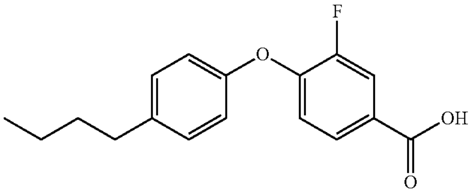 [SMILES: CCCCc1ccc(Oc2ccc(C(=O)O)cc2F)cc1]

Following general procedure B, to a solution of ethyl 4-(4-butylphenoxy) fluorobenzoate (1.42 g, 4.5 mmol) in EtOH (9 mL) was added 2 M aqueous NaOH (5 mL, 10 mmol) and the reaction was stirred at room temperature overnight. 1 M aqueous HCl was added to adjust a pH of 1-2. The aqueous layer was extracted with EtOAc (3×). The combined organics were washed with brine (2×), dried over $Na_2SO_4$, filtered and concentrated in vacuo. The residue was purified by recrystallization from hot EtOAc to give the title compound as colorless solid (0.56 g, 43%). $^1H$ NMR (300 MHz, $CDCl_3$) δ 11.18 (br, s, 1H), 7.91 (dd, J=11.0, 2.0 Hz, 1H), 7.82 (ddd, J=8.6, 2.0, 1.1 Hz, 1H), 7.26-7.15 (m, 2H), 7.04-6.88 (m, 3H), 2.68-2.57 (m, 2H), 1.70-1.54 (m, 2H), 1.47-1.23 (m, 2H), 0.95 (t, J=7.3 Hz, 3H). $^{13}C$ NMR (75 MHz, $CDCl_3$) δ 171.0 (d, J=2.5 Hz), 153.3, 152.9 (d, J=249.5 Hz), 150.8 (d, J=11.0 Hz), 139.7, 130.1, 127.3 (d, J=3.5 Hz), 124.3 (d, J=6.5 Hz), 119.4, 118.9 (d, J=19.9 Hz), 118.6 (d, J=1.4 Hz), 35.1, 33.8, 22.5, 14.1. HRMS ($C_{17}H_{16}FO_3^-$): expected: 287.1089. found: 287.1062.

Compound 395

Ethyl 4-(4-butylphenoxy)-3-fluorobenzoate

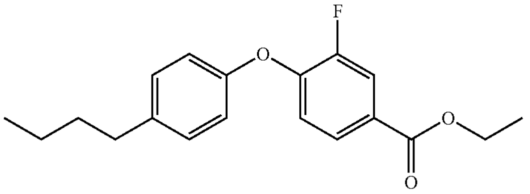 [SMILES: CCCCc1ccc(Oc2ccc(C(=O)OCC)cc2F)cc1]

Following general procedure A, to 4-butylphenol (1.75 mL, 11.4 mmol) and $K_2CO_3$ (1.90 g, 13.8 mmol) in DMSO (18 mL) was added ethyl 3,4-difluorobenzoate (1.37 mL, 9 mmol) and the reaction was then stirred at 80° C. for 24 hours in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over $Na_2SO_4$, filtered and concentrated in vacuo. The residue was purified by silica gel flash chromatography eluting with a 100% to 80% PE-DCM gradient to give the title compound as colorless oil (1.80 g, 63%). $^1H$ NMR (300 MHz, $CDCl_3$) δ 7.84 (dd, J=11.2, 2.0 Hz, 1H), 7.75 (ddd, J=8.5, 2.0, 1.2 Hz, 1H), 7.23-7.12 (m, 2H), 7.01-6.88 (m, 3H), 4.37 (q, J=7.1 Hz, 2H), 2.67-2.55 (m, 2H), 1.68-1.52 (m, 2H), 1.46-1.23 (m, 5H), 0.94 (t, J=7.3 Hz, 3H). $^{13}C$ NMR (75 MHz, $CDCl_3$) δ 165.4 (d, J=2.6 Hz), 153.7, 153.0 (d, J=249.0 Hz), 149.5 (d, J=11.2 Hz), 139.3, 129.9, 126.4 (d, J=3.5 Hz), 126.0 (d, J=6.3 Hz), 119.0, 119.0 (d, J=1.4 Hz), 118.3 (d, J=19.9 Hz), 61.3, 35.1, 33.8, 22.5, 14.4, 14.1. HRMS ($C_{19}H_{22}FO_3^+$): expected: 317.1548. found: 317.1549.

Compound 451

Methyl 5-fluoro-6-(4-(tert-pentyl)phenoxy)nicotinate

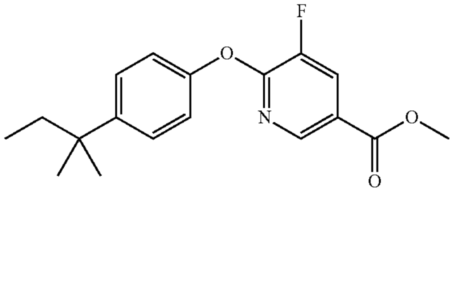 [SMILES: CCC(C)(C)c1ccc(Oc2ncc(C(=O)OC)cc2F)cc1]

Following general procedure C, to a solution of 5-fluoro-6-(4-(tert-pentyl)phenoxy)nicotinic acid (100 mg, 0.33 mmol) in MeOH (2 mL) was added $SOCl_2$ (0.1 mL, 1.4 mmol) at 0° C. and the reaction was then stirred at 80° C. for 3 hours in an argon atmosphere. The reaction was cooled to room temperature and quenched by the addition of saturated aqueous $NaHCO_3$. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 90% PE-EtOAc gradient to give the title compound as colorless solid (30 mg, 29%). $^1H$ NMR (300 MHz, $CDCl_3$) δ 8.56 (d, J=1.9 Hz, 1H), 8.02 (dd, J=10.0, 1.9 Hz, 1H), 7.43-7.31 (m, 2H), 7.17-7.04 (m, 2H), 3.92 (s, 3H), 1.66 (q, J=7.4 Hz, 2H), 1.31 (s, 6H), 0.72 (t, J=7.4 Hz, 3H). $^{13}C$ NMR (75 MHz, $CDCl_3$) δ 164.8 (d, J=1.6 Hz), 155.7 (d, J=11.1 Hz), 150.4, 147.1 (d, J=261.8 Hz), 146.9, 144.4 (d, J=6.1 Hz), 127.4, 125.0 (d, J=17.0 Hz), 122.1 (d, J=1.7 Hz), 120.7, 52.6, 37.9, 37.1, 28.6, 9.3. HRMS ($C_{18}H_{21}FNO_3^+$): expected: 318.1500. found: 318.1555.

Compound 544

4-(4-(Adamantan-1-yl)phenoxy)-3-fluoro-N-hydroxybenzamide

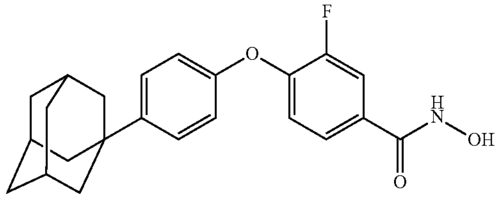 [SMILES: O=C(NO)c1ccc(Oc2ccc(C34CC5CC(CC(C5)C3)C4)cc2)c(F)c1]

Following general procedure D, to a solution of 4-(4-(adamantan-1-yl)phenoxy)-3-fluorobenzoic acid (110 mg, 0.3 mmol) in toluene (2 mL) was added two drops of DMF followed by $SOCl_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. $NEt_3$ (0.7 mL, 5.1 mmol) and hydroxylamine hydrochloride (148 mg, 2.1 mmol) in MeOH (1.5 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography twice, eluting first with a 100% to 40% PE-EtOAc gradient and then with a 100% to 97% DCM-MeOH gradient to give the title compound as colorless solid (60 mg, 52%). $^1H$ NMR (300 MHz, $CDCl_3$/DMSO-$d_6$) δ 11.23 (s, 1H), 9.00 (s, 1H), 7.68 (dd, J=11.6, 2.0 Hz, 1H), 7.57 (ddd, J=8.5, 2.1, 1.1 Hz, 1H), 7.37-7.25 (m, 2H), 6.97 (t, J=8.4 Hz, 1H), 6.96-6.86 (m, 2H), 2.12-1.97 (m, 4H), 1.84 (d, J=2.9 Hz, 6H), 1.80-1.63 (m, 6H). $^{13}C$ NMR (75 MHz, $CDCl_3$/DMSO-$d_6$) δ 162.4, 153.2, 152.4 (d, J=247.5 Hz), 146.6, 146.3 (d, J=11.1 Hz), 128.4 (d, J=5.7 Hz), 126.0, 123.5, 119.5, 117.4, 115.5 (d, J=19.6 Hz), 42.6, 36.1, 35.3, 28.2. HRMS ($C_{23}H_{23}FNO_3^-$): expected: 380.1667. found: 380.1541.

Compound 644

6-(4-Cyclohexylphenoxy)-5-fluoro-N-hydroxynicotinamide

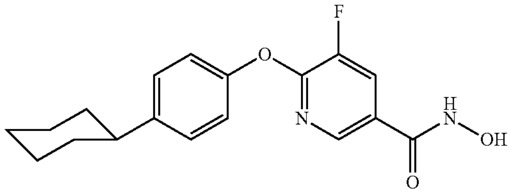 [SMILES: O=C(NO)c1cnc(Oc2ccc(C3CCCCC3)cc2)c(F)c1]

Following general procedure D, to a solution of 6-(4-cyclohexylphenoxy) fluoronicotinic acid (120 mg, 0.4 mmol) in toluene (2.5 mL) was added two drops of DMF followed by $SOCl_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. Hydroxylamine hydrochloride (208 mg, 3 mmol) in a solution of $NEt_3$ (1.0 mL, 7.2 mmol) and MeOH (2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 30% PE-EtOAc gradient to give the title compound as colorless solid (110 mg, 88%). $^1H$ NMR (300 MHz, $CDCl_3$/DMSO-$d_6$) δ 11.32 (s, 1H), 9.12 (s, 1H), 8.28 (d, J=1.9 Hz, 1H), 8.06-7.94 (m, 1H), 7.26-7.15 (m, 2H), 7.08-6.97 (m, 2H), 1.88-1.75 (m, 4H), 1.75-1.64 (m, 1H), 1.48-1.31 (m, 4H), 1.31-1.13 (m, 2H). $^{13}C$ NMR (75 MHz, $CDCl_3$/DMSO-$d_6$) δ 161.0, 153.2 (d, J=11.3 Hz), 150.4, 146.3 (d, J=259.6 Hz), 144.4, 140.6, 127.4, 124.5, 123.1 (d, J=16.7 Hz), 120.7, 43.2, 34.0, 26.2, 25.5. HRMS ($C_{18}H_{18}FN_2O_3^-$): expected: 329.1307. found: 329.1279.

Compound 703

4-(4-(1-(Trifluoromethyl)cyclopropyl)phenoxy)benzoic acid

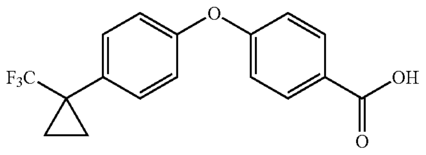 [SMILES: O=C(O)c1ccc(Oc2ccc(C3(C(F)(F)F)CC3)cc2)cc1]

Following general procedure B, to a solution of ethyl 4-(4-(1-(trifluoromethyl)cyclopropyl)phenoxy)benzoate (0.86 g, 2.5 mmol) in EtOH (20 mL) was added 2 M aqueous NaOH (10 mL, 20 mmol) and the reaction was stirred at room temperature overnight. 1 M aqueous HCl was added to adjust a pH of 1-2. The aqueous layer was extracted with EtOAc (3×). The combined organics were washed with brine (2×), dried over $Na_2SO_4$, filtered and concentrated in vacuo. The residue was purified by silica gel flash chromatography eluting with a 90% to 75% PE-EtOAc (+0.2% AcOH) gradient to give the title compound as slightly yellow solid (0.75 g, 95%). $^1H$ NMR (300 MHz, $CDCl_3$) δ 11.15 (br, s, 1H), 8.15-8.04 (m, 2H), 7.54-7.43 (m, 2H), 7.09-6.98 (m, 4H), 1.38 (dd, J=6.7, 5.1 Hz, 2H), 1.07-1.01 (m, 2H). $^{13}C$ NMR (75 MHz, $CDCl_3$) δ 171.8, 162.3, 155.7, 133.2, 132.6, 132.5, 126.5 (q, J=273.4 Hz), 124.0, 119.9, 117.8, 27.8 (q, J=33.7 Hz), 10.0 (q, J=2.4 Hz). HRMS ($C_{17}H_{12}F_3O_3^-$): expected: 321.0744. found: 321.0712.

Compound 712

Methyl 4-(4-(1-(trifluoromethyl)cyclopropyl)phenoxy)benzoate

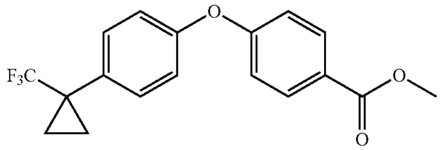 [SMILES: COC(=O)c1ccc(Oc2ccc(C3(C(F)(F)F)CC3)cc2)cc1]

Following general procedure C, to a solution of 4-(4-(1-(Trifluoromethyl)cyclopropyl)phenoxy)benzoic acid (112 mg, 0.35 mmol) in toluene (2 mL) was added two drops of DMF followed by $SOCl_2$ (0.1 mL, 1.4 mmol) at room temperature and the reaction was then stirred at 80° C. for 3.5 hours in an argon atmosphere. The reaction was cooled to room temperature and the volatiles evaporated on a rotary evaporator. A solution of $NEt_3$ (0.6 mL, 4.4 mmol) in MeOH (1.2 mL) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 85% PE-EtOAc gradient to give the title compound as colorless oil (176 mg, 93%). $^1H$ NMR (300 MHz, $CDCl_3$) δ 8.07-7.96 (m, 2H), 7.52-7.41 (m, 2H), 7.07-6.95 (m, 4H), 3.90 (s, 3H), 1.41-1.31 (m, 2H), 1.09-0.97 (m, 2H). $^{13}C$ NMR (75 MHz, $CDCl_3$) δ 166.7, 161.4, 156.0, 133.1, 132.2, 131.9, 126.4 (q, J=273.0 Hz), 125.0, 119.7, 117.9, 52.2, 27.8 (q, J=33.6 Hz), 10.0 (q, J=2.5 Hz). HRMS ($C_{18}H_{16}F_3O_{3+}$): expected: 337.1046. found: 337.1036.

Compound 729

Ethyl 4-(2-chloro-4-(1-(trifluoromethyl)cyclopropyl)phenoxy)-benzoate

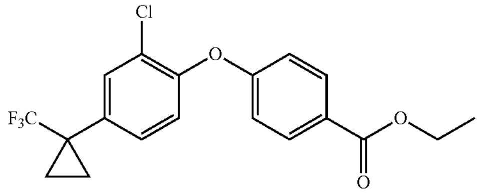 [SMILES: CCOC(=O)c1ccc(Oc2ccc(C3(C(F)(F)F)CC3)cc2Cl)cc1]

Following general procedure A, to 2-chloro-4-(1-(trifluoromethyl)cyclopropyl)phenol (245 mg, 1.5 mmol) and $K_2CO_3$ (220 mg 1.6 mmol) in DMSO (2 mL) was added ethyl 4-fluorobenzoate (0.15 mL, 1.1 mmol) and the reaction was then stirred at 120° C. for 2 days in an argon atmosphere. $K_2CO_3$ (220 mg 1.6 mmol) was added and the reaction was then stirred at 150° C. for 9 hours in an argon atmosphere. The reaction was cooled to room temperature and quenched by the addition of water. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 70% PE-DCM gradient to give the title compound as yellow oil (100 mg, 18%). $^1$H NMR (300 MHz, $CDCl_3$) δ 8.08-7.97 (m, 2H), 7.58 (d, J=2.1 Hz, 1H), 7.41-7.27 (m, 1H), 7.03 (d, J=8.4 Hz, 1H), 7.03-6.88 (m, 2H), 4.36 (q, J=7.1 Hz, 2H), 1.44-1.33 (m, 5H), 1.11-1.00 (m, 2H). $^{13}$C NMR (75 MHz, $CDCl_3$) δ 166.0, 160.7, 151.3, 133.9, 133.8, 131.7, 131.1, 126.2, 126.0 (q, J=273.4 Hz), 125.5, 121.6, 116.8, 60.9, 27.6 (q, J=33.1 Hz), 14.4, 10.0 (q, J=2.3 Hz). HRMS ($C_{19}H_{17}ClF_3O_3^+$): expected: 385.0813. found: 385.0796.

Compound 730

6-(4-(1-(Trifluoromethyl)cyclopropyl)phenoxy)nicotinic acid

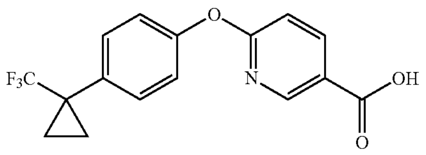

Following general procedure B, to a solution of ethyl 6-(4-(1-(trifluoromethyl)cyclopropyl)phenoxy)nicotinate (1.47 g, 4.2 mmol) in EtOH (20 mL) was added 2 M aqueous NaOH (10 mL, 20 mmol) and the reaction was stirred at room temperature overnight. 1 M aqueous HCl was added to adjust a pH of 1-2. The aqueous layer was extracted with EtOAc (3×). The combined organics were washed with brine (2×), dried over $Na_2SO_4$, filtered and concentrated in vacuo. The residue was purified by silica gel flash chromatography eluting with a 90% to 75% PE-EtOAc (+0.2% AcOH) gradient to give the title compound as colorless solid (1.21 g, 90%). $^1$H NMR (300 MHz, $CDCl_3$/DMSO-$d_6$) δ 12.16 (s, 1H), 8.80 (d, J=2.4 Hz, 1H), 8.30 (dd, J=8.6, 2.3 Hz, 1H), 7.51 (dd, J=8.1, 1.6 Hz, 2H), 7.19-7.08 (m, 2H), 6.97 (d, J=8.6 Hz, 1H), 1.41-1.30 (m, 2H), 1.18-1.02 (m, 2H). $^{13}$C NMR (75 MHz, $CDCl_3$/DMSO-$d_6$) δ 166.1, 165.3, 152.9, 149.8, 140.5, 132.2, 132.2, 125.9 (q, J=273.1 Hz), 121.8, 120.7, 110.5, 27.1 (q, J=33.5 Hz), 9.3 (q, J=2.4 Hz). HRMS ($C_{16}H_{13}F_3NO_3^+$): expected: 324.0842. found: 324.0847.

Compound 749

Ethyl 6-(4-(1-(perfluoroethyl)cyclopropyl)phenoxy)nicotinate

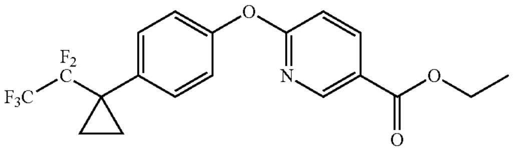 [SMILES: CCOC(=O)c1ccc(Oc2ccc(C3(C(F)(F)C(F)(F)F)CC3)cc2)nc1]

Following general procedure A, to 4-(1-(perfluoroethyl)cyclopropyl)phenol (330 mg, 1.3 mmol) and $K_2CO_3$ (305 mg 2.2 mmol) in DMSO (2.7 mL) was added ethyl 6-chloronicotinate (0.2 mL, 1.3 mmol) and the reaction was then stirred at 80° C. for 3 days in an argon atmosphere. The reaction was cooled to room temperature and quenched by the addition of water. The aqueous layer was extracted with EtOAc (3×). The combined organics were washed first with 1 M aqueous NaOH (1×) then washed with brine (1×), dried over $Na_2SO_4$, filtered and concentrated in vacuo. The residue was purified by silica gel flash chromatography eluting with a 100% to 90% PE-EtOAc gradient to give the title compound as yellow oil (445 mg, 88%). $^1$H NMR (300 MHz, $CDCl_3$) δ 8.83 (dd, J=2.4, 0.7 Hz, 1H), 8.28 (dd, J=8.6, 2.4 Hz, 1H), 7.48 (d, J=8.6 Hz, 2H), 7.14-7.07 (m, 2H), 6.93 (dd, J=8.6, 0.7 Hz, 1H), 4.38 (q, J=7.1 Hz, 2H), 1.43-1.34 (m, 5H), 1.12-1.04 (m, 2H). $^{13}$C NMR (75 MHz, $CDCl_3$) δ 166.14, 165.10, 153.39, 150.44, 140.84, 133.21, 133.12, 121.86, 121.20, 111.12, 61.31, 25.88 (t, J=23.9 Hz), 14.42, 10.02 (t, J=4.0 Hz). The two multiplets of the $CF_2$ (tq) and the $CF_3$ (qt) are too weak to be resolved. HRMS ($C_{19}H_{17}F_5NO_3^+$): expected: 402.1123. found: 402.1124.

Compound 784

N,N-Dimethyl-4-(4-(1-(trifluoromethyl)cyclopropyl)phenoxy)-benzamide

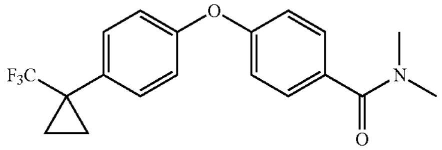

Following general procedure D, to a solution of 4-(4-(1-(Trifluoromethyl)cyclopropyl)phenoxy)benzoic acid (101 mg, 0.3 mmol) in toluene (2 mL) was added two drops of DMF followed by $SOCl_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (1.2 mL, 2.5 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 15% PE-EtOAc gradient to give the title compound as colorless oil (110 mg, 100%). $^1$H NMR (300 MHz, $CDCl_3$) δ 7.48-7.37 (m, 4H), 7.06-6.92 (m, 4H), 3.06 (d, J=9.8 Hz, 6H), 1.39-1.28 (m, 2H), 1.07-0.95 (m, 2H). $^{13}$C NMR (75 MHz, $CDCl_3$) δ 171.2, 158.2, 156.7, 133.0, 131.6, 131.4, 129.3, 126.5 (q, J=272.1 Hz), 119.0, 118.6, 39.8 (br), 35.6 (br), 27.7 (q, J=33.7 Hz), 10.0 (q, J=2.5 Hz). HRMS ($C_{19}H_{19}F_3NO_2^+$): expected: 350.1363. found: 350.1351.

Compound 820

N,N-Dimethyl-6-(4-(1-(trifluoromethyl)cyclopropyl)phenoxy)-nicotinamide

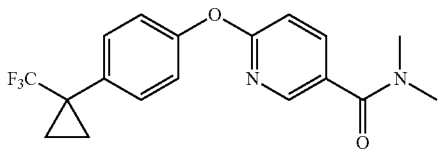

Following general procedure D, to a solution of 6-(4-(1-(trifluoromethyl)cyclopropyl)phenoxy)nicotinic acid (162 mg, 0.5 mmol) in toluene (2 mL) was added two drops of DMF followed by $SOCl_2$ (0.1 mL, 1.4 mmol) at room temperature and the reaction was then stirred at 80° C. for 3 hours in an argon atmosphere. The reaction was cooled to room temperature and the volatiles evaporated on a rotary evaporator. 2 M dimethylamine in THF (2.5 mL, 5 mmol) was added and the reaction was stirred at room temperature overnight in an argon atmosphere. The reaction was quenched by the addition 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with a 90% to 30% PE-EtOAc gradient to give the title compound as colorless solid (172 mg, 100%). $^1H$ NMR (300 MHz, $CDCl_3$) δ 8.28 (dd, J=2.4, 0.8 Hz, 1H), 7.82 (dd, J=8.5, 2.4 Hz, 1H), 7.54-7.44 (m, 2H), 7.16-7.06 (m, 2H), 6.96 (dd, J=8.5, 0.8 Hz, 1H), 3.18-2.96 (m, 6H), 1.40-1.29 (m, 2H), 1.10-0.98 (m, 2H). $^{13}C$ NMR (75 MHz, $CDCl_3$) δ 168.8, 163.9, 153.5, 146.7, 139.3, 132.7, 132.7, 127.1, 126.3 (q, J=274.0 Hz), 121.0, 111.4, 39.7 (br), 35.63 (br), 27.7 (q, J=33.6 Hz), 9.8 (q, J=2.5 Hz). HRMS ($C_{18}H_{18}F_3N_2O_2^+$): expected: 351.1315. found: 351.1293.

Synthesis of Intermediates (±)-4-(Bicyclo[2.2.1]heptan-2-yl)phenol, Mixture of Endo and Exo

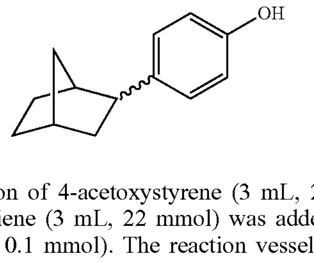

To a solution of 4-acetoxystyrene (3 mL, 20 mmol) in dicyclopentadiene (3 mL, 22 mmol) was added hydroquinone (10 mg, 0.1 mmol). The reaction vessel was purged with argon and sealed. The reaction mixture was stirred at 160° C. for 24 h. The reaction mixture was filtered through silica and washed with DCM. The solution was concentrated in vacuo and used in the next step without further purification.

The resulting oil was dissolved in EtOAc (40 mL). Under an argon atmosphere, palladium on charcoal (5% Pd, 0.2 g, 0.1 mmol) was added and the reaction vessel was flushed with Hz. The reaction was stirred strongly for 22 h at room temperature. The reaction mixture was then purged back with argon, filtered through celite, washed with EtOAc, and concentrated in vacuo. The crude mixture was then filtered on silica (PE/EtOAc), concentrated in vacuo and used in the next step without further purification.

The resulting oil was dissolved in EtOH (40 mL), and 2 M aqueous NaOH (20 mL, 40 mmol) was added. The reaction mixture was stirred for 17 h at room temperature. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 0% PE-DCM gradient. Recrystallization in hot PE afforded the title compound as white needles (1.5 g, 40% over three steps, 7:1 mixture endo:exo)

(±)-4-(Bicyclo[2.2.2]octan-2-yl)phenol

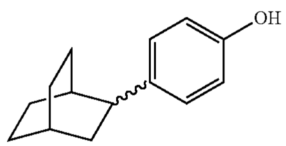 [SMILES: Oc1ccc(C2CC3CCC2CC3)cc1]

To a solution of 4-acetoxystyrene (3 mL, 20 mmol) in cyclohexadiene (2.1 mL, 22 mmol) was added hydroquinone (10 mg, 0.1 mmol). The reaction vessel was purged with argon and sealed. The reaction mixture was stirred at 160° C. for 24 h. The reaction mixture was filtered through silica and washed with DCM. The solution was concentrated in vacuo and used in the next step without further purification.

The resulting oil was dissolved in EtOAc (40 mL). Under an argon atmosphere, palladium on charcoal (5% Pd, 0.2 g, 0.1 mmol) was added and the reaction vessel was flushed with Hz. The reaction was stirred strongly for 22 h. The reaction mixture was then purged back with argon, filtered through celite, washed with EtOAc, and concentrated in vacuo. The crude mixture was then filtered on silica (PE/DCM), concentrated in vacuo and used in the next step without further purification.

The resulting oil was dissolved in EtOH (40 mL), and 2 M aqueous NaOH (20 mL, 40 mmol) was added. The reaction mixture was stirred for 17 h at room temperature. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 0% PE-DCM gradient. Recrystallization in hot PE afforded the title compound as white needles (0.6 g, 15% over three steps)

4-(1-(Trifluoromethyl)cyclopropyl)phenol

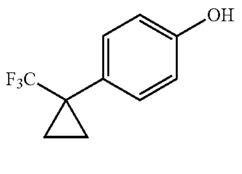 [SMILES: Oc1ccc(C2(C(F)(F)F)CC2)cc1]

Following a procedure from Anderson, K. W. et al., *J. Am. Chem. Soc.,* 2006, 128 (33), 10694-10695, to a solution of KOH (2.6 g, 46.3 mmol), $Pd_2dba_3$ (278 mg, 0.30 mmol), and di-tert-butyl-[2-(2,4,6-triisopropylphenyl)phenyl]phosphate (510 mg, 1.20 mmol) in degassed 1,4-dioxane (7.5 mL) and water (7.5 mL) under argon was added 1-bromo-4-(1-(trifluoromethyl)cyclopropyl)benzene (3.98 g, 15.0 mmol). The reaction vessel was then sealed and immerged in a pre-heated oil bath at 100° C. The reaction was stirred for 4-10 h. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 90% PE-EtOAc gradient to give the title compound as a yellow oil (3.0 g, 99%).

2-Chloro-4-(1-(trifluoromethyl)cyclopropyl)phenol

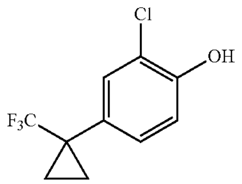 [SMILES: Oc1ccc(C2(C(F)(F)F)CC2)cc1Cl]

To a solution of 4-(1-(trifluoromethyl)cyclopropyl)phenol (1.03 g, 5.1 mmol) in DCE (25 mL) under argon at 0° C. were added N-chlorosuccinimide (737 mg, 5.52 mmol) and aluminium trichloride (740 mg, 5.55 mmol). The reaction mixture was stirred at 0° C. for 3 h, before being quenched with water. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 80% PE-EtOAc gradient to give the title compound as a yellow oil (380 mg, 31%).

6-Chloro-5-fluoronicotinic acid

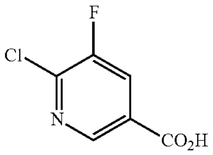 [SMILES: O=C(O)c1cnc(Cl)c(F)c1]

To a solution of 2-chloro-3-fluoro-5-methylpyridine (512 mg, 3.52 mmol) in pyridine (2.5 mL) and water (2.5 mL) was added one portion of potassium permanganate (1.1 g, 6.9 mmol). The reaction mixture was heated to 100° C. Two more equal portion of potassium permanganate (for a total of 3.3 g, 20.7 mmol) were added after respectively 1 h and 2 h of stirring at 100° C. When needed, the solid accumulated in the condenser were washed down with water and pyridine. After another 1 h of stirring at 100° C., the reaction mixture was cooled down to room temperature. The reaction mixture was quenched with saturated aqueous $Na_2S_2O_3$ and stirred 30 minutes. The mixture was filtered, then acidified to pH 2 with HCl 5 M. The aqueous layer was extracted with EtOAc (3×). The combined organics were washed with brine (1×), dried over $Na_2SO_4$, filtered and concentrated in vacuo. The residue was purified by silica gel flash chromatography eluting with 90% to 70% PE-EtOAc gradient to give the title compound as a white solid (300 mg, 49%).

6-Chloro-5-fluoronicotinic acid ethyl ester

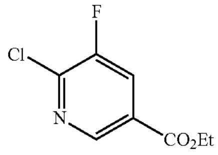

To a solution of 6-chloro-5-fluoronicotinic acid (5.1 g, 29.1 mmol) in EtOH (150 mL) at 0° C. was added $SOCl_2$ (4.5 mL, 61.7 mmol). The mixture was heated at reflux for 4 h. The reaction mixture was allowed to cool down to room temperature, and the reaction was quenched with saturated aqueous $NaHCO_3$. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 80% PE-EtOAc gradient to give the title compound as a white solid (5.28 mg, 89%).

1-(4-Bromophenyl)-N-cyclohexylethan-1-imine

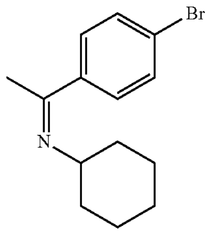 [SMILES: C/C(=N/C1CCCCC1)c1ccc(Br)cc1]

Following a procedure from Mercadante, M. A., et al., *Chemical Science,* 2014, 5, 3983-3994, to a solution of 4'-bromoacetophenone (10.0 g, 50.2 mmol) and p-toluenesulfonic acid monohydrate (100 mg, 0.53 mmol) in toluene (70 mL) was added cyclohexylamine (6.1 mL, 53.5 mmol) and the mixture was stirred at reflux with a Dean-Stark for 21 h. The reaction mixture was allowed to cool down to room temperature and PE was added (100 mL). The p-toluenesulfonic acid precipitated and could be filtered off. The solid was washed with PE (2×). The filtrate was concentrate in vacuo to afford crude product that was recrystallized from hot PE to give the title compound as slightly yellow flakes (12.4 g, 88%).

(Iodomethyl)dimethylphenylsilane

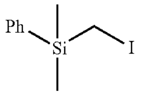

Following a procedure from Mercadante, M. A., et al., *Chemical Science,* 2014, 5, 3983-3994, to a solution of (chloromethyl)dimethylphenylsilane (4.9 mL, 27 mmol) in acetone (30 mL) was added sodium iodide (7.1 g, 47.3 mmol). The reaction mixture was then stirred at reflux for 19 h. The mixture was concentrated in vacuo, filtered over celite, and the solid washed with PE (60 mL). The solution was concentrated in vacuo. The residue was purified by silica gel flash chromatography eluting with 100% to 70% PE-DCM gradient to give the title compound as a yellow oil (7.1 g, 95%).

1-(4-Bromophenyl)-3-(dimethyl(phenyl)silyl)propan-1-one

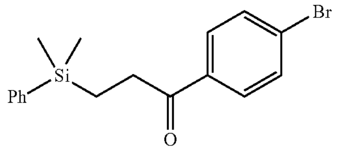 [SMILES: C[Si](C)(CCC(=O)c1ccc(Br)cc1)c1ccccc1]

Following a procedure from Mercadante, M. A., et al., *Chemical Science,* 2014, 5, 3983-3994, to a solution of 1-(4-bromophenyl)-N-cyclohexylethan-1-imine (5.6 g, 20 mmol) in THF (10 mL) at 0° C. was slowly added freshly prepared LDA in THF (approximatively 1.5 M, 15 mL, 22 mmol) dropwise. The mixture was stirred 1 h at 0° C. before adding (iodomethyl)dimethylphenylsilane (6.1 g, 22 mmol). The reaction was stirred for another 1 h at 0° C. before quenching with a buffer aqueous solution of sodium acetate (29.5 g, 360 mmol), acetic acid (10.3 mL, 180 mmol) in water (11 mL). The mixture was stirred for 15 minutes before being diluted with water. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 95% PE-EtOAc gradient to give the title compound as a yellow solid (5.24 g, 75%).

Trimethyl(perfluoroethyl)silane

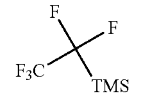

A solution of n-BuLi (2.3 M in cyclohexane, 9 mL, 20.7 mmol) in THF (40 mL) was stirred at −90° C. (Acetone/$N_2$). The system was purged with an atmosphere of pentafluoroethane and the system was kept between −78° C. and −90° C. for 1 h, then slowly warmed to −65° C. and stirred for another 0.5 h. A solution of TMSCl (2.55 mL, 20 mmol) in THF (5 mL) was added and the mixture was allowed to warm-up slowly in the acetone bath and stirred for 15 h at room temperature. The solution was then distilled to obtain the title compound as a solution in THF (65 mL).

4-(1-(Perfluoroethyl)cyclopropyl)phenol

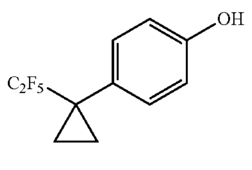

Following a procedure from Mercadante, M. A., et al., *Chemical Science,* 2014, 5, 3983-3994, to the solution of trimethyl(perfluoroethyl)silane in THF previously obtained (60 mL) at 0° C. was added 1-(4-bromophenyl)-3-(dimethyl(phenyl)silyl)propan-1-one (4.9 g, 14.2 mmol). The mixture was stirred for 10 minutes and TBAF (1 M solution in THF, 0.14 mL, 0.14 mmol) was added and the reaction mixture was stirred at room temperature for 7.5 h. The reaction mixture was cooled down to 0° C., water (1.4 mL) and TBAF (1 M solution in THF, 1.4 mL, 1.4 mmol) were added and the reaction mixture was stirred at room temperature for 14 h. The reaction was quenched with water. The aqueous layer was extracted with EtOAc (3×). The combined organics were washed with brine (1×), dried over $Na_2SO_4$, filtered and concentrated in vacuo. The residue was purified by silica gel flash chromatography eluting with a 100% to 95% PE-EtOAc gradient to give 3-(4-bromophenyl)-5-(dimethyl(phenyl)silyl)-1,1,1,2,2-pentafluoropentan-3-ol as a mixture with the starting 1-(4-bromophenyl)-3-(dimethyl(phenyl)silyl)propan-1-one (4.9 g, 1:1 ratio by NMR) due to similar polarity.

To a solution of the previous alcohol/ketone mixture (4.5 g, containing approximately 5.5 mmol of 3-(4-bromophenyl)-5-(dimethyl(phenyl)silyl)-1,1,1,2,2-pentafluoropentan-3-ol) in THF (25 mL) at 0° C. was added NaH (60 wt % in oil, 565 mg, 14.1 mmol). The mixture was stirred at room temperature for 45 minutes. The reaction was cooled down to 0° C. and MsCl (0.9 mL, 11.6 mmol) was added dropwise. After stirring at room temperature for 2 h, the reaction mixture was cooled down to 0° C. and quenched with water. The aqueous layer was extracted with EtOAc (3×). The combined organics were washed with water, saturated aqueous $NaHCO_3$, brine (1×), dried over $Na_2SO_4$, filtered and concentrated in vacuo.

To the resulting oil at 0° C. was added a mixture of pyridine (0.9 mL, 11.2 mmol) and 1,1,1,3,3,3-Hexafluoropropan-2-ol (8 mL). The flask was sealed and the reaction mixture was stirred for 12.5 h. The reaction was quenched with water. The aqueous layer was extracted with PE (3×). The combined organics were washed with aqueous HCl 1 M, water, saturated aqueous $NaHCO_3$ and brine (1×), dried over $Na_2SO_4$, filtered and concentrated in vacuo (water bath at 25° C., no lower than 200 mbar, the desired product is volatile). The residue was purified by silica gel flash chromatography eluting with 100% PE to give 1-bromo-4-(1-(perfluoroethyl)cyclopropyl)benzene. As it is a highly volatile product, the PE was not fully removed and the product was directly subjected to the next step. By further eluting the column with 9:1 PE/EtOAc, 1.7 g of the starting 1-(4-bromophenyl)-3-(dimethyl(phenyl)silyl)propan-1-one was recovered.

Following a procedure from Anderson, K. W. et al., *J. Am. Chem. Soc.,* 2006, 128 (33), 10694-10695, to a solution of KOH (900 m 16.0 mmol), $Pd_2dba_3$ (93 mg, 0.10 mmol), and di-tert-butyl-[2-(2,4,6-triisopropylphenyl)phenyl]phosphate (170 mg, 0.40 mmol) in degassed 1,4-dioxane (2 mL) and water (2 mL) under argon was added 1-bromo-4-(1-(perfluoroethyl)cyclopropyl)benzene (obtained in the previous step) in 1,4-dioxane (0.5 mL) and water (0.5 mL). The reaction vessel was then sealed and immerged in a pre-heated oil bath at 100° C. The reaction was stirred for 4-10 h. The reaction was quenched with 1 M aqueous HCl. The aqueous layer was extracted with EtOAc (3×). The combined organics were washed with brine (1×), dried over $Na_2SO_4$, filtered and concentrated in vacuo. The residue was purified by silica gel flash chromatography eluting with 100% to 90% PE-EtOAc gradient to give the title compound as a yellow oil (1.04 g, 29% over 4 steps, 44% BRSM).

The compounds listed in Table XIV have been identified by TLC using pre-coated silica TLC sheets and common organic solvents such as petroleum ether, ethyl acetate, dichloromethane, methanol, or acetic acids as eluent, preferably as binary or tertiary solvent mixtures thereof, UV light at a wavelength of 254 or 366 nm, and/or common staining solutions such as phosphomolybdic acid, potassium permanganate, or ninhydrin.

The compounds listed in Table XIV have furthermore been identified by mass spectrometry using formic acid in the mobile phase for detection of positive ions, while no additive was used for negative ions. Ammonium Carbonate was used if the molecule was difficult to ionize. Representative compounds have also been identified by nuclear magnetic resonance spectroscopy. Chemical shifts (6) were reported in parts per million (ppm) relative to residual solvent peaks rounded to the nearest 0.01 ppm for proton and 0.1 ppm for carbon (ref.: $CHCl_3$ [$^1H$: 7.26 ppm, $^{13}C$: 77.2 ppm], DMSO [$^1H$: 2.50 ppm, $^{13}C$: 39.5 ppm]). Coupling constants (J) were reported in Hz to the nearest 0.1 Hz. Peak multiplicity was indicated as follows: s (singlet), d (doublet), t (triplet), q (quartet), hept (heptet), m (multiplet), and br (broad).

The invention claimed is:

1. A compound selected from the group consisting of:

(i) a compound of formula I, (I)

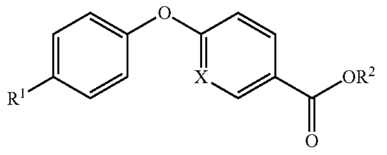

wherein X is CH or N, $R^1$=$C_2$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$-$C_3$ alkyl optionally halogenated or perhalogenated, wherein all cycloalkyl, cycloalkenyl, bicycloalkyl, bicycloalkenyl and tricycloalkyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$-$C_3$ alkyl optionally halogenated or perhalogenated, wherein all alkyl, alkenyl, alkynyl, cycloalkyl, cycloalkenyl, bicycloalkyl, bicycloalkenyl and tricycloalkyl residues can be perhalogenated;

$R^2$=H, $C_1$-$C_6$ alkyl, $C_3$-$C_6$ cycloalkyl, wherein all alkyl residues can be linear or branched, and can be unsubstituted or substituted with one or more substituents independently selected from: —F, —Cl, —Br, —I; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated;

or a salt or solvate thereof, (ii) a compound of formula II, (II)

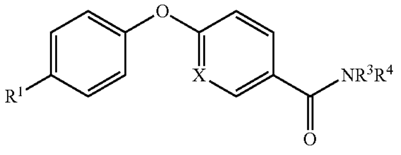

wherein X is defined as in formula I, $R^1$=$C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$-$C_3$ alkyl optionally halogenated or perhalogenated, wherein all cycloalkyl, cycloalkenyl, bicycloalkyl, bicycloalkenyl and tricycloalkyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$-$C_3$ alkyl optionally halogenated or perhalogenated, wherein all alkyl, alkenyl, alkynyl, cycloalkyl, cycloalkenyl, bicycloalkyl, bicycloalkenyl and tricycloalkyl residues can be perhalogenated;

$R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, wherein all alkyl and cycloalkyl residues can be perhalogenated;

$R^4$=$C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated, or a salt or solvate thereof, wherein when $R^4$ is $C_1$-$C_6$ alkyl, the alkyl residues can be linear or branched, and are substituted with one or more substituents independently selected from: —F, —Cl, —Br, —I; and $C_1$-$C_3$ alkyl halogenated or perhalogenated; and $OC_1$-$C_3$ alkyl optionally halogenated or perhalogenated, (iii) a compound of formula III, (III)

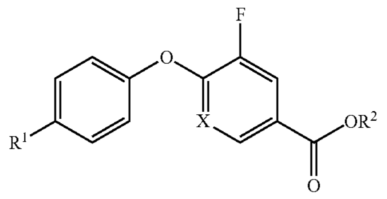

wherein X, $R^1$ and $R^2$ are defined as in formula I, or a salt or solvate thereof, (iv) a compound of formula IV, (IV)

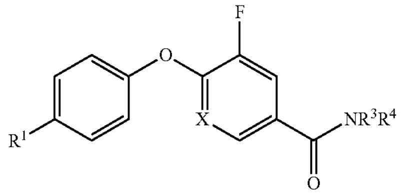

wherein X is defined as in formula I, and $R^1$ and $R^3$ are defined as in formula II, $R^4$=H, $C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated, or a salt or solvate thereof, (v) a compound of formula V, (V)

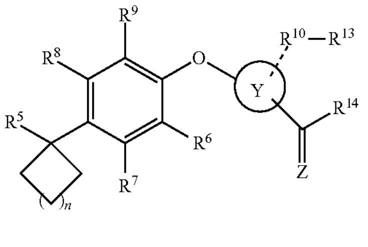

wherein n=0-5, which comprises cyclopropyl (n=0), cyclobutyl (n=1), cyclopentyl (n=2), cyclohexyl (n=3), cycloheptyl (n=4) and cyclooctyl (n=5), wherein the said cyclopropyl, cyclobutyl, cyclopentyl, cyclohexyl, cycloheptyl and cyclooctyl groups can be unsubstituted or substituted with one or more substituents independently selected from: —F, —Cl, —Br, —I, —CN, —NCO, —NCS; and $C_1$-$C_3$ alkyl optionally halogenated or perhalogenated; and $OC_1$-$C_3$ alkyl optionally halogenated or perhalogenated, wherein the said cyclopropyl, cyclobutyl, cyclopentyl, cyclohexyl, cycloheptyl and cyclooctyl groups can be perhalogenated;

$R^5$=$C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, wherein all alkyl, alkenyl and alkynyl residues can be linear or branched, and are perhalogenated, and wherein all cycloalkyl and cycloalkenyl residues are perhalogenated, or wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$-$C_3$ alkyl optionally halogenated or perhalogenated, and wherein all cycloalkyl and cycloalkenyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$-$C_3$ alkyl optionally halogenated or perhalogenated, $R^6$-$R^9$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, Y=a six-membered aromatic ring selected from benzene, pyridine, pyrimidine, pyridazine or pyrazine;

wherein the benzene ring is not substituted, or it is substituted with one to four of the substituents independently selected from $R^{10}$-$R^{13}$, and wherein the pyridine ring is not substituted, or it is substituted at the carbon positions with one to three of the substituents independently selected from $R^{10}$-$R^{12}$, and wherein the N-atom of the pyridine ring may be in ortho-position relative to the ether bond, and wherein the pyrimidine ring is not substituted, or it is substituted at the carbon positions with one or two of the substituents independently selected from $R^{10}$-$R^{11}$, and wherein the N-atoms of the pyrimidine ring may be in ortho-position relative to the ether bond, and wherein the pyridazine ring is not substituted, or it is substituted at the carbon positions with one or two of the substituents independently selected from $R^{10}$-$R^{11}$, and wherein an N-atom of the pyridazine ring may be in ortho-position relative to the ether bond, and wherein the pyrazine ring is not substituted, or it is substituted at the carbon positions with one or two of the substituents independently selected from $R^{10}$-$R^{11}$, and wherein an N-atom of the pyrazine ring may be in ortho-position relative to the ether bond, $R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from —F, —Cl, —Br, —I; and $C_1$-$C_3$ alkyl optionally halogenated or perhalogenated; and $OC_1$-$C_3$ alkyl optionally halogenated or perhalogenated, Z=O or S, $R^{14}$=$OR^2$ or $NR^3R^4$ wherein $R^2$ is defined as in formula I, and wherein $R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, wherein all alkyl and cycloalkyl residues can be perhalogenated;

and wherein $R^4$=H, $C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated, and a salt or solvate thereof;

and wherein compounds as indicated below are excluded:

TABLE Ia

| Compound | R | $R^2$ | X |
|---|---|---|---|
| I-A | tert-butyl | H | CH |
| I-B | tert-butyl | ethyl | CH |
| I-C | tert-pentyl | H | CH |
| I-D | tert-pentyl | ethyl | CH |
| I-E | cyclo-hexyl | H | CH |
| I-F | cyclo-hexyl | ethyl | CH |
| I-G | adamant-1-yl | H | CH |
| I-H | adamant-1-yl | ethyl | CH |
| I-I | methyl | H | N |
| I-J | methyl | ethyl | N |
| I-K | tert-butyl | H | N |
| I-L | tert-butyl | ethyl | N |
| I-M | tert-pentyl | H | N |
| I-N | tert-pentyl | ethyl | N |
| I-O | cyclo-hexyl | H | N |
| I-P | cyclo-hexyl | ethyl | N |
| I-Q | isopropyl | H | CH |
| I-R | phenyl | H | CH |
| I-S | methyl | H | CH |
| I-T | tert-butyl | methyl | N |

TABLE Ia-continued

| Compound | R | $R^2$ | X |
|---|---|---|---|
| I-U | methyl | methyl | N |
| I-V | methyl | methyl | CH |
| I-W | methyl | ethyl | CH |
| I-X | n-hexyl | H | CH |
| I-Y | n-octyl | H | CH |
| I-Z | n-dodecyl | H | CH |
| I-AA | iso-propyl | H | N |

TABLE IIa

| Compound | $R^1$ | $R^3$ | $R^4$ | X |
|---|---|---|---|---|
| II-A | tert-butyl | H | H | N |
| II-B | methyl | H | methyl | CH |
| II-C | methyl | methyl | methyl | CH |

TABLE IIIa

| Compound | $R^1$ | $R^2$ | X |
|---|---|---|---|
| III-A | tert-butyl | H | CH |
| III-B | tert-butyl | ethyl | CH |
| III-C | phenyl | H | CH. |

2. The compound of claim 1, wherein in the compound of Formula I, II, III and IV, $R^1$ is selected from the group consisting of ethyl, n-propyl, n-butyl, n-pentyl, n-hexyl, iso-propyl, tert-butyl, tert-pentyl, 3-pentyl, $—CF_2CF_3$, $—(CF_2)_2CF_3$, $—(CF_2)_3CF_3$, $—CH(CF_3)_2$, $—CF(CF_3)_2$, cyclopropyl, cyclobutyl, cyclopentyl, cyclohexyl, cycloheptyl, norbornyl, bicyclo[2.2.2]octyl, adamantyl, and 9-methylbicyclo[3.3.1]nonyl.

3. The compound of claim 1, wherein in the compound of Formula I, III and V, $R^2$ is selected from the group consisting of H, methyl and ethyl wherein said methyl and ethyl is optionally fluorinated or perfluorinated.

4. The compound of claim 1, wherein in the compound of Formula II, IV and V, $R^3$ is H or methyl, wherein said methyl is optionally fluorinated or perfluorinated.

5. The compound of claim 1, wherein in the compound of Formula II, $R^4$ is selected from the group consisting of OH and methyl, and in the compound of Formula IV and V, $R^4$ is selected from the group consisting of H, OH and methyl wherein in the case of Formula II said methyl is fluorinated or perfluorinated and wherein in the case of Formula V said methyl is optionally fluorinated or perfluorinated.

6. The compound of claim 1, wherein in the compound of Formula V, n is 0 as constituting cyclopropyl.

7. The compound of claim 6, wherein said cyclopropyl is unsubstituted.

8. The compound of claim 1, wherein in the compound of Formula V, $R^5$ is a perfluorinated alkyl, alkenyl, alkynyl, cycloalkyl or cycloalkenyl residue.

9. The compound of claim 1, wherein in the compound of Formula V, $R^5$ is $—CF_3$ or $—CF_2CF_3$.

10. The compound of claim 1, wherein in the compound of Formula V, $R^6$-$R^8$ are H and $R^9$ is selected from the group consisting of —H, —F, —Cl or $—CH_3$.

11. The compound of claim 1, wherein in the compound of Formula V, Y=benzene or pyridine being not substituted with any of the residues selected from $R^{10}$-$R^{13}$, or being substituted with one of the substituents selected from $R^{10}$-$R^{13}$ being —F at the carbon atom in ortho-position relative to the ether bond.

12. The compound of claim 1, wherein in the compound of Formula V, Z=O.

13. The compound of claim 1, wherein all alkyl residues of $R^4$ can be linear or branched, and are substituted with one or more substituents independently selected from the group consisting of —F, —Cl, —Br, —I; $OC_1$-$C_3$ alkyl and halogenated $C_1$-$C_3$ alkyl.

14. The compound of claim 1, wherein said $C_1$-$C_3$ alkyl is perhalogenated, and said $OC_1$-$C_3$ alkyl is halogenated or perhalogenated.

15. A pharmaceutical composition, comprising a) an active agent selected from the group consisting of (i) a compound of formula I, (I)

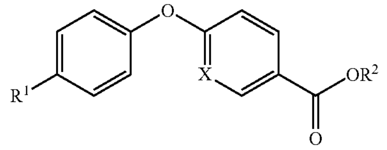

wherein X is CH or N, $R^1$=$C_2$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$-$C_3$ alkyl optionally halogenated or perhalogenated, wherein all cycloalkyl, cycloalkenyl, bicycloalkyl, bicycloalkenyl and tricycloalkyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$-$C_3$ alkyl optionally halogenated or perhalogenated, wherein all alkyl, alkenyl, alkynyl, cycloalkyl, cycloalkenyl, bicycloalkyl, bicycloalkenyl and tricycloalkyl residues can be perhalogenated;

$R^2$=H, $C_1$-$C_6$ alkyl, $C_3$-$C_6$ cycloalkyl, wherein all alkyl residues can be linear or branched, and can be unsubstituted or substituted with one or more substituents independently selected from: —F, —Cl, —Br, —I; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated;

or a salt or solvate thereof, (ii) a compound of formula II, (II)

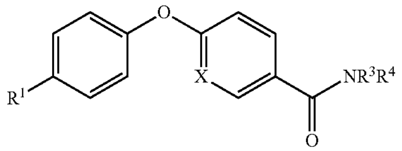

wherein X is defined as in formula I, $R^1$=$C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, $C_4$-$C_{12}$ bicycloalkyl, $C_6$-$C_{12}$ bicycloalkenyl, $C_5$-$C_{14}$ tricycloalkyl, wherein all alkyl, alkenyl and alkynyl residues can be linear or branched, and can be unsubstituted or substituted with one or more substituents independently selected from: F, Cl, Br, I, CN, NCO, NCS; and $OC_1$-$C_3$ alkyl optionally halogenated or perhalogenated, wherein all cycloalkyl, cycloalkenyl, bicycloalkyl, bicycloalkenyl and tricycloalkyl residues can be unsubstituted or substituted with one or more substituents independently selected from: F, Cl, Br, I, CN, NCO, NCS; and $C_1$-$C_3$ alkyl optionally halogenated or perhalogenated, and $OC_1$-$C_3$ alkyl optionally halogenated or perhalogenated, wherein all alkyl, alkenyl, alkynyl, cycloalkyl, cycloalkenyl, bicycloalkyl, bicycloalkenyl and tricycloalkyl residues can be perhalogenated;

$R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, wherein all alkyl and cycloalkyl residues can be perhalogenated;

$R^4$=$C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated;

or a salt or solvate thereof, wherein when $R^4$ is $C_1$-$C_6$ alkyl, the alkyl residues can be linear or branched, and are substituted with one or more substituents independently selected from: —F, —Cl, —Br, —I; and $C_1$-$C_3$ alkyl halogenated or perhalogenated; and $OC_1$-$C_3$ alkyl optionally halogenated or perhalogenated, (iii) a compound of formula III, (III)

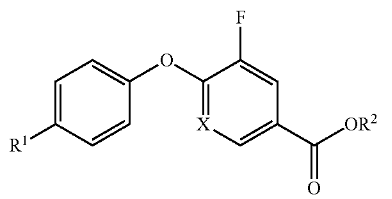

wherein X, $R^1$ and $R^2$ are defined as in formula I, or a salt or solvate thereof, (iv) a compound of formula IV, (IV)

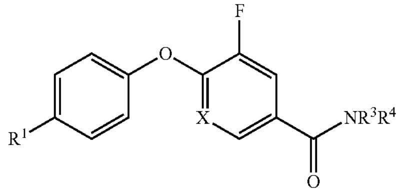

wherein X is defined as in formula I, and $R^1$ and $R^3$ are defined as in formula II, and $R^4$=H, $C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated, or a salt or solvate thereof, (v) a compound of formula V, (V)

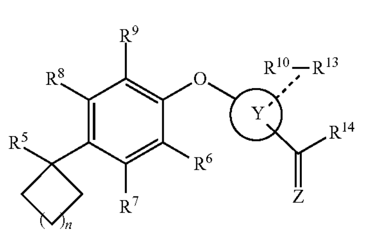

wherein n=0-5, which comprises cyclopropyl (n=0), cyclobutyl (n=1), cyclopentyl (n=2), cyclohexyl (n=3), cycloheptyl (n=4) and cyclooctyl (n=5), wherein the said cyclopropyl, cyclobutyl, cyclopentyl, cyclohexyl, cycloheptyl and cyclooctyl groups can be unsubstituted or substituted with one or more substituents independently selected from: —F, —Cl, —Br, —I, —CN, —NCO, —NCS; and $C_1$-$C_3$ alkyl optionally halogenated or perhalogenated; and $OC_1$-$C_3$ alkyl optionally halogenated or perhalogenated, wherein the said cyclopropyl, cyclobutyl, cyclopentyl, cyclohexyl, cycloheptyl and cyclooctyl groups can be perhalogenated;

$R^5$=$C_1$-$C_{12}$ alkyl, $C_2$-$C_{12}$ alkenyl, $C_2$-$C_{12}$ alkynyl, $C_3$-$C_8$ cycloalkyl, $C_3$-$C_8$ cycloalkenyl, wherein all alkyl, alkenyl and alkynyl residues can be linear or branched, and are perhalogenated, and wherein all cycloalkyl and cycloalkenyl residues are perhalogenated, or wherein all alkyl, alkenyl and alkynyl residues can be linear or branched, and can be unsubstituted or substituted with one or more substituents independently selected from: —F, —Cl, —Br, —I, —CN, —NCO, —NCS; and $OC_1$-$C_3$ alkyl optionally halogenated or perhalogenated, and wherein all cycloalkyl and cycloalkenyl residues can be unsubstituted or substituted with one or more substituents independently selected from: —F, —Cl, —Br, —I, —CN, —NCO, —NCS; and $C_1$-$C_3$ alkyl optionally halogenated or perhalogenated, and $OC_1$-$C_3$ alkyl optionally halogenated or perhalogenated, $R^6$-$R^9$ are independently from each other selected from —H, —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, Y=a six-membered aromatic ring selected from benzene, pyridine, pyrimidine, pyridazine or pyrazine;

wherein the benzene ring is not substituted, or it is substituted with one to four of the substituents independently selected from $R^{10}$-$R^{13}$, and wherein the pyridine ring is not substituted, or it is substituted at the carbon positions with one to three of the substituents independently selected from $R^{10}$-$R^{12}$, and wherein the N-atom of the pyridine ring may be in ortho-position relative to the ether bond, and wherein the pyrimidine ring is not substituted, or it is substituted at the carbon positions with one or two of the substituents independently selected from $R^{10}$-$R^{11}$, and wherein the N-atoms of the pyrimidine ring may be in ortho-position relative to the ether bond, and wherein the pyridazine ring is not substituted, or it is substituted at the carbon positions with one or two of the substituents independently selected from $R^{10}$-$R^{11}$, and wherein an N-atom of the pyridazine ring may be in ortho-position relative to the ether bond, and wherein the pyrazine ring is not substituted, or it is substituted at the carbon positions with one or two of the substituents independently selected from $R^{10}$-$R^{11}$, and wherein an N-atom of the pyrazine ring may be in ortho-position relative to the ether bond, $R^{10}$-$R^{13}$ are independently from each other selected from —F, —Cl, —Br, —I, linear or branched $C_1$-$C_4$ alkyl, linear or branched $C_2$-$C_4$ alkenyl, $C_2$-$C_4$ alkynyl, $C_3$-$C_5$ cycloalkyl, and wherein all alkyl, alkenyl, alkynyl and cycloalkyl residues can be unsubstituted or substituted with one or more substituents independently selected from —F, —Cl, —Br, —I; and $C_1$-$C_3$ alkyl optionally halogenated or perhalogenated; and $OC_1$-$C_3$ alkyl optionally halogenated or perhalogenated, Z=O or S, $R^{14}$=$OR^2$ or $NR^3R^4$ wherein $R^2$ is defined as in formula I, and wherein $R^3$=H, $C_1$-$C_6$ alkyl, or $C_3$-$C_6$ cycloalkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated, and $OC_1$-$C_3$ alkyl optionally halogenated or perhalogenated, wherein all alkyl and cycloalkyl residues can be perhalogenated;

and wherein $R^4$=H, $C_1$-$C_6$ alkyl, $C_3$-$C_6$ cycloalkyl, OH or $OC_1$-$C_6$ alkyl, wherein all alkyl residues can be linear or branched, and can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all cycloalkyl residues can be unsubstituted or substituted with one or more substituents independently selected from: —F, —Cl, —Br, —I; and $C_1$-$C_3$ alkyl optionally halogenated or perhalogenated; and $OC_1$-$C_3$ alkyl optionally halogenated or perhalogenated, wherein all alkyl and cycloalkyl residues can be perhalogenated;

or a salt or solvate thereof;

and wherein compounds as indicated below are excluded:

TABLE Ia

| Compound | $R^1$ | $R^2$ | X |
|---|---|---|---|
| I-A | tert-butyl | H | CH |
| I-B | tert-butyl | ethyl | CH |
| I-C | tert-pentyl | H | CH |
| I-D | tert-pentyl | ethyl | CH |
| I-E | cyclo-hexyl | H | CH |
| I-F | cyclo-hexyl | ethyl | CH |
| I-G | adamant-1-yl | H | CH |
| I-H | adamant-1-yl | ethyl | CH |
| I-I | methyl | H | N |
| I-J | methyl | ethyl | N |
| I-K | tert-butyl | H | N |
| I-L | tert-butyl | ethyl | N |
| I-M | tert-pentyl | H | N |
| I-N | tert-pentyl | ethyl | N |
| I-O | cyclo-hexyl | H | N |
| I-P | cyclo-hexyl | ethyl | N |
| I-Q | isopropyl | H | CH |
| I-R | phenyl | H | CH |
| I-S | methyl | H | CH |
| I-T | tert-butyl | methyl | N |
| I-U | methyl | methyl | N |
| I-V | methyl | methyl | CH |
| I-W | methyl | ethyl | CH |
| I-X | n-hexyl | H | CH |

TABLE Ia-continued

| Compound | $R^1$ | $R^2$ | X |
|---|---|---|---|
| I-Y | n-octyl | H | CH |
| I-Z | n-dodecyl | H | CH |
| I-AA | iso-propyl | H | N |

TABLE IIa

| Compound | $R^1$ | $R^3$ | $R^4$ | X |
|---|---|---|---|---|
| II-A | tert-butyl | H | H | N |
| II-B | methyl | H | methyl | CH |
| II-C | methyl | methyl | methyl | CH |

TABLE IIIa

| Compound | $R^1$ | $R^2$ | X |
|---|---|---|---|
| III-A | tert-butyl | H | CH |
| III-B | tert-butyl | ethyl | CH |
| III-C | phenyl | H | CH |

and b) carriers, diluents and/or adjuvants suitable for administration to patients.

16. The composition of claim 15 for the use as an immunotherapeutic agent or as an adjuvant for immunotherapy.

17. The composition according to claim 15, further comprising a second active agent.

18. The composition according to claim 17, wherein said second active agent is selected from the group consisting of chemotherapeutic agents, peptide antibiotics, alkylating agents, topoisomerase inhibitors, kinase inhibitors, inhibitors and activators of signaling pathways, retinoids, hormone signaling modulators, histone deacetylase inhibitors, other Notch enhancers not encompassed by the compounds of the present invention, Notch Signaling-activating peptides or antibodies, immune response modulating agents and anti-inflammatory agents and ACE inhibitors, beta-blockers, myostatin inhibitors, PDE-5 inhibitors and antihistamines.

19. The composition according to claim 18, wherein said second active agent is selected from the group consisting of Cytarabin, Gemcitabine, Azathioprine, Mercaptopurine, Fluorouracil, Thioguanine, Hydroxyurea, Azacitidine, Capecitabine, Doxifluridine, Methotrexate, Cisplatin, Oxaliplatin, Carboplatin and Nedaplatin, Doxorubicin, Epirubicin, Valrubicin, Idarubicin, Daunorubicin, Sabarubicin, Pixantrone, Mitoxantrone, Actinomycin, Bleomycin, Mechlorethamine, Chlorambucil, Melphalan, Nitrosoureas, Dacarbazine, Temozolomide, Cyclophosphamide, Docetaxel, Paclitaxel, Abraxane, Cabazitaxel, Vinblastine, Vindesine, Vinorelbine, Vincristine, Irinotecan, Topotecan, Teniposide, Etoposide, Erlotinib, Lapatinib, Dasatinib, Imatinib, Afatinib, Vemurafenib, Dabrafenib, Nilotinib, Cetuximab, Trametinib, Palbociclib, Cobimetinib, Cabozantinib, Pegaptanib, Crizotinib, Olaparib, Panitumumab, Cabozantinib, Ponatinib, Regorafenib, Entrectinib, Ranibizumab, Ibrutinib, Trastuzumab, Rituximab, Alemtuzumab, Gefitinib, Bevacizumab, Lenvatinib, Bosutinib, Axitinib, Pazopanib, Everolimus, Temsirolimus, Ruxolitinib, Tofacitinib, Sorafenib, Sunitinib, Aflibercept, Bortezomib, Vandetanib; Vismodegib, Sonidegib, retinol, tretinoin, isotretinoin, alitretinoin, bexarotene, tazarotene, acitretin, adapalene, etretinate, Raloxifene, Tamoxifen, Fulvestrant, Lasofoxifene, Toremifene, Bicalutamide, Flutamide, Anastrozole, Letrozole, Exemestane, Vorinostat, Romidepsin, Panobinostat, Belinostat, Chidamide, Ingenol mebutate, Valproic acid, Resveratrol, hesperetin, chrysin, phenethyl isothiocyanate, thiocoraline, N-methylhemeanthidine chloride, Imiquimod, Ipilimumab, Atezolizumab, Ofatumumab, Rituximab, Nivolumab, Pembrolizumab, Dexamethason, Betamethason, Prednisone, Prednisolone, Methylprednisolone, Triamcinolon-hexacetonid, Mometasonfuroat, Clobetasolpropionat, acetylsalicylic acid, salicylic acid and other salicylates, Diflunisal, Ibuprofen, Dexibuprofen, Naproxen, Fenoprofen, Ketoprofen, Dexketoprofen, Loxoprofen, Flurbiprofen, Oxaprozin, Indomethacin, Ketorolac, Tolmetin, Diclofenac, Etodolac, Aceclofenac, Nabumetone, Sulindac, Mefenamic acid, Meclofenamic acid, Flufenamic acid, Tolfenamic acid, Celecoxib, Parecoxib, Etoricoxib and Firocoxib.

20. A kit comprising the compound according to claim 1 and a second active agent, wherein said compound and said second active agent are in separate dose forms which can be co-administered or administered separately.

21. A compound selected from the group consisting of:

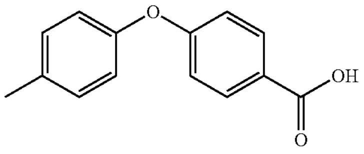

4-(p-tolyoxy)benzoic acid

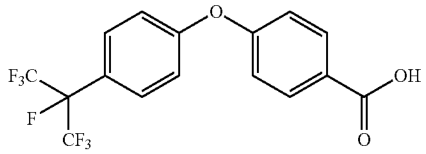

4-(4-(perfluoropropan-2-yl)phenoxy)benzoic acid

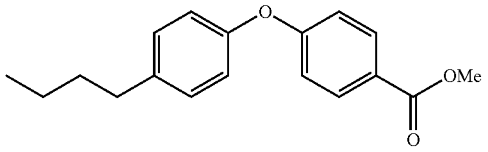

methyl 4-(4-butylphenoxy)benzoate

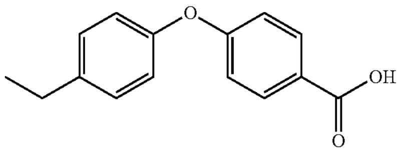

4-(4-ethylphenoxy)benzoic acid

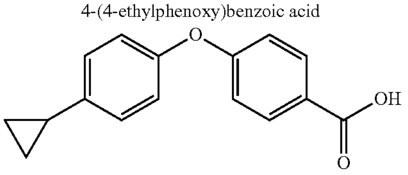

4-(4-cyclopropylphenoxy)benzoic acid

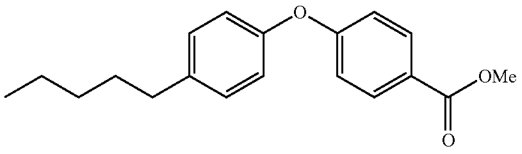

methyl 4-(4-pentylphenoxy)benzoate

-continued

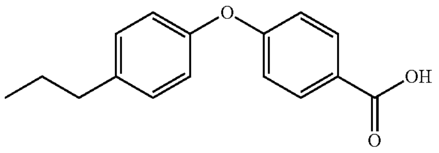

4-(4-propylphenoxy)benzoic acid

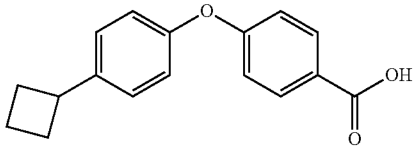

4-(4-cyclobutylphenoxy)benzoic acid

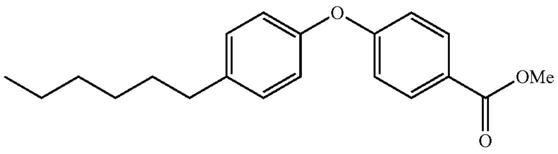

methyl 4-(4-hexylphenoxy)benzoate

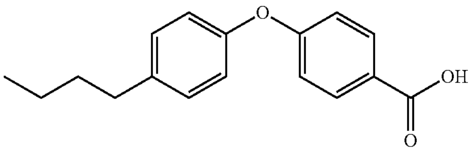

4-(4-butylphenoxy)benzoic acid

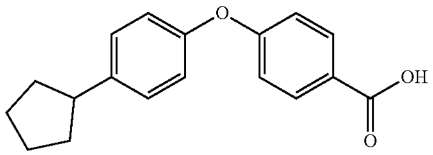

4-(4-cyclopentylphenoxy)benzoic acid

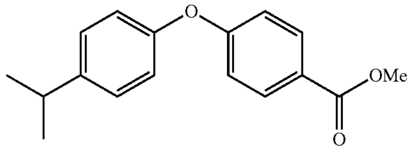

methyl 4-(4-isopropylphenoxy)benzoate

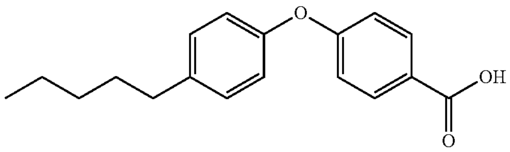

4-(4-pentylphenoxy)benzoic acid

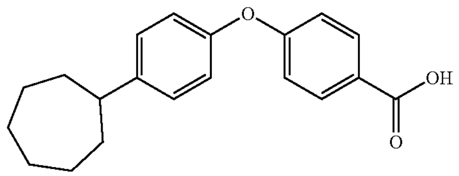

4-(4-cycloheptylphenoxy)benzoic acid

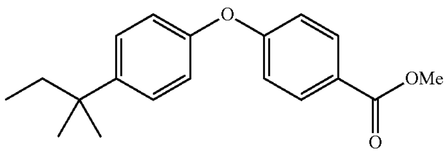

methyl 4-(4-(tert-pentyl)phenoxy)benzoate

-continued

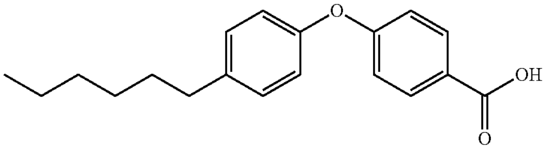

4-(4-hexylphenoxy)benzoic acid

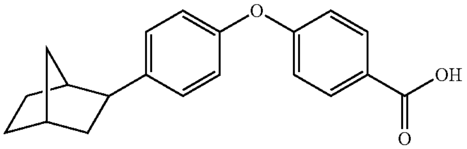

4-(4-((1S,4R)-bicyclo[2.2.1]heptan-2-yl)phenoxy)benzoic acid

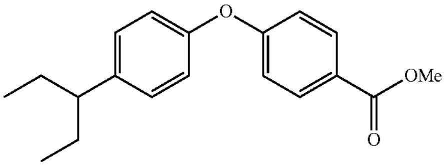

methyl 4-(4-(pentan-3-yl)phenoxy)benzoate

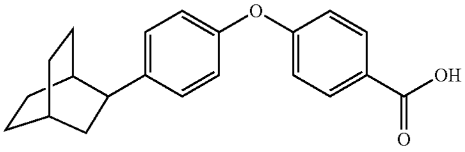

4-(4-((1s,4s)-bicyclo[2.2.2]octan-2-yl)phenoxy)benzoic acid

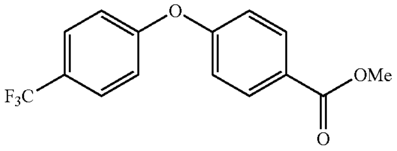

methyl 4-(4-(trifluoromethyl)phenoxy)benzoate

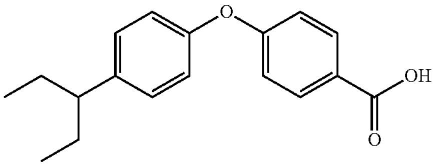

4-(4-(pentan-3-yl)phenoxy)benzoic acid

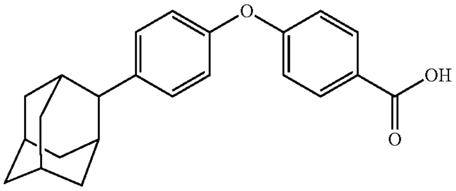

4-(4-((1r,3r,5r,7r)-adamantan-2-yl)phenoxy)benzoic acid

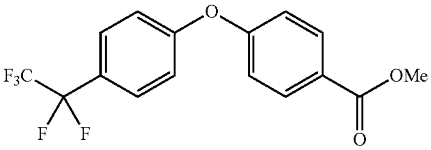

methyl 4-(4-(perfluoroethyl)phenoxy)benzoate

-continued

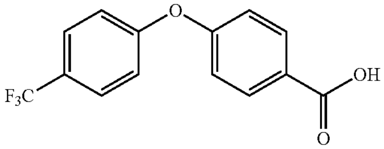

4-(4-(trifluoromethyl)phenoxy)benzoic acid

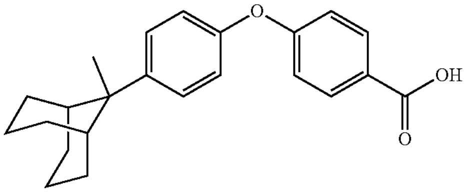

4-(4-((1R,5S)-9-methylbicyclo[3.3.1]nonan-9-yl)phenoxy)benzoic acid

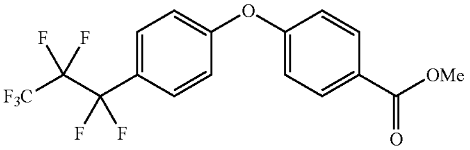

methyl 4-(4-perfluoropropyl)phenoxy)benzoate

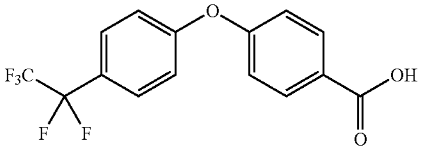

4-(4-(perfluoroethyl)phenoxy)benzoic acid

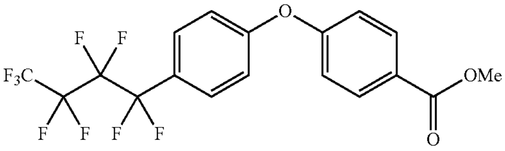

methyl 4-(4-(perfluorobutyl)phenoxy)benzoate

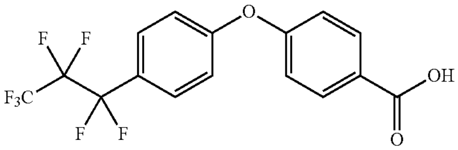

4-(4-(perfluoropropyl)phenoxy)benzoic acid

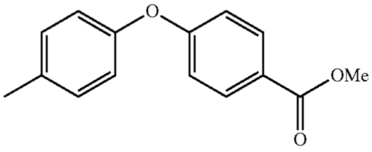

methyl 4-(p-tolyloxy)benzoate

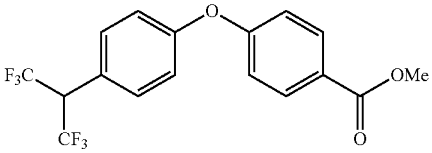

methyl 4-(4-(1,1,1,3,3,3-hexafluoropropan-2-yl)phenoxy)benozate

-continued

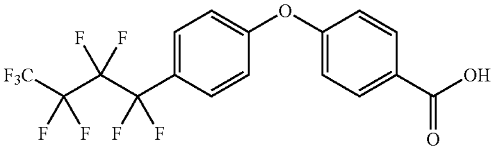

4-(4-(perfluorobutyl)phenoxy)benzoic acid

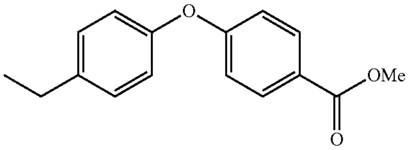

methyl 4-(4-ethylphenoxy)benzoate

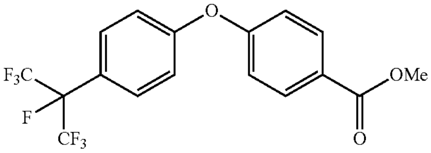

methyl 4-(4-(perfluoropropan-2-yl)phenoxy)benzoate

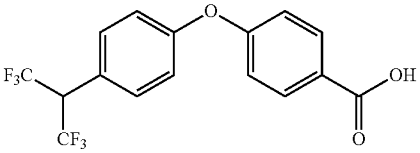

4-(4-(1,1,1,3,3,3-hexafluoropropan-2-yl)phenoxy)benzoic acid

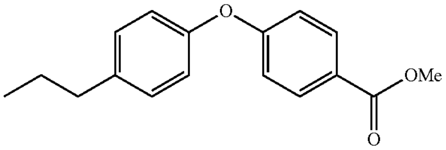

methyl 4-(4-propylphenoxy)benzoate

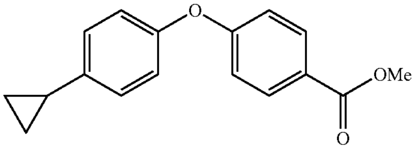

methyl 4-(4-cyclopropylphenoxy)benzoate

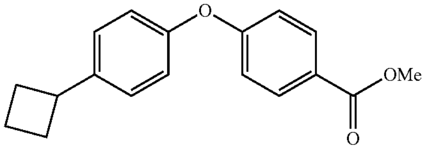

methyl 4-(4-cyclobutylphenoxy)benzoate

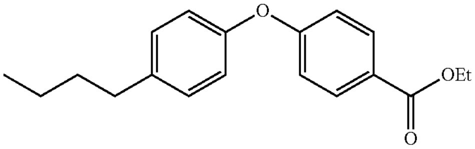

ethyl 4-(4-butylphenoxy)benzoate

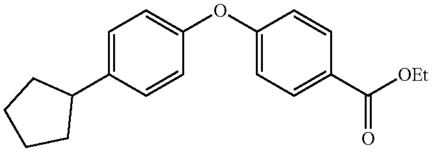

ethyl 4-(4-cyclopentylphenoxy)benzoate

-continued

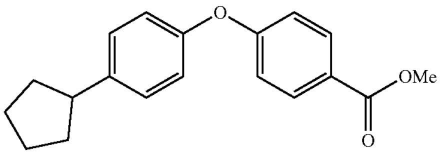

methyl 4-(4-cyclopentylphenoxy)benzoate

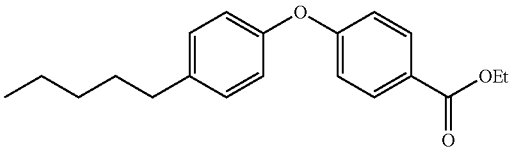

ethyl 4-(4-pentylphenoxy)benzoate

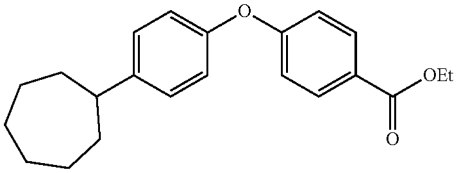

ethyl 4-(4-cycloheptylphenoxy)benzoate

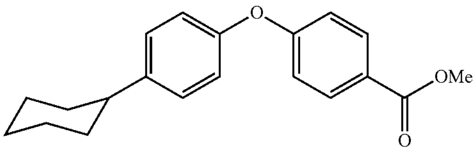

methyl 4-(4-cyclohexylphenoxy)benzoate

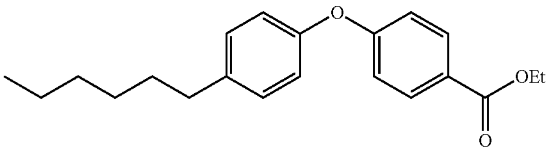

ethyl 4-(4-hexylphenoxy)benzoate

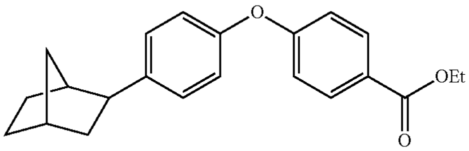

ethyl 4-(4-((1S,4R)-bicyclo[2.2.1]heptan-2-yl)phenoxy)benzoate

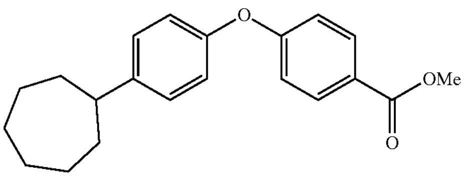

methyl 4-(4-cycloheptylphenoxy)benzoate

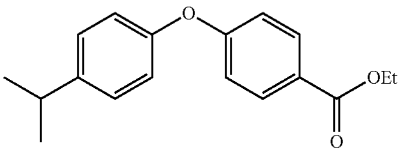

ethyl 4-(4-isopropylphenoxy)benzoate

-continued

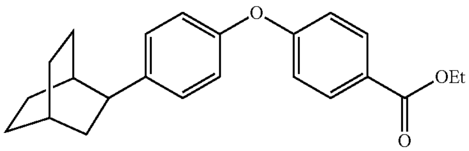

ethyl 4-(4-((1s,4s)-bicyclo[2.2.2]octan-2-yl)phenoxy)benzoate

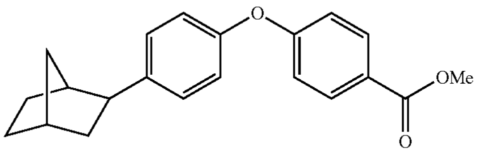

methyl 4-(4-((1S,4R)-bicyclo[2.2.1]heptan-2-yl)phenoxy)benzoate

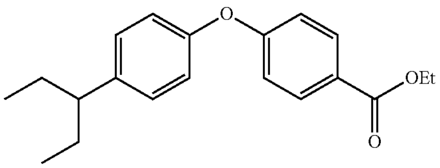

ethyl 4-(4-(pentan-3-yl)phenoxy)benzoate

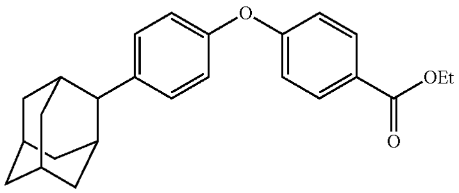

ethyl 4-(4-((1r,3r,5r,7r)-adamantan-2-yl)phenoxy)benzoate

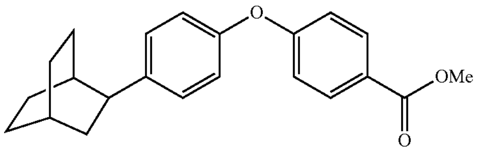

methyl 4-(4-((1s,4s)-bicyclo[2.2.2]octan-2-yl)phenoxy)benzoate

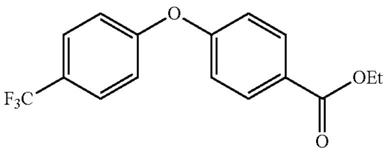

ethyl 4-(4-(trifluoromethyl)phenoxy)benzoate

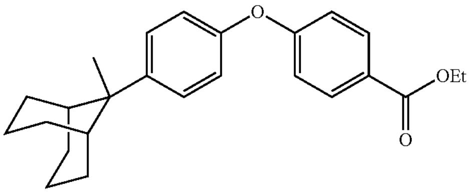

ethyl 4-(4-((1R,5S)-9-methylbicyclo[3.3.1]nonan-9-yl)phenoxy benzoate

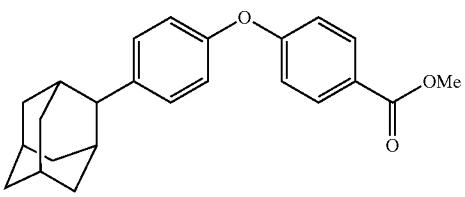

methyl 4-(4-((3r,5r,7r)-adamantan-1-yl)phenoxy)benzoate

-continued

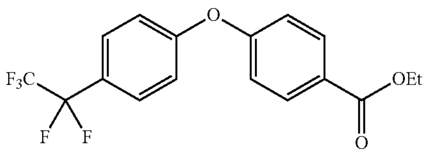

ethyl 4-(4-(perfluoroethyl)phenoxy)benzoate

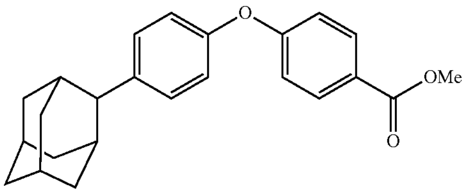

methyl 4-(4-((1r,3r,5r,7r)-adamantan-2-yl)phenoxy)benzoate

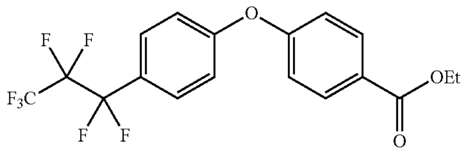

ethyl 4-(4-perfluoropropyl)phenoxy)benzoate

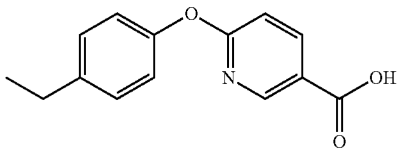

6-(4-ethylphenoxy)nicotinic acid

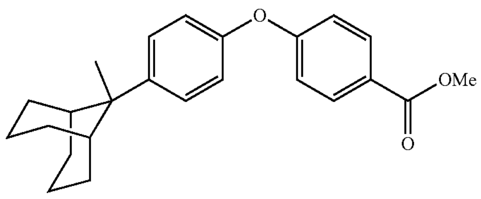

methyl 4-(4-((1R,5S)-9-methylbicyclo[3.3.1]nonan-9-yl)phenoxy) benzoate

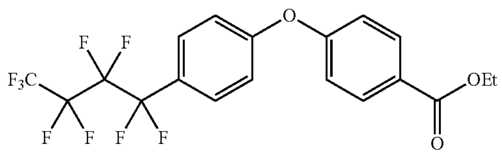

ethyl 4-(4-(perfluorobutyl)phenoxy)benzoate

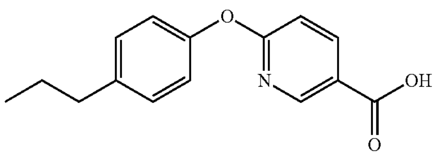

6-(4-propylphenoxy)nicotinic acid

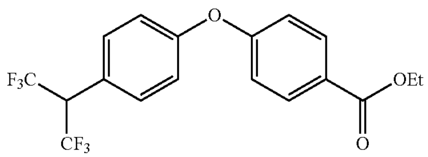

ethyl 4-(4-(1,1,1,3,3,3-hexafluoropropan-2-yl)phenoxy)benzoate

-continued

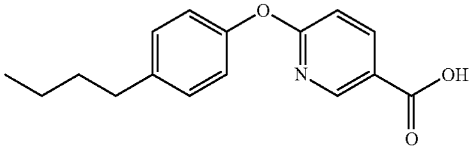

6-(4-butylphenoxy)nicotinic acid

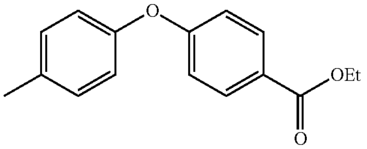

ethyl 4-(p-tolyloxy)benzoate

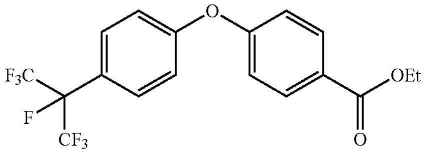

ethyl 4-(4-(perfluoropropan-2-yl)phenoxy)benzoate

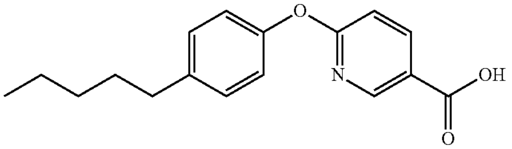

6-(4-pentylphenoxy)nicotinic acid

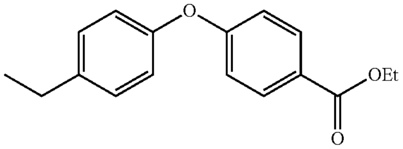

ethyl 4-(4-ethylphenoxy)benzoate

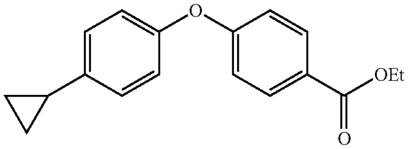

ethyl 4-(4-cyclopropylphenoxy)benzoate

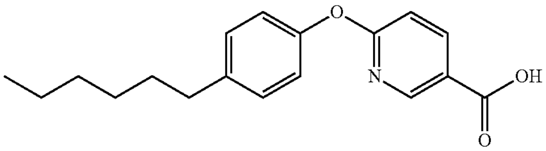

6-(4-hexylphenoxy)nicotinic acid

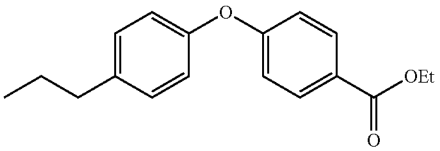

ethyl 4-(4-propylphenoxy)benzoate

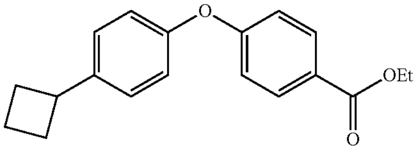

ethyl 4-(4-cyclobutylphenoxy)benzoate

-continued

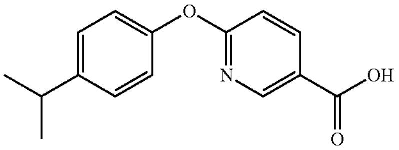

6-(4-isopropylphenoxy)nicotinic acid

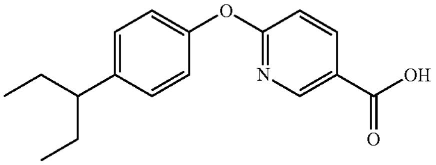

6-(4-(pentan-3-yl)phenoxy)nicotinic acid

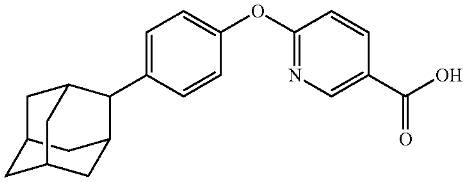

6-(4-((1r,3r,5r,7r)-adamantan-2-yl)phenoxy)nicotinic acid

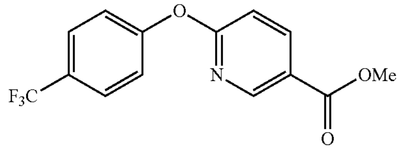

methyl 6-(4-(trifluoromethyl)phenoxy)nicotinate

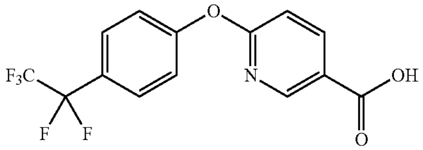

6-(4-(perfluoroethyl)phenoxy)nicotinic acid

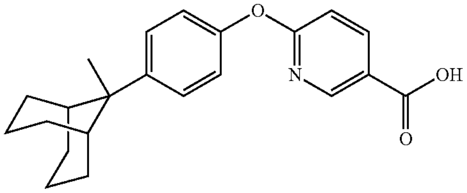

6-(4-((1R,5S)-9-methylbicyclo[3.3.1]nonan-9-yl)phenoxy)nicotinic acid

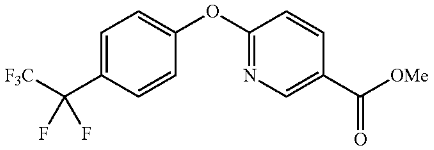

methyl 6-(4-(perfluoroethyl)phenoxy)nicotiniate

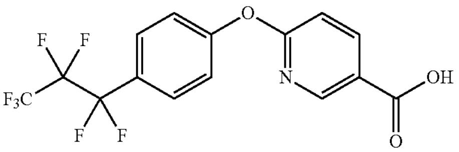

6-(4-(perfluoropropyl)phenoxy)nicotinic acid

-continued

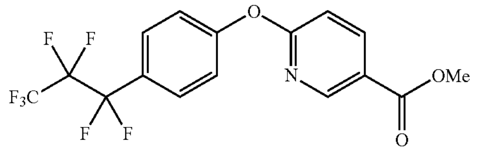

methyl 6-(4-(perfluoropropyl)phenoxy)nicotinate

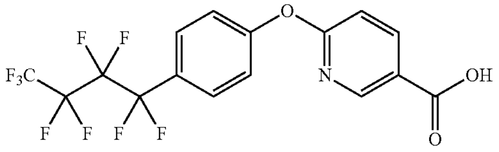

6-(4-(perfluorobutyl)phenoxy)nicotinic acid

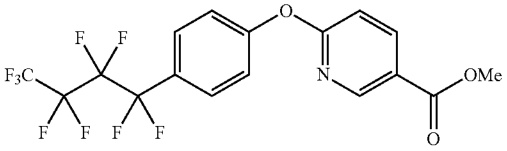

methyl 6-(4-(perfluorobutyl)phenoxy)nicotinate

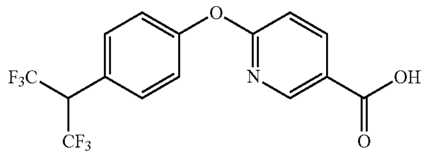

6-(4-(1,1,1,3,3,3-hexafluoropropan-2-yl)phenoxy)nicotinic acid

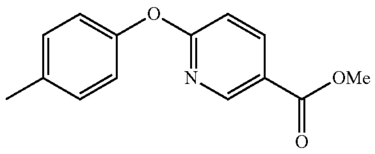

methyl 6-(p-tolyoxy)nicotinate

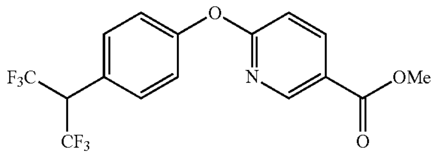

methyl 6-(4-(1,1,1,3,3,3-hexafluoropropan-2-yl)phenoxy)nicotinate

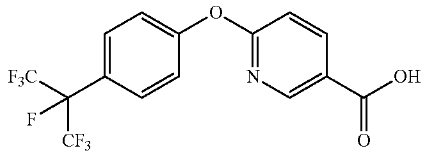

6-(4-(perfluoropropan-2-yl)phenoxy)nicotinic acid

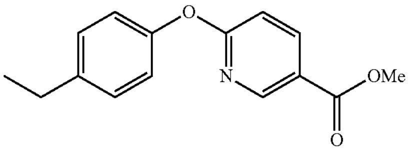

methyl 6-(4-ethylphenoxy)nicotinate

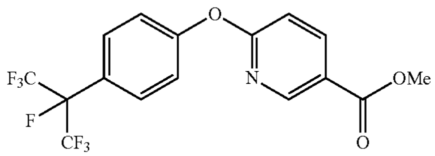

methyl 6-(4-(perfluoropropan-2-yl)phenoxy)nicotinate

-continued

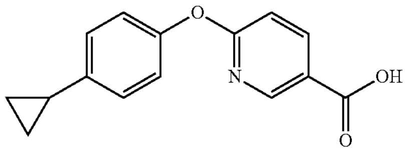

6-(4-cyclopropylphenoxy)nicotinic acid

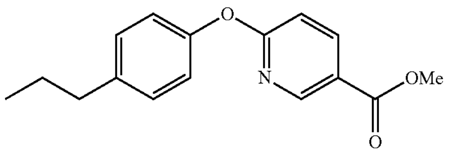

methyl 6-(4-propylphenoxy)nicotinate

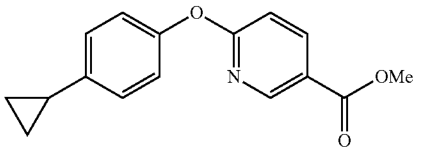

methyl 6-(4-cyclopropylphenoxy)nicotinate

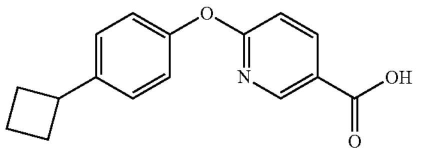

6-(4-cyclobutylphenoxy)nicotinic acid

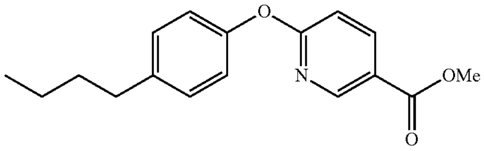

methyl 6-(4-butylphenoxy)nicotinate

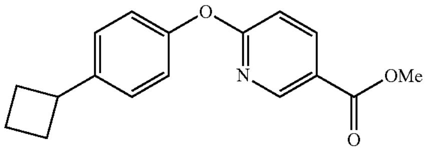

methyl 6-(4-cyclobutylphenoxy)nicotinate

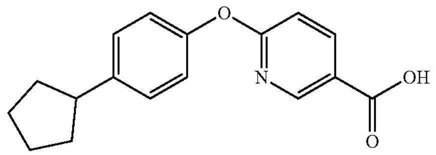

6-(4-cyclopentylphenoxy)nicotinic acid

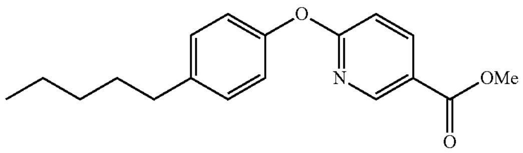

methyl 6-(4-pentylphenoxy)nicotinate

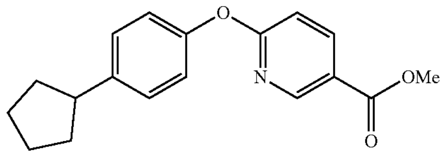

methyl 6-(4-cyclopentylphenoxy)nicotinate

-continued

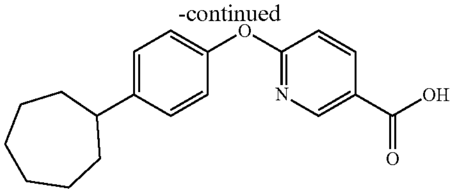

6-(4-cycloheptylphenoxy)nicotinic acid

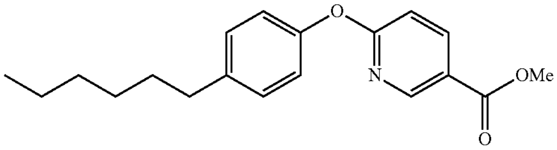

methyl 6-(4-hexylphenoxy)nicotinate

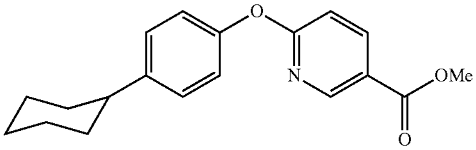

methyl 6-(4-cyclohexylphenoxy)nicotinate

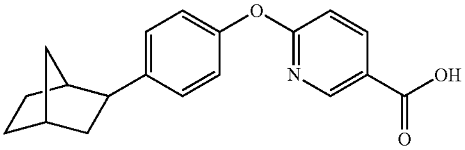

6-(4-((1S,4R)-bicyclo[2.2.1]heptan-2-yl)phenoxy)nicotinic acid

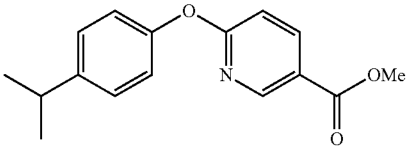

methyl 6-(4-isopropylphenoxy)nicotinate

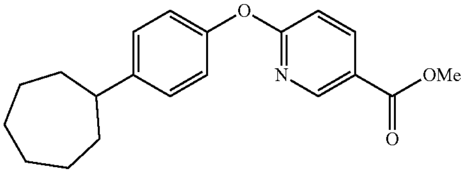

methyl 6-(4-cycloheptylphenoxy)nicotinate

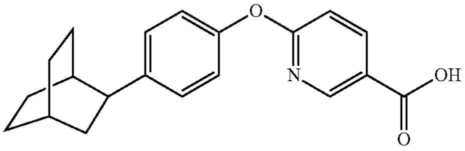

6-(4-((1s,4s)-bicyclo[2.2.2.]octan-2-yl)phenoxy)nicotinic acid

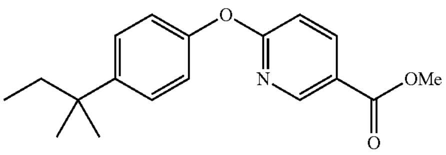

methyl 6-(4-(tert-pentyl)phenoxy)nicotinate

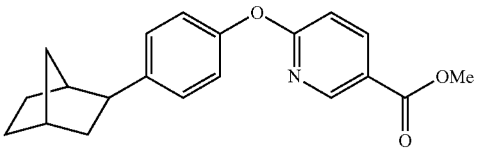

methyl 6-(4-((1S,4R)-bicyclo[2.2.1]heptan-2-yl)phenoxy)nicotinate

-continued

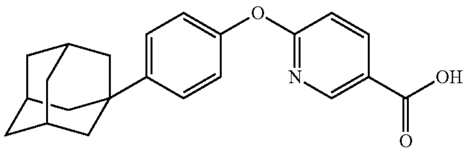

6-(4-((3r,5r,7r)-adamantan-1-yl)phenoxy)nicotinic acid

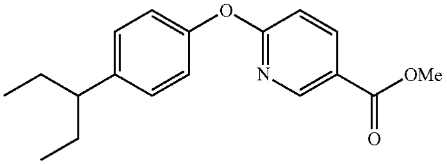

methyl 6-(4-(pentan-3-yl)phenoxy)nicotinate

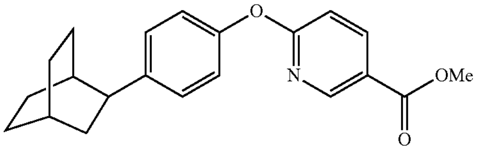

methyl 6-(4-((1s,4s)-bicyclo[2.2.2.]octan-2-yl)phenoxy)nicotinate

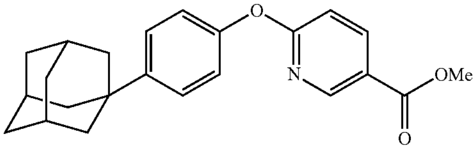

methyl 6-(4-((3r,5r,7r)-adamantan-1-yl)phenoxy)nicotinate

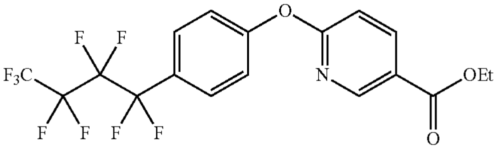

ethyl 6-(4-(perfluorobutyl)phenoxy)nicotinate

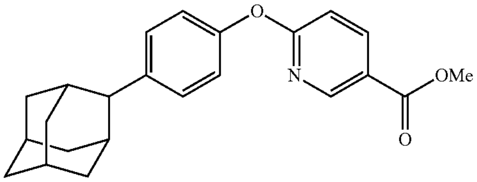

methyl 6-(4-((1r,3r,5r,7r)-adamantan-2-yl)phenoxy)nicotinate

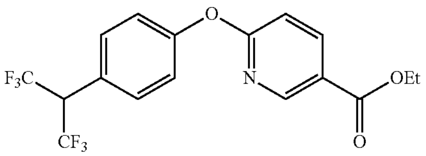

ethyl 6-(4-(1,1,1,3,3,3,-hexafluoropropan-2-yl)phenoxy)nicotinate

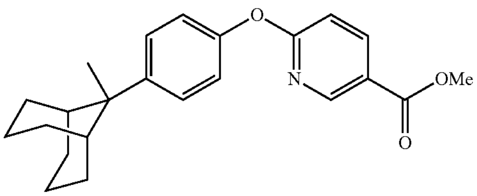

methyl 6-(4-((1R,5S)-9-methylbicyclo[3.3.1]nonan-9-yl)phenoxy)nicotinate

-continued

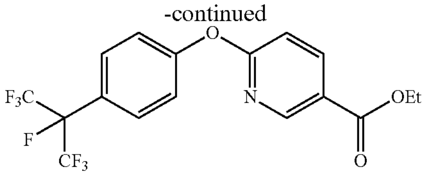

ethyl 6-(4-(perfluoropropan-2-yl)phenoxy)nicotinate

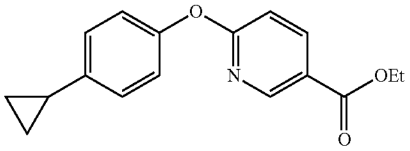

ethyl 6-(4-(cyclopropyl)phenoxy)nicotinate

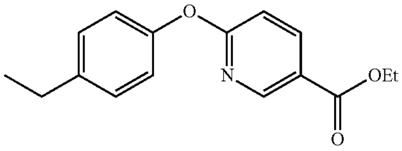

ethyl 6-(4-(ethylphenoxy)nicotinate

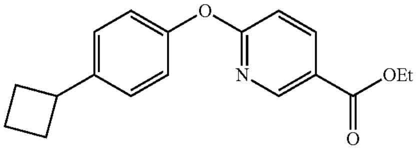

ethyl 6-(4-(cyclobutylphenoxy)nicotinate

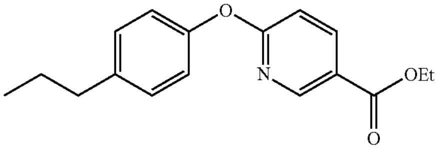

ethyl 6-(4-propylphenoxy)nicotinate

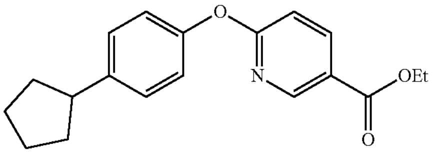

ethyl 6-(4-cyclopentylphenoxy)nicotinate

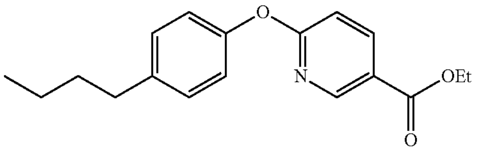

ethyl 6-(4-butylphenoxy)nicotinate

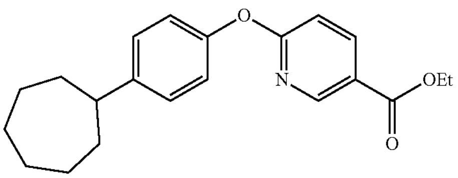

ethyl 6-(4-cycloheptylphenoxy)nicotinate

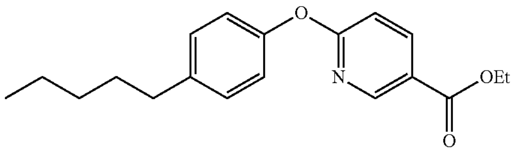

ethyl 6-(4-pentylphenoxy)nicotinate

-continued

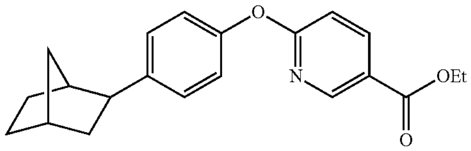

ethyl 6-(4-((1S,4R)-bicyclo[2.2.1]heptan-2-yl)phenoxy)nicotinate

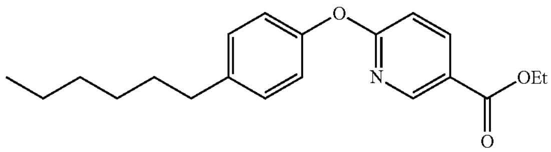

ethyl 6-(4-hexylphenoxy)nicotinate

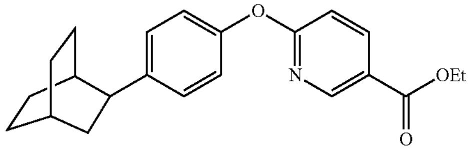

ethyl 6-(4-((1s,4s)-bicyclo[2.2.2.]octan-2-yl)phenoxy)nicotinate

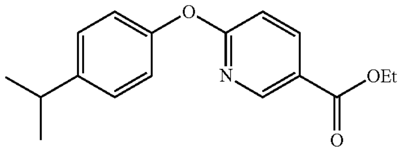

ethyl 6-(4-isopropylphenoxy)nicotinate

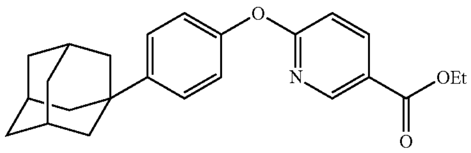

ethyl 6-(4-((3r,5r,7r)-adamantan-1-yl)phenoxy)nicotinate

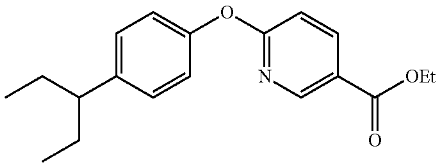

ethyl 6-(4-pentan-3-yl)phenoxy)nicotinate

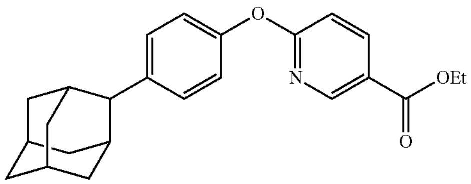

ethyl 6-(4-((1r,3r,5r,7r)-adamantan-2-yl)phenoxy)nicotinate

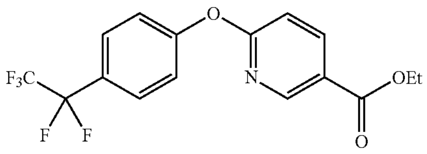

ethyl 6-(4-(perfluoroethyl)phenoxy)nicotinate

-continued

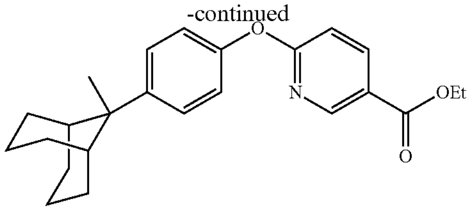

ethyl 6-(4-((1R,5S)-9-methylbicyclo[3.3.1]nonan-9-yl)phenoxy)nicotinate

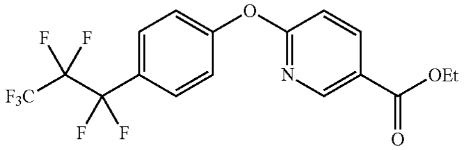

ethyl 6-(4-(perfluoropropyl)phenoxy)nicotinate

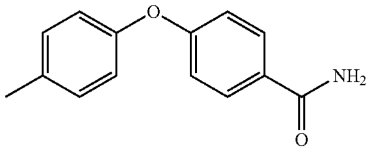

4-(p-tolyoxy)benzamide

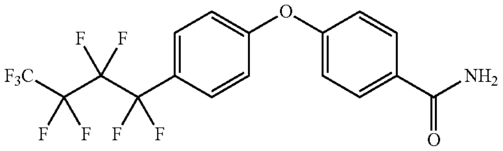

4-(4-(perfluorobutyl)phenoxy)benzamide

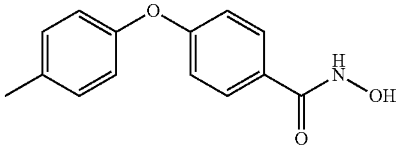

N-hydroxy-4-(p-tolyoxy)benzamide

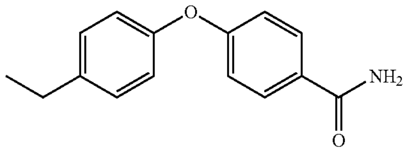

4-(4-ethylphenoxy)benzamide

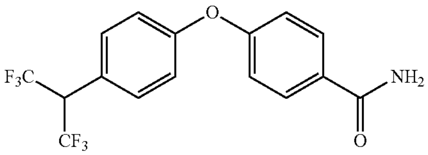

4-(4-(1,1,1,3,3,3,-hexafluoropropan-2-yl)phenoxy)benzamide

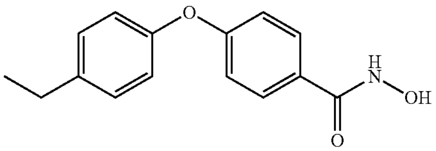

4-(4-ethylphenoxy)-N-hydroxybenzamide

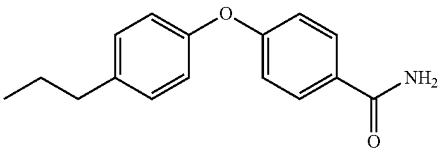

4-(4-propylphenoxy)benzamide

-continued

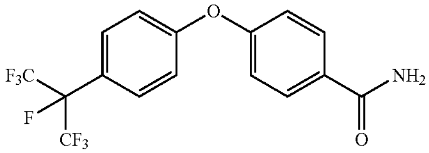

4-(4-(perfluoropropan-2-yl)phenoxy)benzamide

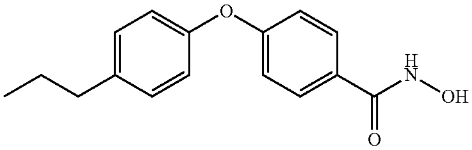

N-hydroxy-4-(4-propylphenoxy)benzamide

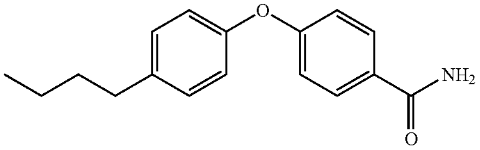

4-(4-butylphenoxy)benzamide

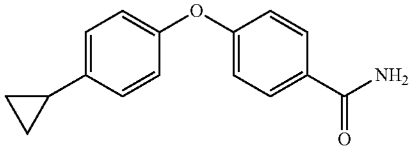

4-(4-cyclopropylphenoxy)benzamide

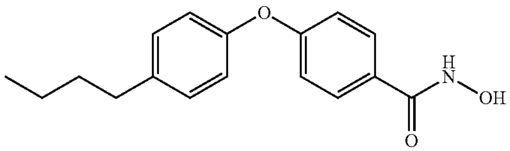

4-(4-butylphenoxy)-N-hydroxybenzamide

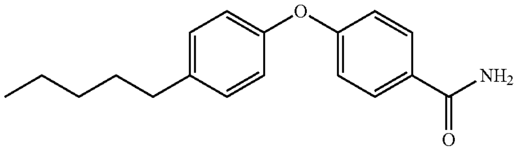

4-(4-pentylphenoxy)benzamide

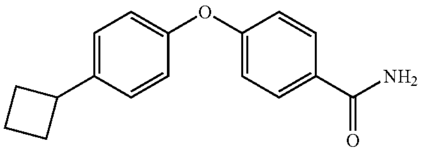

4-(4-cyclobutylphenoxy)benzamide

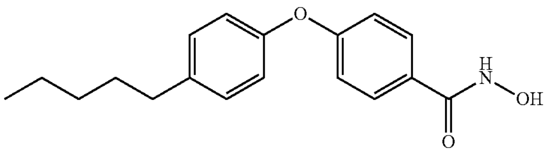

N-hydroxy-4-(4-pentylphenoxy)benzamide

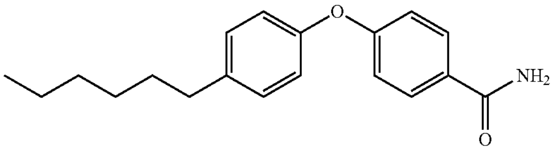

4-(4-hexylphenoxy)benzamide

-continued

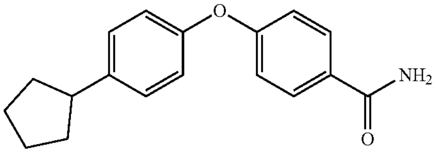

4-(4-cyclopentylphenoxy)benzamide

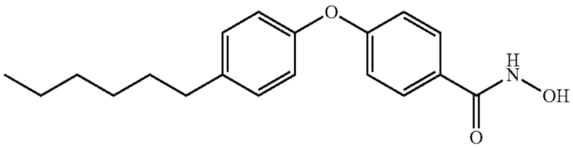

4-(4-hexylphenoxy)-N-hydroxybenzamide

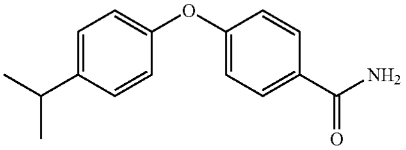

4-(4-isopropylphenoxy)benzamide

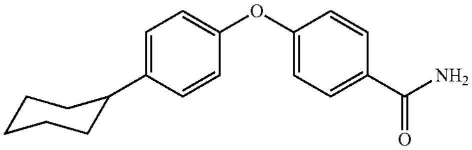

4-(4-cyclohexylphenoxy)benzamide

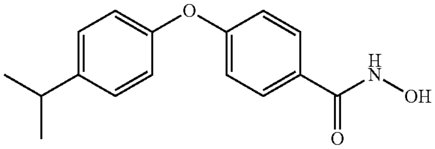

N-hydroxy-4-(4-isopropylphenoxy)benzamide

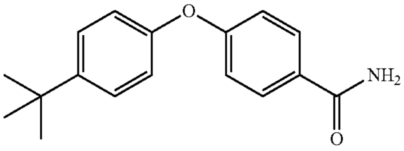

4-(4-(tert-butyl)phenoxy)benzamide

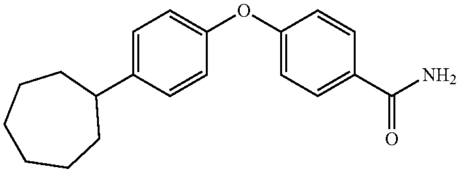

4-(4-cycloheptylphenoxy)benzamide

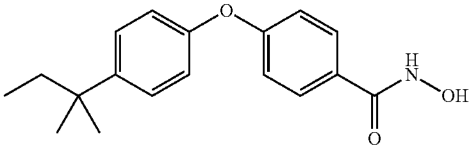

N-hydroxy-4-(4-tert-pentyl)phenoxy)benzamide

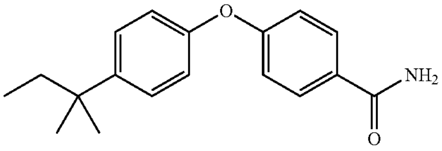

4-(4-tert-pentyl)phenoxy)benzamide

-continued

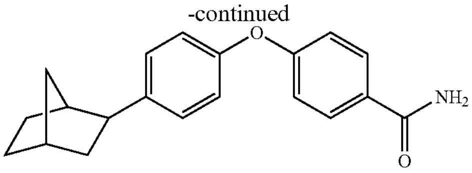

4-(4-((1S,4R)-bicyclo[2.2.1]heptan-2-yl)phenoxy)benzamide

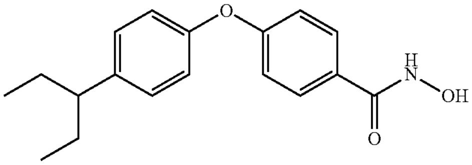

N-hydroxy-4-(4-(pentan-3-yl)phenoxy)benzamide

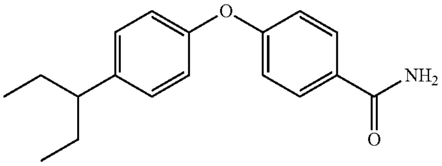

4-(4-(pentan-3-yl)phenoxy)benzamide

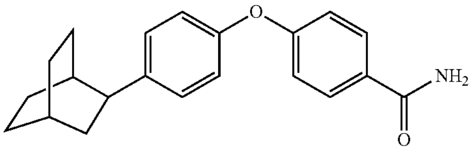

4-(4-((1S,4s)-bicyclo[2.2.1]octan-2-yl)phenoxy)benzamide

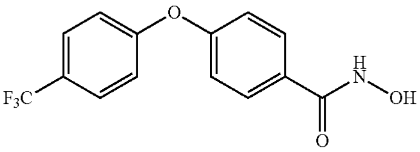

N-hydroxy-4-(4-(trifluoromethyl)phenoxy)benzamide

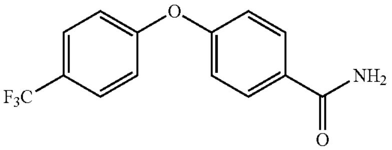

4-(4-(trifluorometh1)phenoxy)benzamide

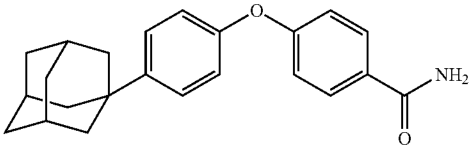

4-(4-((3r,5r,7r)-adamantan-1-yl)phenoxy)benzamide

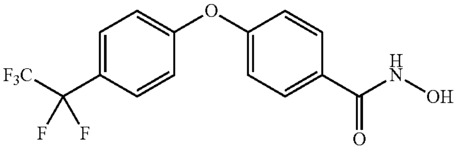

N-hydroxy-4-(4-(perfluoroethyl)phenoxy)benzamide

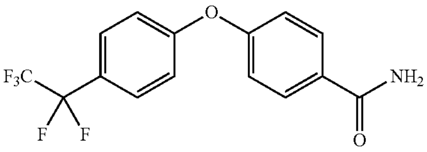

4-(4-(perfluoroethyl)phenoxy)benzamide

-continued

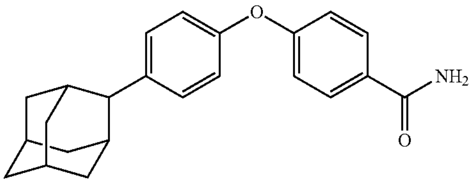

4-(4-((1r,3r,5r,7r)-adamantan-2-yl)phenoxy)benzamide

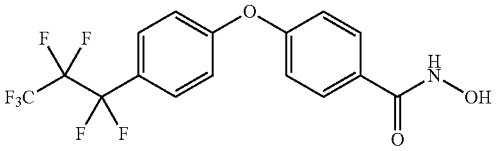

N-hydroxy-4-(4-(perfluoropropyl)phenoxy)benzamide

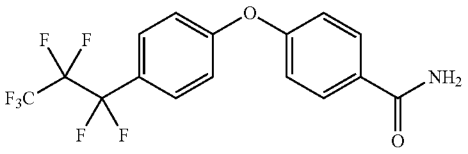

4-(4-(perfluoropropyl)phenoxy)benzamide

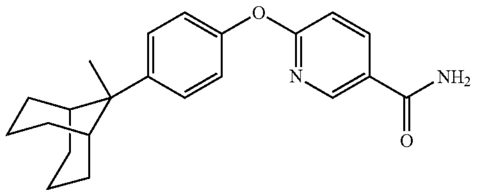

4-(4-((1R,5S)-9-methylbicyclo[3.3.1]nonan-9-yl)phenoxy)benzamide

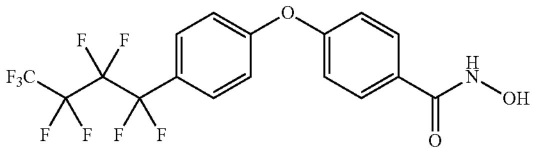

N-hydroxy-4-(4-(perfluorobutyl)phenoxy)benzamide

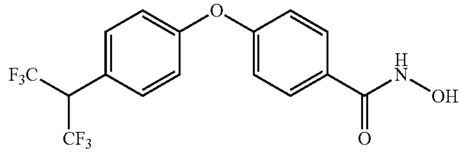

4-(4-(1,1,1,3,3,3-hexafluoropropan-2-yl)phenoxy)-N-hydroxybenzamide

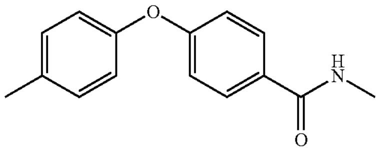

N-methyl-4-(p-tolyloxy)benzamide

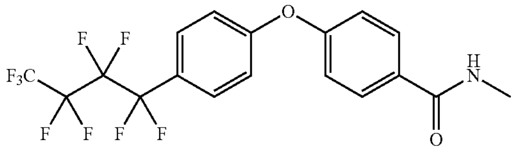

N-methyl-4-(4-perfluorobutyl)phenoxy)benzamide

-continued

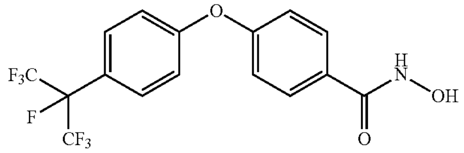

N-hydroxy-4-(4-(perfluoropropan-2-yl)phenoxy)benzamide

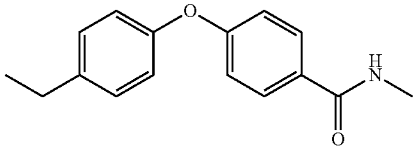

4-(4-ethylphenoxy)-N-methylbenzamide

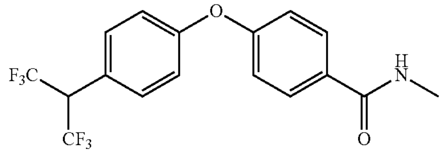

4-(4-(1,1,1,3,3,3-hexafluoropropan-2-yl)phenoxy)-N-methylbenzamide

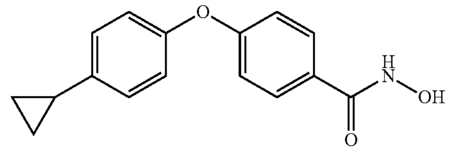

4-(4-cyclopropylphenoxy)-N-hydroxybenzamide

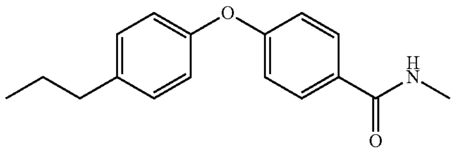

N-methyl-4-(4-propylphenoxy)benzamide

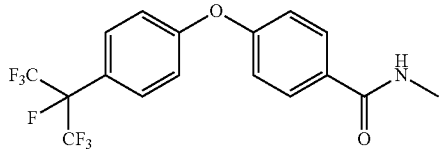

N-methyl-4-(4-(perfluoropropan-2-yl)phenoxy)benzamide

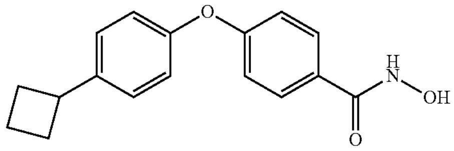

4-(4-cyclobutylphenoxy)-N-hydroxybenzamide

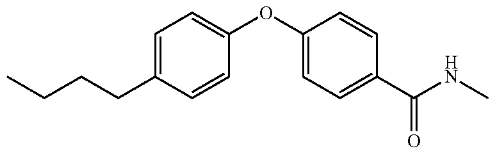

4-(4-butylphenoxy)-N-methylbenzamide

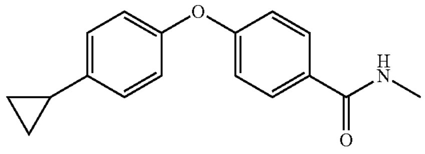

4-(4-cyclopropylphenoxy)-N-methylbenzamide

-continued

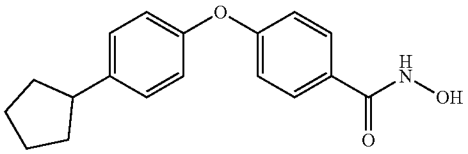

4-(4-cyclopentylphenoxy)-N-hydroxybenzamide

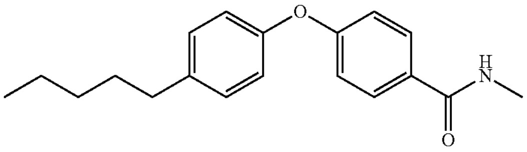

N-methyl-4-(4-pentylphenoxy)benzamide

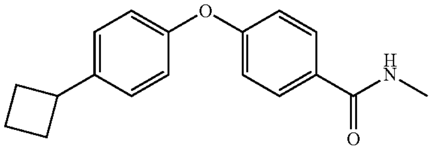

4-(4-cyclobutylphenoxy)-N-methylbenzamide

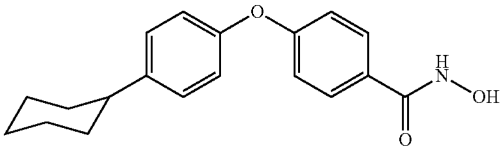

4-(4-cyclohexlyphenoxy)-N-hydroxybenzamide

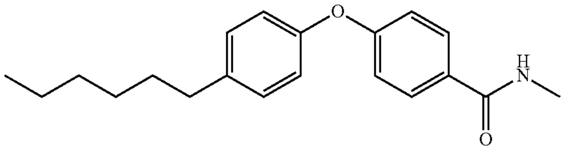

4-(4-hexylphenoxy)-N-methylbenzamide

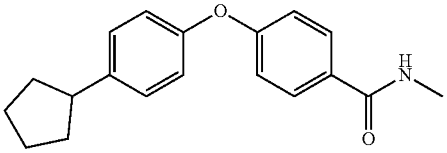

4-(4-cyclopentylphenoxy)-N-methylbenzamide

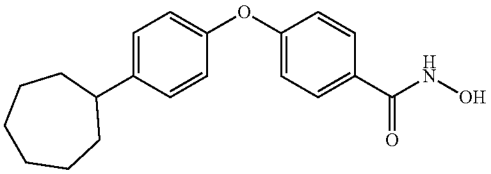

4-(4-cycloheptylphenoxy)-N-hydroxybenzamide

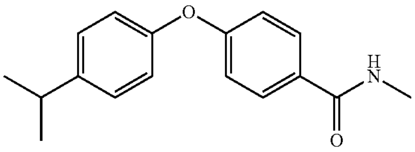

4-(4-isopropylphenoxy)-N-methylbenzamide

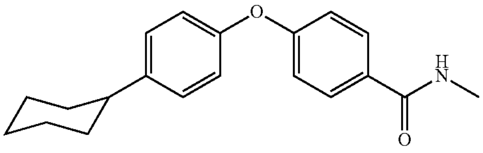

4-(4-cyclohexylphenoxy)-N-methylbenzamide

-continued

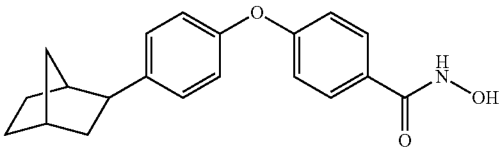

4-(4-((1S,4R)-bicyclo[2.2.1]heptan-2-yl)phenoxy)-N-hydroxybenzamide

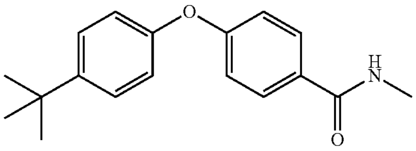

4-(4-tert-butyl)phenoxy)-N-methylbenzamide

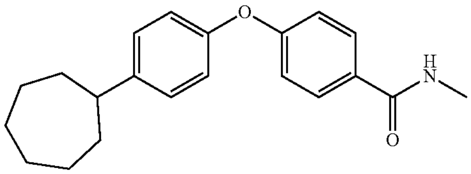

4-(4-cycloheptylphenoxy)-N-methylbenzamide

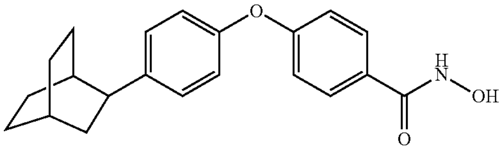

4-(4-((1s,4s)-bicyclo[2.2.2]octan-2-yl)phenoxy)-N-hydroxybenzamide

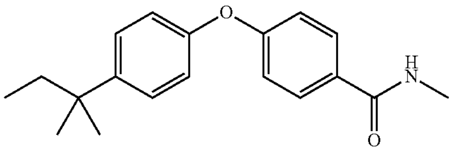

N-methyl-4-(4-(tert-phenyl)phenoxy)benzamide

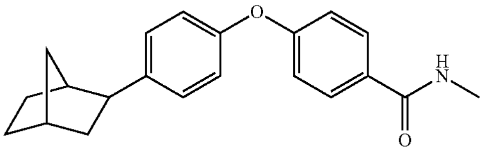

4-(4-((1S,4R)-bicyclo[2.2.1]heptan-2-yl)phenoxy)-N-methylbenzamide

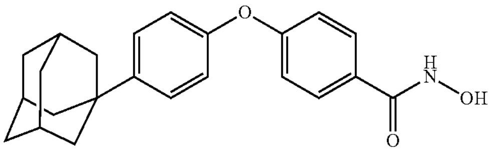

4-(4-((3r,5r,7r)-adamantan-1-yl)phenoxy)-N-hydroxybenzamide

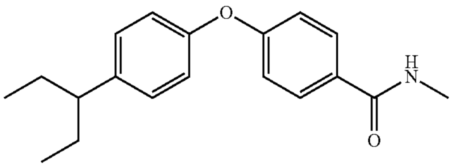

N-methyl-4-(4-(pentan-3-yl)phenoxy)benzamide

-continued

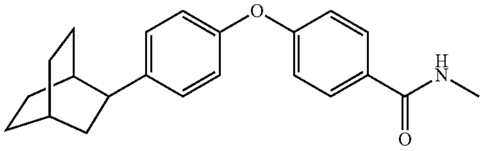

4-(4-((1s,4s)-bicyclo[2.2.2]octan-2-yl)phenoxy)-N-methylbenzamide

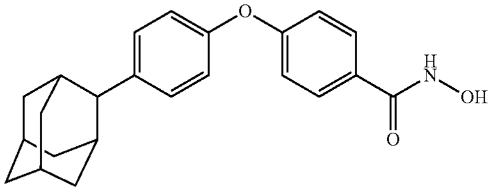

4-(4-((1r,3r,5r,7r)-adamantan-2-yl)phenoxy)-N-hydroxybenzamide

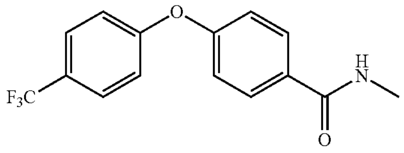

N-methyl-4-(4-(trifluoromethyl)phenoxy)benzamide

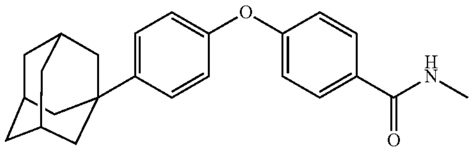

4-(4-((3r,5r,7r)-adamantan-1-yl)phenoxy)-N-methylbenzamide

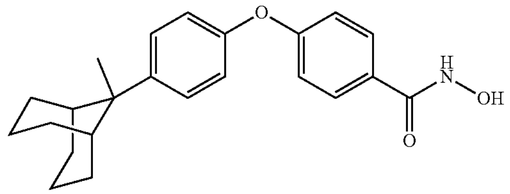

N-hydroxy-4-(4-((1R,5S)-9-methylbicylo[3.3.1]nonan-9-yl)phenoxy) benzamide

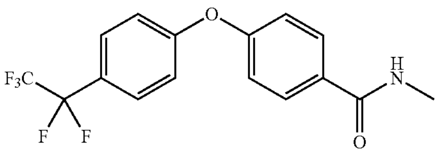

N-methyl-4-(4-(perfluoroethyl)phenoxy)benzamide

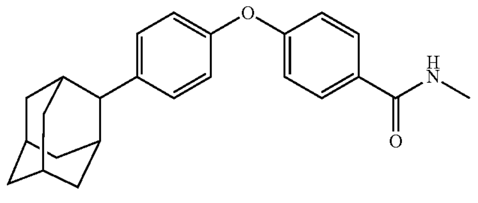

4-(4-((1r,3r,5r,7r)-adamantan-2-yl)phenoxy)-N-methylbenzamide

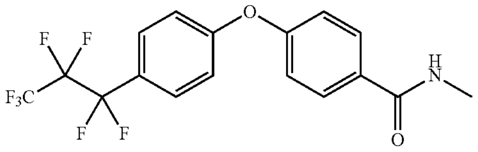

N-methyl-4-(4-(perfluoropropyl)phenoxy)benzamide

-continued

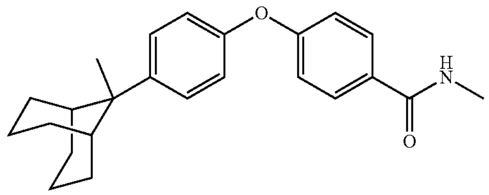

N-methyl-4-(4-((1R,5S)-9-methylbicyclo[3.3.1]nonan-9-yl)phenoxy) benzamide

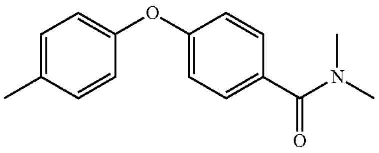

N,N-dimethyl-4-(p-tolyloxy)benzamide

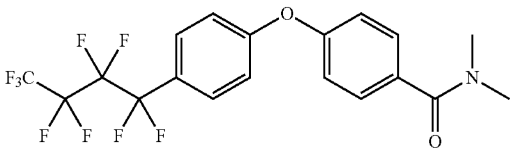

N-N-dimethyl-4-(4-perfluorobutyl)phenoxy)benzamide

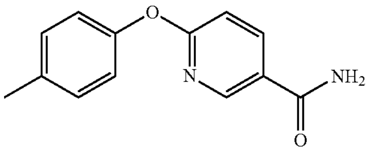

6-(p-tolyloxy)nicotinamide

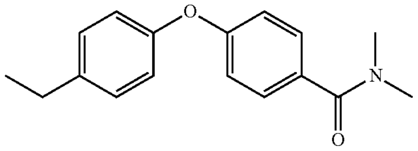

4-(4-ethylphenoxy)-N,N-dimethylbenzamide

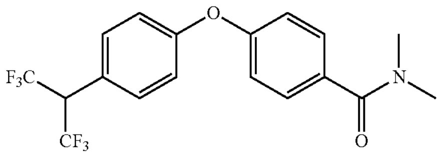

4-(4-(1,1,1,3,3,3-hexafluoropropan-2-yl)phenoxy)-N,N-dimethylbenzamide

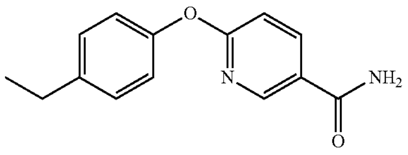

6-(4-ethylphenoxy)nicotinamide

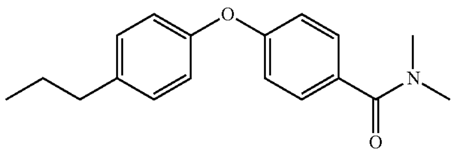

N,N-dimethyl-4-(4-propylphenoxy)benzamide

-continued

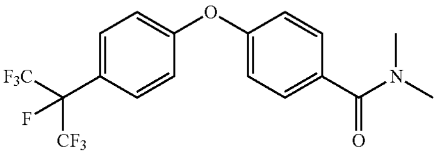

N,N-dimethyl-4-(4-(perfluoropropan-2-yl)phenoxy)benzamide

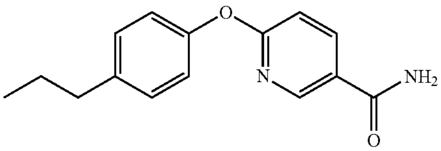

6-(4-propylphenoxy)nicotinamide

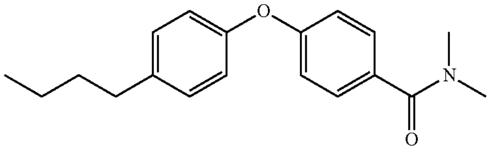

4-(4-butylphenoxy)-N,N-dimethylbenzamide

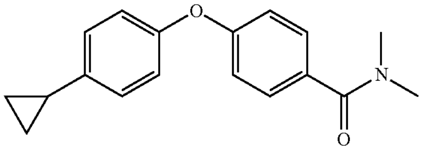

4-(4-cyclopropylphenoxy)-N,N-dimethylbenzamide

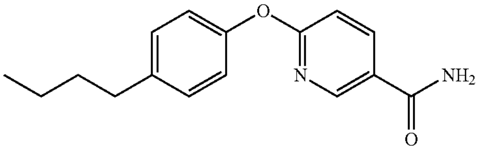

6-(4-butylphenoxy)nicotinamide

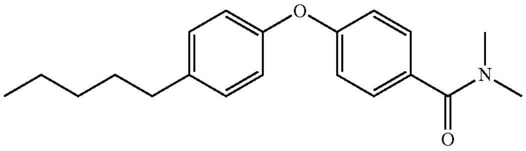

N,N-dimethyl-4-(4-pentylphenoxy)benzamide

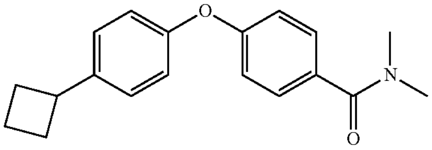

4-(4-cyclobutylphenoxy)-N,N-dimethylbenzamide

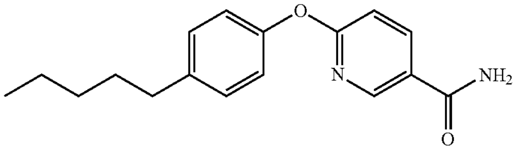

6-(4-pentylphenoxy)nicotinamide

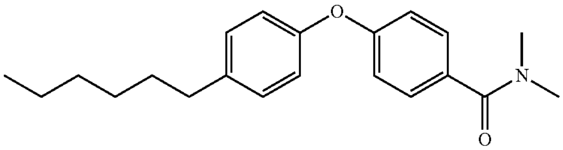

4-(4-hexylphenoxy)-N,N-dimethylbenzamide

-continued

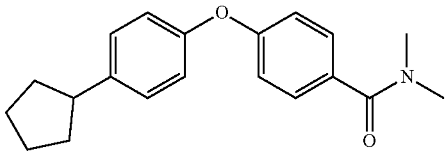

4-(4-cyclopentylphenoxy)-N,N-dimethylbenzamide

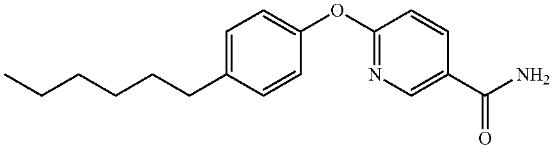

6-(4-hexylphenoxy)nicotinamide

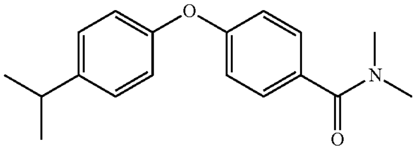

4-(4-isopropylphenoxy)-N,N-dimethylbenzamide

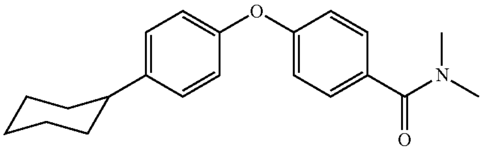

4-(4-cyclohexylphenoxy)-N,N-dimethylbenzamide

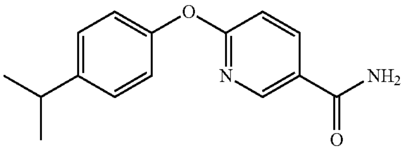

6-(4-isopropylphenoxy)nicotinamide

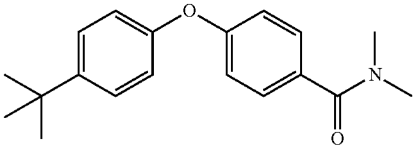

4-(4-(tert-butyl)phenoxy-N,N-dimethylbenzamide

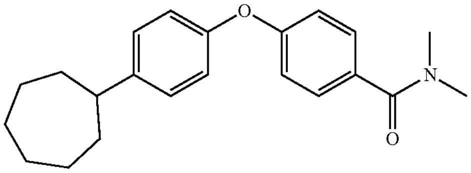

4-(4-cycloheptylphenoxy)-N,N-dimethylbenzamide

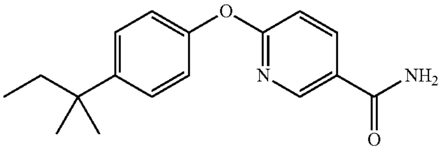

6-(4-(tert-pentyl)phenoxy)nicotinamide

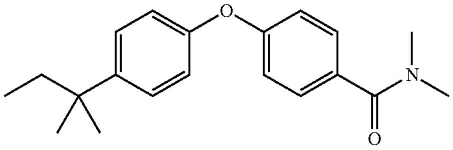

N,N-dimethyl-4-(4-(tert-pentyl)phenoxy)benzamide

-continued

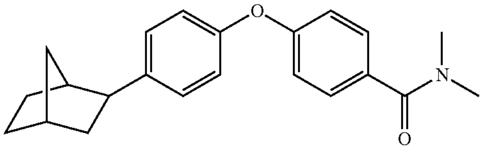

4-(4-((1S,4R)-bicyclo[2.2.1]heptan-2-yl)phenoxy)-N,N-dimethylbenzamide

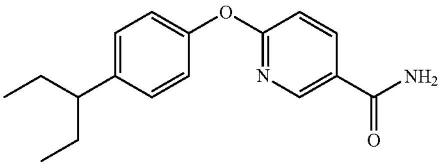

6-(4-(pentan-3-yl)phenoxy)nicotinamide

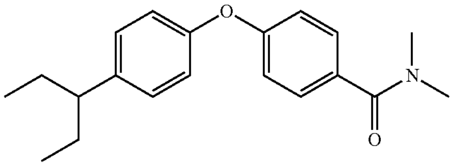

N,N-dimethyl-4-(4-(pentan-3-yl)phenoxy)benzamide

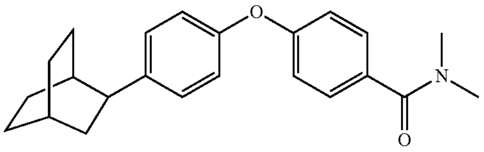

4-(4-((1s,4s)-bicyclo[2.2.2]octan-2-yl)phenoxy)-N,N-dimethylbenzamide

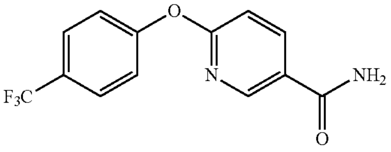

6-(4-(trifluoromethyl)phenoxy)nicotinamide

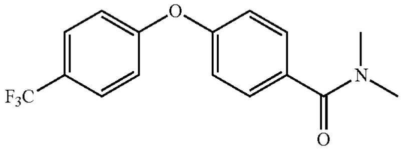

N,N-dimethyl-4-(4-(trifluoromethyl)phenoxy)benzamide

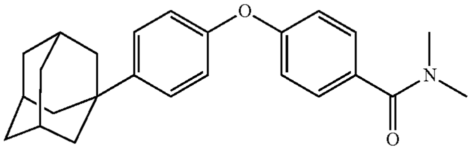

4-(4-((3r,5r,7r)-adamantan-1-yl)phenoxy-N,N-dimethylbenzamide

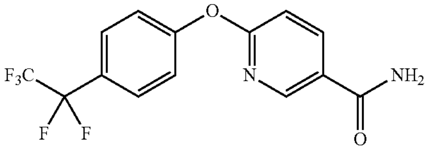

6-(4-(perfluoroethyl)phenoxy)nicotinamide

-continued

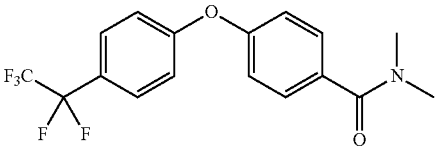

N,N-dimethyl-4-(4-(perfluoroethyl)phenoxy)benzamide

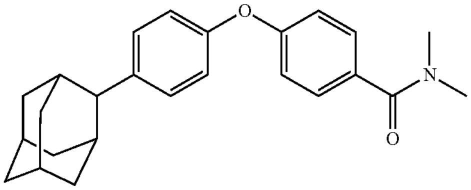

4-(4-((1r,3r,5r,7r)-adamantan-2-yl)phenoxy)-N,N-dimethylbenzamide

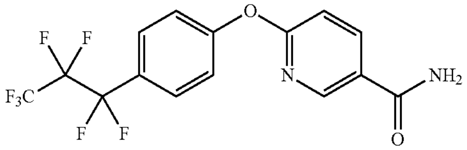

6-(4-(perfluoropropyl)phenoxy)nicotinamide

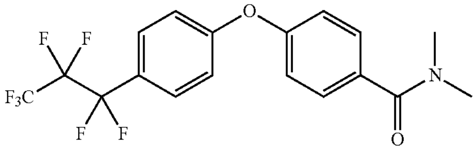

N,N-dimethyl-4-(4-(perfluoropropyl)phenoxy)benzamide

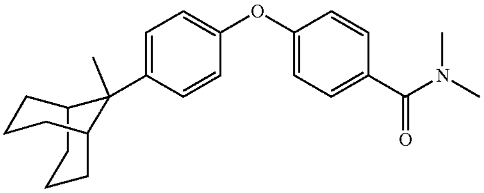

N,N-dimethyl-4-(4-((1R,5S)-9-methylbicyclo[3.3.1]nonan-9-yl)phenoxy)benzamide

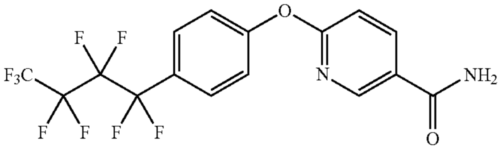

6-(4-(perfluorobutyl)phenoxy)nicotinamide

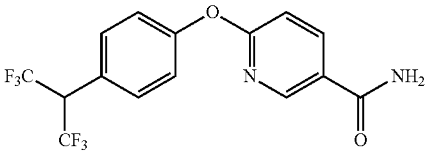

6-(4-(1,1,1,3,3,3-hexafluoropropan-2-yl)phenoxy)nicotinamide

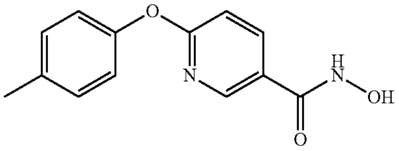

N-hydroxy-6-(p-tolyoxy)nicotinamide

-continued

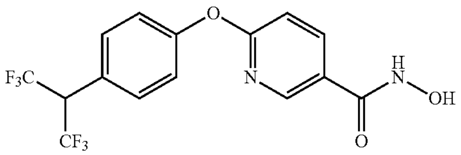

6-(4-(1,1,1,3,3,3-hexafluoropropan-2-yl)phenoxy)-N-hydroxynicotinamide

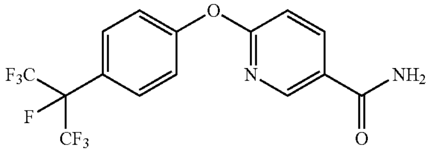

6-(4-(perfluoropropan-2-yl)phenoxy)nicotinamide

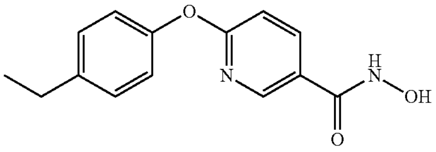

6-(4-ethylphenoxy)-N-hydroxynicotinamide

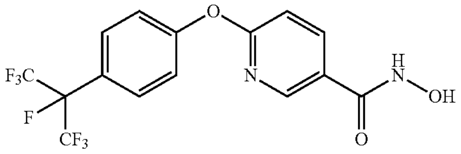

N-hydroxy-6-(4-(perfluoropropan-2-yl)phenoxy)nicotinamide

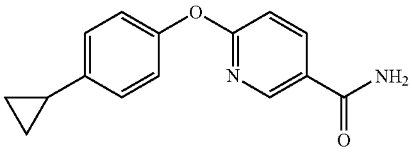

6-(4-cyclopropylphenoxy)nicotinamide

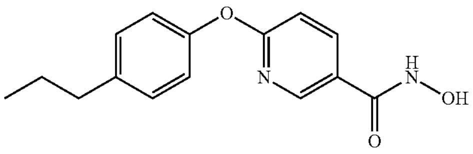

N-hydroxy-6-(4-propylphenoxy)nicotinamide

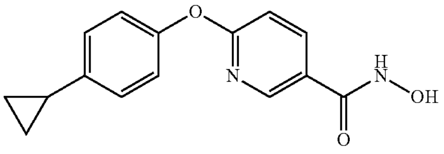

6-(4-cyclopropylphenoxy)-N-hydroxynicotinamide

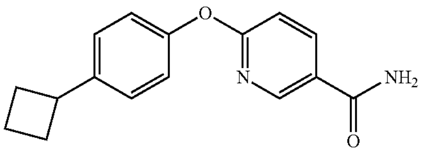

6-(4-cyclobutylphenoxy)nicotinamide

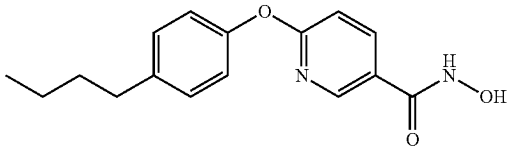

6-(4-butylphenoxy)-N-hydroxynicotinamide

-continued

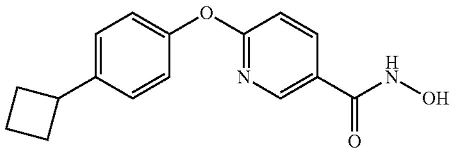

6-(4-cyclobutylphenoxy)-N-hydroxynicotinamide

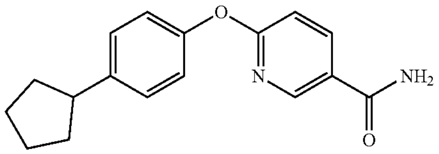

6-(4-cyclopentylphenoxy)nicotinamide

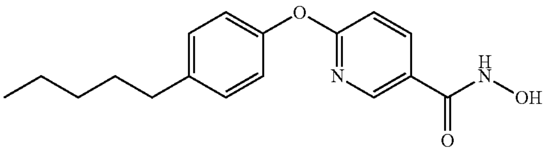

N-hydroxy-6-(4-pentylphenoxy)nicotinamide

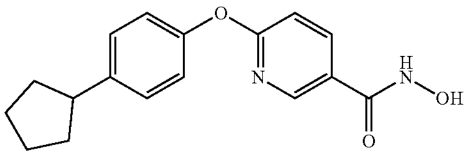

6-(4-cyclopentylphenoxy)-N-hydroxynicotinamide

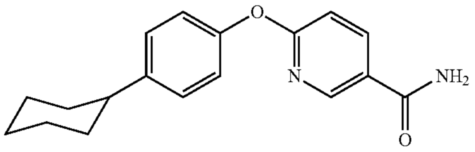

6-(4-cyclohexylphenoxy)nicotinamide

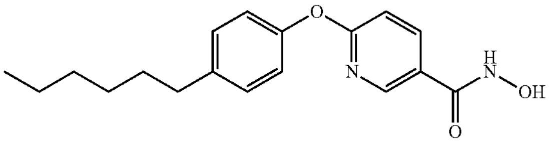

6-(4-hexylphenoxy)-N-hydroxynicotinamide

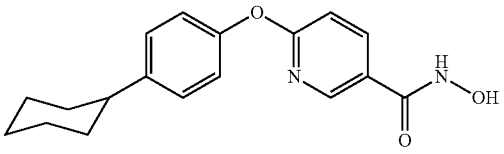

6-(4-cyclohexylphenoxy)-N-hydroxynicotinamide

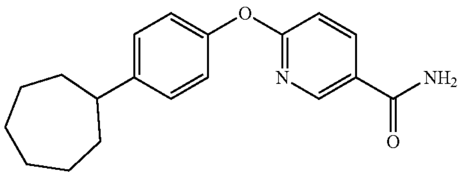

6-(4-cycloheptylphenoxy)nicotinamide

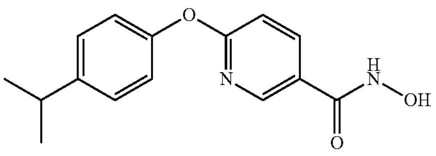

N-hydroxy-6-(4-isopropylphenoxy)nicotinamide

-continued

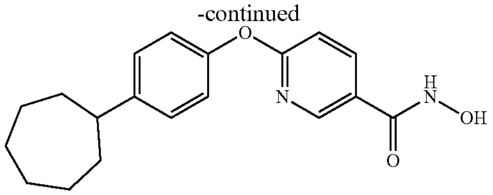

6-(4-cycloheptylphenoxy)-N-hydroxynicotinamide

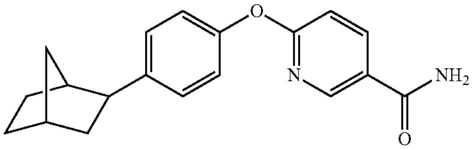

6-(4-((1S,4R)-bicyclo[2.2.1]heptan-2-yl)phenoxy)nicotinamide

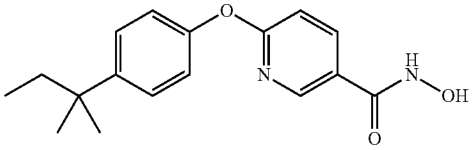

N-hydroxy-6-(4-(tert-pentyl)phenoxy)nicotinamide

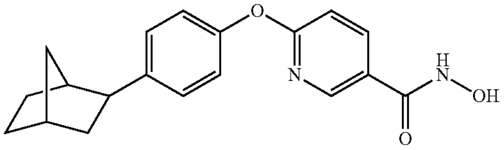

6-(4-((1S,4R)-bicyclo[2.2.1]heptan-2-yl)phenoxy)-N-hydroxynicotinamide

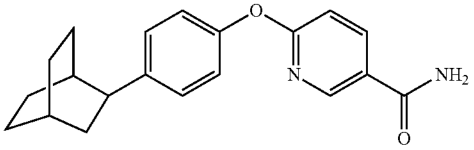

6-(4-((1s,4s)-bicyclo[2.2.2]octan-2-yl)phenoxy)nicotinamide

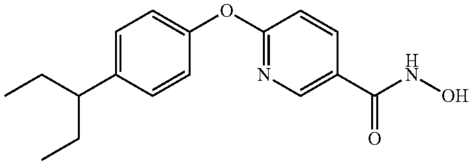

N-hydroxy-6-(4-(pentan-3-yl)phenoxy)nicotinamide

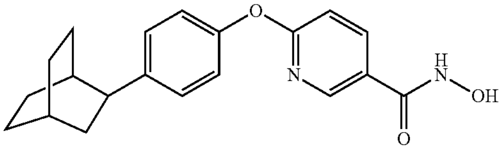

6(4-((1s,4s)-bicyclo[2.2.2]octan-2-yl)phenoxy)-N-hydroxynicotinamide

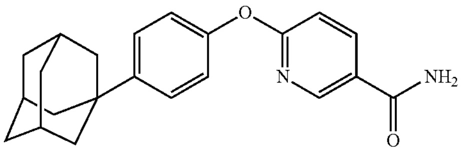

6-(4-((3r,5r,7r)-adamantan-1-yl)phenoxy)nicotinamide

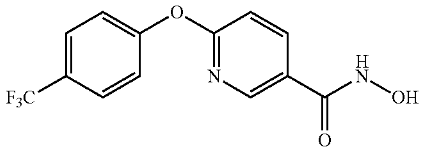

N-hydroxy-6-(4-(trifluoromethyl)phenoxy)nicotinamide

-continued

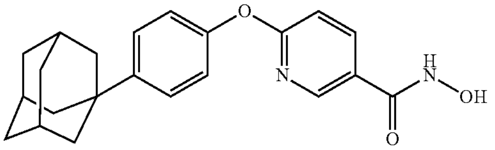

6-(4-((3r,5r,7r)-adamantan-1-yl)phenoxy)-N-hydroxynicotinamide

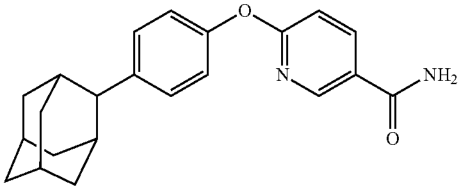

6-(4-((1r,3r,5r,7r)-adamantan-2-yl)phenoxy)nicotinamide

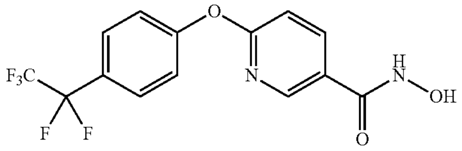

N-hydroxy-6-(4-(perfluoroethyl)phenoxy)nicotinamide

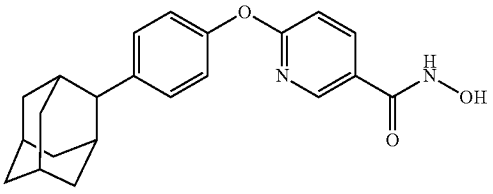

6-(4-((1r,3r,5r,7r)-adamantan-2-yl)phenoxy)-N-hydroxynicotinamide

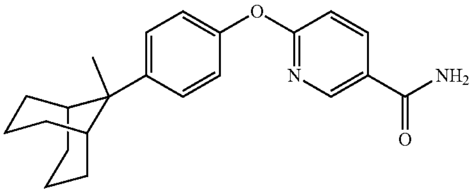

6-(4-((1R,5S)-9-methylbicyclo[3.3.1]nonan-9-yl)phenoxy)nicotinamide

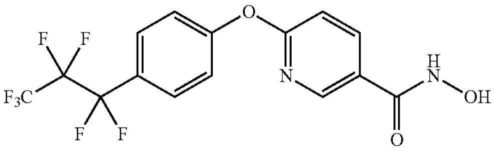

N-hydroxy-6-(4-(perfluoropropyl)phenoxy)nicotinamide

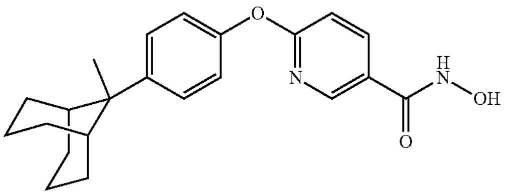

N-hydroxy-6-(4-((1R,5S)-9-methylbicyclo[3.3.1]nonan-9-yl)phenoxy)nicotinamide

-continued

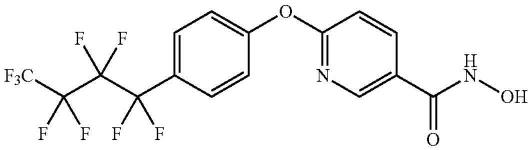

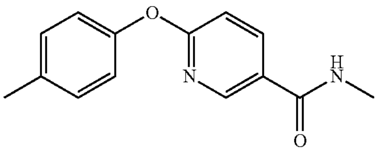

N-methyl-6-(p-tolyloxy)nicotinamide

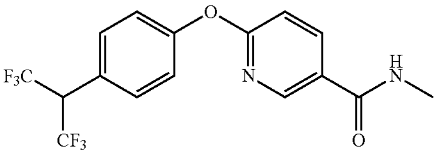

6-(4-(1,1,1,3,3,3-hexafluoropropan-2-yl)phenoxy)-N-methylnicotinamide

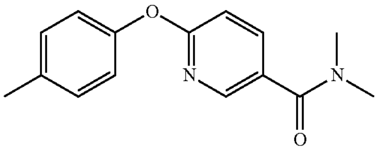

N,N-dimethyl-6-(p-tolyloxy)nicotinamide

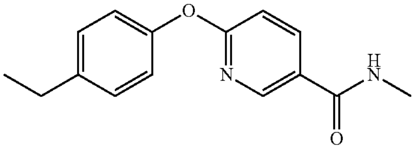

6-(4-ethylphenoxy)-N-methylnicotinamide

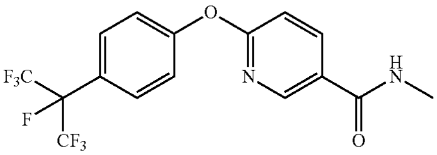

N-methyL-6-(4-(perfluoropropan-2-yl)phenoxy)nicotinamide

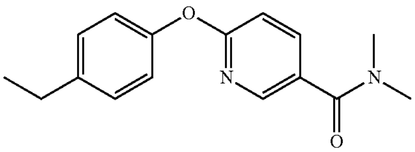

6-(4-ethylphenoxy)-N,N-dimethylnicotinamide

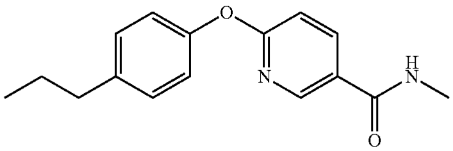

N-methyl-6-(4-propylphenoxy)nicotinamide

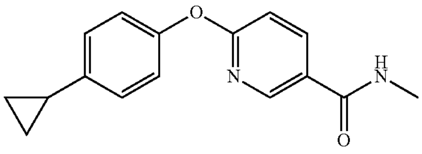

6-(4-cyclopropylphenoxy)-N-methylnicotinamide

-continued

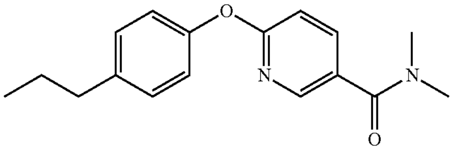

N,N-dimethyl-6-(4-propylphenoxy)nicotinamide

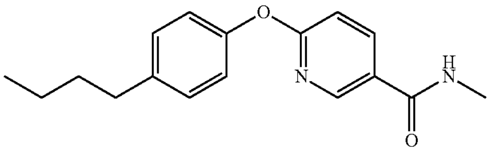

6-(4-butylphenoxy)-N-methylnicotinamide

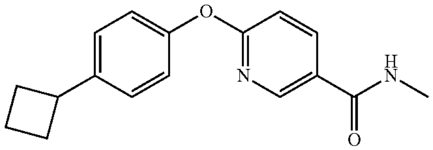

6-(4-cyclobutylphenoxy)-N-methylnicotinamide

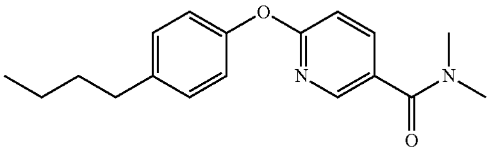

6-(4-butylphenoxy)-N,N-dimethylnicotinamide

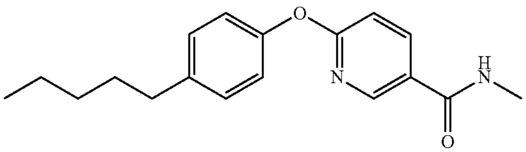

N-methyl-6-(4-pentylphenoxy)nicotinamide

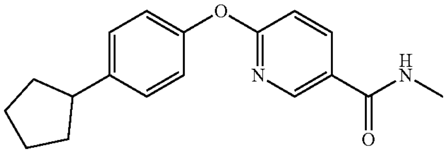

6-(4-cyclopentylphenoxy)-N-methylnicotinamide

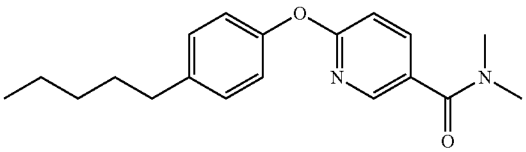

N,N-dimethyl-6-(4-pentylphenoxy)nicotinamide

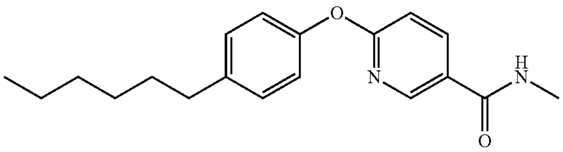

6-(4-hexylphenoxy)-N-methylnicotinamide

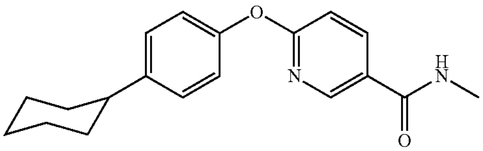

6-(4-cyclohexylphenoxy)-N-methylnicotinamide

-continued

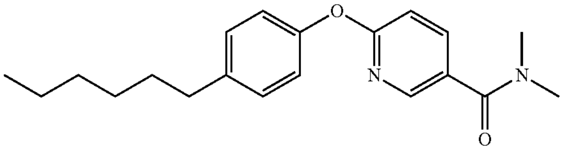

6-(4-hexylphenoxy)-N,N-dimethylnicotinamide

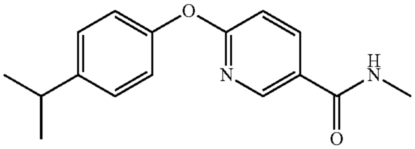

6-(4-isopropylphenoxy)-N-methylnicotinamide

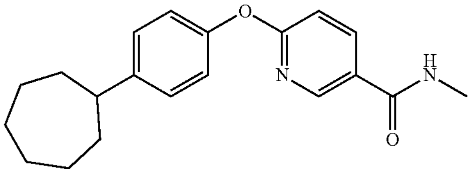

6-(4-cycloheptylphenoxy)-N-methylnicotinamide

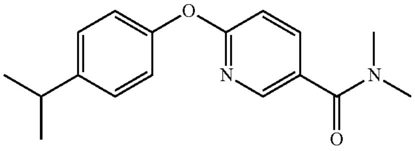

6-(4-isopropylphenoxy)-N,N-dimethylnicotinamide

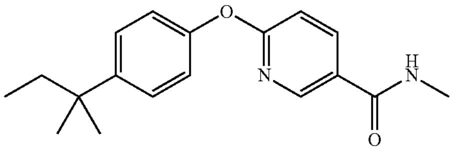

N-methyl-6-(4-(tert-pentyl)phenoxy)nicotinamide

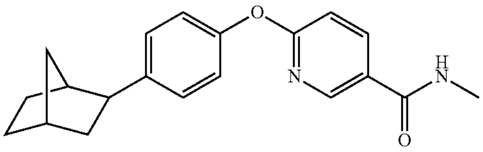

6-(4-((1S,4R)-bicyclo[2.2.1]heptan-2-yl)phenoxy)-N-methylnicotinamide

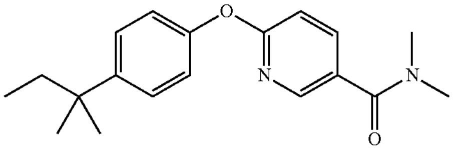

N,N-dimethyl-6-(4-(tert-pentyl)phenoxy)nicotinamide

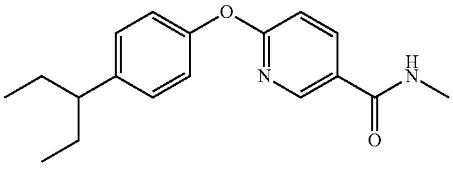

N-methyl-6-(4-(pentan-3-yl)phenoxy)nicotinamide

-continued

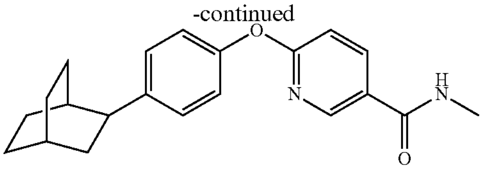

6-(4-((1s,4s)-bicyclo[2.2.2]octan-2-yl)phenoxy)-N-methylnicotinamide

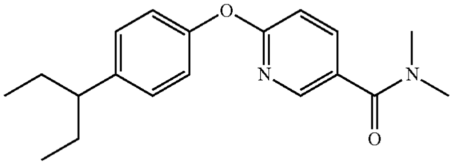

N,N-dimethyl-6-(4-(pentan-3-yl)phenoxy)nicotinamide

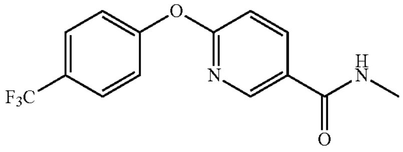

N-methyl-6-(4-(trifluoromethyl)phenoxy)nicotinamide

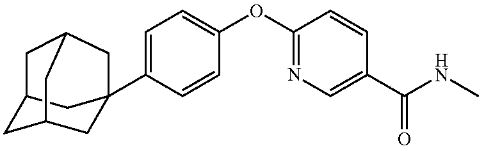

6-(4-((3r,5r,7r)-adamantan-1-yl)phenoxy)-N-methylnicotinamide

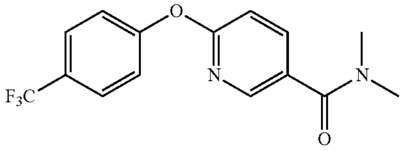

N,N-dimethyl-6-(4-(trifluoromethyl)phenoxy)nicotinamide

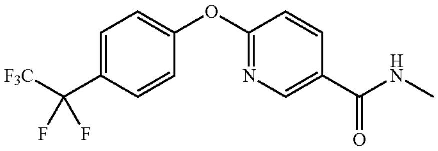

N-methyl-6-(4-(perfluoromethyl)phenoxy)nicotinamide

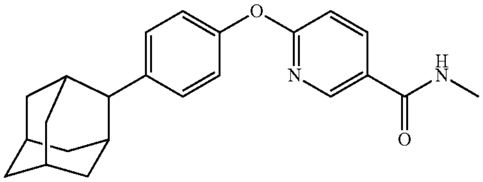

6-(4-((1r,3r,5r,7r)-adamantan-2-yl)phenoxy)-N-methylnicotinamide

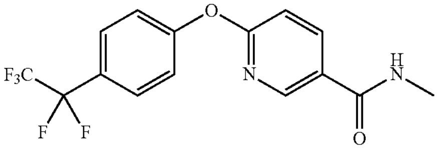

N,N-dimethyl-6-(4-(perfluoromethyl)phenoxy)nicotinamide

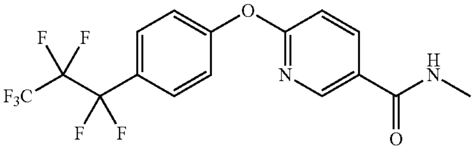

N-methyl-6-(4-(perfluoropropyl)phenoxy)nicotinamide

-continued

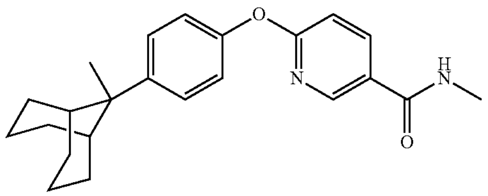

N-methyl-6-(4-((1R,5S)-9-methylbicyclo[3.3.1]nonan-9-yl)phenoxy)nicotinamide

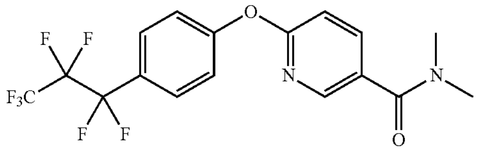

N,N-dimethyl-6-(4-(perfluoropropyl)phenoxy)nicotinamide

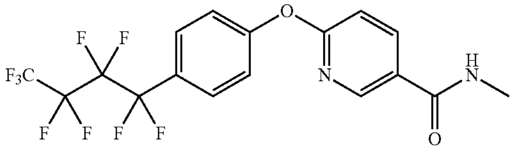

N-methyl-6-(4-(perfluorobutyl)phenoxy)nicotinamide

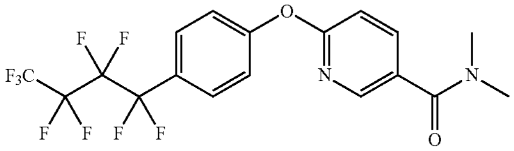

N,N-dimethyl-6-(4-(perfluorobutyl)phenoxy)nicotinamide

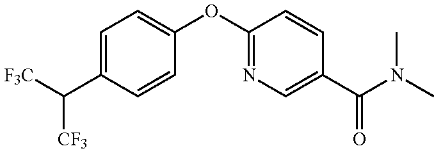

6-(4-(1,1,1,3,3,3-hexafluoropropan-2-yl)phenoxy)-N,N-dimethylnicotinamide

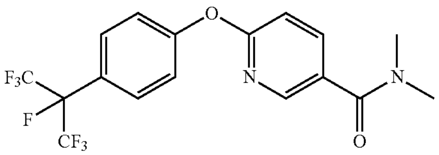

N,N-dimethyl-6-(4-(perfluoropropan-2-yl)phenoxy)nicotinamide

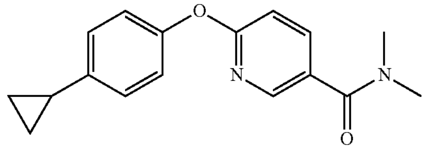

6-(4-cyclopropylphenoxy)-N,N-dimethylnicotinamide

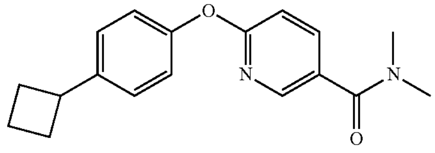

6-(4-cyclobutylphenoxy)-N,N-dimethylnicotinamide

-continued

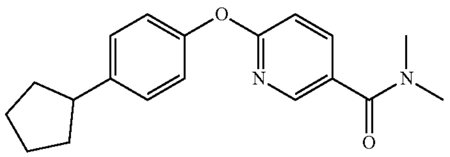

6-(4-cyclopentylphenoxy)-N,N-dimethylnicotinamide

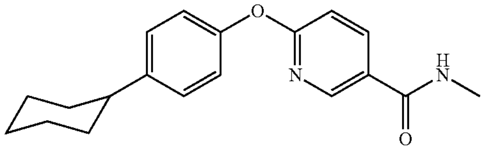

6-(4-cyclohexylphenoxy)-N,N-dimethylnicotinamide

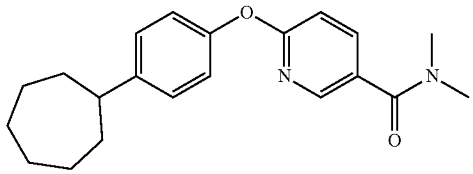

6-(4-cycloheptylphenoxy)-N-N-dimethylnicotinamide

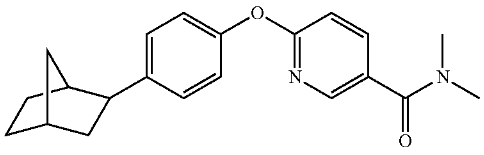

6-(4-((1S,4R)-bicyclo[2.2.1]heptan-2-yl)phenoxy)-N,N-dimethylnicotinamide

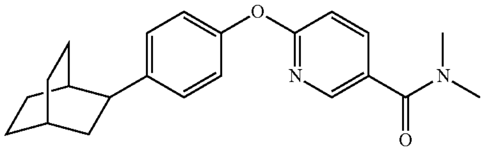

6-(4-((1s,4s)-bicyclo[2.2.2]octan-2-yl)phenoxy)-N,N-dimethylnicotinamide

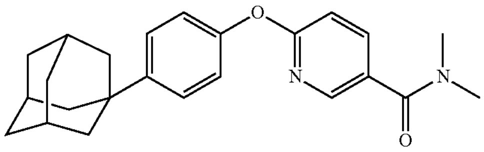

6-(4-((3r,5r,7r)-adamantan-1-yl)phenoxy)-N,N-dimethylnicotinamide

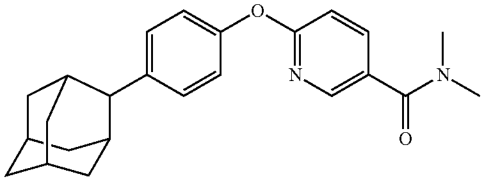

6-(4-((1r,3r,5r,7r)-adamantan-2-yl)phenoxy)-N,N-dimethylnicotinamide

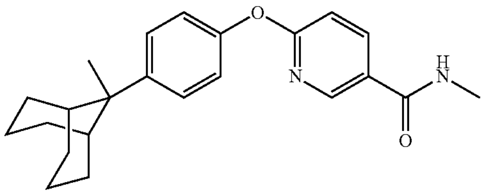

N,N-methyl-6-(4-((1R,5S)-9-methylbicyclo[3.3.1]nonan-9-yl)phenoxy) nicotinamide

-continued

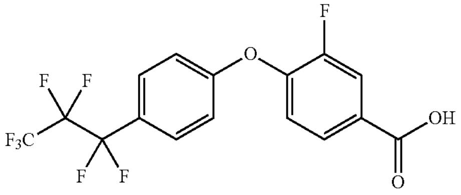

3-fluoro-4-(4-(perfluoropropyl)phenoxy)benzoic acid

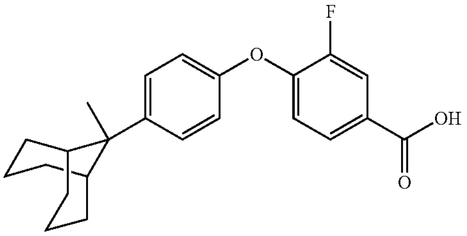

3-fluoro-4-(4-((1R,5S)-9-methylbicyclo[3.3.1]nonan-9-yl)phenoxy)benzoic acid

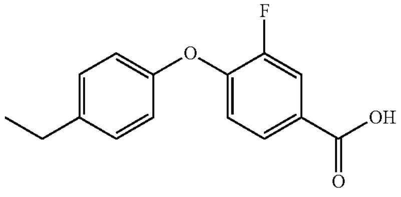

4-(4-ethylphenoxy)-3-fluorobenzoic acid

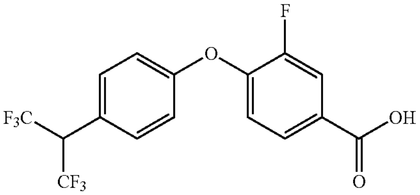

3-fluoro-4-(4-(1,1,1,3,3,3-hexafluoropropan-2-yl)phenoxy)benzoic acid

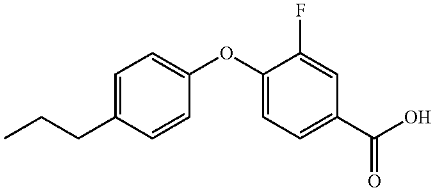

3-fluoro-4-(4-propylphenoxy)benzoic acid

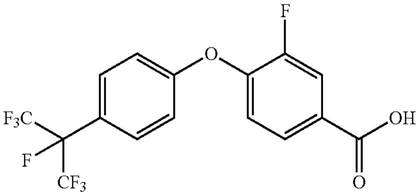

3-fluoro-4-(4-(perfluoropropan-2-yl)phenoxy)benzoic acid

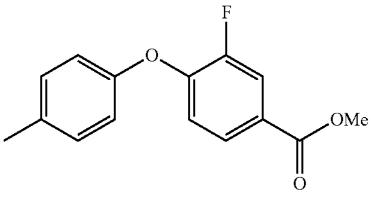

methyl 3-fluoro-4-(p-tolyloxy)benzoale

-continued

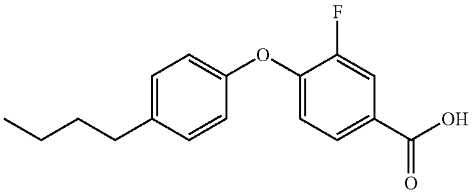

4-(4-butylphenoxy)-3-fluorobenzoic acid

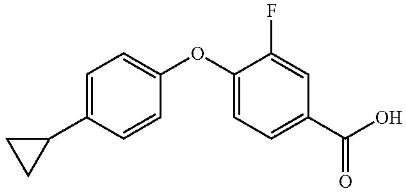

4-(4-cyclopropylphenoxy)-3-fluorobenzoic acid

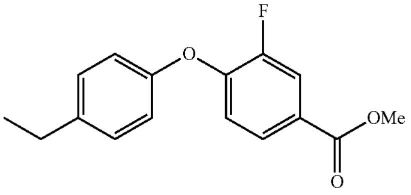

methyl 4-(4-ethylphenoxy)-3-fluorobenzoate

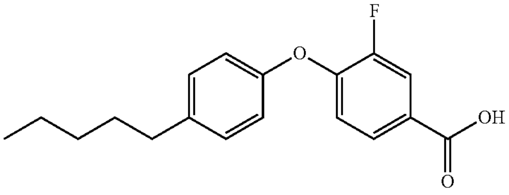

3-fluoro-4-(4-pentylphenoxy)benzoic acid

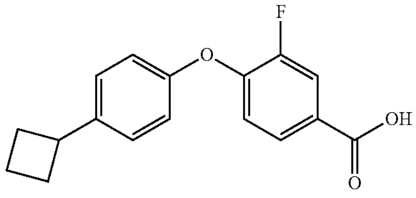

4-(4-cyclobutylphenoxy)-3-fluorobenzoic acid

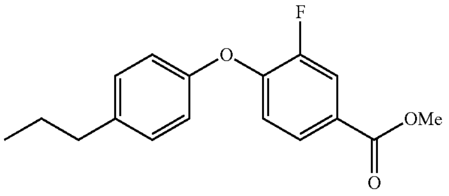

methyl 3-fluoro-4-(4-propylphenoxy)benzoate

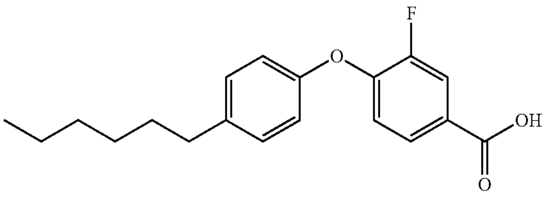

3-fluoro-4-(4-hexylphenoxy)benzoic acid

-continued

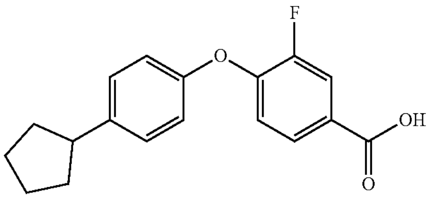

4-(4-cyclopentylphenoxy)-3-fluorobenzoic acid

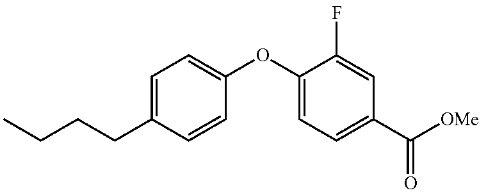

methyl 4-(4-butylphenoxy)-3-fluorobenzoate

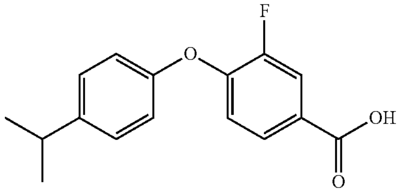

3-fluoro-4-(4-isopropylphenoxy)benzoic acid

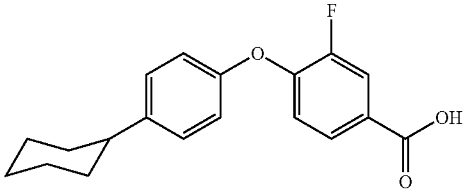

4-(4-cyclohexylphenoxy)-3-fluorobenzoic acid

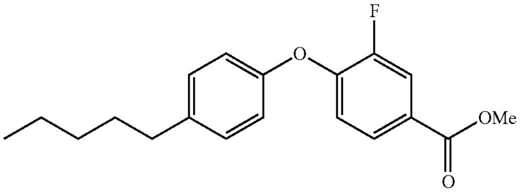

methyl 3-fluoro-4-(4-pentylphenoxy)benzoate

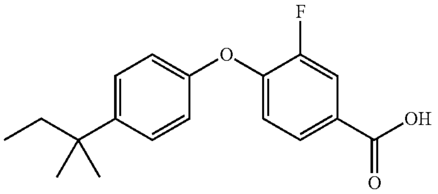

3-fluoro-4-(4-(tert-pentyl)phenoxy)benzoic acid

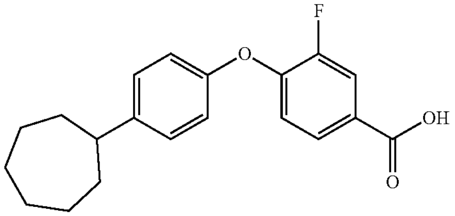

4-(4-cycloheptylphenoxy)-3-fluorobenzoic acid

-continued

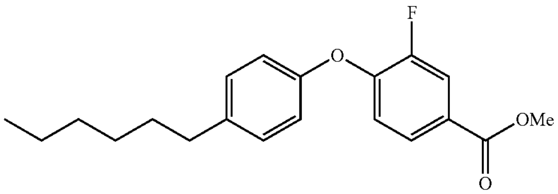

methyl 3-fluoro-4-(4-hexylphenoxy)benzoate

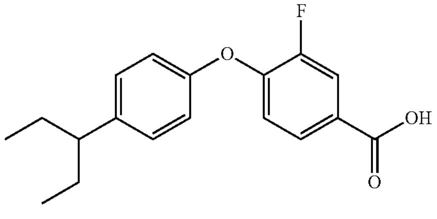

3-fluoro-4-(4-(pentan-3-yl)phenoxy)benzoic acid

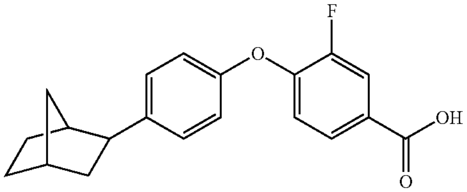

6-(4-((1S,4R)-bicyclo[2.2.1]heptan-2-yl)phenoxy)-3-fluorobenzoic acid

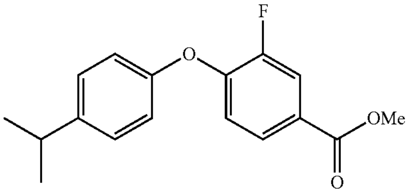

methyl 3-fluoro-4-(4-isopropylphenoxy)benzoate

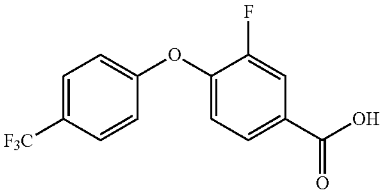

3-fluoro-4-(4-(trifluoromethyl)phenoxy)benzoic acid

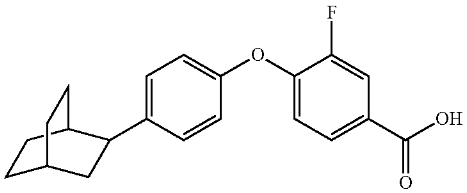

4-(4-((1s,4s)-bicyclo[2.2.2]octan-2-yl)phenoxy)-3-fluorobenzoic acid

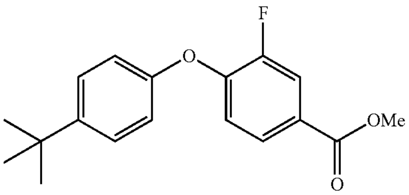

methyl 4-(4-(tert-butyl)phenoxy)-3-fluorobenzoate

-continued

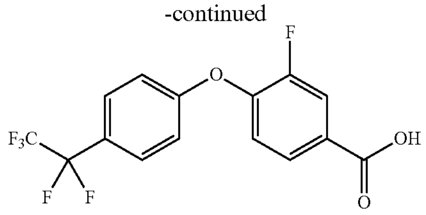

3-fluoro-4-(4-(perfluoroethyl)phenoxy)benzoic acid

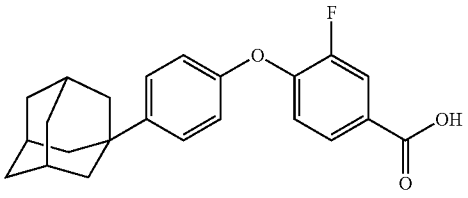

4-(4-((3r,5r,7r)-adamantan-1-yl)phenoxy)-3-fluorobenzoic acid

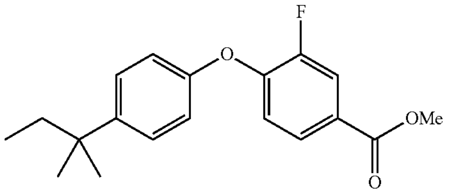

methyl 3-fluoro-4-(4-(tert-pentyl)phenoxy)benzoate

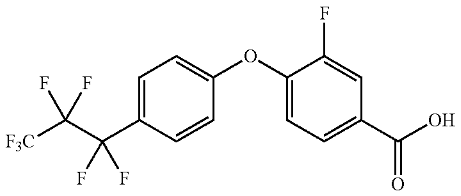

3-fluoro-4-(4-(perfluoropropyl)phenoxy)benzoic acid

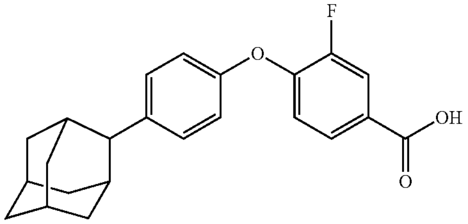

4-(4-((1r,3r,5r,7r)-adamantan-2-yl)phenoxy)-3-fluorobenzoic acid

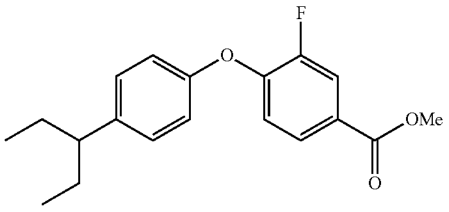

methyl 3-fluoro-4-(4-(pentan-3-yl)phenoxy)benzoate

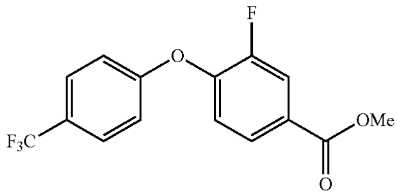

methyl 3-fluoro-4-(4-(trifluoromethyl)phenoxy)benzoate

-continued

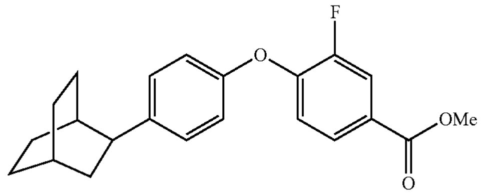

methyl 4-(4-((1s,4s)-bicyclo[2.2.2]octan-2-yl)phenoxy)-3-fluorobenzoate

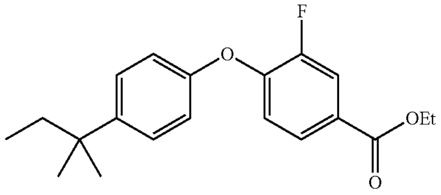

ethyl 3-fluoro-4-(4-(tert-pentyl)phenoxy)benzoate

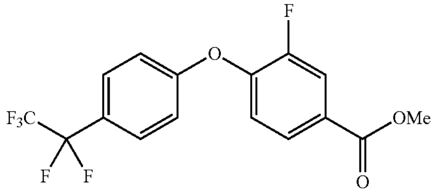

methyl 3-fluoro-4-(4-(perfluoroethyl)phenoxy)benzoate

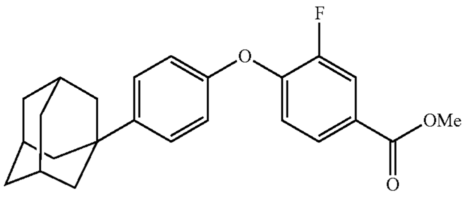

methyl 4-(4-((3r,5r,7r)-adamantan-1-yl)phenoxy)-3-fluorobenzoate

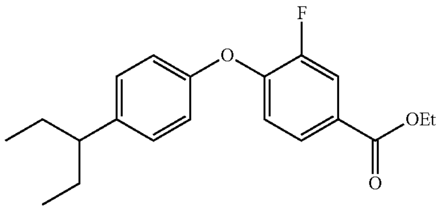

ethyl 3-fluoro-4-(4-(pentan-3-yl)phenoxy)benzoate

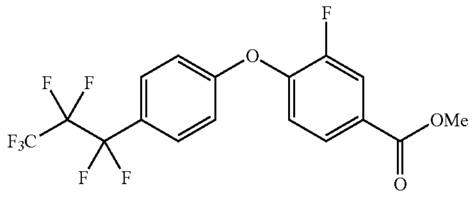

methyl 3-fluoro-4-(4-(perfluoropropyl)phenoxy)benzoate

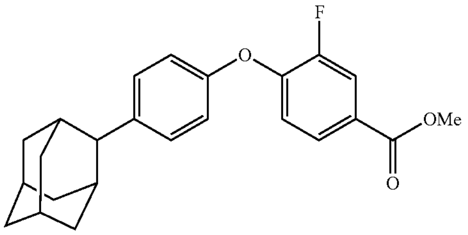

methyl 4-(4-((1r,3r,5r,7r)-adamantan-2-yl)phenoxy)-3-fluorobenzoate

-continued

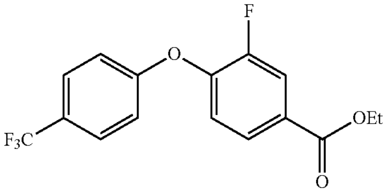

ethyl 3-fluoro-4-(4-(trifluoromethyl)phenoxy)benzoate

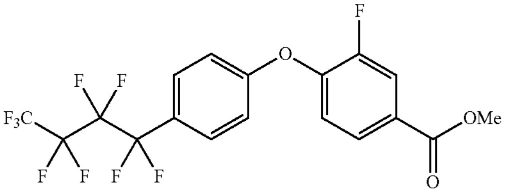

methyl 3-fluoro-4-(4-(perfluorobutyl)phenoxy)benzoate

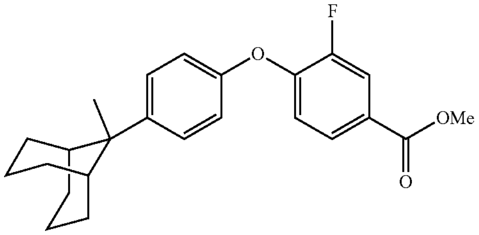

methyl 3-fluoro-4-(4-((1R,5S)-9-methylbicyclo[3.3.1]nonan-9-yl) phenoxy)benzoate

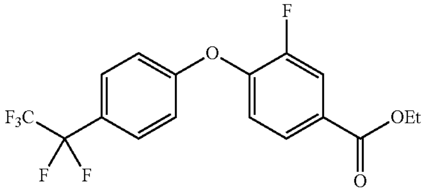

ethyl 3-fluoro-4-(4-(perfluoroethyl)phenoxy)benzoate

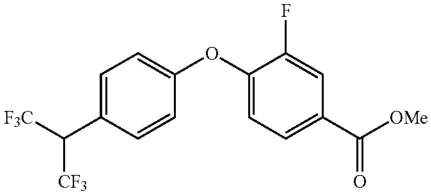

methyl 3-fluoro-4-(4-(1,1,1,3,3,3-hexafluoropropan-2-yl)phenoxy)benzoate

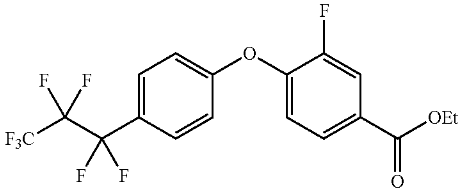

ethyl 3-fluoro-4-(4-(perfluoropropyl)phenoxy)benzoate

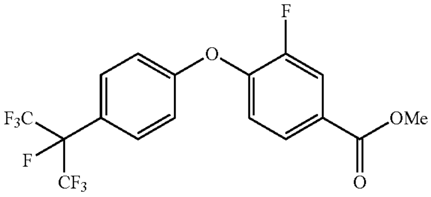

methyl 3-fluoro-4-(4-(perfluoropropan-2-yl)phenoxy)benzoate

-continued

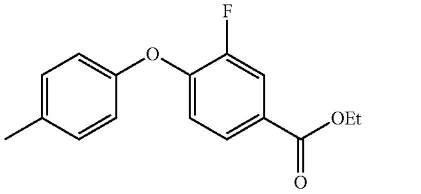

ethyl 3-fluoro-4-(p-tolyloxy)benzoate

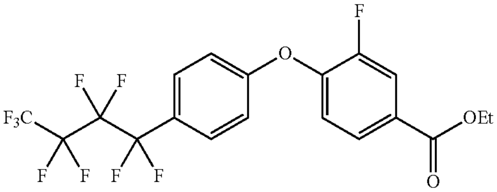

ethyl 3-fluoro-4-(4-(perfluorobutyl)phenoxy)benzoate

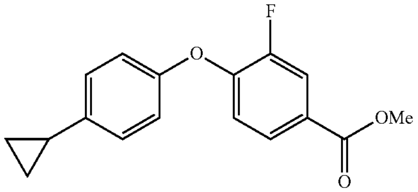

methyl 4-(4-cyclopropylphenoxy)-3-fluorobenzoate

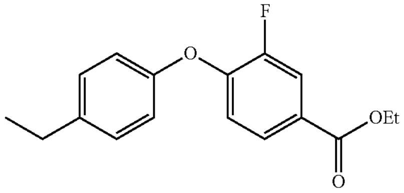

ethyl 4-(4-ethylphenoxy)-3-fluorobenzoate

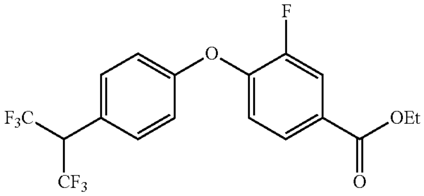

ethyl 3-fluoro-4-(4-(1,1,1,3,3,3-hexafluoropropan-2-yl)phenoxy) benzoate

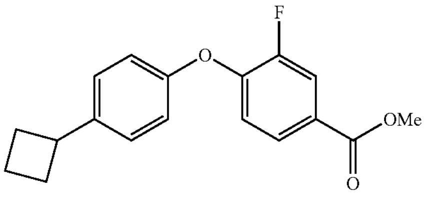

methyl 4-(4-cyclobutylphenoxy)-3-fluorobenzoate

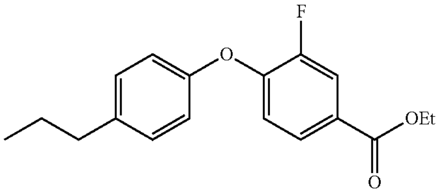

ethyl 3-fluoro-4-(4-propylphenoxy)benzoate

-continued

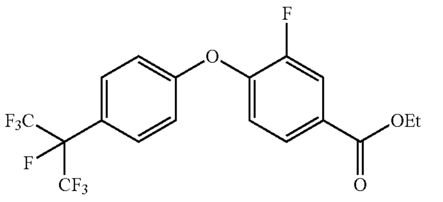

ethyl 3-fluoro-4-(4-(perfluoropropan-2-yl)phenoxy)benzoate

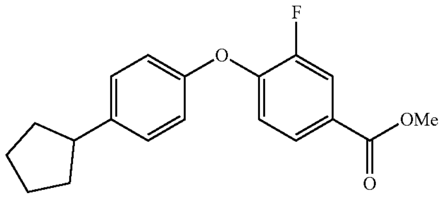

methyl 4-(4-cyclopentylphenoxy)-3-fluorobenzoate

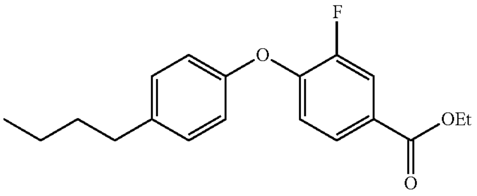

ethyl 4-(4-butylphenoxy)-3-fluorobenzoate

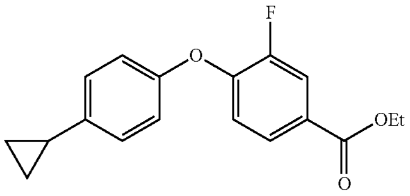

ethyl 4-(4-cyclopropylphenoxy)-3-fluorobenzoate

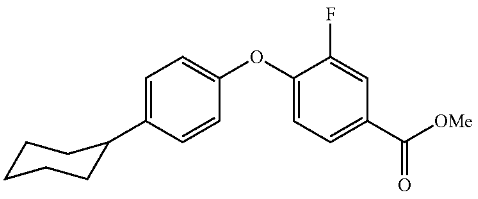

methyl 4-(4-cyclohexylphenoxy)-3-fluorobenzoate

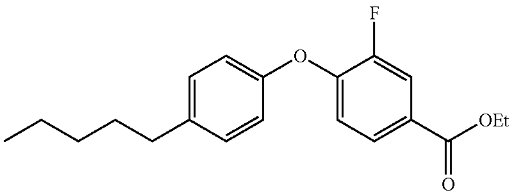

ethyl 3-fluoro-4-(4-pentylphenoxy)benzoate

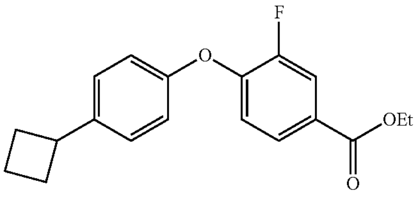

ethyl 4-(4-cyclobutylphenoxy)-3-fluorobenzoate

-continued

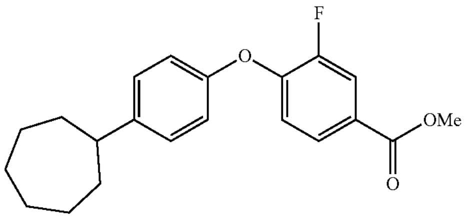

methyl 4-(4-cycloheptylphenoxy)-3-fluorobenzoate

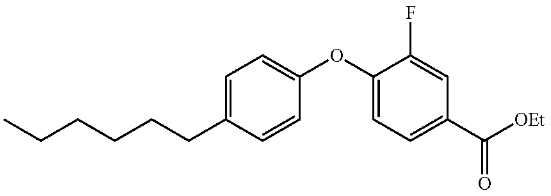

ethyl 3-fluoro-4-(4-hexylphenoxy)benzoate

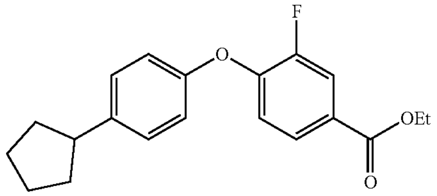

ethyl 4-(4-cyclopentylphenoxy)-3-fluorobenzoate

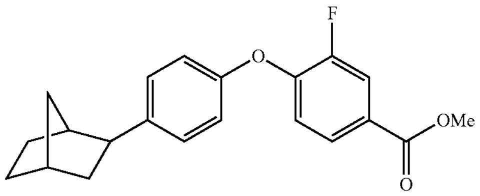

methyl 4-(4-((1S,4R)-bicyclo[2.2.1]heptan-2-yl)phenoxy)-3-fluorobenzoate

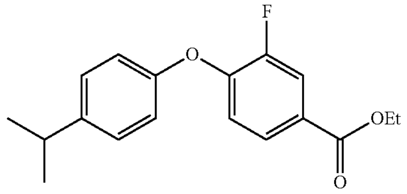

ethyl 3-fluoro-4-(4-isopropylphenoxy)benzoate

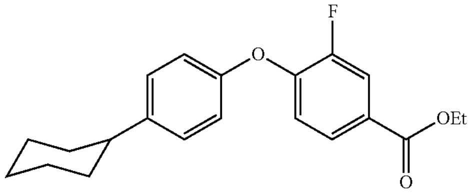

ethyl 4-(4-cyclohexylphenoxy)-3-fluorobenzoate

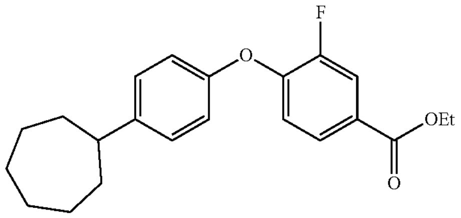

ethyl 4-(4-cycloheptylphenoxy)-3-fluorobenzoate

-continued

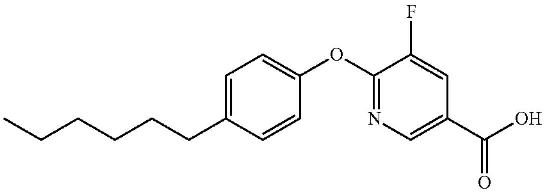
5-fluoro-6-(4-hexylphenoxy)nicotinic acid

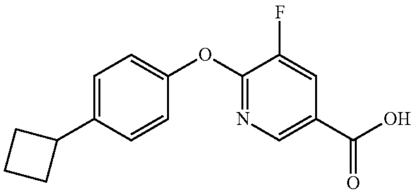
6-(4-cyclobutylphenoxy)-5-fluoronicotinic acid

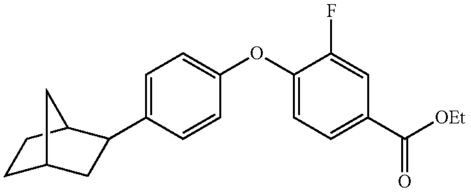
ethyl 4-(4-((1S,4R)-bicyclo[2.2.1]heptan-2-yl)phenoxy)-3-fluorobenzoate

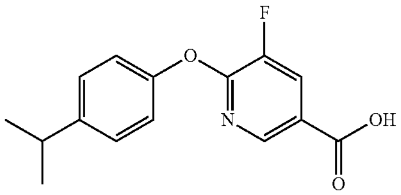
5-fluoro-6-(4-isopropylphenoxy)nicotinic acid

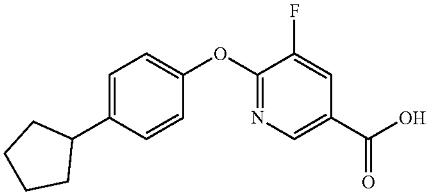
6-(4-cyclopentylphenoxy)-5-fluoronicotinic acid

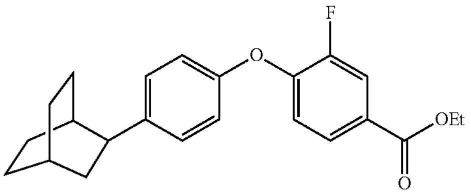
ethyl 4-(4-((1s,4s)-bicyclo[2.2.2]octan-2-yl)phenoxy)-3-fluorobenzoate

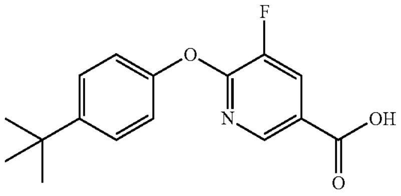
6-(4-(tert-butyl)phenoxy)-5-fluoronicotinic acid

-continued

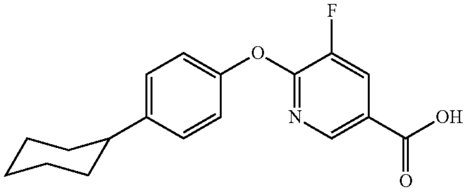
6-(4-cyclohexylphenoxy)-5-fluoronicotinic acid

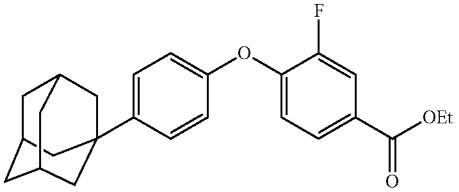
ethyl 4-(4-((3r,5r,7r)-adamantan-1-yl)phenoxy)-3-fluorobenzoate

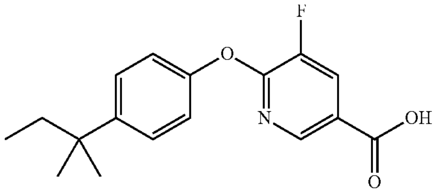
5-fluoro-6-(4-(tert-pentyl)phenoxy)nicotinic acid

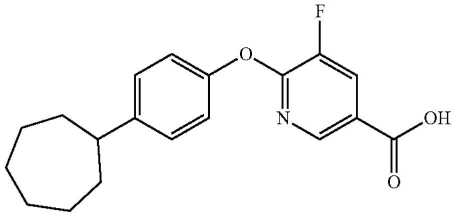
6-(4-cycloheptylphenoxy)-5-fluoronicotinic acid

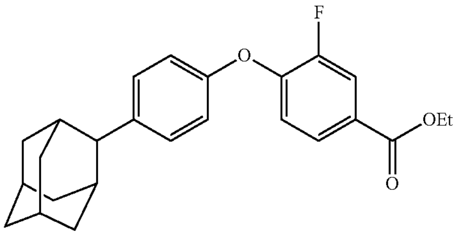
ethyl 4-(4-((1r,3r,5r,7r)-adamantan-2-yl)phenoxy)-3-fluorobenzoate

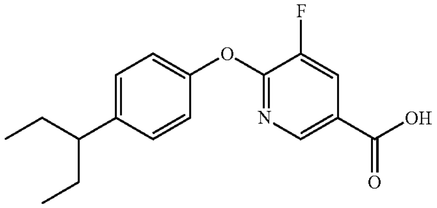
5-fluoro-6-(4-(pentan-3-yl)phenoxy)nicotinic acid

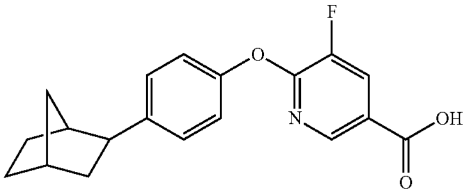
6-(4-((1S,4R)-bicyclo[2.2.1]heptan-2-yl)phenoxy)-5-fluoronicotinic acid -continued

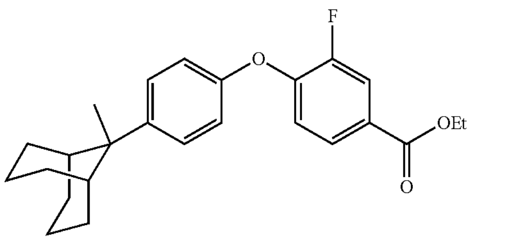

ethyl 3-fluoro-4-(4-((1R,5S)-9-methylbicyclo[3.3.1]nonan-9-yl)phenoxy)benzoate

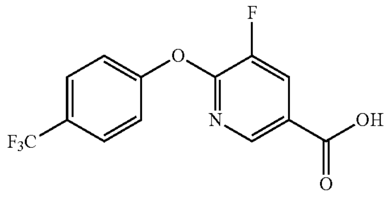

5-fluoro-6-(4-(trifluoromethyl)phenoxy)nicotinic acid

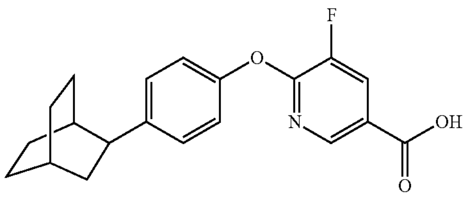

6-(4-((1s,4s)-bicyclo[2.2.2]octan-2-yl)phenoxy)-5-fluoronicotinic acid

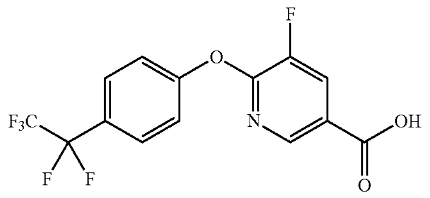

5-fluoro-6-(4-(perfluoroethyl)phenoxy)nicotinic acid

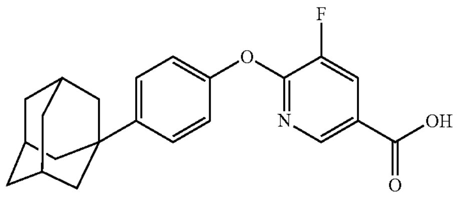

6-(4-((3r,5r,7r)-adamantan-1-yl)phenoxy)-5-fluoronicotinic acid

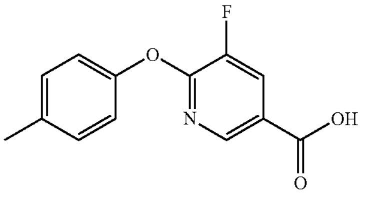

5-fluoro-6-(p-tolyloxy)nicotinic acid

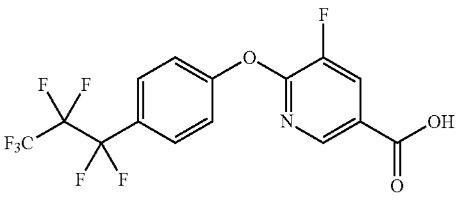

5-fluoro-6-(4-(perfluoropropyl)phenoxy)nicotinic acid

-continued

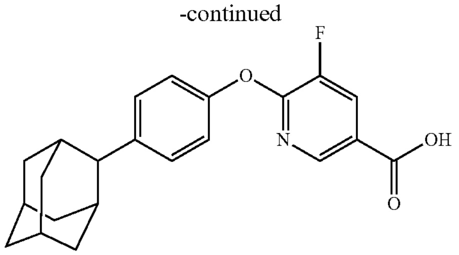

6-(4-((1r,3r,5r,7r)-adamantan-2-yl)phenoxy)-5-fluoronicotinic acid

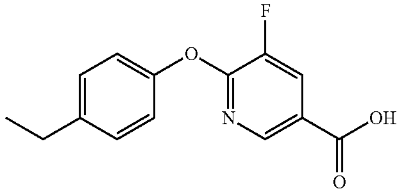

6-(4-ethylphenoxy)-5-fluoronicotinic acid

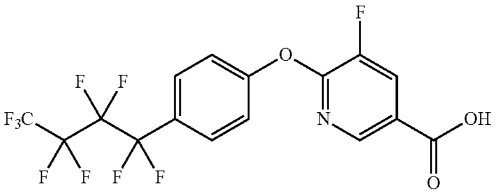

5-fluoro-6-(4-(perfluorobutyl)phenoxy)nicotinic acid

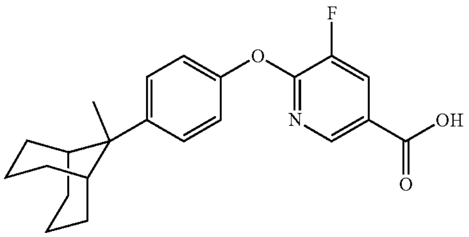

5-fluoro-6-(4-((1R,5S)-9-methylbicyclo[3.3.1]nonan-9-yl)phenoxy)nicotinic acid

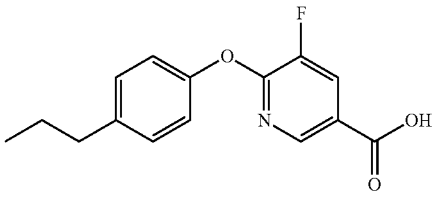

5-fluoro-6-(4-propylphenoxy)nicotinic acid

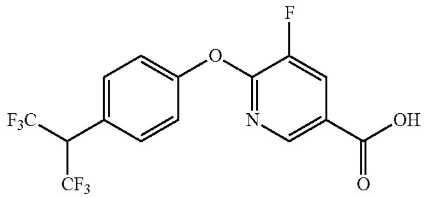

5-fluoro-6-(4-(1,1,1,3,3,3-hexafluoropropan-2-yl)phenoxy)nicotinic acid

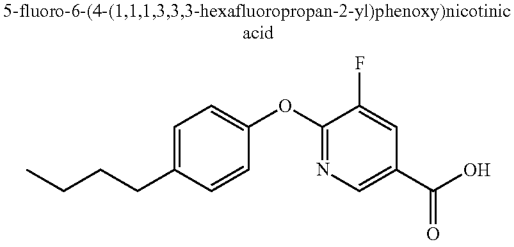

6-(4-butylphenoxy)-5-fluoronicotinic acid

-continued

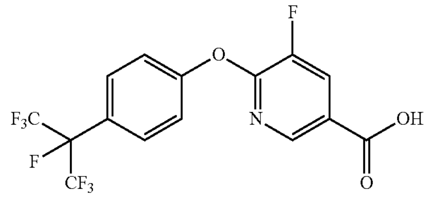

5-fluoro-6-(4-(perfluoropropan-2-yl)phenoxy)nicotinic acid

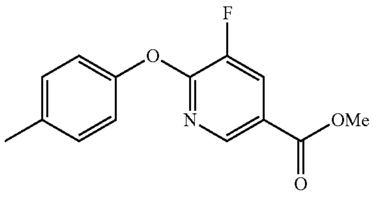

methyl 5-fluoro-6-(p-tolyloxy)nicotinate

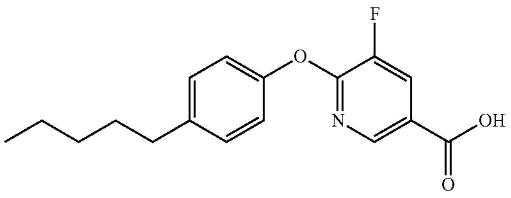

5-fluoro-6-(4-pentylphenoxy)nicotinic acid

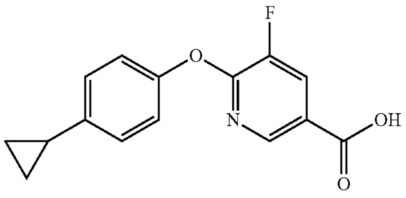

6-(4-cyclopropylphenoxy)-5-fluoronicotinic acid

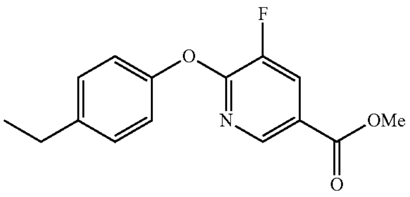

methyl 6-(4-ethylphenoxy)-5-fluoronicotinate

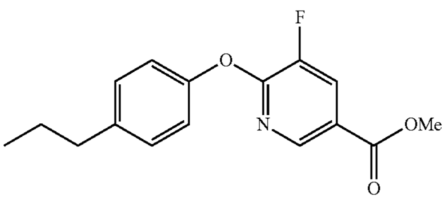

methyl 5-fluoro-6-(4-propylphenoxy)nicotinate

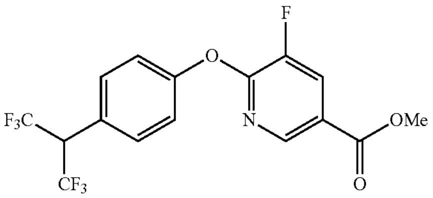

methyl 5-fluoro-6-(4-(1,1,1,3,3,3-hexafluoropropan-2-yl)phenoxy) nicotinate

-continued

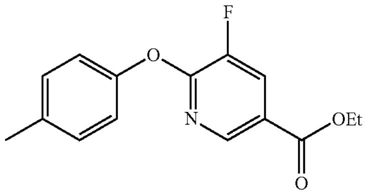

ethyl 5-fluoro-6-(p-tolyloxy)nicotinate

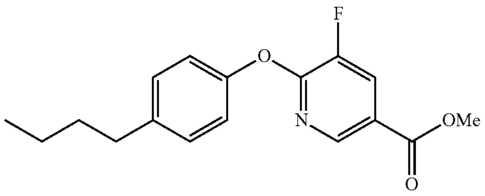

methyl 6-(4-butylphenoxy)-5-fluoronicotinate

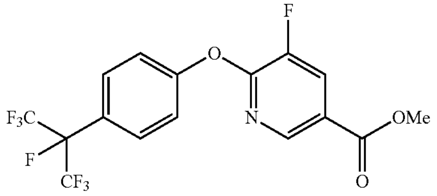

methyl 5-fluoro-6-(4-(perfluoropropan-2-yl)phenoxy)nicotinate

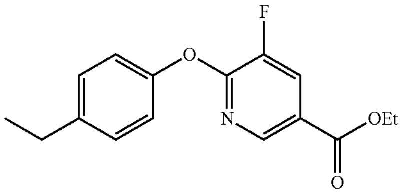

ethyl 6-(4-ethylphenoxy)-5-fluoronicotinate

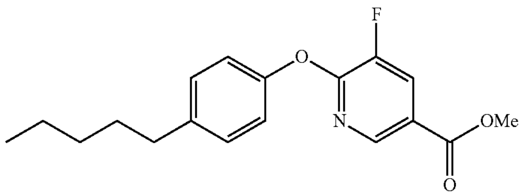

methyl 5-fluoro-6-(4-pentylphenoxy)nicotinate

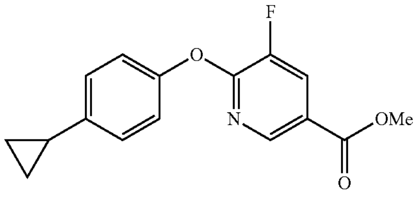

methyl 6-(4-cyclopropylphenoxy)-5-fluoronicotinate

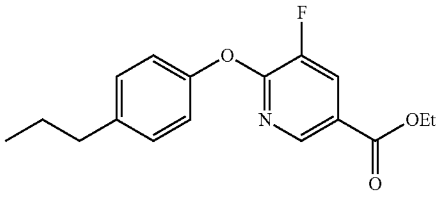

ethyl 5-fluoro-6-(4-propylphenoxy)nicotinate

-continued

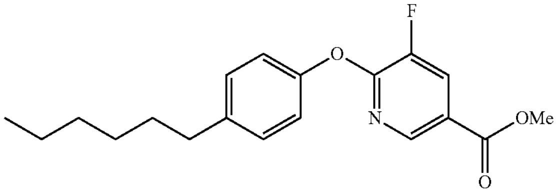

methyl 5-fluoro-6-(4-hexylphenoxy)nicotinate

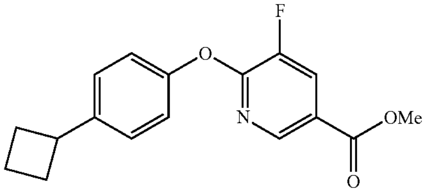

methyl 6-(4-cyclobutylphenoxy)-5-fluoronicotinate

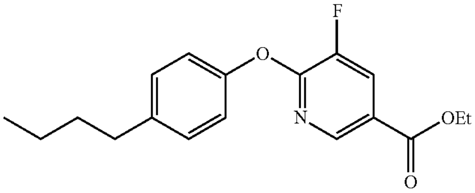

ethyl 6-(4-butylphenoxy)-5-fluoronicotinate

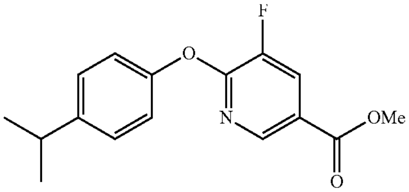

methyl 5-fluoro-6-(4-isopropylphenoxy)nicotinate

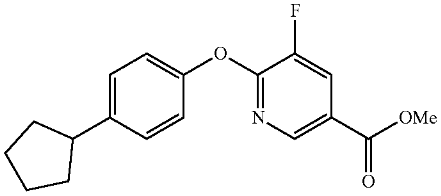

methyl 6-(4-cyclopentylphenoxy)-5-fluoronicotinate

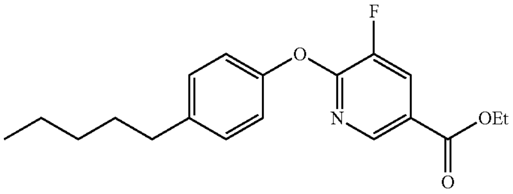

ethyl 5-fluoro-6-(4-pentylphenoxy)nicotinate

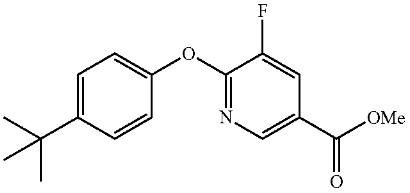

methyl 6-(4-(tert-butyl)phenoxy)-5-fluoronicotinate

-continued

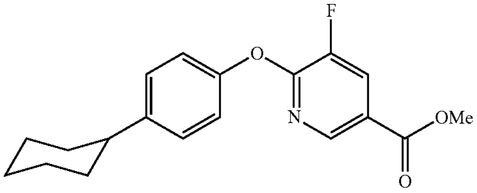

methyl 6-(4-cyclohexylphenoxy)-5-fluoronicotinate

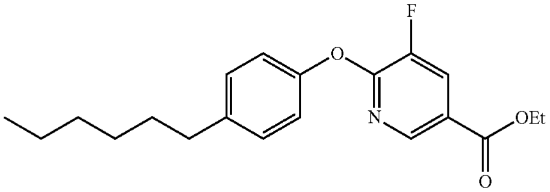

ethyl 5-fluoro-6-(4-hexylphenoxy)nicotinate

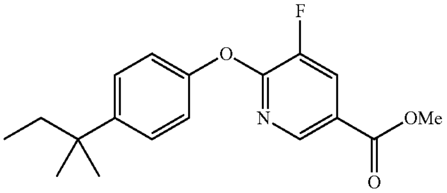

methyl 5-fluoro-6-(4-(tert-pentyl)phenoxy)nicotinate

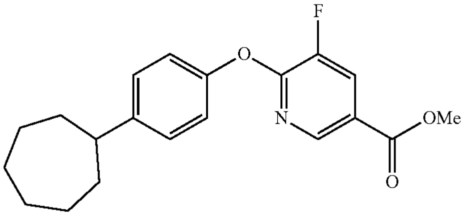

methyl 6-(4-cycloheptylphenoxy)-5-fluoronicotinate

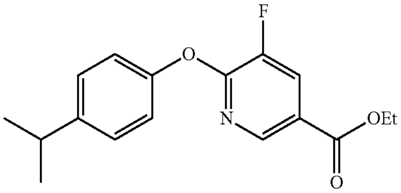

ethyl 5-fluoro-6-(4-isopropylphenoxy)nicotinate

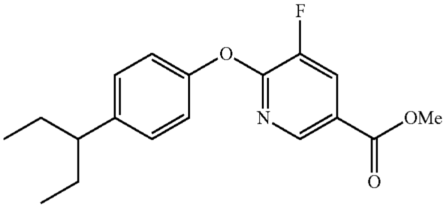

methyl 5-fluoro-6-(4-(pentan-3-yl)phenoxy)nicotinate

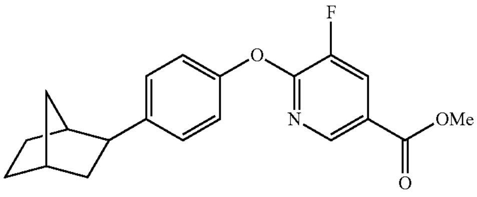

methyl 6-(4-((1S,4R)-bicyclo[2.2.1]heptan-2-yl)phenoxy)-5-fluoronicotinate

-continued

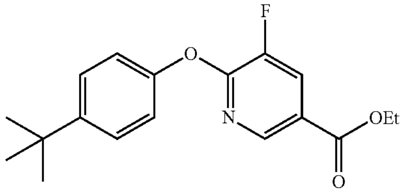

ethyl 6-(4-(tert-butyl)phenoxy)-5-fluoronicotinate

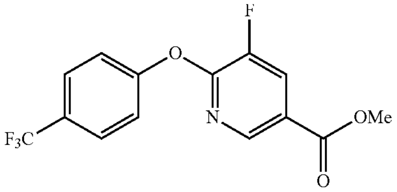

methyl 5-fluoro-6-(4-(trifluoromethyl)phenoxy)nicotinate

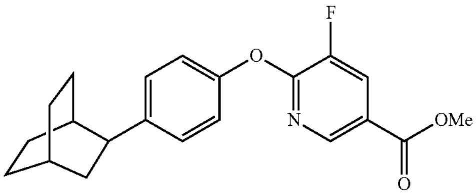

methyl 6-(4-((1s,4s)-bicyclo[2.2.2]octan-2-yl)phenoxy)-5-fluoronicotinate

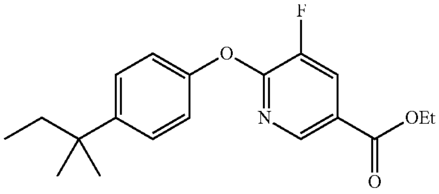

ethyl 5-fluoro-6-(4-(tert-pentyl)phenoxy)nicotinate

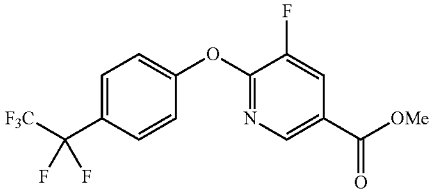

methyl 5-fluoro-6-(4-(perfluoroethyl)phenoxy)nicotinate

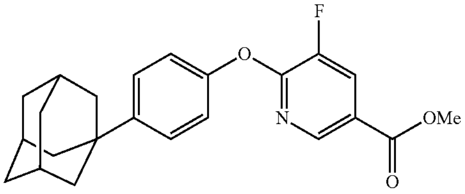

methyl 6-(4-((3r,5r,7r)-adamantan-1-yl)phenoxy)-5-fluoronicotinate

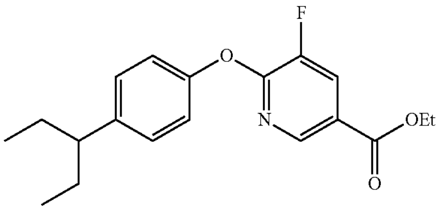

ethyl 5-fluoro-6-(4-(pentan-3-yl)phenoxy)nicotinate

-continued

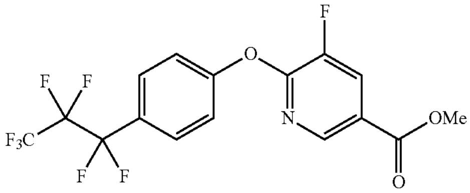

methyl 5-fluoro-6-(4-(perfluoropropyl)phenoxy)nicotinate

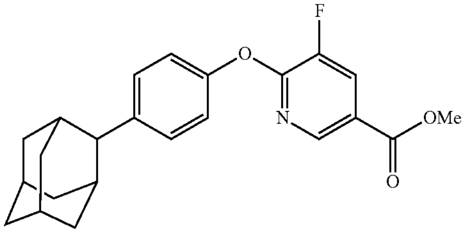

methyl 6-(4-((1r,3r,5r,7r)-adamantan-2-yl)phenoxy)-5-fluoronicotinate

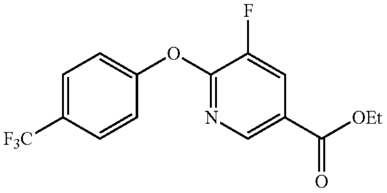

ethyl 5-fluoro-6-(4-(trifluoromethyl)phenoxy)nicotinate

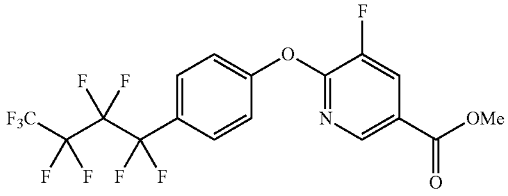

methyl 5-fluoro-6-(4-(perfluorobutyl)phenoxy)nicotinate

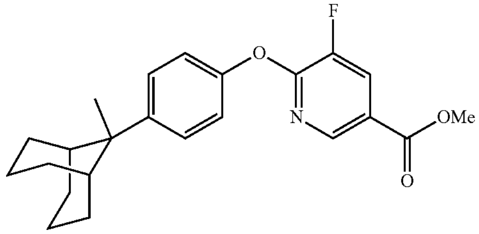

methyl 5-fluoro-6-(4-((1R,5S)-9-methylbicyclo[3.3.1]nonan-9-yl)phenoxy)nicotinate

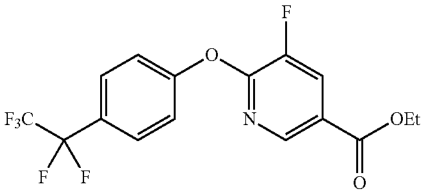

ethyl 5-fluoro-6-(4-(perfluoroethyl)phenoxy)nicotinate

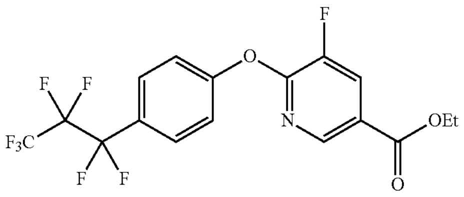

ethyl 5-fluoro-6-(4-(perfluoropropyl)phenoxy)nicotinate

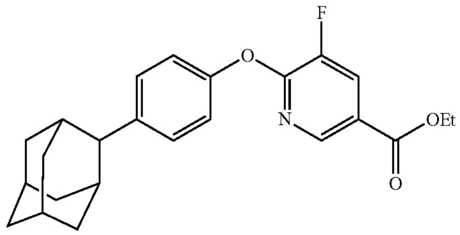

ethyl 6-(4-((1r,3r,5r,7r)-adamantan-2-yl)phenoxy)-5-fluoronicotinate

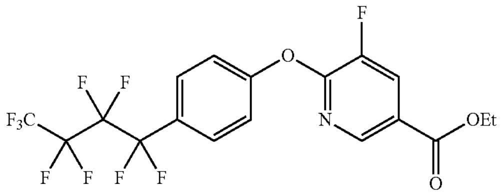

ethyl 5-fluoro-6-(4-(perfluorobutyl)phenoxy)nicotinate

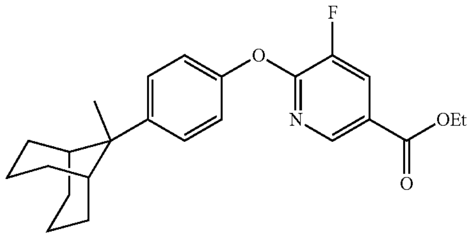

ethyl 5-fluoro-6-(4-((1R,5S)-9-methylbicyclo[3.3.1]nonan-9-yl)phenoxy) nicotinate

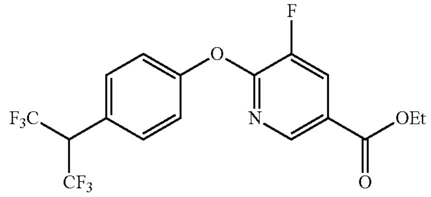

ethyl 5-fluoro-6-(4-(1,1,1,3,3,3-hexafluoropropan-2-yl)phenoxy)nicotinate

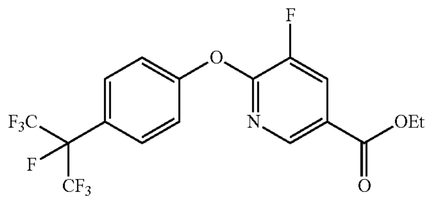

ethyl 5-fluoro-6-(4-(perfluoropropan-2-yl)phenoxy)nicotinate

-continued

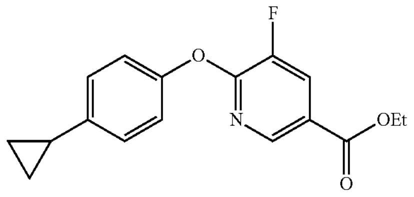

ethyl 6-(4-cyclopropylphenoxy)-5-fluoronicotinate

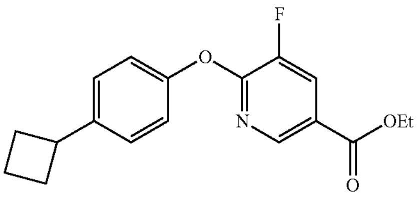

ethyl 6-(4-cyclobutylphenoxy)-5-fluoronicotinate

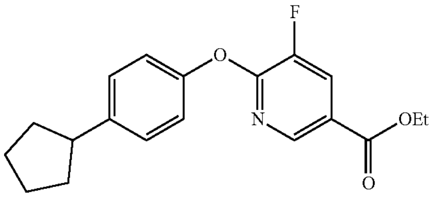

ethyl 6-(4-cyclopentylphenoxy)-5-fluoronicotinate

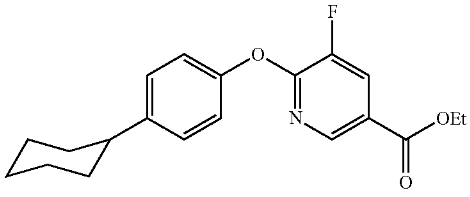

ethyl 6-(4-cyclohexylphenoxy)-5-fluoronicotinate

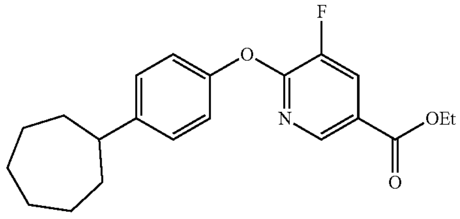

ethyl 6-(4-cycloheptylphenoxy)-5-fluoronicotinate

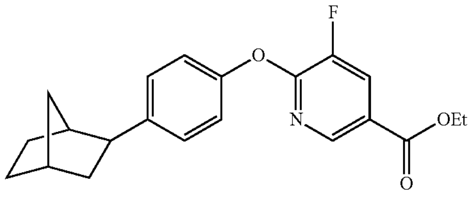

ethyl 6-(4-((1S,4R)-bicyclo[2.2.1]heptan-2-yl)phenoxy)-5-fluoronicotinate

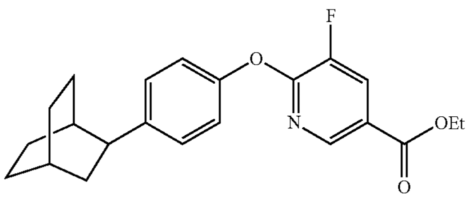

ethyl 6-(4-((1s,4s)-bicyclo[2.2.2]octan-2-yl)phenoxy)-5-fluoronicotinate

-continued

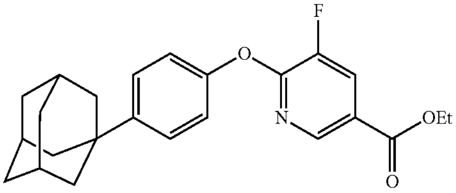

ethyl 6-(4-((3r,5r,7r)-adamantan-1-yl)phenoxy)-5-fluoronicotinate

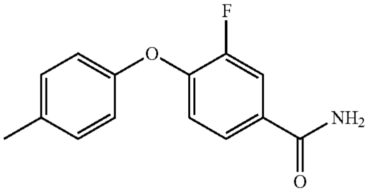

3-fluoro-4-(p-tolyloxy)benzamide

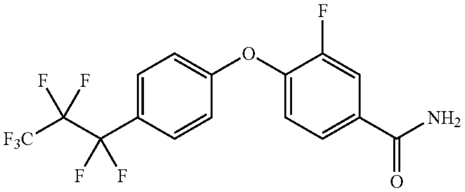

3-fluoro-4-(4-(perfluoropropyl)phenoxy)benzamide

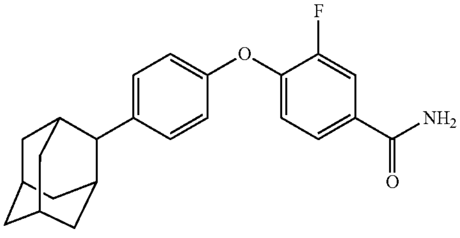

4-(4-((1r,3r,5r,7r)-adamantan-2-yl)phenoxy)-3-fluorobenzamide

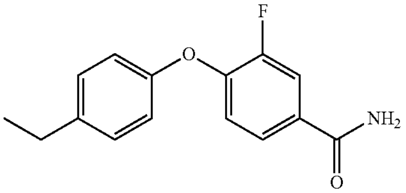

4-(4-ethylphenoxy)-3-fluorobenzamide

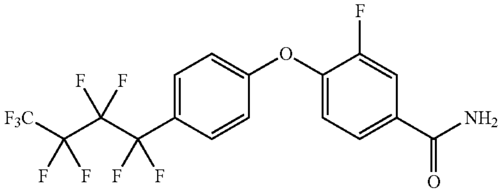

3-fluoro-4-(4-(perfluorobutyl)phenoxy)benzamide

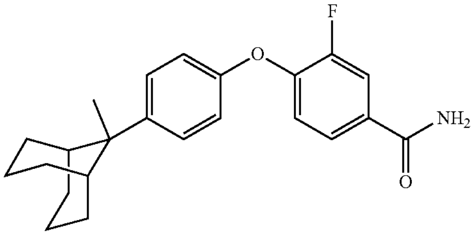

3-fluoro-4-(4-((1R,5S)-9-methylbicyclo[3.3.1]nonan-9-yl)phenoxy) benzamide

-continued

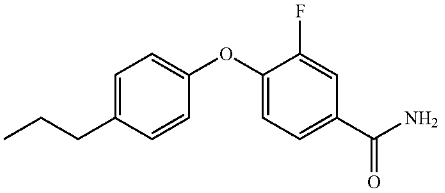

3-fluoro-4-(4-(propylphenoxy)benzamide

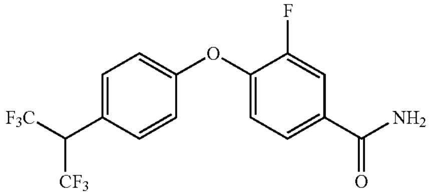

3-fluoro-4-(4-(1,1,1,3,3,3-hexafluoropropan-2-yl)phenoxy)benzamide

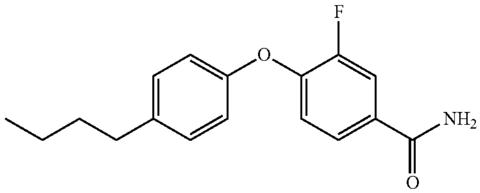

4-(4-butylphenoxy)-3-fluorobenzamide

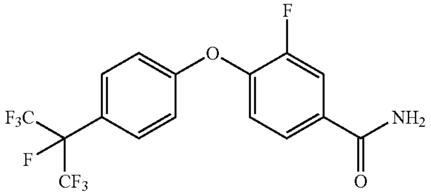

3-fluoro-4-(4-(perfluoropropan-2-yl)phenoxy)benzamide

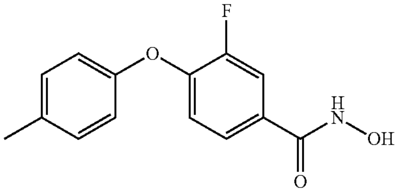

3-fluoro-N-hydroxy-4-(p-tolyloxy)benzamide

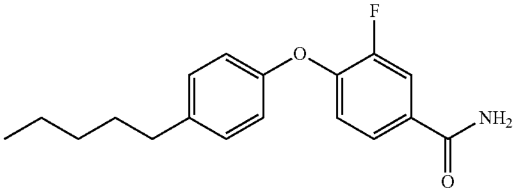

3-fluoro-4-(4-pentylphenoxy)benzamide

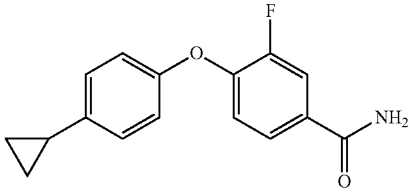

4-(4-cyclopropylphenoxy)-3-fluorobenzamide

-continued

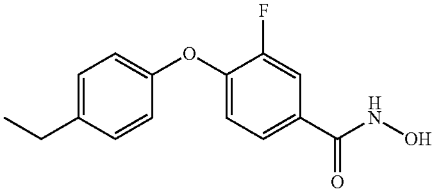

4-(4-ethylphenoxy)-3-fluoro-N-hydroxybenzamide

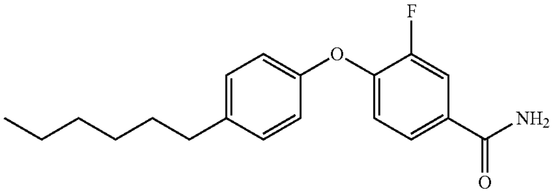

3-fluoro-4-(4-hexylphenoxy)benzamide

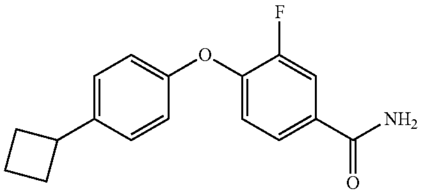

4-(4-cyclobutylphenoxy)-3-fluorobenzamide

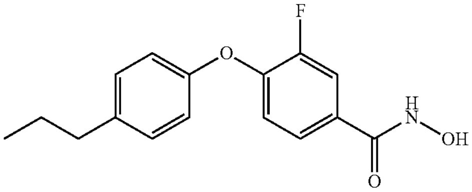

3-fluoro-N-hydroxy-4-(4-propylphenoxy)benzamide

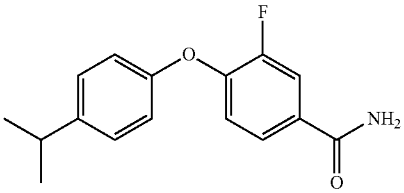

3-fluoro-4-(4-isopropylphenoxy)benzamide

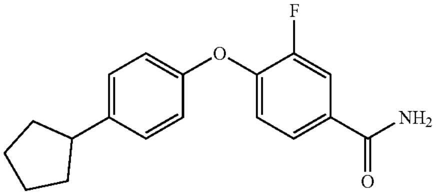

4-(4-cyclopentylphenoxy)-3-fluorobenzamide

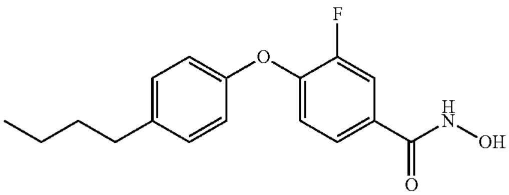

4-(4-butylphenoxy)-3-fluoro-N-hydroxybenzamide

-continued

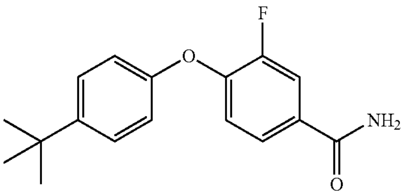

4-(4-(tert-butyl)phenoxy)-3-fluorobenzamide

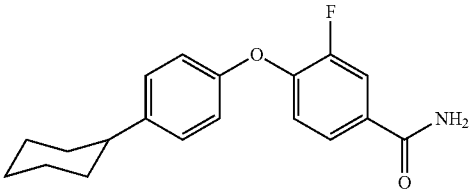

4-(4-cyclohexylphenoxy)-3-fluorobenzamide

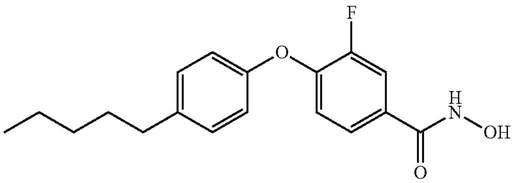

3-fluoro-N-hydroxy-4-(4-pentylphenoxy)benzamide

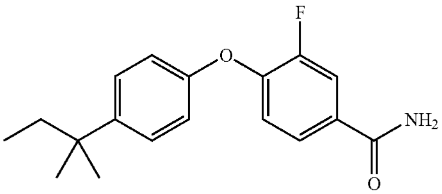

3-fluoro-4-(4-(tert-pentyl)phenoxy)benzamide

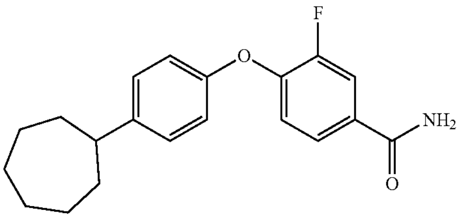

4-(4-cycloheptylphenoxy)-3-fluorobenzamide

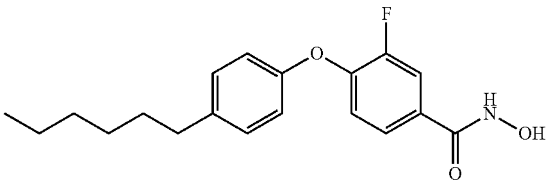

3-fluoro-4-(4-hexylphenoxy)-N-hydroxybenzamide

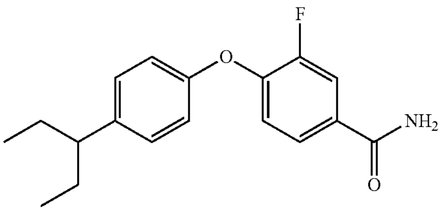

3-fluoro-4-(4-pentan-3-yl)phenoxy)benzamide

-continued

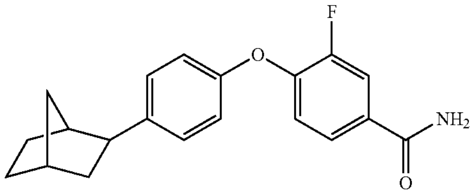

4-(4-((1S,4R)-bicyclo[2.2.1]heptan-2-yl)phenoxy)-3-fluorobenzamide

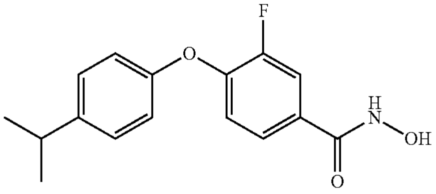

3-fluoro-N-hydroxy-4-(4-isopropylphenoxy)benzamide

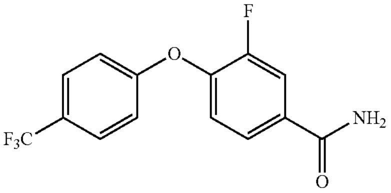

3-fluoro-4-(4-(trifluoromethyl)phenoxy)benzamide

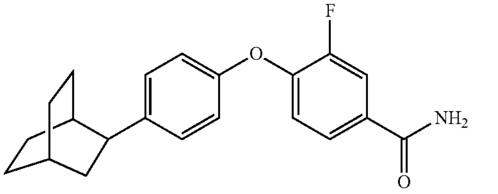

4-(4-((1s,4s)-bicyclo[2.2.2]octan-2-yl)phenoxy)-3-fluorobenzamide

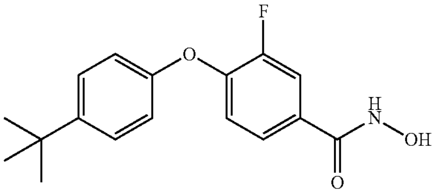

4-(4-(tert-butyl)phenoxy)-3-fluoro-N-hydroxybenzamide

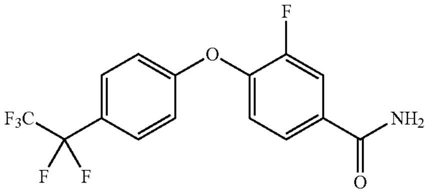

3-fluoro-4-(4-(perfluoroethyl)phenoxy)benzamide

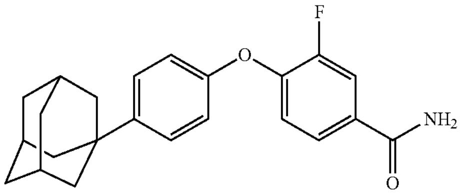

4-(4-((3r,5r,7r)-adamantan-1-yl)phenoxy)-3-fluorobenzamide

-continued

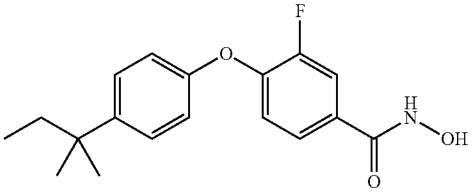

3-fluoro-N-hydroxy-4-(4-(tert-pentyl)phenoxy)benzamide

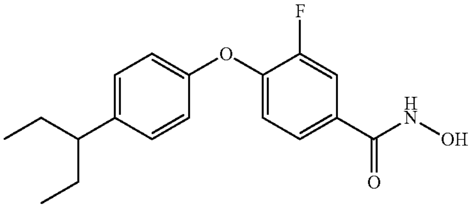

3-fluoro-N-hydroxy-4-(4-(pentan-3-yl)phenoxy)benzamide

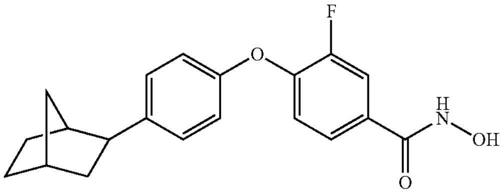

4-(4-((1S,4R)-bicyclo[2.2.1]heptan-2-yl)phenoxy)-3-fluoro-N-hydroxybenzamide

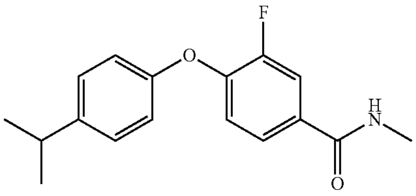

3-fluoro-4-(4-isopropylphenoxy)-N-methylbenzamide

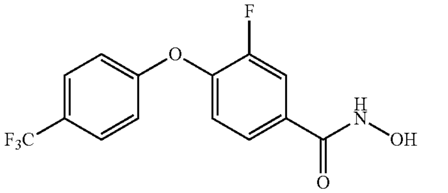

3-fluoro-N-hydroxy-4-(4-(trifluoromethyl)phenoxy)benzamide

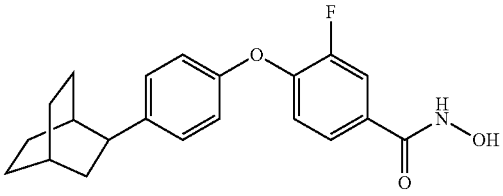

4-(4-((1s,4s)-bicyclo[2.2.2]octan-2-yl)phenoxy)-3-fluoro-N-hydroxybenzamide

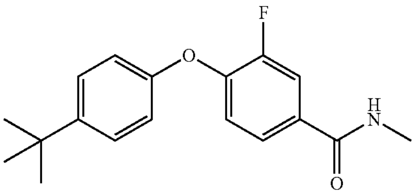

4-(4-(tert-butyl)phenoxy)-3-fluoro-N-methylbenzamide

-continued

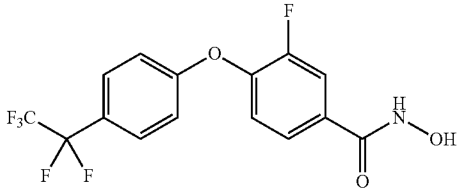

3-fluoro-N-hydroxy-4-(4-(perfluoroethyl)phenoxy)benzamide

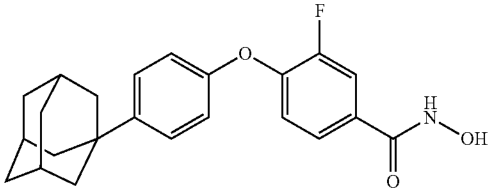

4-(4-((3r,5r,7r)-adamantan-1-yl)phenoxy)-3-fluoro-N-hydroxybenzamide

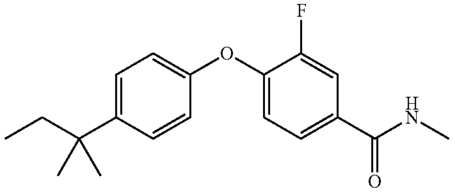

3-fluoro-N-methyl-4-(4-(tert-pentyl)phenoxy)benzamide

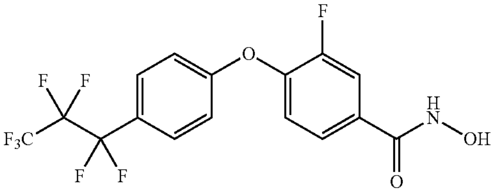

3-fluoro-N-hydroxy-4-(4-perfluoropropyl)phenoxy)benzamide

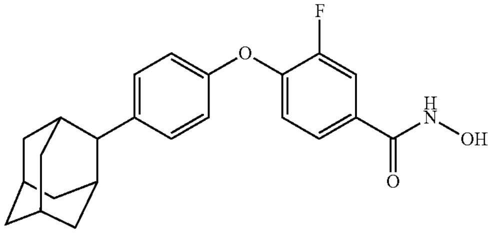

4-(4-((1r,3r,5r,7r)-adamantan-2-yl)phenoxy)-3-fluoro-N-hydroxybenzamide

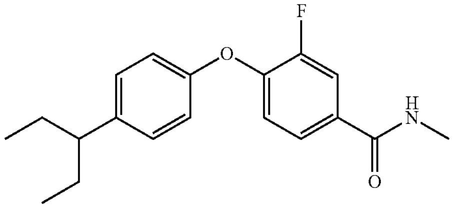

3-fluoro-N-methyl-4-(4-(pentan-3-yl)phenoxy)benzamide

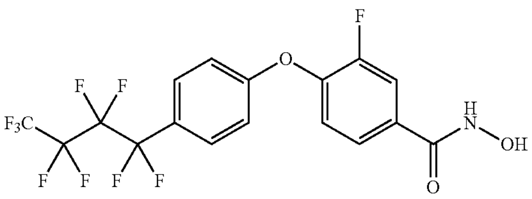

3-fluoro-N-hydroxy-4-(4-(perfluorobutyl)phenoxy)benzamide

-continued

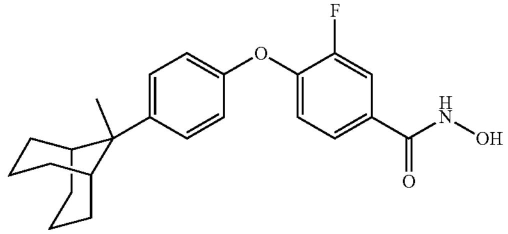

3-fluoro-N-hydroxy-4-(4-((1R,5S)-9-methylbicyclo[3.3.1]nonan-9-yl)phenoxy)benzamide

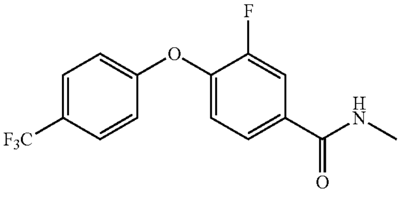

3-fluoro-N-methyl-4-(4-(trifluoromethyl)phenoxy)benzamide

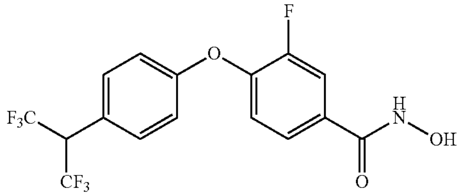

3-fluoro-4-(4-(1,1,1,3,3,3-hexafluoropropan-2-yl)phenoxy)-N-hydroxybenzamide

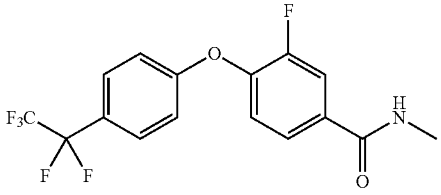

3-fluoro-N-methyl-4-(4-(perfluoroethyl)phenoxy)benzamide

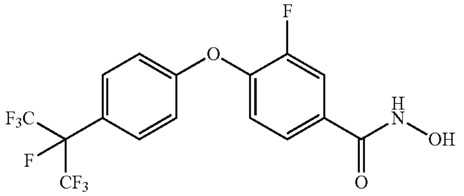

3-fluoro-N-hydroxy-4-(4-(perfluoropropan-2-yl)phenoxy)benzamide

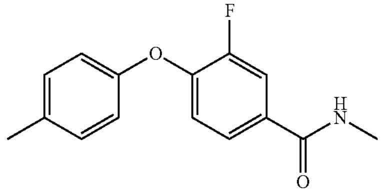

3-fluoro-N-methyl-4-(p-tolyloxy)benzamide

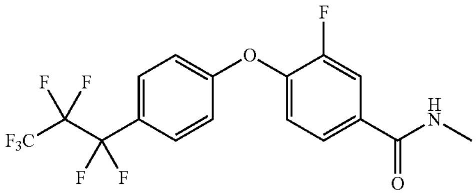

3-fluoro-N-methyl-4-(4-(perfluoropropyl)phenoxy)benzamide

-continued

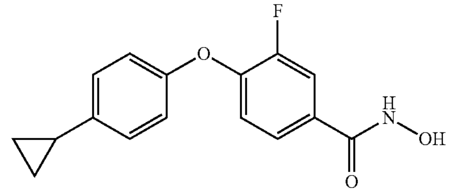

4-(4-cyclopropylphenoxy)-3-fluoro-N-hydroxybenzamide

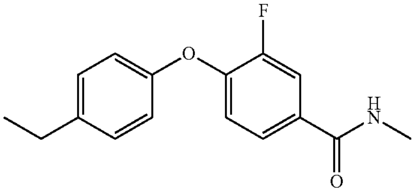

4-(4-ethylphenoxy)-3-fluoro-N-methylbenzamide

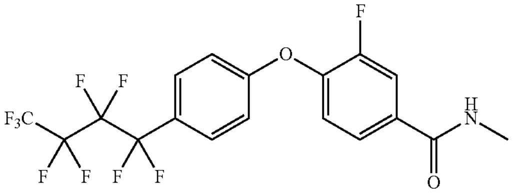

3-fluoro-N-methyl-4-(4-(perfluorobutyl)phenoxy)benzamide

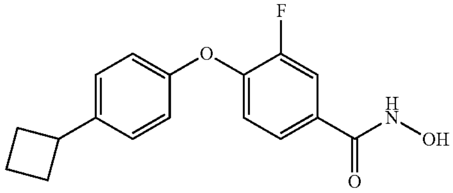

4-(4-cyclobutylphenoxy)-3-fluoro-N-hydroxybenzamide

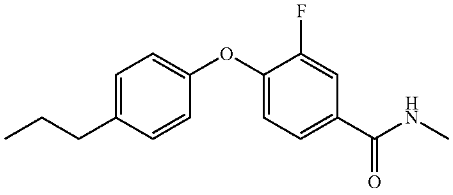

3-fluoro-N-methyl-4-(4-propylphenoxy)benzamide

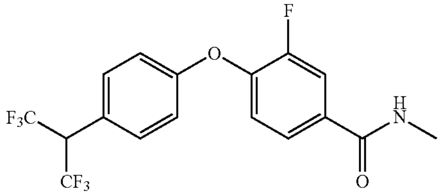

3-fluoro-4-(4-(1,1,1,3,3,3-hexafluoropropan-2-yl)phenoxy)-N-methylbenzamide

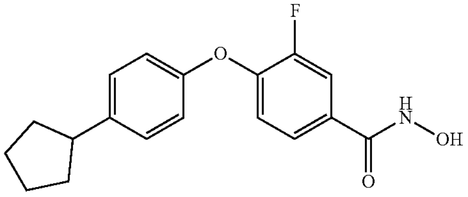

4-(4-cyclopentylphenoxy)-3-fluoro-N-hydroxybenzamide

-continued

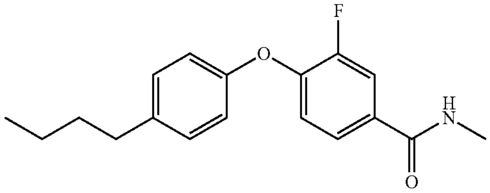

4-(4-butylphenoxy)-3-fluoro-N-methylbenzamide

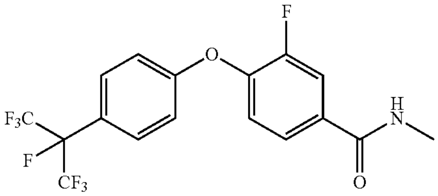

3-fluoro-N-methyl-4-(4-(perfluoropropan-2-yl)phenoxy)benzamide

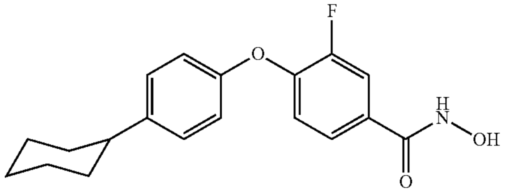

4-(4-cyclohexylphenoxy)-3-fluoro-N-hydroxybenzamide

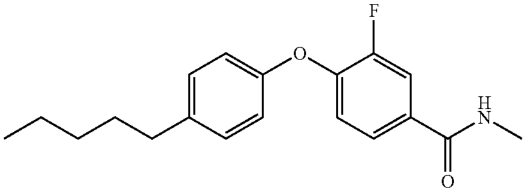

3-fluoro-N-methyl-4-(4-pentylphenoxy)benzamide

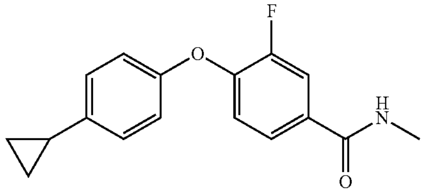

4-(4-cyclopropylphenoxy)-3-fluoro-N-methylbenzamide

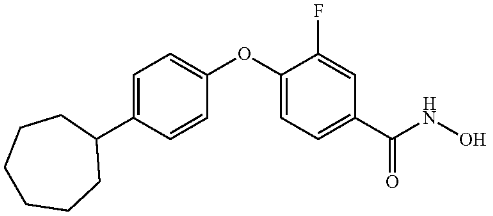

4-(4-cycloheptylphenoxy)-3-fluoro-N-hydroxybenzamide

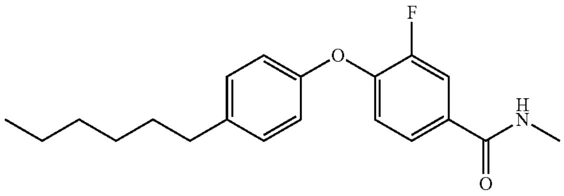

3-fluoro-4-(4-hexylphenoxy)-N-methylbenzamide

-continued

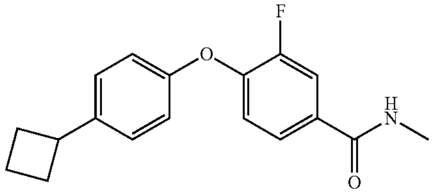

4-(4-cyclobutylphenoxy)-3-fluoro-N-methylbenzamide

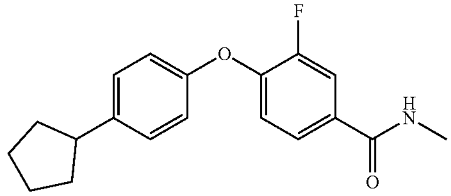

4-(4-cyclopentylphenoxy)-3-fluoro-N-methylbenzamide

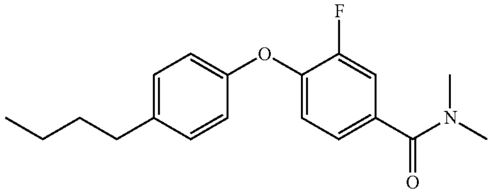

4-(4-butylphenoxy)-3-fluoro-N,N-dimethylbenzamide

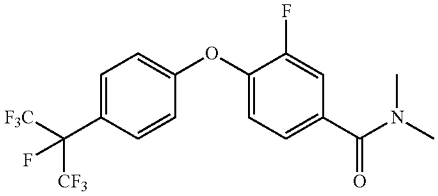

3-fluoro-N,N-dimethyl-4-(4-(perfluoropropan-2-yl)phenoxy)benzamide

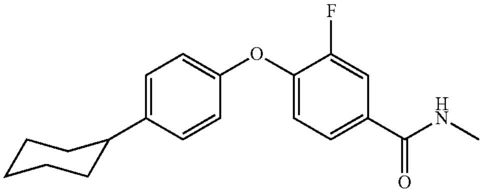

4-(4-cyclohexylphenoxy)-3-fluoro-N-methylbenzamide

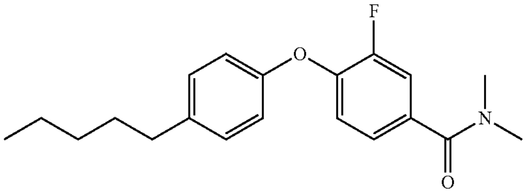

3-fluoro-N,N-dimethyl-4-(4-pentylphenoxy)benzamide

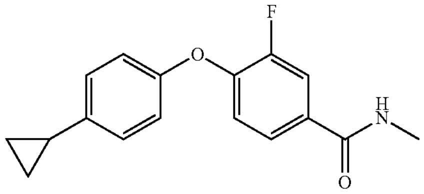

4-(4-cyclopropylphenoxy)-3-fluoro-N,N-dimethylbenzamide

-continued

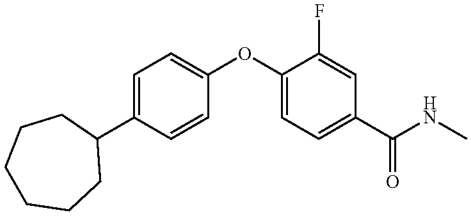

4-(4-cycloheptylphenoxy)-3-fluoro-N-methylbenzamide

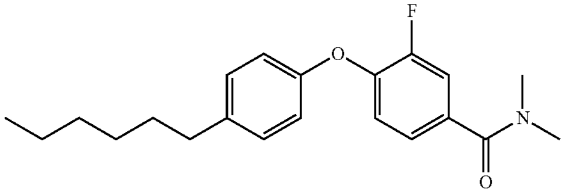

3-fluoro-4-(4-hexylphenoxy)-N,N-dimethylbenzamide

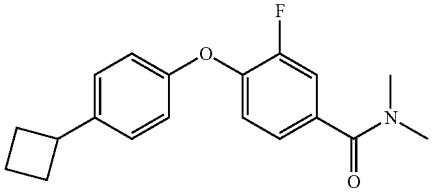

4-(4-cyclobutylphenoxy)-3-fluoro-N,N-dimethylbenzamide

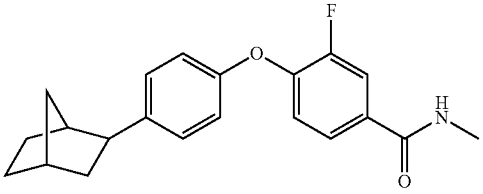

4-(4-((1S,4R)-bicyclo[2.2.1]heptan-2-yl)phenoxy)-3-fluoro-N-methylbenzamide

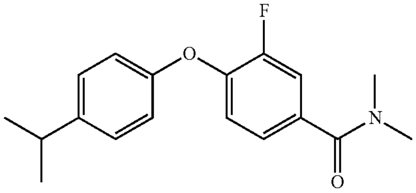

3-fluoro-4-(4-isopropylphenoxy)-N,N-dimethylbenzamide

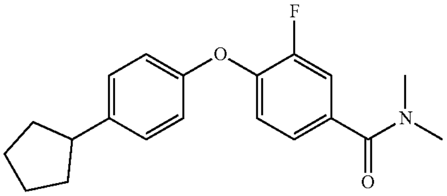

4-(4-cyclopentylphenoxy)-3-fluoro-N,N-dimethylbenzamide

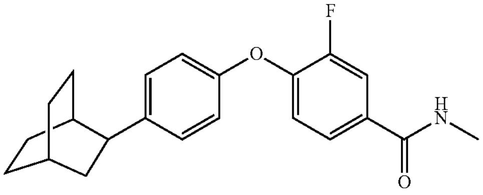

4-(4-((1s,4s)-bicyclo[2.2.2]octan-2-yl)phenoxy)-3-fluoro-N-methylbenzamide

-continued

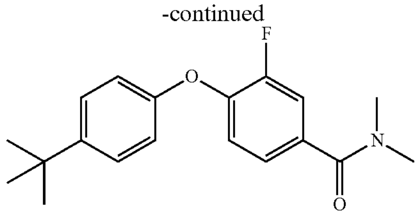

4-(4-(tert-butyl)phenoxy)-3-fluoro-N,N-dimethylbenzamide

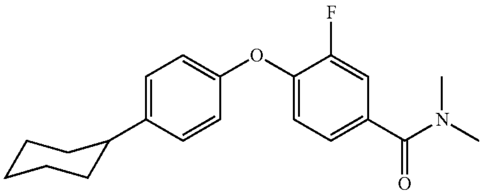

4-(4-cyclohexylphenoxy)-3-fluoro-N,N-dimethylbenzamide

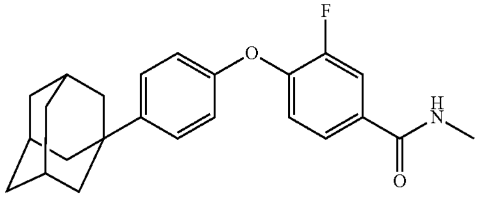

4-(4-((3r,5r,7r)-adamantan-1-yl)phenoxy)-3-fluoro-N-methylbenzamide

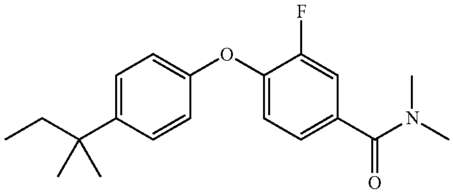

3-fluoro-N,N-dimethyl-4-(4-tert-pentyl)phenoxy)benzamide

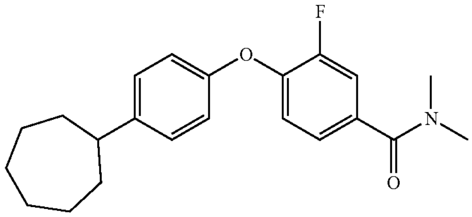

4-(4-cycloheptylphenoxy)-3-fluoro-N,N-dimethylbenzamide

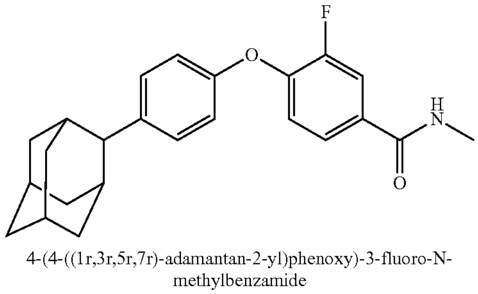

4-(4-((1r,3r,5r,7r)-adamantan-2-yl)phenoxy)-3-fluoro-N-methylbenzamide

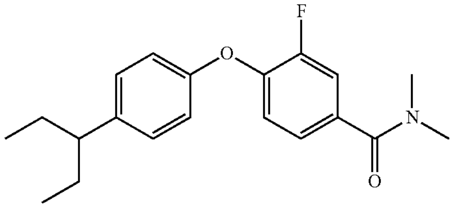

3-fluoro-N,N-dimethyl-4-(4-(pentan-3-yl)phenoxy)benzamide

-continued

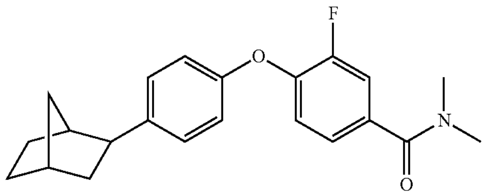

4-(4-((1S,4R)-bicyclo[2.2.1]heptan-2-yl)phenoxy)-3-fluoro-N,N-dimethylbenzamide

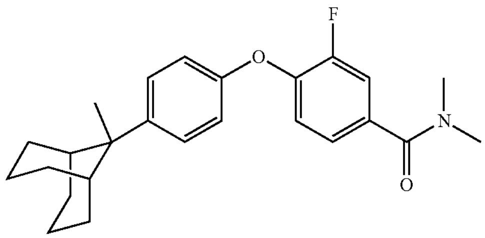

3-fluoro-N-methyl-4-((1R,5S)-9-methylbicyclo[3,3,1]nonan-9-yl)phenoxy)benzamide

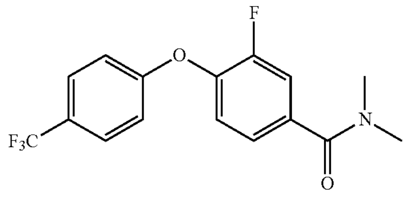

3-fluoro-N,N-dimethyl-4-(4-trifluoromethyl)phenoxy)benzamide

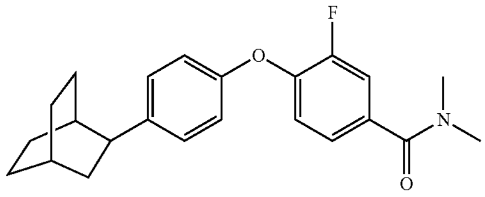

4-(4-((1s,4s)-bicyclo[2,2,2]octan-2-yl)phenoxy)-3-fluoro-N,N-dimethylbenzamide

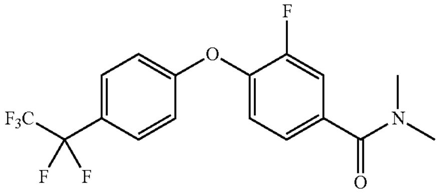

3-fluoro-N,N-dimethyl-4-(4-(perfluoroethyl)phenoxy)benzamide

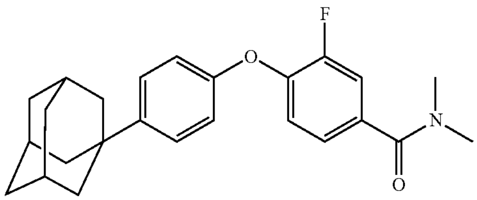

4-(4-((3r,5r,7r)-adamantan-1-yl)phenoxy)-3-fluoro-N-N-dimethylbenzamide

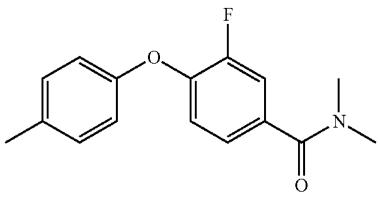

3-fluoro-N,N-dimethyl-4-(p-tolyloxy)benzamide

-continued

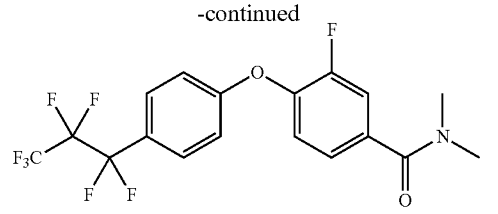

3-fluoro-N,N-dimethyl-4-(4-(perfluoropropyl)phenoxy)benzamide

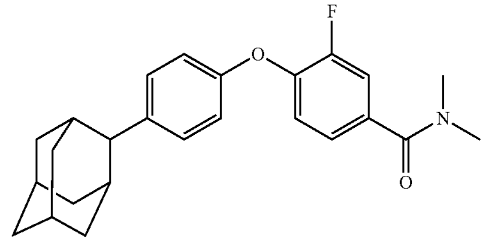

4-(4-((1r,3r,7r)-adamantan-2-yl)phenoxy)-3-fluoro-N-N-dimethylbenzamide

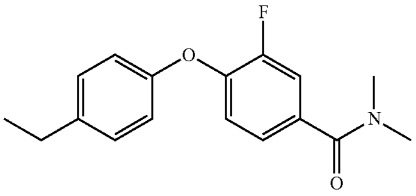

4-(4-ethylphenoxy)-3-fluoro-N,N-dimethylbenzamide

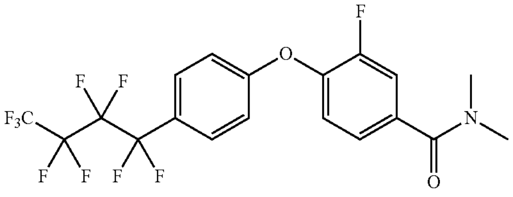

3-fluoro-N,N-dimethyl-4-(4-(perfluorobutyl)phenoxy)benzamide

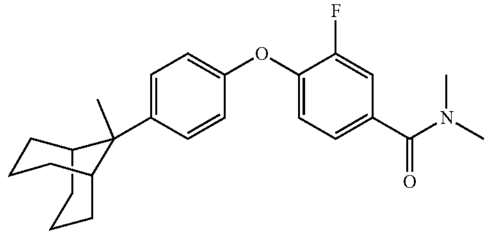

3-fluoro-N,N-dimethyl-4-(4-((1R,5S,)-9-methylbicyclo[3.3.1]nonan-9-yl)phenoxy)benzamide

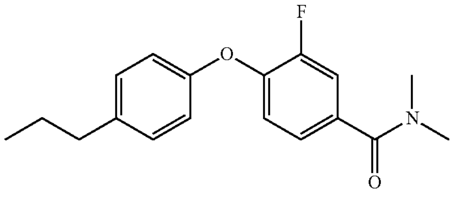

3-fluoro-N,N-dimethyl-4-(4-propylphenoxy)benzamide

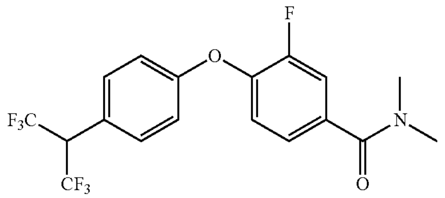

3-fluoro-4-(4-(1,1,1,3,3,3-hexafluoropropan-2-yl)phenoxy)-N, N-dimethylbenzamide -continued

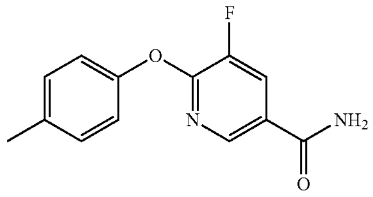

5-fluoro-6-(p-tolyloxy)nicotinamide

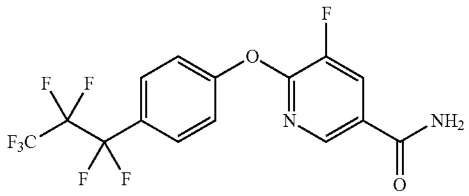

5-fluoro-6-(4-(perfluoropropyl)phenoxy)nicotinamide

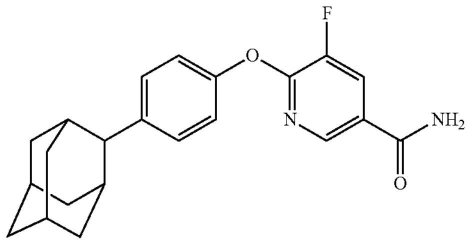

6-(4-((1r,3r,5r,7r)-adamantan-2-yl)phenoxy-5-fluoronicotinamide

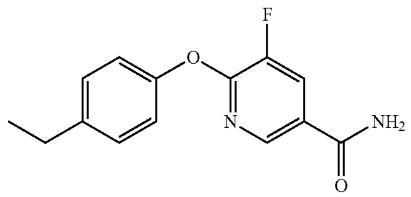

6-(4-ethylphenoxy)-5-fluoronicotinamide

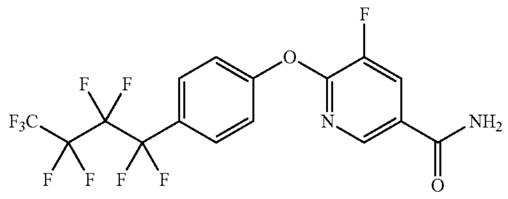

5-fluoro-6-(4-(perfluorobutyl)phenoxy)nicotinamide

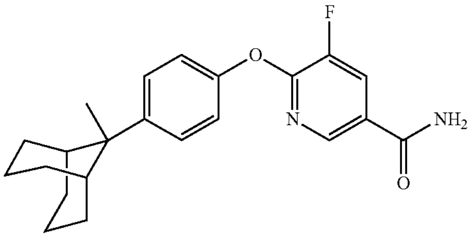

5-fluoro-6-(4-((1R,5S)-9-methylbicyclo[3.3.1]nonan-9-yl)phenoxy)nicotinamide

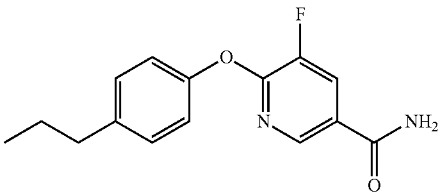

5-fluoro-6-(4-propylphenoxy)nicotinamide

-continued

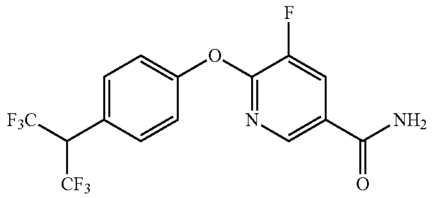

5-fluoro-6-(4-(1,1,1,3,3,3-hexafluoropropan-2-yl)phenoxy)nicotinamide

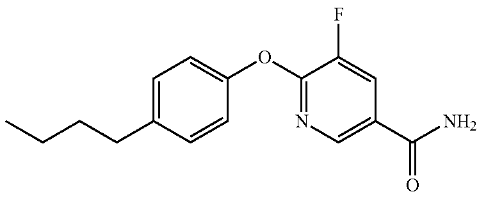

6-(4-butylphenoxy)-5-fluoronicotinamide

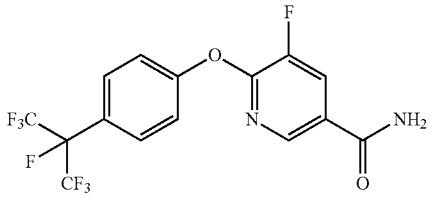

5-fluoro-6-(4-(perfluoropropan-2-yl)phenoxy)nicotinamide

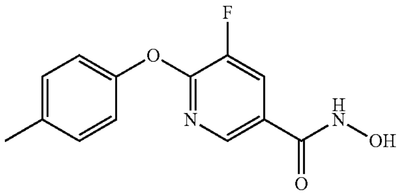

5-fluoro-N-hydroxy-6-(p-tolyloxy)nicotinamide

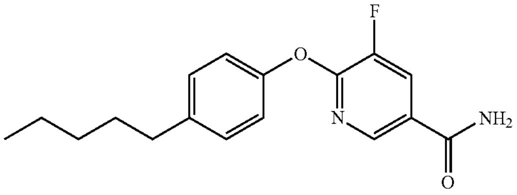

5-fluoro-6-(4-pentylphenoxy)nicotinamide

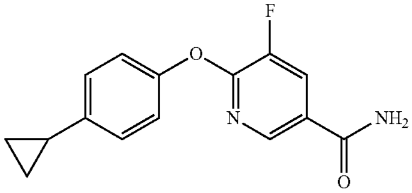

6-[4-cyclopropylphenoxy)-5-fluoronicotinamide

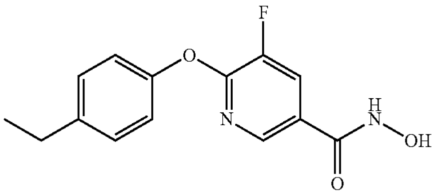

6-(4-ethylphenoxy)-5-fluoro-N-hydroxynicotinamide

-continued

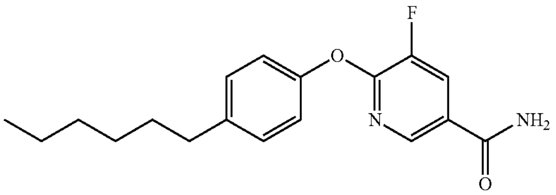

5-fluoro-6-(4-hexylphenoxy)nicotinamide

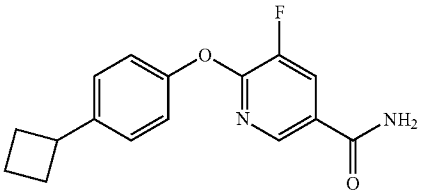

6-(4-cyclobutylphenoxy)-5-fluoronicotinamide

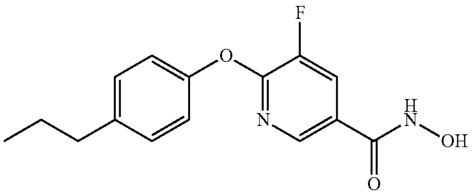

5-fluoro-N-hydroxy-6-(4-propylphenoxy)nicotinamide

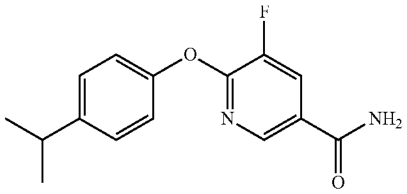

5-fluoro-6-(4-isopropylphenoxy)nicotinamide

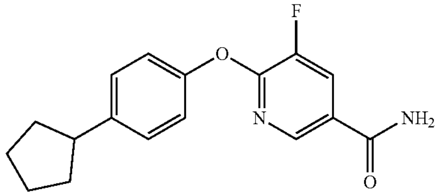

6-(4-cyclopentylphenoxy)-5-fluoronicotinamide

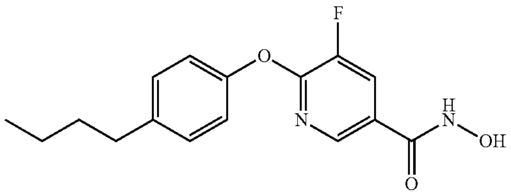

6-(4-butylphenoxy)~5-fluoro-N-hydroxynicotinamide

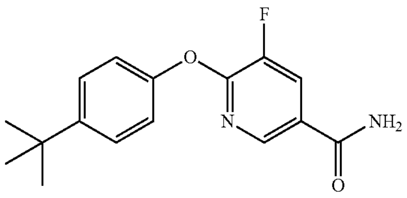

6-(4-(tert-butyl)phenoxy)-5-fluoronicotinamide

-continued

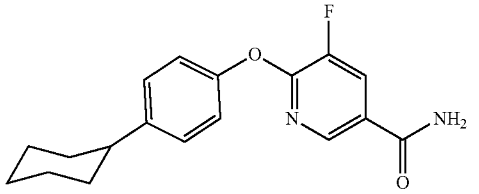

6-(4-cyclohexylphenoxy)-5-fluoronicotinamide

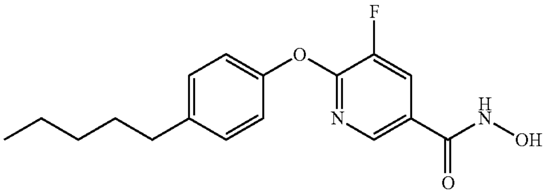

5-fluoro-N-hydroxy-6-(4-pentylphenoxy)nicotinamide

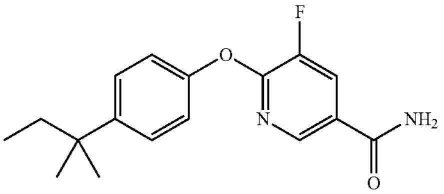

5-fluoro-6-(4-(tert-pentyl)phenoxy)nicotinamide

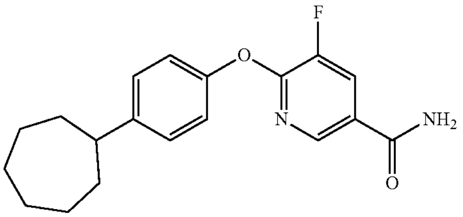

5-(4-cycloheptylphenoxy)-5-fluoronicotinamide

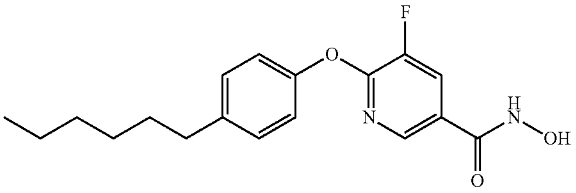

5-fluoro-6-(4-hexylphenoxy)-N-hydroxynicotinamide

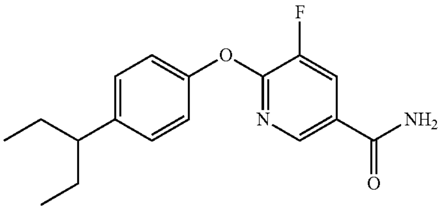

5-fluoro-6-(4-(pentan-3-yl)phenoxy)nicotinamide

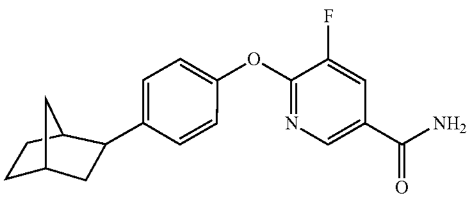

6-(4-((1S,4R)-bicyclo[2.2.1]heptan-2-yl)phenoxy)-5-fluoronicotinamide

-continued

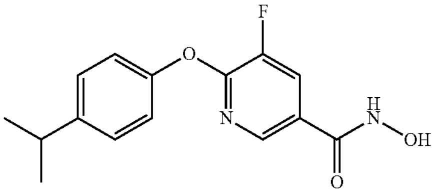

5-fluoro-N-hydroxy-6-(4-isopropylphenoxy)nicotinamide

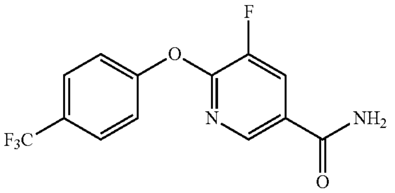

5-fluoro-6-(4-(trifluoromethyl)phenoxy)nicotinamide

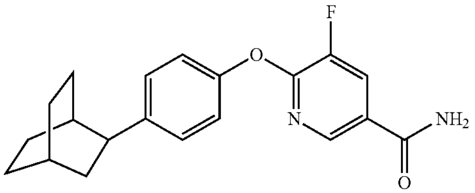

6-(4-((1s,4s)-bicyclo[2.2.2]octan-2-yl)phenoxy)-5-fluoronicotinamide

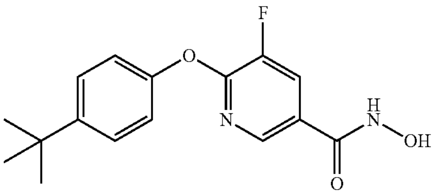

6-(4-(tert-butyl)phenoxy)-5-fluoro-N-hydroxynicotinamide

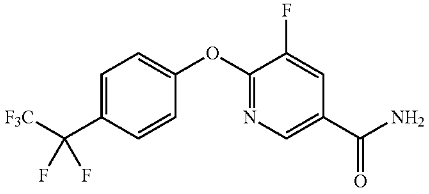

5-fluoro-6-(4-(perfluoroethyl)phenoxy)nicotinamide

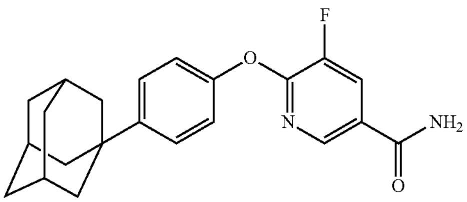

6-(4-((3r,5r,7r)-adamantan-1-yl)phenoxy)-5-fluoronicotinamide

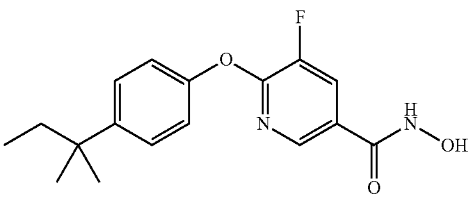

-continued

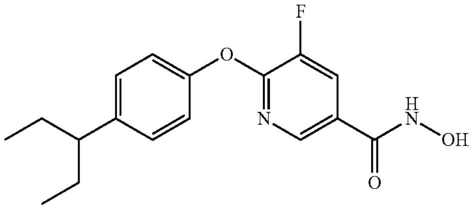

5-fluoro-N-hydroxy-6-(4-(pentan-3-yl)phenoxy)nicotinamide

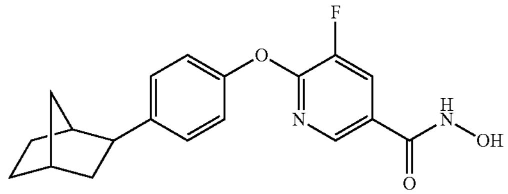

6-(4-((1S,4R)bicyclo[2.2.1]heptan-2-yl)phenoxy)-5-fluoro- N-hydroxynicotinamide

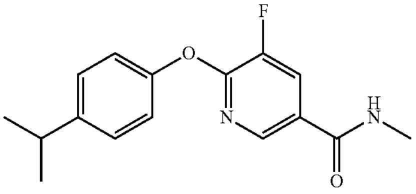

5-fluoro-6-(4-isopropylphenoxy)-N-methylnicotinamide

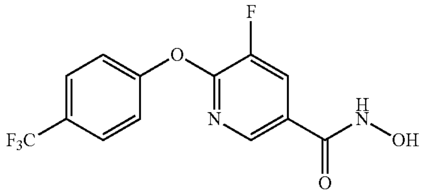

5-fluoro-N-hydroxy-6-(4-(trifluoromethyl)phenoxy)nicotinamide

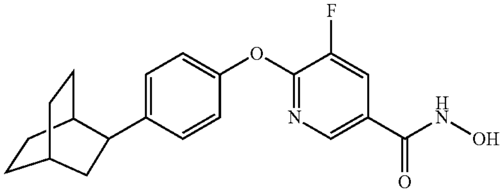

6-(4-((1s,4s)-bicyclo[2.2.2]octan-2-yl)phenoxy)-5-fluoro-N-hydroxynicotinamide

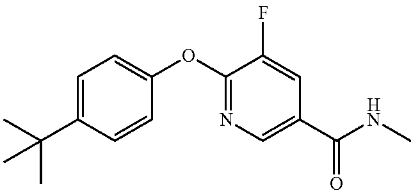

6-(4-(tert-butyl)phenoxy)-5-fluoro-N-methylnicotinamide

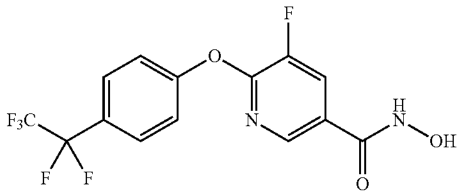

5-fuoro-N-hydroxy-6-(4-(perfluoroethyl)phenoxy)nicotinamide

-continued

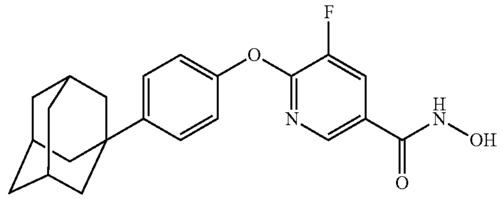

6-(4-((3r,5r,7r)-adamamantan-1-yl)phenoxy)-5-fluoro-N-hydroxynicotinamide

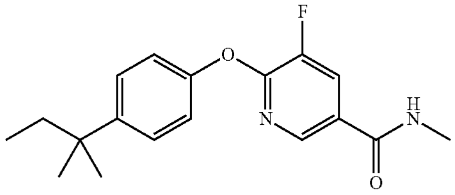

5-fluoro-N-methyl-6-(4-(tert-pentyl)phenoxy)nicotinamide

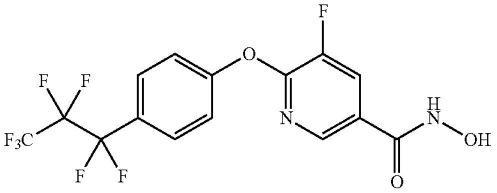

5-fluoro-N-hydroxy-6-(4-(perfluoropropyl)phenoxy)nicotinamide

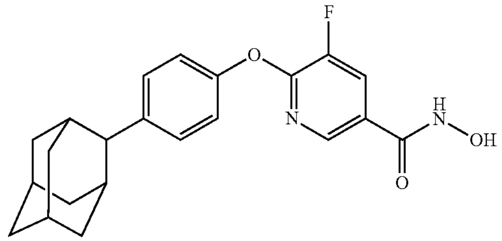

6-(4-((1r,3r,5r,7r)-adamantan-2-yl)phenoxy)-5-fluoro-N-hydroxynicotinamide

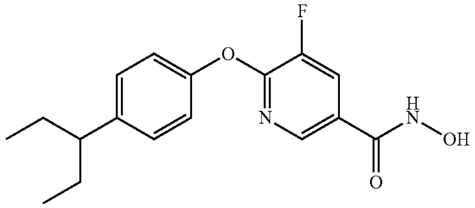

5-fluoro-N-methyl-6-(4-(pentan-3-yl)phenoxy)nicotinamide

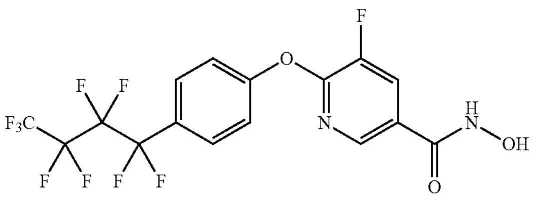

5-fluoro-N-hydroxy-6-(4-perfluorobutyl)phenoxy)nicotinamide

-continued

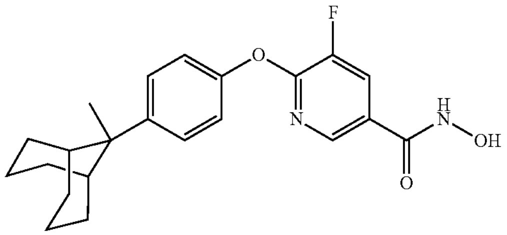

5-fluoro-N-hydroxy-6-(4-((1R,5S)-9-methylbicyclo[3.3.1]nonan-9-yl)phenoxy)nicotinamide

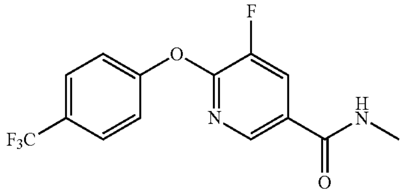

5-fluoro-N-methyl-6-(4-(trifluoromethyl)phenoxy)nicotinamide

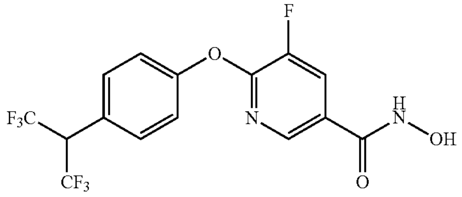

5-fluoro-6-(4-(1,1,1,3,3,3-hexafluoropropan-2-yl)phenoxy)-N-hydroxynicotinamide

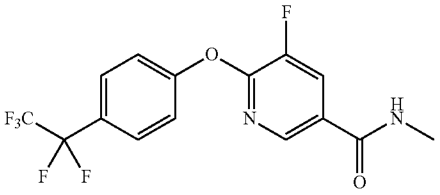

5-fluorro-N-methyl-6-(4-(perfluoroethyl)phenoxy)nicotinamide

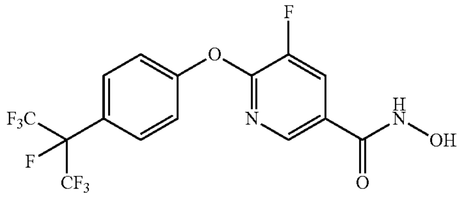

5-fluoro-N-hydroxy-6-(4-(perfluoropropan-2-yl)phenoxy)nicotinamide

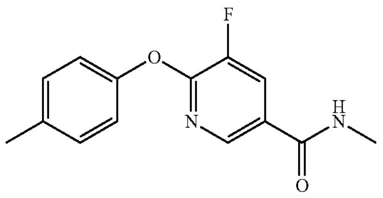

5-fluoro-N-methyl-6-(p-tolyloxy)nicotinamide

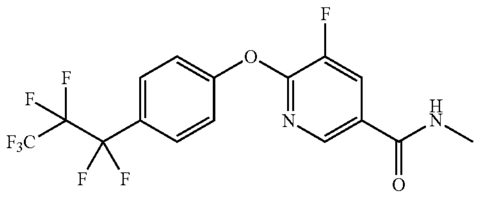

5-fluoro-N-methyl-6-(4-(perfluoropropyl)phenoxy)nicotinamide

-continued

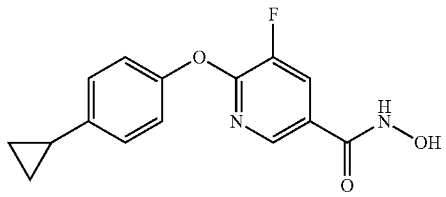

6-(4-cyclopropylphenoxy)-5-fluoro-N-hydroxynicotinamide

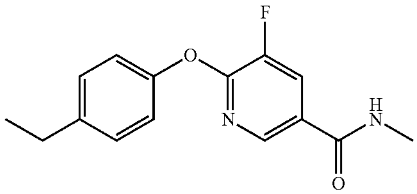

6-(4-ethylphenoxy)-5-fluoro-N-methylnicotinamide

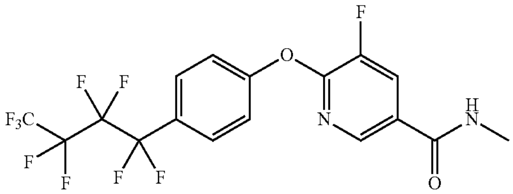

5-fluoro-N-methyl-6-(4-(perfluorobutyl)phenoxyy)nicotinamide

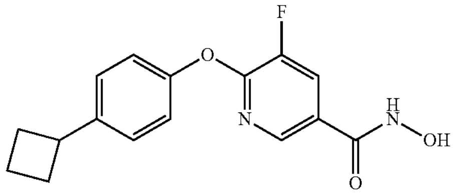

6-(4-cyclobutylphenoxy)-5-fluoro-N-hydroxynicotinamide

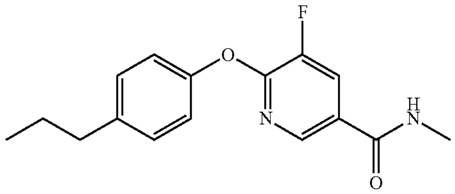

5-fluoro-N-methyl-6-(4-propylphenoxy)nicotinamide

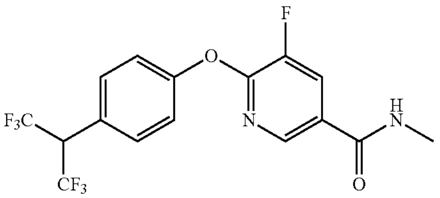

5-fluoro-6-(4-(1,1,1,3,3,3-hexafluoropropan-2-yl)phenoxy)-N-methylnicotinamide

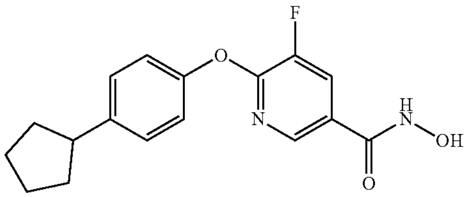

6-(4-cyclopentylphenoxy)-5-fluoro-N-hydroxynicotinamide

-continued

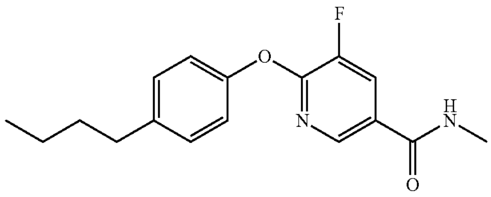

6-(4-butylphenoxy)-5-fluoro-N-methynicotinamide

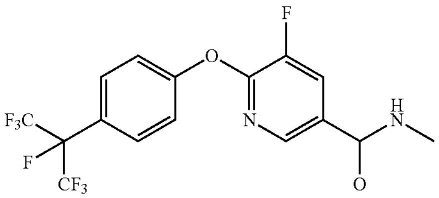

5-fluoro-N-mexhyl-6-(4-(perfluoropropan-2-yl)phenoxy)nicotinamide

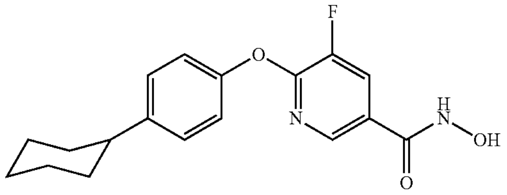

6-(4-cyclohexyphenoxy)-5-fluoro-N-hydroxynicotinamide

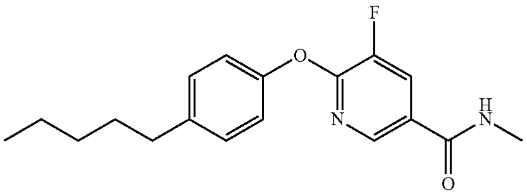

5-fluoro-N-methyl-6-(4-pentylphenoxy)nicotinamide

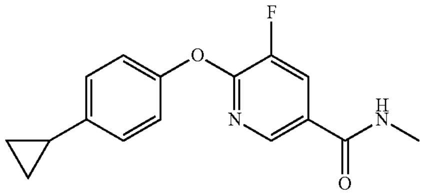

6-(4-cyclopropylphenoxy)-5-fluoro-N-methylnicotinamide

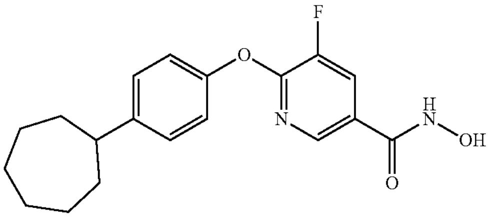

6-(4-cycloheptylphenoxy)-5-fluoro-N-hydroxynicotinamide

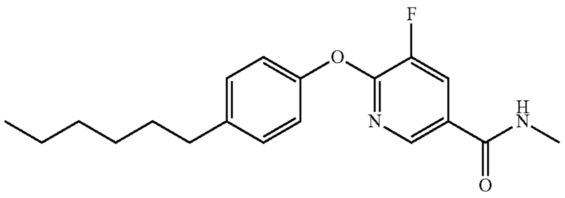

5-fluoro-6-(4-hexylphenoxy)-N-methylnicotinamide

-continued

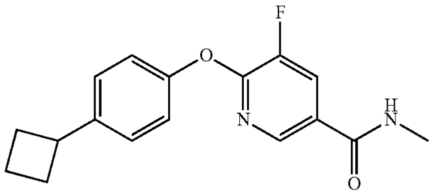

6-(4-cyclobutylphenoxy)-5-fluoro-N-methylniconamide

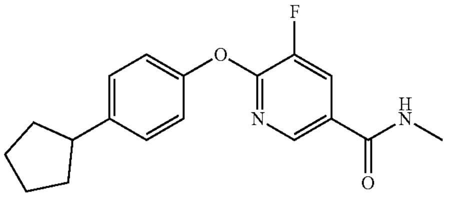

6-(4-cyclopentylphenoxy)-5-fluoro-N-methylnicotinamide

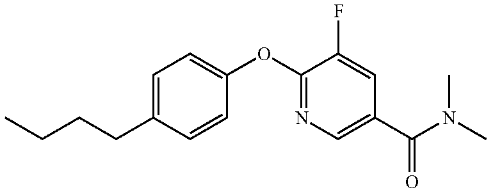

6-(4-butylphenoxy)-5-fluoro-N,N-dimethylnicotinamide

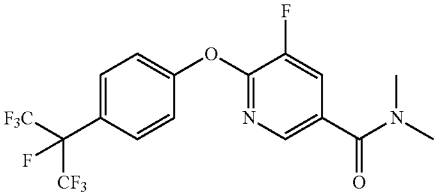

5-fluoro-N,N-dimethyl-6-(4-(perfluoropropan-2-yl)phenoxy)nicotinamide

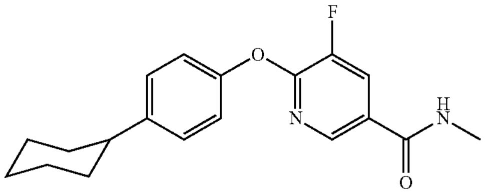

6-(4-cyclohexylphenoxy)-5-fluoro-N-methylnicotinamide

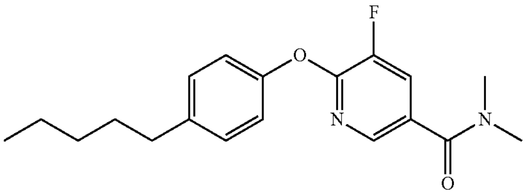

5-fluoro-N,N-dimethyl-6-(4-pentylphenoxy)nicotinamide

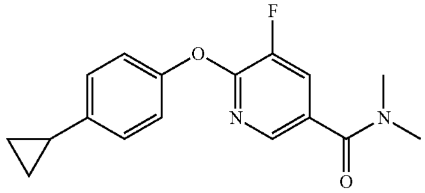

6-(4-cyclopropylphenoxy)-5-fluoro-N,N-dimethylnicotinamide

-continued

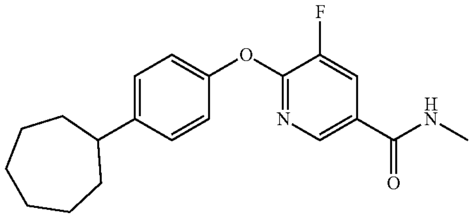

6-(4-cycloheptylphenoxy)-5-fluoro-N-methylnicotinamide

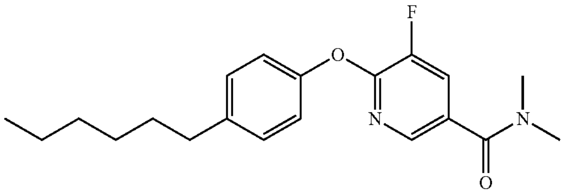

5-fluoro-6-(4-hexylphenoxy)-N,N-dimethylnicotinamide

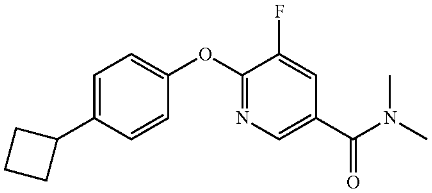

6-(4-cyclobutylphenoxy)-5-fluoro-N,N-dimethylnicotinamide

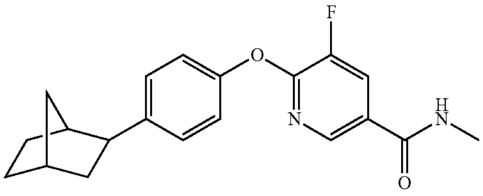

6-(4-((1S,4R)-bicyclo[2,2,1]heptan-2-yl)phenoxy)-5-fluoro-N-methylnicotinamide

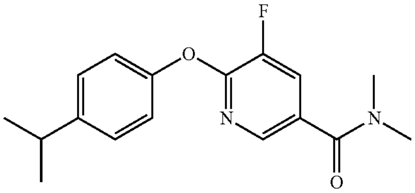

5-fluoro-6-(4-isopropylphenoxy)-N,N-dimethylnicotinamide

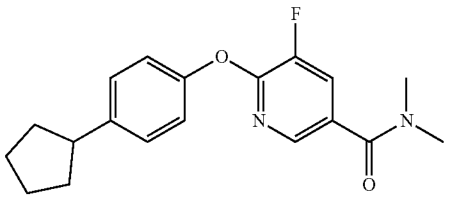

6-(4-cyclopentylphenoxy)-5-fluoro-N,N-dimethylnicotinamide

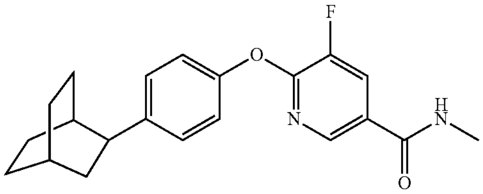

6-(4-((1s,4s)-bicyclo[2.2.2]octan-2-yl)phenoxy)-5-fluoro-N-methylnicotinamide

-continued

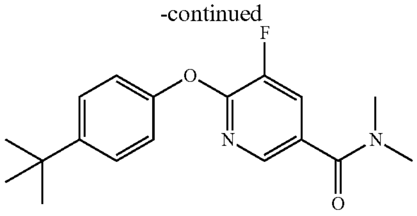

6-(4-(tert-butyl)phenoxy)-5-fluoro-N,N-dimethylnicotinamide

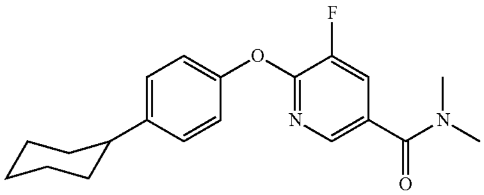

6-(4-cyclohexylphenoxy)-5-fluoro-N,N-dimethylnicotinamide

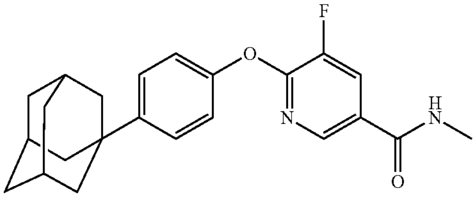

6-(4-((3r,5r,7r)-adamantan-1-yl)phenoxy)-5-fluoro-N-methylnicotinamide

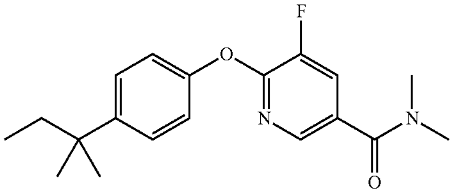

5-fluoro-N,N-dimethyl-6-(4-(tert-pentyl)phenoxy)nicotinamide

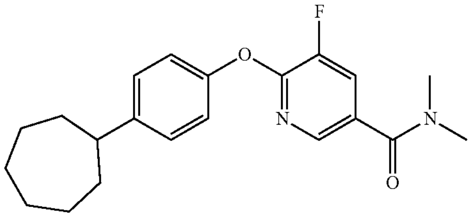

6-(4-cycloheptylphenoxy)-5-fluoro-N,N-dimethylnicotinamide

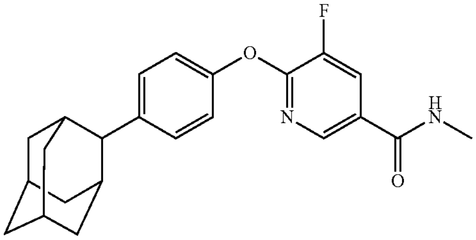

6-(4-((3r,5r,7r)-adamantan-2-yl)phenoxy)-5-fluoro-N-methylnicotinamide

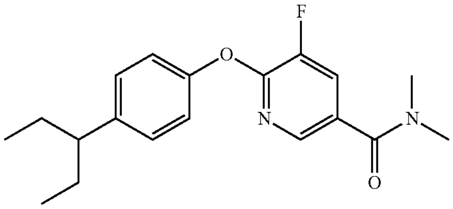

5-fluoro-N,N-dimethyl-6-(4-(pentan-3-yl)phenoxy)nicotinamide

-continued

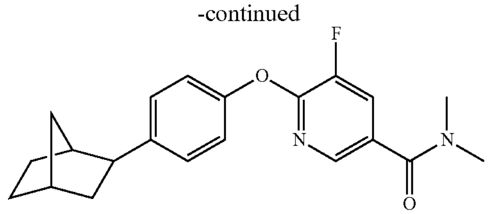

6-(4-((1S,4R)-bicyclo[2.2.1]heptan-2-yl)phenoxy)-5-fluoro-N,N-dimethylnicotinamide

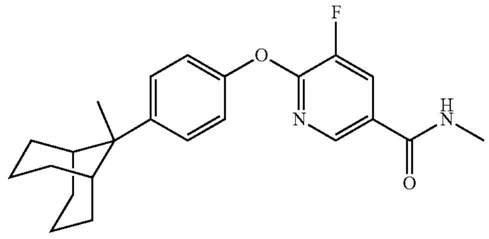

5-fluoro-N-methyl-6-(4-((1R,5S)-9-methylbicyclo[3.3.1]nonan-9-yl)phenoxy)nicotinamide

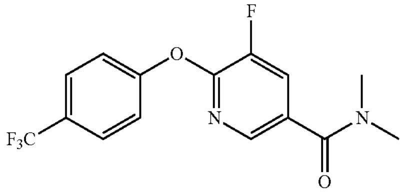

5-fluoro-N,N-dimethyl-6-(4-trifluoromethyl)phenoxy)nicotinamide

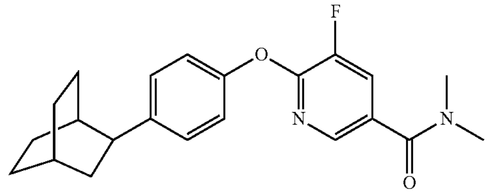

6-(4-((1s,4s)-bicyclo[2.2.2]octan-2-yl)phenoxy)-5-fluoro-N,N-dimethylnicotinamide

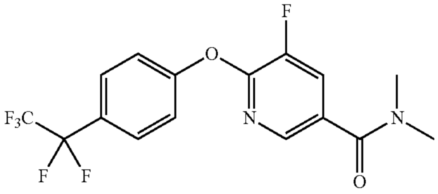

5-fluoro-N,N-dimethyl-6-(4-(perfluoroethyl)phenoxy)nicotinamide

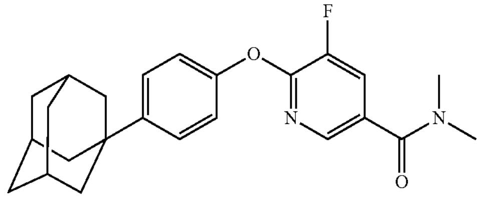

6-(4-((3r,5r,7r)-adamantan-1-yl)phenoxy)-5-fluoro-N-N-dimethylnicotinamide

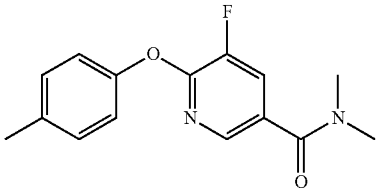

5-fluoro-N,N-dimethyl-6-(p-tolyloxy)nicotinamide

-continued

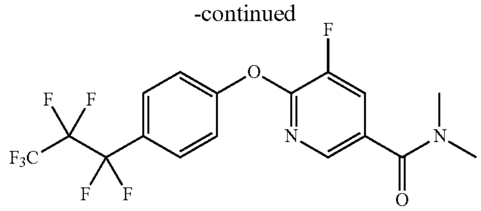

5-fluoro-N,N-dimethyl-6-(4-(perfluoropropyl)phenoxy)nicotinamide

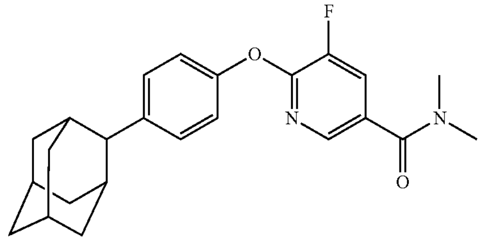

6-(4-((1r,3r,5r,7r)-adamantan-2-yl)phenoxy)-5-fluoro-N,N-dimethylnicotinamide

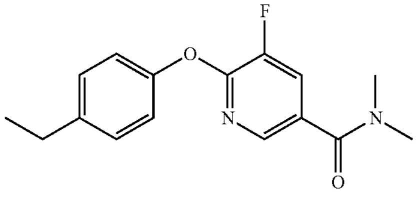

6-(4-ethylphenoxy)-5-fluoro-N,N-dimethylnicotinamide

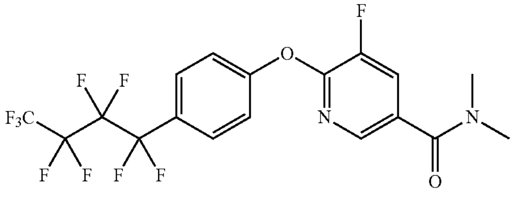

5-fluoro-N,N-dimethyl-6-(4-(perfluorobutyl)phenoxy)nicotinamide

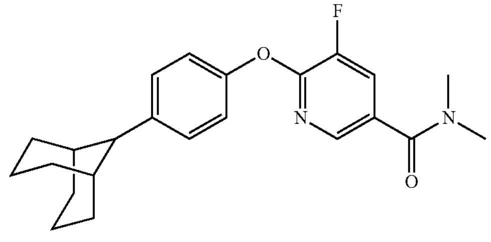

5-fluoro-N,N-dimethyl-4-(4-((1R,5S)-9-methylbicyclo[3.3.1]nonan-9-yl)phenoxy)nicotinamide

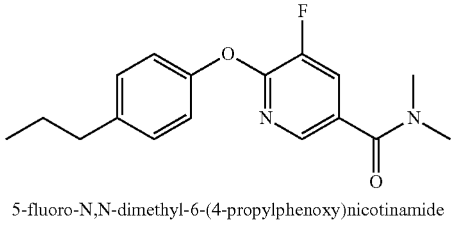

5-fluoro-N,N-dimethyl-6-(4-propylphenoxy)nicotinamide

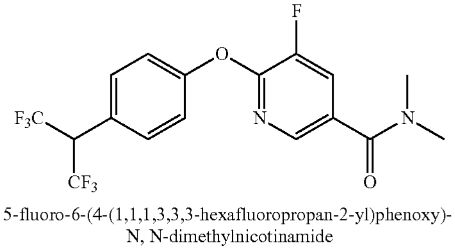

5-fluoro-6-(4-(1,1,1,3,3,3-hexafluoropropan-2-yl)phenoxy)-N, N-dimethylnicotinamide -continued

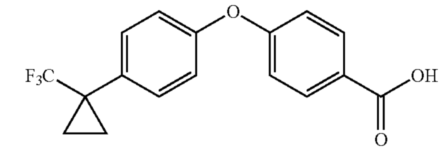

4-(4-(1-(trifluoromethyl)cycloproply)phenoxy) benzoic acid

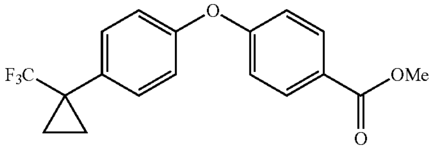

methyl 4-(4-(1-(trifluoromethyl)cyclopropyl) phenoxy)benzoate

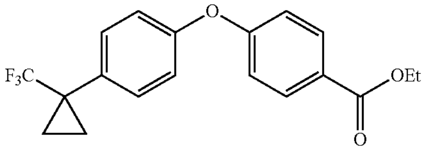

ethyl 4-(4-(1-(trifluoromethyl)cyclopropyl) phenoxy)benzoate

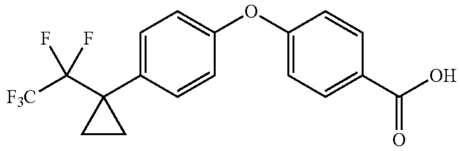

4-4-(1-(perfluoroethyl)cyclopropyl)phenoxy) benzoic acid

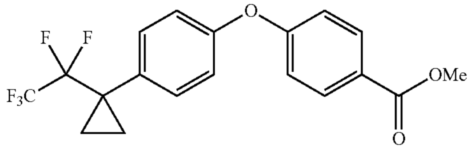

methyl 4-(4-(1-(perfluoroethyl)cyclopropyl) phenoxy)benzoate

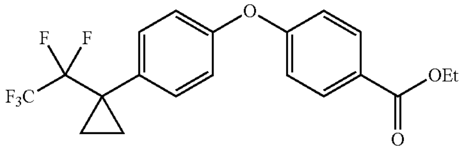

ethyl 4-(4-(1-(perfluoroethyl)cyclopropyl) phenoxy)benzoate

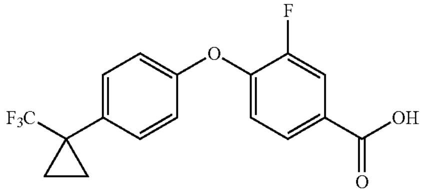

3-fluoro-4-(4-(1-(trifluoromethyl)cyclopropyl)phenoxy) benzoic acid

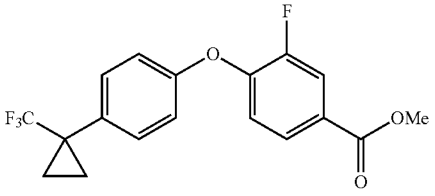

methyl 3-fluoro-4-(4-(1-(trifluoromethyl)cyclopropyl) phenoxy)benzoate

-continued

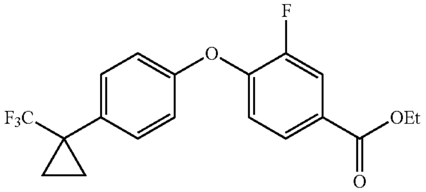

ethyl 3-fluoro-4-(4-(1-(trifluoromethyl)cyclopropyl) phenoxy)benzoate

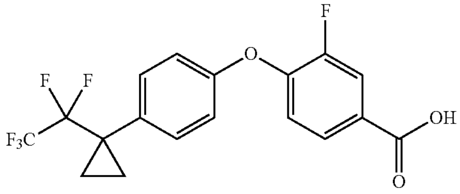

3-fluoro-4-4-(1-(perfluoroethyl)cyclopropyl)phenoxy) benzoic acid

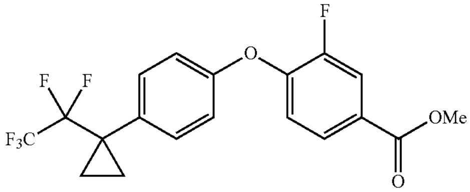

methyl 3-fluoro-4-(4-(1-(perfluoroethyl)cyclopropyl) phenoxy)benzoate

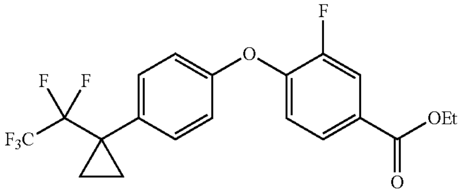

ethyl 3-fluoro-4-(4-(1-(perfluoroethyl)cyclopropyl) phenoxy)benzoate

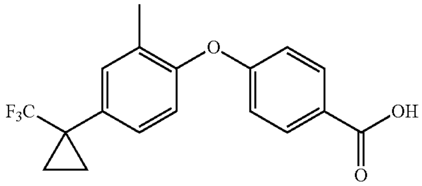

4-(2-methyl-4-(1-(trifluoromethyl)cyclopropyl)phenoxy) benzoic acid

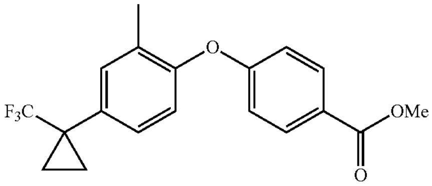

methyl 4-(2-methyl 4-(1-(trifluoromethyl)cyclopropyl) phenoxy)benzoate

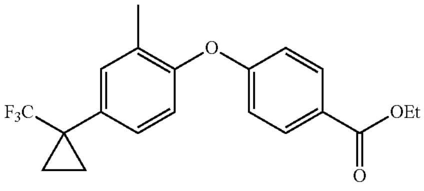

ethyl 4-(2-methyl 4-(1-(trifluoromethyl)cyclopropyl) phenoxy)benzoate

-continued

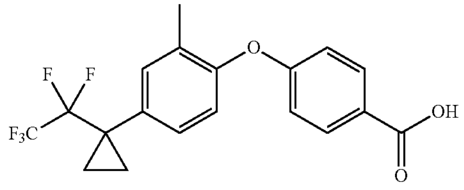

4-(2-methyl-4-(1-(perfluoroethyl)cyclopropyl) phenoxy)benzoic acid

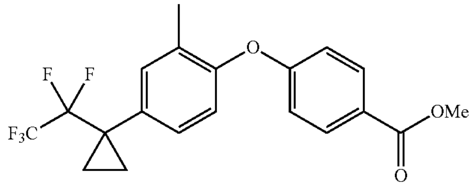

methyl 4-(2-methyl-4-(1-(perfluoroethyl)cyclopropyl) phenoxy)benzoate

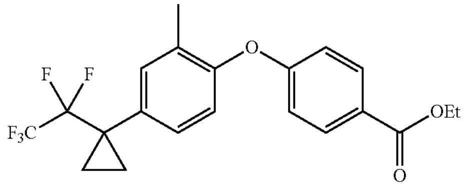

ethyl 4-(2-methyl-4-(1-(perfluoroethyl)cyclopropyl) phenoxy)benzoate

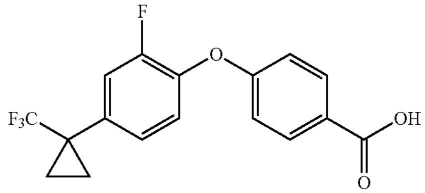

4-(2-fluoro-4-(1-(trifluoromethyl)cyclopropyl) phenoxy)benzoic acid

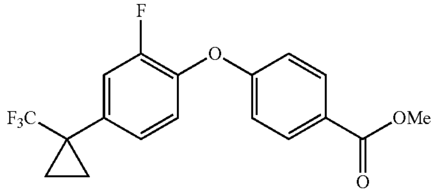

methyl 4-(2-fluoro-4-(1-(trifluoromethyl)cyclopropyl) phenoxy)benzoate

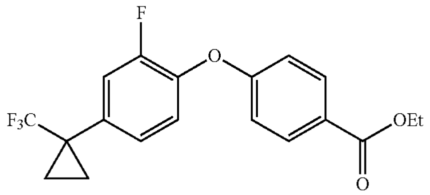

ethyl 4-(2-fluoro-4-(1-(trifluoromethyl)cyclopropyl) phenoxy)benzoate

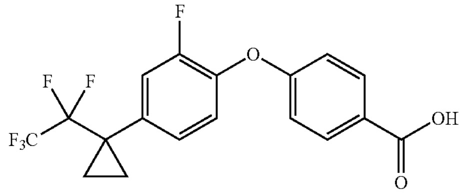

4-(2-fluoro-4-(1-(perfluoroethyl)cyclopropyl) phenoxy)benzoic acid

-continued

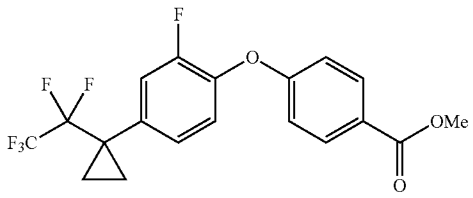

methyl 4-(2-fluoro-4-(1-(perfluoroethyl)cyclopropyl) phenoxy)benzoate

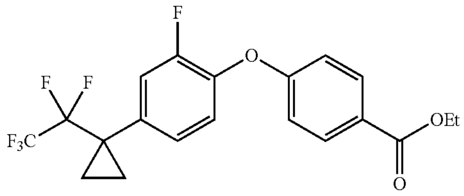

ethyl 4-(2-fluoro-4-(1-(perfluoroethyl)cyclopropyl) phenoxy)benzoate

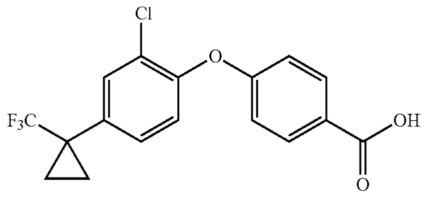

4-(2-chloro-4-(1-(trifluoromethyl)cyclopropyl)phenoxy) benzoic acid

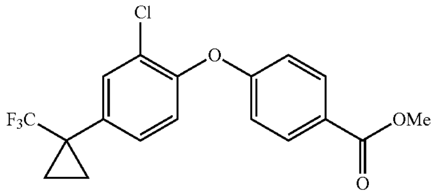

methyl 4-(2-chloro-4-(1-(trifluoromethyl)cyclopropyl) phenoxy)benzoate

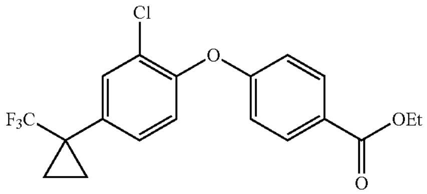

ethyl 4-(2-chloro-4-(1-(trifluoromethyl)cyclopropyl) phenoxy)benzoate

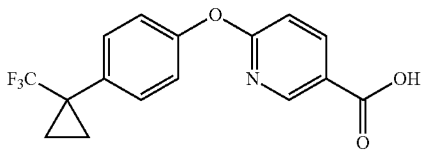

6-(4-(1-(trifluoromethyl)cyclopropyl)phenoxy) nicotinic acid

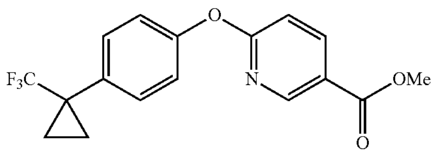

methyl 6-(4-(1-(trifluoromethyl)cyclopropyl) phenoxy)nicotinate

-continued

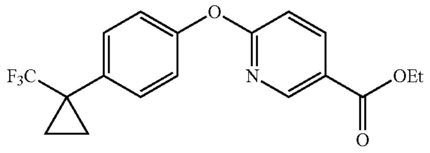

ethyl 6-(4-(1-(trifluoromethyl)cyclopropyl) phenoxy)nicotinate

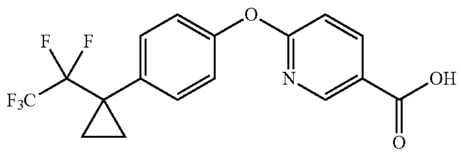

6-(4-(1-(perfluoroethyl)cyclopropyl)phenoxy) nicotinic acid

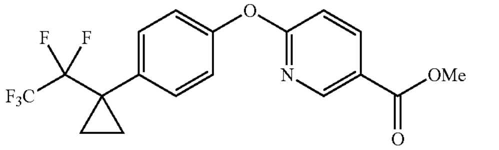

methyl 6-(4-(1-(perfluoroethyl)cyclopropyl) phenoxy)nicotinate

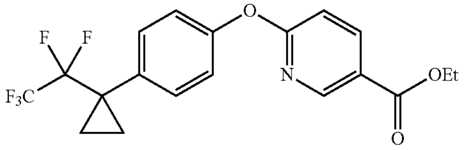

ethyl 6-(4-(1-(perfluoroethyl)cyclopropyl) phenoxy)nicotinate

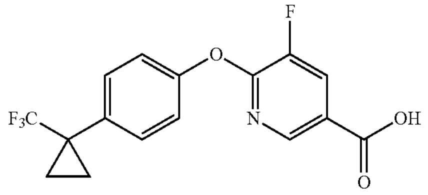

5-fluoro-6-(4-(1-(trifluoromethyl)cyclopropyl)phenoxy) nicotinic acid

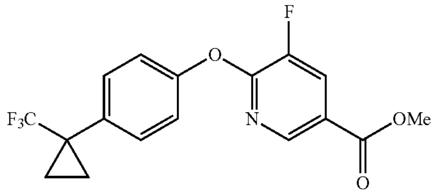

methyl 5-fluoro-6-(4-(1-(trifluoromethyl)cyclopropyl) phenoxy)nicotinate

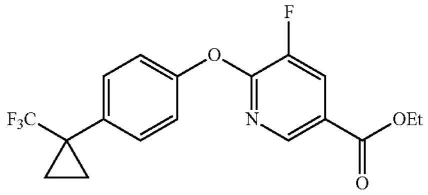

ethyl 5-fluoro-6-(4-(1-(trifluoromethyl)cyclopropyl) phenoxy)nicotinate

-continued

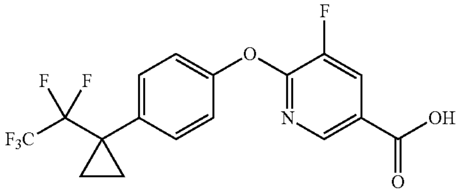

5-fluoro-6-(4-(1 (perfluoroethyl)cyclopropyl)phenoxy) nicotinic acid

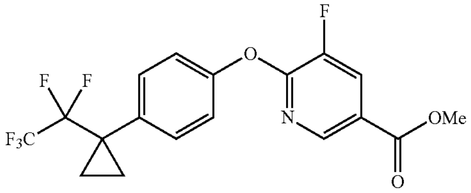

methyl 5-fluoro-6-(4-(1-(perfluoroethyl)cyclopropyl) phenoxy)nicotinate

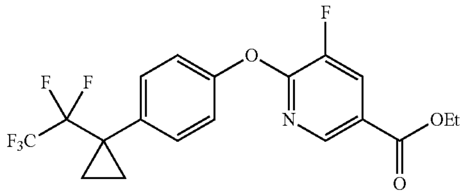

ethyl 5-fluoro-6-(4-(1-(perfluoroethyl)cyclopropyl) phenoxy)nicotinate

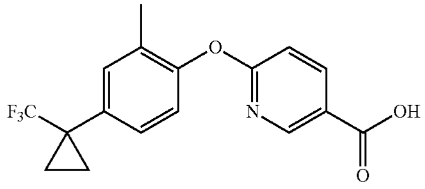

6-(2-methyl-4-(1-(trifluoromethyl)cyclopropyl)phenoxy) nicotinic acid

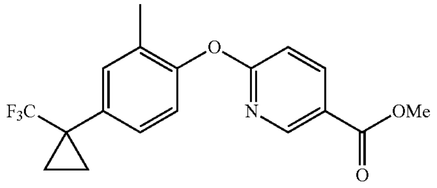

methyl 6-(2-methyl-4-(1-(trifluoromethyl)cyclopropyl) phenoxy)nicotinate

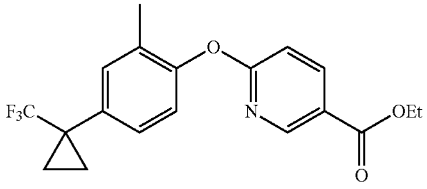

ethyl 6-(2-methyl-4-(1-(trifluoromethyl)cyclopropyl) phenoxy)nicotinate

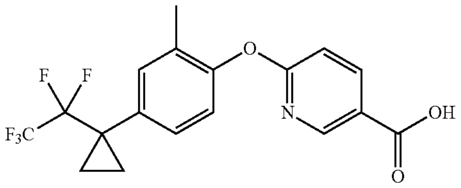

6-(2-methyl-4-(1-(perfluoroethyl)cyclopropyl)phenoxy) nicotinic acid

-continued

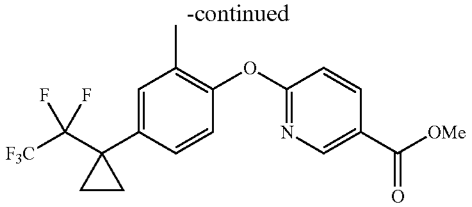

methyl 6-(2-methyl-4-(1-(perfluoroethyl)cyclopropyl) phenoxy)nicotinate

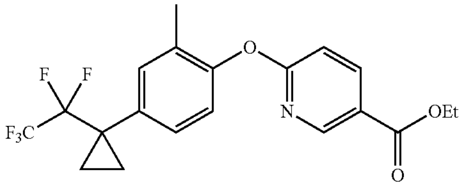

ethyl 6-(2-methyl-4-(1-(perfluoroethyl)cyclopropyl) phenoxy)nicotinate

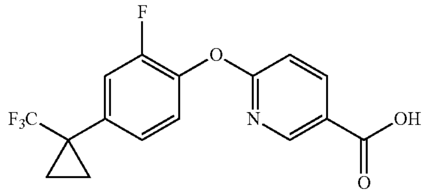

6-(2-fluoro-4-(1-(trifluoromethyl)cyclopropyl)phenoxy) nicotinic acid

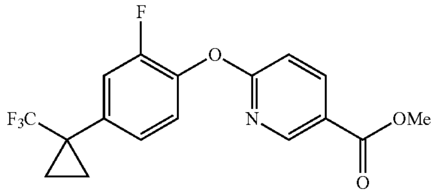

methyl 6-(2-fluoro-4-(1-(trifluoromethyl)cyclopropyl) phenoxy)nicotinate

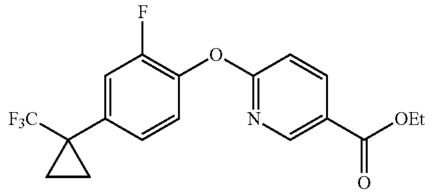

ethyl 6-(2-fluoro-4-(1-(trifluoromethyl)cyclopropyl) phenoxy)nicotinate

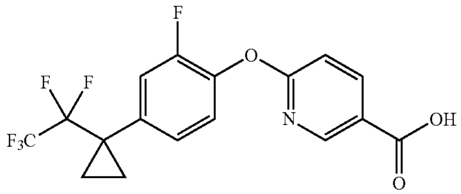

6-(2-fluoro-4-(1-(perfluoroethyl)cyclopropyl)phenoxy) nicotinic acid

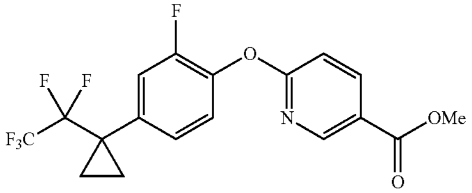

methyl 6-(2-fluoro-4-(1-(perfluoroethyl)cyclopropyl) phenoxy)nicotinate

-continued

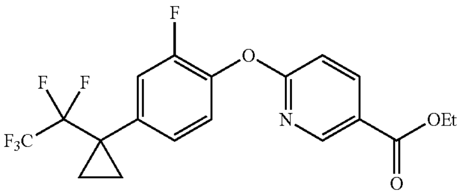

ethyl 6-(2-fluoro-4-(1-(perfluoroethyl)cyclopropyl) phenoxy)nicotinate

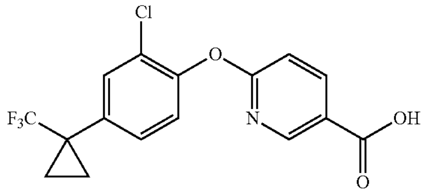

6-(2-chloro-4-(1-(trifluoromethyl)cyclopropyl)phenoxy) nicotinic acid

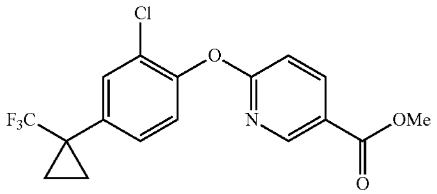

methyl 6-(2-chloro-4-(1-(trifluoromethyl)cyclopropyl) phenoxy)nicotinate

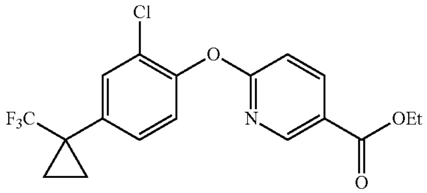

ethyl 6-(2-chloro-4-(1-(trifluoromethyl)cyclopropyl) phenoxy)nicotinate

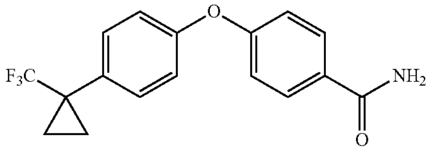

4-(4-(1-(trifluoromethyl)cyclopropyl)phenoxy)benzamide

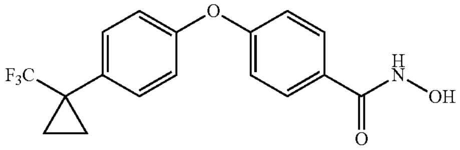

N-hydroxy-4-(4-(1-(trifluoromethyl)cyclopropyl)phenoxy)benzamide

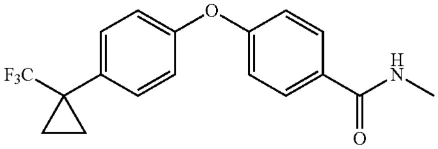

N-methyl-4-(4-(1-(trifluoromethyl)cyclopropyl)phenoxy)benzamide

-continued

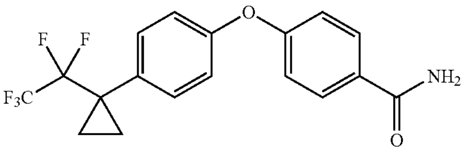

4-(4-(1-(perfluoroethyl)cyclopropyl)phenoxy)benzamide

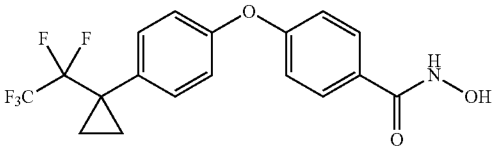

N-hydroxy-4-(4-(1-(perfluoroethyl)cyclopropyl)phenoxy)benzamide

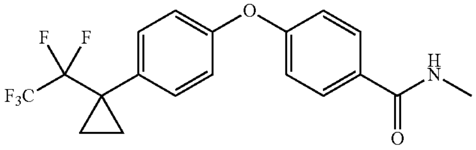

N-methyl-4-(4-(1-perfluoroethyl)cyclopropyl)phenoxy)benzamide

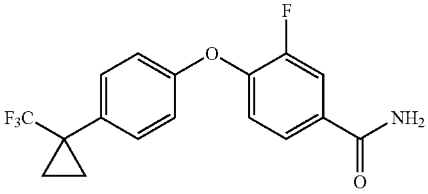

3-fluoro-4-(4-(1-(trifluoromethyl)cyclopropyl)phenoxy)benzamide

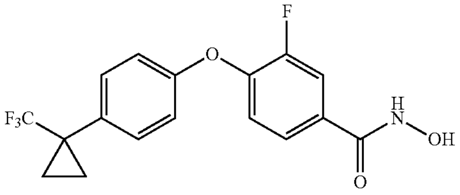

3-fluoro-N-hydroxy-4-(4-(1-(trifluoromethyl)cyclopropyl)phenoxy) benzamide

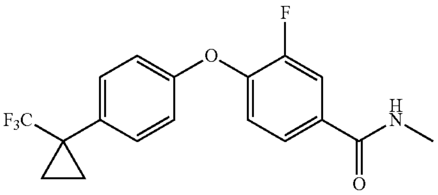

3-fluoro-N-methyl-4-(4-(1-(trifluoromethyl)cyclopropyl)phenoxy) benzamide

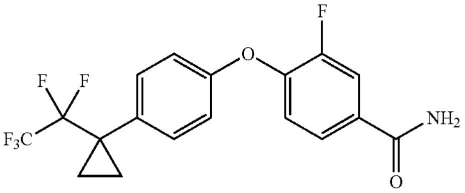

3-fluoro-4-(4-(1-(perfluoroethyl)cyclopropyl)phenoxy)benzamide

-continued

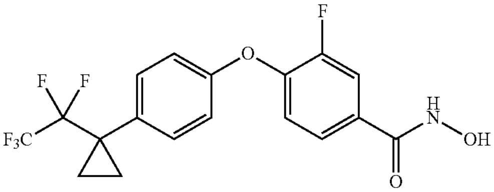

3-fluoro-N-hydroxy-4-(4-(1-(perfluoroethyl)cyclopropyl)phenoxy) benzamide

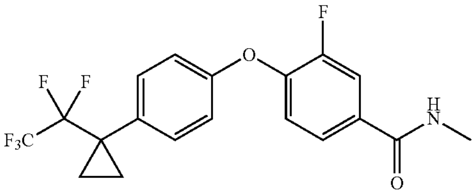

3-fluoro-N-methyl-4-(4-(1-(perfluoroethyl)cyclopropyl)phenoxy) benzamide

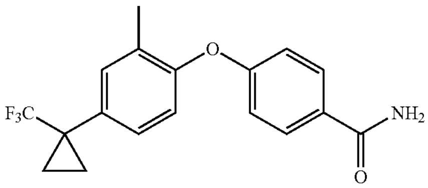

4-(2-methyl-4-(1-(trifluoromethyl)cyclopropyl)phenoxy)benzamide

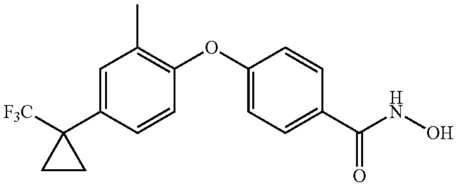

N-hydroxy-4-(2-methyl-4-(1-(trifluoromethyl)cyclopropyl)phenoxy) benzamide

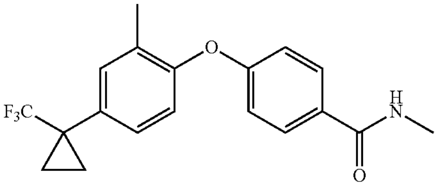

N-methyl-4-(2-methyl-4-(1-(trifluoromethyl)cyclopropyl)phenoxy) benzamide

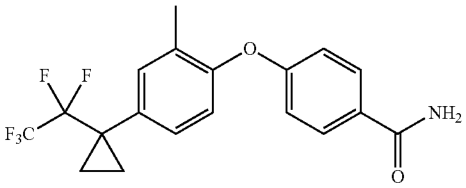

4-(2-methyl-4-(1-(perfluoroethyl)cyclopropyl)phenoxy)benzamide

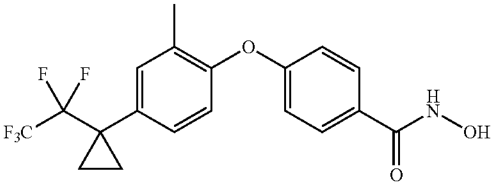

N-hydroxy-4-(2-methyl-4-(1-(perfluoroethyl)cyclopropyl)phenoxy) benzamide

-continued

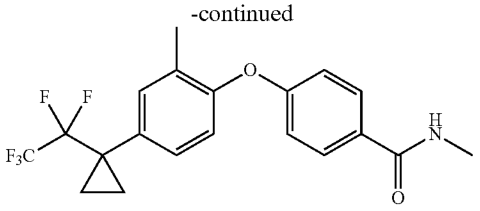

N-methyl-4-(2-methyl-4-(1-(perfluoroethyl)cyclopropyl)phenoxy)benzamide

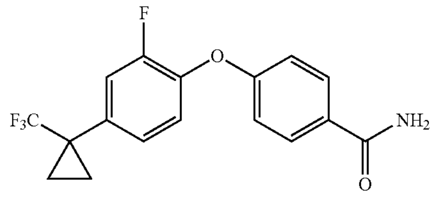

4-(2-fluoro-4-(1-(trifluoromethyl)cyclopropyl)phenoxy)benzamide

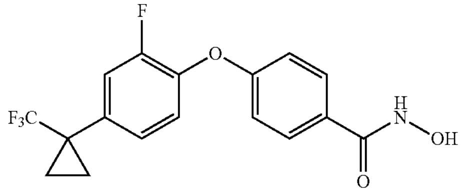

4-(2-fluoro-4-(1-(trifluoromethyl)cyclopropyl)phenoxy)-N-hydroxybenzamide

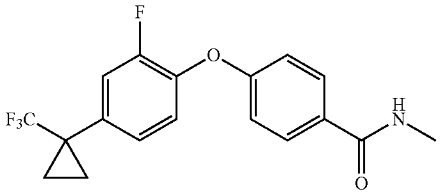

4-(2-fluoro-4-(1-(trifluoromethyl)cyclopropyl)phenoxy)-N-methylbenzamide

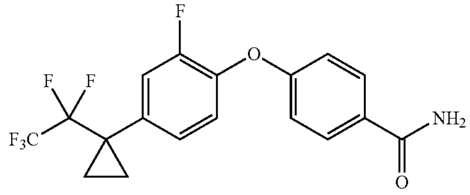

4-(2-fluoro-4-(1-(perfluoroethyl)cyclopropyl)phenoxy)benzamide

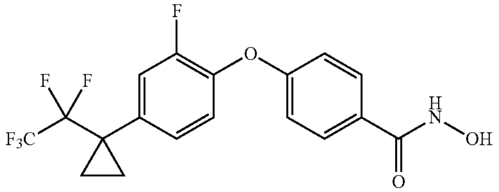

4-(2-fluoro-4-(1-(perfluoroethyl)cyclopropyl)phenoxy)-N-hydroxybenzamide

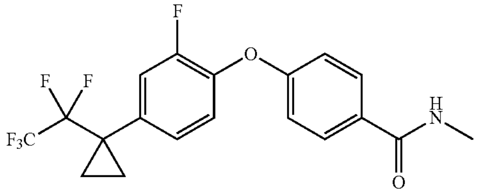

4-(2-fluoro-4-(1-(perfluoroethyl)cyclopropyl)phenoxy)-N-methylbenzamide

-continued

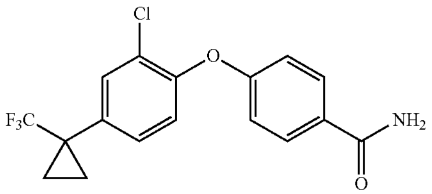

4-(2-chloro-4-(1-(trifluoromethyl)cyclopropyl)phenoxy)benzamide

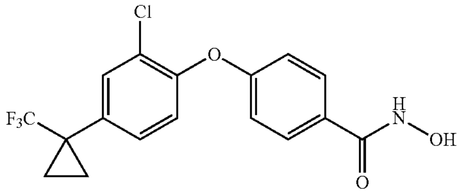

4-(2-chloro-4-(1-(trifluoromethyl)cylopropyl)phenoxy)-N-hydroxybenzamide

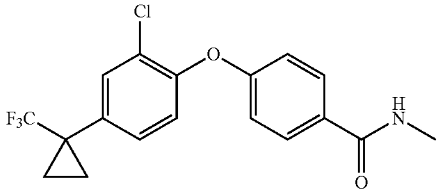

4-(2-chloro-4-(1-(trifluoromethyl)cyclopropyl)phenoxy)-N-methylbenzamide

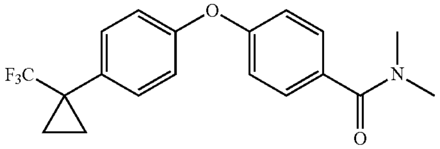

N,N-dimethyl-4-(4-(1-(trifluoromethyl)cyclopropyl)phenoxy)benzamide

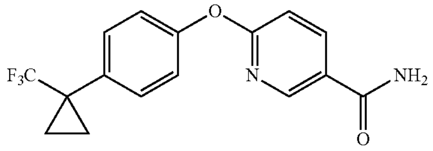

6-(4-(trifluoromethyl)cyclopropyl)phenoxy)nicotinamide

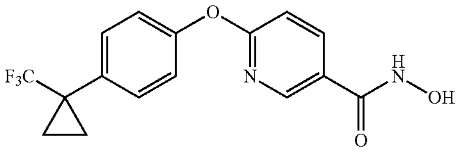

N-hydroxy-6-(4-(1-(trifluoromethyl)cyclopropyl)phenoxy)nicotinamide

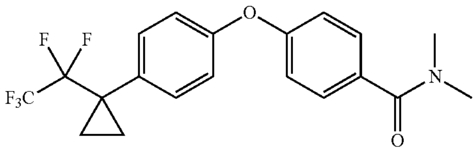

N-N-dimethyl-4-(4-(1-(perfluoroethyl)cyclopropyl)phenoxy)benzamide

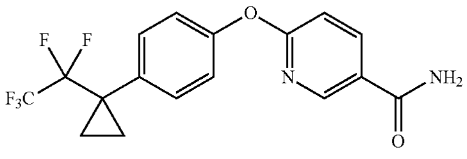

6-(4-(1-(perfluoroethyl)cyclopropyl)phenoxy)nicotinamide

-continued

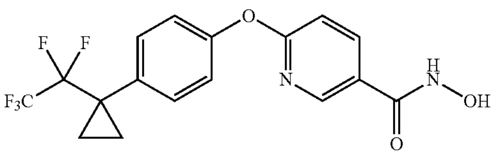

N-hydroxy-6-(4-(1-perfluoroethyl)cyclopropyl)phenoxy)nicotinamide

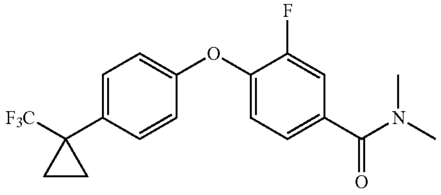

3-fluoro-N,N-dimethyl-4-(4-(1-(trifluoromethyl)cyclopropyl)phenoxy) benzamide

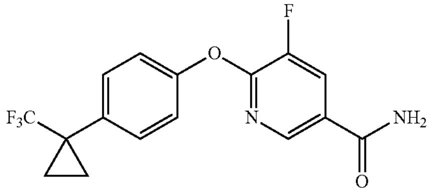

5-fluoro-6-(4-(1-(trifluoromethyl)cyclopropyl)phenoxy)nicotinamide

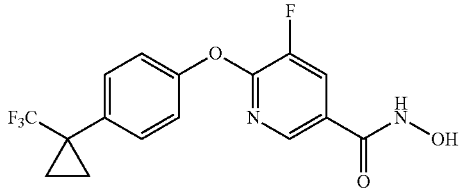

5-fluoro-N-hydroxy-6-(4-(1-(trifluoromethyl)cyclopropyl)phenoxy) nicotinamide

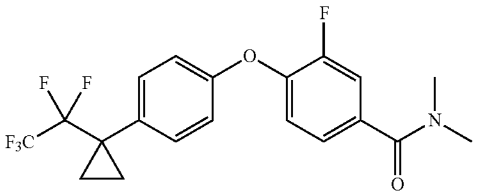

3-fluoro-N,N-dimethyl-4-(4-(1-(perfluoroethyl)cyclopropyl)phenoxy) benzamide

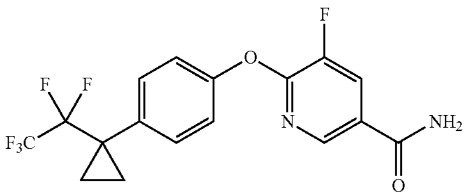

5-fluoro-6-(4-(1-(perfluoroethyl)cyclopropyl)phenoxy)nicotinamide

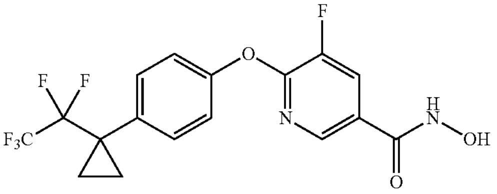

5-fluoro-N-hydroxy-6-(4-(1-(perfluoroethyl)cyclopropyl)phenoxy) nicotinamide

-continued

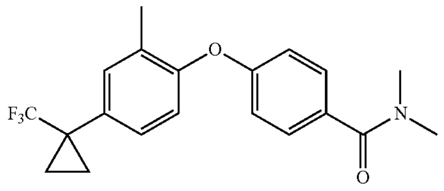

N,N-dimethyl-4-(2-methyl-4-(1-(trifluoromethyl)cyclopropyl)phenoxy) benzamide

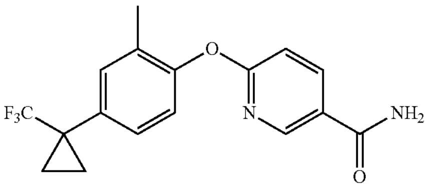

6-(2-methyl-4-(1-(trifluoromethyl)cyclopropyl)phenoxy)nicotinamide

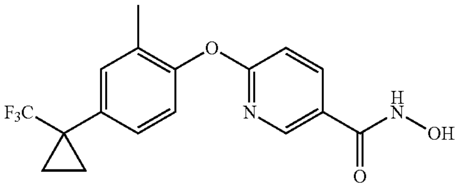

N-hydroxy-6-(2-methyl-4-(1-(trifluoromethyl)cyclopropyl)phenoxy) nicotinamide

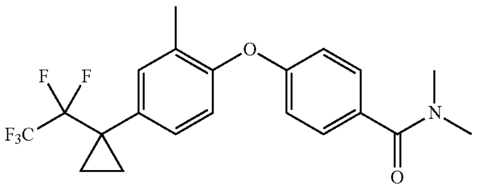

N,N-dimethyl-4-(2-methyl-4-(1-perfluoroethyl)cyclopropyl)phenoxy) benzamide

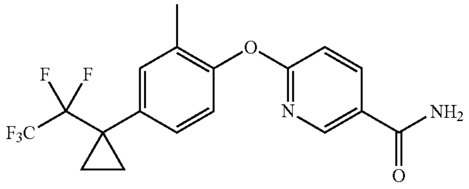

6-(2-methyl-4-(1-(perfluoroethyl)cyclopropyl)phenoxy)nicotinamide

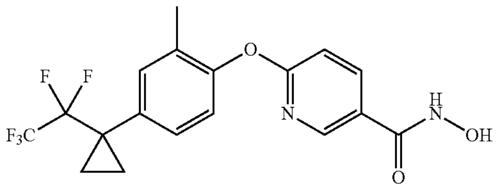

N-hydroxy-6-(2-methyl-4-(1-(perfluoroethyl)cyclopropyl)phenoxy) nicotinamide

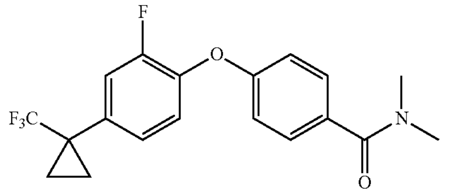

4-(2-fluoro-4-(1-(trifluoromethyl)cyclopropyl)phenoxy)-N,N,-dimethylbenzamide

-continued

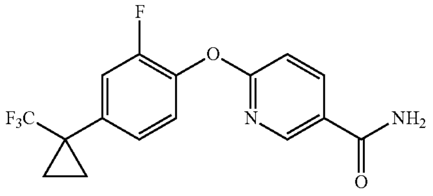

6-(2-fluoro-4-(1-(trifluoromethyl)cyclopropyl)phenoxy)nicotinamide

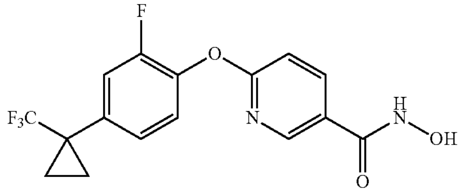

6-(2-fluoro-4-(1-(trifluoromethyl)cyclopropyl)phenoxy)-N-hydroxynicotinamide

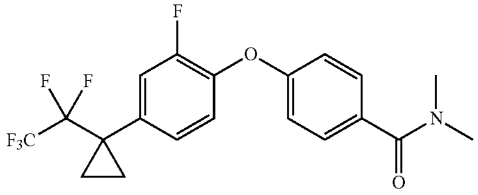

4-(2-fluoro-4-(1-(perfluoroethyl)cyclopropyl)phenoxy)-N,N-dimethylbenzamide

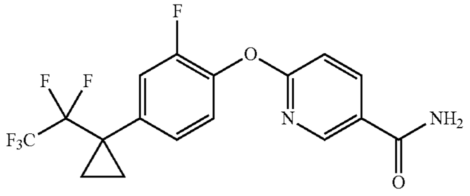

6-(2-fluoro-4-(1-(perfluoroethyl)cyclopropyl)phenoxy)nicotinamide

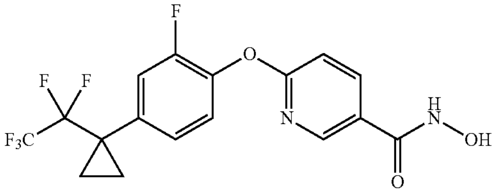

6-(2-fluoro-4-(1-(perfluoroethyl)cyclopropyl)phenoxy)-N-hydroxynicotinamide

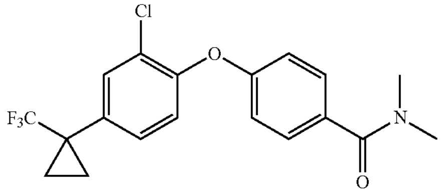

4-(2-chloro-4-(1-(trifluoromethyl)cyclopropyl)phenoxy)-N,N-dimethylbenzamide

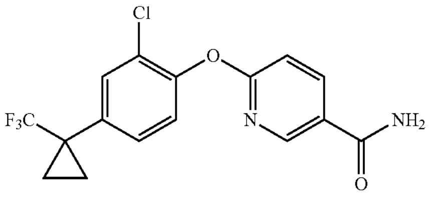

6-(2-chloro-4-(1-(trifluoromethyl)cyclopropyl)phenoxy)nicotinamide

-continued

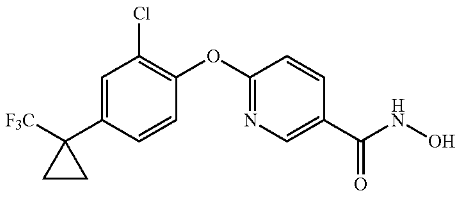

6-(2-chloro-4-(1-(trifluoromethyl)cyclopropyl)phenoxy)-N-hydroxynicotinamide

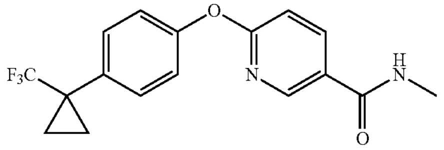

N-methyl-4-(4-(1-(trifluoromethyl)cyclopropyl)phenoxy)benzamide

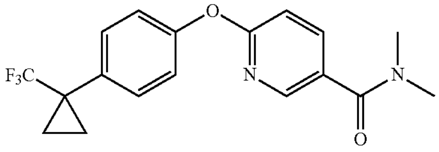

N,N-dimethyl-6-(4-(1-(trifluoromethyl)cyclopropyl)phenoxy)nicotinamide

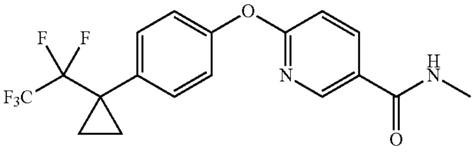

N-methyl-4-(4-(1-(perfluoroethyl)cyclopropyl)phenoxy)benzamide

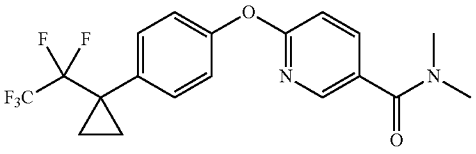

N,N-dimethyl-6-(4-(1-(perfluoroethyl)cyclopropyl)phenoxy)nicotinamide

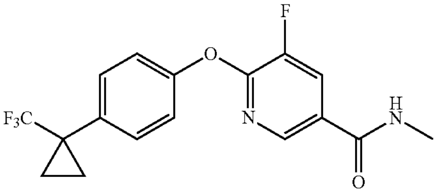

3-fluoro-N-methyl-4-(4-(1-(trifluoromethyl)cyclopropyl)phenoxy)benzamide

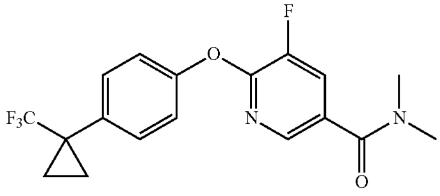

5-fluoro-N,N-dimethyl-6-(4-(1-(trifluoromethyl)cyclopropyl)phenoxy)nicotinamide

-continued

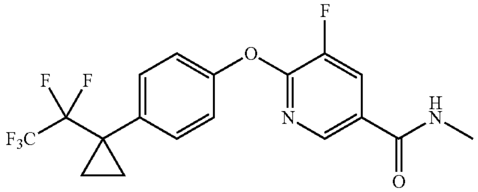

3-fluoro-N-methyl-4-(4-(1-(perfluoroethyl)cyclopropyl)phenoxy) benzamide

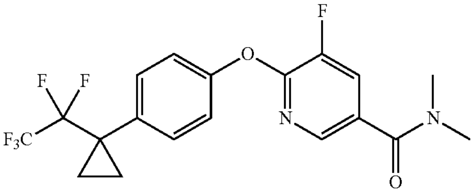

5-fluoro-N,N-dimethyl-6-(4-(1-(perfluoroethyl)cyclopropyl)phenoxy) nicotinamide

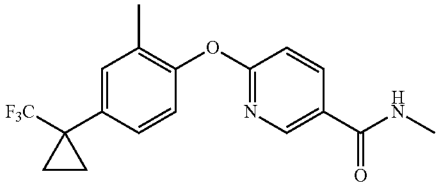

N-methyl-4-(2-methyl-4-(1-(trifluoromethyl)cyclopropyl)phenoxy) benzamide

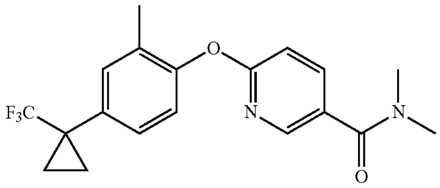

N,N-dimethyl-6-(2-methyl-4-(1-(trifluoromethyl)cyclopropyl)phenoxy) nicotinamide

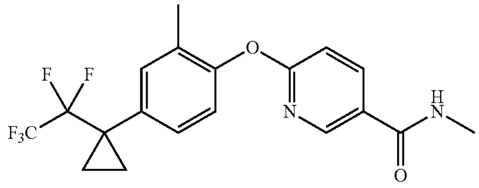

N-methyl-4-(2-methyl-4-(1-(perfluoroethyl)cyclopropyl)phenoxy) benzamide

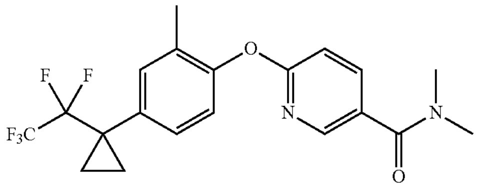

N,N-dimethyl-6-(2-methyl-4-(1-(perfluoroethyl)cyclopropyl)phenoxy) nicotinamide

-continued

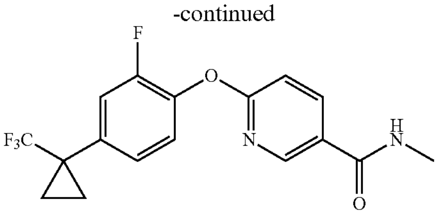

4-(2-fluoro-4-(1-(trifluoromethyl)cyclopropyl)phenoxy)-N-methylbenzamide

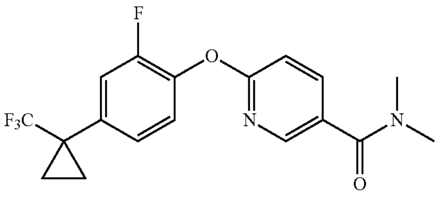

6-(2-fluoro-4-(1-(trifluoromethyl)cyclopropyl)phenoxy)-N,N-dimethylnicotinamide

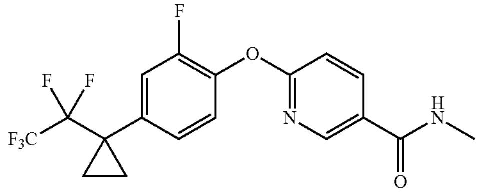

4-(2-fluoro-4-(1-(perfluoroethyl)cyclopropyl)phenoxy)-N-methylbenzamide

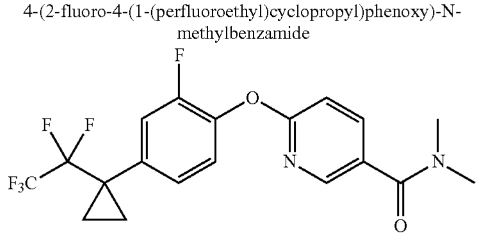

6-(2-fluoro-4-(1-(perfluoroethyl)cyclopropyl)phenoxy)-N,N-dimethylnicotinamide

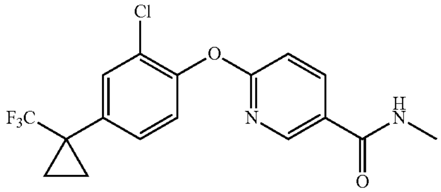

4-(2-chloro-4-(1-(trifluoromethyl)cyclopropyl)phenoxy)-N-methylbenzamide

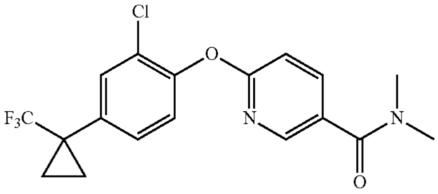

6-(2-chloro-4-(1-(trifluoromethyl)cyclopropyl)phenoxy)-N,N-dimethylnicotinamide

22. A pharmaceutical composition, comprising a) an active agent selected from the group consisting of the compound of claim 21 or a salt or solvate thereof; and b) a carrier, diluent and/or adjuvant suitable for administration to patients.

23. The composition of claim 15, wherein $R^1$ is selected from the group consisting of methyl, ethyl, n-propyl, n-butyl, n-pentyl, n-hexyl, iso-propyl, tert-butyl, tert-pentyl, 3-pentyl, $-CF_3$, $-CF_2CF_3$, $-(CF_2)_2CF_3$, $-(CF_2)_3CF_3$, $-CH(CF_3)_2$, $-CF(CF_3)_2$, cyclopropyl, cyclobutyl, cyclopentyl, cyclohexyl, cycloheptyl, norbornyl, bicyclo[2.2.2]octyl, adamantyl, and 9-methylbicyclo[3.3.1]nonyl.

24. The composition of claim 15, wherein $R^3$ is H or methyl.

25. The composition of claim 24, wherein $R^3$ is methyl and said methyl is fluorinated or perfluorinated.

26. The composition of claim 15, wherein all alkyl residues of $R^4$ can be linear or branched, and are substituted with one or more substituents independently selected from the group consisting of —F, —Cl, —Br, —I; $OC_1$-$C_3$ alkyl and halogenated $C_1$-$C_3$ alkyl.

27. The composition of claim 26, wherein any substituent that is a $C_1$-$C_3$ alkyl is perhalogenated, and any substitutent that is a $OC_1$-$C_3$ alkyl is halogenated or perhalogenated.

28. The composition of claim 15, wherein in the compound of Formula II, $R^4$ is selected from the group consisting of OH and methyl.

29. The compound of claim 28, wherein $R^4$ is methyl and said methyl is fluorinated or perfluorinated.

* * * * *